US012729193B2

(12) United States Patent
Nasveschuk et al.

(10) Patent No.: US 12,729,193 B2
(45) Date of Patent: Sep. 8, 2026

(54) TRICYCLIC LIGANDS FOR DEGRADATION OF IKZF2 OR IKZF4

(71) Applicant: C4 Therapeutics, Inc., Watertown, MA (US)

(72) Inventors: Christopher G. Nasveschuk, Stoneham, MA (US); James A Henderson, Weston, MA (US); Moses Moustakim, Cambridge, MA (US); Andrew Charles Good, Watertown, MA (US); David Proia, Newton, MA (US)

(73) Assignee: C4 Therapeutics, Inc., Watertown, MA (US)

( * ) Notice: Subject to any disclaimer, the term of this patent is extended or adjusted under 35 U.S.C. 154(b) by 511 days.

(21) Appl. No.: 18/134,985

(22) Filed: Apr. 14, 2023

(65) Prior Publication Data

US 2023/0339902 A1 Oct. 26, 2023

Related U.S. Application Data

(63) Continuation of application No. PCT/US2021/055102, filed on Oct. 14, 2021.

(60) Provisional application No. 63/091,875, filed on Oct. 14, 2020.

(51) Int. Cl.

| | |
|---|---|
| ***C07D 401/14*** | (2006.01) |
| ***C07D 401/04*** | (2006.01) |
| ***C07D 405/14*** | (2006.01) |
| ***C07D 471/04*** | (2006.01) |

(52) U.S. Cl.

CPC ......... *C07D 401/14* (2013.01); *C07D 401/04* (2013.01); *C07D 405/14* (2013.01); *C07D 471/04* (2013.01)

(58) Field of Classification Search

CPC .. C07D 401/14; C07D 401/04; C07D 405/14; C07D 471/04

USPC .................................................... 514/210.21

See application file for complete search history.

(56) References Cited

U.S. PATENT DOCUMENTS

| | | | |
|---|---|---|---|
| 5,635,517 | A | 6/1997 | Muller et al. |
| 8,648,096 | B2 | 2/2014 | Muller et al. |
| 9,732,064 | B2 | 8/2017 | Muller et al. |
| 9,796,698 | B2 | 10/2017 | Muller et al. |
| 9,801,868 | B2 | 10/2017 | Muller et al. |

(Continued)

FOREIGN PATENT DOCUMENTS

| | | |
|---|---|---|
| CA | 2198028 | 2/1996 |
| WO | WO 2002/059109 A2 | 8/2002 |

(Continued)

OTHER PUBLICATIONS

U.S. Appl. No. 18/134,990, filed Apr. 14, 2023, Nasveschuk, Christopher et al.*

(Continued)

*Primary Examiner* — Jeffrey S Lundgren
*Assistant Examiner* — Heather Dahlin
(74) *Attorney, Agent, or Firm* — Knowles Intellectual Property Strategies, LLC

(57) ABSTRACT

Tricyclic compounds that degrade IKZF2 and/or IKZF4 are provided for medical therapy, including abnormal cellular proliferation, including cancer, inflammatory disorders, neurodegenerative disorders or autoimmune disorders.

20 Claims, 3 Drawing Sheets

Specification includes a Sequence Listing.

(56) References Cited

U.S. PATENT DOCUMENTS

| | | | | |
|---|---|---|---|---|
| 9,834,538 | B2 | 12/2017 | Muller et al. | |
| 9,920,027 | B2 | 3/2018 | Ruchelman et al. | |
| 10,125,114 | B2 | 11/2018 | Bradner et al. | |
| 11,185,543 | B2 | 11/2021 | Alexander et al. | |
| 11,407,732 | B1 * | 8/2022 | Henderson et al. | C07D 401/04 |
| 2002/0147343 | A1 | 10/2002 | Chen et al. | |
| 2009/0298882 | A1 | 12/2009 | Muller et al. | |
| 2014/0356322 | A1 | 12/2014 | Crews et al. | |
| 2014/0377293 | A1 | 12/2014 | Zeldis | |
| 2016/0272639 | A1 | 9/2016 | Crew et al. | |
| 2018/0008574 | A1 | 1/2018 | Xu et al. | |
| 2019/0119285 | A1 | 4/2019 | Ndubaku et al. | |
| 2019/0233433 | A1 | 8/2019 | Crews et al. | |
| 2019/0328722 | A1 | 10/2019 | Ge et al. | |
| 2020/0000776 | A1 | 1/2020 | Ge et al. | |
| 2020/0061033 | A1 | 2/2020 | Lee et al. | |
| 2021/0206743 | A1 | 7/2021 | Lee et al. | |
| 2022/0213115 | A1 * | 7/2022 | Baculi et al. | C07D 491/107 |
| 2023/0322803 | A1 * | 10/2023 | Degnan et al. | C07D 498/04 |
| 2024/0360150 | A1 | 10/2024 | Fu et al. | |
| 2024/0383886 | A1 * | 11/2024 | Veits et al. | C07D 417/14 |

FOREIGN PATENT DOCUMENTS

| | | | | |
|---|---|---|---|---|
| WO | WO-2005/030132 | A2 | 4/2005 | |
| WO | WO 2008/027542 | A2 | 3/2008 | |
| WO | WO 2008/033567 | A1 | 3/2008 | |
| WO | WO 2008/039489 | A2 | 4/2008 | |
| WO | WO 2008/115516 | A2 | 9/2008 | |
| WO | WO 2009/042177 | A1 | 4/2009 | |
| WO | WO 2009/139880 | A1 | 11/2009 | |
| WO | WO 2009/145899 | A1 | 12/2009 | |
| WO | WO 2010/053732 | A1 | 5/2010 | |
| WO | WO 2012/175481 | A1 | 12/2012 | |
| WO | WO 2015/085172 | A2 | 6/2015 | |
| WO | WO-2015/160845 | A2 | 10/2015 | |
| WO | WO-2016/119690 | A1 | 8/2016 | |
| WO | WO-2017/197046 | A1 | 11/2017 | |
| WO | WO 2017/197056 | A1 | 11/2017 | |
| WO | WO 2017/201069 | A1 | 11/2017 | |
| WO | WO-2018/144649 | A1 | 8/2018 | |
| WO | WO-2018/237026 | A1 | 12/2018 | |
| WO | WO 2019/038717 | A1 | 2/2019 | |
| WO | WO 2019/148055 | A1 | 8/2019 | |
| WO | WO 2019/191112 | A1 | 10/2019 | |
| WO | WO-2019/201123 | A1 | 10/2019 | |
| WO | WO 2019/241274 | A1 | 12/2019 | |
| WO | WO 2020/006233 | A1 | 1/2020 | |
| WO | WO 2020/006262 | A1 | 1/2020 | |
| WO | WO 2020/006265 | A1 | 1/2020 | |
| WO | WO 2020/010177 | A1 | 1/2020 | |
| WO | WO 2020/010227 | A1 | 1/2020 | |
| WO | WO 2020/012334 | A1 | 1/2020 | |
| WO | WO-2020/012337 | A1 | 1/2020 | |
| WO | WO-2020/128972 | A1 | 6/2020 | |
| WO | WO-2020/165833 | A1 | 8/2020 | |
| WO | WO-2020/165834 | A1 | 8/2020 | |
| WO | WO2020210630 | A1 * | 10/2020 | C07D 209/92 |
| WO | WO 2021/041664 | A1 | 3/2021 | |
| WO | WO 2021/127586 | A1 | 6/2021 | |
| WO | WO-2022/032132 | A1 | 2/2022 | |
| WO | WO-2022/081927 | A1 | 4/2022 | |
| WO | WO-2022/081928 | A1 | 4/2022 | |

OTHER PUBLICATIONS

U.S. Appl. No. 17/723,199, filed Apr. 18, 2022, James A. Henderson et al.*

Asatsuma-Okumura T, Ito T, Handa H. Molecular mechanisms of cereblon-based drugs. Pharmacology & therapeutics. Oct. 1, 2019; 202:132-9. (Year: 2019).*

Agafonov, Roman et al. "Quantitative and high throughput method for measuring complex formation between target proteins and E3 ubiquitin ligase," C4 Therapeutics Presentation (2017).

Bartlett et al. "The evolution of thalidomide and its IMiD derivatives as anticancer agents" Nat Rev Cancer, 4(4):314-322, Apr. 2004.

Berndsen et al. "New insights into ubiquitin E3 ligase mechanism" Nat. Struct. & Mol. Biol., 21:4, 301-307, Apr. 2014.

Burslem, George M. et al. "Efficient synthesis of immunomodulatory drug analogues enables exploration of structure-degradation relationships" Chem Med Chem Comm, vol. 13:15, pp. 1508-1512 (2018).

C4 Therapeutics Presentation—S. Fisher, "Degrader Drugs: From cellular activity to in vivo pharmacology Discovery on Target," 21 pages, Sep. 18, 2019.

C4 Therapeutics Presentation—Huang et al., "CAMD Methods Development in Protein Degrader Space," 41 pages, Sep. 17, 2019.

C4 Therapeutics Presentation—C. Nasveschuk, "Degrader Drug Space: What Rules?" HT-ADME Conference Cambridge, MA, Jun. 20, 2019.

Chamberlain et al. "Structure of the human cereblon-DDB1-lenalidomide complex reveals basis for responsiveness to thalidomide analogs" Nature Structural & Molecule Biology, 21:9, 803-809, Sep. 2014.

Chang, X. et al. "What is the functional role of the thalidomide binding protein cereblon?" Int J Biochem Mol Bio., 2(3):287-294 (2011).

Contino-Pepin et al. "Preliminary biological evaluations of new thalidomide analogues for multiple sclerosis application", Bioorganic & Medicinal Chemistry Letters, 19(3), 878-881 (2009).

Deshaies et al. "Ring domain E3 ubiquitin ligases" Ann. Rev. Biochem., 78:399-434 (2009).

Duan et al. "Targeting Brd4 for cancer therapy: Inhibitors and degraders", MedChem Commun; 9. 1779-1802 (2018).

Fischer et al. "Structure of the DDB1-CRBN E3 ubiquitin ligase in complex with thalidomide" Nature, 512, 49-53, Aug. 7, 2014.

Fischer et al. "The Molecular Basis of CRL4DDB2/CSA Ubiquitin Ligase Architecture, Targeting, and Activation," Cell, 147, 1024-1039, Nov. 23, 2011.

Fisher, Stewart L., et al.; "Targeted protein degradation and the enzymology of degraders," Elsevier, Current Opinion in Chemical Biology, 44:47-55 (2018).

Hansen, Joshua D., et al.; "Discovery of CRBN E3 Ligase Modulator CC-92480 for the Treatment of Relapsed and Refractory Multiple Myeloma," Journal of Medicinal Chemistry, 63, 6648-6676 (2020).

International Application No. PCT/US21/55102, International Search Report and Written Opinion dated Feb. 2, 2022, 7 pages.

Ito et al. "Identification of a Primary Target of thalidomide teratogenicity", Science, 327, 1345-1350, Mar. 12, 2010.

Jacques et al. "Differentiation of anti-inflammatory and antitumorigenic properties of stabilized enantiomers of thalidomide analogs" PNAS, 112:19, E1471-E1479, May 12, 2015.

Kazantsev et al. Ligands for cereblon: 2017-2021 patent overview, Expert Opinion on Therapeutic Patents, 32:2, 171-190, Feb. 1, 2022.

Kronke et al. "Lenalidomide Causes Selective Degradation of IKZF1 and IKZF3 in Multiple Myeloma Cells" Science, 343(6168):301-305 (2014).

Kronke et al. "Lenalidomide induces ubiquitination and degradation of CDK1[alpha] in del(5q) MDS" Nature, 523(7559):183-188, Jul. 9, 2015.

Liu et al. Drug Discovery Targeting Bromodomain-Containing Protein 4, J. Med. Chem., 60 4533-4558 (2017).

Lu et al. "The myeloma drug lenalidomide promotes the cereblon-dependent destruction of Ikaros proteins" Science, 343:305-309 (2014).

Matyskiela, Mary E. et al. "A Cereblon Modulator (CC-220) with Improved Degradation of Ikaros and Aiolos," Journal of Medicinal Chemistry, 61, 535-542, (2018).

Norris et al. "Design and synthesis of novel cereblon binders for use in targeted protein degradation," Journal of Medicinal Chemistry, 66:23, 16388-16409, Nov. 22, 2023.

PubChem SID 434110878, available Sep. 28, 2020 [retrieved on Jan. 26, 2022]; https://pubchem.ncbi.nlm.nih.gov/substance/434110878].

(56) References Cited

OTHER PUBLICATIONS

Rok Frlan et al.; "Evaluation of US 2016/0115161A1: Isoindoline compounds and methods of their use," Expert Opinion on Therapeutic Patents, 27:6, 637-641 (2017).
Ruchelman et al. "Isosteric analogs of lenalidomide and pomalidomide: Synthesis and biological activity" Bioorganic and Medicinal Chemistry Letters, 23, 360-365 (2013).
Schneekloth et al. "Chemical approaches to controlling intracellular protein degradation" Chembiochem, 6(1):40-46 (2005).
Schneekloth et al. "Chemical Genetic Control of Protein Levels: Selective in Vivo Targeted Degradation" Journal of the American Chemical Society, 126:12, 3748-3754 (2004).
Schneekloth et al. "Targeted Intracellular Protein Degradation Induced by a Small Molecule: En Route to Chemical Proteomics" Bioorganic and Medicinal Chemistry Letters, 18:5904-5908 (2008).
Kim, Sung et al.; "A novel cereblon modulator for targeted protein degradation" European Journal of Medicinal Chemistry; vol. 166, 65-74 (2019).
C4 Therapeutics Presentation—Zeid, Rhamy; Targeted protein degradation as a novel therapeutic approach, High Throughput Chemistry & Chemical Biology Gordon Research Conference; pp. 40 (2017).
Zhou et al. "Harnessing the Ubiquitination Machinery to Target the Degradation of Specific Cellular Proteins" Molecular Cell, 6, 751-756, Sep. 2000.
US, U.S. Pat. No. 10,646,575, B2, U.S. Appl. No. 16/186,339, Phillips et al., May 12, 2020.
US, U.S. Pat. No. 10,660,968, B2, U.S. Appl. No. 16/186,334, Phillips et al., May 26, 2020.
US, U.S. Pat. No. 10,849,982, B2, U.S. Appl. No. 16/186,341, Phillips et al., Dec. 1, 2020.
US, U.S. Pat. No. 10,905,768, B2, U.S. Appl. No. 16/872,225, Phillips et al., Feb. 2, 2021.
US, U.S. Pat. No. 11,185,592, B2, U.S. Appl. No. 16/882,236, Phillips et al., Nov. 30, 2021.
US, U.S. Pat. No. 11,254,672, B2, U.S. Appl. No. 16/809,325, Norcross et al., Feb. 22, 2022.
US, U.S. Pat. No. 11,401,256, B2, U.S. Appl. No. 16/809,345, Norcross et al., Aug. 2, 2022.
US, U.S. Pat. No. 11,407,732, B2, U.S. Appl. No. 17/498,617, Henderson et al., Aug. 9, 2022.
US, U.S. Pat. No. 11,459,335, A1, U.S. Appl. No. 16/721,650, Phillips et al., Oct. 4, 2022.
US, U.S. Pat. No. 11,524,949, A1, U.S. Appl. No. 16/874,475, Phillips et al., Dec. 13, 2022.
US, U.S. Pat. No. 11,584,748, A1, U.S. Appl. No. 17/072,896, Nasveschuk et al., Feb. 21, 2023.
US, U.S. Pat. No. 11,623,929, A1, U.S. Appl. No. 17/103,621, Nasveschuk et al., Apr. 11, 2023.
US, U.S. Pat. No. 11,673,902, B2, U.S. Appl. No. 17/843,769, Nasveschuk et al., Jun. 13, 2023.
US, U.S. Pat. No. 11,691,972, A1, U.S. Appl. No. 17/541,035, Nasveschuk et al., Jul. 4, 2023.
US, U.S. Pat. No. 11,401,256, A1, U.S. Appl. No. 16/809,345, Norcross et al., Aug. 2, 2022.
US, U.S. Pat. No. 11,753,197, A1, U.S. Appl. No. 17/031,550, Henderson et al., Sep. 12, 2023.
US, U.S. Pat. No. 11,802,131, A1, U.S. Appl. No. 16/809,336, Norcross et al., Oct. 31, 2023.
US, U.S. Pat. No. 11,787,802, A1, U.S. Appl. No. 17/576,582, Norcross et al., Oct. 17, 2023.
US, 2021/0198256, A1, U.S. Appl. No. 17/192,634, Nasveschuk et al., Jul. 1, 2021.
US, 2022/0313826, A1, U.S. Appl. No. 17/107,781, Phillips et al., Oct. 6, 2022.
US, 2022/0313827, A1, U.S. Appl. No. 17/121,389, Phillips et al., Oct. 6, 2022.
US, 2022/0372016, A1, U.S. Appl. No. 17/351,935, Phillips et al., Nov. 24, 2022.
US, 2023/0014124, A1, U.S. Appl. No. 17/164,446, Phillips et al., Jan. 19, 2023.
US, 2023/0019060, A1, U.S. Appl. No. 17/465,583, Nasveschuk et al., Jan. 19, 2023.
US, 2023/0060334, A1, U.S. Appl. No. 17/901,775, Nasveschuk et al., Mar. 2, 2023.
US, 2023/0082430, A1, U.S. Appl. No. 17/723,199, Henderson et al., Mar. 16, 2023.
US, 2023/0095223, A1, U.S. Appl. No. 17/524,558, Phillips et al., Mar. 20, 2023.
US, 2023/0145336, A1, U.S. Appl. No. 18/084,380, Nasveschuk et al., May 11, 2023.
US, 2023/0190760, A1, U.S. Appl. No. 18/106,893, Proia et al., Jun. 22, 2023.
US, 2023/0192643, A1, U.S. Appl. No. 17/878,753, Norcross et al., Jun. 22, 2023.
US, 2023/0233692, A1, U.S. Appl. No. 18/105,735, Henderson et al., Jul. 27, 2023.
US, 2023/0279023, A1, U.S. Appl. No. 17/959,144, Phillips et al., Sep. 7, 2023.
US, 2023/0372496, A1, U.S. Appl. No. 18/134,971, Nasveschuk et al., Nov. 23, 2023.
U.S. Appl. No. 18/240,231, Henderson et al., filed Aug. 30, 2023.
U.S. Appl. No. 18/100,992, Nasveschuk et al., filed Jan. 24, 2023.
U.S. Appl. No. 18/117,978, Nasveschuk et al., filed Mar. 6, 2023.
U.S. Appl. No. 18/134,990, Nasveschuk et al., filed Apr. 14, 2023.
U.S. Appl. No. 18/144,800, Nasveschuk et al., filed May 8, 2023.
U.S. Appl. No. 17/965,569, Nasveschuk et al., filed Oct. 13, 2022.
U.S. Appl. No. 18/079,815, Phillips et al., filed Dec. 12, 2022.
U.S. Appl. No. 18/370,186, Norcross et al., filed Sep. 19, 2023.
U.S. Appl. No. 18/385,277, Norcross et al., filed Oct. 30, 2023.
U.S. Appl. No. 18/516,589, Nasveschuk et al., filed Nov. 21, 2023.
U.S. Appl. No. 18/534,395, Nasveschuk et al., filed Dec. 8, 2023.
CAS Registry No. 2655648-70-5. Database Registry Chemical Abstracts Service, Columbus, Ohio, Entered STN: Jul. 15, 2021.
CAS Registry No. 2655647-40-6. Database Registry Chemical Abstracts Service, Columbus, Ohio, Entered STN: Jul. 15, 2021.
CAS Registry No. 2504233-68-3. Database Registry Chemical Abstracts Service, Columbus, Ohio, Entered STN: Nov. 4, 2020.
CAS Registry No. 19031-28-8. Database Registry Chemical Abstracts Service, Columbus, Ohio, Entered STN: Nov. 16, 1984.
CAS Registry No. 21283-86-3. Database Registry Chemical Abstracts Service, Columbus, Ohio, Entered STN: Nov. 16, 1984.
Bjorklund et al. "Rate of CRL4CRBN substrate Ikaros and Aiolos degradation underlies differential activity of lenalidomide and pomalidomide in multiple myeloma cells by regulation of c-Myc and IRF4". Blood Cancer Journal (2015) vol. 5, e354, published Oct. 2, 2015.
Cippitelli et al., "Role of Aiolos and Ikaros in the Antitumor and Immunomodulatory Activity of IMiDs in Multiple Myeloma: Better to Lose Than to Find Them" Int. J. Mol. Sci., vol. 22, Issue 1103, published Jan. 22, 2021.
Chen, et al. "Multiple Functions of Ikaros in Hematological Malignancies, Solid Tumor and Autoimmune Diseases." Gene, vol. 684, Feb. 2019, pp. 47-52. Science Direct, https://doi.org/10.1016/j.gene.2018.10.045. (Year: 2019).
Dokunikhin, N.S. and Gaeva, L.A. Benz[c,d]Indoline Derivatives. II. 6-Benzoylbenz[c,d]indoline-2-one, 1-Methyl-6-Benzoylbenz[c,d]indoline-2-one and the Products of Their Cyclization. J. Gen. Chem. USSR, v. 28, No. 11, 2944-2948, 1958.
Hörig, H. and Pullman, W. "From bench to clinic and back: perspective on the 1st IQPC translational research conference" J. Translational Med. 2004, vol. 2 Article 44.
Suarez, et al. "IKAROS Expression Profiles Characterize Different Autoimmune Diseases." Translational Medicine Communications, vol. 3, No. 1, Dec. 2018, p. 11. BioMed Central, https://doi.org/10.1186/s41231-018-0030-3.
Yan Jingxiu and Zhao Lidong "Effects of thalidomide and baicalein on proliferation, apoptosis and CRBN protein expression in HEL cells", Journal of Xuzhou Medical University, 2017, 37(9): 566-570 (Chinese).
U.S. Pat. No. 11,992,531-B2, May 28, 2024, Phillips et al., U.S. Appl. No. 17/107,781.

(56) References Cited

OTHER PUBLICATIONS

U.S. Pat. No. 12,048,747-B2, Jul. 30, 2024, Phillips et al., U.S. Appl. No. 17/121,389.
U.S. Pat. No. 12,048,748-B2, Jul. 30, 2024, Phillips et al., U.S. Appl. No. 17/524,558.
U.S. Pat. No. 12,049,464-B2, Jul. 30, 2024, Nasveschuk et al., U.S. Appl. No. 17/901,775.
U.S. Pat. No. 12,076,405-B2, Sep. 3, 2023, Phillips et al., U.S. Appl. No. 17/164,446.
U.S. Pat. No. 12,091,397-B2, Sep. 17, 2024, Norcross et al., U.S. Appl. No. 17/878,753.
U.S. Pat. No. 12,157,735-B2, Dec. 3, 2024, Nasveschuk et al., U.S. Appl. No. 17/965,569.
U.S. Pat. No. 12,180,225-B2, Dec. 31, 2024, Phillips et al., U.S. Appl. No. 17/959,144.
U.S. Pat. No. 12,227,504-B2, Feb. 18, 2025, Nasveschuk et al., U.S. Appl. No. 18/100,992.
U.S. Pat. No. 12,365,681-B2, Jul. 22, 2025, Norcross et al., U.S. Appl. No. 18/370,186.
U.S. Pat. No. 12,371,442-B2, Jul. 29, 2025, Nasveschuk et al., U.S. Appl. No. 18/144,800.
U.S. Pat. No. 12,421,220-B2, Sep. 23, 2025, Nasveschuk et al., U.S. Appl. No. 18/972,557.
U.S. Pat. No. 12,441,740-B2, Oct. 14, 2024, Phillips et al., U.S. Appl. No. 18/973,867.
U.S. Pat. No. 12,454,521-B2, Oct. 28, 2025, Phillips et al., U.S. Appl. No. 17/351,935.
U.S. Pat. No. 12,486,253-B2, Dec. 2, 2025, Nasveschuk et al., U.S. Appl. No. 18/980,700.
U.S. Pat. No. 12,486,290-B2, Dec. 2, 2025, Nasveschuk et al., U.S. Appl. No. 19/205,510.
U.S. Pat. No. 12,528,797-B2, Jan. 20, 2026, Nasveschuk et al., U.S. Appl. No. 17/465,583.
U.S. Pat. No. 12,559,492-B2, Feb. 24, 2026, Nasveschuk et al., U.S. Appl. No. 18/084,380.
U.S. Pat. No. 12,570,626-B2, Mar. 10, 2026, Phillips et al., U.S. Appl. No. 18/079,815.
US-2023/0024096-A1, Jan. 26, 2023, Duplessis et al., U.S. Appl. No. 17/771,204.
US-2024/0018118-A1, Jan. 18, 2024, Nasveschuk et al., U.S. Appl. No. 18/134,990.
US-2024/0018156-A1, Jan. 18, 2024, Nasveschuk et al., U.S. Appl. No. 18/117,978.
US-2024/0158418-A1, May 16, 2024, Nasveschuk et al., U.S. Appl. No. 18/516,589.
US-2024/0199581-A1, Jun. 20, 2024, Nasveschuk et al., U.S. Appl. No. 18/534,395.
US-2024-0199638-A1, Jun. 20, 2024, Norcross et al., U.S. Appl. No. 18/385,277.
US-2024/0245677-A1, Jul. 25, 2024, Jackson et al., U.S. Appl. No. 18/600,097.
US-2024/0391912-A1, Nov. 28, 2024, Henderson et al., U.S. Appl. No. 18/797,261.
US-2024/0398959-A1, Dec. 5, 2024, Phillips et al., U.S. Appl. No. 18/642,602.
US-2025-0057957-A1, Feb. 20, 2025, Phillips et al., U.S. Appl. No. 18/774,801.
US-2025-0084055-A1, Mar. 13, 2025, Norcross et al., U.S. Appl. No. 18/806,363.
US-2025/0084081-A1, Mar. 13, 2025, Nasveschuk et al., U.S. Appl. No. 18/945,284.
US-2025/0121069-A1, Apr. 17, 2025, Phillips et al., U.S. Appl. No. 18/775,662.
US-2025/0121070-A1, Apr. 17, 2025, Nasveschuk et al., U.S. Appl. No. 18/979,247.
US-2025/0127903-A1, Apr. 24, 2025, Phillips et al., U.S. Appl. No. 18/774,794.
US-2025/0282780 A1, Sep. 11, 2025, Nasveschuk et al., U.S. Appl. No. 19/053,297.
US-2025/0289827-A1, Sep. 18, 2025, Yu et al., U.S. Appl. No. 19/224,081.
US-2025-0368631 A1, Dec. 4, 2025, Nasveschuk et al., U.S. Appl. No. 19/303,022.
US-2025/0382285-A1, Dec. 18, 2025, Nasveschuk et al., U.S. Appl. No. 19/303,091.
US-2026/0015338-A1, Jan. 15, 2026, Phillips et al., U.S. Appl. No. 19/336,041.
US-2026/0015362-A1, Jan. 15, 2026, Phillips et al., U.S. Appl. No. 19/336,152.
US 2026-0042782 A1, Feb. 12, 2026, Nasveschuk et al., U.S. Appl. No. 19/363,434.
U.S. Appl. No. 19/255,607, filed Jun. 30, 2025, Norcross et al.
U.S. Appl. No. 19/384,750, filed Nov. 10, 2025, Nasveschuk et al.
U.S. Appl. No. 19/545,998, filed Feb. 20, 2026, Phillips et al.

* cited by examiner 3 5 2 4 1 6 8 7 9

TRICYCLIC LIGANDS FOR DEGRADATION OF IKZF2 OR IKZF4

CROSS-REFERENCE TO RELATED APPLICATIONS

This application is a continuation of International Patent Application No. PCT/US2021/055102, filed on Oct. 14, 2021, which claims benefit of and priority to U.S. Provisional Application No. 63/091,875, filed on Oct. 14, 2020, each of which is hereby incorporated by reference herein in its entirety.

FIELD OF THE INVENTION

The invention provides tricyclic cereblon binders for the degradation of IKZF2 (Helios) and/or IKZF4 (Eos) by the ubiquitin proteasomal pathway for the treatment of medical disorders mediated by these transcription factors.

INCORPORATION BY REFERENCE

The contents of the XML file named "16010-057WO1US1_ST26_2023-03-23.xml" which was created on Mar. 23, 2023, and is 3.64 KB in size, are hereby incorporated by reference in their entirety.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

The Ikaros ("IKZF") family is a series of zinc-finger protein transcription factors that are important for certain physiological processes, particularly lymphocyte development (see Fan, Y. and Lu, D. "The Ikaros family of zinc-finger proteins" Acta Pharmaceutica Sinica B, 2016, 6:513-521). Ikaros ("IKZF1") was first discovered in 1992 (see Georgopoulos, K. et al. "Ikaros, an early lymphoid-specific transcription factor and a putative mediator for T cell commitment" Science, 1992, 258:802-812), and over the subsequent two decades four additional homologs have been identified: Helios ("IKZF2"), Aiolos ("IKZF3"), Eos ("IKZF4"), and Pegasus ("IKZF5") (see John, L. B., and Ward, A. C. The Ikaros gene family: transcriptional regulators of hematopoiesis and immunity" Mol Immunol, 2011, 48:1272-1278). Each homolog gene can produce several protein isoforms through alternative splicing, theoretically allowing for the generation of a large number of protein complexes through different combinations of the various homologs. Highly conserved among members of this family is a set of two $Cys_2His_2$ zinc finger motifs at the C-terminus that mediates protein interactions among various members of the protein family. Up to four zinc finger motifs at the N-terminus are present for recognition of DNA sequences, with the number of these N-terminal zinc fingers varying due to alternative splicing. Isoforms without these N-terminal zinc fingers show a dominant negative effect on transcriptional activation (see Winandy, S. et al. "A dominant mutation in the Ikaros gene leads to rapid development of leukemia and lymphoma" Cell, 1995, 83:289-299).

The distribution of various members of the Ikaros protein family within the body varies significantly. Ikaros, Helios, and Aiolos are mainly present in lymphoid cells and their corresponding progenitors, with Ikaros additionally also detected in the brain, and Ikaros and Helios also detected in erythroid cells. Eos and Pegasus are more widely spread, and found in skeletal muscle, the liver, the brain, and the heart (see Perdomo, J. et al. "Eos and Pegasus, two members of the Ikaros family of proteins with distinct DNA binding activities: J Biol Chem, 2000, 275:38347-38354; Schmitt, C. et al. "Aiolos and Ikaros: regulators of lymphocyte development, homeostasis and lymphoproliferation" Apoptosis, 2002, 7:277-284; Yoshida, T. and Georgopoulos, K. "Ikaros fingers on lymphocyte differentiation" Int J Hematol, 2014, 100:220-229).

Regulatory T cells (Tregs) are a specialized subpopulation of T cells that suppress the immune response to maintain homeostasis, self-tolerance and autoimmunity (PMID: 20672742). Tregs can inhibit T cell proliferation and cytokine production. A number of subsets of Tregs exist.

Tregs suppress CD4+ and CD8+ T cells by consuming IL-2, restricting IL-2 expression and upregulating CTLA4 to suppress antigen presenting cells (APCs). Tregs also produce cytokines (IL-10, IL-35 and TGF-β) to inhibit effector T-cell activation, as well as to secrete granzyme and/or perforin to destroy effector cells. In addition, Tregs generate adenosine from ATP in the tumor microenvironment that can prevent optimal T cell activation.

Tregs work antagonistically to other T cells that attack tumors or cancers. In cancer environments, an excess of Treg activity can prevent the immune system from destroying cancer cells. In autoimmune disease, too few Tregs can allow other autoimmune cells to attack the body's own tissue. The percentage of Tregs in circulation in multiple myeloma patients is significantly higher than in healthy people, and multiple myeloma patients with high Tregs live shorter lives.

Tregs are a subset of CD4+ T cells that express $FoxP_3$ (forkhead box $P_3$), which is a transcription factor that is a master regulator of the regulatory pathway in the development and function of regulatory T cells. $FoxP_3$ is a marker for both natural Treg cells (nTregs) and adaptive/induced T regulatory cells (a/iTregs). Multiple studies have shown that $FoxP_3$ plays an important role in cancer development.

IKZF2 and IKZF4 are selectively expressed in Treg cells but not effector or memory cells. $FoxP_3$/IKZF4/CtBP1 forms an inhibitory complex that suppresses gene expression (IL-2, IFN-7) in Tregs and maintains its suppressive signature. Knocking down IKZF4 in Tregs abrogates the cell's ability to suppress immune responses and enables partial effector function. Mir-17 targets IKZF4 for degradation and its overexpression diminishes the suppression activity of Treg. Tregs lacking MiR-17 exhibit increased suppression.

Syngeneic tumor-bearing mice treated with mouse $FoxP_3$ antisense oligos significantly attenuate tumor growth. It is becoming more clear that IKZF4 plays a critical role in controlling many of the suppressive functions of Tregs by interacting with $FoxP_3$.

IKZF2 regulates Treg differentiation through a distinct mechanism from IKZF4. IKZF2 knockout in $FoxP_3$-expressing Tregs promotes loss of inhibitory properties (with an increase in IL-2) and expression of T-effector cytokines via STAT5 (which regulates $FoxP_3$). Like IKZF4 knock-outs, IKZF2 knock-outs are unable to prevent autoimmune disease in an inflammatory bowel disease model. IKZF2 is highly expressed in leukemic stem cells and contributes to leukemogenesis. IKZF2 regulates chromatin accessibility of and maintains expression of self-renewal transcription factors, HOXA9 and MYC in leukemic stem cells. IKZF2 inhibits myeloid differentiation by suppressing the accessibility of myeloid differentiation genes containing C/EBP motifs Unlike IKZF1 and IKZF3, it is suggested that IKZF4 may function as a positive regulator of $T_H1$ genes. IKZF4 expression has been shown to correlate with expression of $T_H1$ genes at both the transcript and protein levels. Therefore, IKZF4 may have an opposing role to IKZF1 and IKZF3 in the regulation of $T_H1$ differentiation and function. Also, unlike IKZF1 and IKZF3, IKZF4 may negatively regulate $T_H17$ differentiation. Likewise, IKZF4 appears to oppose the functions of IKZF1 and IKZF3 in $T_{FH}$ cells.

IKZF2 and IKZF4 have not been, and may not be able to be, selectively targeted with conventional small molecule inhibitor drugs.

There has been little research and thus progress on the identification and use of drugs that can selectively degrade IKZF2 and/or IKZF4.

Novartis has an IKZF2/4 protein degrader in clinical trials. See Adcock, et.al., Novartis AG, WO 2020/012334; Beckwith, et.al, Novartis AG, WO 2020/012337; Visser, et.al., Novartis AG, WO 2019/038717; and Binazzi, et.al., Novartis AG, WO 2020/128972.

Dana Farber Cancer Institute has also filed patent applications in this general area: Gray, et.al., Dana-Farber Cancer Institute, WO 2020/006264; and Verano, et.al., Dana Farber Cancer Institute, WO 2020/117759, and WO 2021/087093. Bristol-Myers Squibb Company has also filed on IKZF2 degraders, for example, WO 2021/101919 and WO 2021/194914.

Ionis Pharmaceuticals and Astra Zeneca have reported a high-affinity oligonucleotide (AZD8701) that targets $FoxP_3$ and inhibits the immunosuppressive function of regulatory T-cells and produces an anti-tumor effect in syngeneic mice (AACR Annual Meeting Abst 5561; April 2018).

PCT/US2019/24094 and PCT/US2020/02678 filed by C4 Therapeutics, Inc. disclose cereblon binders for degradation of Ikaros (IKZF1/3).

WO 2021/127586 filed by Calico Life Sciences LLC and AbbVie Inc. describes PTPN1 and PTPN2 ligands covalently bound to various cereblon ligands.

Despite these efforts there remains a need for compounds that catalyze the selective degradation of zinc finger proteins such as IKZF2 and IKZF4 for medical therapy, including for the treatment of disorders that involve abnormal cellular proliferation, including tumors and cancers.

SUMMARY OF THE INVENTION

It has been discovered that certain tricyclic glutarimide compounds can degrade IKZF2 and/or IKZF4. Further, in certain embodiments, these tricyclic compounds exhibit selectivity in their degradation of IKZF2 and/or IKZF4 over IKZF1 or IKZF3. Thus, new tricyclic compounds are provided that can be administered in an effective amount to a host, typically a human, to treat medical disorders that are responsive to drugs that selectively degrade IKZF2 and/or IKZF4, including for example abnormal cellular proliferation, including cancer, inflammatory disorders, neurodegenerative disorders, and autoimmune disorders. The invention includes the described IKZF2 and/or IKZF4 degraders and their pharmaceutically acceptable salts along with their uses and manufacture.

In certain embodiments, the tricyclic compounds of the present invention have degradation selectivity in vitro for IKZF2 and/or IKZF4 over IKZF1 and/or IKZF3 of at least about 1.5, 2, 3, 5, or even 10-fold in a standard HiBiT bioluminescence assay.

In certain embodiments by selectively degrading IKZF2 and/or IKZF4, the tricyclic glutarimides described herein or their pharmaceutically acceptable salts can be used to treat diseases that are in immunosuppressed environments due to the presence of Treg cells and/or other associated cytokines and mediators that reduce the host's normal immune response to the disease. In one non-limiting embodiment, a host biopsy can be tested for the biomarker $FoxP_3$, or upregulation of IL-10, IL-35 or TGF$\beta$, to determine optimal therapy.

A selected compound disclosed herein, its pharmaceutically acceptable salt, or its pharmaceutically acceptable composition can be used to treat a disorder mediated by IKZF2 or IKZF4, for example, a solid tumor such as lung cancer, including small cell lung carcinoma or non-small cell lung carcinoma (for example those refractory to PD-1 or PD-L1), melanoma (for example those refractory to PD-1 or PD-L1), breast cancer (including triple negative breast cancer) or a hematopoietic malignancy such as multiple myeloma, leukemia, acute myeloid leukemia, acute lymphoblastic leukemia, chronic lymphoblastic leukemia, a myelodysplastic syndrome, or other target indications. In certain embodiments, the cancer is CLL with increased $FoxP_3$ CD4+ cells. It is known that Jurkat cells (T-ALL) express IKZF2 and IKZF4, and therefore these compounds can be used to treat T-ALL. Additional examples of cancers mediated by IKZF2 or IKZF4 include T-cell leukemia, T-cell lymphoma, Hodgkin's lymphoma, non-Hodgkin's lymphoma, myeloid leukemia, nasopharyngeal cancer, microsatellite stable colorectal cancer, thymoma, and carcinoid.

In certain embodiments, the selective degrader of IKZF2 and/or IKZF4 is administered to a host in need thereof in combination with another active agent, for example, a checkpoint inhibitor, CAR-T therapy, a targeted antibody, an antibody drug conjugate or other standard of care therapy for the cancer or abnormal cell proliferation treated. In certain embodiments, the patient has cancer that has progressed on immune checkpoint inhibitor therapy, has a high tumor burden, is over about 60 or 65 years old or has an increased number of Treg markers. When used in combination with another compound or biologic that treats immunosuppression, it may lead to an enhanced activation and effector function of CD4+ T cells, CD8+ T cells, B cells, NK cells, macrophages or dendritic cells.

The invention provides a compound of Formula I:

(I)

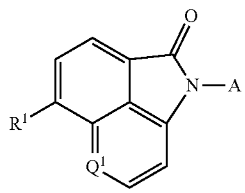

or a pharmaceutically acceptable salt, N-oxide, isotopic derivative, or prodrug thereof, optionally in a pharmaceutically acceptable carrier to form a composition;

wherein:

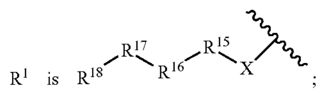

$Q^1$ is CH or N;

X is selected from bond, alkyl, aliphatic, heterocycle (which can be bound through C and/or N in the ring), aryl, heteroaryl, bicycle, —$NR^{27}$—, —$NR^{10}$—, —$CR^{40}R^{41}$—, —O—, —C(O)—, —C($NR^{27}$)—, —C(S)—, —S(O)—, —$S(O)_2$— and —S—; each of which is optionally substituted, as allowed by valence, to form a stable compound, with 1, 2, 3, or 4 substituents independently selected from non-hydrogen $R^{40}$;

$R^{15}$, $R^{16}$, and $R^{17}$ are independently at each occurrence selected from the group consisting of a bond, alkyl, —C(O)—, —C(O)O—, —OC(O)—, —$SO_2$—, —S(O)—, —C(S)—, —C(O)$NR^{27}$—, —$NR^{27}$C(O)—, —O—, —S—, —$NR^{27}$—, —$NR^{10}$—, —C($R^{40}R^{41}$)—, bicycle, alkene, alkyne, haloalkyl, alkoxy, aryl, heterocycle, aliphatic, cycloalkyl, heteroaliphatic, and heteroaryl; each of which is optionally substituted, as allowed by valence to form a stable compound, with 1, 2, 3, or 4 substituents independently selected from $R^{40}$; and wherein no more than two of $R^{15}$, $R^{16}$, and $R^{17}$ are selected to be bond;

$R^{18}$ is selected from hydrogen, halogen, cyano, —C(O)$R^{27}$, —C(O)$OR^{27}$, alkyl, —C(O)$NR^{10}R^{27}$, —$NR^{27}$C(O)$R^{27}$, —$NR^{10}R^{27}$, —$OR^{27}$, —$SR^{27}$, alkene, alkyne, haloalkyl, alkoxy, aryl, heterocycle, aliphatic, heteroaliphatic, heteroaryl; each of which is optionally substituted, as allowed by valence to form a stable compound, with 1, 2, 3, or 4 substituents independently selected from $R^{40}$; and wherein X, $R^{15}$, $R^{16}$, $R^{17}$ and $R^{18}$ are selected in combination as known by those of skill in the art to provide a stable $R^1$ moiety under ambient conditions of use and desired shelf life, for example of at least about 2, 3, 4, 5 or 6 months or more; typically X, $R^{15}$, $R^{16}$, $R^{17}$ and $R^{18}$ are selected such that no more than 1, 2, or 3 heteroatoms can be connected sequentially;

$R^{27}$ is independently at each occurrence selected from the group consisting of hydrogen, alkyl, arylalkyl, heteroarylalkyl, alkene, alkyne, aryl, heteroaryl, heterocycle, cycloalkyl, aliphatic and heteroaliphatic;

$R^{40}$ is independently at each occurrence selected from hydrogen, aliphatic, heteroaliphatic, cyano, nitro, alkyl, halogen (including specifically F, Cl, Br), haloalkyl, —$OR^{10}$, —$SR^{10}$, —S(O)$R^{12}$, —$SO_2R^{12}$, and —$NR^{10}R^{11}$;

$R^{41}$ is aliphatic, aryl, heteroaryl, or hydrogen;

A is selected from:

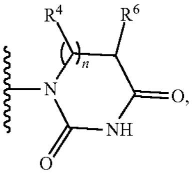
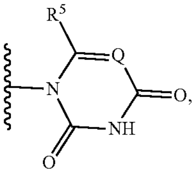
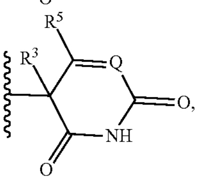
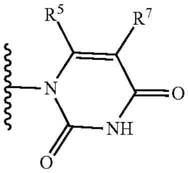
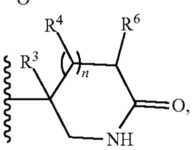
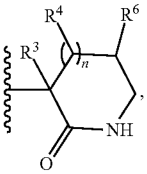
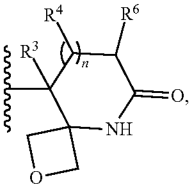
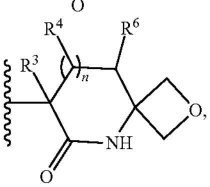
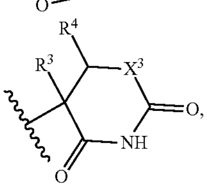
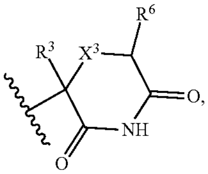
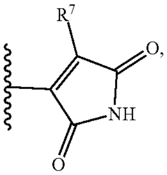
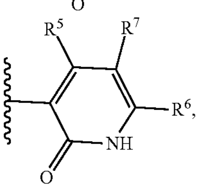
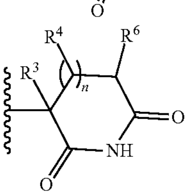

and

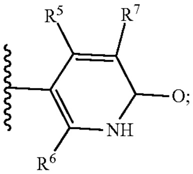

n is 0, 1, or 2;

$X^3$ is $NR^{10}$, $NR^{6'}$, O, or S;

Q is $CR^7$ or N;

$R^3$ is hydrogen, alkyl, halogen, or haloalkyl;

or $R^3$ and $R^6$ are combined to form a 1 or 2 carbon attachment;

or $R^3$ and $R^4$ are combined to form a 1, 2, 3, or 4 carbon attachment;

or $R^3$ and an $R^4$ group adjacent to $R^3$ are combined to form a double bond.

$R^4$ and $R^5$ are independently selected from hydrogen, alkyl, halogen, haloalkyl, —$OR^{10}$, —$SR^{10}$, —$S(O)R^{12}$, —$SO_2R^{12}$, and —$NR^{10}R^{11}$;

$R^6$ and $R^7$ are independently selected from hydrogen, alkyl, halogen, haloalkyl, —$OR^{10}$, —$SR^{10}$, —$S(O)R^{12}$, —$SO_2R^{12}$, and —$NR^{10}R^{11}$, $R^{6'}$ is hydrogen, alkyl, or haloalkyl;

or $R^3$ and $R^{6'}$ are combined to form a 1 or 2 carbon attachment.

each $R^{10}$ and $R^{11}$ are independently selected from hydrogen, aliphatic, alkyl, haloalkyl, heterocycle, aryl, heteroaryl, —$C(O)R^{12}$, —$S(O)R^{12}$, and —$SO_2R^{12}$;

each $R^{12}$ is independently selected from hydrogen, alkyl, haloalkyl, heterocycle, aryl, heteroaryl, —$NR^{13}R^{14}$, and $OR^{13}$; and each instance of $R^{13}$ and $R^{14}$ is independently selected from hydrogen, alkyl, and haloalkyl.

Every combination of variables, substituents, embodiments and the compounds that result from these combinations, is deemed specifically and individually disclosed, as such depiction is for convenience of space only and not intended to describe only a genus or even a subgenus of compounds, as known by those of skill in the art, but instead to provide each species hereunder that is a stable compound under ambient conditions of use and desired shelf life, for example of at least about 2, 3, 4, 5 or 6 months or more.

In certain embodiments, the compounds described herein bind to cereblon, increasing the interaction between cereblon and IKZF2 or IKZF4 and leading to the subsequent ubiquitination and degradation of the protein in the proteasome.

In some embodiments, therefore, based on this discovery, compounds and methods are provided for the treatment of a patient with a disorder mediated by IKZF2 or IKZF4, which is in certain embodiments a lymphoid disorder. In certain embodiments, the disorder is a leukemia. In certain embodiments, the disorder is a lymphoid leukemia. In certain embodiments, the disorder is a lymphoblastic leukemia. In some embodiments, the disorder is a hematological malignancy, for example multiple myeloma, a myelodysplastic syndrome such as 5q-syndrome, acute lymphoblastic leukemia, Hodgkin's lymphoma, non-Hodgkin's lymphoma, myeloid leukemia, acute myeloid leukemia, chronic myeloid leukemia, or chronic lymphocytic leukemia. In another embodiment, a selected compound of the present invention is administered to achieve immunomodulation and to reduce angiogenesis.

In other embodiments, compounds and methods are presented for the treatment of a disorder including, but not limited to, benign growth, neoplasm, tumor, cancer, abnormal cellular proliferation, immune disorders, inflammatory disorders, graft-versus-host rejection, viral infection, bacterial infection, an amyloid-based proteinopathy, a proteinopathy, or a fibrotic disorder. Further, other disorders are described below which can be treated with an effective amount of a compound described herein.

In certain embodiments, any of the compounds described herein have at least one desired substitution of an atom, at an amount about the natural abundance of the isotope, i.e., enriched.

Other features and advantages of the present invention will be apparent from the following detailed description and claims.

Thus, the present invention includes at least the following features:

(a) a compound of Formula I as described herein, or a pharmaceutically acceptable salt, isotopic derivative (including a deuterated derivative), or prodrug thereof;

(b) a compound of Formula I as described herein, or a pharmaceutically acceptable salt, isotopic derivative, or prodrug thereof, for the treatment of a disorder that is mediated by IKZF2 or IKZF4;

(c) a method of treating a patient, typically a human, in need thereof comprising administering an effective amount of a compound of Formula I as described herein, or a pharmaceutically acceptable salt thereof, wherein the patient has a disorder described herein, for example a disorder mediated by IKZF2 or IKZF4;

(d) a method of treating a patient, typically a human, in need thereof comprising administering an effective amount of a compound of Formula I as described herein, or a pharmaceutically acceptable salt thereof, wherein the patient has a hematological malignancy such as multiple myeloma, leukemia, lymphoblastic leukemia, chronic lymphocytic leukemia, acute myeloid leukemia, chronic myeloid leukemia, Hodgkin's lymphoma, or non-Hodgkin's lymphoma;

(e) a method of treating a patient, typically a human, in need thereof comprising administering an effective amount of a compound of Formula I as described herein, or a pharmaceutically acceptable salt thereof, wherein the patient has a solid malignancy such as non-small cell lung carcinoma, small cell lung carcinoma, breast cancer, melanoma, prostate cancer, colon cancer, pancreatic cancer; or a cancer that generally exhibits an immunosuppressed environment;

(f) a method of treating a patient, typically a human, in need thereof comprising administering an effective amount of a compound of Formula I as described herein, or a pharmaceutically acceptable salt thereof, wherein the patient has a solid malignancy such as non-small cell lung carcinoma, small cell lung carcinoma, breast cancer, melanoma, prostate cancer, colon cancer, pancreatic cancer; or a cancer that generally exhibits an immunosuppressed environment, and wherein the patient is also administered an anti PD-1 or anti PD-L1 agent;

(g) use of a compound of Formula I as described herein, or a pharmaceutically acceptable salt, isotopic derivative, or prodrug thereof, in an effective amount in the treatment of a patient, typically a human, with any one of the disorders described herein, including those mediated by IKZF2 or IKZF4;

(h) use of a compound of Formula I as described herein, or a pharmaceutically acceptable salt, isotopic derivative, or prodrug thereof in the manufacture of a medicament for the treatment of a medical disorder sensitive to the compound, as further described herein;

(i) a method of manufacture of a medicament for the treatment of a disorder described herein in a host characterized in that a compound of Formula I is used in the manufacture;

(j) a compound of Formula I as described herein, or a pharmaceutically acceptable salt, isotopic derivative, or prodrug thereof, for the treatment of cancer in a host, including any of the cancers described herein;

(k) use of a compound of Formula I as described herein, or a pharmaceutically acceptable salt, isotopic derivative, or prodrug thereof in the manufacture of a medicament for the treatment of cancer, including any of the cancers described herein;

(l) a method of manufacturing a medicament for the treatment of cancer in a host, including any of the cancers described herein, characterized in that a compound of Formula I is used in the manufacture;

(m) a compound of Formula I as described herein, or a pharmaceutically acceptable salt, isotopic derivative, or prodrug thereof, for the treatment of a tumor in a host, including any of the tumors described herein;

(n) use of a compound of Formula I as described herein, or a pharmaceutically acceptable salt, isotopic derivative, or prodrug thereof in the manufacture of a medicament for the treatment of a tumor, including any of the tumors described herein;

(o) a method of manufacturing a medicament for the treatment of a tumor in a host, including any of the tumors described herein, characterized in that a compound of Formula I is used in the manufacture;

(p) a compound of Formula I as described herein, or a pharmaceutically acceptable salt, isotopic derivative, or prodrug thereof, for the treatment of an immune, autoimmune, inflammatory, neurodegenerative or fibrotic disorder in a host;

(q) use of a compound of Formula I as described herein, or a pharmaceutically acceptable salt, isotopic derivative, or prodrug thereof in the manufacture of a medicament for the treatment of an immune, autoimmune, inflammatory, neurodegenerative or fibrotic disorder;

(r) a method of manufacturing a medicament for the treatment of an immune, autoimmune, inflammatory, neurodegenerative or fibrotic disorder in a host characterized in that a compound of Formula I is used in the manufacture;

(s) a compound of Formula I as described herein, or a pharmaceutically acceptable salt, isotopic derivative, or prodrug thereof, for the treatment of a hematological malignancy such as multiple myeloma, leukemia, lymphoblastic leukemia, chronic lymphocytic leukemia, acute myeloid leukemia, chronic myeloid leukemia, Hodgkin's lymphoma, or non-Hodgkin's lymphoma;

(t) a compound of Formula I as described herein, or a pharmaceutically acceptable salt, isotopic derivative, or prodrug thereof, for the treatment of a solid malignancy such as non-small cell lung carcinoma, small cell lung carcinoma, breast cancer, melanoma, prostate cancer, colon cancer, pancreatic cancer; or cancers generally that exhibit an immunosuppressed environment;

(u) use of a compound of Formula I as described herein, or a pharmaceutically acceptable salt, isotopic derivative, or prodrug thereof in the manufacture of a medicament for the treatment of a hematological malignancy such as multiple myeloma, leukemia, lymphoblastic leukemia, chronic lymphocytic leukemia, acute myeloid leukemia, chronic myeloid leukemia, Hodgkin's lymphoma, or non-Hodgkin's lymphoma;

(v) a method of manufacturing a medicament for the treatment of a hematological malignancy such as multiple myeloma, leukemia, lymphoblastic leukemia, chronic lymphocytic leukemia, acute myeloid leukemia, chronic myeloid leukemia, Hodgkin's lymphoma, or non-Hodgkin's lymphoma;

(w) a pharmaceutical composition comprising an effective host-treating amount of a compound of Formula I as described herein or a pharmaceutically acceptable salt, isotopic derivative, or prodrug thereof with a pharmaceutically acceptable carrier or diluent;

(x) a compound a described herein as a mixture of enantiomers or diastereomers (as relevant), including the racemate;

(y) a compound as described herein in enantiomerically or diastereomerically (as relevant) enriched form, including an isolated enantiomer or diastereomer (i.e. greater than 85, 90, 95, 97, or 99% pure); and (z) a process for the manufacture of therapeutic products that contain an effective amount of a compound of Formula I as described herein.

DETAILED DESCRIPTION OF THE INVENTION

I. Definitions

Figure 1:
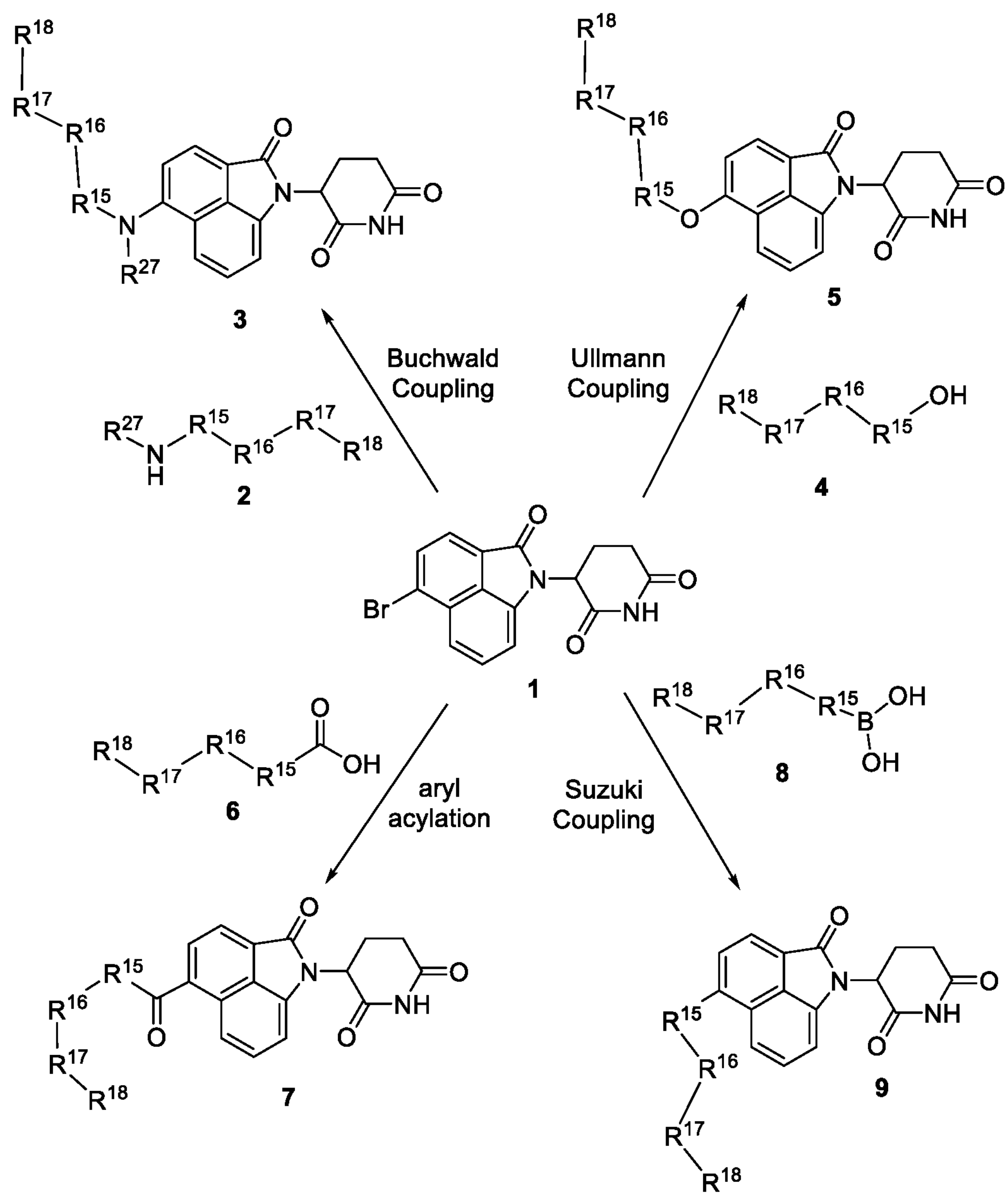
FIG. 1 is a synthetic scheme showing non-limiting examples of syntheses that can be used with intermediate 3-(5-bromo-2-oxobenzo[cd]indol-1(2H)-yl)piperidine-2,6-dione to add a range of $R^1$ groups.
Figure 2:
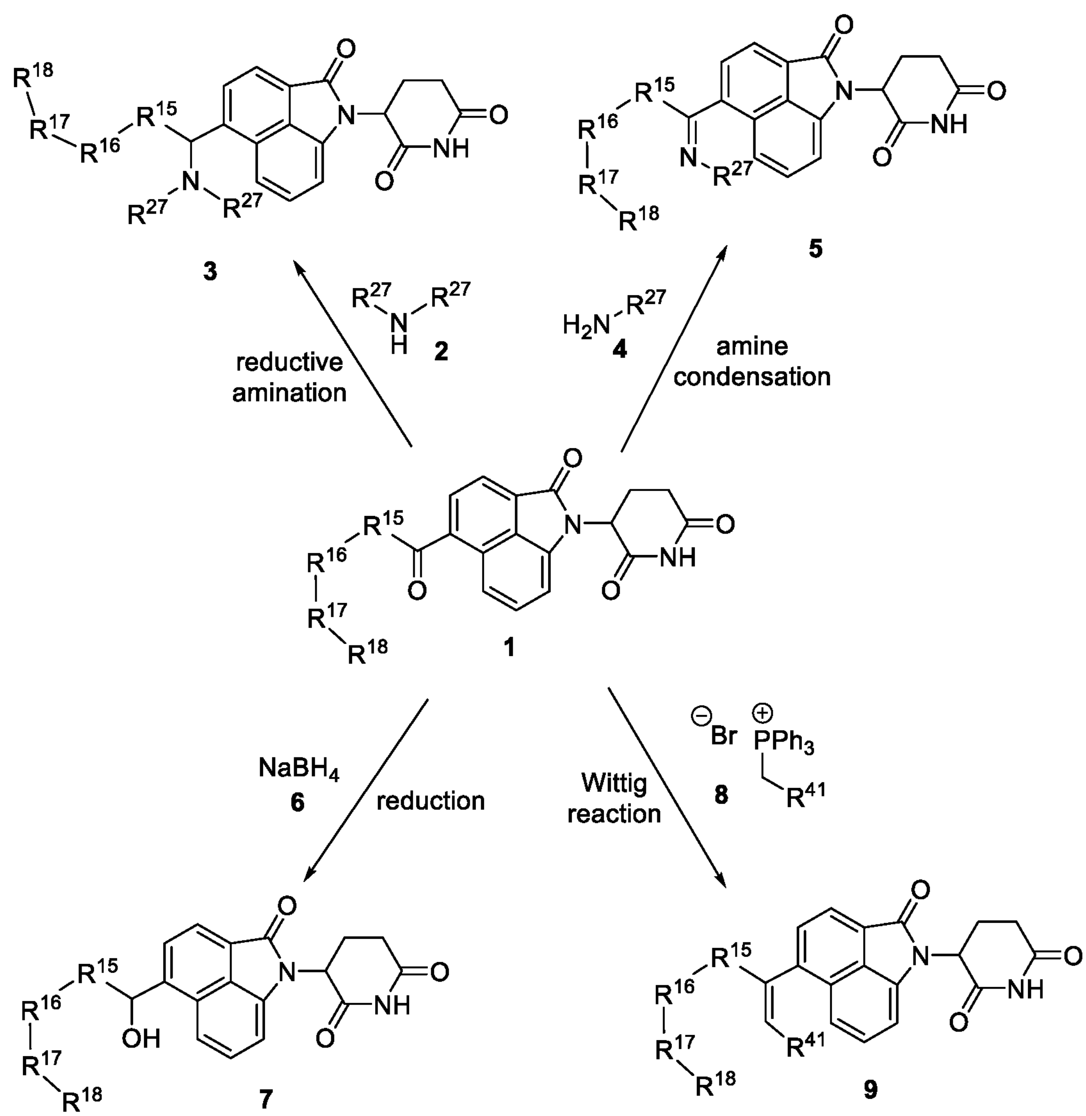
FIG. 2 is a synthetic scheme showing non-limiting examples of syntheses that can be used with intermediate 1-(2,6-dioxopiperidin-3-yl)-2-oxo-1,2-dihydrobenzo[cd]indole-5-carbaldehyde derivative to functionalize a range of $R^1$ groups.
Figure 3:
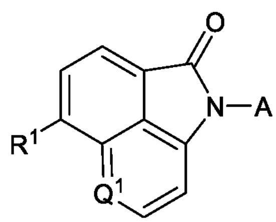
FIG. 3 is a representative formula of IKZF2/4 degrading compounds of the present invention.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice and testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Compounds are described using standard nomenclature. Unless defined otherwise, all technical and scientific terms used herein have the same meaning as is commonly understood by one of skill in the art to which this invention belongs.

In certain embodiments of each compound described herein, the compound may be in the form of a racemate, enantiomer, mixture of enantiomers, diastereomer, mixture of diastereomers, tautomer, N-oxide, or isomer, such as a rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds described herein with at least one desired isotopic substitution of an atom, at an amount above the natural abundance of the isotope, i.e., enriched. Isotopes are atoms having the same atomic number but different mass numbers, i.e., the same number of protons but a different number of neutrons. If isotopic substitutions are used, the common replacement is at least one deuterium for hydrogen.

More generally, examples of isotopes that can be incorporated into compounds of the invention include isotopes of hydrogen, carbon, nitrogen, oxygen, fluorine, and chlorine such as $^{2}H$, $^{3}H$, $^{11}C$, $^{13}C$, $^{1}C$, $^{15}N$, $^{17}O$, $^{18}O$, $^{18}F$, $^{35}S$, and $^{36}Cl$ respectively. In one non-limiting embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. Additionally, any hydrogen atom present in the compound of the invention may be substituted with an $^{18}F$ atom, a substitution that may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated. In certain embodiments, at least one deuterium is placed on an atom that has a bond which is broken during metabolism of the compound in vivo, or is one, two or three atoms remote form the metabolized bond (e.g., which may be referred to as an α, β or γ, or primary, secondary or tertiary isotope effect).

The compounds of the present invention may form a solvate with a solvent (including water). Therefore, in one non-limiting embodiment, the invention includes a solvated form of the compounds described herein. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, $-(C{=}O)NH_2$ is attached through carbon of the keto ($C{=}O$) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. In one non-limiting embodiment, the alkenyl contains from 2 to about 12 carbon atoms, more generally from 2 to about 6 carbon atoms or from 2 to about 4 carbon atoms. In certain embodiments the alkenyl is $C_2$, $C_2$-$C_3$, $C_2$-$C_4$, $C_2$-$C_5$, or $C_2$-$C_6$. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. In one non-limiting embodiment, the alkynyl contains from 2 to about 12 carbon atoms, more generally from 2 to about 6 carbon atoms or from 2 to about 4 carbon atoms. In certain embodiments the alkynyl is $C_2$, $C_2$-$C_3$, $C_2$-$C_4$, $C_2$-$C_5$, or $C_2$-$C_6$. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Halo" and "Halogen" is independently fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more cycloalkyl or heterocycle groups wherein the radical or point of attachment is on the aryl ring, and in such instances, the number of carbon atoms continue to designate the number of carbon atoms in the aryl ring system. The one or more fused cycloalkyl or heterocycle groups can be a 4 to 7-membered saturated or partially unsaturated cycloalkyl or heterocycle groups.

"Arylalkyl" refers to either an alkyl group as defined herein substituted with an aryl group as defined herein or to an aryl group as defined herein substituted with an alkyl group as defined herein.

The term "heterocycle" denotes saturated and partially saturated heteroatom-containing ring radicals, wherein there are 1, 2, 3, or 4 heteroatoms independently selected from nitrogen, sulfur, boron, silicone, and oxygen. Heterocyclic rings may comprise monocyclic 3-10 membered rings, as well as 5-16 membered bicyclic ring systems (which can include bridged, fused, and spiro-fused bicyclic ring systems). It does not include rings containing —O—O—, —O—S— or —S—S— portions. Examples of saturated heterocycle groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

"Heterocycle" also includes groups wherein the heterocyclic radical is fused/condensed with an aryl or carbocycle radical, wherein the point of attachment is the heterocycle ring. "Heterocycle" also includes groups wherein the heterocyclic radical is substituted with an oxo group (i.e. ). For example a partially unsaturated condensed heterocyclic group containing 1 to 5 nitrogen atoms, for example, indoline or isoindoline; a partially unsaturated condensed heterocyclic group containing 1 to 2 oxygen atoms and 1 to 3 nitrogen atoms; a partially unsaturated condensed heterocyclic group containing 1 to 2 sulfur atoms and 1 to 3 nitrogen atoms; and a saturated condensed heterocyclic group containing 1 to 2 oxygen or sulfur atoms.

The term "heterocycle" also includes "bicyclic heterocycle". The term "bicyclic heterocycle" denotes a heterocycle as defined herein wherein there is one bridged, fused, or spirocyclic portion of the heterocycle. The bridged, fused, or spirocyclic portion of the heterocycle can be a carbocycle, heterocycle, or aryl group as long as a stable molecule results. Unless excluded by context the term "heterocycle" includes bicyclic heterocycles. Bicyclic heterocycle includes groups wherein the fused heterocycle is substituted with an oxo group. Non-limiting examples of bicyclic heterocycles include:

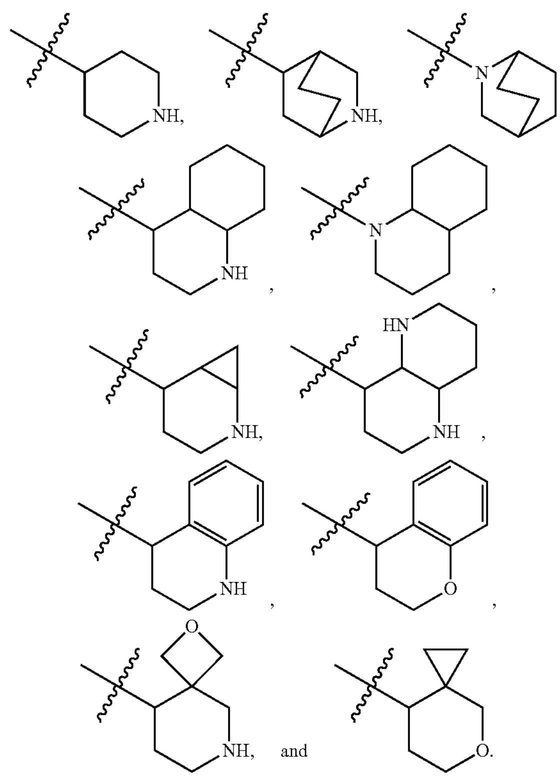

The term "heteroaryl" denotes stable aromatic ring systems that contain 1, 2, 3, or 4 heteroatoms independently selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4- triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. In certain embodiments the "heteroaryl" group is a 8, 9, or 10 membered bicyclic ring system. Examples of 8, 9, or 10 membered bicyclic heteroaryl groups include benzofurazanyl, benzothiophenyl, benzothiazolyl, benzoxazolyl, quinazolinyl, quinoxalinyl, naphthyridinyl, quinolinyl, isoquinolinyl, benzofuranyl, indolyl, indazolyl, and benzotriazolyl.

"Heteroarylalkyl" refers to either an alkyl group as defined herein substituted with a heteroaryl group as defined herein or to a heteroaryl group as defined herein substituted with an alkyl group as defined herein.

As used herein, "carbocyclic", "carbocycle" or "cycloalkyl" includes a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double bonds. The term "cycloalkyl" also includes ring systems wherein the cycloalkyl ring, as defined above, is fused with one heterocycle, aryl or heteroaryl ring wherein the point of attachment is on the cycloalkyl ring, and in such instances, the number of carbons continue to designate the number of carbons in the carbocyclic ring system. The term "cycloalkyl" also includes ring systems wherein the cycloalkyl ring, as defined above, has a spirocyclic heterocycle, aryl or heteroaryl ring wherein the point of attachment is on the cycloalkyl ring, and in such instances, the number of carbons continue to designate the number of carbons in the carbocyclic ring system. The term "cycloalkyl" also includes bicyclic or polycyclic fused, bridged, or spiro ring systems that contain from 5 to 14 carbon atoms and zero heteroatoms in the non-aromatic ring system. Representative examples of "cycloalkyl" include, but are not limited to,

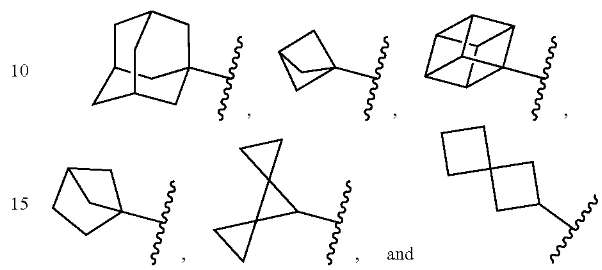

, , , , , and .

The term "bicycle" refers to a ring system wherein two rings are fused together and each ring is independently selected from carbocycle, heterocycle, aryl, and heteroaryl. Non-limiting examples of bicycle groups include:

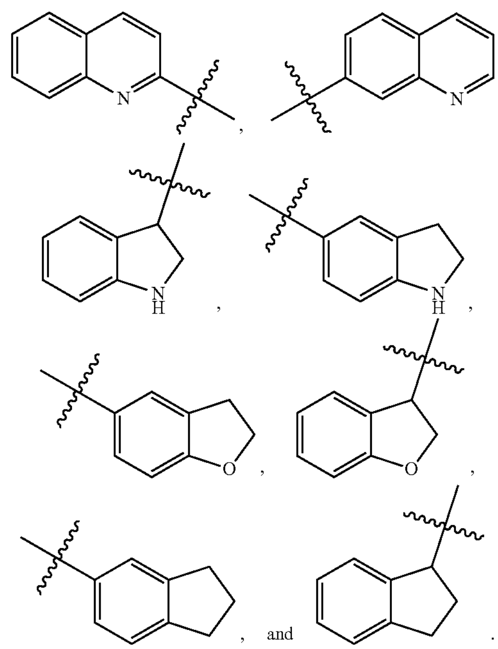

, , , , , , , , , and .

When the term "bicycle" is used in the context of a bivalent residue such as $R^{15}$, $R^{16}$, or $R^{17}$, the attachment points can be on separate rings or on the same ring. In certain embodiments both attachment points are on the same ring. In certain embodiments both attachment points are on different rings. Non-limiting examples of bivalent bicycle groups include:

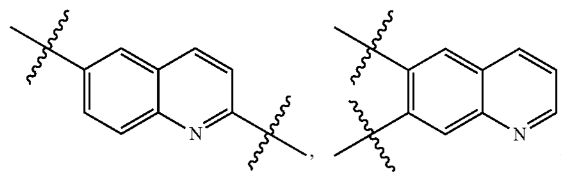

, ,

-continued

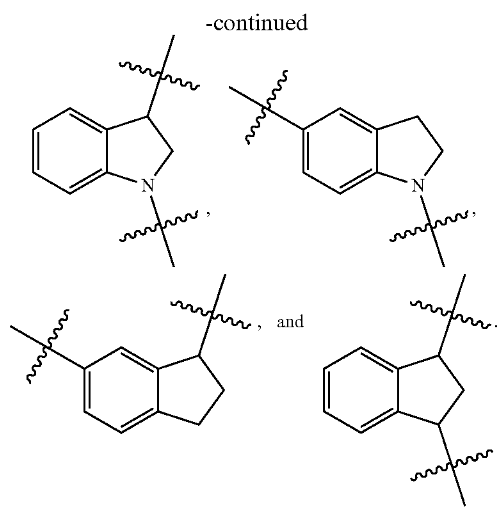

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of a compound includes, e.g., subcutaneous (s.c.), intravenous (i.v.), intramuscular (i.m.), or intrasternal injection, or infusion techniques.

As used herein, "pharmaceutical compositions" is a composition comprising at least one active agent such as a selected active compound as described herein, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, a "pharmaceutically acceptable salt" is a derivative of the disclosed compound in which the parent compound is modified by making inorganic and organic, acid or base addition salts thereof with a biologically acceptable lack of toxicity. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" means a diluent, excipient, or vehicle that an active agent is used or delivered in.

A "pharmaceutically acceptable excipient" means an excipient that is useful in preparing a pharmaceutical composition/combination that is generally safe, and neither biologically nor otherwise inappropriate for administration to a host, typically a human. In certain embodiments, an excipient is used that is acceptable for veterinary use.

A "patient" or "host" or "subject" is a human or non-human animal in need of treatment, of any of the disorders as specifically described herein. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

In certain embodiments "prodrug" is a version of the parent molecule that is metabolized or chemically converted to the parent molecule in vivo, for example in a mammal or a human. Non-limiting examples of prodrugs include esters, amides, for example off a primary or secondary amine, carbonates, carbamates, phosphates, ketals, imines, oxazolidines, and thiazolidines. A prodrug can be designed to release the parent molecule upon a change in pH (for example in the stomach or the intestine) or upon action of an enzyme (for example an esterase or amidase).

In certain embodiments "stable" means the less than 10%, 5%, 3%, or 1% of the compound degrades under ambient conditions with a shelf life of at least 3, 4, 5, or 6-months. In certain embodiments a compound stored at ambient conditions is stored at about room temperature and exposed to air and a relative humidity of less than about 40%, 50%, 60%, or 70%. In certain embodiments a compound stored at ambient conditions is stored at about room temperature under inert gas (such as argon or nitrogen). Typically, moieties described herein do not have more than one or two heteroatoms bound to each other directly unless the moiety is heteroaromatic.

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

II. Compounds of the Present Invention

Embodiments of "Alkyl"

In certain embodiments "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In certain embodiments "alkyl" has one carbon.

In certain embodiments "alkyl" has two carbons.

In certain embodiments "alkyl" has three carbons.

In certain embodiments "alkyl" has four carbons.

In certain embodiments "alkyl" has five carbons.

In certain embodiments "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

Embodiments of "Haloalkyl"

In certain embodiments "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In certain embodiments "haloalkyl" has one carbon.

In certain embodiments "haloalkyl" has one carbon and one halogen.

In certain embodiments "haloalkyl" has one carbon and two halogens.

In certain embodiments "haloalkyl" has one carbon and three halogens.

In certain embodiments "haloalkyl" has two carbons.

In certain embodiments "haloalkyl" has three carbons.

In certain embodiments "haloalkyl" has four carbons.

In certain embodiments "haloalkyl" has five carbons.

In certain embodiments "haloalkyl" has six carbons.

Non-limiting examples of "haloalkyl" include:

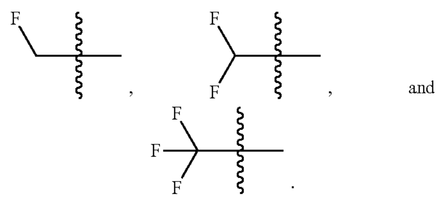

, , and .

Additional non-limiting examples of "haloalkyl" include:

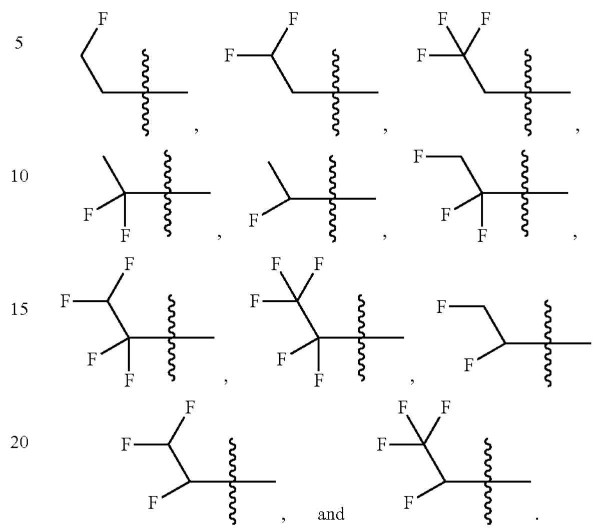

, and .

Additional non-limiting examples of "haloalkyl" include:

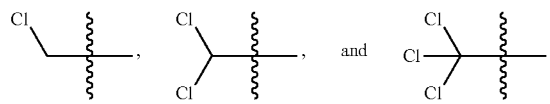

, , and .

Additional non-limiting examples of "haloalkyl" include:

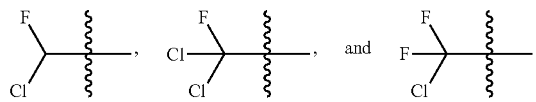

, , and .

Embodiments of "Aryl"

In certain embodiments "aryl" is a 6 carbon aromatic group (phenyl)

In certain embodiments "aryl" is a 10 carbon aromatic group (napthyl)

In certain embodiments "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example,

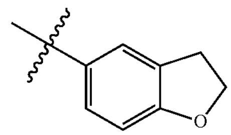 [SMILES: *c1ccc2c(c1)CCO2]

is an "aryl" group.

However,

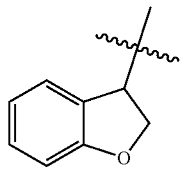 [SMILES: *C1COc2ccccc21]

is a “heterocycle” group.

In certain embodiments “aryl” is a 6 carbon aromatic group fused to a cycloalkyl wherein the point of attachment is the aryl ring. Non-limiting examples of “aryl” include dihydro-indene and tetrahydronaphthalene wherein the point of attachment for each group is on the aromatic ring.

For example,

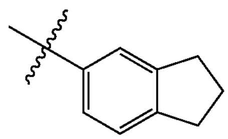 [SMILES: *c1ccc2c(c1)CCC2]

is an “aryl” group.

However,

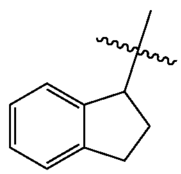 [SMILES: *C1CCc2ccccc21]

is a “cycloalkyl” group.

Embodiments of “Heteroaryl”

In certain embodiments “heteroaryl” is a 5 membered aromatic group containing 1, 2, 3, or 4 nitrogen atoms.

Non-limiting examples of 5 membered “heteroaryl” groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered “heteroaryl” groups include:

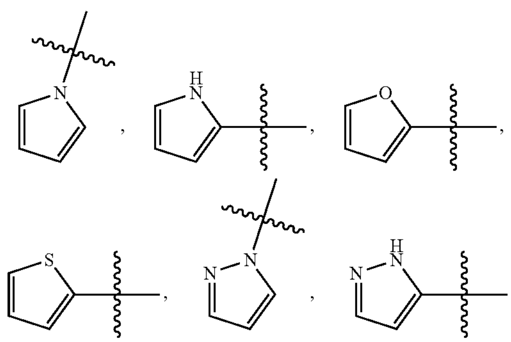

-continued

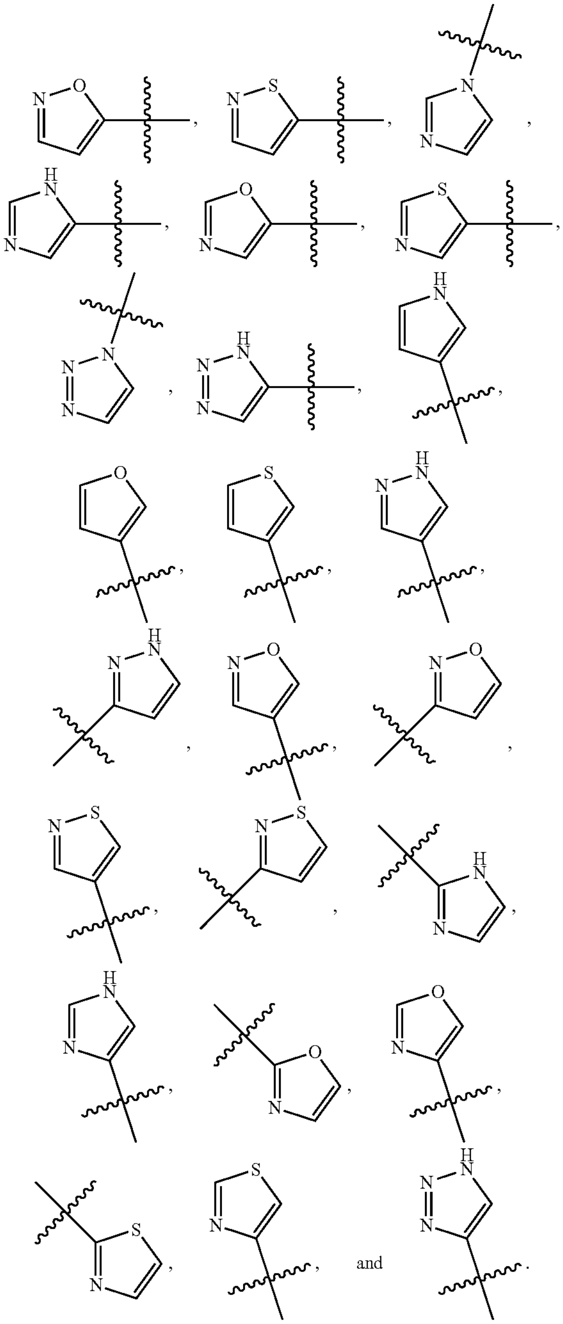

In certain embodiments “heteroaryl” is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered “heteroaryl” groups with 1 or 2 nitrogen atoms include:

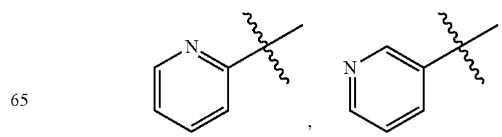

-continued

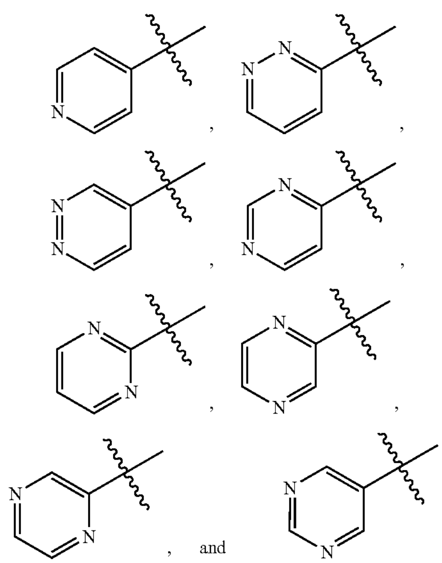

In certain embodiments "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

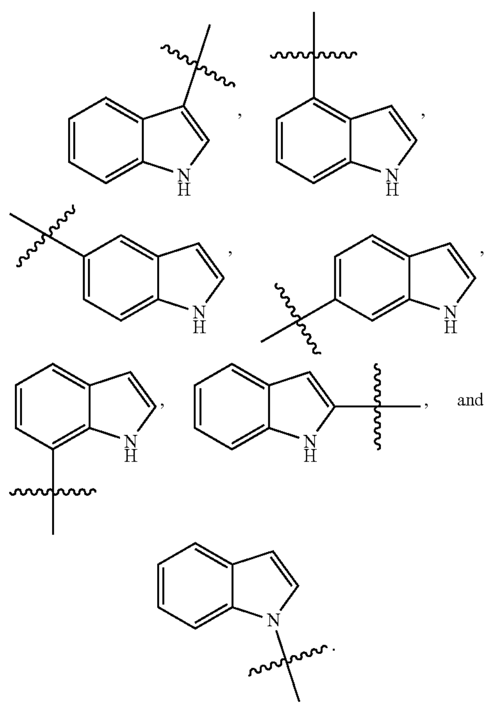

Additional non-limiting examples of "heteroaryl" groups that are bicyclic include:

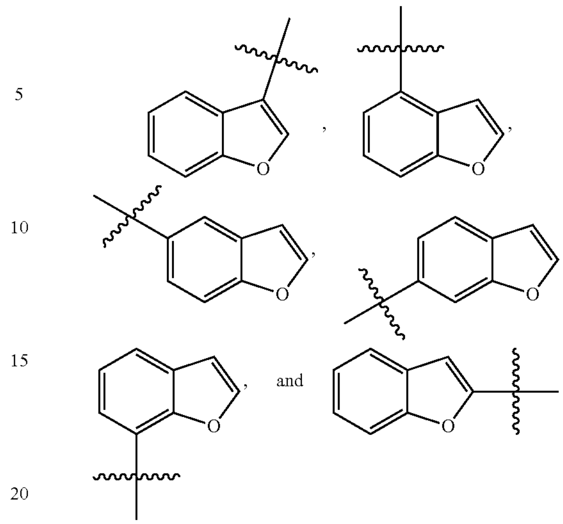

Additional non-limiting examples of "heteroaryl" groups that are bicyclic include:

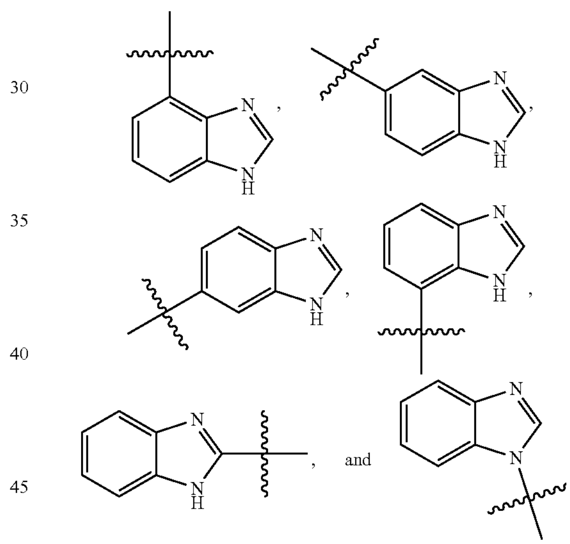

In certain embodiments "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

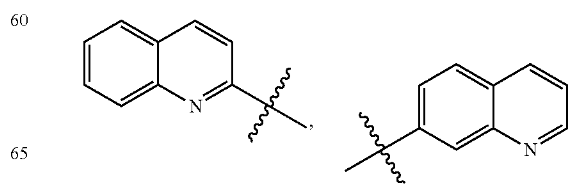

-continued

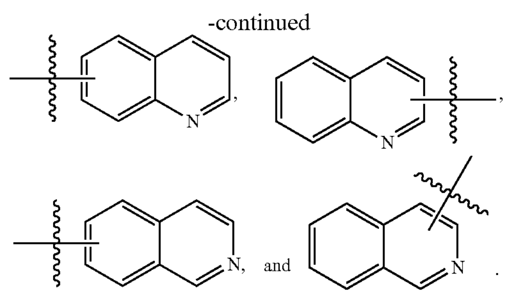

Embodiments of "Cycloalkyl"

In certain embodiments "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In certain embodiments "cycloalkyl" has three carbons.

In certain embodiments "cycloalkyl" has four carbons.

In certain embodiments "cycloalkyl" has five carbons.

In certain embodiments "cycloalkyl" has six carbons.

In certain embodiments "cycloalkyl" has seven carbons.

In certain embodiments "cycloalkyl" has eight carbons.

In certain embodiments "cycloalkyl" has nine carbons.

In certain embodiments "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example

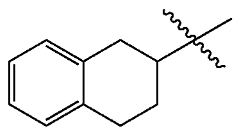 [SMILES: *C1CCc2ccccc2C1]

is an "cycloalkyl" group.

However,

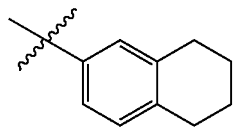 [SMILES: *c1ccc2c(c1)CCCC2]

is an aryl group.

Additional examples of "cycloalkyl" groups include

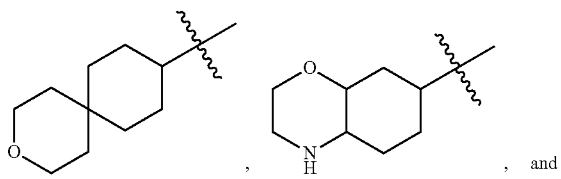

, , and

-continued

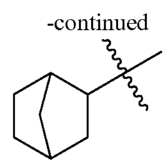

Embodiments of "Heterocycle"

In certain embodiments "heterocycle" refers to a cyclic ring with one nitrogen and 3, 4, 5, 6, 7, or 8 carbon atoms.

In certain embodiments "heterocycle" refers to a cyclic ring with one nitrogen and one oxygen and 3, 4, 5, 6, 7, or 8 carbon atoms.

In certain embodiments "heterocycle" refers to a cyclic ring with two nitrogens and 3, 4, 5, 6, 7, or 8 carbon atoms.

In certain embodiments "heterocycle" refers to a cyclic ring with one oxygen and 3, 4, 5, 6, 7, or 8 carbon atoms.

In certain embodiments "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

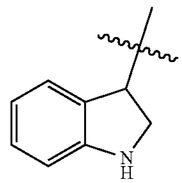 [SMILES: *C1CNc2ccccc21]

is a "heterocycle" group.

However,

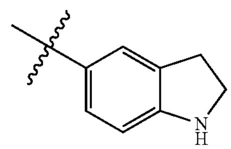 [SMILES: *c1ccc2c(c1)CCN2]

is an "aryl" group.

Non-limiting examples of "heterocycle" also include:

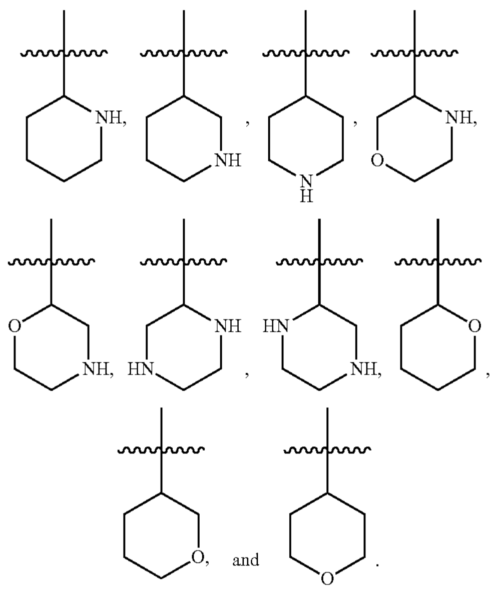

Additional non-limiting examples of "heterocycle" include:

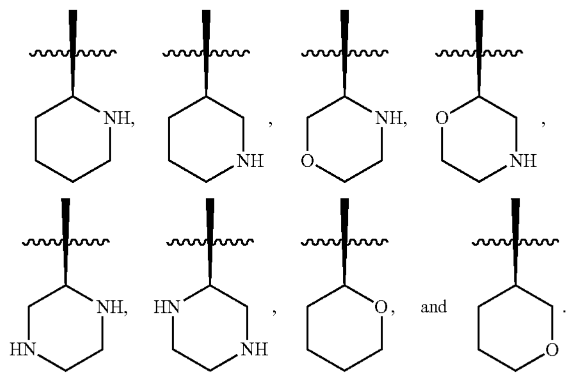

Additional non-limiting examples of "heterocycle" include:

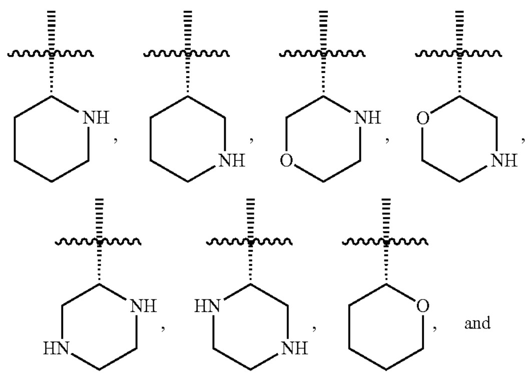

-continued

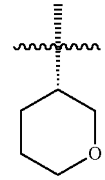

Non-limiting examples of "heterocycle" also include:

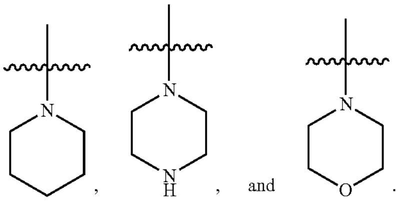

Non-limiting examples of "heterocycle" also include:

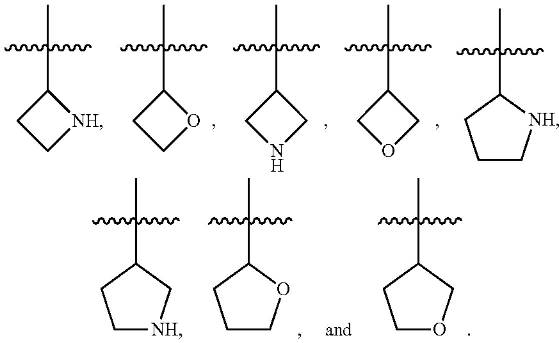

Additional non-limiting examples of "heterocycle" include:

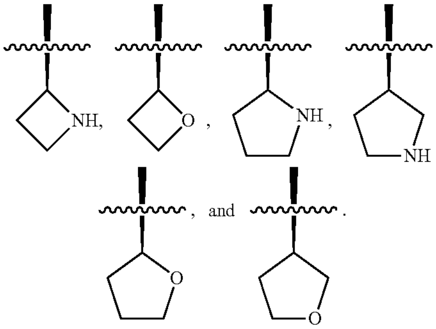

Additional non-limiting examples of "heterocycle" include:

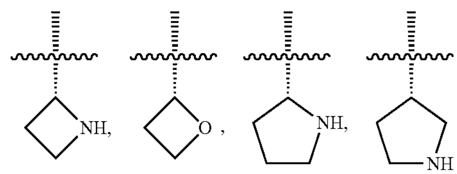

-continued

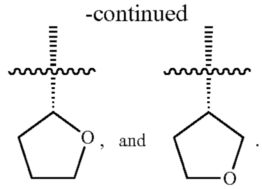

Optional Substituents

In certain embodiments a moiety described herein that can be substituted with 1, 2, 3, or 4 substituents is substituted with one substituent.

In certain embodiments a moiety described herein that can be substituted with 1, 2, 3, or 4 substituents is substituted with two substituents.

In certain embodiments a moiety described herein that can be substituted with 1, 2, 3, or 4 substituents is substituted with three substituents.

In certain embodiments a moiety described herein that can be substituted with 1, 2, 3, or 4 substituents is substituted with four substituents.

Embodiments of $R^1$

In certain embodiments, $R^1$ is selected from:

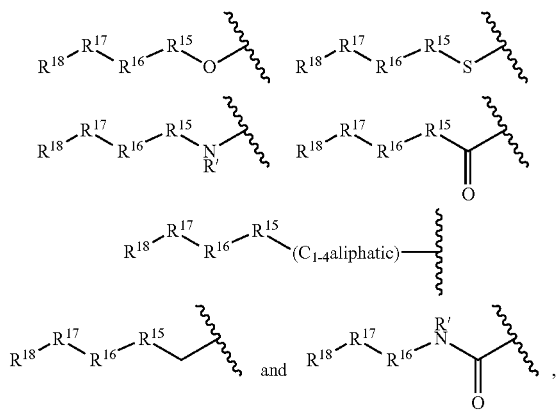

wherein each R' is independently selected from hydrogen, alkyl, haloalkyl, aryl, heterocycle, and heteroaryl.

In certain embodiments, $R^1$ is a heterocycle group optionally substituted with 1 or 2 substituents selected from R'.

In certain embodiments, $R^1$ is a 6-membered heterocycle group with one or two nitrogen atoms.

In certain embodiments, $R^1$ is a 6-membered heterocycle group with one or two oxygen atoms In certain embodiments, $R^1$ is selected from:

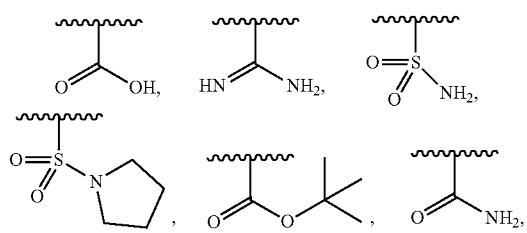

-continued

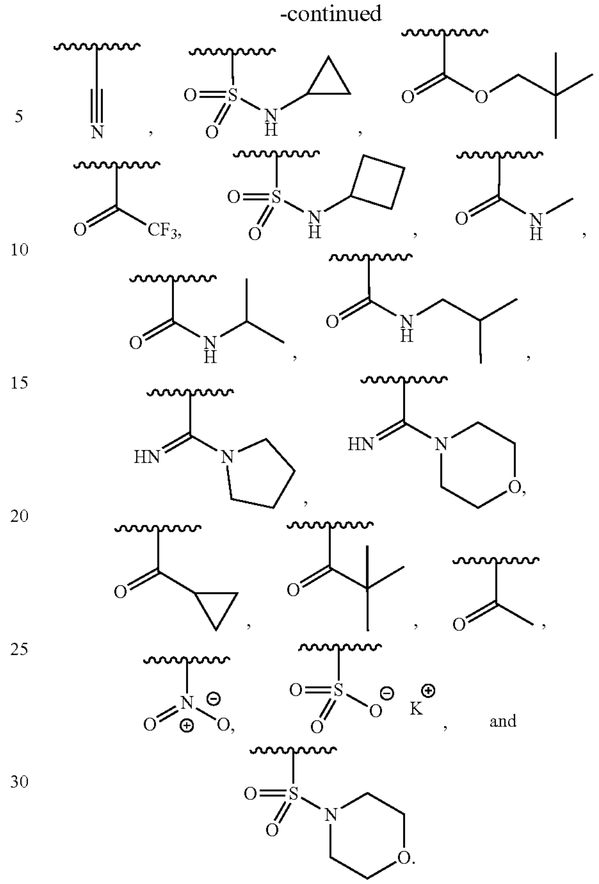

In certain embodiments, $R^1$ is selected from:

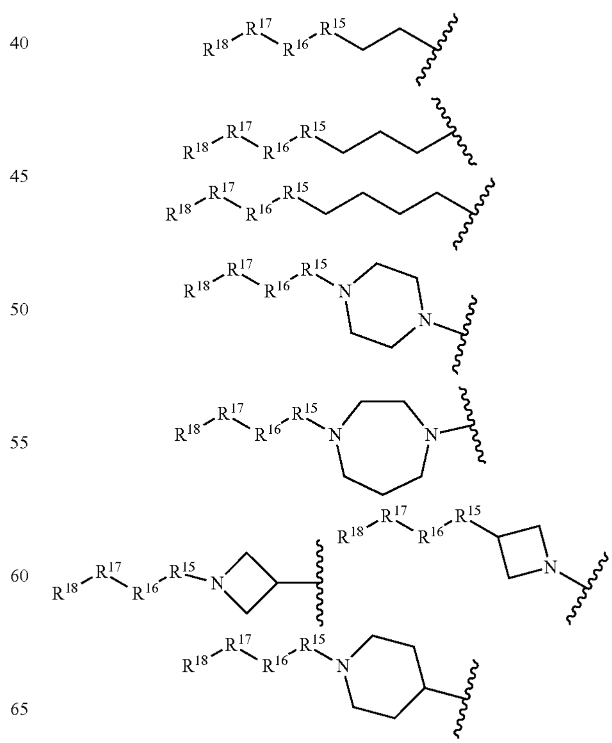

-continued
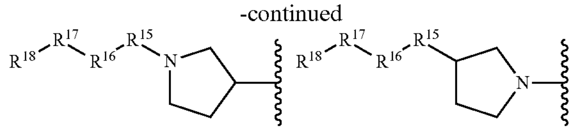
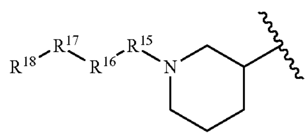
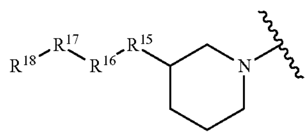
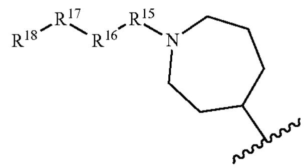
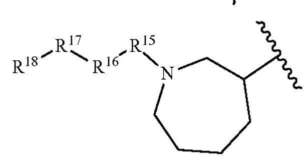
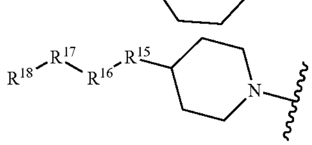
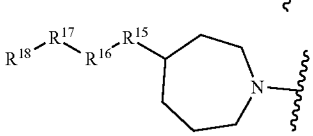
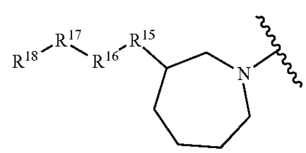
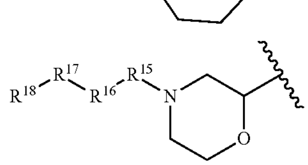
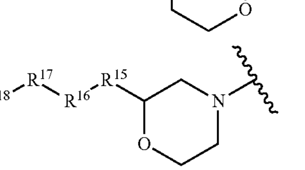
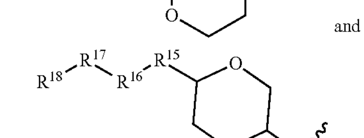
and
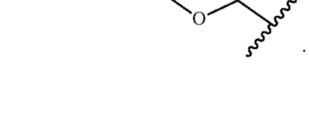
.
In certain embodiments, $R^1$ is selected from:
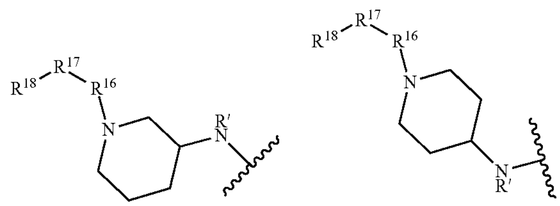
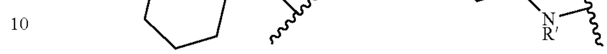
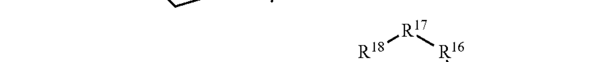
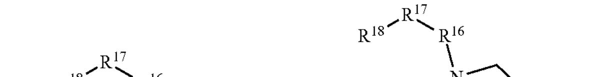
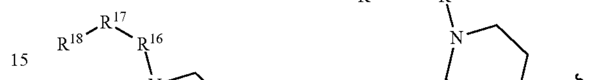
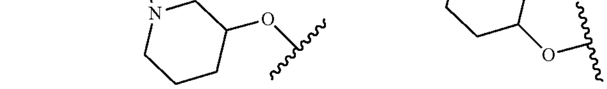
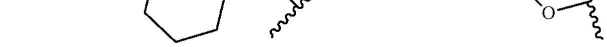
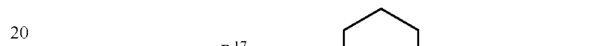
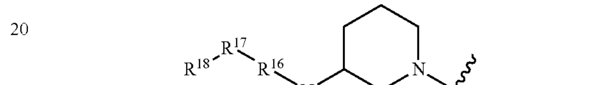
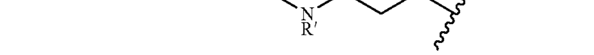
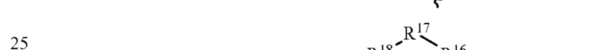
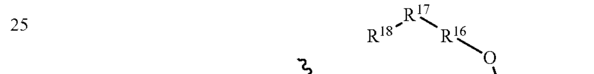
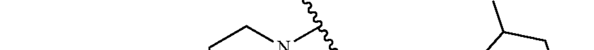
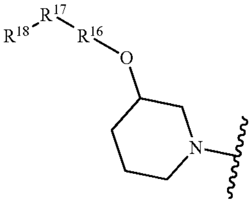
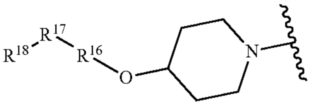
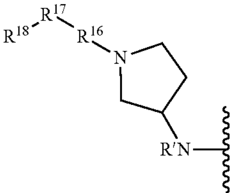
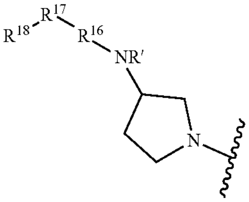
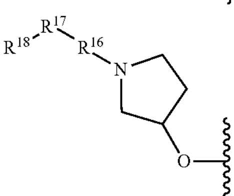
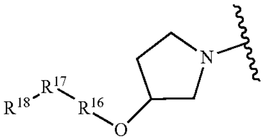
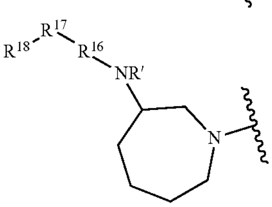
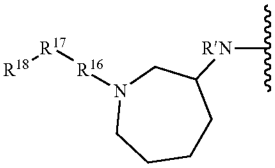
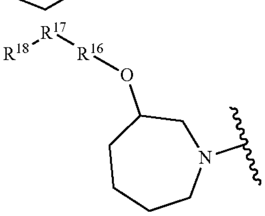
and -continued
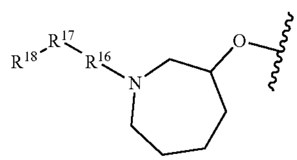
In certain embodiments $R^1$ is selected from:
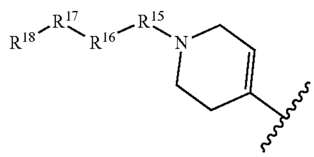
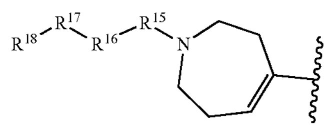
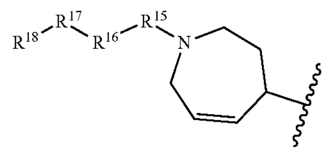
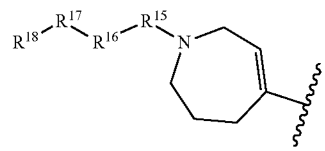
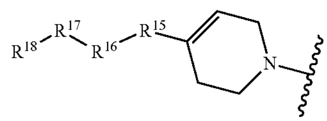
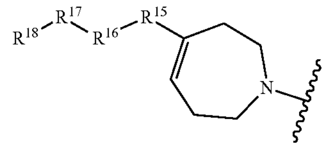
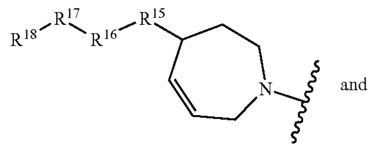
and
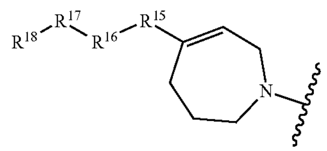
In certain embodiments, $R^1$ is selected from:
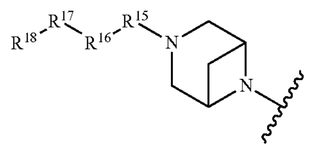
-continued
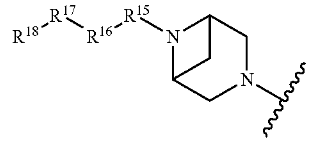
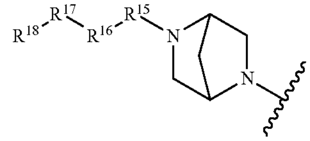
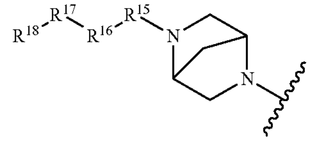
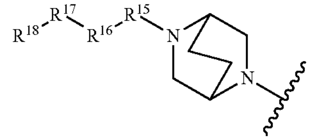
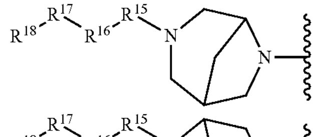
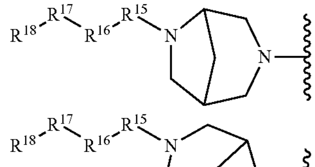
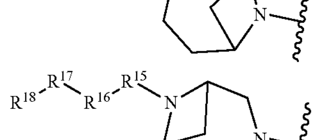
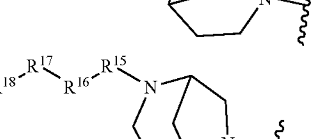
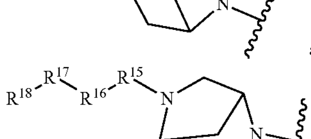
and
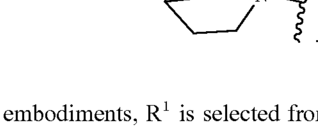
In certain embodiments, $R^1$ is selected from:
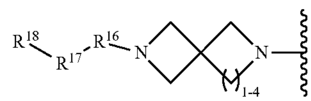
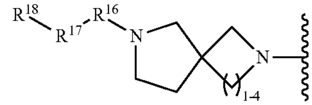
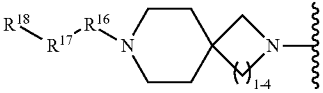

-continued
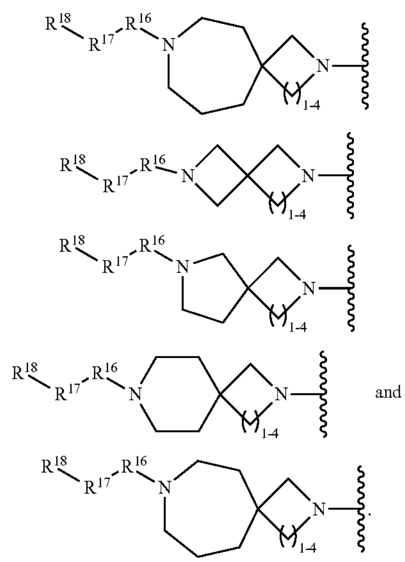
and
In certain embodiments, $R^1$ is selected from:
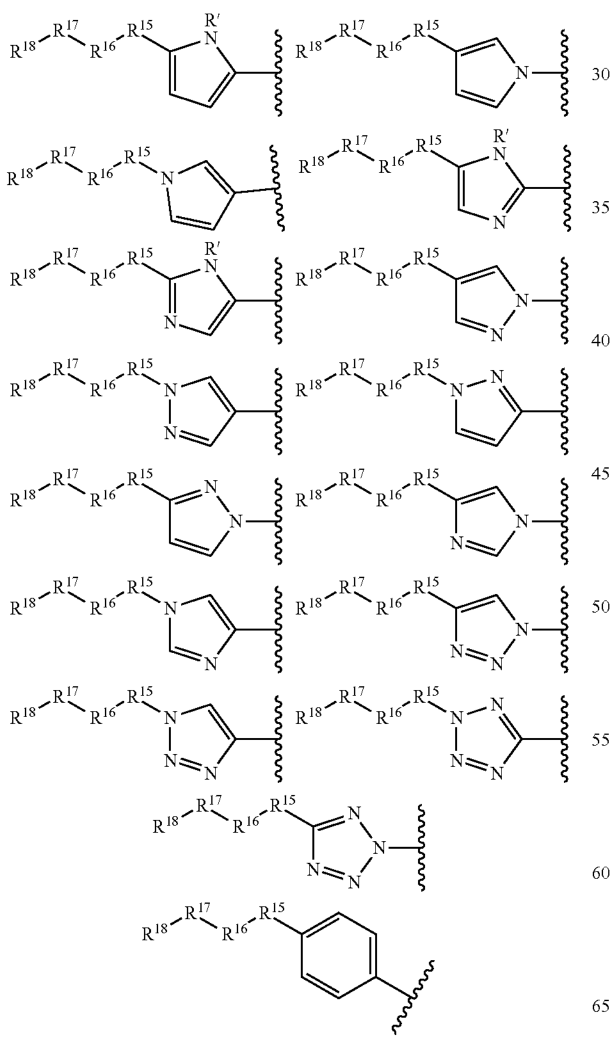
-continued
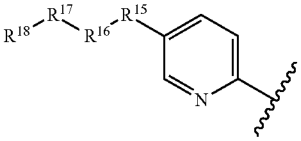
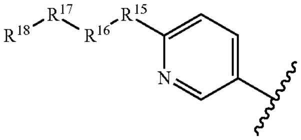
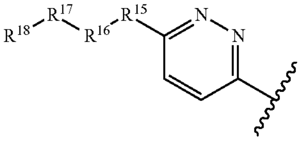
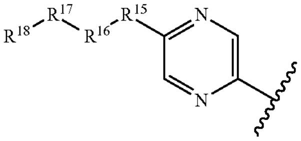
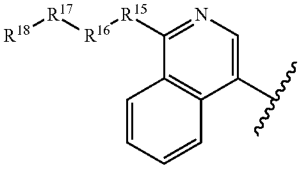
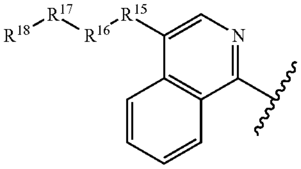
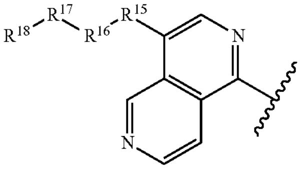
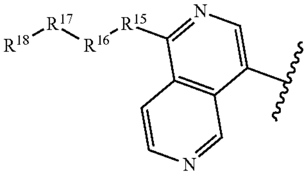
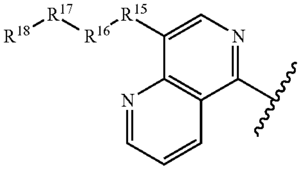
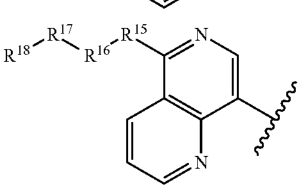

-continued
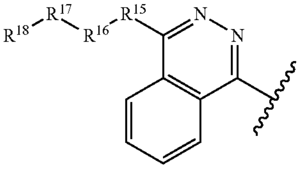
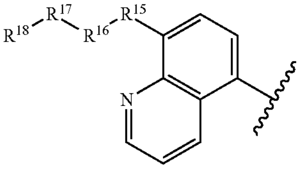
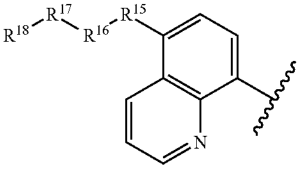
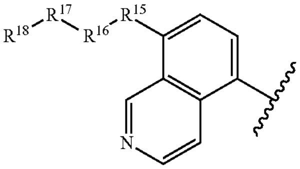
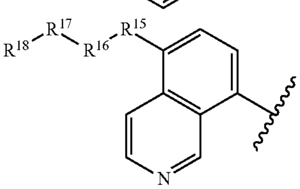
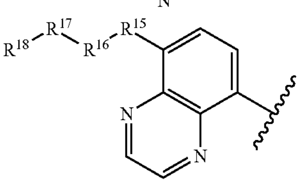
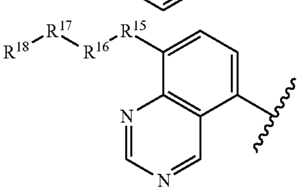
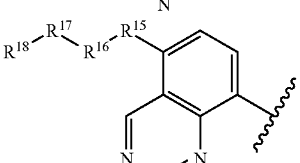
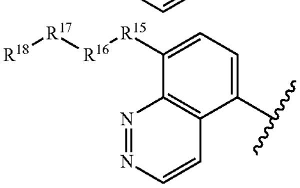
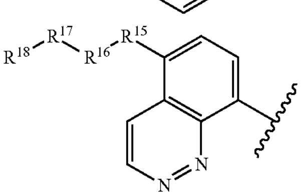
and
-continued
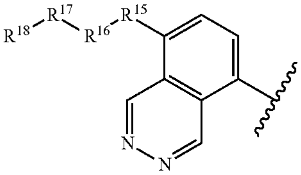
.
In certain embodiments, $R^1$ is selected from:
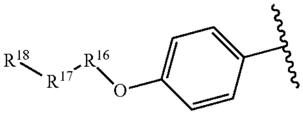
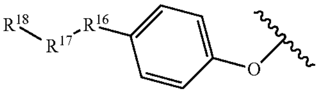
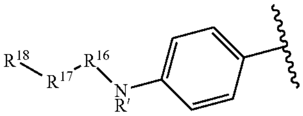
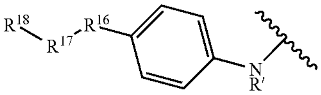
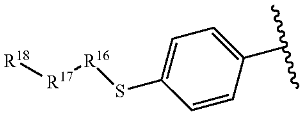
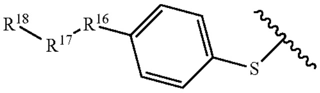
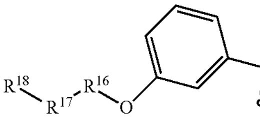
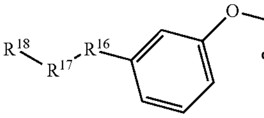
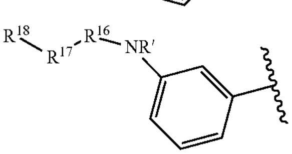
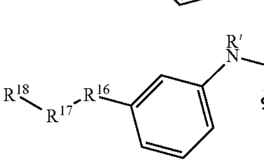
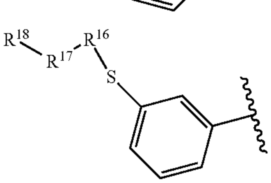

-continued
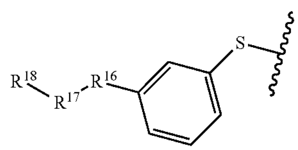
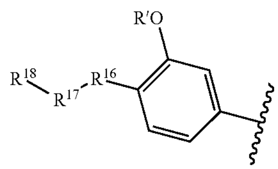
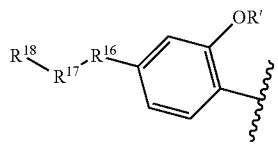
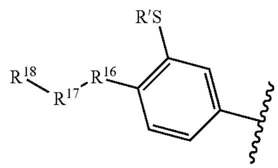
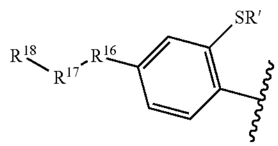
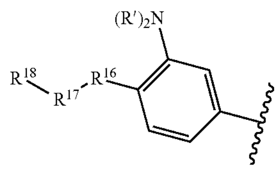
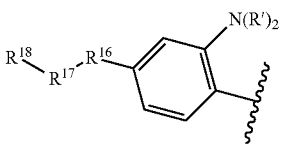
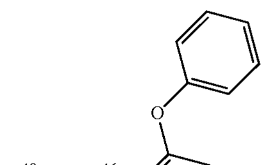
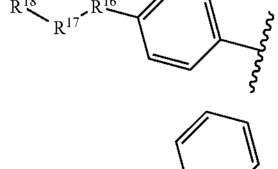
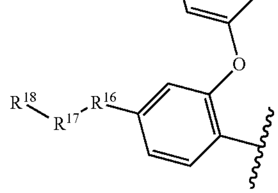
-continued
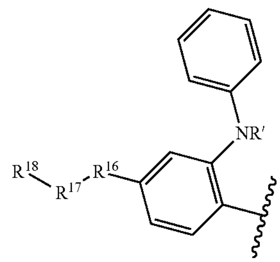
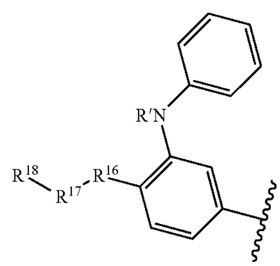
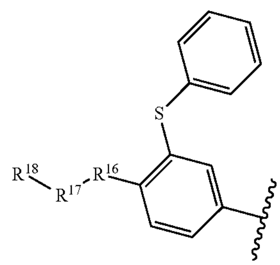
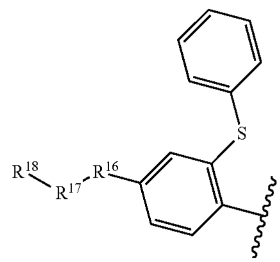
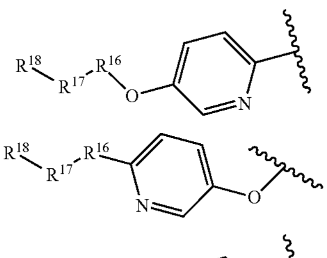
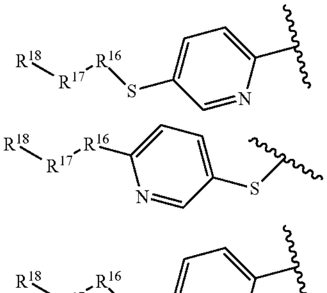
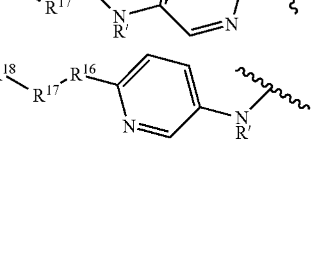

-continued
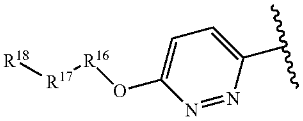
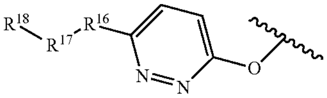
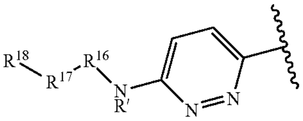
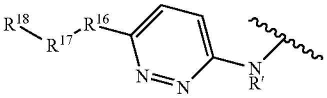
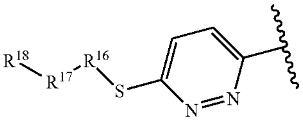
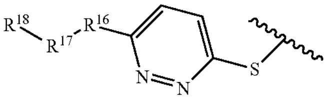
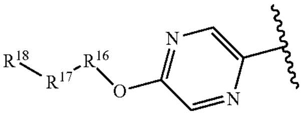
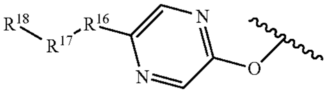
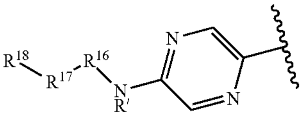
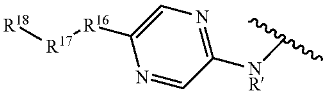
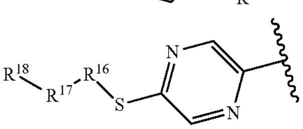
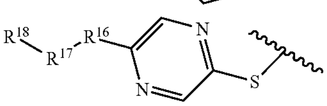
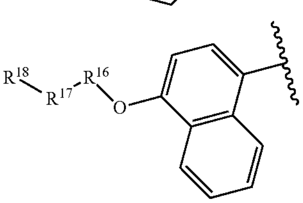
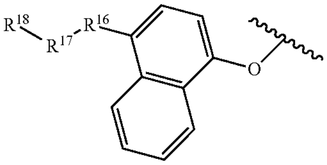
-continued
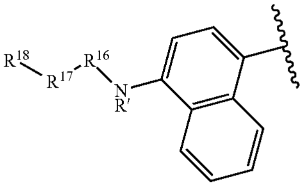
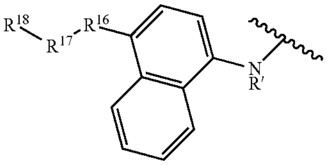
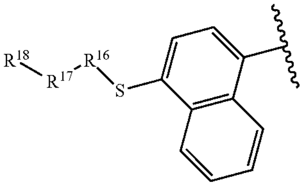
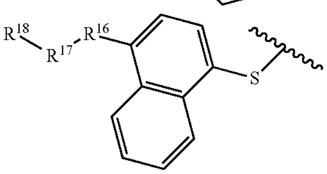
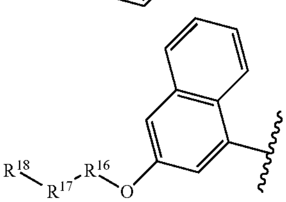
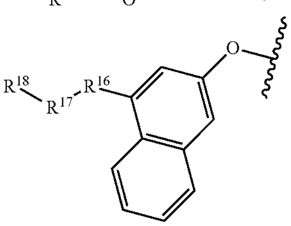
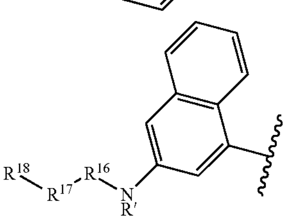
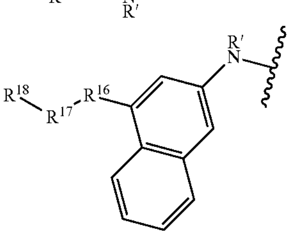
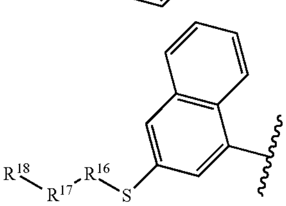

-continued
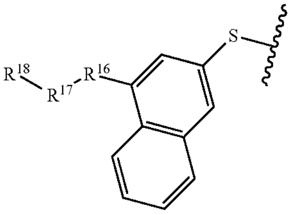
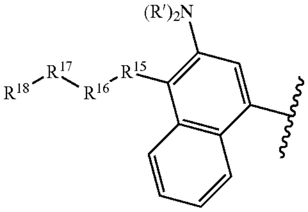
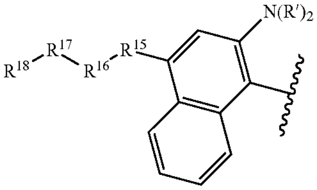
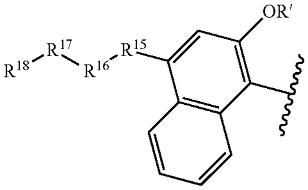
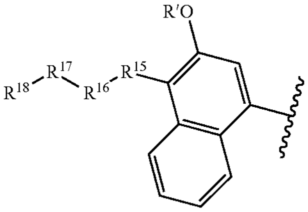
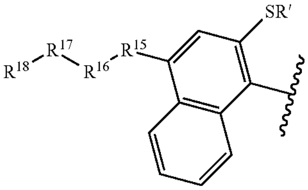
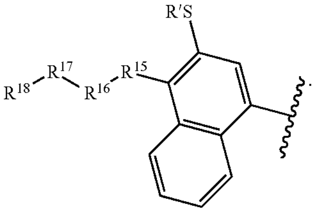
In certain embodiments, $R^1$ is selected from:
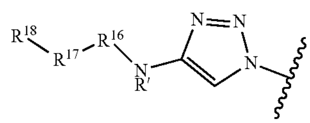
-continued
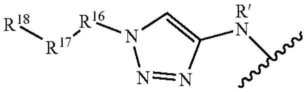
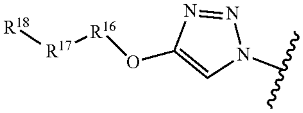
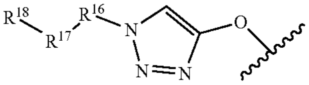
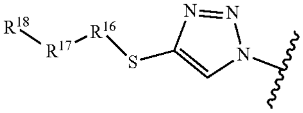
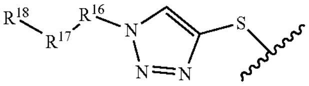
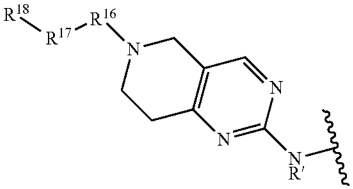
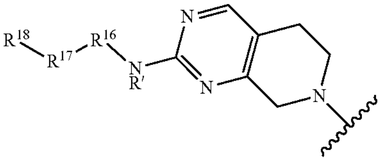
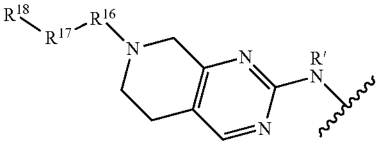
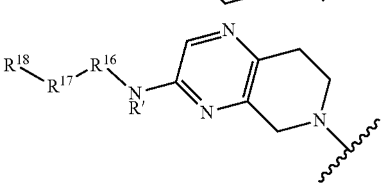
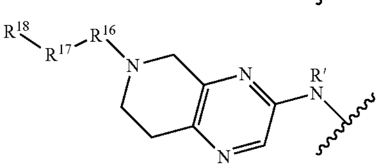
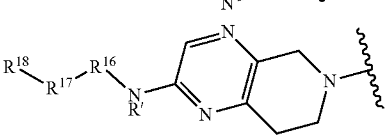
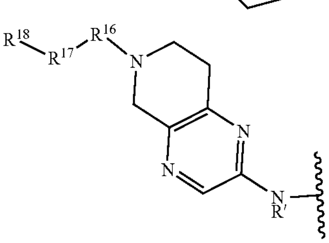

-continued
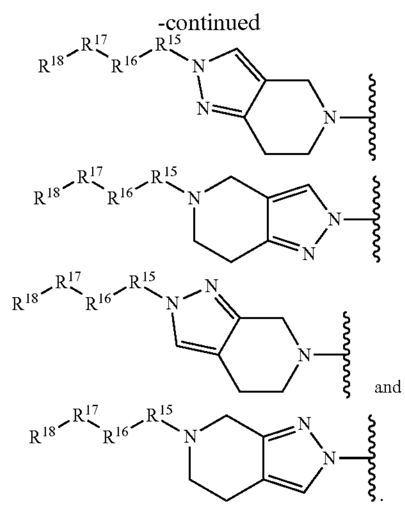
and .
In certain embodiments, $R^1$ is selected from:
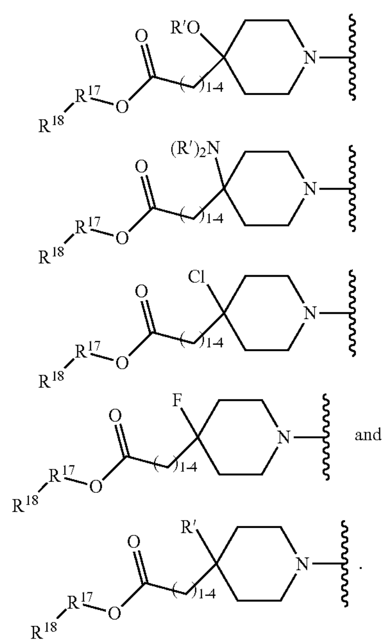
and .
In certain embodiments, $R^1$ is selected from:
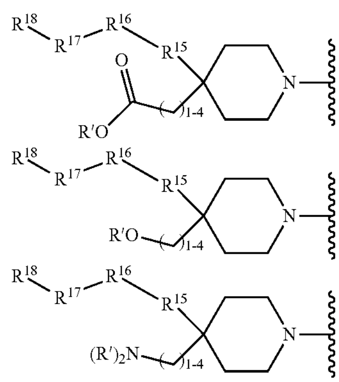
-continued
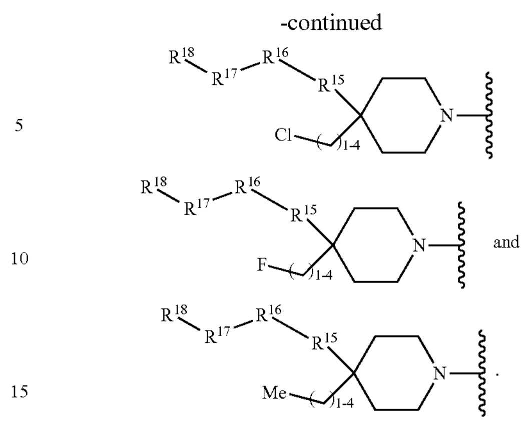
and .
In certain embodiments, $R^1$ is selected from:
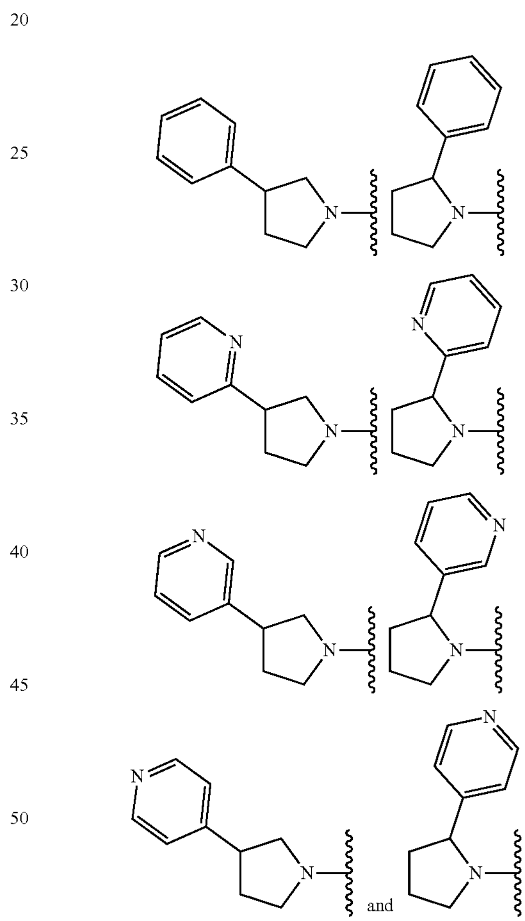
and .
In certain embodiments, $R^1$ is selected from:
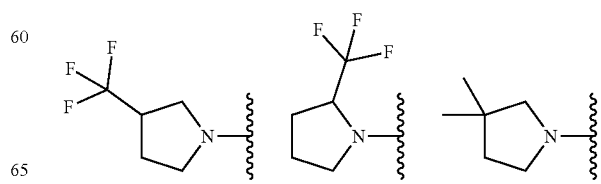

-continued
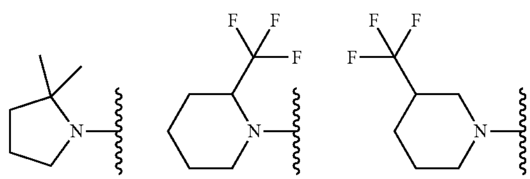
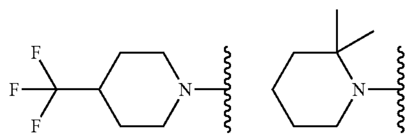
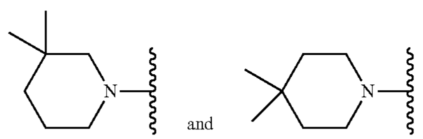
and
In certain embodiments, $R^1$ is selected from:
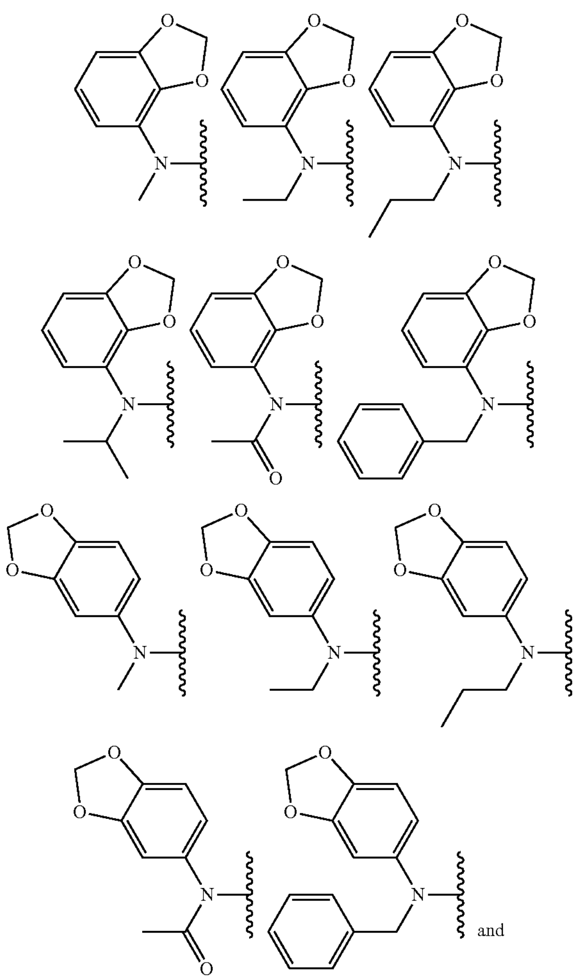
and
-continued
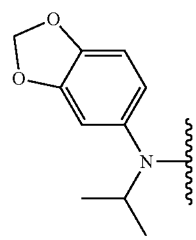
In certain embodiments, $R^1$ is selected from:
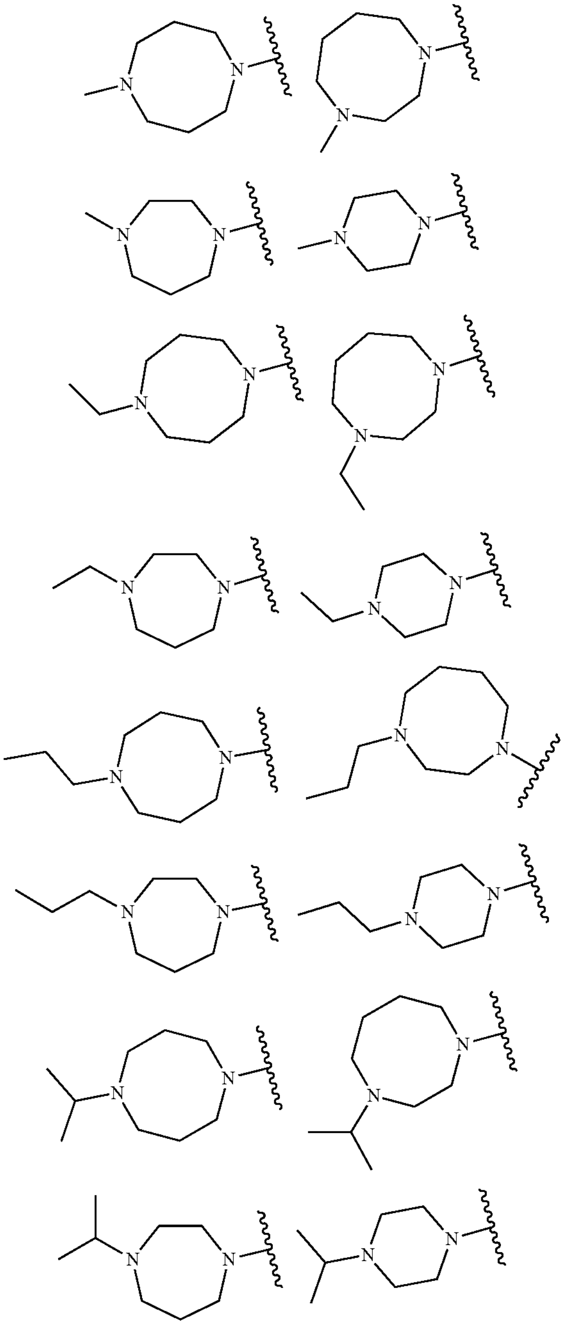

-continued
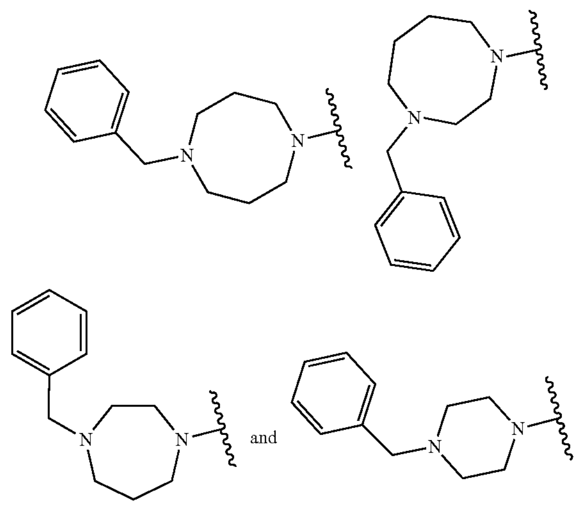
and
In certain embodiments, $R^1$ is selected from:
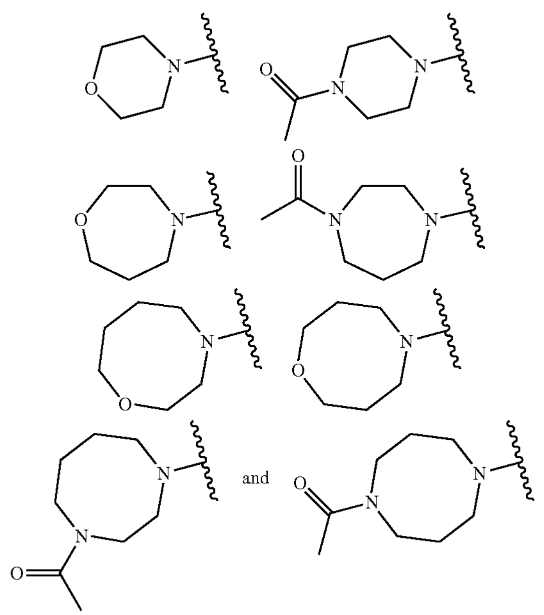
and
In certain embodiments, $R^1$ is selected from:
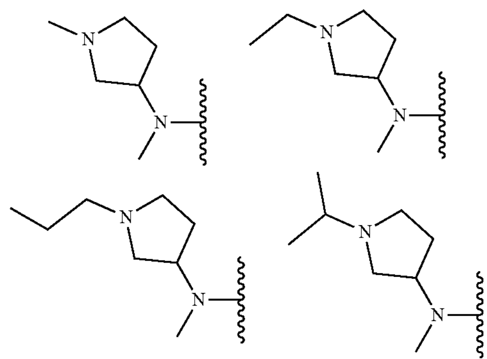
-continued
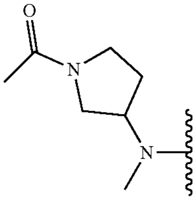
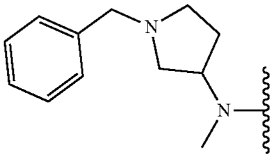
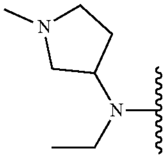
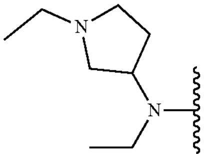
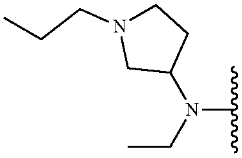
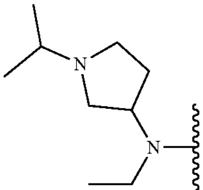
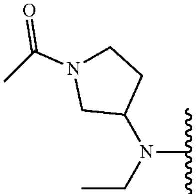
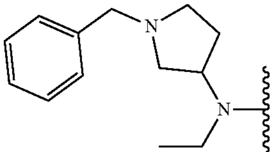
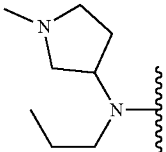
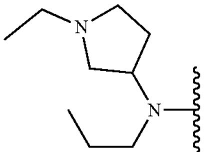
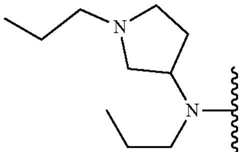
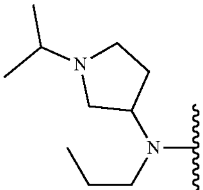
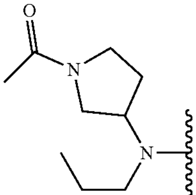
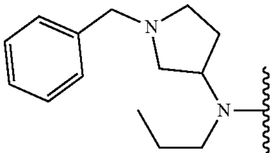
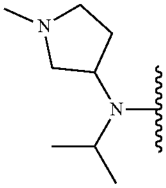
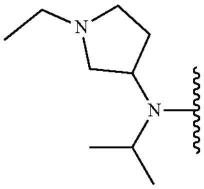

-continued
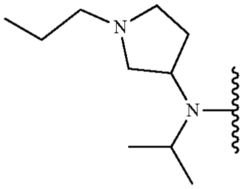 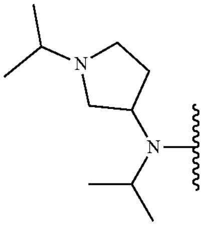
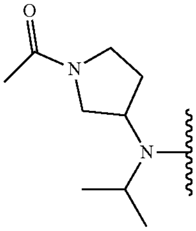 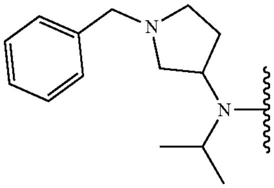
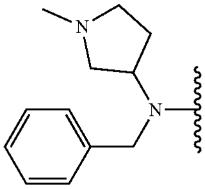 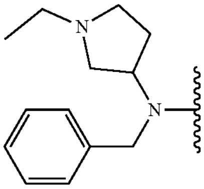
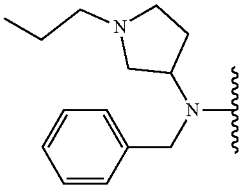 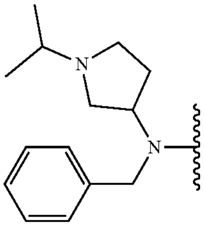
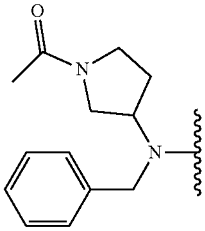 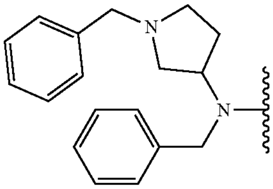
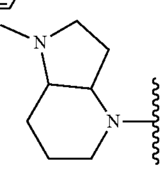 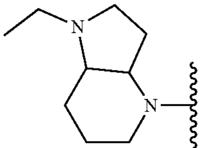
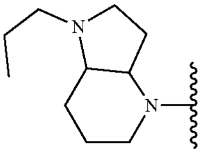 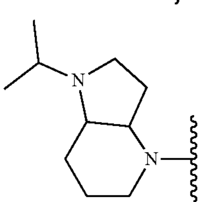
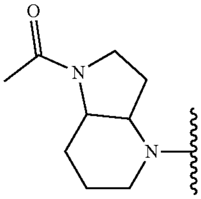 and 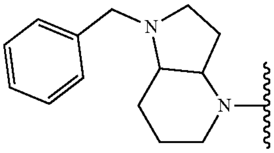
In certain embodiments, $R^1$ is selected from:
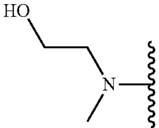 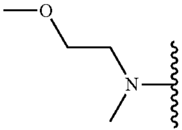
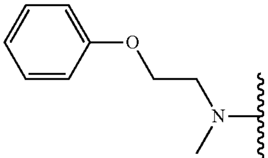 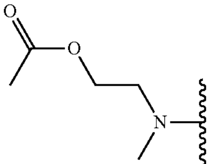
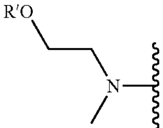 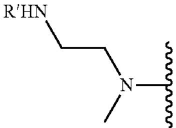 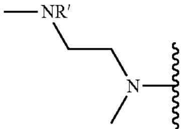
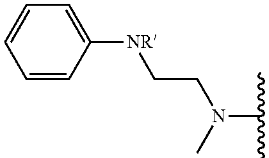 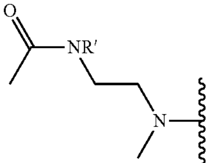
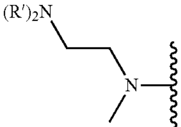 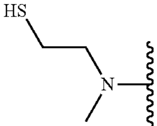 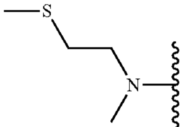
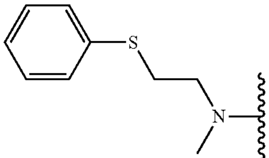 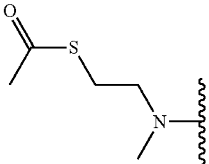
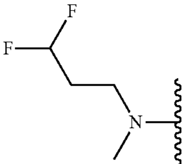 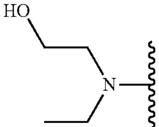 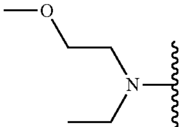
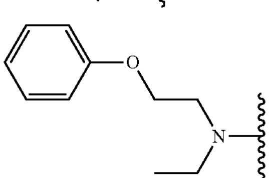 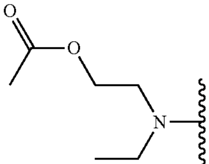
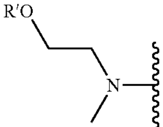 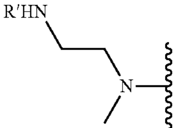 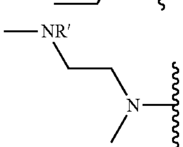
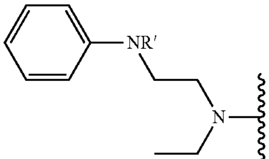 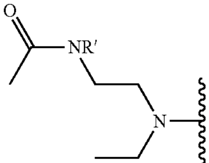

-continued
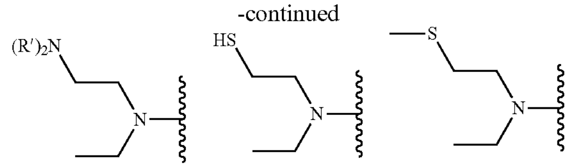
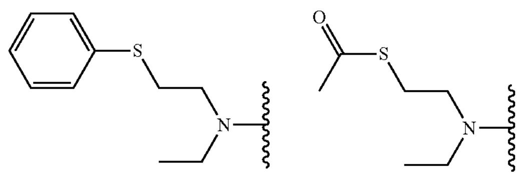
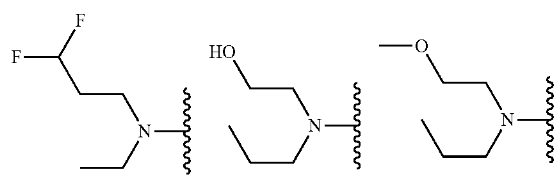
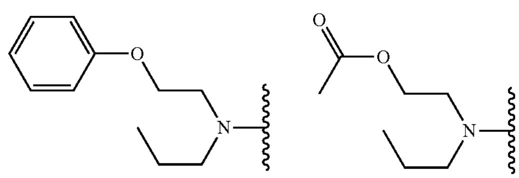
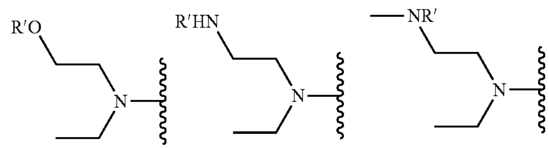
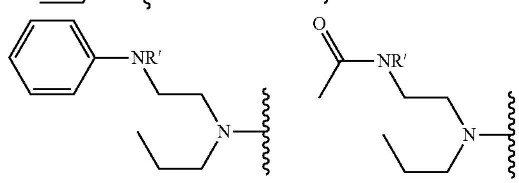
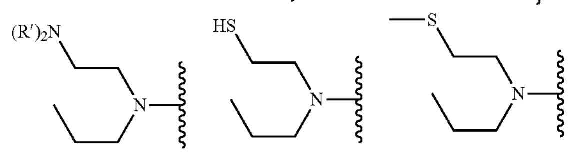
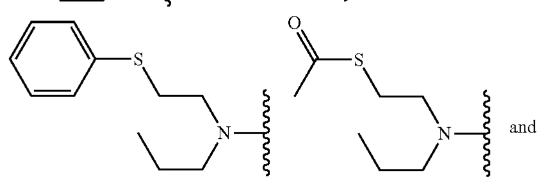
and
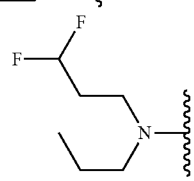
.
In certain embodiments, $R^1$ is selected from:
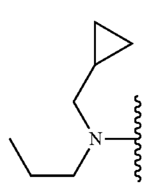
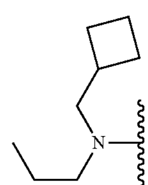
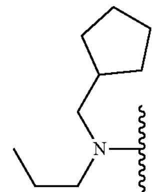
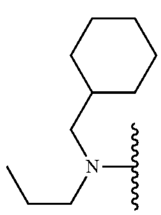
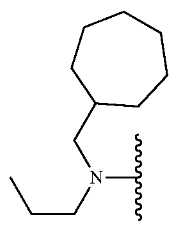
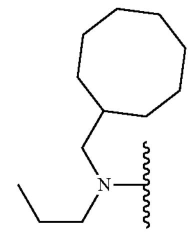
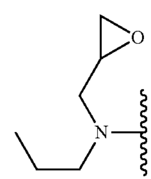
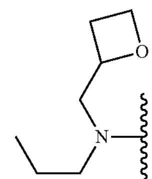
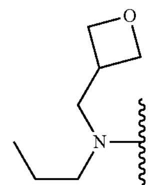
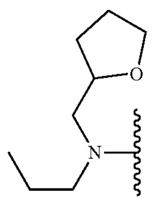
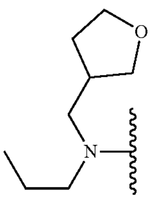
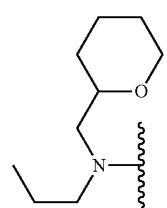
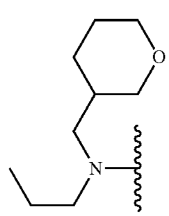
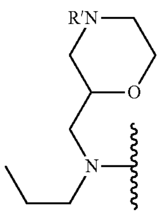
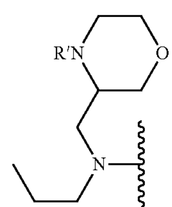
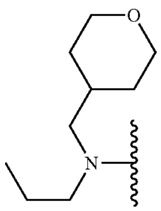
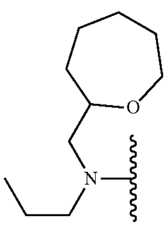
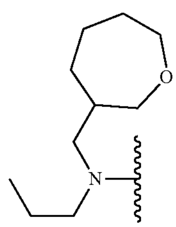
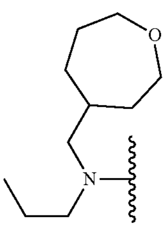
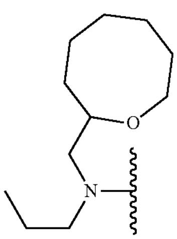
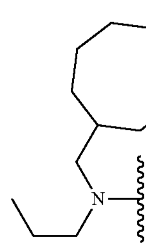

-continued
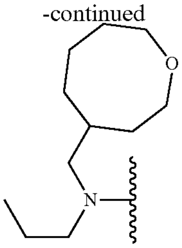
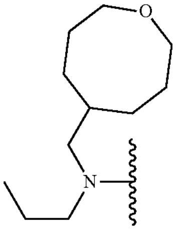 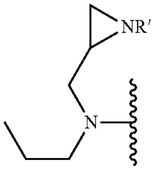 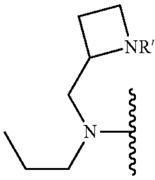
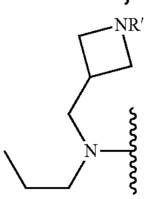 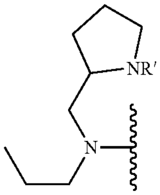 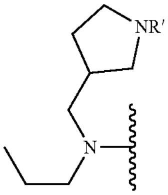
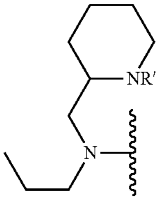 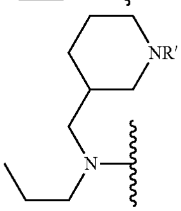 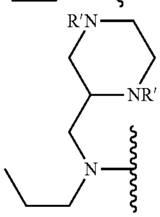
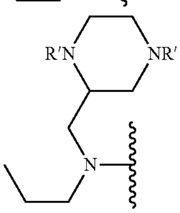 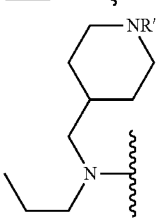 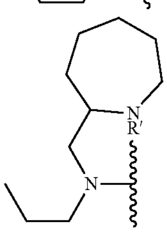
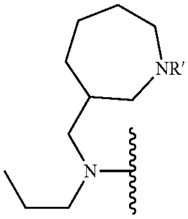 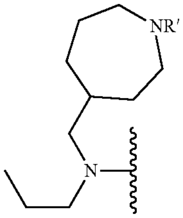 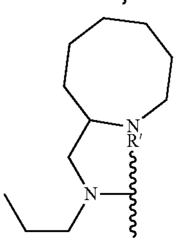
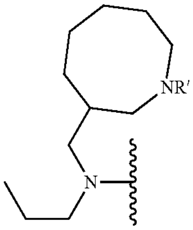 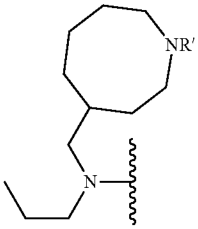 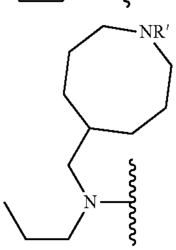
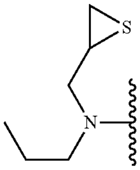 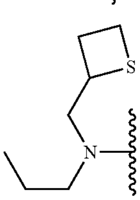 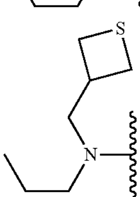
-continued
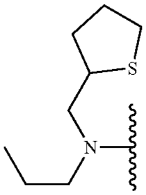 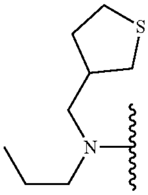 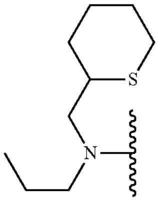
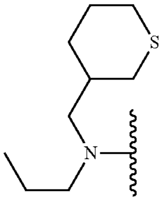 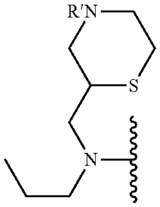 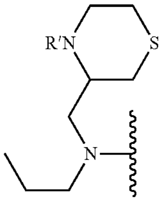
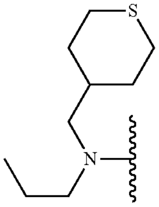 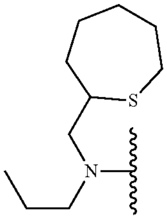 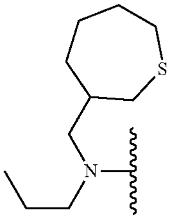
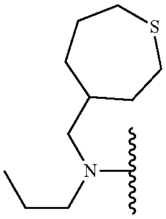 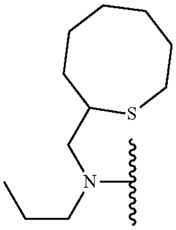 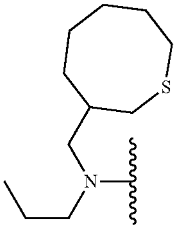
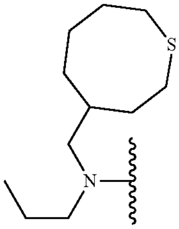 and 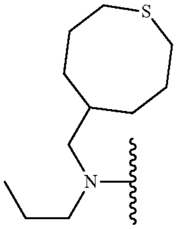.
In certain embodiments, $R^1$ is selected from:
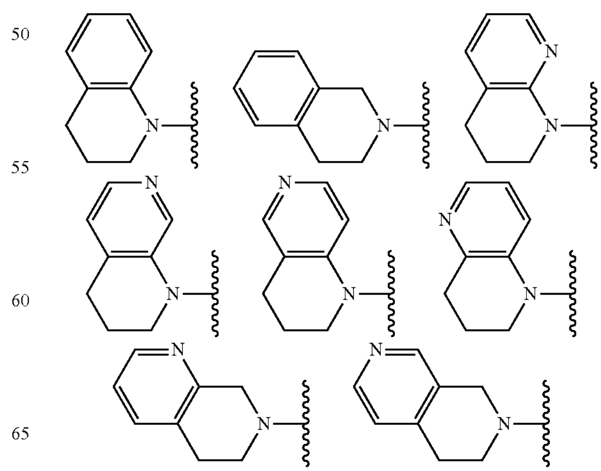

-continued
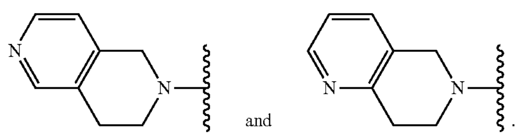
and
In certain embodiments, $R^1$ is selected from:
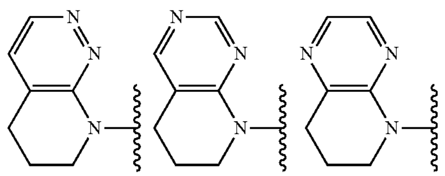
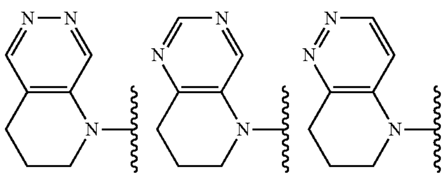
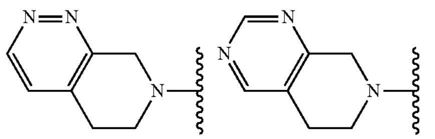
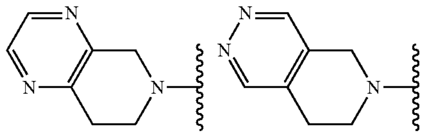
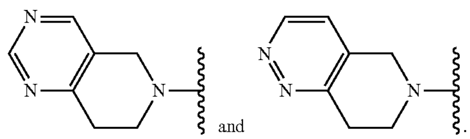
and
In certain embodiments, $R^1$ is selected from:
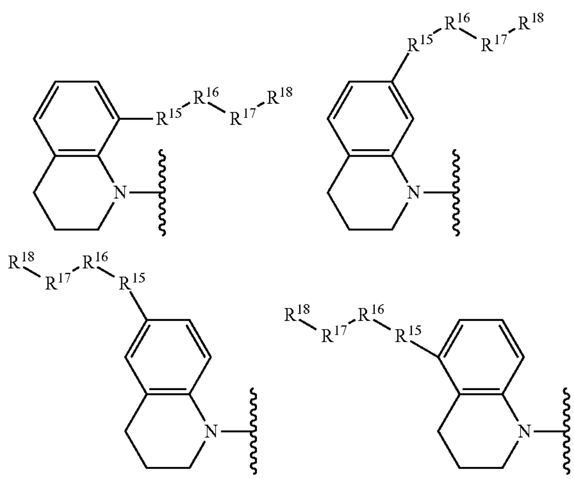
-continued
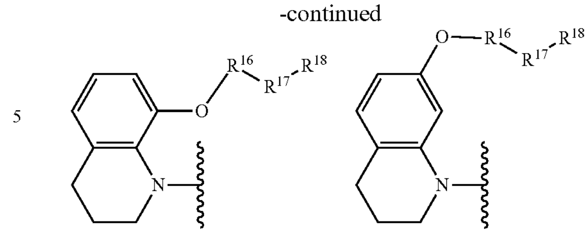
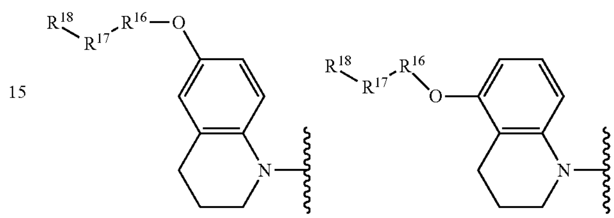
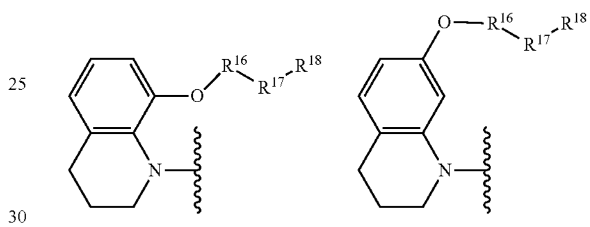
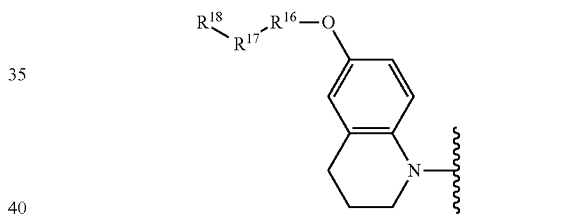
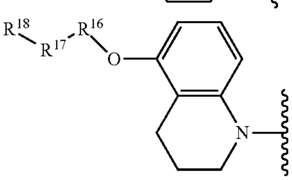
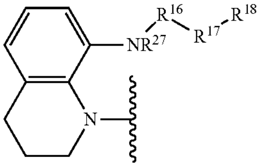
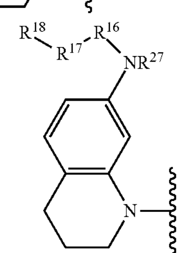
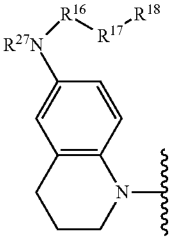
and
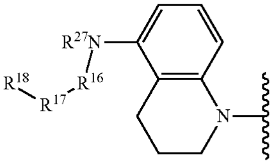

In certain embodiments, $R^1$ is selected from:
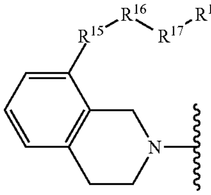
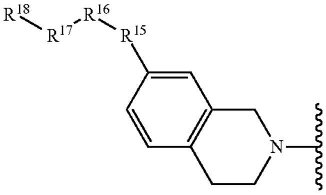
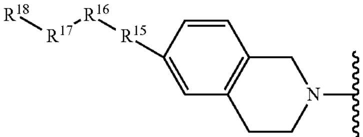
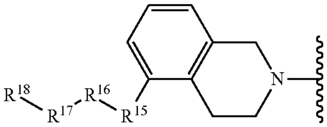
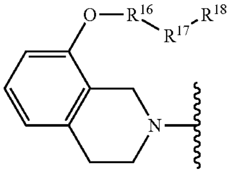
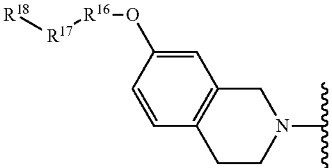
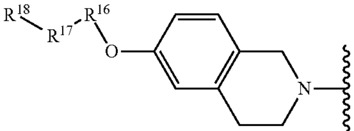
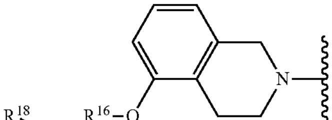
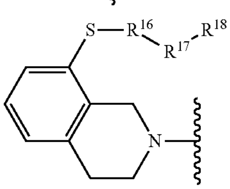
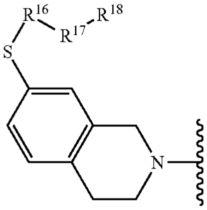
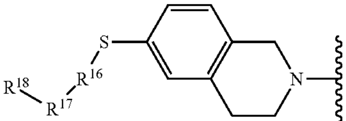
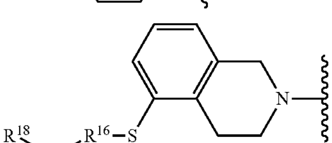
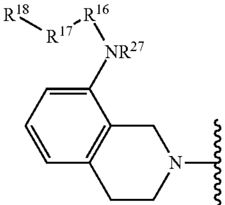
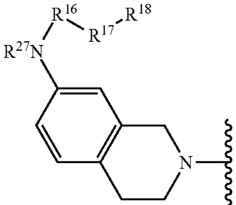
-continued
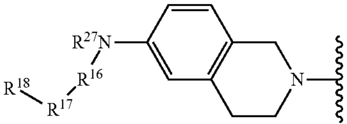
and
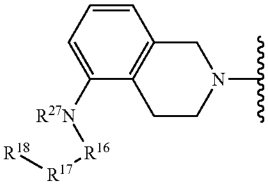
.
In certain embodiments, $R^1$ is selected from:
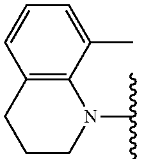
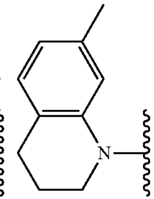
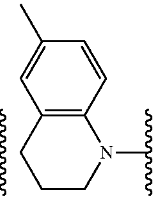
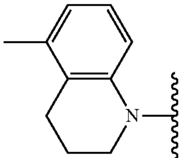
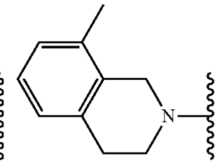
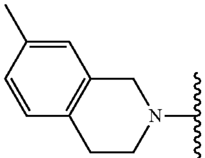
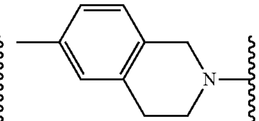
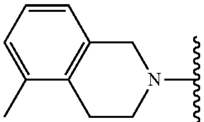
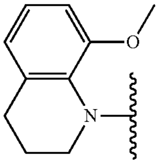
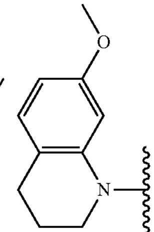
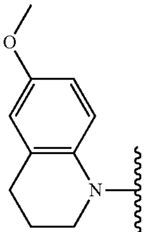
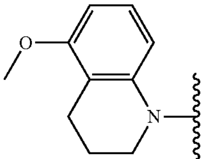
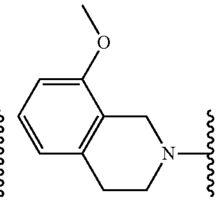
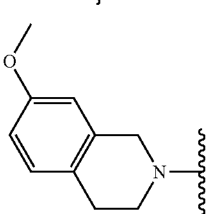
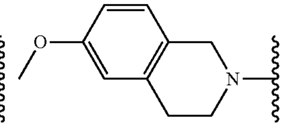

-continued
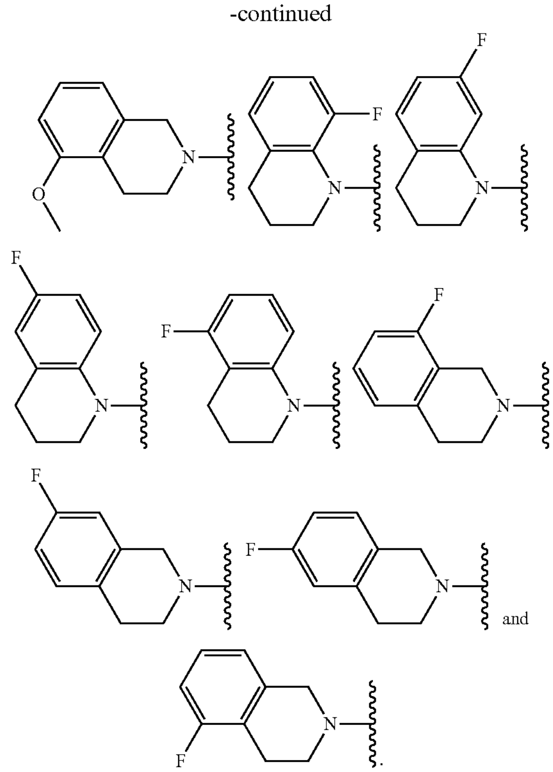
and
In certain embodiments, $R^1$ is selected from:
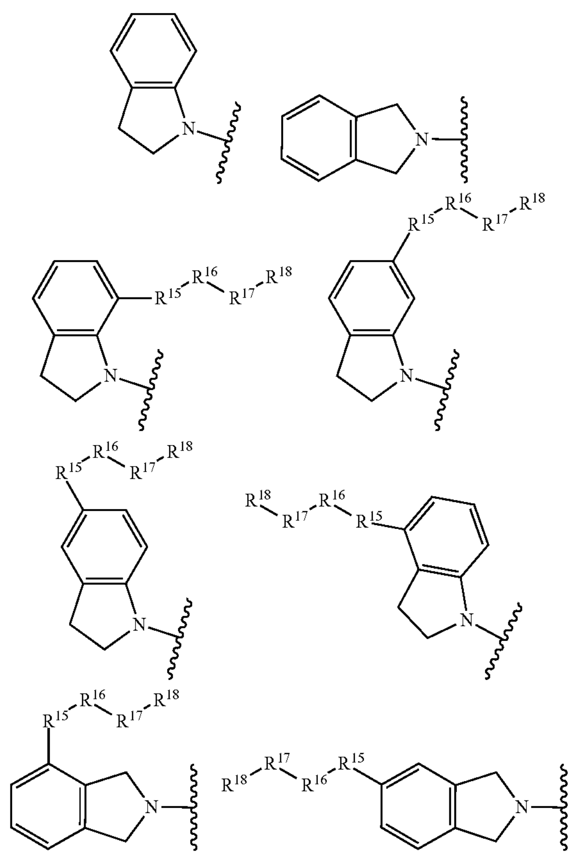
-continued
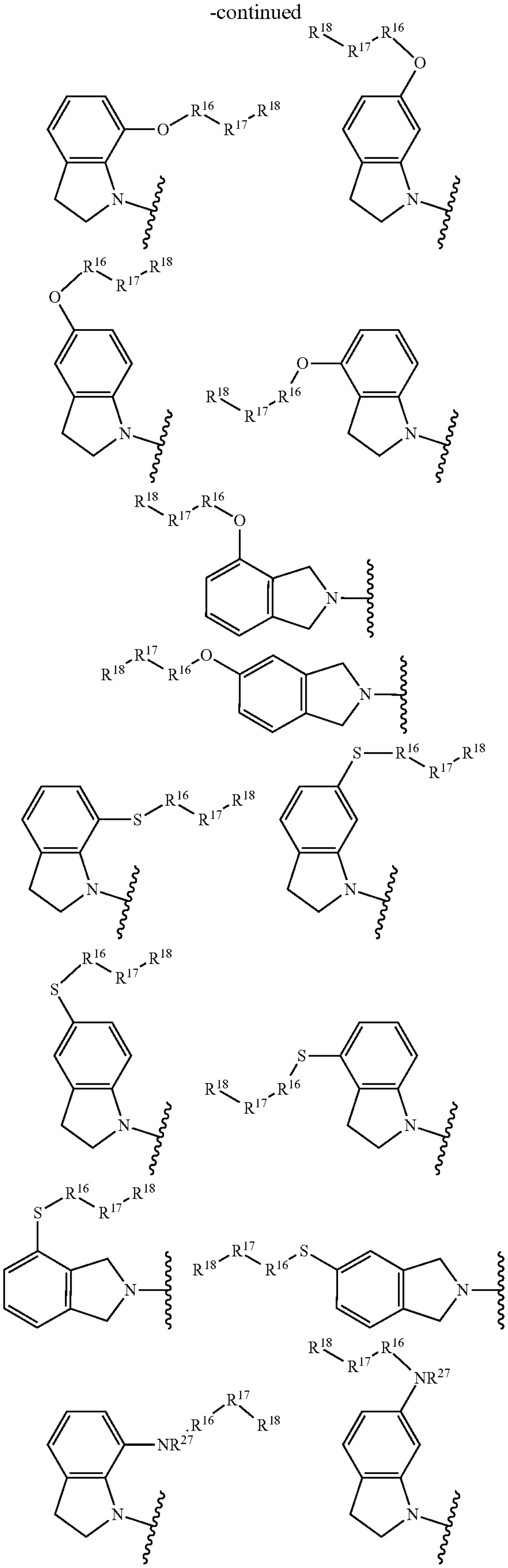

-continued
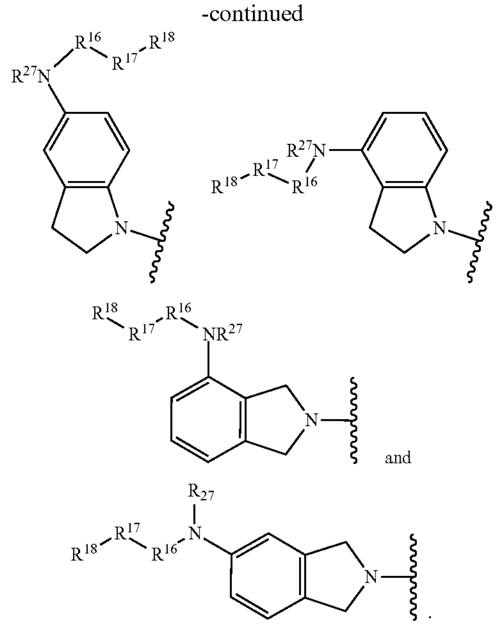
and
In certain embodiments, $R^1$ is selected from:
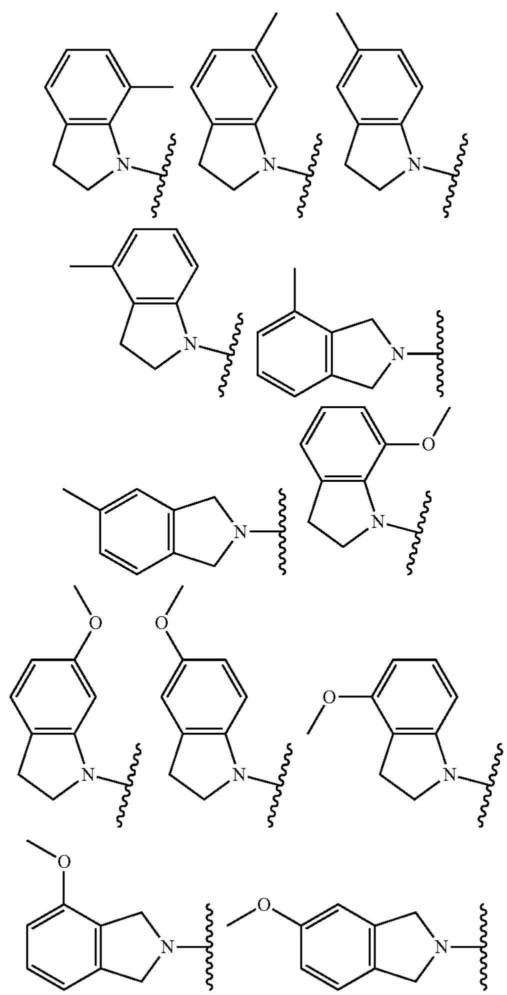
-continued
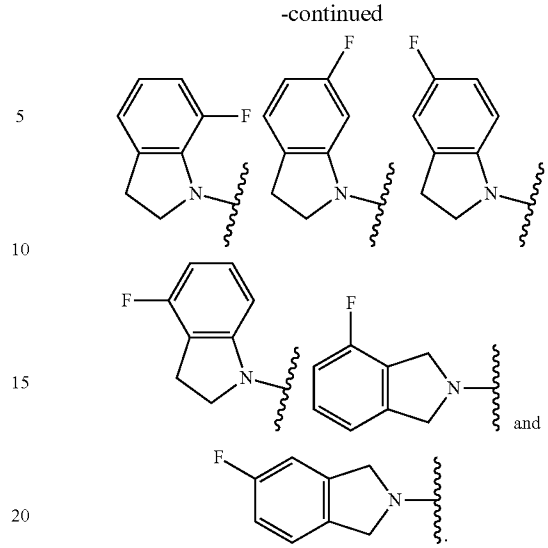
and
In certain embodiments, $R^1$ is selected from:
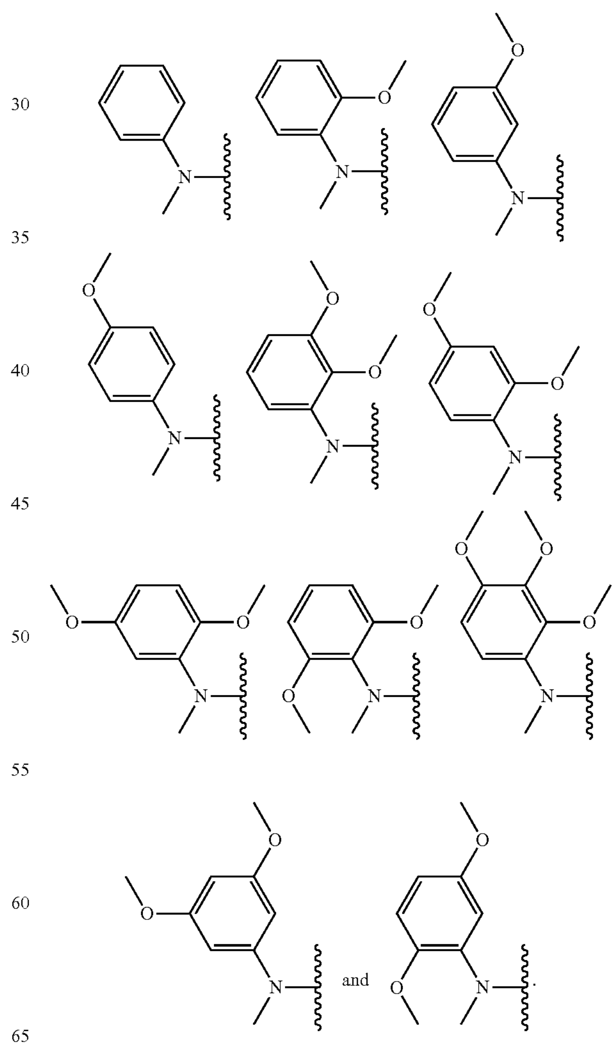
and In certain embodiments, $R^1$ is selected from:
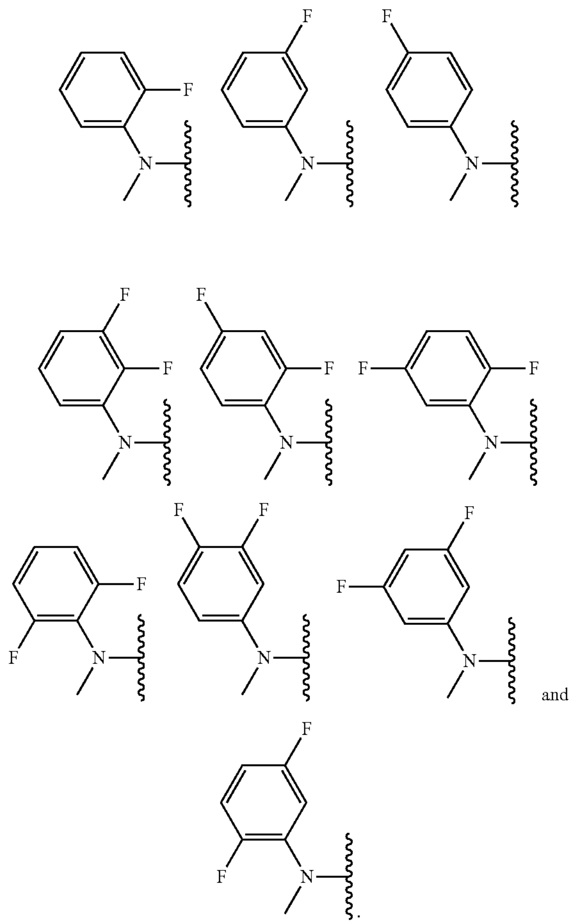
and
In certain embodiments, $R^1$ is selected from:
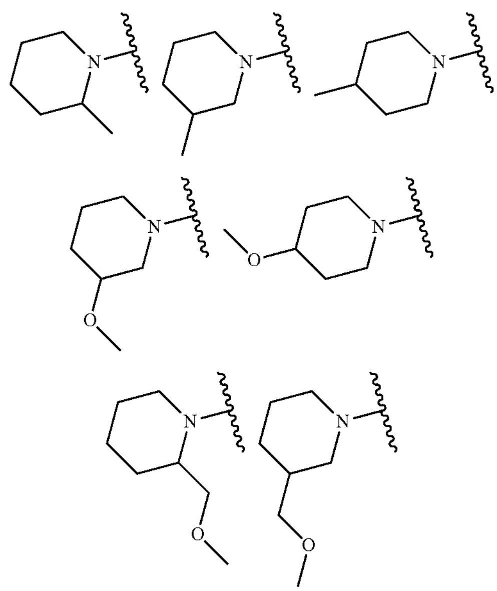
-continued
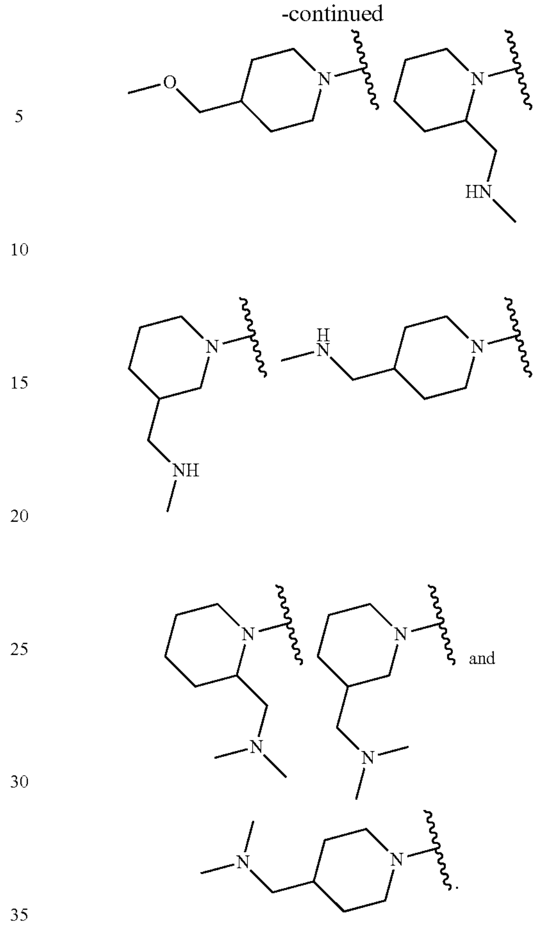
and
In certain embodiments, $R^1$ is selected from:
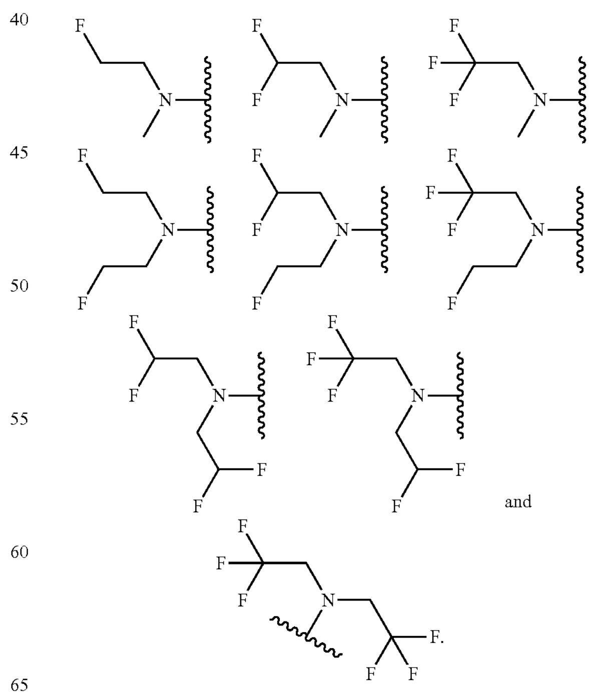
and In certain embodiments, $R^1$ is selected from:
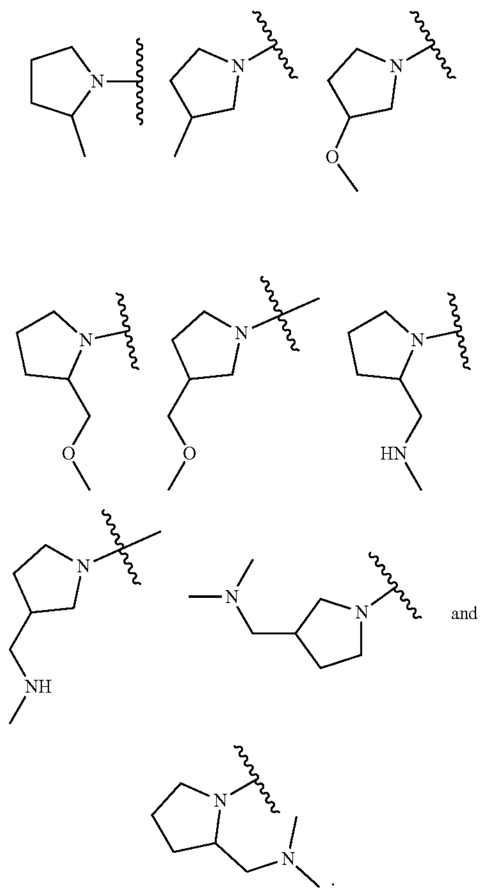
and
In certain embodiments, $R^1$ is selected from:
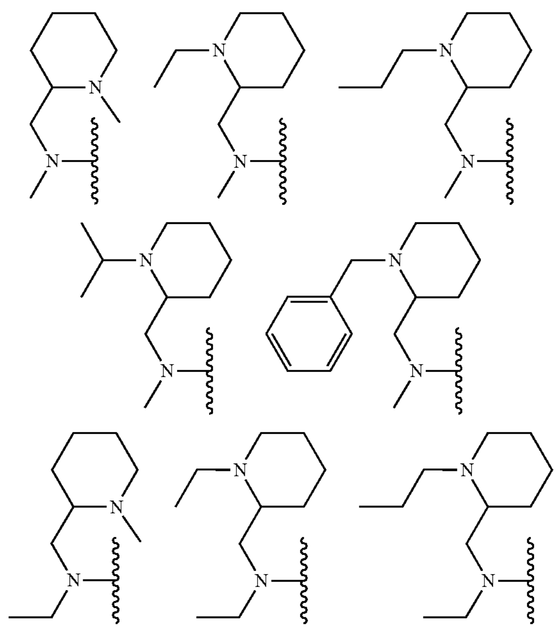
-continued
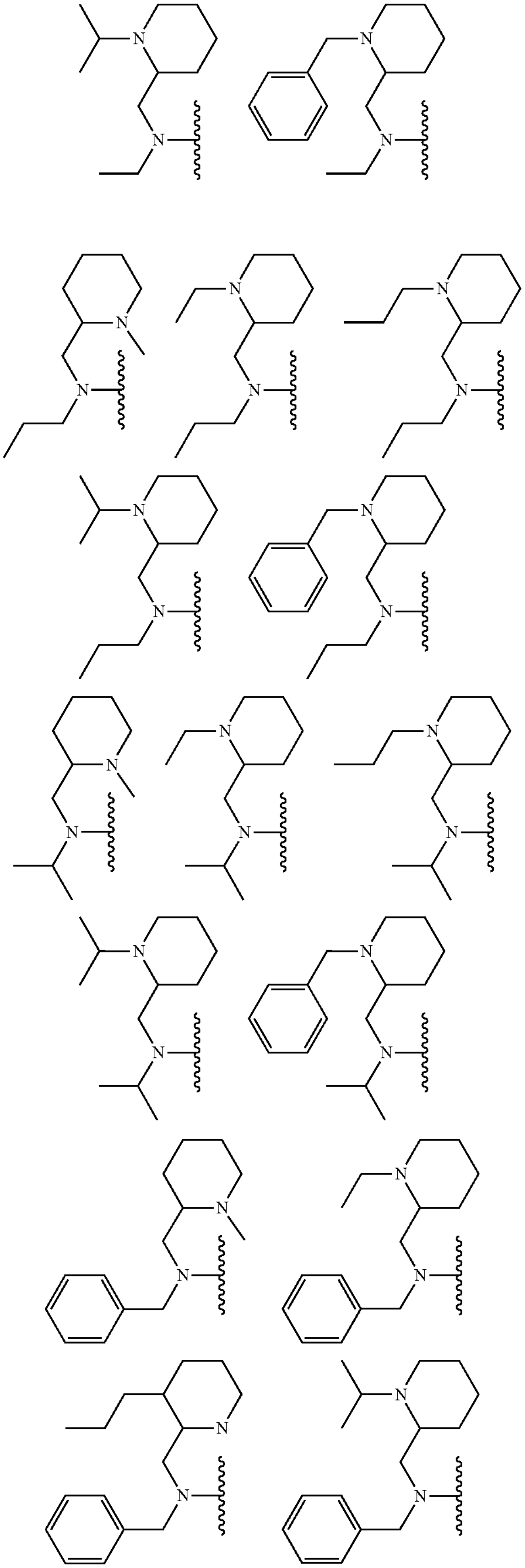

-continued
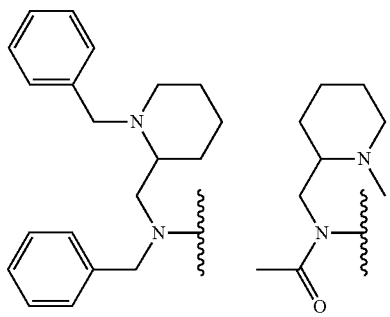
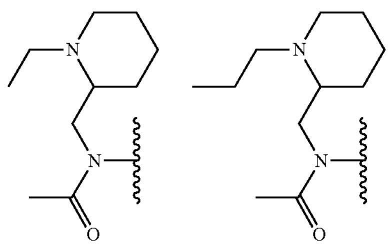
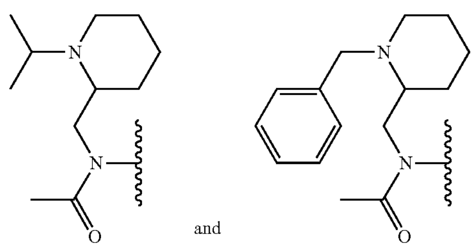
and .
In certain embodiments, $R^1$ is selected from:
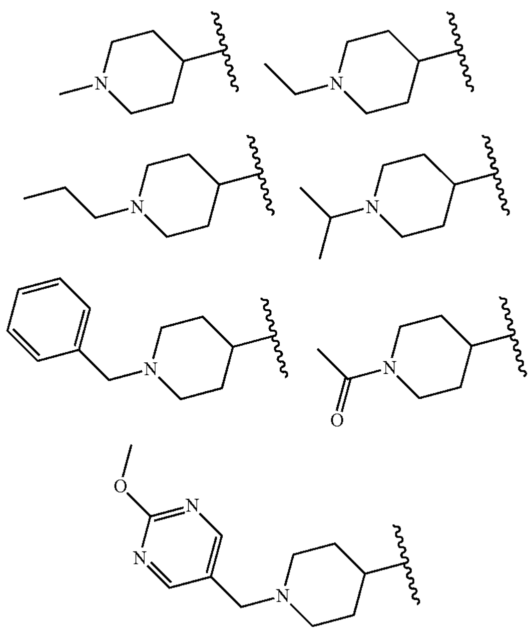
-continued
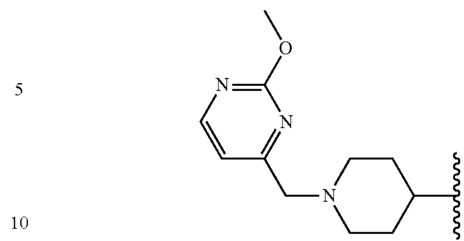
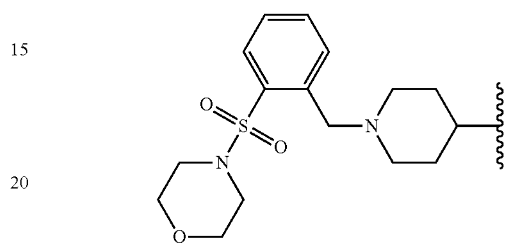
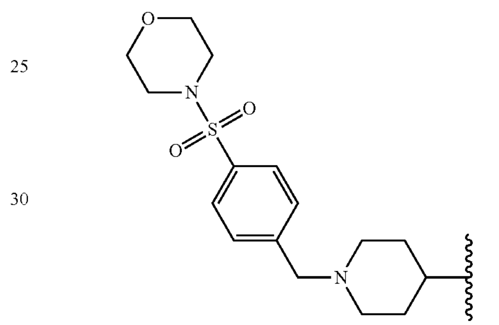
and
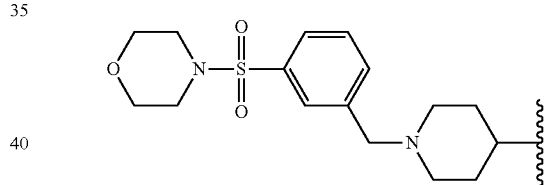
.
In certain embodiments, $R^1$ is selected from:
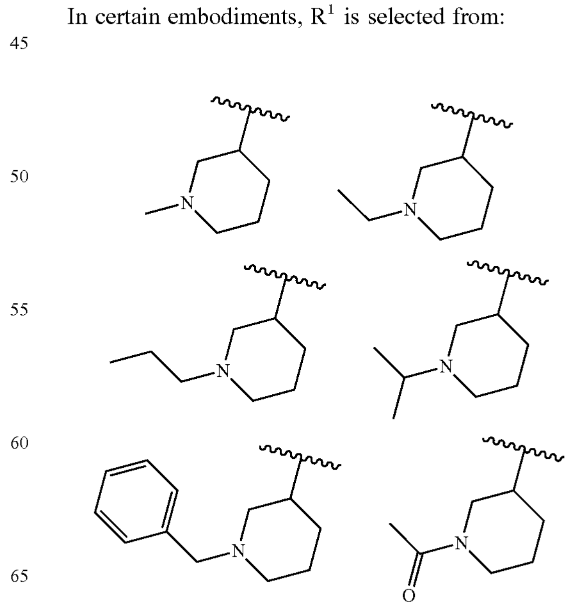

-continued
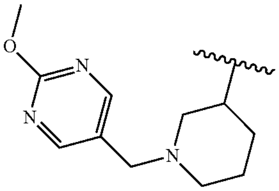
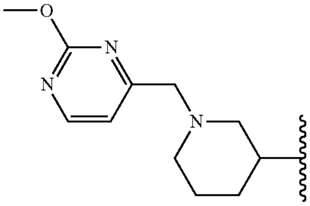
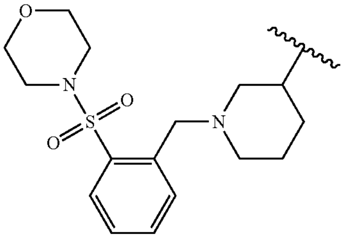
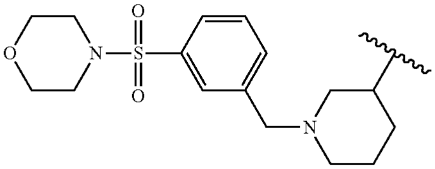
and
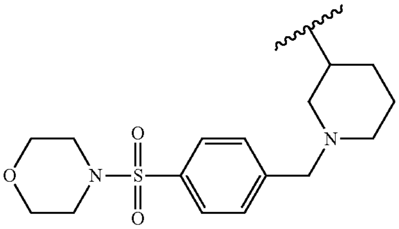
In certain embodiments, $R^1$ is selected from:
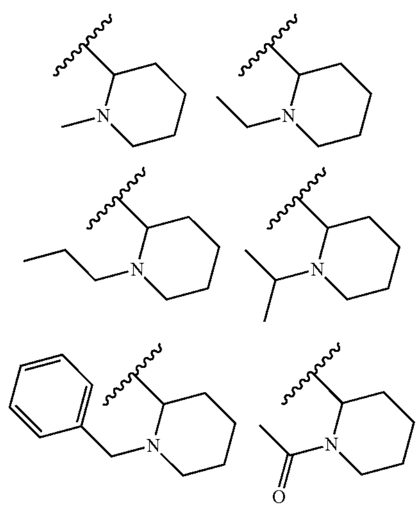
-continued
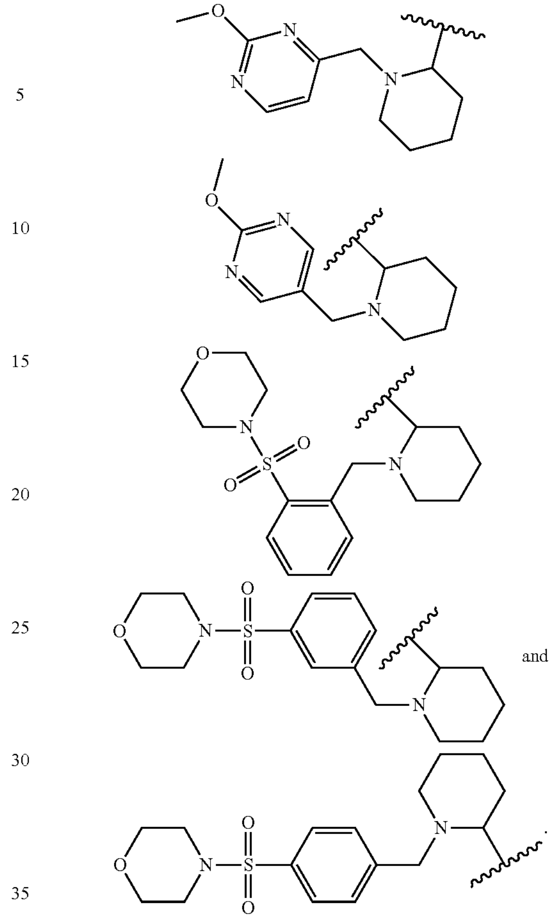
and
In certain embodiments, $R^1$ is selected from:
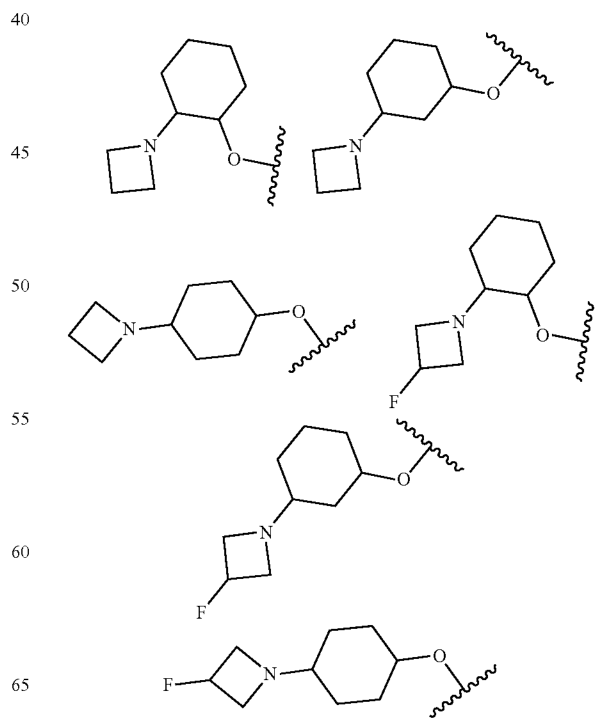

-continued
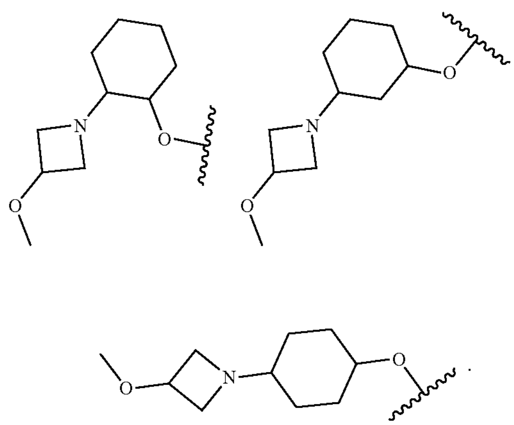
and
In certain embodiments, $R^1$ is selected from:
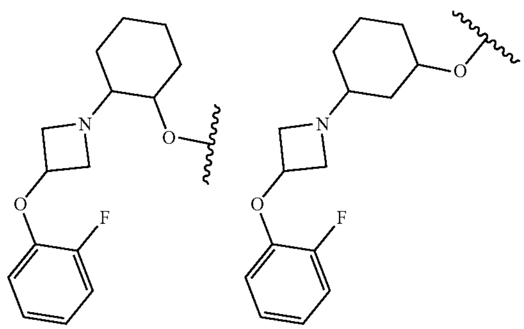
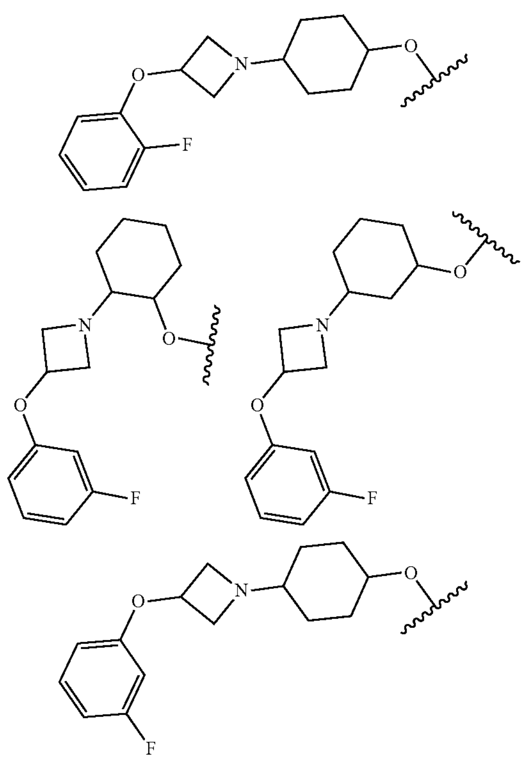
-continued
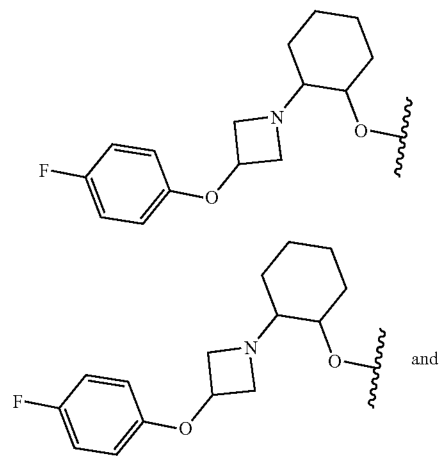
and
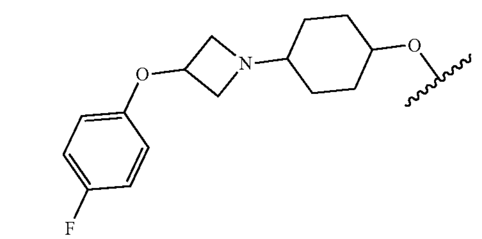
In certain embodiments, $R^1$ is selected from:
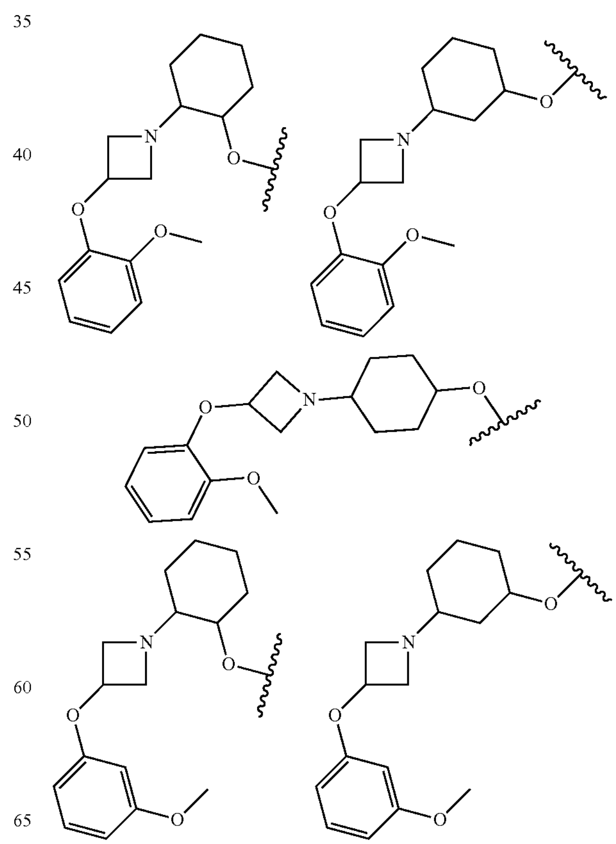

-continued
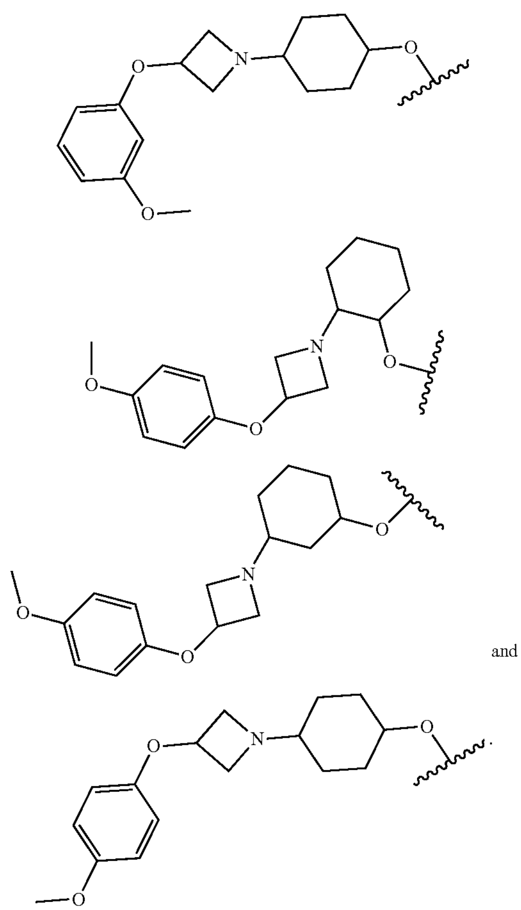
and
In certain embodiments, $R^1$ is selected from:
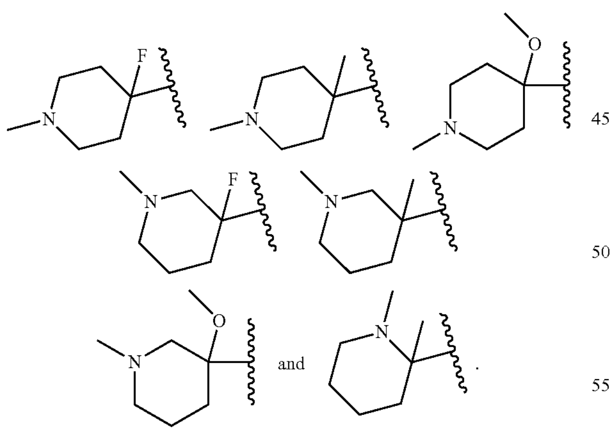
and
In certain embodiments, $R^1$ is selected from:
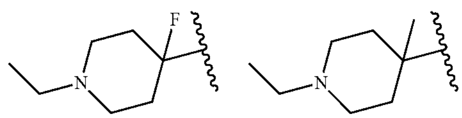
-continued
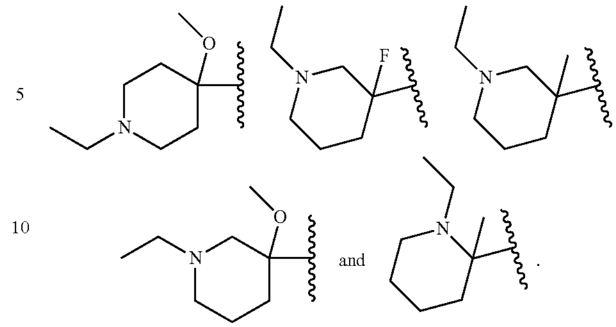
and
In certain embodiments, $R^1$ is selected from:
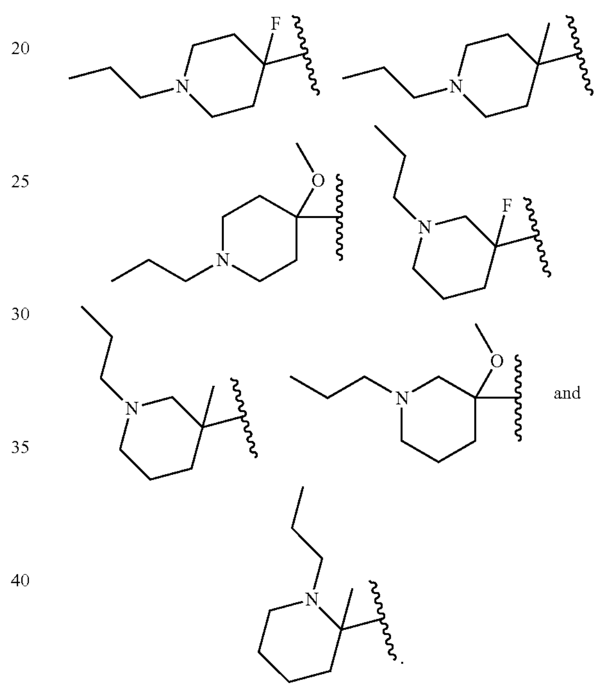
and
In certain embodiments, $R^1$ is selected from:
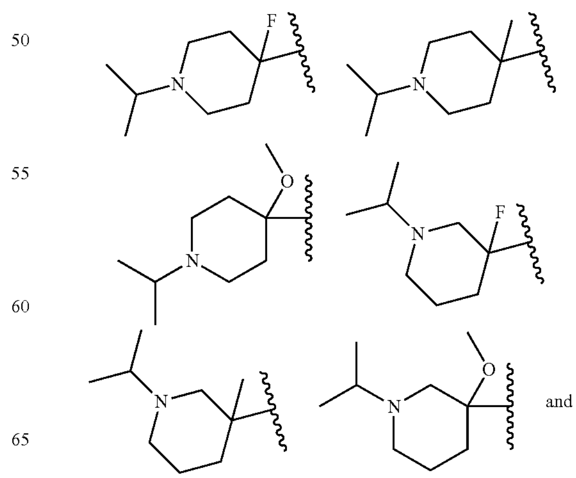
and -continued
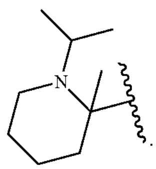
In certain embodiments, $R^1$ is selected from:
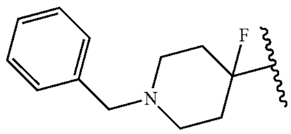
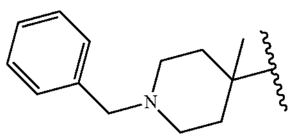
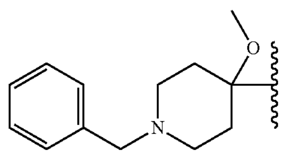
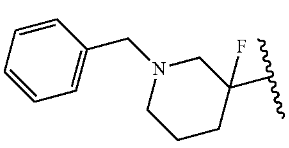
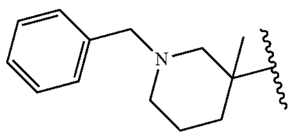
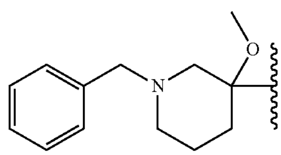
and
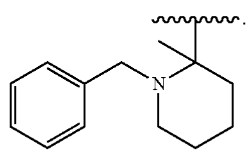
In certain embodiments, $R^1$ is selected from:
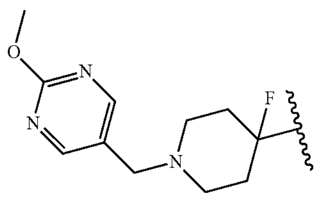
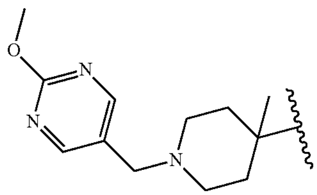
-continued
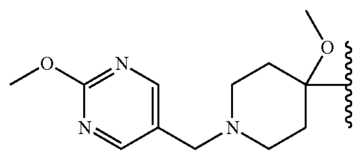
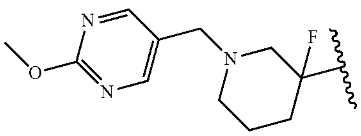
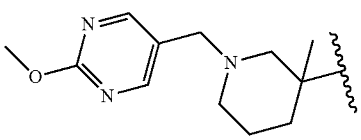
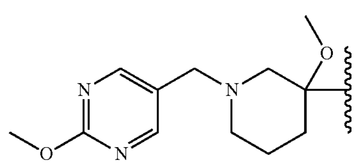
and
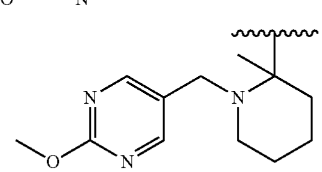
In certain embodiments, $R^1$ is selected from:
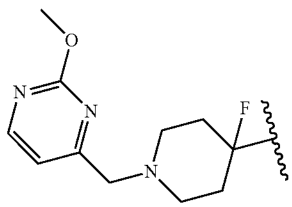
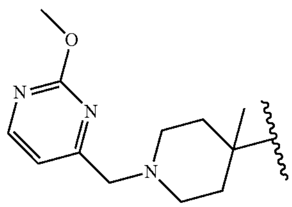
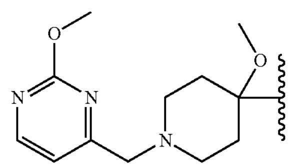
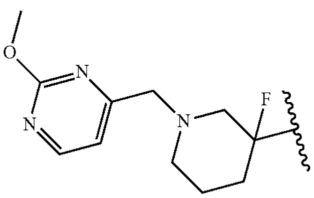

-continued
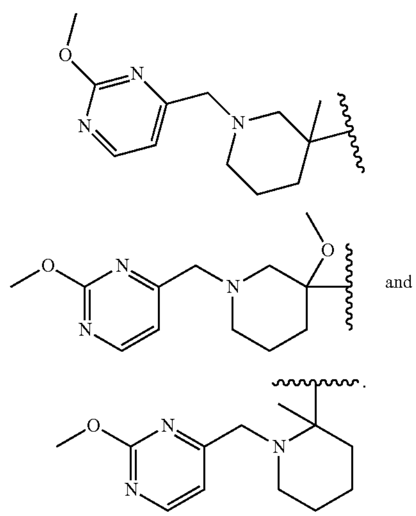
and
In certain embodiments, $R^1$ is selected from:
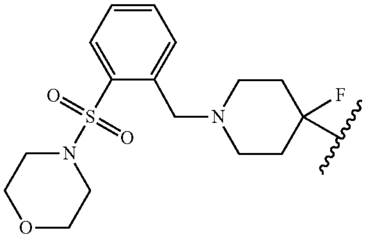
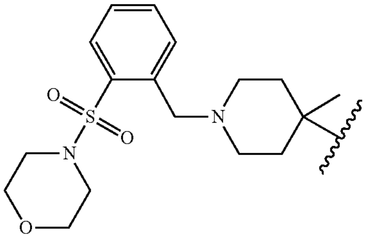
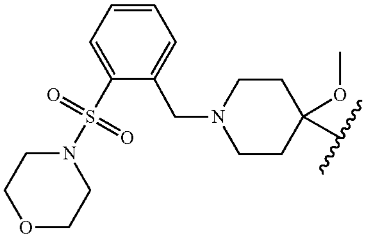
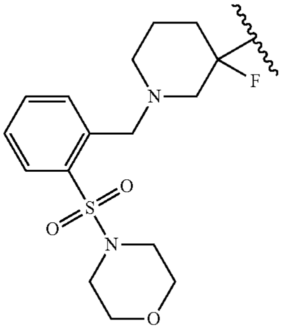
-continued
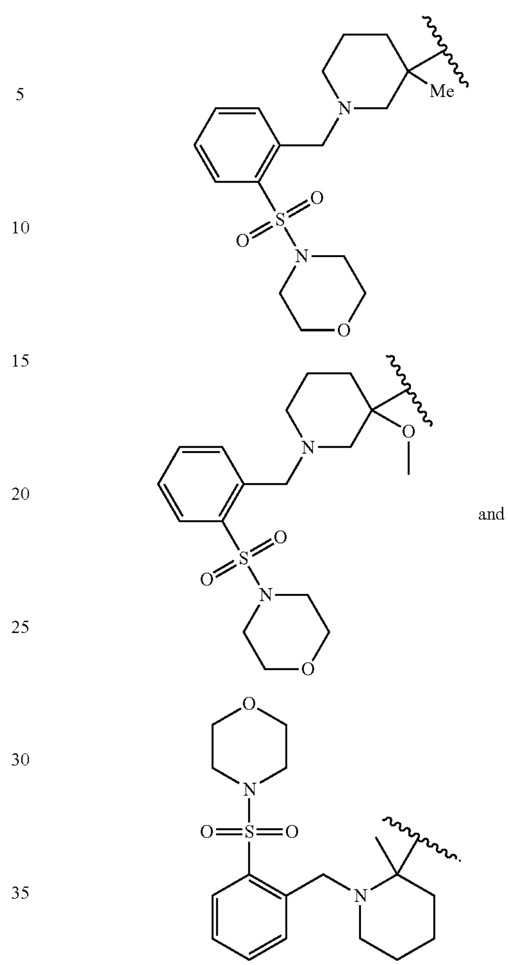
and
In certain embodiments, $R^1$ is selected from:
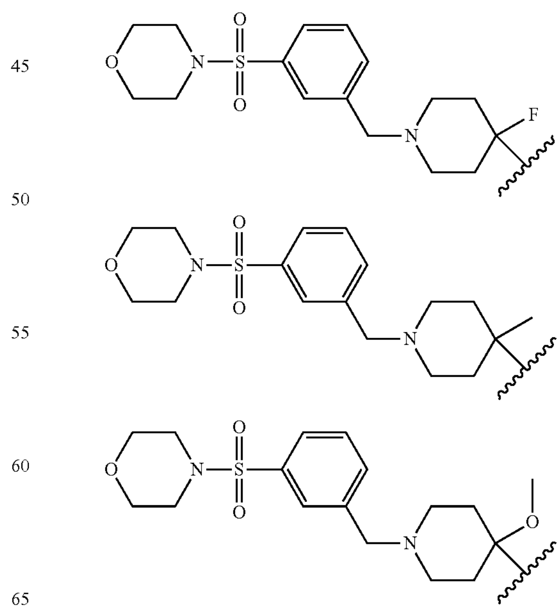

-continued
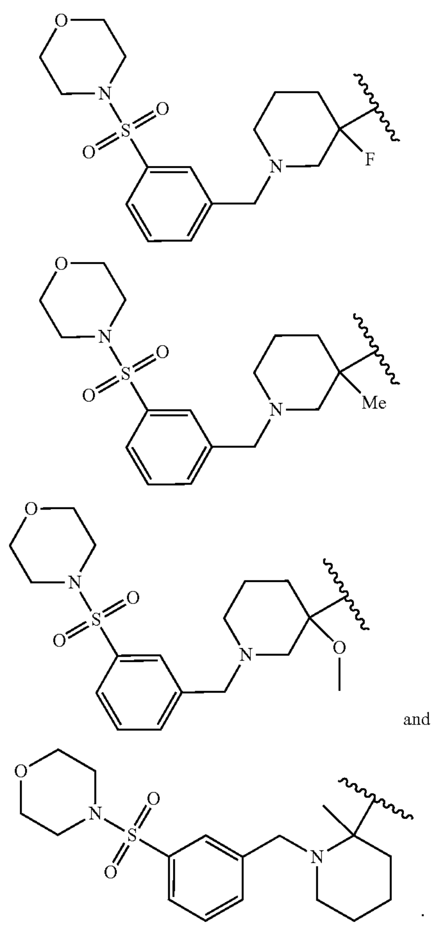
and
In certain embodiments, $R^1$ is selected from:
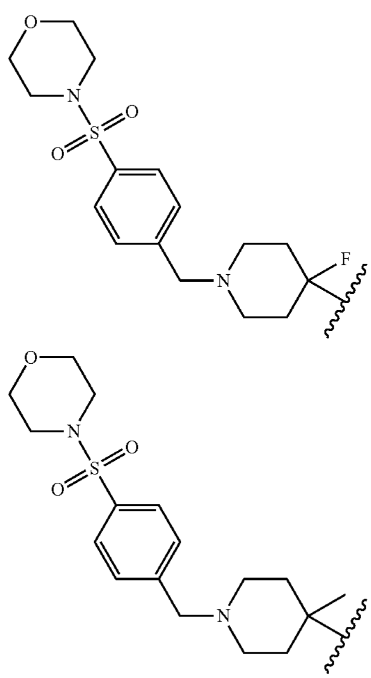
-continued
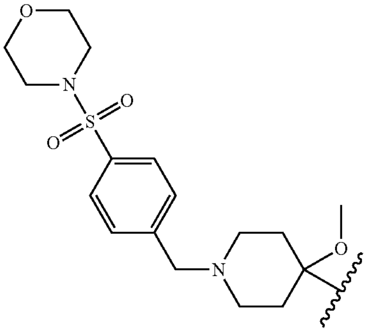
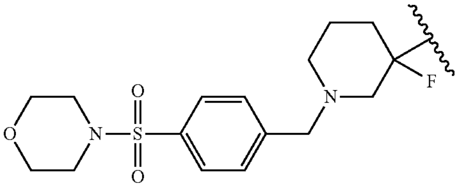
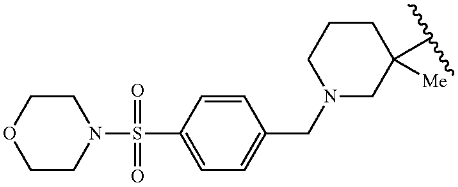
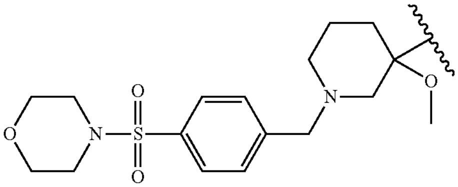
and
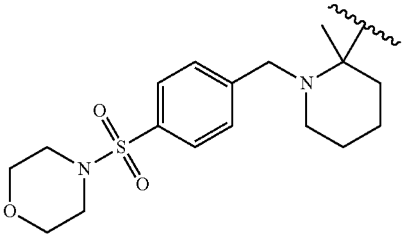
In certain embodiments, $R^1$ is selected from:
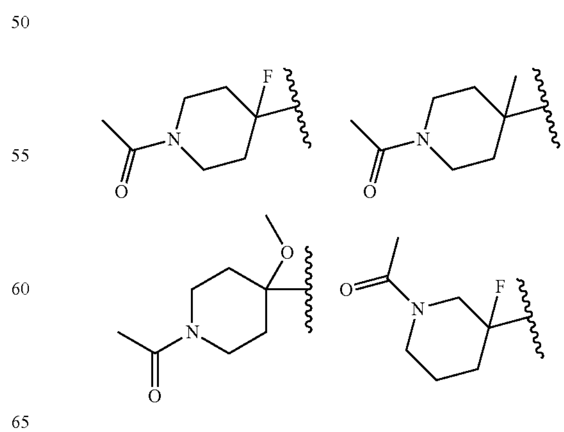

-continued
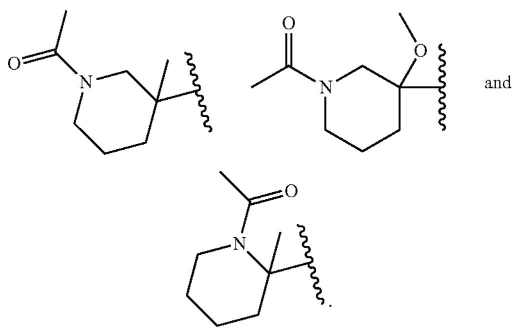
and
In certain embodiments, $R^1$ is selected from:
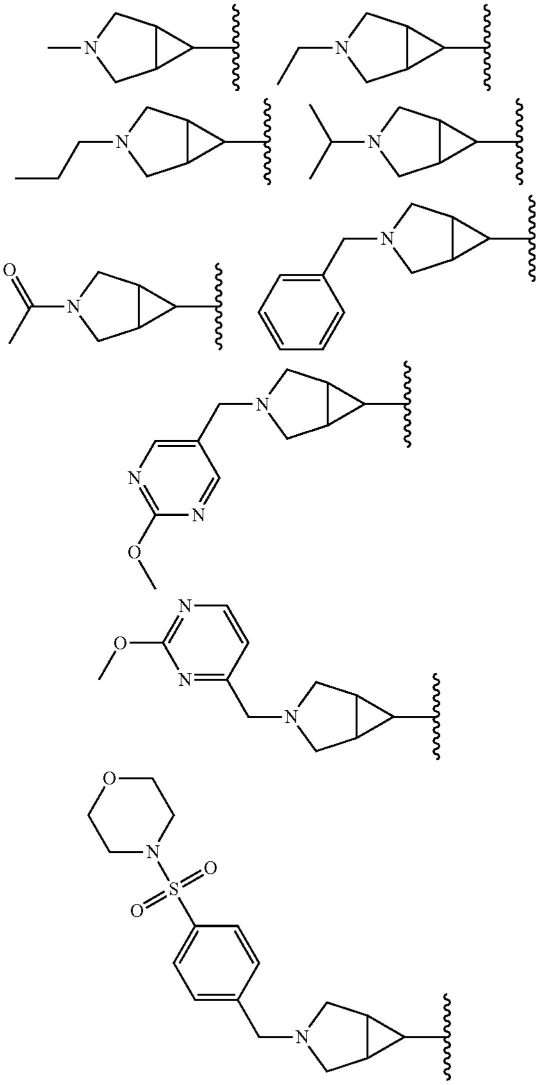
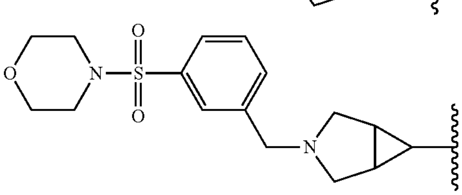
and
-continued
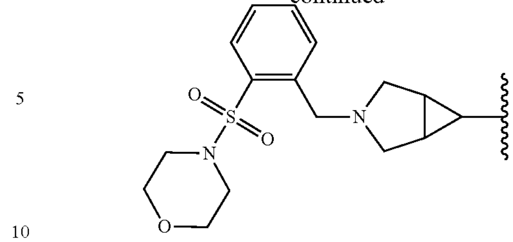
In certain embodiments, $R^1$ is selected from:
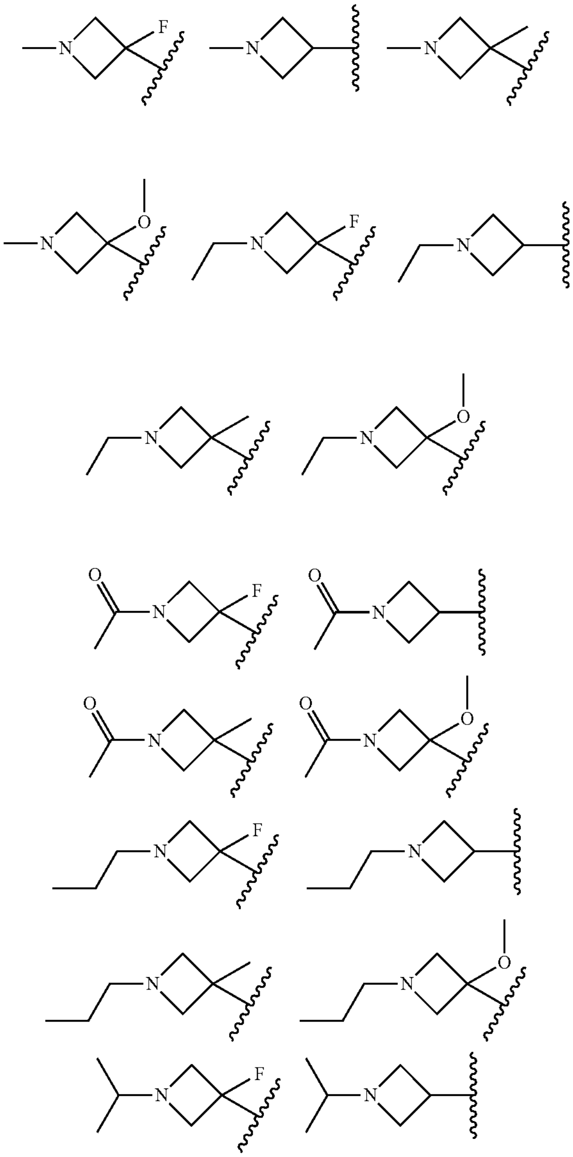
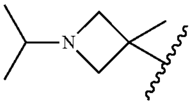
and
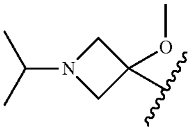

In certain embodiments, $R^1$ is selected from:
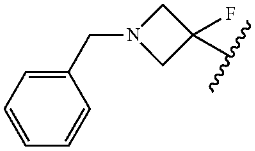
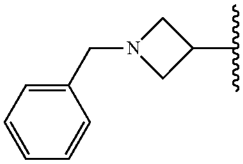
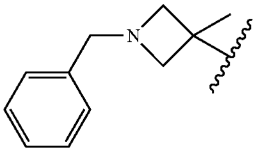
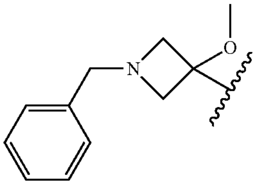
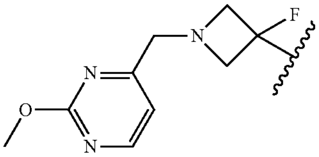
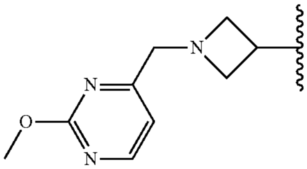
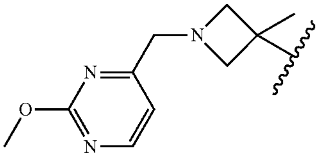
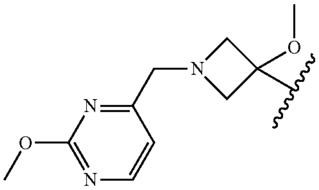
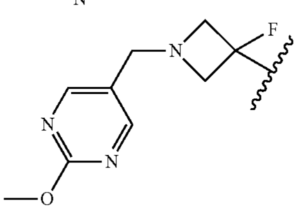
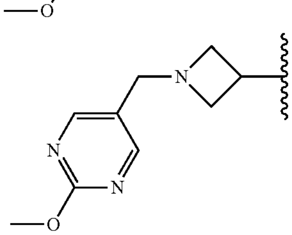
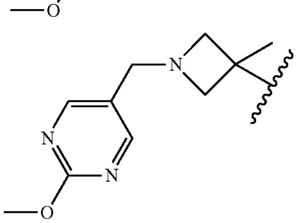
-continued
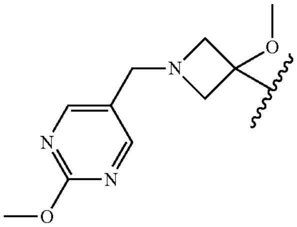
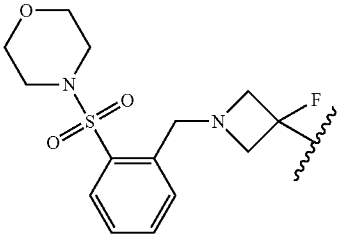
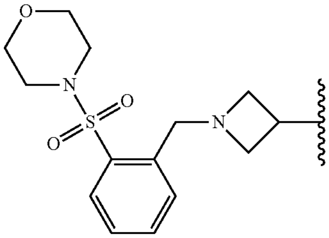
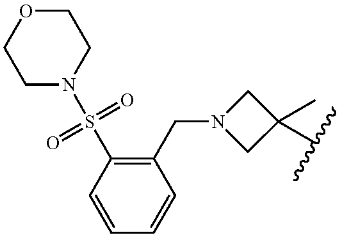
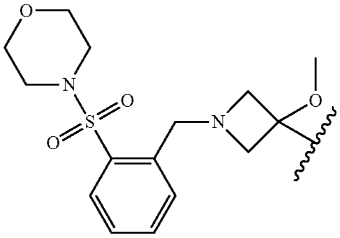
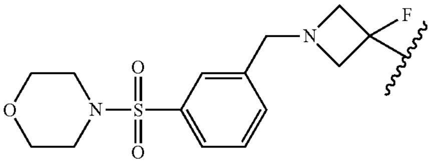
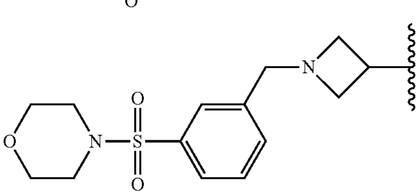
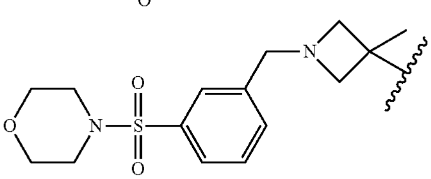

-continued
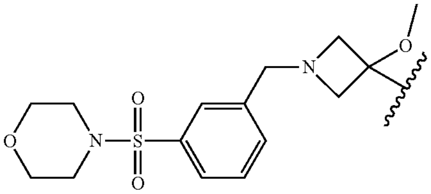
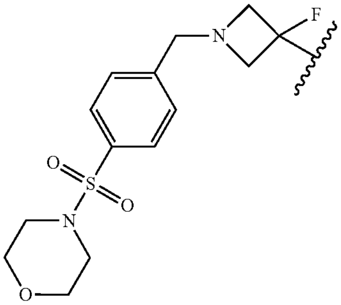
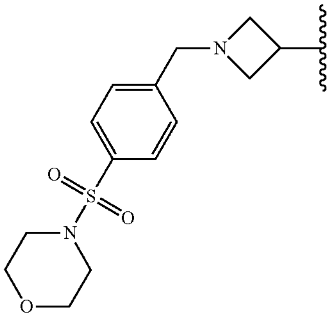
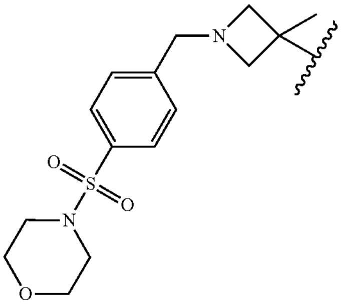
and
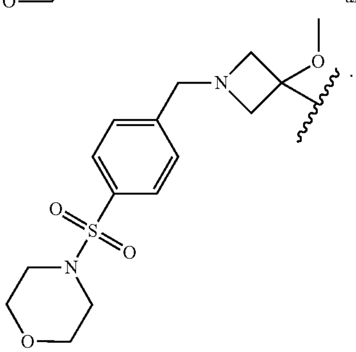
.
In certain embodiments, $R^1$ is selected from:
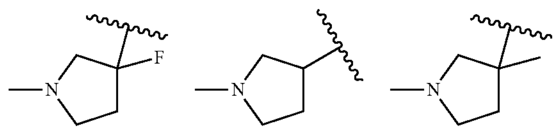
-continued
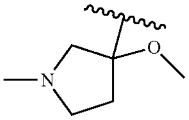
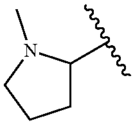
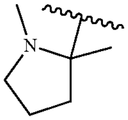
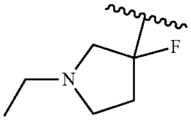
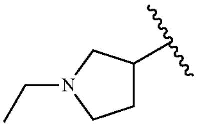
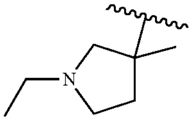
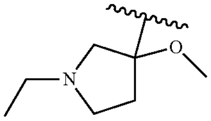
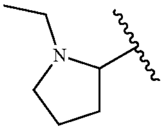
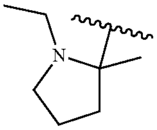
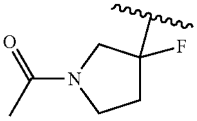
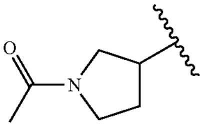
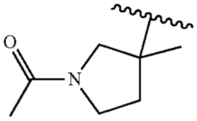
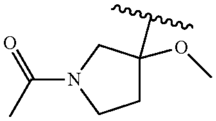
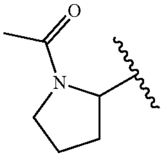
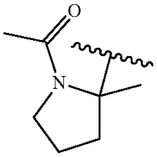
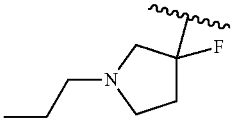
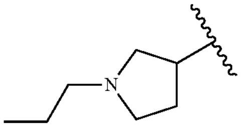
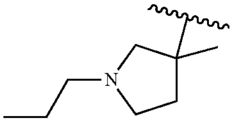
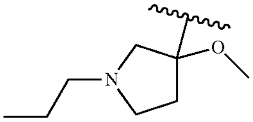
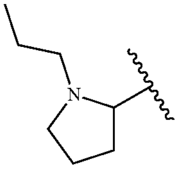
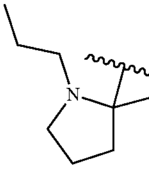
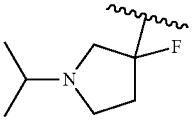
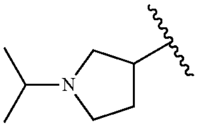
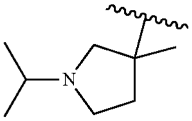
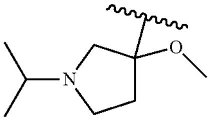

-continued
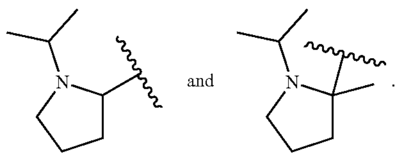
In certain embodiments $R^1$ is selected from:
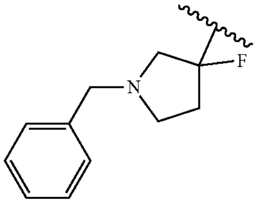
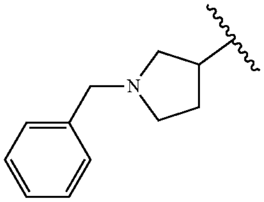
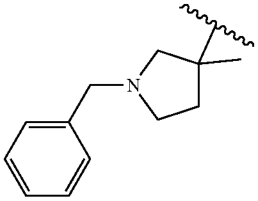
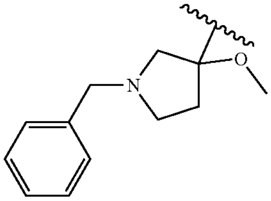
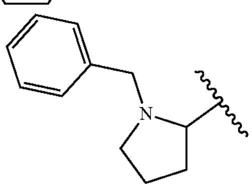
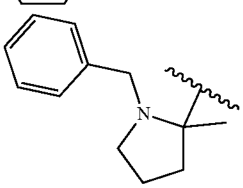
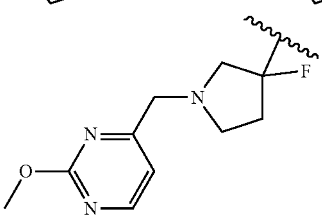
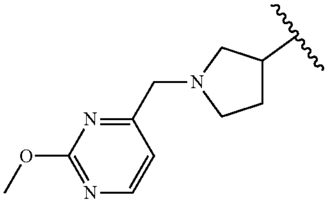
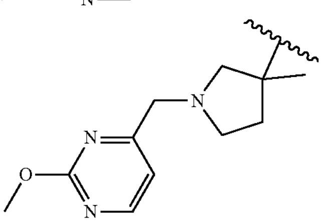
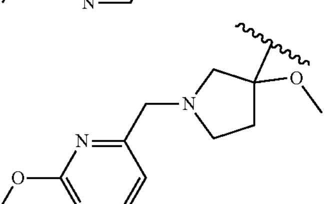
-continued
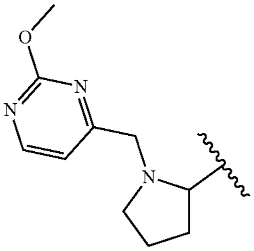
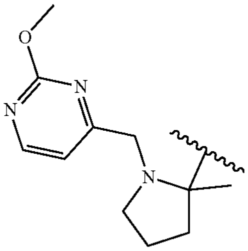
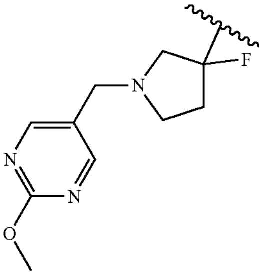
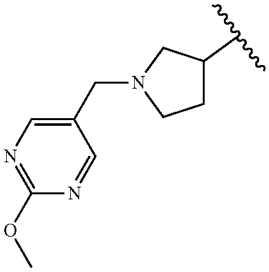
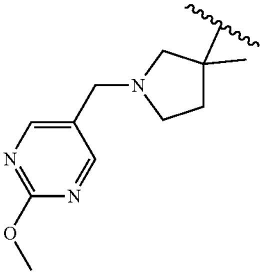
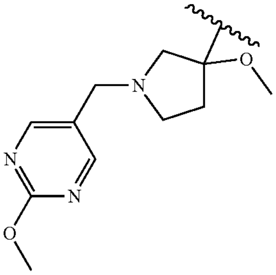
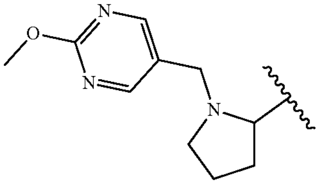
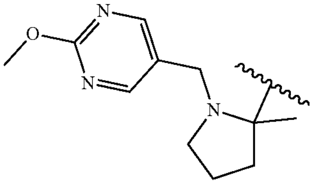
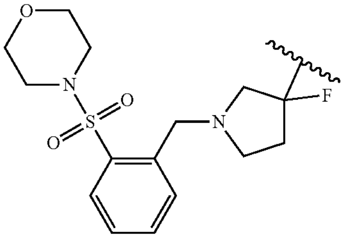
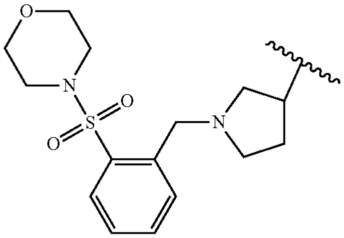

-continued
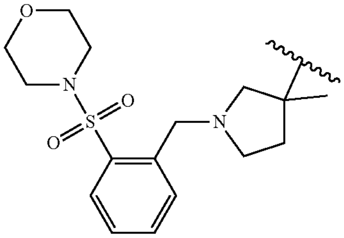
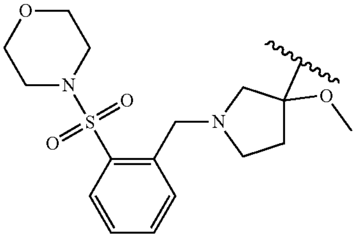
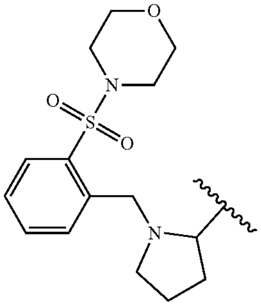
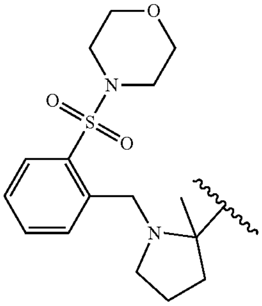
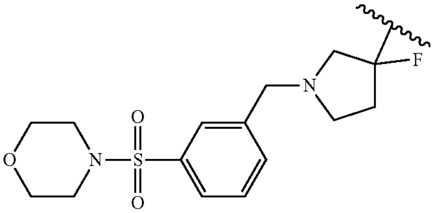
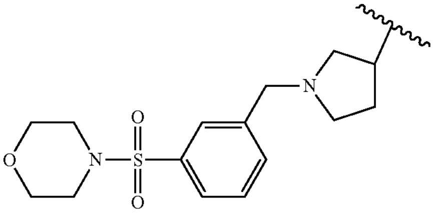
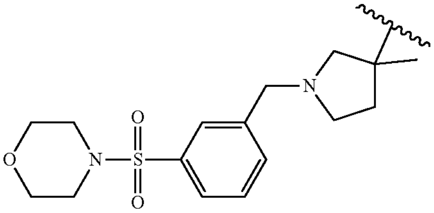
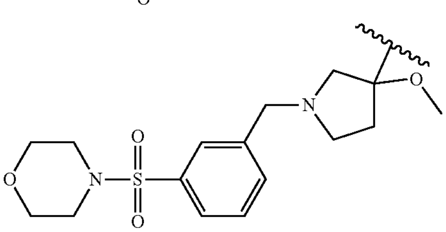
-continued
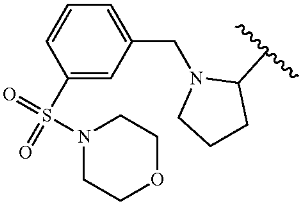
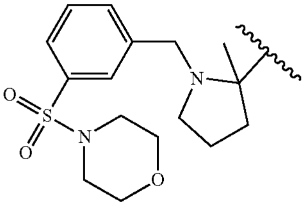
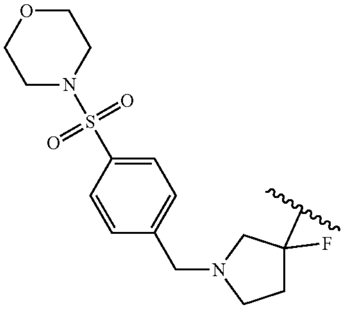
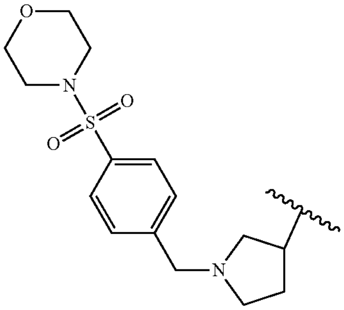
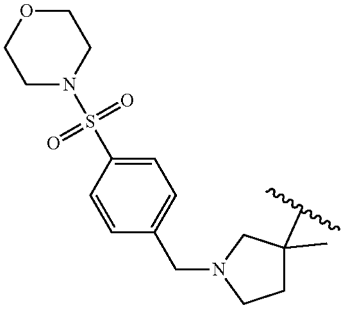
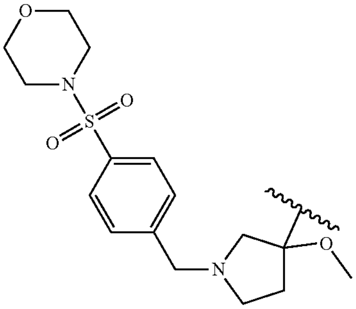

-continued
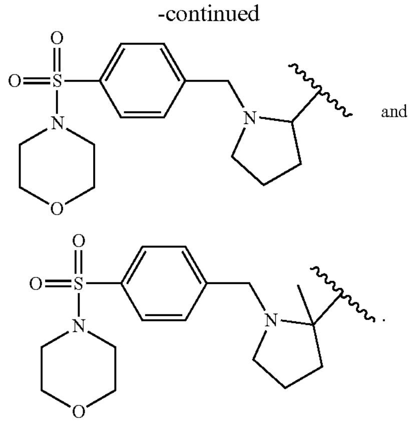
and
In certain embodiments, $R^1$ is selected from:
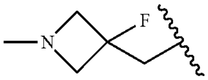 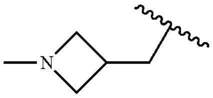
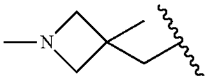 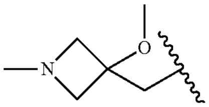
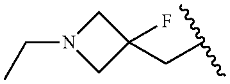 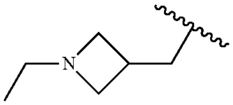
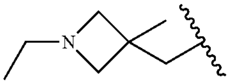 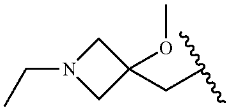
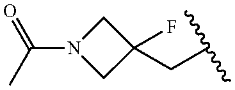 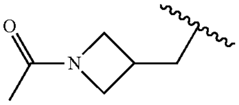
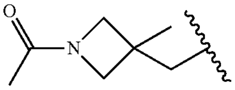 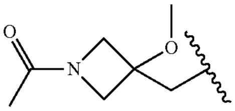
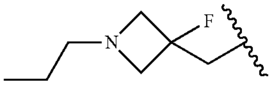 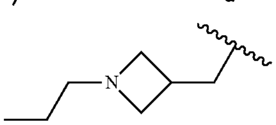
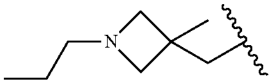 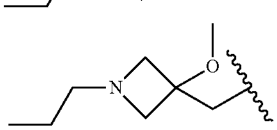
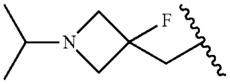 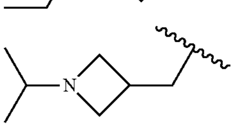
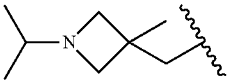 and 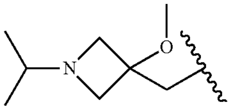
In certain embodiments, $R^1$ is selected from:
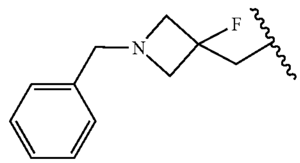
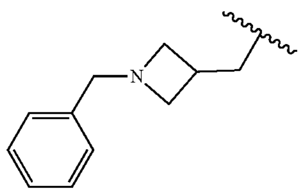
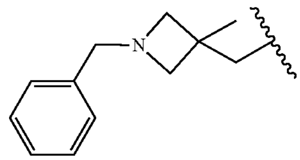
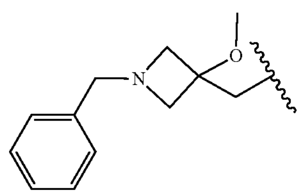
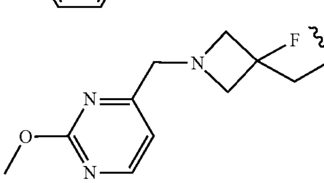
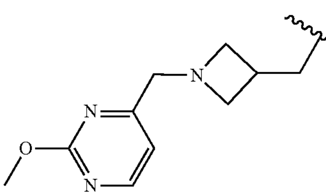
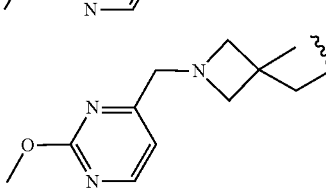
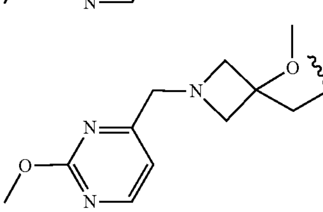
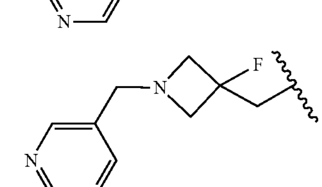
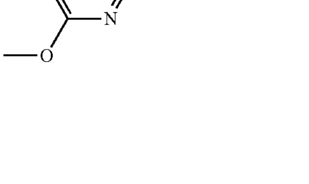
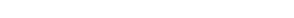

-continued
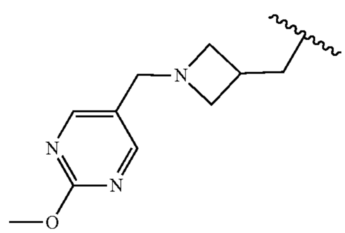
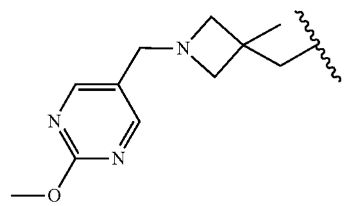
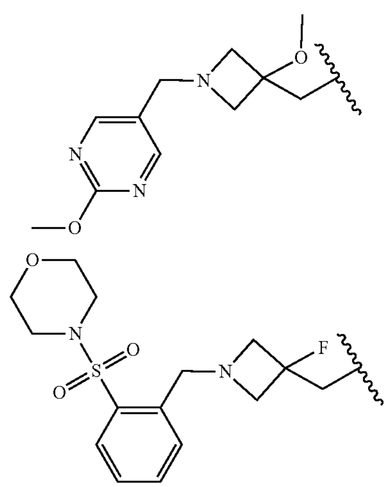
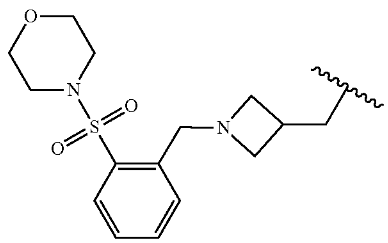
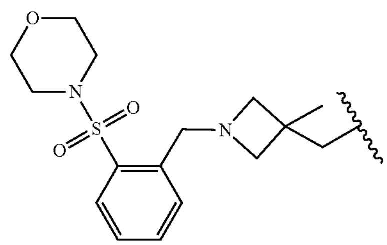
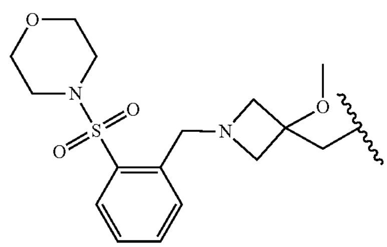
-continued
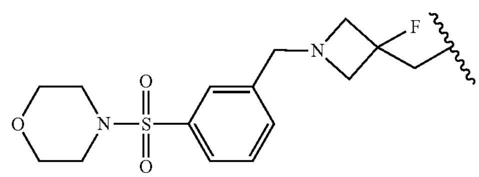
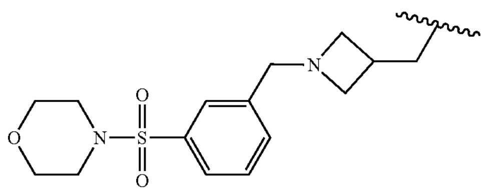
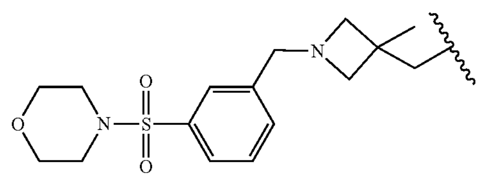
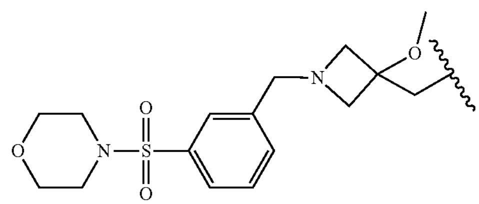
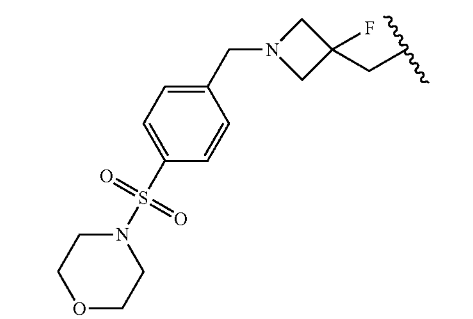
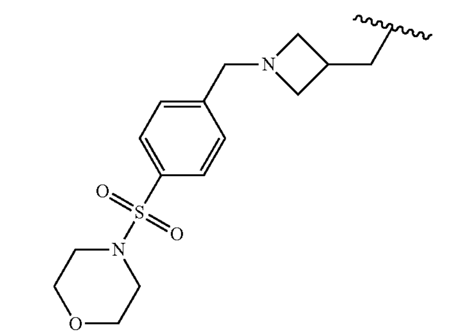
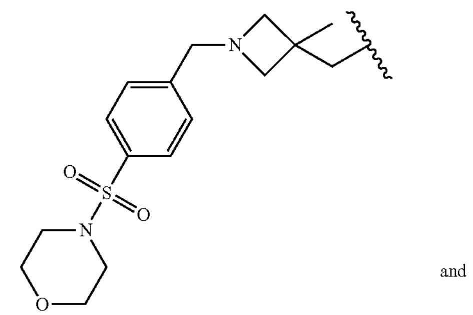
and -continued
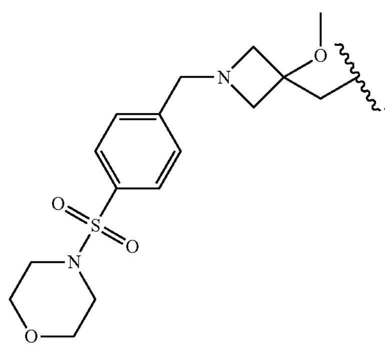
In certain embodiments, $R^1$ is selected from:
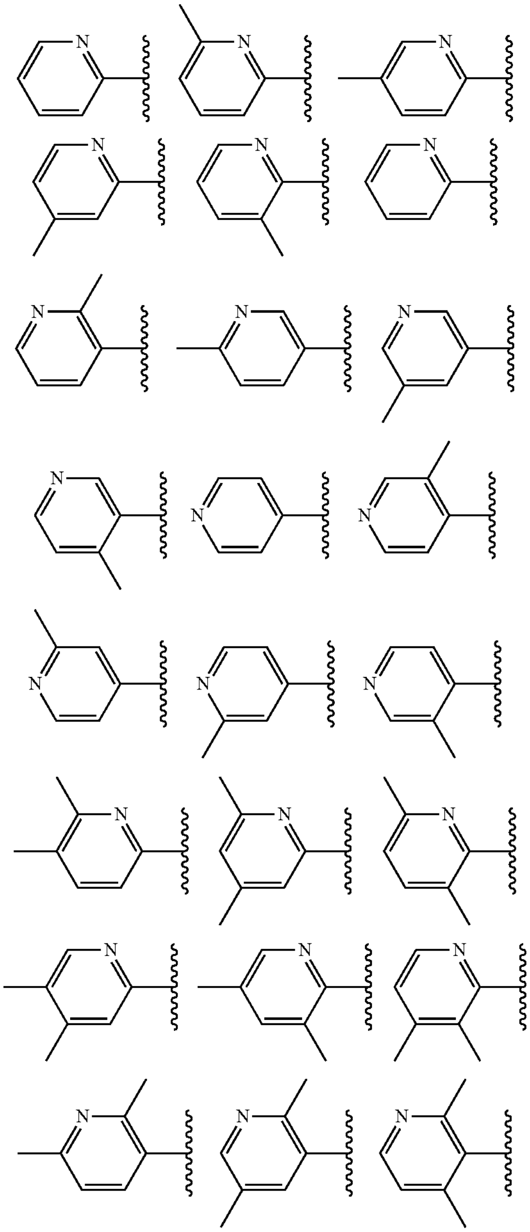
-continued
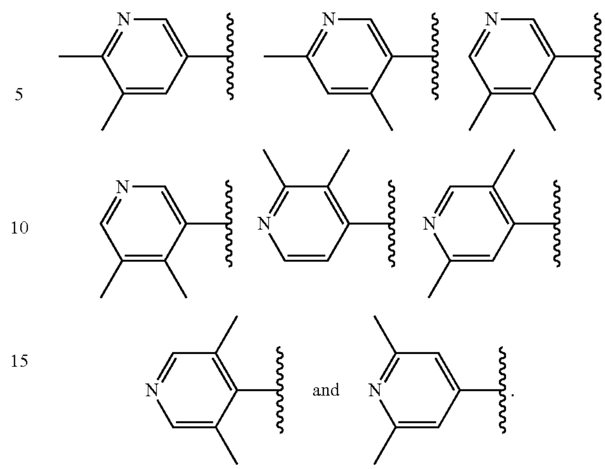
and
In certain embodiments, $R^1$ is selected from:
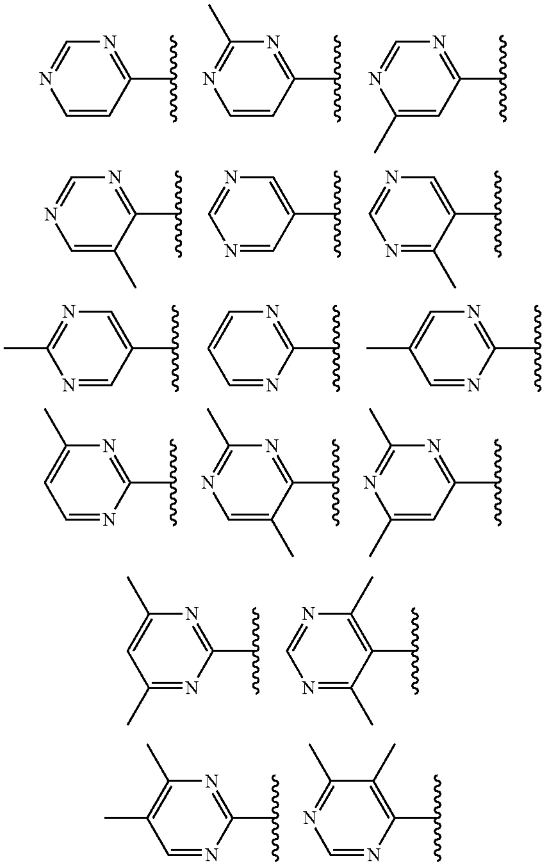
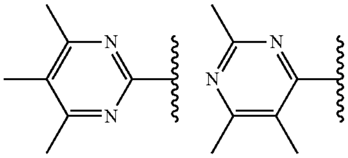
and -continued
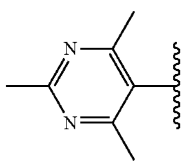
In certain embodiments, $R^1$ is selected from:
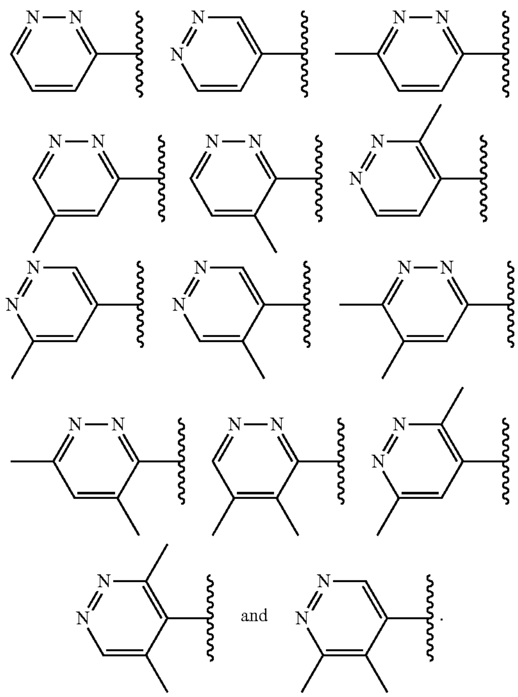
and
In certain embodiments, $R^1$ is selected from:
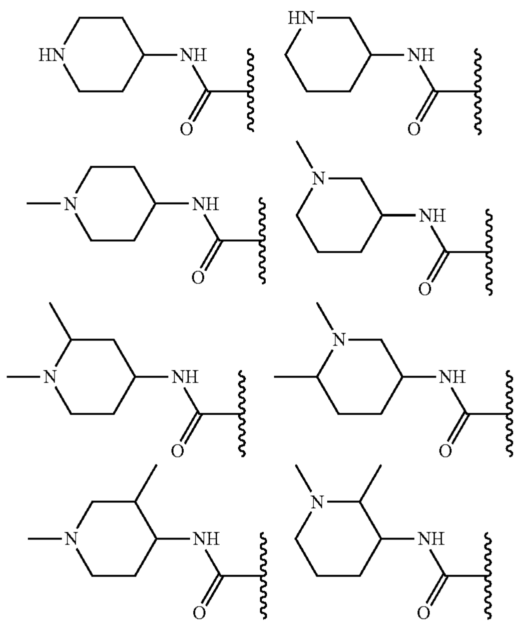
-continued
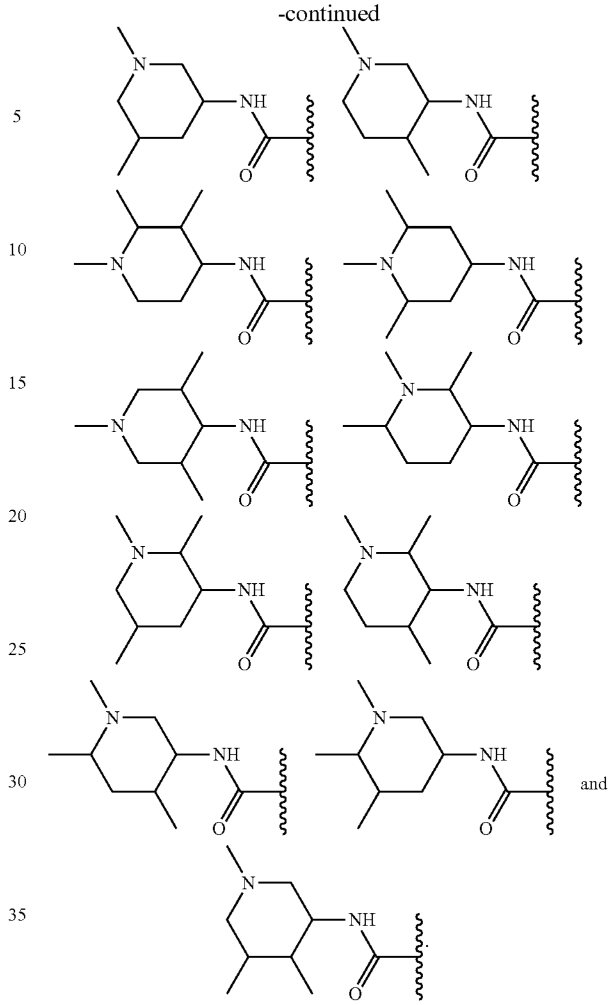
and
In certain embodiments, $R^1$ is selected from:
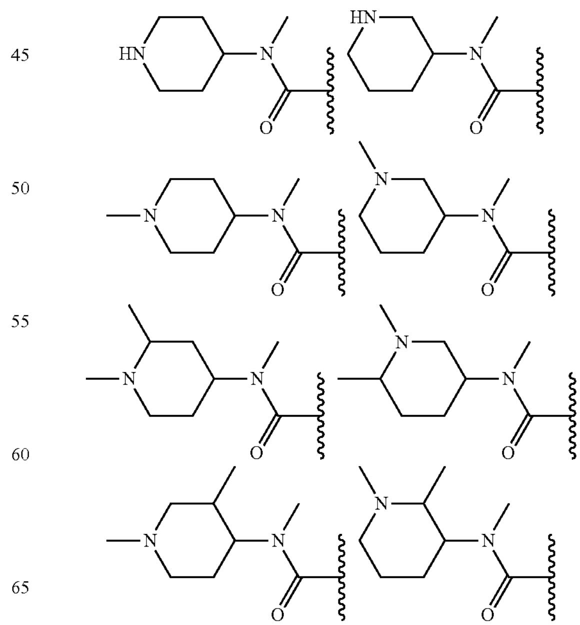

-continued
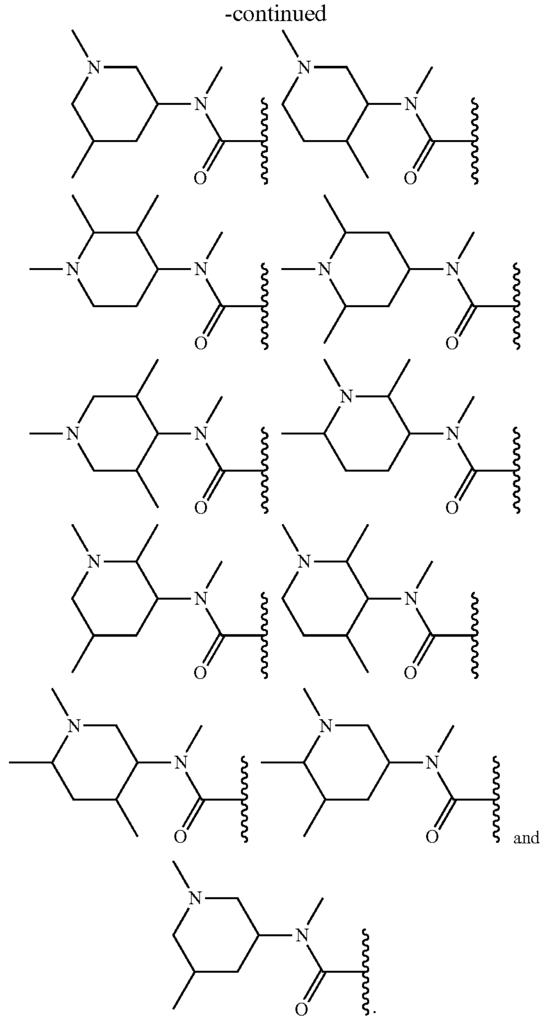
and
In certain embodiments, $R^1$ is selected from:
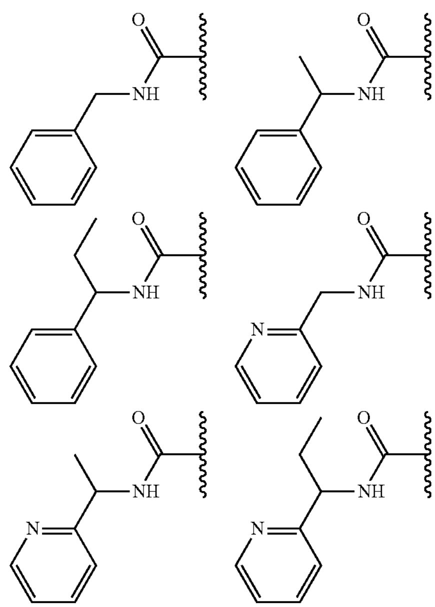
-continued
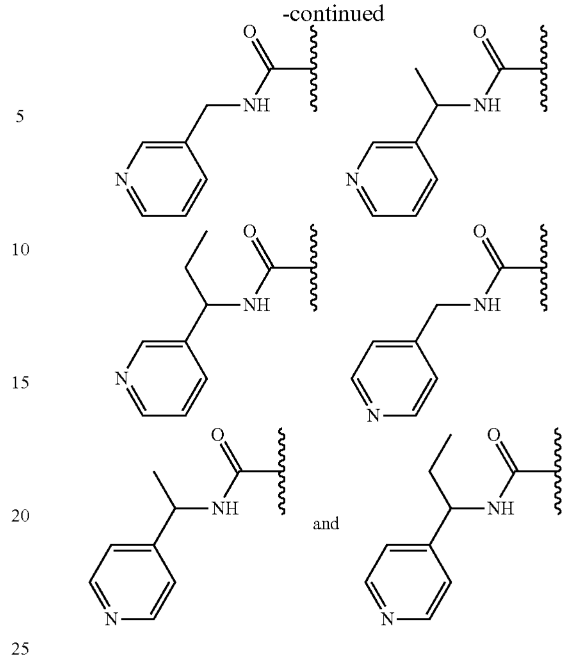
and
In certain embodiments, $R^1$ is selected from:
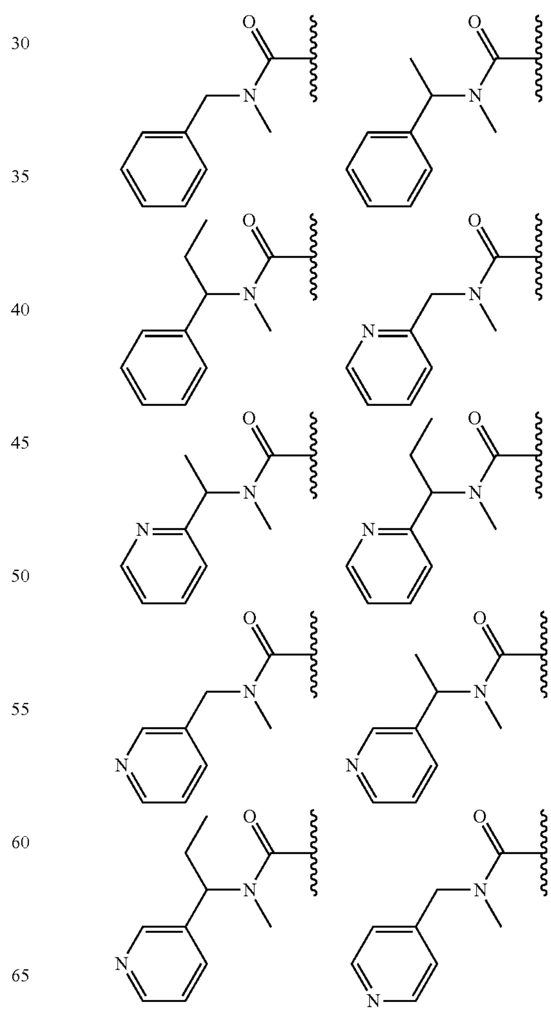

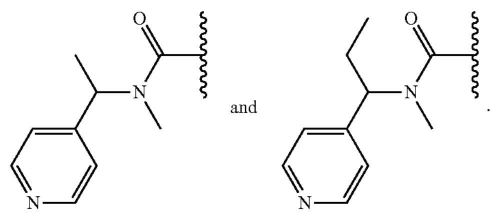
and
In certain embodiments, $R^1$ is selected from:
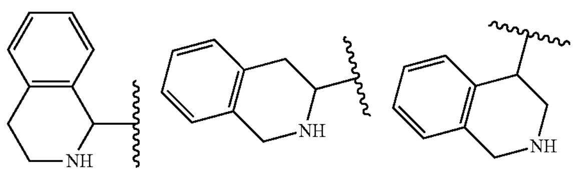
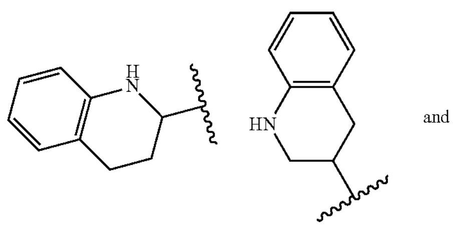
and
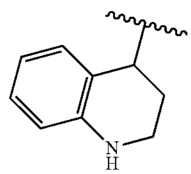
In certain embodiments, $R^1$ is selected from:
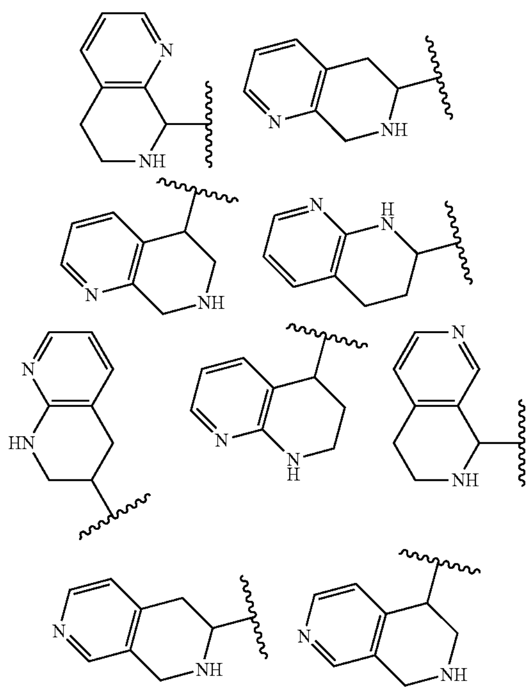
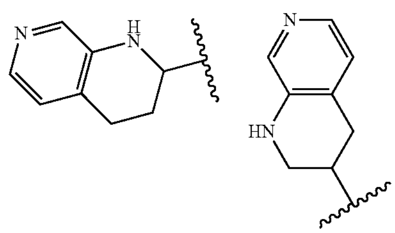
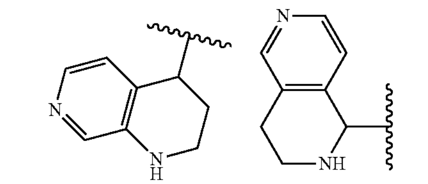
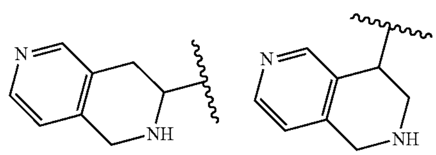
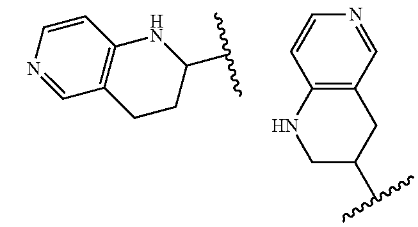
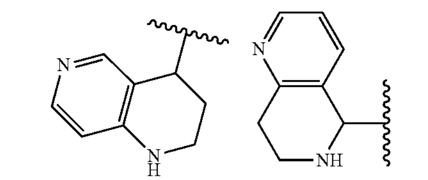
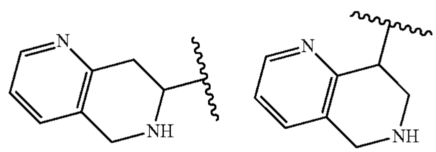
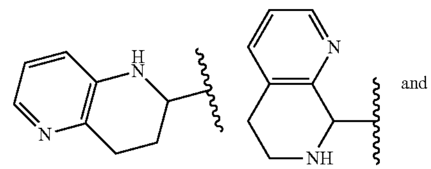
and -continued
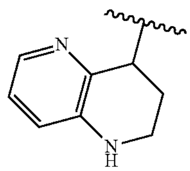
.
In certain embodiments, $R^1$ is selected from:
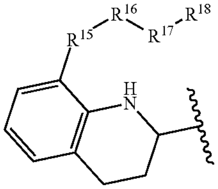
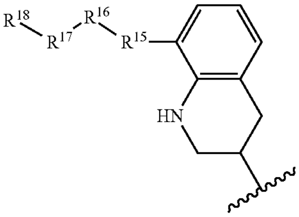
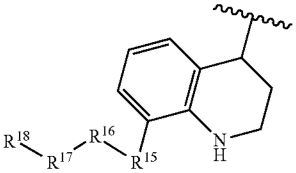
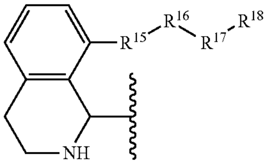
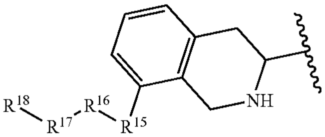
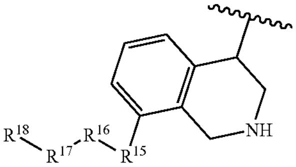
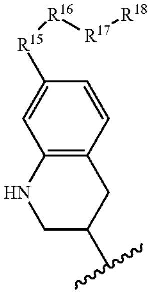
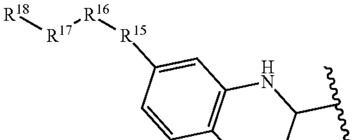
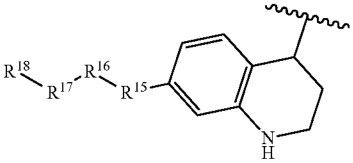
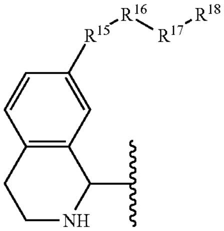
-continued
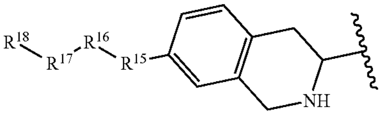
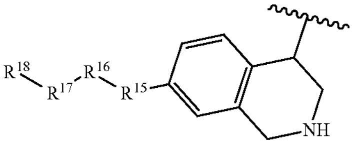
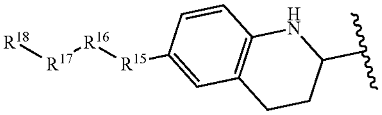
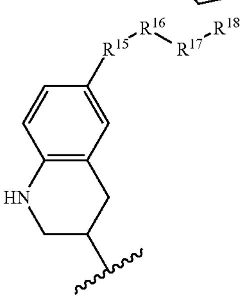
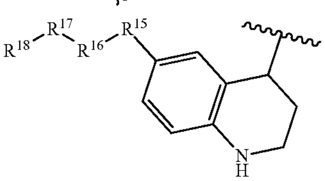
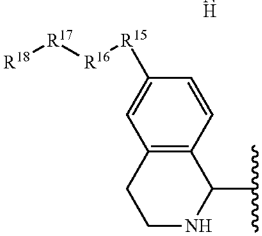
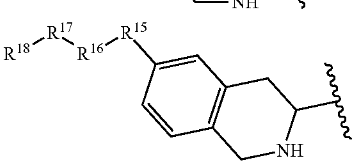
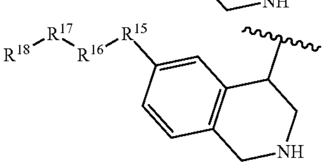
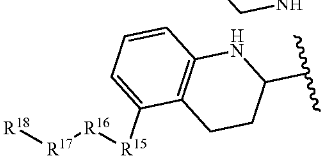
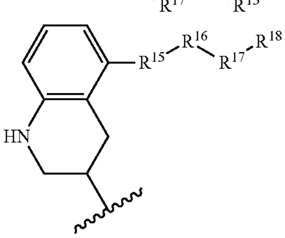
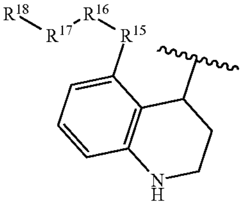

-continued
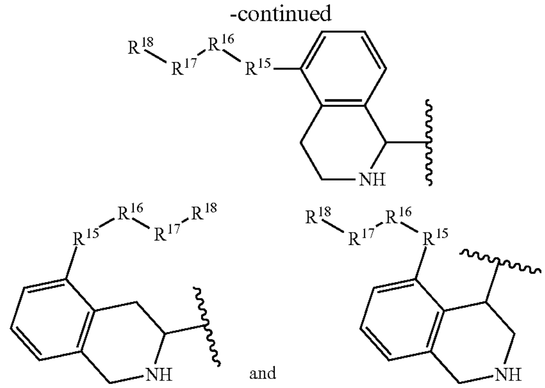
and
In certain embodiments, $R^1$ is selected from:
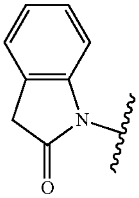
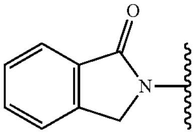
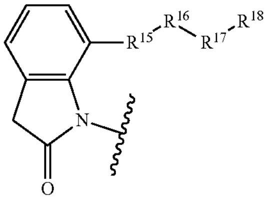
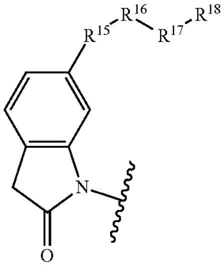
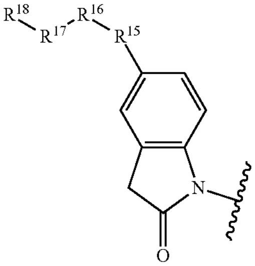
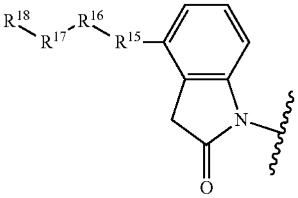
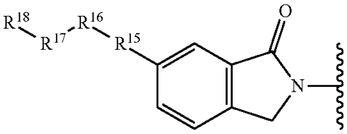
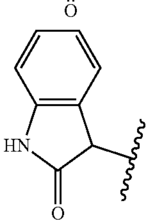
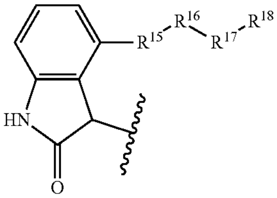
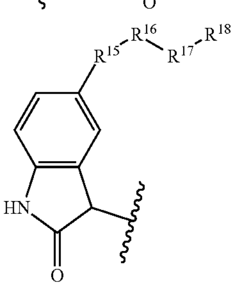
-continued
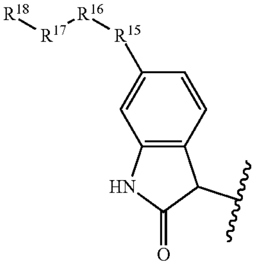
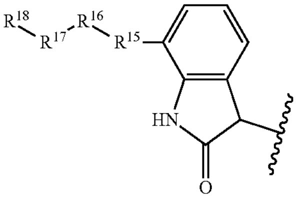
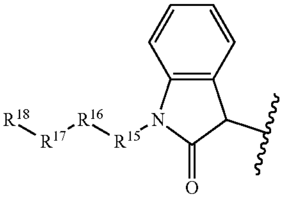
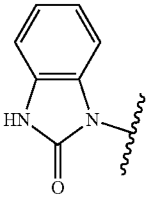
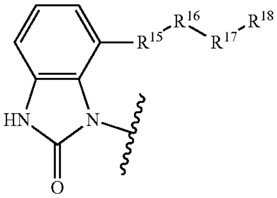
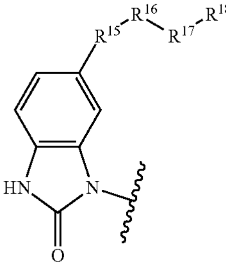
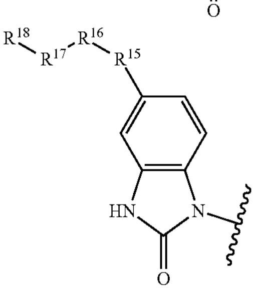
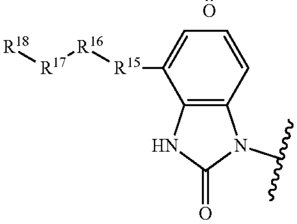
and
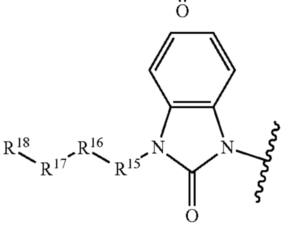
In certain embodiments, $R^1$ is selected from:
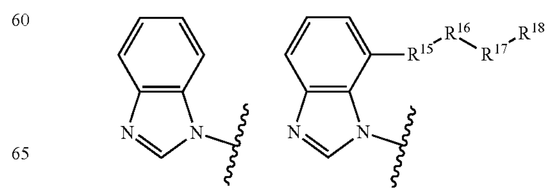

-continued
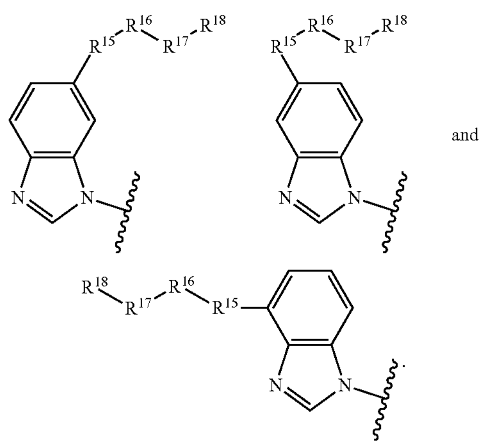
In certain embodiments, $R^1$ is selected from:
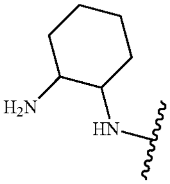
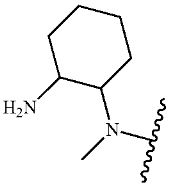
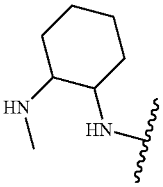
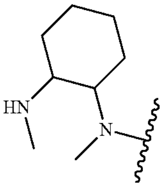
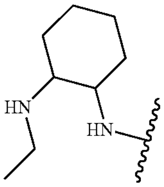
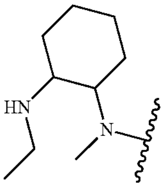
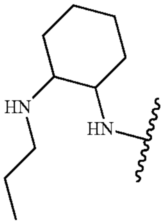
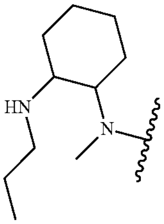
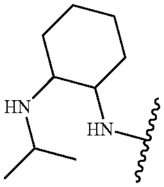
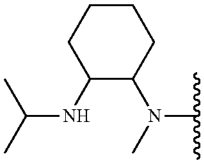
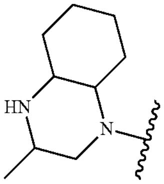
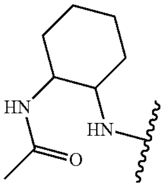
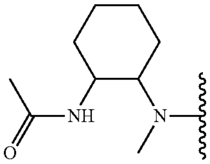
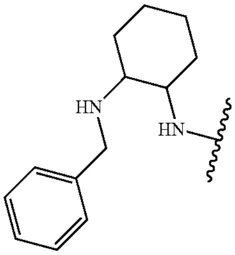
-continued
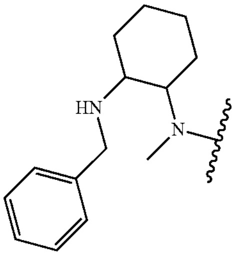
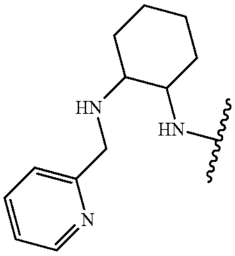
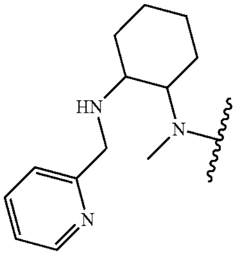
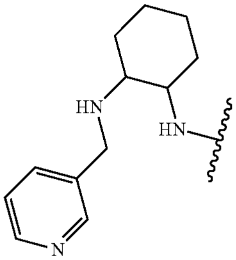
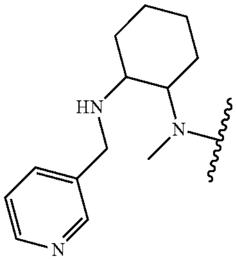
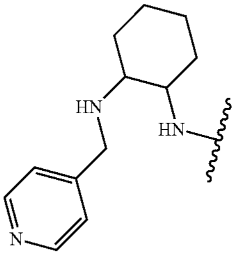
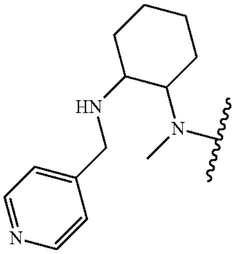
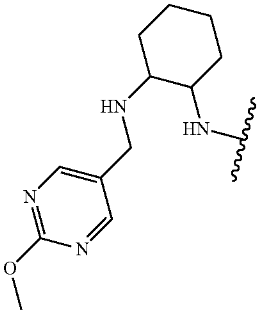
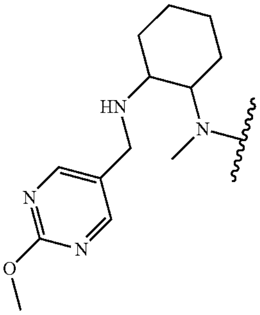
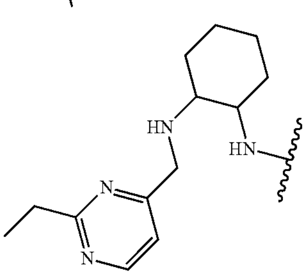
and -continued
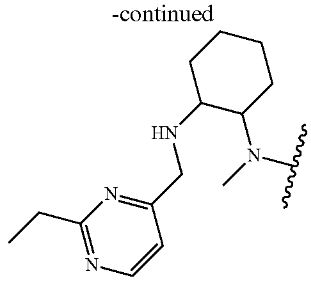
.
In certain embodiments, Riis selected from:
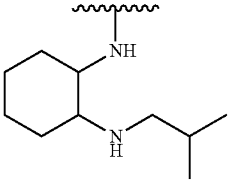
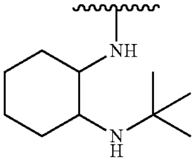
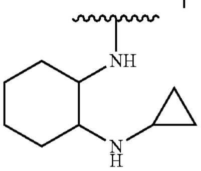
,
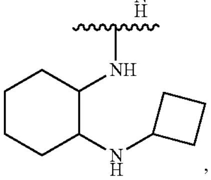
,
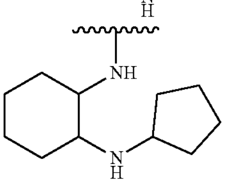
,
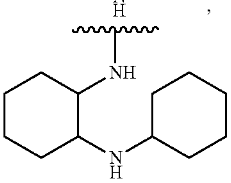
,
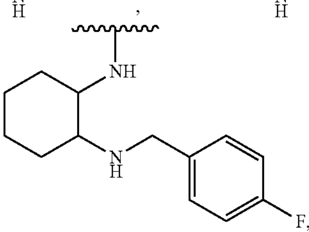
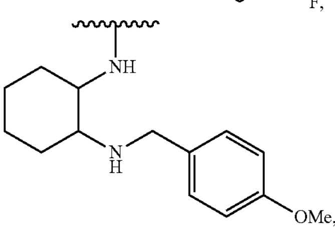
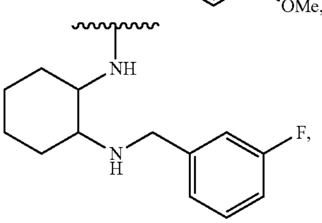
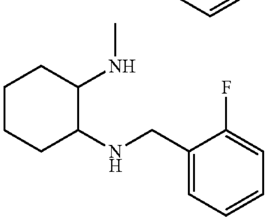
,
-continued
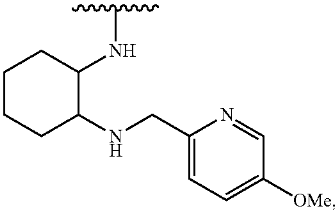
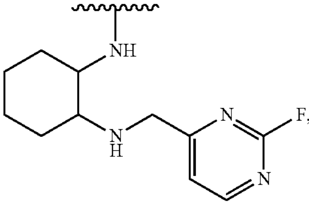
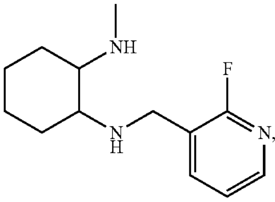
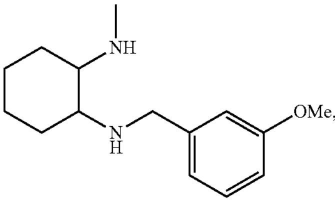
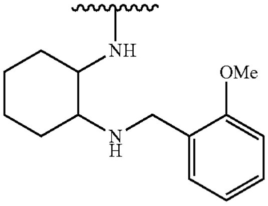
, and
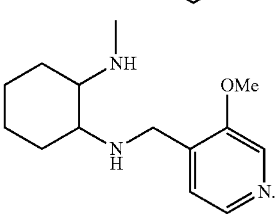
In certain embodiments, $R^1$ is selected from:
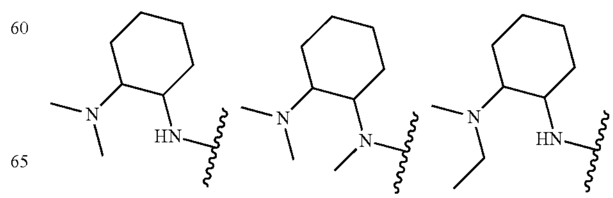

-continued
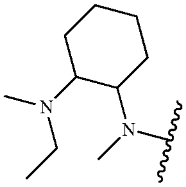
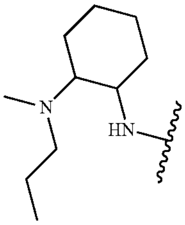
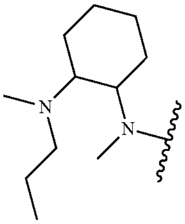
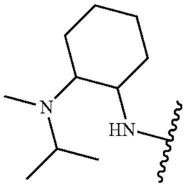
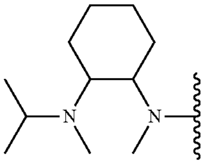
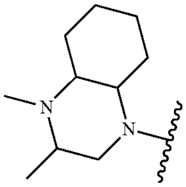
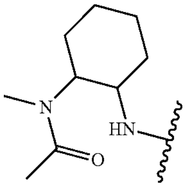
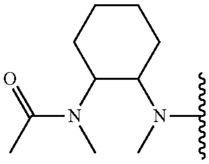
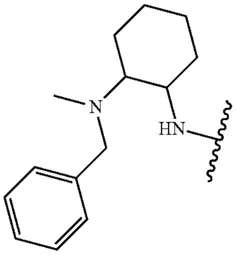
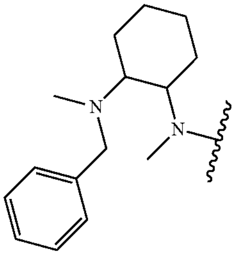
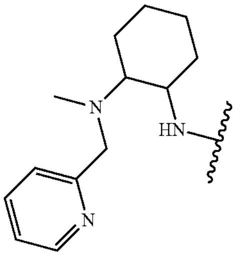
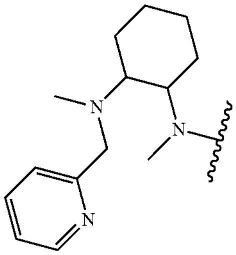
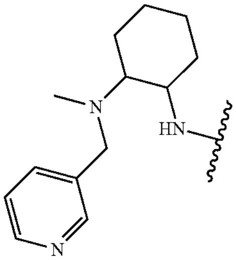
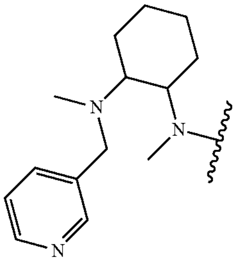
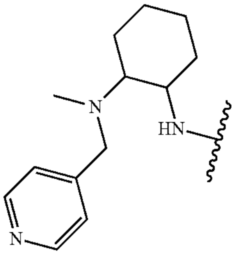
-continued
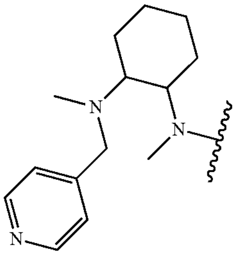
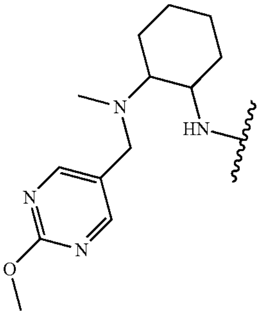
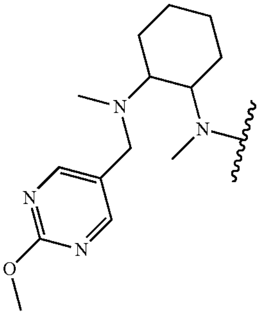
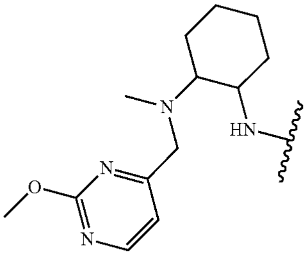
and
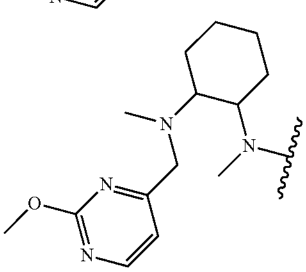.
In certain embodiments, $R^1$ is selected from
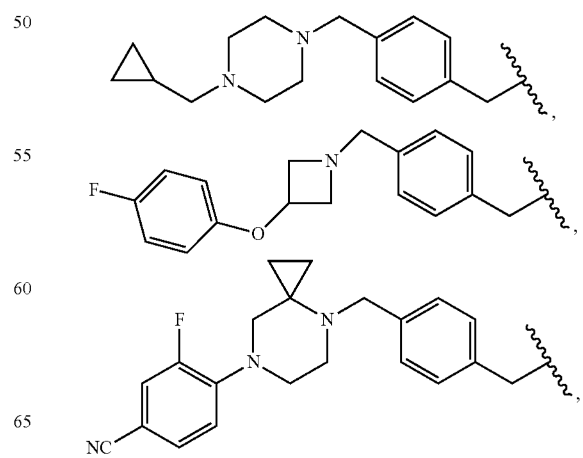
,
,
, -continued
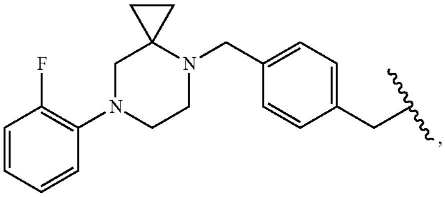
,
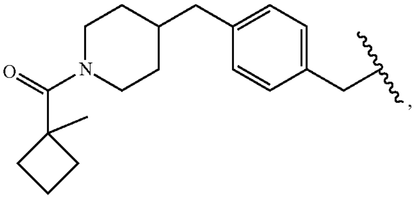
,
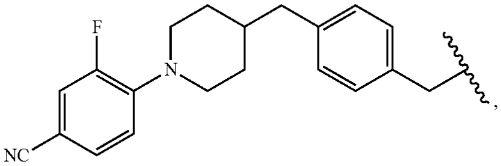
,
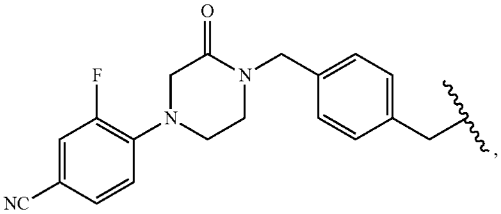
,
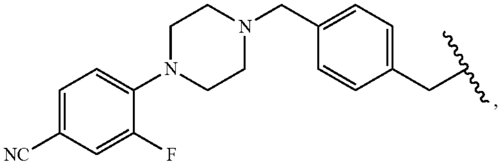
,
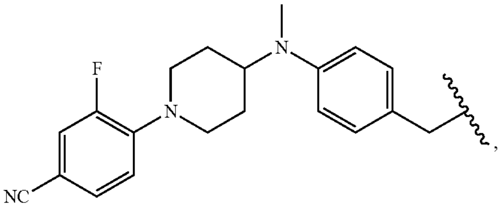
,
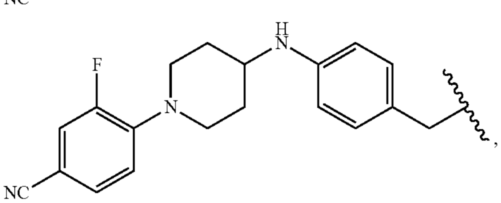
,
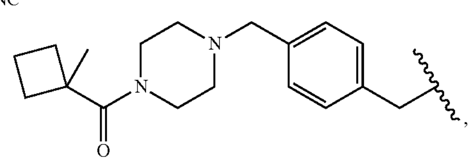
,
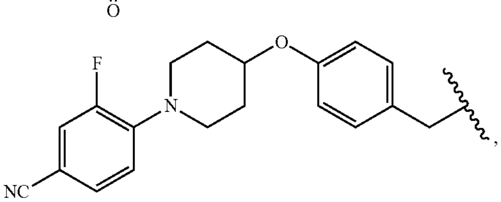
,
-continued
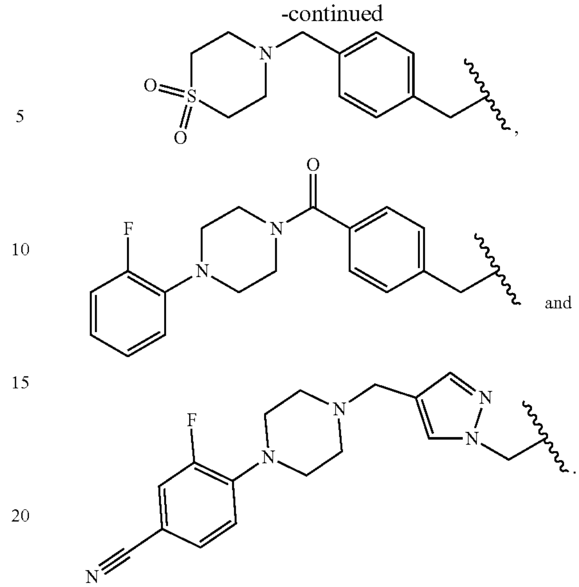
In certain embodiments $R^1$ is selected from:
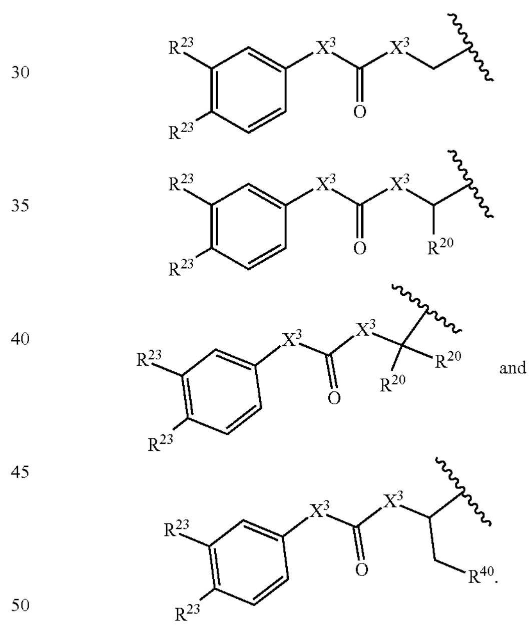
In certain embodiments, $R^1$ is selected from:
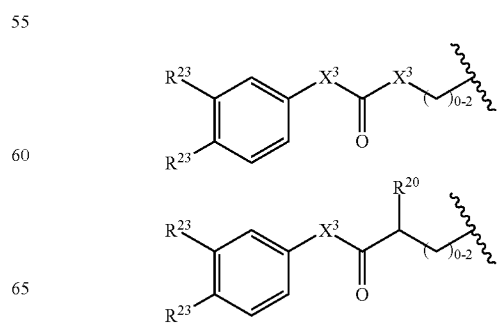

-continued
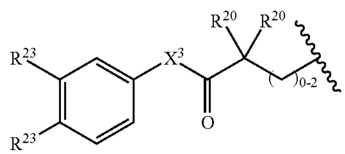
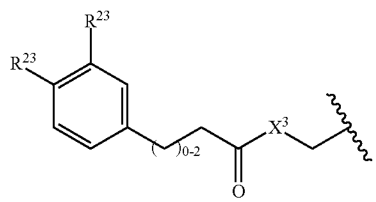
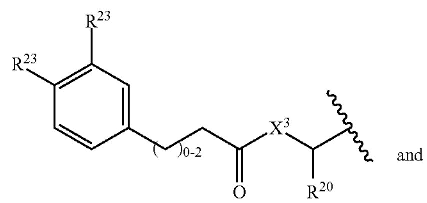
and
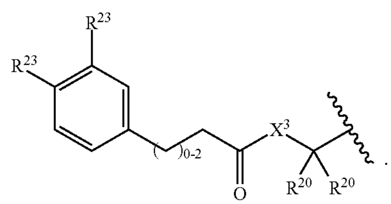
In certain embodiments, R is selected from:
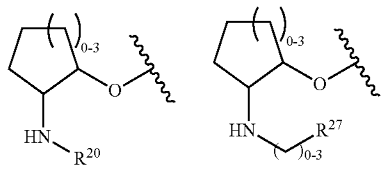
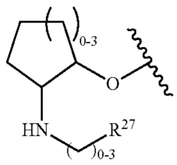
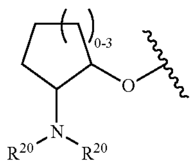
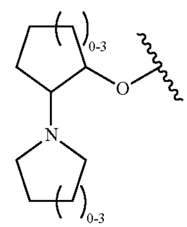
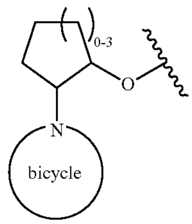
and
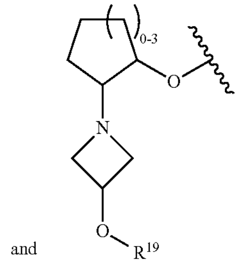
In certain embodiments, $R^1$ is selected from:
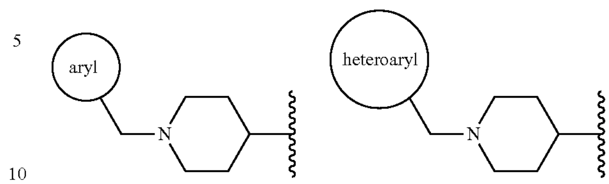
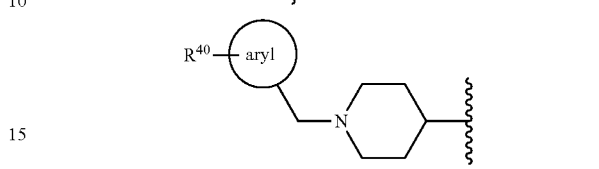
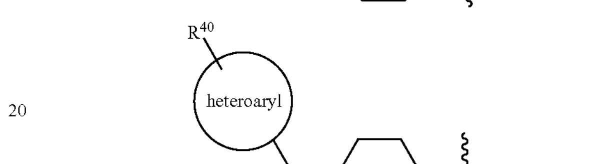
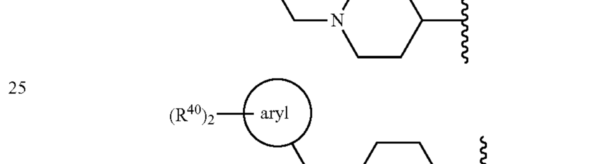
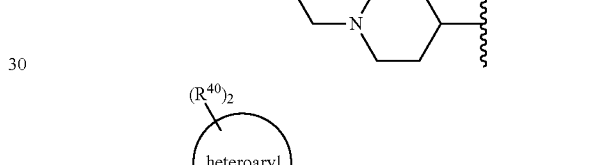
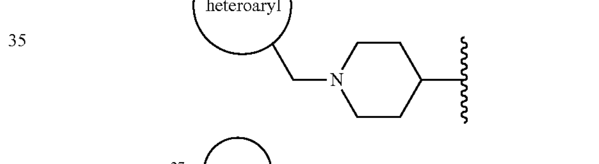
and
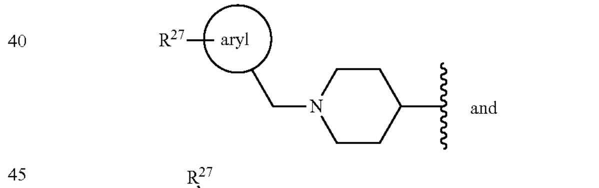
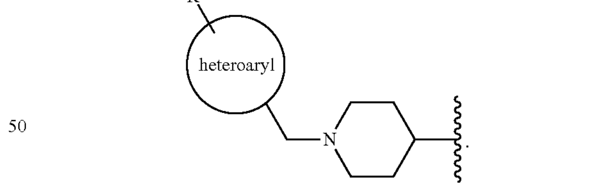
In certain embodiments the $R^1$ is selected from:
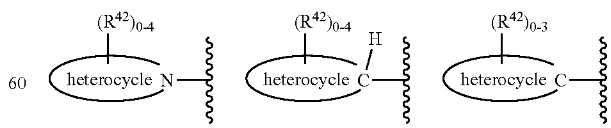
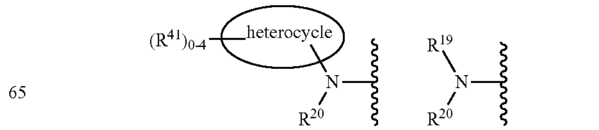

-continued

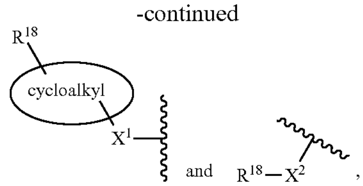

and , or a pharmaceutically acceptable salt thereof, where:

$R^{42}$ is hydrogen, alkyl, haloalkyl, aryl, heteroaryl, cycloalkyl, heterocyclic, aliphatic, or heteroaliphatic;

$X^1$ is $NR^{19}$, O, or S;

$X^2$ is $CH_2$ or C(O);

$R^{19}$ is selected from alkyl, hydrogen, —C(O)$NR^{10}R^{27}$, —C(O)$OR^{27}$, —C(O)$R^{27}$, alkene, alkyne, haloalkyl, alkoxy, aryl, heterocycle, aliphatic, heteroaliphatic, heteroaryl; each of which is optionally substituted, as allowed by valence to form a stable compound, with 1, 2, 3, or 4 substituents independently selected from $R^{40}$;

$R^{20}$ is aliphatic, including alkyl; and $R^{23}$ is hydrogen, alkyl, halogen, or haloalkyl.

In certain embodiments the $R^1$ is selected from:

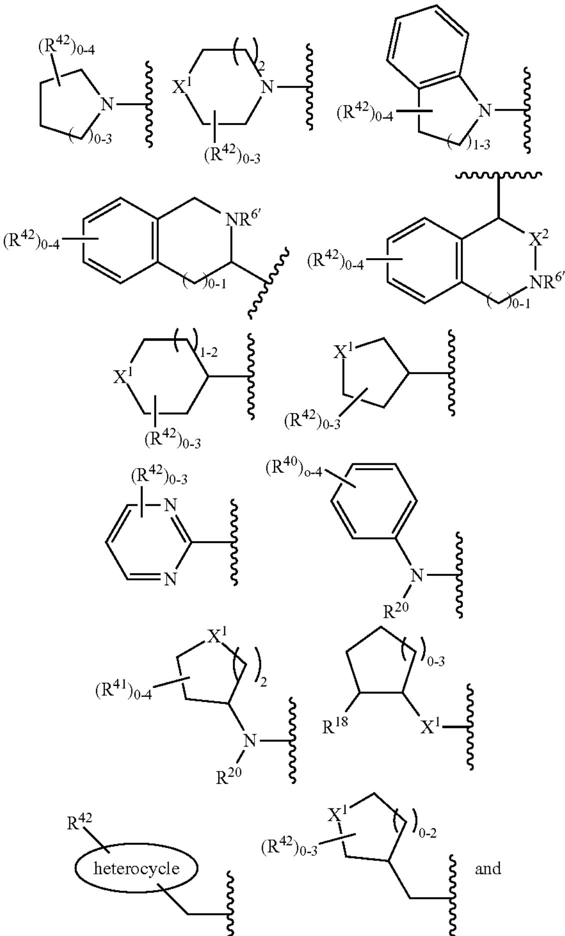

and

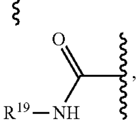

, or a pharmaceutically acceptable salt thereof.

Non-limiting Embodiments of A

In certain embodiments, A is selected from:

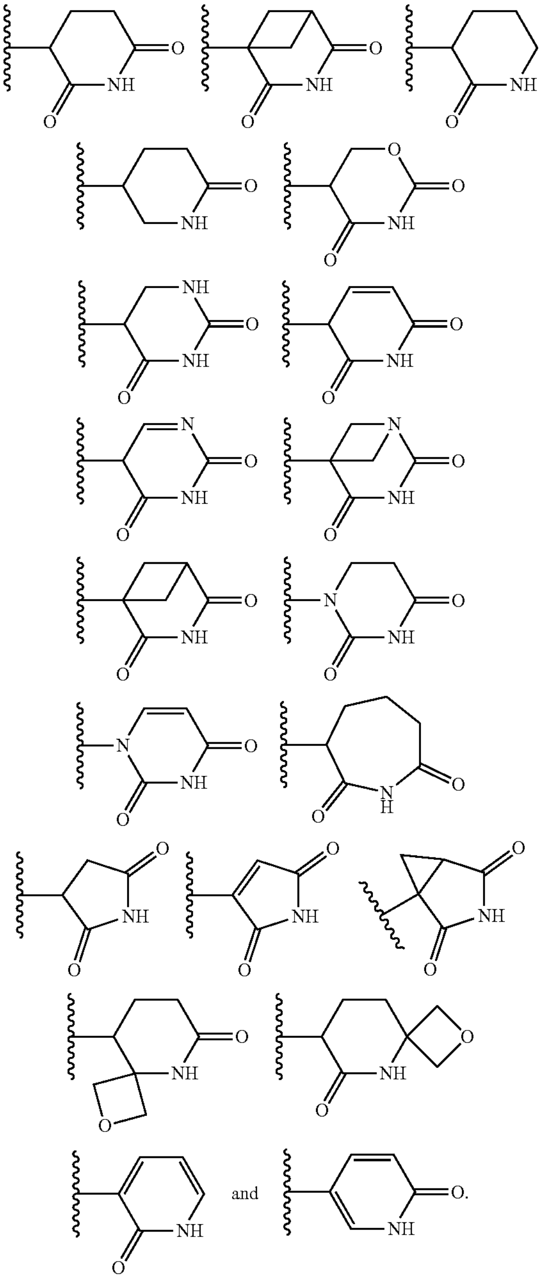

and .

In certain embodiments, A is selected from:

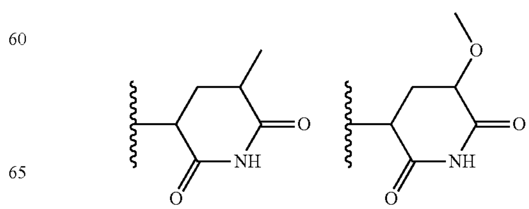

-continued
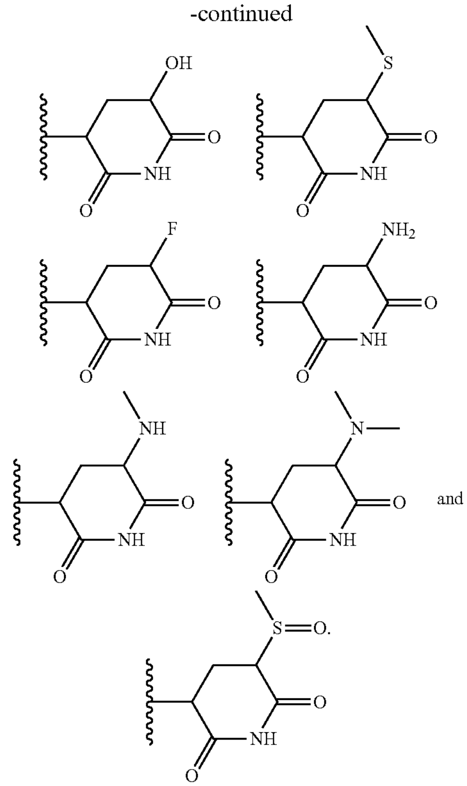
and
In certain embodiments, A is selected from:
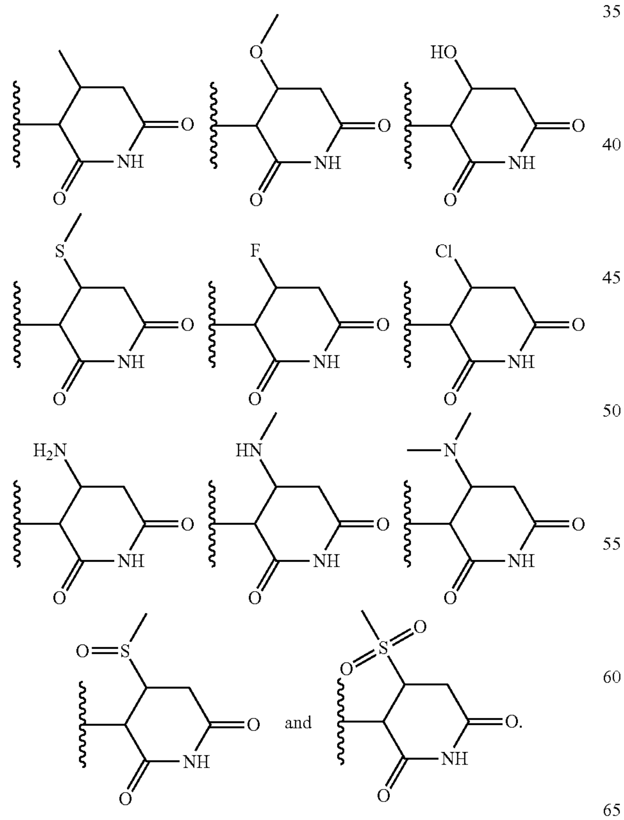
and
In certain embodiments, A is selected from:
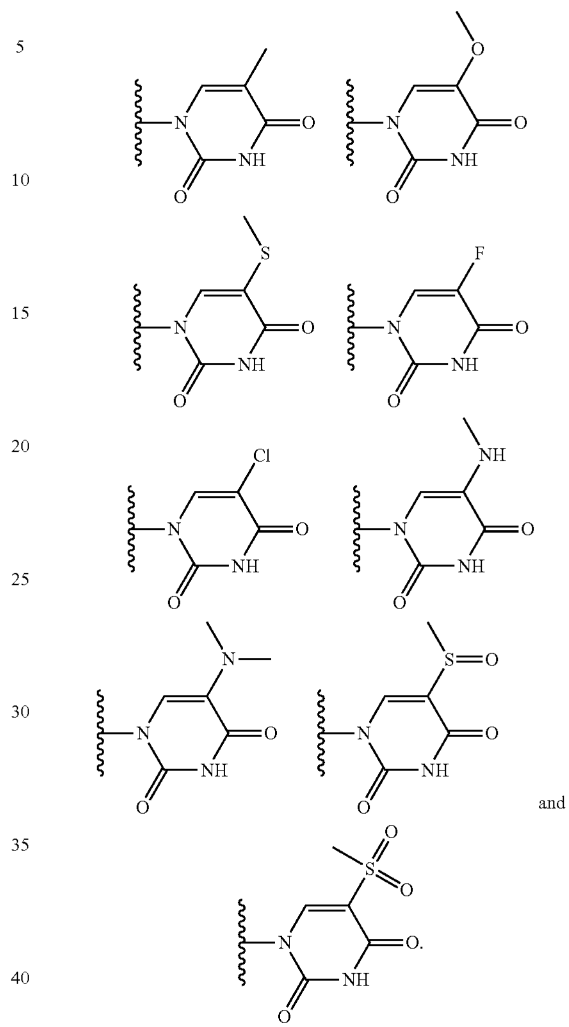
and
In certain embodiments, A is selected from:
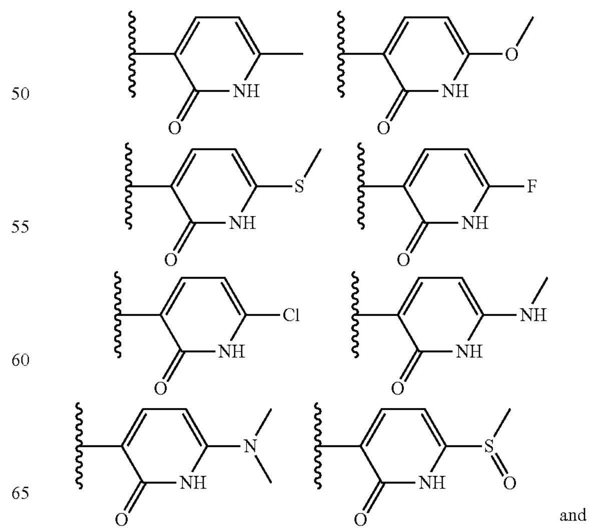
and -continued

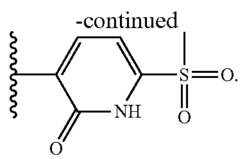

In certain embodiments, A is selected from:

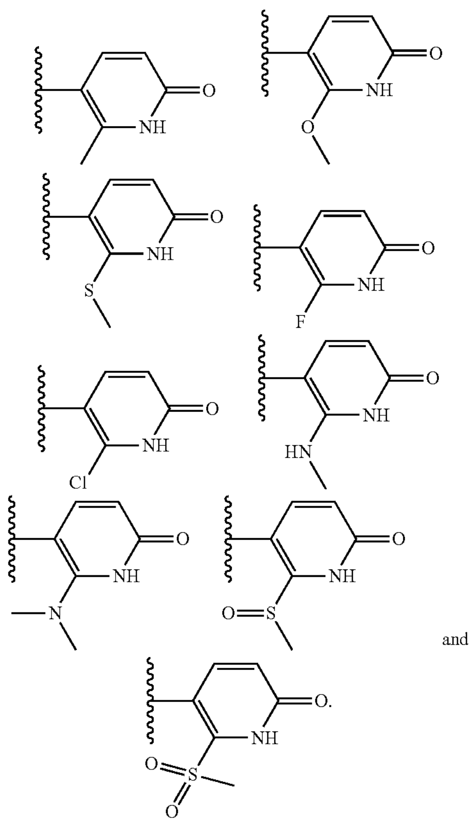

and

In certain embodiments the compound of Formula I is of formula

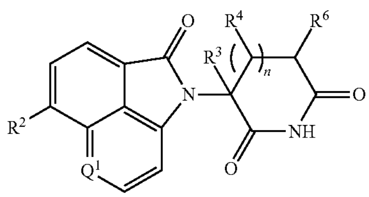

or a pharmaceutically acceptable salt, thereof;

wherein:

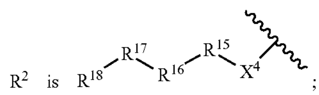

and $X^4$ is selected from alkyl, aliphatic, aryl, heteroaryl, bicycle, —$NR^{27}$—, —$NR^{10}$—, —$CR^{40}R^{41}$—, —O—, —C(O)—, —C($NR^{27}$)—, —C(S)—, —S(O)—, —$S(O)_2$—, —S—, piperidine which is bound to the tricycle through the N in the piperidine ring, 6-membered heterocycle with 2, 3, or 4 heteroatoms, and 4-, 5-, or 7-membered heterocycle with 1, 2, 3, or 4 heteroatoms; each of which is optionally substituted, as allowed by valence, to form a stable compound, with 1, 2, 3, or 4 substituents independently selected from non-hydrogen $R^{40}$.

In certain embodiments the compound of the present invention is selected from:

I-1

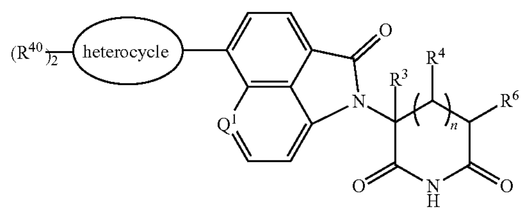

I-2

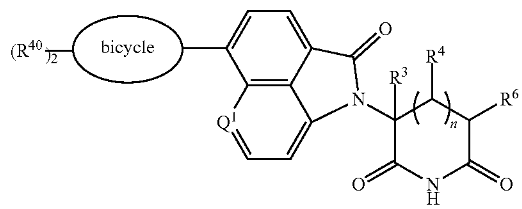

I-3

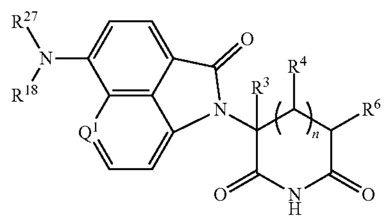

I-4

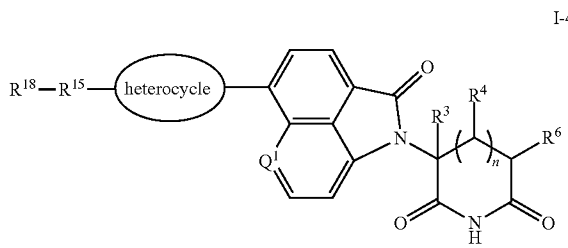

I-5

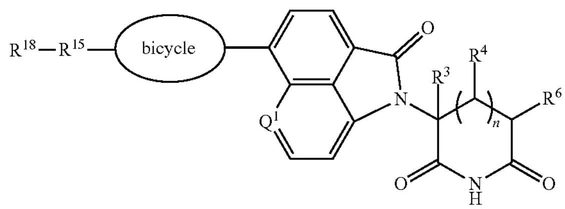

-continued
I-6
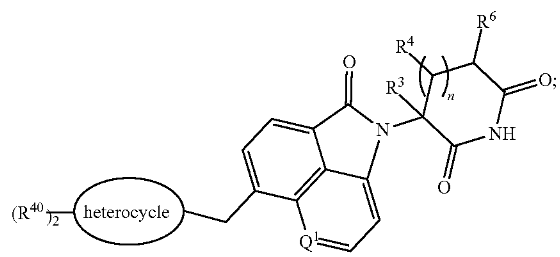
or a pharmaceutically acceptable salt thereof.
In certain embodiments the compound of the present invention is selected from:
I-7
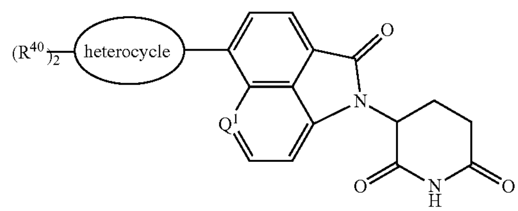
I-8
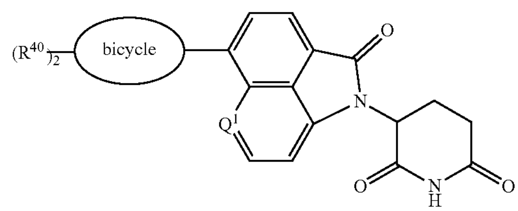
I-9
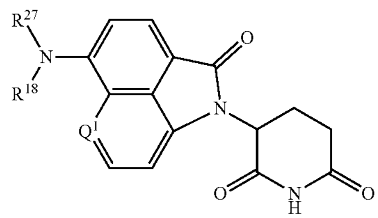
I-10
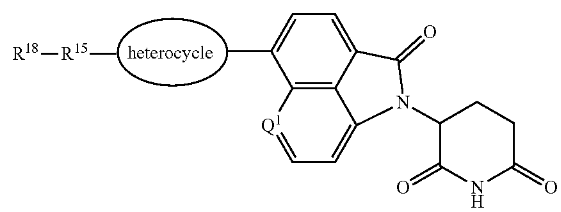
I-11
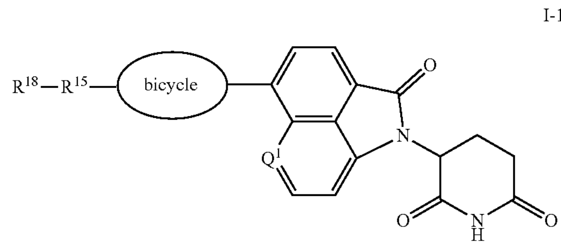
-continued
I-12
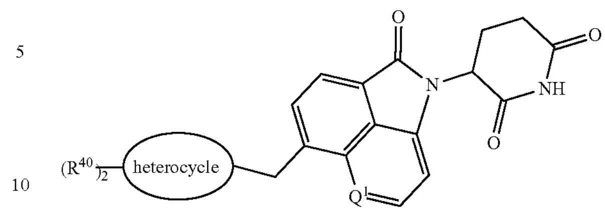
or a pharmaceutically acceptable salt thereof.
In certain embodiments the compound of the present invention is selected from:
I-13
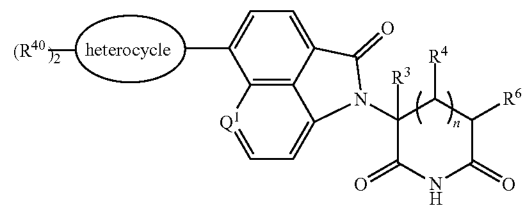
I-14
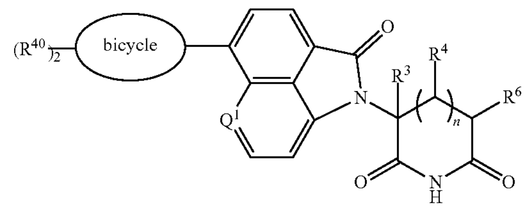
I-15
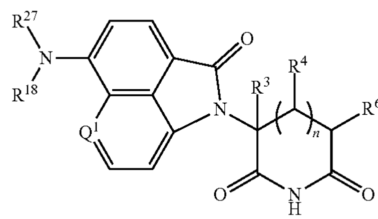
I-16
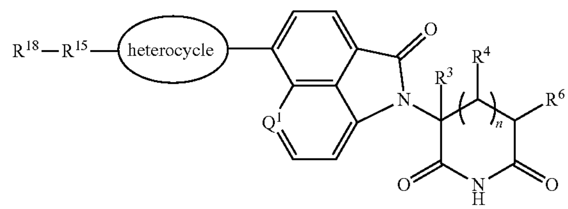
I-17
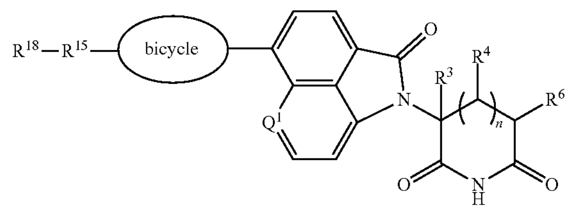

-continued

I-18

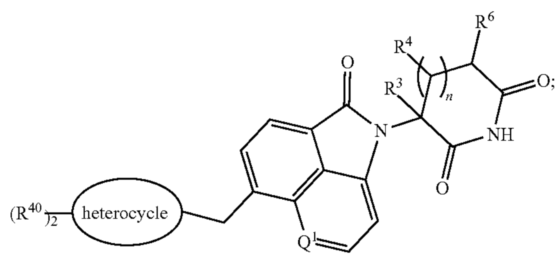

or a pharmaceutically acceptable salt thereof.

Embodiments of X

In certain embodiments, X is bond.

In certain embodiments, X is oxygen.

In certain embodiments, X is sulfur.

In certain embodiments, X is an —$NR^{27}$—.

In certain embodiments, X is a —$NR^{10}$—.

In certain embodiments, X is —$CR^{40}R^{41}$—.

In certain embodiments, X is —C(O)—

In certain embodiments, X is —$C(NR^{27})$—.

In certain embodiments, X is a —C(S)—.

In certain embodiments, X is a —$S(O)_2$—.

In certain embodiments, X is a —C(S)—.

In certain embodiments, X is a —C(S)—.

In certain embodiments, X is a —C(S)—.

In certain embodiments, X is a 5-membered aromatic heterocycle with attachment points in a 1,3 orientation.

In certain embodiments, X is a 5-membered aromatic heterocycle with attachment points in a 1,2 orientation.

In certain embodiments, X is a 6-membered aromatic heterocycle with attachment points in a 1,2 orientation.

In certain embodiments, X is a 6-membered aromatic heterocycle with attachment points in a 1,3 orientation.

In certain embodiments, X is a 6-membered aromatic heterocycle with attachment points in a 1,4 orientation.

In certain embodiments, X is a 6-membered aromatic heterocycle with attachment points in a 1,3 orientation.

In certain embodiments, X is a 5-membered heterocycle with attachment points in a 1,2 orientation In certain embodiments, X is a 5-membered heterocycle with attachment points in a 1,3 orientation.

In certain embodiments, X is a 6-membered heterocycle with attachment points in a 1,2 orientation.

In certain embodiments, X is a 6-membered heterocycle with attachment points in a 1,3 orientation.

In certain embodiments, X is a 6-membered heterocycle with attachment points in a 1,4 orientation.

In certain embodiments, X is a bicyclic heterocycle with one heteroatom

In certain embodiments, X is a bicyclic heterocycle with two heteroatoms.

In certain embodiments, X is a bicyclic heterocycle with one heteroatom and one attachment is bound to Nitrogen and one is bound to carbon In certain embodiments, X is a bicyclic heterocycle with one heteroatom, and both attachment points are bound to carbon In certain embodiments, X is a bicyclic heterocycle with two heteroatoms and both points of attachment are bound to Nitrogen.

In certain embodiments, X is a bicyclic heterocycle with two heteroatoms.

In certain embodiments, X is a fused bicyclic alkane.

In certain embodiments, X is a spiro-bicyclic alkane.

In certain embodiments X is selected from:

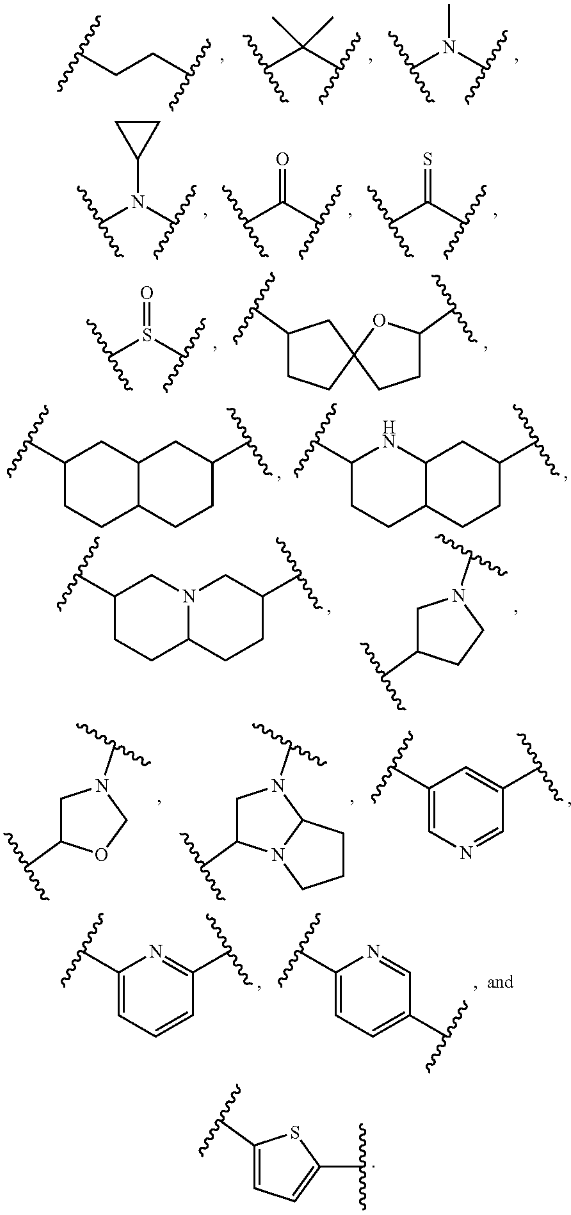

Embodiments of $R^4$ and $R^5$

In certain embodiments, $R^4$ is hydrogen.

In certain embodiments, $R^4$ is alkyl.

In certain embodiments, $R^4$ is fluorine.

In certain embodiments, $R^4$ is chlorine.

In certain embodiments, $R^4$ is bromine.

In certain embodiments, $R^4$ is haloalkyl.

In certain embodiments, $R^4$ is —$OR^{10}$.

In certain embodiments, $R^4$ is —$SR^{10}$.

In certain embodiments, $R^4$ is —$S(O)R^{12}$.

In certain embodiments, $R^4$ is —$SO_2R^{12}$.

In certain embodiments, $R^4$ is —$NR^{10}R^{11}$.

In certain embodiments, $R^5$ is hydrogen.

In certain embodiments, $R^5$ is alkyl.

In certain embodiments, $R^5$ is haloalkyl.

In certain embodiments, $R^5$ is —$OR^{10}$.

In certain embodiments, $R^5$ is —$SR^{10}$.

In certain embodiments, $R^5$ is —$S(O)R^{12}$.

In certain embodiments, $R^5$ is —$SO_2R^{12}$.

In certain embodiments, $R^5$ is —$NR^{10}R^{11}$.

In certain embodiments, $R^4$ and $R^5$ are selected from:

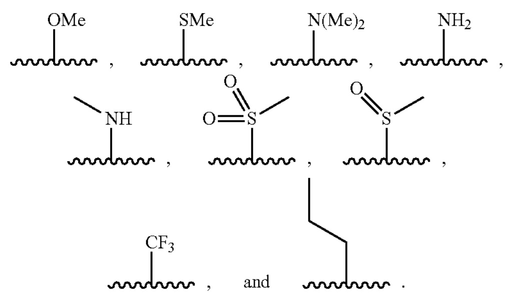

Embodiments of $R^6$ and $R^7$

In certain embodiments, $R^6$ is hydrogen.

In certain embodiments, $R^6$ is alkyl.

In certain embodiments, $R^6$ is fluorine.

In certain embodiments, $R^6$ is chlorine.

In certain embodiments, $R^6$ is bromine.

In certain embodiments, $R^6$ is haloalkyl.

In certain embodiments, $R^6$ is —$OR^{10}$.

In certain embodiments, $R^6$ is —$SR^{10}$.

In certain embodiments, $R^6$ is —$S(O)R^{12}$.

In certain embodiments, $R^6$ is —$SO_2R^{12}$.

In certain embodiments, $R^6$ is —$NR^{10}R^{11}$.

In certain embodiments, $R^7$ is hydrogen.

In certain embodiments, $R^7$ is alkyl.

In certain embodiments, $R^7$ is fluorine.

In certain embodiments, $R^7$ is chlorine.

In certain embodiments, $R^7$ is bromine.

In certain embodiments, $R^7$ is haloalkyl.

In certain embodiments, $R^7$ is —$OR^{10}$.

In certain embodiments, $R^7$ is —$SR^{10}$.

In certain embodiments, $R^7$ is —$S(O)R^{12}$.

In certain embodiments, $R^7$ is —$SO_2R^{12}$.

In certain embodiments, $R^7$ is —$N^{10}R^{11}$.

In certain embodiments, $R^6$ and $R^7$ are selected from:

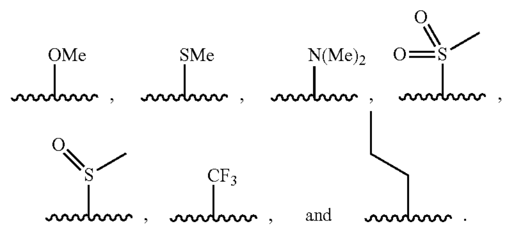

Embodiments of $R^{10}$ and $R^{11}$

In certain embodiments $R^{10}$ and $R^{11}$ are hydrogen.

In certain embodiments $R^{10}$ is hydrogen.

In certain embodiments $R^{11}$ is hydrogen.

In certain embodiments $R^{10}$ is alkyl.

In certain embodiments $R^{10}$ is methyl.

In certain embodiments $R^{10}$ is aliphatic.

In certain embodiments $R^{10}$ is haloalkyl.

In certain embodiments $R^{10}$ is heterocycle.

In certain embodiments $R^{10}$ is aryl.

In certain embodiments $R^{10}$ is heteroaryl.

In certain embodiments $R^{10}$ is —$C(O)R^{12}$.

In certain embodiments $R^{10}$ is —$S(O)R^{12}$.

In certain embodiments $R^{10}$ is —$SO_2R^{12}$.

In certain embodiments $R^{11}$ is alkyl.

In certain embodiments $R^{11}$ is methyl.

In certain embodiments $R^{11}$ is aliphatic.

In certain embodiments $R^{11}$ is haloalkyl.

In certain embodiments $R^{11}$ is heterocycle.

In certain embodiments $R^{11}$ is aryl.

In certain embodiments $R^{11}$ is heteroaryl.

In certain embodiments $R^{11}$ is —$C(O)R^{12}$.

In certain embodiments $R^{11}$ is —$S(O)R^{12}$.

In certain embodiments $R^{11}$ is —$SO_2R^{12}$.

Embodiments of $R^{12}$

In certain embodiments, $R^{12}$ is hydrogen.

In certain embodiments, $R^{12}$ is alkyl.

In certain embodiments, $R^{12}$ is haloalkyl.

In certain embodiments, $R^{12}$ is heterocycle.

In certain embodiments, $R^{12}$ is aryl.

In certain embodiments, $R^{12}$ is heteroaryl.

In certain embodiments, $R^{12}$ is —$NR^{13}R^{14}$.

In certain embodiments, $R^{12}$ is $OR^{13}$.

Embodiments $R^{15}$, $R^{16}$, and $R^{17}$

In certain embodiments $R^{15}$ is bond.

In certain embodiments $R^{15}$ is alkyl.

In certain embodiments $R^{15}$ is aliphatic.

In certain embodiments $R^{15}$ is aryl.

In certain embodiments $R^{15}$ is a bicycle.

In certain embodiments $R^{15}$ is alkene.

In certain embodiments $R^{15}$ is alkyne.

In certain embodiments $R^{15}$ is haloalkyl.

In certain embodiments $R^{15}$ is alkoxy.

In certain embodiments $R^{15}$ is heteroaryl.

In certain embodiments $R^{15}$ is a heterocycle.

In certain embodiments $R^{15}$ is cycloalkyl.

In certain embodiments $R^{15}$ is heteroaliphatic.

In certain embodiments $R^{15}$ is —$NR^{27}$.

In certain embodiments $R^{15}$ is —$NR^{10}$.

In certain embodiments $R^{15}$ is —$CR^{40}R^{41}$—

In certain embodiments $R^{15}$ is oxygen.

In certain embodiments $R^{15}$ is —C(O)—.

In certain embodiments, $R^{15}$ is —C(S)—.

In certain embodiments $R^{15}$ is sulfur.

In certain embodiments $R^{15}$ is —C(S)—.

In certain embodiments, $R^{15}$ is —OC(O)—.

In certain embodiments, $R^{15}$ is —C(O)O—.

In certain embodiments $R^{15}$ is an —$C(O)N^{27}$—.

In certain embodiments $R^{15}$ is an —$NR^{27}C(O)$—.

In certain embodiments $R^{15}$ is a —$NR^{10}$—.

In certain embodiments $R^{15}$ is a 6-membered aryl group with attachment points in a 1,2 orientation.

In certain embodiments $R^{15}$ is a 6-membered aryl group with attachment points in a 1,3 orientation.

In certain embodiments $R^{15}$ is a 6-membered aryl group with attachment points in a 1,4 orientation.

In certain embodiments $R^{15}$ is a 6-membered aryl group with attachment points in a 1,2 orientation.

In certain embodiments $R^{15}$ is a heteroaryl group with attachment points in a 1,2 orientation.

In certain embodiments $R^{15}$ is a heteroaryl group with attachment points in a 1,2 orientation.

In certain embodiments $R^{15}$ is a aryl group with attachment points in a 1,2 orientation.

In certain embodiments $R^{16}$ is bond.

In certain embodiments $R^{16}$ is alkyl.

In certain embodiments $R^{16}$ is aliphatic.

In certain embodiments $R^{16}$ is aryl.

In certain embodiments $R^{16}$ is a bicycle.

In certain embodiments $R^{16}$ is alkene.

In certain embodiments $R^{16}$ is alkyne.

In certain embodiments $R^{16}$ is haloalkyl.

In certain embodiments $R^{16}$ is alkoxy.

In certain embodiments $R^{16}$ is heteroaryl.

In certain embodiments $R^{16}$ is a heterocycle.

In certain embodiments $R^{16}$ is cycloalkyl.

In certain embodiments $R^{16}$ is heteroaliphatic.

In certain embodiments $R^{16}$ is —$NR^{27}$—.

In certain embodiments $R^{16}$ is —$NR^{10}$.

In certain embodiments $R^{16}$ is —$CR^{40}R^{41}$—

In certain embodiments $R^{16}$ is oxygen.

In certain embodiments $R^{16}$ is —C(O)—.

In certain embodiments, $R^{16}$ is —C(S)—.

In certain embodiments $R^{16}$ is sulfur.

In certain embodiments $R^{16}$ is —C(S)—.

In certain embodiments, $R^{16}$ is —OC(O)—.

In certain embodiments, $R^{16}$ is —C(O)O—.

In certain embodiments $R^{16}$ is an —C(O)$NR^{27}$—.

In certain embodiments $R^{16}$ is an —$NR^{27}$C(O)—.

In certain embodiments $R^{16}$ is a —$NR^{10}$—.

In certain embodiments $R^{16}$ is a 6-membered aryl group with attachment points in a 1,2 orientation.

In certain embodiments $R^{16}$ is a 6-membered aryl group with attachment points in a 1,3 orientation.

In certain embodiments $R^{16}$ is a 6-membered aryl group with attachment points in a 1,4 orientation.

In certain embodiments $R^{16}$ is a 6-membered aryl group with attachment points in a 1,2 orientation.

In certain embodiments $R^{16}$ is a heteroaryl group with attachment points in a 1,2 orientation.

In certain embodiments $R^{16}$ is a heteroaryl group with attachment points in a 1,2 orientation.

In certain embodiments $R^{16}$ is a aryl group with attachment points in a 1,2 orientation.

In certain embodiments $R^{17}$ is bond.

In certain embodiments $R^{17}$ is alkyl.

In certain embodiments $R^{17}$ is aliphatic.

In certain embodiments $R^{17}$ is aryl.

In certain embodiments $R^{17}$ is a bicycle.

In certain embodiments $R^{17}$ is alkene.

In certain embodiments $R^{17}$ is alkyne.

In certain embodiments $R^{17}$ is haloalkyl.

In certain embodiments $R^{17}$ is alkoxy.

In certain embodiments $R^{17}$ is heteroaryl.

In certain embodiments $R^{17}$ is a heterocycle.

In certain embodiments $R^{17}$ is cycloalkyl.

In certain embodiments $R^{17}$ is heteroaliphatic.

In certain embodiments $R^{17}$ is —$NR^{27}$—.

In certain embodiments $R^{17}$ is —$NR^{10}$.

In certain embodiments $R^{17}$ is —$CR^{40}R^{41}$—

In certain embodiments $R^{17}$ is oxygen.

In certain embodiments $R^{17}$ is —C(O)—.

In certain embodiments, $R^{17}$ is —C(S)—.

In certain embodiments $R^{17}$ is sulfur.

In certain embodiments $R^{17}$ is —C(S)—.

In certain embodiments, $R^{17}$ is —OC(O)—.

In certain embodiments, $R^{17}$ is —C(O)O—.

In certain embodiments $R^{17}$ is an —C(O)$N^{27}$—.

In certain embodiments $R^{17}$ is an —$NR^{27}$C(O)—.

In certain embodiments $R^{17}$ is a —$NR^{10}$—.

In certain embodiments $R^{17}$ is a 6-membered aryl group with attachment points in a 1,2 orientation.

In certain embodiments $R^{17}$ is a 6-membered aryl group with attachment points in a 1,3 orientation.

In certain embodiments $R^{17}$ is a 6-membered aryl group with attachment points in a 1,4 orientation.

In certain embodiments $R^{17}$ is a 6-membered aryl group with attachment points in a 1,2 orientation.

In certain embodiments $R^{17}$ is a heteroaryl group with attachment points in a 1,2 orientation.

In certain embodiments $R^{17}$ is a heteroaryl group with attachment points in a 1,2 orientation.

In certain embodiments $R^{17}$ is a aryl group with attachment points in a 1,2 orientation.

In certain embodiments, $R^{18}$ is hydrogen

In certain embodiments, $R^{18}$ is halogen.

In certain embodiments, $R^{18}$ is cyano.

In certain embodiments, $R^{18}$ is —C(O)$OR^{27}$.

In certain embodiments, $R^{18}$ is alkyl.

In certain embodiments, $R^{18}$ is —C(O)$NR^{10}R^{27}$.

In certain embodiments, $R^{18}$ is —$NR^{27}$C(O)$R^{27}$.

In certain embodiments, $R^{18}$ is —$NR^{10}R^{27}$.

In certain embodiments, $R^{18}$ is $SR^{27}$.

In certain embodiments, $R^{18}$ is haloalkyl.

In certain embodiments, $R^{18}$ is alkoxy.

In certain embodiments, $R^{18}$ is aryl.

In certain embodiments, $R^{18}$ is heterocycle.

In certain embodiments, $R^{18}$ is aliphatic.

In certain embodiments, $R^{18}$ is heteroaliphatic.

In certain embodiments, $R^{18}$ is heteroaryl.

In certain embodiments, $R^{18}$ is —$OR^{27}$.

Embodiments of $R^{19}$

In certain embodiments, $R^{19}$ is alkyl.

In certain embodiments, $R^{19}$ is hydrogen.

In certain embodiments, $R^{19}$ is —C(O)$NR^{10}R^{27}$.

In certain embodiments, $R^{19}$ is —C(O)$OR^{27}$.

In certain embodiments, $R^{19}$ is —C(O)$R^{27}$.

In certain embodiments, $R^{19}$ is alkene.

In certain embodiments, $R^{19}$ is alkyne.

In certain embodiments, $R^{19}$ is haloalkyl.

In certain embodiments, $R^{19}$ is alkoxy.

In certain embodiments, $R^{19}$ is aryl.

In certain embodiments, $R^{19}$ is heterocycle.

In certain embodiments, $R^{19}$ is aliphatic.

In certain embodiments, $R^{19}$ is heteroaliphatic.

In certain embodiments, $R^{19}$ is heteroaryl.

Embodiments of $R^{20}$

In certain embodiments, $R^{20}$ is aliphatic.

In certain embodiments, $R^{20}$ is alkyl.

In certain embodiments, $R^{20}$ is selected from:

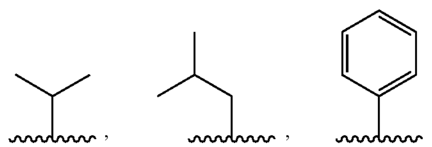

-continued

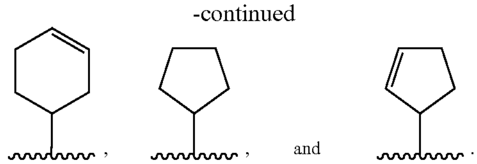

, , and .

Embodiments of $R^{23}$

In certain embodiments, $R^{23}$ is hydrogen.
In certain embodiments, $R^{23}$ is fluorine.
In certain embodiments, $R^{23}$ is bromine.
In certain embodiments, $R^{23}$ is chlorine.
In certain embodiments, $R^{23}$ is haloalkyl.
In certain embodiments, $R^{23}$ is selected from:

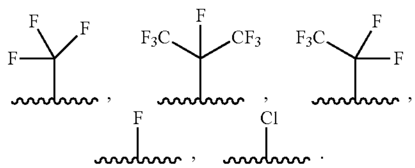

Embodiments of $R^{27}$

In certain embodiments, $R^{27}$ is hydrogen.
In certain embodiments, $R^{27}$ is alkyl.
In certain embodiments, $R^{27}$ is arylalkyl.
In certain embodiments, $R^{27}$ is heteroarylalkyl.
In certain embodiments, $R^{27}$ is alkene.
In certain embodiments, $R^{27}$ is alkyne.
In certain embodiments, $R^{27}$ is aryl.
In certain embodiments, $R^{27}$ is heteroaryl.
In certain embodiments, $R^{27}$ is heterocycle.
In certain embodiments, $R^{27}$ is cycloalkyl.
In certain embodiments, $R^{27}$ is aliphatic.
In certain embodiments, $R^{27}$ is heteroaliphatic.
In certain embodiments, $R^{27}$ is selected from:

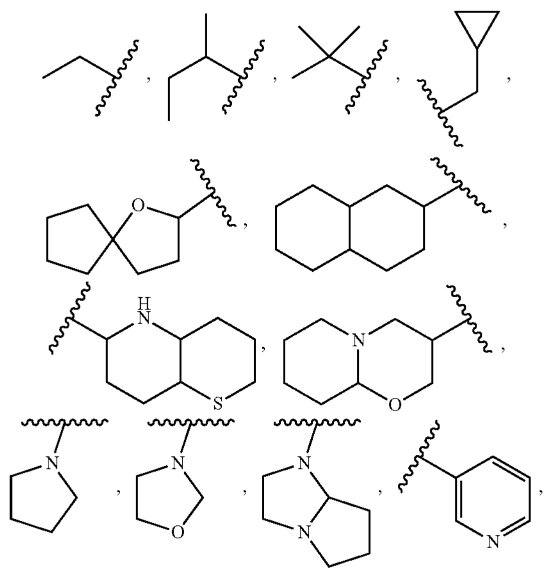

-continued

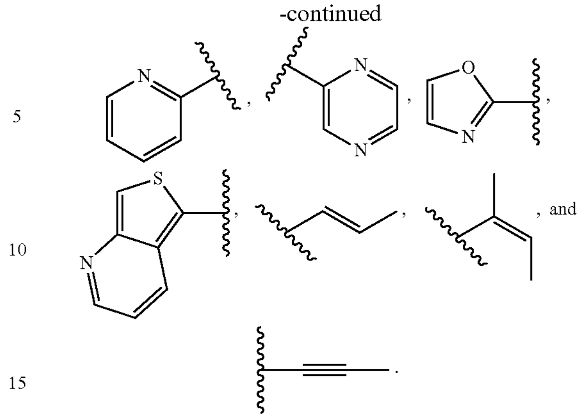

Embodiments of $R^{40}$

In certain embodiments, $R^{40}$ is hydrogen.
In certain embodiments, $R^{40}$ is aliphatic.
In certain embodiments, $R^{40}$ is heteroaliphatic.
In certain embodiments, $R^{40}$ is cyano.
In certain embodiments, $R^{40}$ is nitro.
In certain embodiments, $R^{40}$ is alkyl.
In certain embodiments, $R^{40}$ is fluorine.
In certain embodiments, $R^{40}$ is chlorine.
In certain embodiments, $R^{40}$ is bromine.
In certain embodiments, $R^{40}$ is haloalkyl.
In certain embodiments, $R^{40}$ is $—OR^{10}$.
In certain embodiments, $R^{40}$ is $—SR^{10}$.
In certain embodiments, $R^{40}$ is $—S(O)R^{12}$.
In certain embodiments, $R^{40}$ is $—SO_2R^{12}$.
In certain embodiments, $R^{40}$ is $—NR^{10}R^{11}$.
In certain embodiments, $R^{40}$ is selected from:

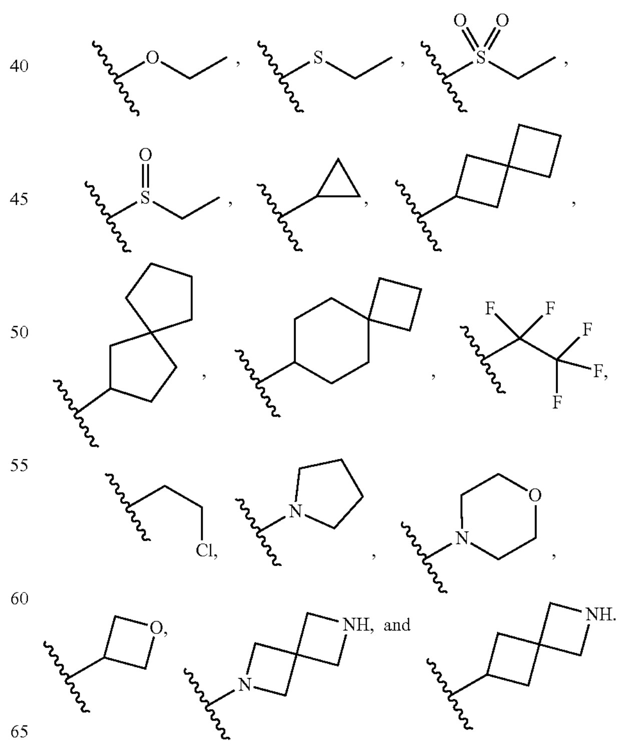

Embodiments of $R^{41}$

In certain embodiments, $R^{41}$ is aliphatic.
In certain embodiments, $R^{41}$ is heteroaryl.
In certain embodiments, $R^{41}$ is hydrogen.
In certain embodiments, $R^{41}$ is aliphatic.
In certain embodiments, $R^{41}$ is aliphatic.
In certain embodiments, $R^{41}$ is aliphatic.
In certain embodiments, $R^{41}$ is selected from:

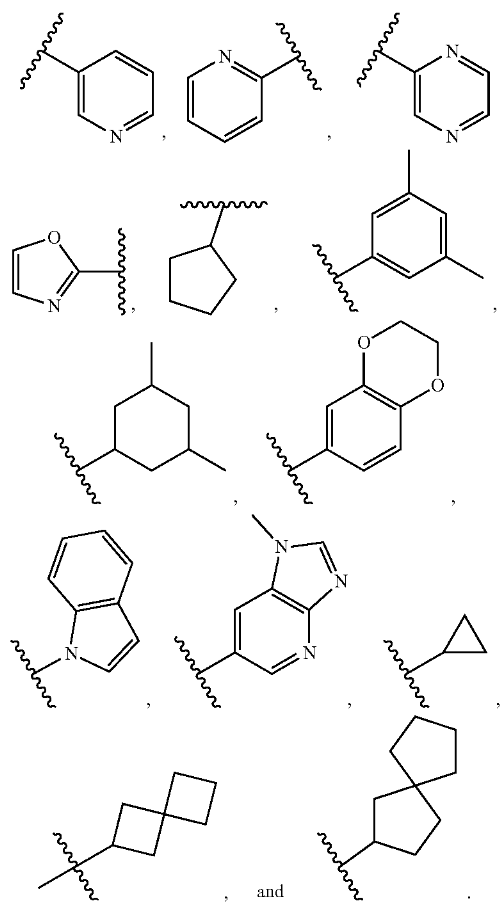

Embodiments of $R^{42}$

In certain embodiments, $R^{42}$ is selected from:

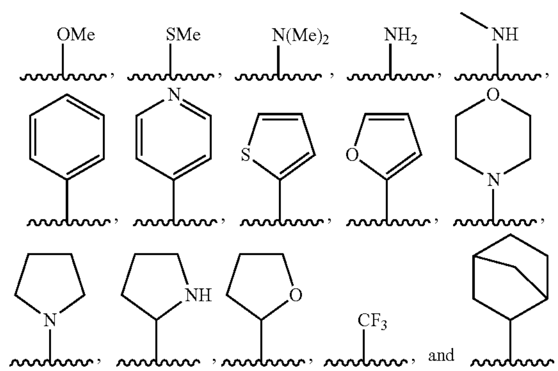

Non-Limiting Examples of Compounds of Formula I

Representative examples of compounds of Formula I include:

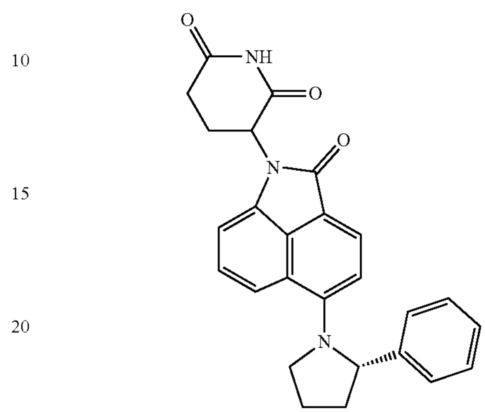

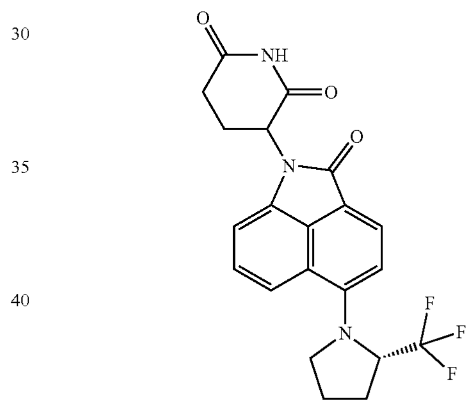

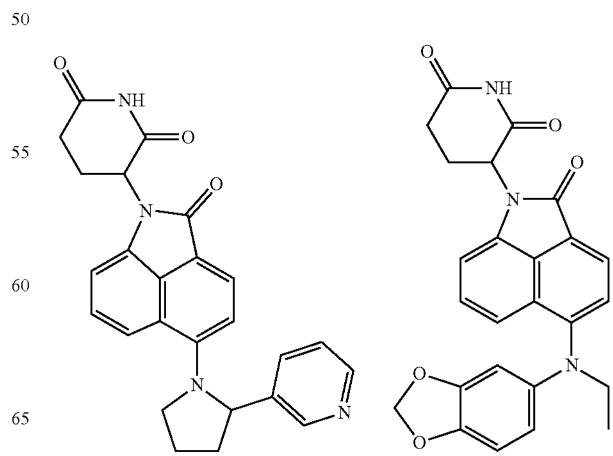

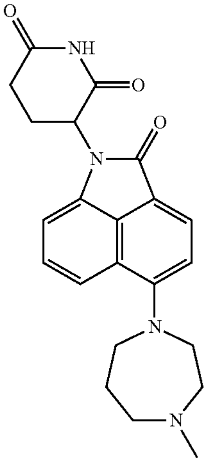
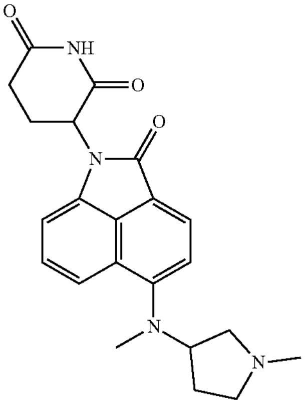
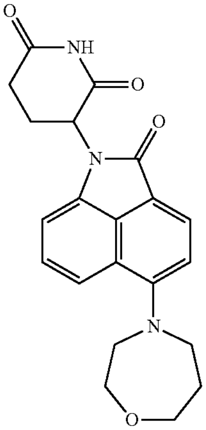
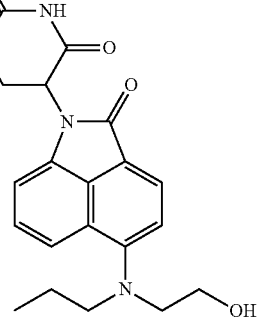
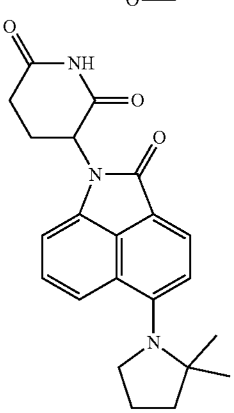
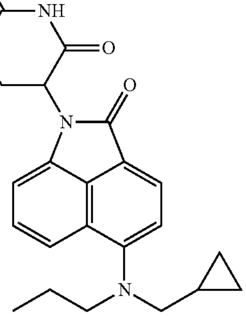
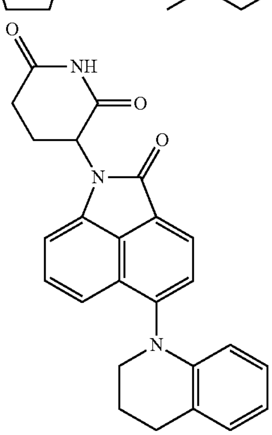
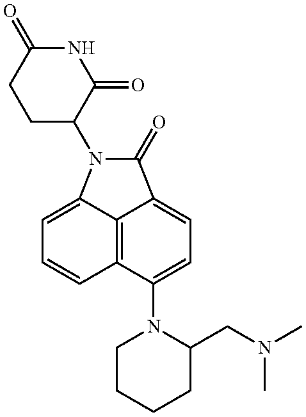
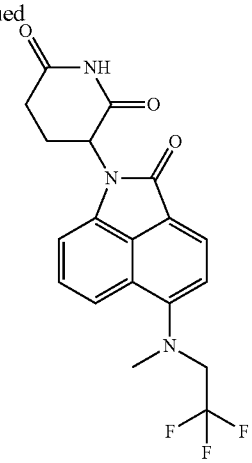
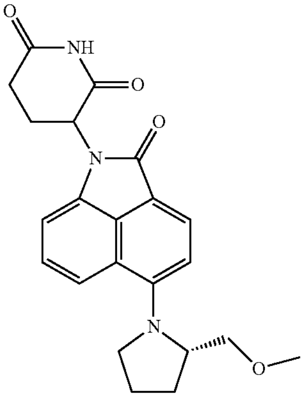
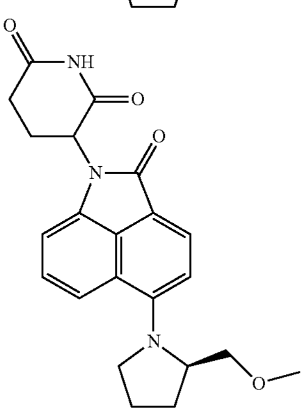
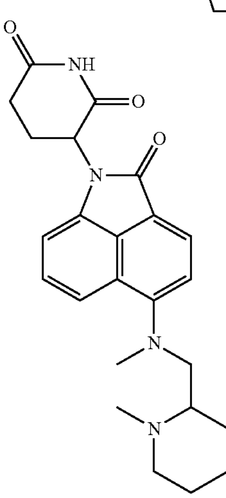
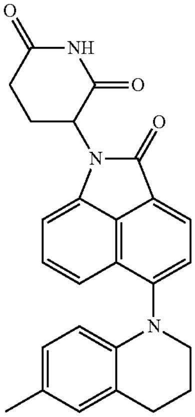

-continued
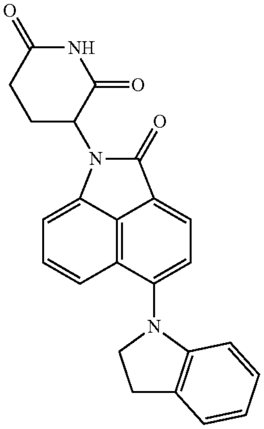
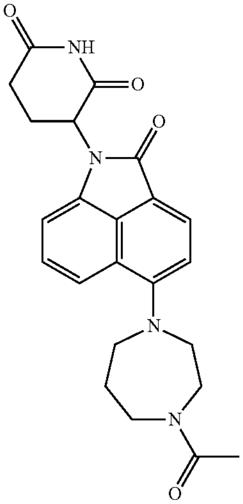
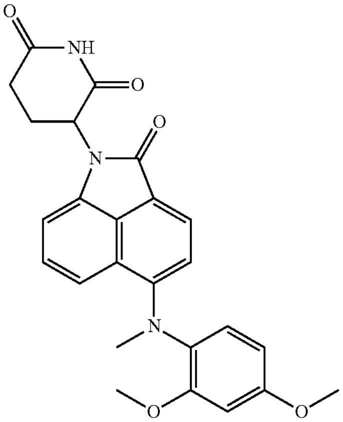
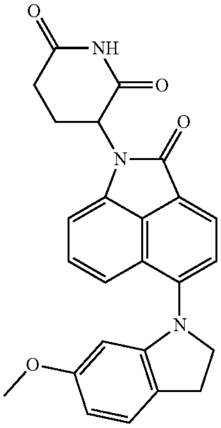
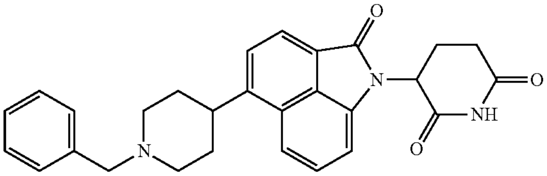
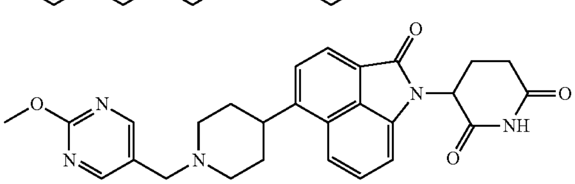
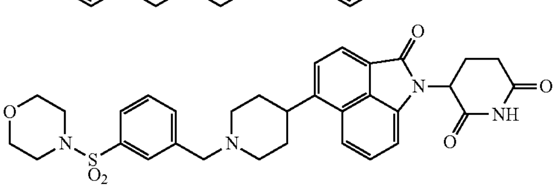
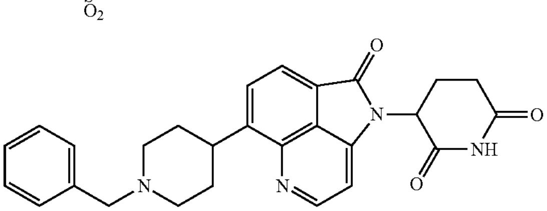
-continued
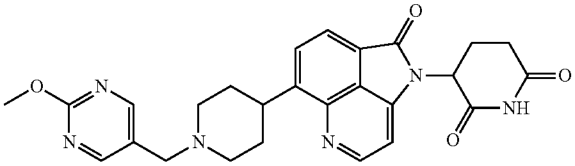
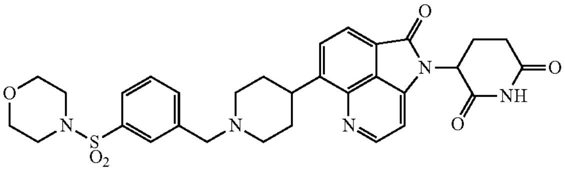
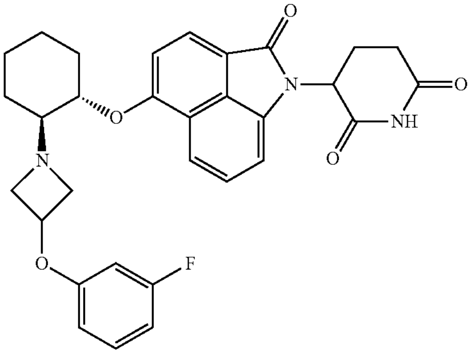
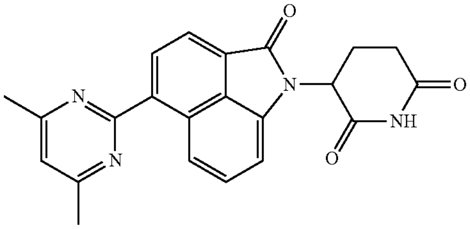
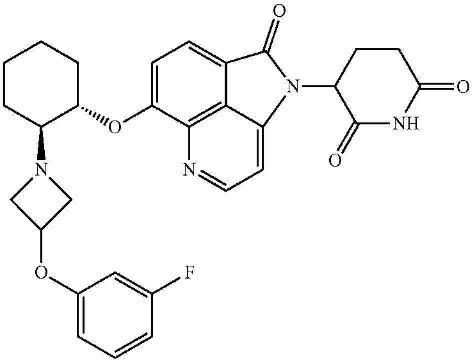
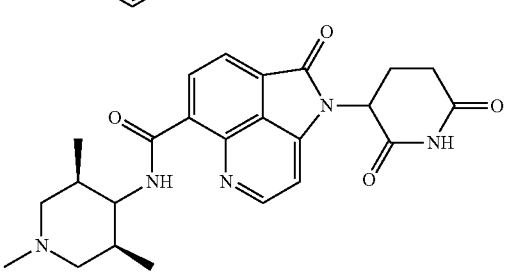

-continued
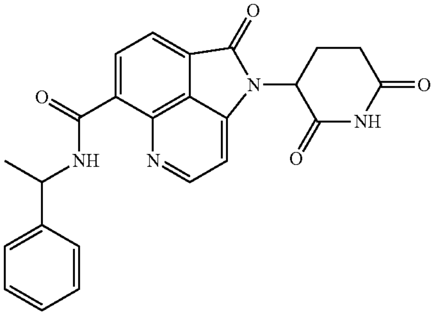
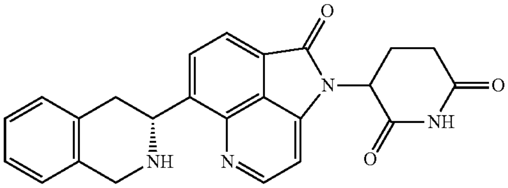
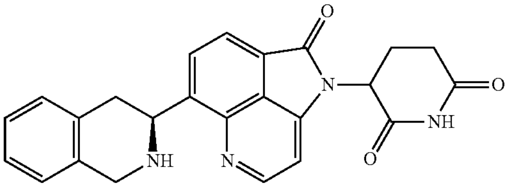
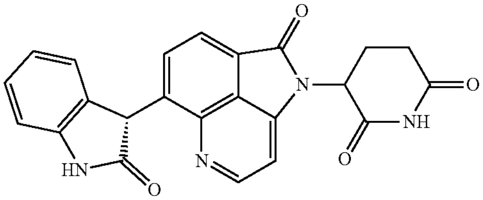
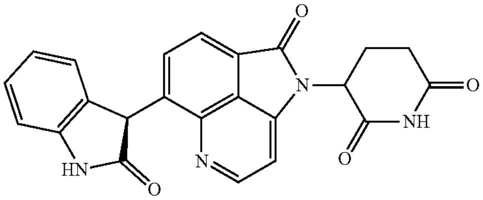
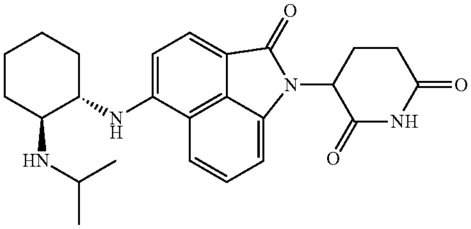
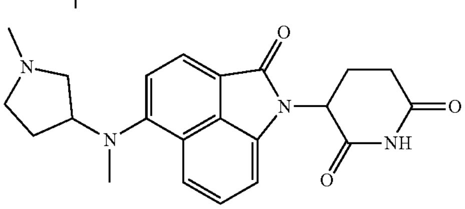
-continued
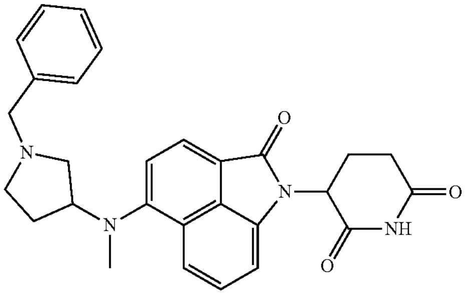
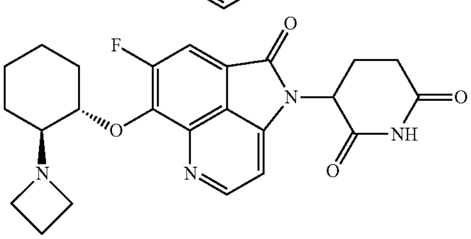
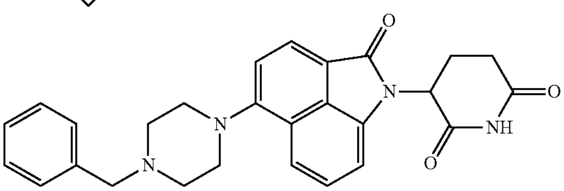
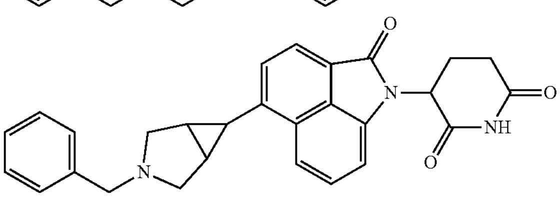
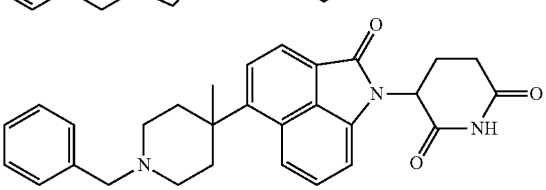
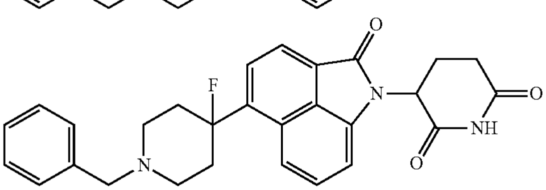
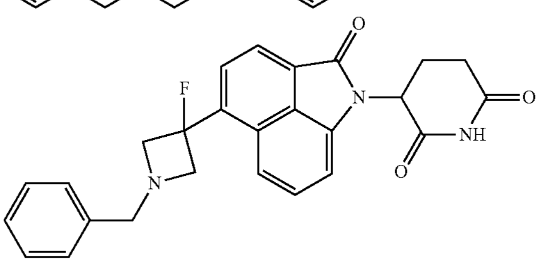
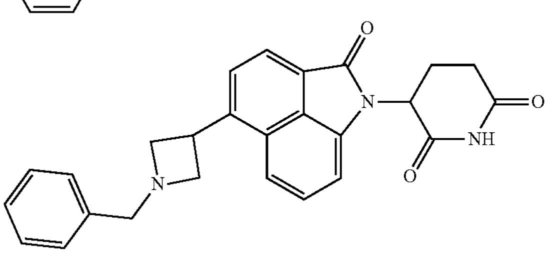

-continued
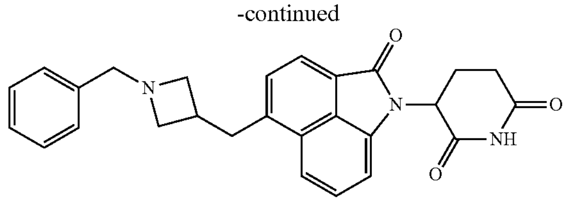
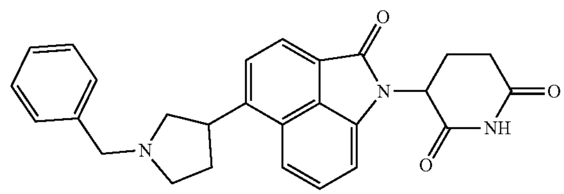
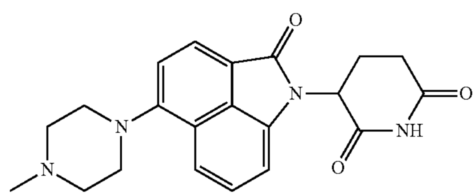
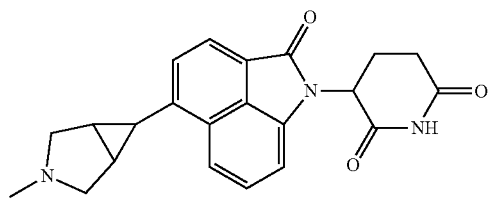
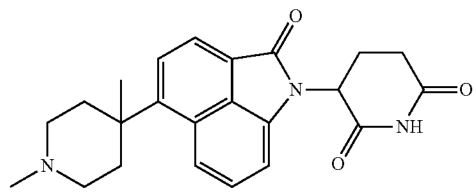
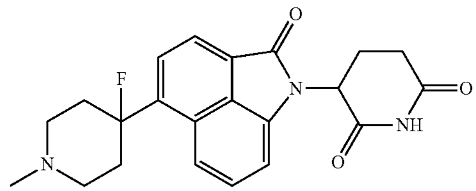
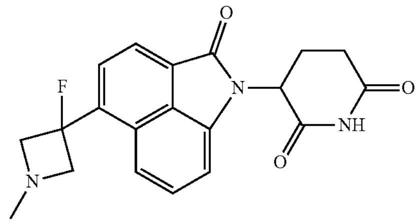
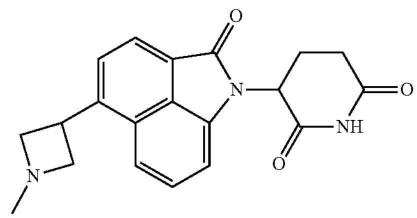
-continued
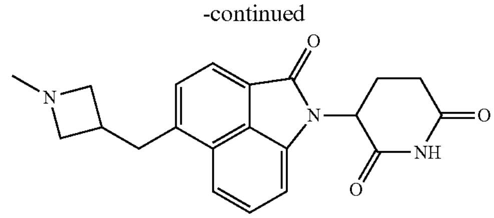
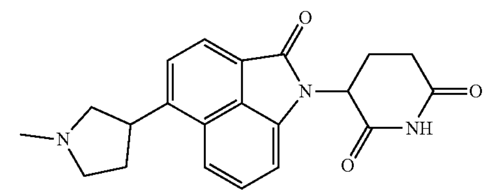
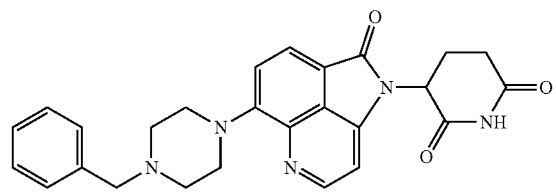
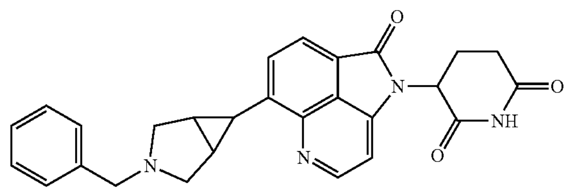
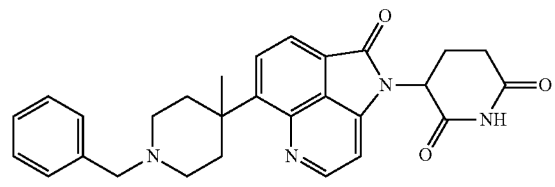
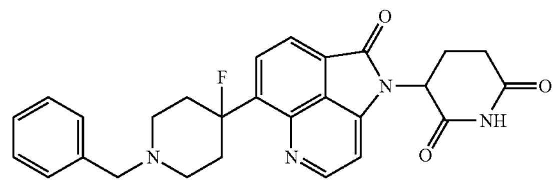
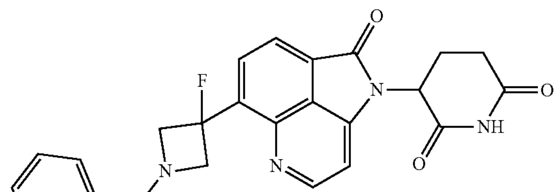
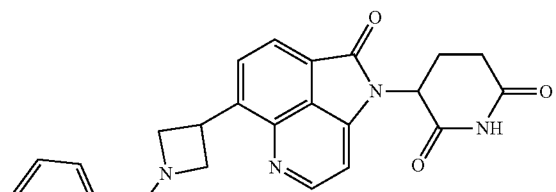

-continued
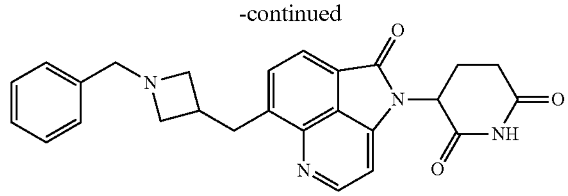
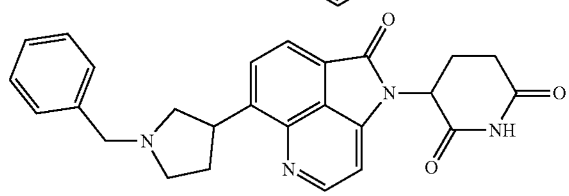
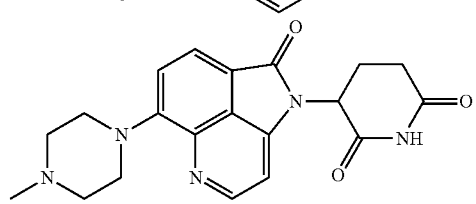
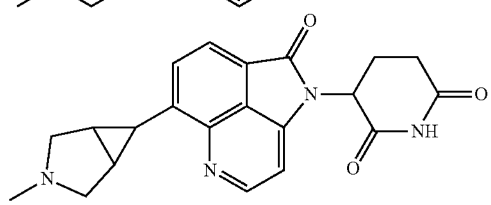
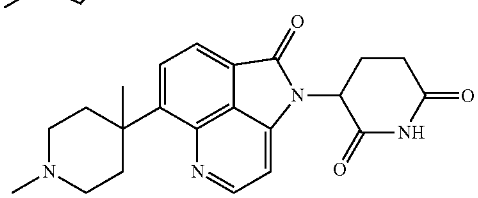
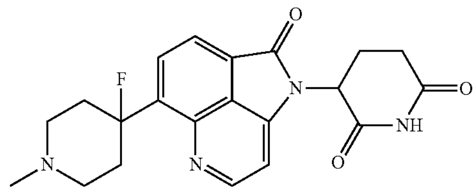
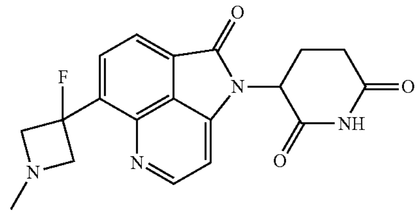
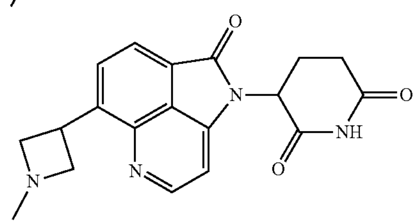
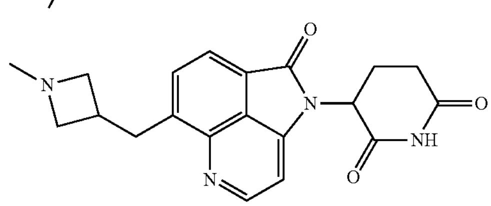
-continued
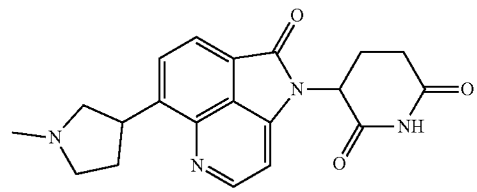
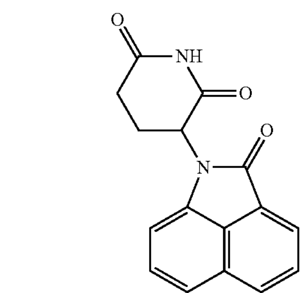
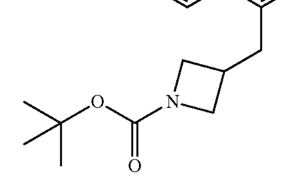
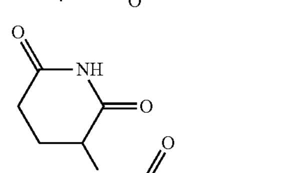
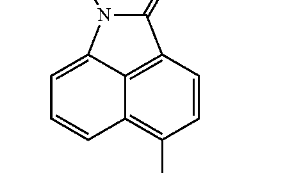
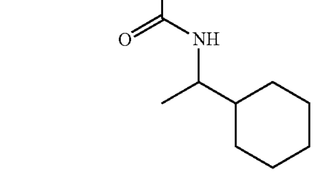
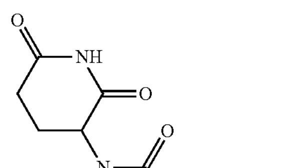
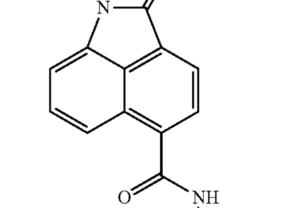
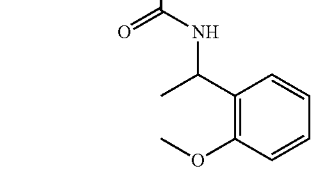
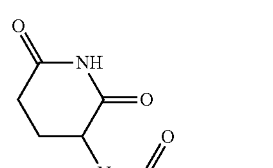
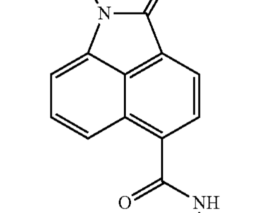
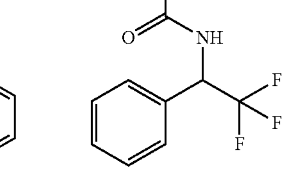

-continued
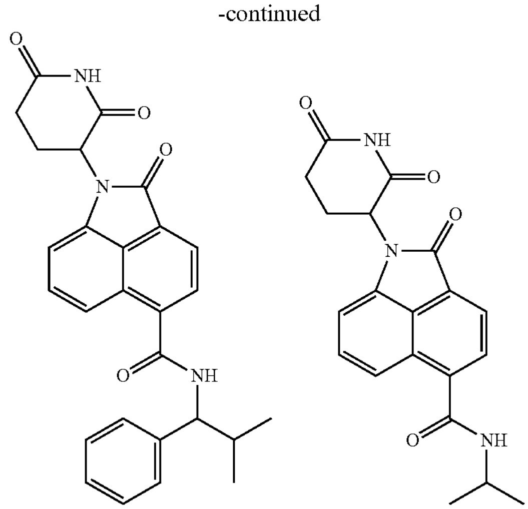
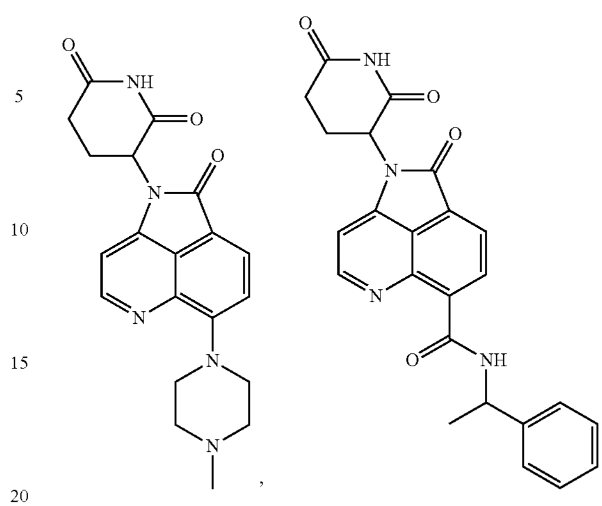
,
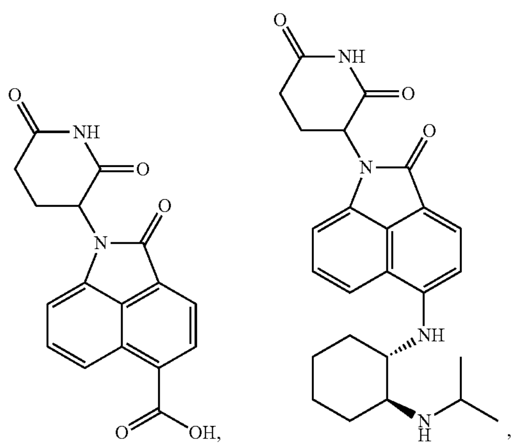
,
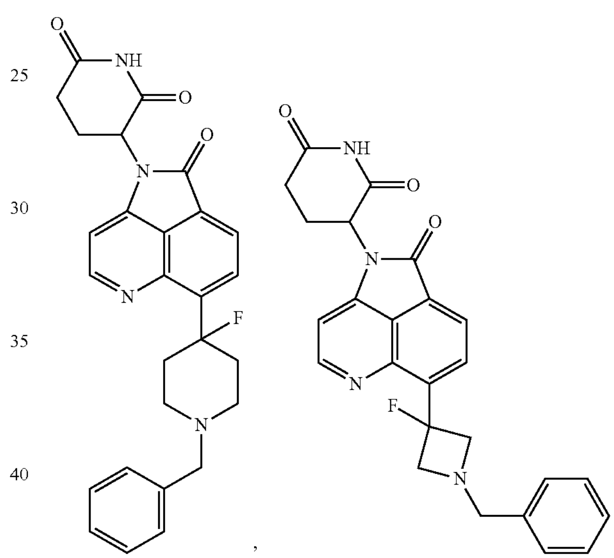
,
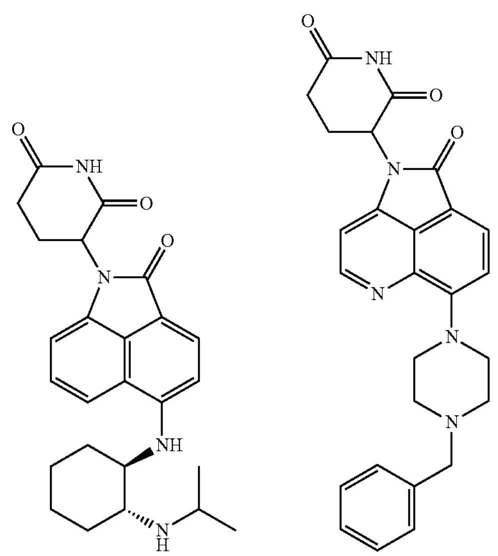
,
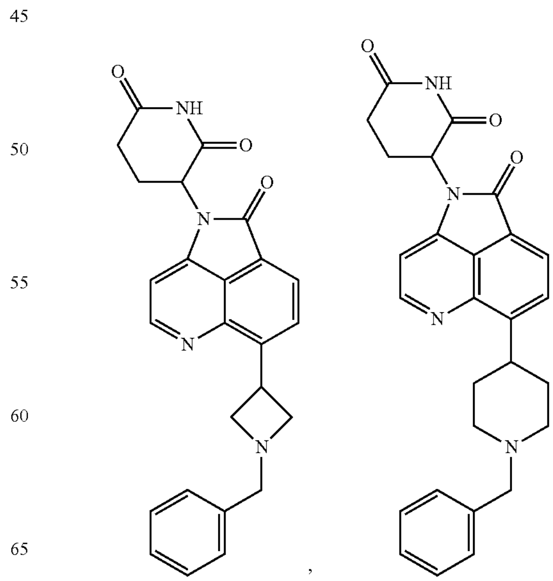
, -continued

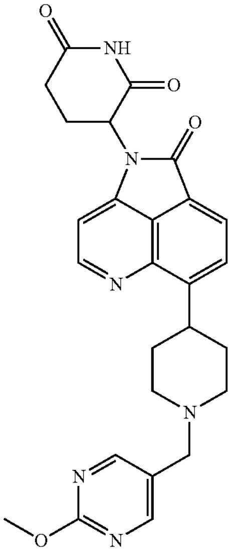

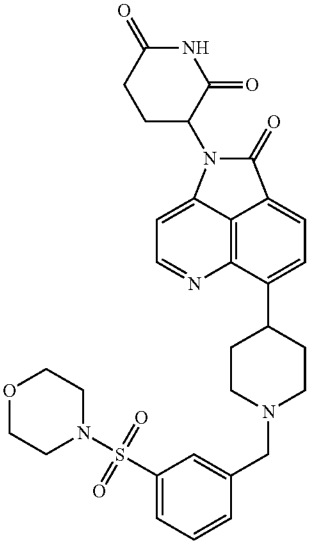

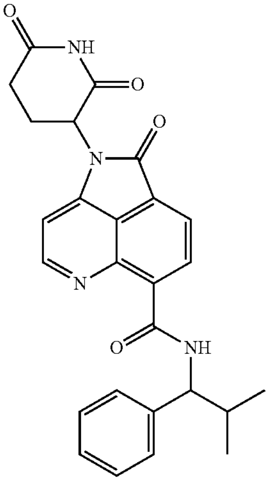

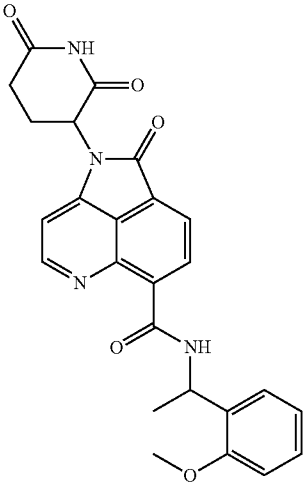

-continued

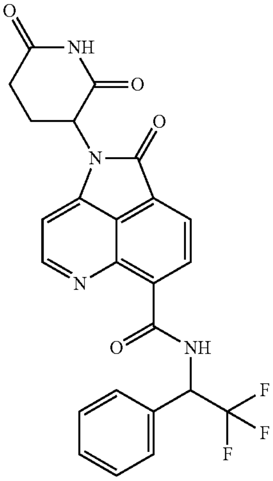

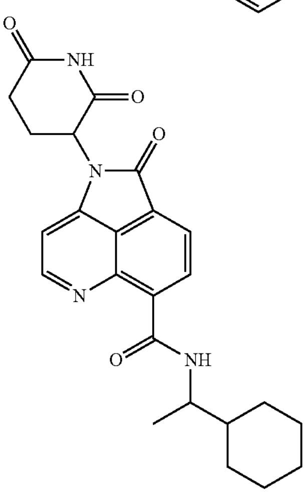

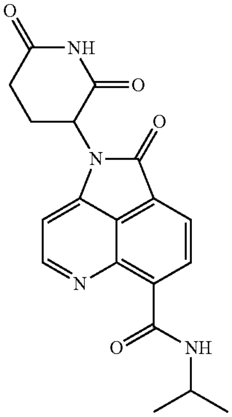

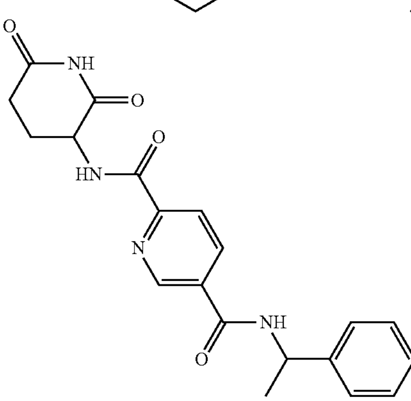

or a pharmaceutically acceptable salt thereof.

Non-limiting Isotopic Embodiments

In certain embodiments the compound is isotopically labeled. In certain embodiments at least one R group independently selected from $R^1$, $R^2$, $R^3$, $R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, R', $R^{19}$, $R^{20}$, $R^{23}$, $R^{27}$, $R^{40}$, $R^{41}$, or $R^{42}$ is isotopically labeled with 1, 2, or more isotopes as allowed by valence. In certain embodiments the isotopic label is deuterium. In certain embodiments, at least one deuterium is placed on an atom that has a bond which is broken during metabolism of the compound in vivo, or is one, two or three atoms remote form the metabolized bond (e.g., which may be referred to as an α, β or γ, or primary, secondary or tertiary isotope effect). In another embodiment the isotopic label is $^{13}C$. In another embodiment the isotopic label is $^{18}F$.

III. Methods of Treatment

Any of the tricyclic compounds described herein can be used in an effective amount to treat a host, including a human, in need thereof, optionally in a pharmaceutically acceptable carrier to treat any of the disorders described herein. In certain embodiments, the method comprises administering an effective amount of the active compound or its salt as described herein, optionally including a pharmaceutically acceptable excipient, carrier, or adjuvant (i.e., a pharmaceutically acceptable composition), optionally in combination or alternation with an additional therapeutically active agent or combination of agents.

In certain embodiments, the compound of the present invention selectively degrades IKZF2 and/or 4 over one or more of IKZF1 and/or 3 and/or 5.

In certain embodiments the disorder treated by a compound of the present invention is an immunomodulatory disorder. In certain embodiments the disorder treated by a compound of the present invention is mediated by angiogenesis. In certain embodiments the disorder treated by a compound of the present invention is related to the lymphatic system.

In certain embodiments a compound of the present invention pharmaceutical salt thereof, optionally in a pharmaceutical composition as described herein is used to degrade IKZF2 or IKZF4, which is a mediator of the disorder affecting the patient, such as a human. The control of protein level afforded by any of the compounds of the present invention provides treatment of a disease state or condition, which is modulated through IKZF2 or IKZF4 by lowering the level of that protein in the cell, e.g., cell of a patient, or by lowering the level of downstream proteins in the cell. In certain embodiments, the method comprises administering an effective amount of the compound as described herein, optionally including a pharmaceutically acceptable excipient, carrier, adjuvant (i.e., a pharmaceutically acceptable composition), optionally in combination or alternation with an additional therapeutically active agent or combination of agents.

In certain embodiments, a compound of the present invention is used to treat a disorder including, but not limited to, benign growth, neoplasm, tumor, cancer, abnormal cellular proliferation, immune disorder, inflammatory disorder, graft-versus-host rejection, viral infection, bacterial infection, an amyloid-based proteinopathy, a proteinopathy, or a fibrotic disorder.

The term "disease state" or "condition" when used in connection with any of the compounds is meant to refer to any disease state or condition that is mediated by IKZF2 or IKZF4, such as cellular proliferation, or by proteins that are downstream of IKZF2 or IKZF4, and where degradation of such protein in a patient may provide beneficial therapy or relief of symptoms to a patient in need thereof. In certain instances, the disease state or condition may be cured.

In certain embodiments, a compound or its corresponding pharmaceutically acceptable salt, isotopic derivative, or prodrug as described herein can be used in an effective amount to treat a host, for example a human, with a lymphoma or lymphocytic or myelocytic proliferation disorder or abnormality. For example, a compound as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, isotopic derivative, or prodrug as described herein can be used in an effective amount to treat a host, for example a human, with a Hodgkin lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In another embodiment, a compound or its corresponding pharmaceutically acceptable salt, isotopic derivative, or prodrug as described herein can be used in an effective amount to treat a host, for example a human, with an immunomodulatory condition. Non-limiting examples of immunomodulatory conditions include: arthritis, lupus, celiac disease, Sjogren's syndrome, polymyalgia rheumatia, multiple sclerosis, ankylosing spondylitis, type 1 diabetes, alopecia areata, vasculitis, and temporal arteritis.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

Abnormal proliferation of B-cells, T-cells, and/or NK cells can result in a wide range of diseases such as cancer, proliferative disorders and inflammatory/immune diseases. A host, for example a human, afflicted with any of these disorders can be treated with an effective amount of a compound as described herein to achieve a decrease in symptoms (palliative agent) or a decrease in the underlying disease (a disease modifying agent).

In certain embodiments, a compound or its corresponding pharmaceutically acceptable salt, isotopic derivative, or prodrug as described herein can be used in an effective amount to treat a host, for example a human, with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; diffuse poorly differentiated lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In certain embodiments, a compound or its corresponding pharmaceutically salt, isotopic derivative, or prodrug as described herein can be used in an effective amount to treat a host, for example a human, with a T-cell or NK-cell lymphoma such as, but not limited to: anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In certain embodiments, a compound or its corresponding pharmaceutically acceptable salt, isotopic derivative, or prodrug as described herein can be used to treat a host, for example a human, with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In certain embodiments, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A compound or its pharmaceutically acceptable salt, isotopic analog, or prodrug as described herein can be used in an effective amount to treat a host, for example a human, with a proliferative condition such as myeloproliferative disorder (MPD), polycythemia vera (PV), essential thrombocythemia (ET), myeloid metaplasia with myelofibrosis (MMM), chronic myelomonocytic leukemia (CMML), hypereosinophilic syndrome (HES), system mast cell disease (SMCD), and the like. In another embodiment, a compound provided herein is useful for the treatment of primary myelofibrosis, post-polycythemia vera myelofibrosis, post-essential thrombocythemia myelofibrosis, and secondary acute myelogenous leukemia.

In certain embodiments, a compound or its pharmaceutically acceptable salt, isotopic analog, or prodrug as described herein can be used in an effective amount to treat a host, for example a human, with a myelodysplastic syndrome (MDS) such as, but not limited to: refractory cytopenia with unilineage dysplasia, refractory anemia with ring sideroblasts (RARS), refractory anemia with ring sideroblasts—thrombocytosis (RARS-t), refractory cytopenia with multilineage dyslplasia (RCMD) including RCMD with multilineage dysplasia and ring sideroblasts (RCMD-RS), Refractory amenias with excess blasts I (RAEB-I) and II (RAEB-II), 5q-syndrome, refractory cytopenia of childhood, and the like.

In certain embodiments a compound of the present invention can provide a therapeutic effect by direct degradation of Helios or Eos which may change the transcriptional regulation of a protein downstream of Helios or Eos.

The term "neoplasia" or "cancer" is used to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma. In certain embodiments the disorder is adenoid cystic carcinoma. In certain embodiments the disorder is NUT midline carcinoma.

In another embodiment, a compound or its pharmaceutically acceptable salt, isotopic derivative or prodrug as described herein can be used in an effective amount to treat a host, for example a human, with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behçet's disease; Berger's disease; Bickerstaffs encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barre syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka Pityriasis lichenoides et varioliformis acuta; Multiple sclerosis; Myasthenia gravis; Myositis; Mênière's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; Polyarteritis nodosa; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjögren's syndrome; Spondyloarthropathy; Stiff person syndrome; Still's disease; Subacute bacterial endocarditis (SBE); Susac's syndrome; Sweet's syndrome; Sydenham chorea; sympathetic ophthalmia; systemic lupus erythematosus; Takayasu's arteritis; temporal arteritis (also known as "giant cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, chronic pain, and rhinitis.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

A compound or its pharmaceutically acceptable salt, isotopic variant, or prodrug as described herein can be used in an effective amount to treat a host, for example a human, with a skin disorder such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, the skin disorder is treated by topical administration of compounds known in the art in combination with the compounds disclosed herein. In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis *coli*, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome#arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubê syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Wolf-Hirschhorn syndrome, Wolff Periodic disease, Weissenbacher-Zweymuller syndrome and Xeroderma pigmentosum, among others.

In certain embodiments, a method is provided for treating a solid tumor, for example non-small cell lung cancer or melanoma comprising administering to a patient an effective amount of a compound of Formula I, or a pharmaceutically acceptable salt, isotopic analog, or prodrug thereof, optionally in a pharmaceutically acceptable carrier to form a composition. In another embodiment, a compound of Formula I, or a pharmaceutically acceptable salt, isotopic analog, or prodrug thereof, optionally in a pharmaceutically acceptable carrier to form a composition, for use in a method of treating a solid tumor, for example non-small cell lung cancer or melanoma, wherein the method comprises administering the compound to a patient.

In certain embodiments, a method is provided for managing the progression of multiple myeloma comprising administering to a patient an effective amount of a compound of Formula I, or a pharmaceutically acceptable salt, isotopic analog, or prodrug thereof, optionally in a pharmaceutically acceptable carrier to form a composition. In another embodiment, a compound of Formula I, or a pharmaceutically acceptable salt, isotopic analog, or prodrug thereof, optionally in a pharmaceutically acceptable carrier to form a composition, for use in a method of managing the progression of multiple myeloma, wherein the method comprises administering the compound to a patient.

In certain embodiments the solid tumor is resistant to treatment with an anti PD-1 agent.

In certain embodiments the solid tumor is refractory to treatment with an anti PD-1 agent.

In certain embodiments the solid tumor is resistant to treatment with an anti PD-L1 agent.

In certain embodiments the solid tumor is refractory to treatment with an anti PD-L1 agent.

In certain embodiments, a method is provided for treating multiple myeloma comprising administering to a patient an effective amount of a compound of Formula I, or a pharmaceutically acceptable salt, isotopic analog, or prodrug thereof, optionally in a pharmaceutically acceptable carrier to form a composition. In another embodiment, a compound of Formula I, or a pharmaceutically acceptable salt, isotopic analog, or prodrug thereof, optionally in a pharmaceutically acceptable carrier to form a composition, for use in a method of treating multiple myeloma, wherein the method comprises administering the compound to a patient.

In certain embodiments, a method is provided for managing the progression of multiple myeloma comprising administering to a patient an effective amount of a compound of Formula I, or a pharmaceutically acceptable salt, isotopic analog, or prodrug thereof, optionally in a pharmaceutically acceptable carrier to form a composition. In another embodiment, a compound of Formula I, or a pharmaceutically acceptable salt, isotopic analog, or prodrug thereof, optionally in a pharmaceutically acceptable carrier to form a composition, for use in a method of managing the progression of multiple myeloma, wherein the method comprises administering the compound to a patient.

In certain embodiments, a method is provided for inducing a therapeutic response as assessed by the International Uniform Response Criteria (IURC) for Multiple Myeloma (described in Durie B. G. M; et al. "International uniform response criteria for multiple myeloma. *Leukemia* 2006, 10(10):1-7) in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve a stringent complete response, complete response, or very good partial response, as assessed by the IURC for Multiple Myeloma in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve an increase in overall survival, progression-free survival, event-free survival, time to process, or disease-free survival in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve an increase in overall survival in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve an increase in progression-free survival in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve an increase in event-free survival in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve an increase in time to progression in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

In another embodiment, a method is provided to achieve an increase in disease-free survival in a patient having multiple myeloma comprising administering to the patient an effective amount of a compound of Formula I, or a pharmaceutically acceptable salt, isotopic analog, or prodrug thereof, optionally in a pharmaceutically acceptable carrier to form a composition.

Methods are also provided to treat patients who have been previously treated for multiple myeloma but are non-responsive to standard therapies in addition to those who have not been previously treated. Additional methods are provided to treat patients who have undergone surgery in an attempt to treat multiple myeloma in addition to those who have not undergone surgery. Methods are also provided to treat patients who have previously undergone transplant therapy in addition to those who have not.

The compounds described herein may be used in the treatment or management of multiple myeloma that is relapsed, refractory, or resistant. In some embodiments, the multiple myeloma is primary, secondary, tertiary, quadruply or quintuply relapsed. In certain embodiments, the compounds described herein may be used to reduce, maintain, or eliminate minimal residual disease (MRD).

The types of multiple myeloma that may be treated with the compounds described herein include, but are not limited to: monoclonal gammopathy of undetermined significance (MGUS); low risk, intermediate risk, or high risk multiple myeloma; newly diagnosed multiple myeloma, including low risk, intermediate risk, or high risk newly diagnosed multiple myeloma); transplant eligible and transplant ineligible multiple myeloma; smoldering (indolent) multiple myeloma (including low risk, intermediate risk, or high risk smoldering multiple myeloma); active multiple myeloma; solitary plasmacytoma; plasma cell leukemia; central nervous system multiple myeloma; light chain myeloma; non-secretory myeloma; Immunoglobulin D myeloma; and Immunoglobulin E myeloma.

In some embodiments, the compounds described herein may be used in the treatment or management of multiple myeloma characterized by genetic abnormalities, for example but not limited to: Cyclin D translocations (for example, t(11;14)(q13;q32); t(6;14)(p21;32); t(12;14)(p13;q32); or t(6;20);); MMSET translocations (for example t(4;14)(p16;q32); MAF translocations (for example t(14;16)(q32;a32); t(20;22); t(16;22)(q11;q13); or t(14;20)(q32;q11); or other chromosome factors (for example deletion of 17p13 or chromosome 13; del(17/17p), nonhyperdiploidy, and gain (1q)).

In certain embodiments, a method is provided for treating or managing multiple myeloma comprising administering to a patient an effective amount of a compound of Formula I, or a pharmaceutically acceptable salt, isotopic analog, or prodrug thereof, optionally in a pharmaceutically acceptable carrier to form a composition, as induction therapy.

In certain embodiments, a method is provided for treating or managing multiple myeloma comprising administering to a patient an effective amount of a compound of Formula I, or a pharmaceutically acceptable salt, isotopic analog, or prodrug thereof, optionally in a pharmaceutically acceptable carrier to form a composition, as consolidation therapy.

In certain embodiments, a method is provided for treating or managing multiple myeloma comprising administering to a patient an effective amount of a compound of Formula I, or a pharmaceutically acceptable salt, isotopic analog, or prodrug thereof, optionally in a pharmaceutically acceptable carrier to form a composition, as maintenance therapy.

In certain embodiments, the multiple myeloma is plasma cell leukemia.

In certain embodiments, the multiple myeloma is high risk multiple myeloma. In some embodiments, the high risk multiple myeloma is relapsed or refractory. In certain embodiments, the high risk multiple myeloma has relapsed within 12 months of the first treatment. In another embodiment, the high risk multiple myeloma is characterized by genetic abnormalities, for example, one or more of del(17/17p) and t(14;16)(q32;q32). In some embodiments, the high risk multiple myeloma is relapsed or refractory to one, two or three previous treatments.

In certain embodiments, the multiple myeloma has a p53 mutation. In certain embodiments, the p53 mutation is a Q331 mutation. In certain embodiments, the p53 mutation is a R273H mutation. In certain embodiments, the p53 mutation is a K132 mutation. In certain embodiments, the p53 mutation is a K132N mutation. In certain embodiments, the p53 mutation is a R337 mutation. In certain embodiments, the p53 mutation is a R337L mutation. In certain embodiments, the p53 mutation is a W146 mutation. In certain embodiments, the p53 mutation is a S261 mutation. In certain embodiments, the p53 mutation is a S261T mutation. In certain embodiments, the p53 mutation is a E286 mutation. In certain embodiments, the p53 mutation is a E286K mutation. In certain embodiments, the p53 mutation is a R175 mutation. In certain embodiments, the p53 mutation is a R175H mutation. In certain embodiments, the p53 mutation is a E258 mutation. In certain embodiments, the p53 mutation is a E258K mutation. In certain embodiments, the p53 mutation is a A161 mutation. In certain embodiments, the p53 mutation is a A161T mutation.

In certain embodiments, the multiple myeloma has a homozygous deletion of p53. In certain embodiments, the multiple myeloma has a homozygous deletion of wild-type p53. In certain embodiments, the multiple myeloma has wild-type p53.

In certain embodiments, the multiple myeloma shows activation of one or more oncogenic drivers. In certain embodiments, the one or more oncogenic drivers are selected from the group consisting of C-MAF, MAFB, FGFR3, MMset, Cyclin D1, and Cyclin D. In certain embodiments, the multiple myeloma shows activation of C-MAF. In certain embodiments, the multiple myeloma shows activation of MAFB. In certain embodiments, the multiple myeloma shows activation of FGFR3 and MMset. In certain embodiments, the multiple myeloma shows activation of C-MAF, FGFR3, and MMset. In certain embodiments, the multiple myeloma shows activation of Cyclin D1. In certain embodiments, the multiple myeloma shows activation of MAFB and Cyclin D1. In certain embodiments, the multiple myeloma shows activation of Cyclin D.

In certain embodiments, the multiple myeloma has one or more chromosomal translocations. In certain embodiments, the chromosomal translocation is t(14;16). In certain embodiments, the chromosomal translocation is t(14;20). In certain embodiments, the chromosomal translocation is t(4; 14). In certain embodiments, the chromosomal translocations are t(4;14) and t(14;16). In certain embodiments, the chromosomal translocation is t(11;14). In certain embodiments, the chromosomal translocation is t(6;20). In certain embodiments, the chromosomal translocation is t(20;22). In certain embodiments, the chromosomal translocations are t(6;20) and t(20;22). In certain embodiments, the chromosomal translocation is t(16;22). In certain embodiments, the chromosomal translocations are t(14;16) and t(16;22). In certain embodiments, the chromosomal translocations are t(14;20) and t(11;14).

In certain embodiments, the multiple myeloma has a Q331 p53 mutation, activation of C-MAF, and a chromosomal translocation at t(14; 16). In certain embodiments, the multiple myeloma has homozygous deletion of p53, activation of C-MAF, and a chromosomal translocation at t(14; 16). In certain embodiments, the multiple myeloma has a K132N p53 mutation, activation of MAFB, and a chromosomal translocation at t(14;20). In certain embodiments, the multiple myeloma has wild type p53, activation of FGFR3 and MMset, and a chromosomal translocation at t(4; 14). In certain embodiments, the multiple myeloma has wild type p53, activation of C-MAF, and a chromosomal translocation at t(14;16). In certain embodiments, the multiple myeloma has homozygous deletion of p53, activation of FGFR3, MMset, and C-MAF, and chromosomal translocations at t(4;14) and t(14;16). In certain embodiments, the multiple myeloma has homozygous deletion of p53, activation of Cyclin D1, and a chromosomal translocation at t(11;14). In certain embodiments, the multiple myeloma has a R337L p53 mutation, activation of Cyclin D1, and a chromosomal translocation at t(11;14). In certain embodiments, the multiple myeloma has a W146 p53 mutation, activation of FGFR3 and MMset, and a chromosomal translocation at t(4; 14). In certain embodiments, the multiple myeloma has a S261T p53 mutation, activation of MAFB, and chromosomal translocations at t(6;20) and t(20;22). In certain embodiments, the multiple myeloma has a E286K p53 mutation, by activation of FGFR3 and MMset, and a chromosomal translocation at t(4; 14). In certain embodiments, the multiple myeloma has a R175H p53 mutation, activation of FGFR3 and MMset, and a chromosomal translocation at t(4; 14). In certain embodiments, the multiple myeloma has a E258K p53 mutation, activation of C-MAF, and chromosomal translocations at t(14;16) and t(16;22). In certain embodiments, the multiple myeloma has wild type p53, activation of MAFB and Cyclin D1, and chromosomal translocations at t(14;20) and t(11;14). In certain embodiments, the multiple myeloma has a A161T p53 mutation, activation of Cyclin D, and a chromosomal translocation at t(11;14).

In some embodiments, the multiple myeloma is transplant eligible newly diagnosed multiple myeloma. In other embodiments, the multiple myeloma is transplant ineligible newly diagnosed multiple myeloma.

In some embodiments, the multiple myeloma shows early progression (for example less than 12 months) following initial treatment. In other embodiments, the multiple myeloma shows early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In certain embodiments, a method is provided for treating or managing relapsed or refractory multiple myeloma in patients with impaired renal function or a symptom thereof comprising administering to a patient an effective amount of a compound of Formula I, or a pharmaceutically acceptable salt, isotopic analog, or prodrug thereof, optionally in a pharmaceutically acceptable carrier to form a composition.

In another embodiment, a method is provided for treating or managing relapsed or refractory multiple myeloma in frail patients comprising administering to a patient an effective amount of a compound of Formula I, or a pharmaceutically acceptable salt, isotopic analog, or prodrug thereof, optionally in a pharmaceutically acceptable carrier to form a composition, wherein the frail patient is characterized by ineligibility for induction therapy or intolerance to dexamethasone treatment. In other embodiments, the frail patient is elderly, for example, older than 65 years old.

In another embodiment, a method is provided for treating or managing fourth line relapsed or refractory multiple myeloma comprising administering to a patient an effective amount of a compound of Formula I, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound of Formula I, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound of Formula I, or a pharmaceutically acceptable salt, isotopic analog, or prodrug thereof, optionally in a pharmaceutically acceptable carrier to form a composition, as maintenance therapy after another therapy or transplant.

In another embodiment, a method is provided for treating or managing high risk multiple myeloma that is relapsed or refractory to one, two, or three previous treatments comprising administering to a patient an effective amount of a compound of Formula I, or a pharmaceutically acceptable salt, isotopic analog, or prodrug thereof, optionally in a pharmaceutically acceptable carrier to form a composition.

In some embodiments, the patient to be treated by one of the compounds described herein has not be treated with multiple myeloma therapy prior to administration. In some embodiments, the patient to be treated by one of the compounds described herein has been treated by multiple myeloma therapy prior to administration. In some embodiments, the patient to be treated by one of the compounds described herein has developed drug resistant to the multiple myeloma therapy. In some embodiments, the patient to be treated by one of the compounds described herein has developed resistance to one, two, or three multiple myeloma therapies, wherein the therapies are selected from a CD38 antibody (CD38 mAB, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avodomide).

The compounds described herein can be used to treat a patient regardless of patient's age. In some embodiments, the subject is 18 years or older. In other embodiments, the subject is more than 18, 25, 35, 40, 45, 50, 55, 60, 65, or 70 years old. In other embodiments, the patient is less than 65 years old. In other embodiments, the patient is more than 65 years old. In certain embodiments, the patient is an elderly multiple myeloma patient, such as a patient older than 65 years old. In certain embodiments, the patient is an elderly multiple myeloma patient, such as a patient older than 75 years old.

It has been reported that certain proteins with a β-hairpin turn containing a glycine at a key position (a "g-loop protein" or "g-loop degron") acts as a "structural degron" for cereblon when the cereblon is also bound to a thalidomide-like molecule (IMiD) neosubstrate protein. Such "g-loop degron" containing proteins generally include a small anti-parallel β-sheet forming a β-hairpin with an α-turn, with a geometric arrangement of three backbone hydrogen bond acceptors at the apex of a turn (positions i, i+1, and i+2), with a glycine residue at a key position (i+3) (see, e.g., Matyskiela, et al, A novel cereblon modulator recruits GSPT1 to the CRL4-CRBN ubiquitin ligase. Nature 535, 252-257 (2016); Sievers et al., Defining the human C2H2 zinc finger degrome targeted by thalidomide analogs through CRBN. Science 362, eaat0572 (2018)). These g-loop degrons have been identified in a number of proteins, including, but not limited to, Sal-like 4 (SALL4), GSPT1, IKFZ1, IKFZ3, and CKla, ZFP91, ZNF93, etc.

In some embodiments, a tricyclic compound of the present invention or pharmaceutical salt thereof, optionally in a pharmaceutical composition as described herein can be administered in an effective amount to a host to degrade a protein containing a g-loop degron, wherein the protein is selected from a protein kinase, C2H2 containing zinc finger protein, an RNA-recognition motif containing protein, a zinc beta ribbon containing protein, a beta-propeller containing protein, a P-loop NTPase containing protein, a really interesting new gene (RING)-finger domain containing protein, an SRC Homology 3 (SH3)-domain containing protein, an immunoglobulin E-set domain containing protein, a Tudor-domain containing protein, a zinc finger FYVE/PHD-type containing protein, an Ig-like domain containing protein, a ubiquitin-like domain containing protein, a concanavalin-like domain containing protein, a C1-domain containing protein, a Pleckstrin homology (PH)-domain containing protein, an OB-fold-domain containing protein, an NADP Rossman-fold-domain containing protein, an Actin-like ATPase domain containing protein, and a helix-turn-helix (HTH)-domain containing protein. In some embodiments, the protein kinase, C2H2 containing zinc finger protein, an RNA-recognition motif containing protein, a zinc beta ribbon containing protein, a beta-propeller containing protein, a P-loop NTPase containing protein, a really interesting new gene (RING)-finger domain containing protein, an SRC Homology 3 (SH3)-domain containing protein, an immunoglobulin E-set domain containing protein, a Tudor-domain containing protein, a zinc finger FYVE/PHD-type containing protein, an Ig-like domain containing protein, a ubiquitin-like domain containing protein, a concanavalin-like domain containing protein, a C1-domain containing protein, a Pleckstrin homology (PH)-domain containing protein, an OB-fold-domain containing protein, an NADP Rossman-fold-domain containing protein, an Actin-like ATPase domain containing protein, or a helix-turn-helix (HTH)-domain containing protein is overexpressed or contains a gain-of-function mutation.

n some embodiments, the degron is stabilized by internal hydrogen bonds from an ASX motif and a ST motif.

In some embodiments, a tricyclic heterobifunctional compound of the present invention or pharmaceutical salt thereof, optionally in a pharmaceutical composition as described herein can be administered in an effective amount to a host to degrade a protein with a "g-loop degron," wherein the "g-loop degron" comprises a [D/N]XX[S/T]G motif, wherein D=aspartic acid, N=asparagine, X can be any amino acid residue, S=serine, T=threonine, and G=glycine. In certain embodiments, the "g-loop degron" containing protein comprises an amino acid sequence of DXXSG, wherein D=aspartic acid, X can be any amino acid residue, S=serine, and G=glycine. In another embodiment, the "g-loop degron" containing protein comprises an amino acid sequence of NXXSG, wherein N=asparagine, X can be any amino acid residue, S=serine, and G=glycine. In yet another embodiment, the "g-loop degron" containing protein comprises an amino acid sequence of DXXTG, wherein D=aspartic acid, X can be any amino acid residue, T=threonine, and G=glycine. In still another embodiment, "g-loop degron" containing protein comprises an amino acid sequence of NXXTG, wherein N=asparagine, X can be any amino acid residue, T=threonine, and G=glycine. In some embodiments, the "g-loop degron" containing protein comprises an amino acid sequence of CXXCG, wherein C=cysteine, X can be any amino acid residue, and G=glycine. In certain embodiments, the "g-loop degron" containing protein comprises an amino acid sequence of NXXNG, wherein N=asparagine, X can be any amino acid residue, and G=glycine.

In some embodiments, a tricyclic heterobifunctional compound of the present invention or pharmaceutical salt thereof, optionally in a pharmaceutical composition as described herein can be administered in an effective amount to a host to degrade a protein with a C2H2 zinc-finger domain containing a "g-loop degron". In some embodiments, the zinc-finger domain has the consensus sequence C-X-X-C-G, wherein C=cysteine, X=any amino acid, and G=glycine. In an alternative embodiment, the protein with a zinc-finger domain has the consensus sequence Q-C-X-X-C-G (SEQ ID NO: 1), wherein C=cysteine, X=any amino acid, G=glycine, and Q=glutamine. In a still further embodiment, the zinc-finger domain has the consensus sequence Q-C-$X_2$-C-G-$X_3$-F-$X_5$-L-$X_2$-H-$X_3$-H (SEQ ID NO: 2), wherein C=cysteine, X=any amino acid, G=glycine, Q=glutamine, F=phenylalanine, L=leucine, and H=histidine. In some embodiments, the $C_2H2$ zinc-finger domain containing $X_2$-C-$X_2$-CG-$X_2$-C-$X_5$ (SEQ ID NO: 3), wherein C=cysteine, X=any amino acid, and G=glycine. In some embodiments, the $C_2H_2$ zinc-finger domain containing protein is over-expressed. In some embodiments, the expression of $C_2H_2$ zinc-finger containing protein is associated with a disease or disorder, including, but not limited to, cancer.

For example, a compound of the present invention, or pharmaceutical salt thereof, optionally in a pharmaceutical composition as described herein is administered to a host to degrade Zinc Finger Protein, Atypical E3 Ubiquitin Ligase (ZFP91). Zinc Finger Protein, Atypical E3 Ubiquitin Ligase contains a $Cys_2$-$His_2$ zinc finger, and protects tumor cell survival and confers chemoresistance through forkhead box A1 (FOXA1) destabilization (see, e.g., Tang, et al. The ubiquitinase ZFP91 promotes tumor cell survival and confers chemoresistance through FOXA1 destabilization, Carcinogenesis, Col. 41(1), January 2020). Zinc Finger Protein, Atypical E3 Ubiquitin Ligase is believed to act through noncanonical NF-κB pathway regulation, and its overexpression leads to increased NF-κB signaling pathway activation has been implicated in a number of cancers, including gastric cancer, breast cancer, colon cancer, kidney cancer, ovarian cancer, pancreatic cancer, stomach cancer, prostate cancer, sarcoma, and melanoma (see, e.g., Paschke, ZFP91 zinc finger protein expression pattern in normal tissues and cancers. Oncol Lett. 2019; March; 17(3):3599-3606). In certain embodiments, a compound of the present invention, or pharmaceutical salt thereof, optionally in a pharmaceutical composition as described herein is used to degrade Zinc Finger Protein, Atypical E3 Ubiquitin Ligase for the treatment of a cancer, including but not limited to, gastric cancer, breast cancer, colon cancer, lung cancer, kidney cancer, ovarian cancer, pancreatic cancer, stomach cancer, prostate cancer, sarcoma, and melanoma. In certain embodiments, a compound of the present invention, or pharmaceutical salt thereof, optionally in a pharmaceutical composition as described herein is used to degrade Zinc Finger Protein, Atypical E3 Ubiquitin Ligase for the treatment of a sarcoma, melanoma, or gastric cancer.

In another embodiment, a compound of the present invention, or pharmaceutical salt thereof, optionally in a pharmaceutical composition as described herein is administered to a host to degrade zinc finger protein 276 (ZFP276).

In yet another embodiment, a compound of the present invention, or pharmaceutical salt thereof, optionally in a pharmaceutical composition as described herein is administered to a host to degrade Zinc finger protein 653 (ZFP653). Zinc finger protein 653 may act as a more general repressor of transcription by competition with GRIP1 and other p160 coactivators for binding to SF1 (see, e.g., Borud et al., Cloning and characterization of a novel zinc finger protein that modulates the transcriptional activity of nuclear receptors. Molec. Endocr. 17: 2303-2319, 2003).

As other examples, a compound of the present invention, or pharmaceutical salt thereof, optionally in a pharmaceutical composition as described herein is administered to a host in an effective amount to degrade Zinc finger protein 692 (ZFP692). Zinc finger protein 692, also known as AICAR response element binding protein (AREBP), contains a Cys2-His2 zinc finger, and is believed to be a key modulator of hepatic glucose production regulated by AMPK in vivo (See Shirai et al., AICAR response element binding protein (AREBP), a key modulator of hepatic glucose production regulated by AMPK in vivo. Biochem Biophys Res Commun. 2011 Oct. 22; 414(2):287-91). The overexpression of and its overexpression has been associated with the promotion of colon adenocarcinoma and metastasis by activating the PI3K/AKT pathway (see, for example, Xing et al., Zinc finger protein 692 promotes colon adenocarcinoma cell growth and metastasis by activating the PI3K/AKT pathway. Int J Oncol. 2019 May; 54(5): 1691-1703), and the development of metastasis in lung adenocarcinomas and lung carcinoma. Knockdown of Zinc finger protein 692 expression via short interfering RNA reduced cell invasion and increased apoptosis in lung carcinoma cells and suppressed lung carcinoma tumor growth in a xenograft model (see, e.g., Zhang et al., ZNF692 promotes proliferation and cell mobility in lung adenocarcinoma. Biochem Biophys Res Commun. 2017 Sep. 2; 490(4):1189-1196). Accordingly, In certain embodiments, a compound of the present invention, or pharmaceutical salt thereof, optionally in a pharmaceutical composition as described herein is used to degrade Zinc finger protein 692 for the treatment of a lung or colon cancer, including a lung adenocarcinoma or carcinoma or a colon adenocarcinoma.

A tricyclic compound of the present invention, or pharmaceutical salt thereof, optionally in a pharmaceutical composition as described herein can also administered in an effective amount to a host to degrade Zinc finger protein 827 (ZFP827). Zinc finger protein 827 is a zinc finger protein that regulates alternative lengthening of telomeres (ALT) pathway by binding nuclear receptors and recruiting the nucleosome remodeling and histone deacetylation (NURD) complex to telomeres to induce homologous recombination (see, e.g., Conomos, D., Reddel, R. R., Pickett, H. A. NuRD-ZNF827 recruitment to telomeres creates a molecular scaffold for homologous recombination. Nature Struct. Molec. Biol. 21: 760-770, 2014). Zinc finger protein 827 has been associated with ALT-associated promyelocytic leukemia (PML) nuclear bodies (APBs) and other telomeric aberrations. Accordingly, in certain embodiments, a compound of the present invention, or pharmaceutical salt thereof, optionally in a pharmaceutical composition as described herein is used to degrade ZNF827 in ALT-associated disorders, including, but not limited to ALT-positive promyelocytic leukemia, osteosarcoma, adrenal/PNS neuroblastoma, breast cancer, glioblastoma, colorectal cancer, pancreatic neuroendocrine tumor (NET), neuroendocrine tumor, colorectal cancer, liver cancer, soft tissue cancers, including leiomyosarcoma, malignant fibrous histiocytoma, liposarcoma, stomach/gastric cancer, testicular cancer, and thyroid cancer.

In other embodiments, a tricyclic compound of the present invention, or pharmaceutical salt thereof, optionally in a pharmaceutical composition as described herein is administered in an effective amount to a host to degrade E4F Transcription Factor 1 protein (E4F1). E4F Transcription Factor 1 is believed to function as a ubiquitin ligase for p53, and is a key posttranslational regulator of p53 that plays an important role in the cellular life-or-death decision controlled by p53 (see, e.g., Le Cam et al., The E4F protein is required for mitotic progression during embryonic cell cycles. Molec. Cell. Biol. 24: 6467-6475, 2004). E4F1 overexpression has been associated with the development of myeloid leukemia cells (see, e.g., Hatachi et al., E4F1 deficiency results in oxidative stress-mediated cell death of leukemic cells. J Exp Med. 2011 Jul. 4; 208(7): 1403-1417). Accordingly, in certain embodiments, a compound of the present invention, or pharmaceutical salt thereof, optionally in a pharmaceutical composition as described herein is used to degrade E4F Transcription Factor 1 for the treatment of a leukemia of myelogenous origin, including but not limited to, acute myelogenous leukemia (AML), undifferentiated AML, myeloblastic leukemia with minimal cell maturation, myeloblastic leukemia with cell maturation, promyelocytic leukemia, myelomonocytic leukemia, myelomonocytic leukemia with eosinophilia, monocytic leukemia, erythroleukemia, megakaryoblastic leukemia, chronic myelogenous leukemia (C-L), juvenile myelomonocytic leukemia (JMML), chronic myelomonocytic leukemia (CMML), a myeloproliferative neoplasm, including for example, polycythemia vera (PV), essential thrombocythemia (ET), myeloid metaplasia with myelofibrosis (MMM), hypereosinophilic syndrome (HES), systemic mast cell disease (SMCD), myelofibrosis, and primary myelofibrosis. E4F1 expression is also essential for survival in p53-deficient cancer cells (see, e.g., Rodier et al., The Transcription Factor E4F1 Coordinates CHK1-Dependent Checkpoint and Mitochondrial Functions. Cell Reports Volume 11, ISSUE 2, P220-233, Apr. 14, 2015). Accordingly, in certain embodiments, a compound of the present invention, or pharmaceutical salt thereof, optionally in a pharmaceutical composition as described herein is used to degrade E4F Transcription Factor 1 for the treatment of a p53-deficient associated disorder, including, but not limited to ovarian cancer, small cell lung cancer, pancreatic cancer, head and neck squamous cell carcinoma, and triple negative breast cancer.

In another aspect, a tricyclic compound of the present invention, or pharmaceutical salt thereof, optionally in a pharmaceutical composition as described herein is administered in an effective amount to a host to degrade Zinc finger protein 517 (ZFP517). Zinc finger protein 517 has been identified as an oncogenic driver in adrenocortical carcinoma (ACC) (see, e.g., Rahane et al., Establishing a human adrenocortical carcinoma (ACC)-specific gene mutation signature. Cancer Genet. 2019; 230:1-12). Accordingly, in certain embodiment, a compound of the present invention, or pharmaceutical salt thereof, optionally in a pharmaceutical composition as described herein is used to Zinc finger protein 517 for the treatment of adrenocortical carcinoma.

In yet another aspect, a tricyclic compound of the present invention, or pharmaceutical salt thereof, optionally in a pharmaceutical composition as described herein is administered in an effective amount to a host to degrade Zinc finger protein 582 (ZFP582). Zinc finger protein 582 is believed to be involved in n DNA damage response, proliferation, cell cycle control, and neoplastic transformation, most notably cervical, esophageal, and colorectal cancer (see, e.g., Huang et al., Methylomic analysis identifies frequent DNA methylation of zinc finger protein 582 (ZNF582) in cervical neoplasms. PLoS One 7: e41060, 2012; Tang et al., Aberrant DNA methylation of PAX1, SOX1 and ZNF582 genes as potential biomarkers for esophageal squamous cell carcinoma. Biomedicine & Pharmacotherapy Volume 120, December 2019, 109488; Harada et al., Analysis of DNA Methylation in Bowel Lavage Fluid for Detection of Colorectal Cancer. Cancer Prev Res; 7(10); 1002-10; 2014). Accordingly, in certain embodiments, a compound of the present invention, or pharmaceutical salt thereof, optionally in a pharmaceutical composition as described herein is used to degrade Zinc finger protein 582 for the treatment of a cancer, including but not limited to cervical cancer, including cervical adenocarcinoma, esophageal cancer, including squamous cell carcinoma and adenocarcinoma, and colorectal cancer.

In another embodiment, a tricyclic compound of the present invention, or pharmaceutical salt thereof, optionally in a pharmaceutical composition as described herein is administered in an effective amount to a host to degrade Zinc finger protein 654 (ZFP654).

Alternatively, a tricyclic compound of the present invention, or pharmaceutical salt thereof, optionally in a pharmaceutical composition as described herein is administered in an effective amount to a host to degrade Zinc finger protein 787 (ZFP787).

A tricyclic compound of the present invention, or pharmaceutical salt thereof, optionally in a pharmaceutical composition as described herein can be administered in an effective amount to a host to degrade Hypermethylated in Cancer 1 (HIC1) protein. Hypermethylated in Cancer 1 protein contains an N-terminal BTB/POZ protein-protein interaction domain and 5 Kruppel-like C2H2 zinc finger motifs in its C-terminal half (see, e.g., Deltour et al., The carboxy-terminal end of the candidate tumor suppressor gene HIC-1 is phylogenetically conserved. Biochim. Biophys. Acta 1443: 230-232, 1998). Expression of Hypermethylated in Cancer 1 protein gene disorder Miller-Dieker syndrome (see, e.g., Grimm et al., Isolation and embryonic expression of the novel mouse gene Hic1, the homologue of HIC1, a candidate gene for the Miller-Dieker syndrome. Hum. Molec. Genet. 8: 697-710, 1999).

A tricyclic compound of the present invention, or pharmaceutical salt thereof, optionally in a pharmaceutical composition as described herein is administered in an effective amount to a host to degrade Hypermethylated in Cancer 2 (HIC2) protein.

A tricyclic compound of the present invention, or pharmaceutical salt thereof, optionally in a pharmaceutical composition as described herein can be administered in an effective amount to a host to degrade GDNF-Inducible Zinc Finger Protein 1 (GZF1). GDNF-Inducible Zinc Finger Protein 1 is a transcriptional regulator that binds to a 12-bp GZF1 response element (GRE) and represses gene transcription (see, e.g., Morinaga et al., GDNF-inducible zinc finger protein 1 is a sequence-specific transcriptional repressor that binds to the HOXA10 gene regulatory region. Nucleic Acids Res. 33: 4191-4201, 2005).

Alternatively, for example, a tricyclic compound of the present invention, or pharmaceutical salt thereof, optionally in a pharmaceutical composition as described herein can be administered in an effective amount to a host to degrade Odd Skipped Related 1 (OSR1) protein. Odd Skipped Related 1 protein contains 3 C2H2-type zinc fingers, a tyrosine phosphorylation site, and several putative PXXP SH3 binding motifs (see, e.g., Katoh, M. Molecular cloning and characterization of OSR1 on human chromosome 2p24. Int. J. Molec. Med. 10: 221-225, 2002).

In another aspect, a tricyclic compound of the present invention, or pharmaceutical salt thereof, optionally in a pharmaceutical composition as described herein is administered in an effective amount to a host to degrade Odd Skipped Related 2 (OSR2) protein.

In yet another embodiment, a selected tricyclic compound of the present invention, or pharmaceutical salt thereof, optionally in a pharmaceutical composition as described herein can be administered to a host in an effective amount to degrade SAL-Like 4 (SALL4) protein. SAL-Like 4 protein has 3 C2H2 double zinc finger domains of the SAL-type, the second of which has a single C2H2 zinc finger attached at its C-terminal end, as well as an N-terminal C2HC zinc finger motif typical for vertebrate SAL-like proteins. SAL-Like 4 protein mutations are associated with the development of Duane-radial ray syndrome (see, e.g., Borozdin et al., SALL4 deletions are a common cause of Okihiro and acro-renal-ocular syndromes and confirm haploinsufficiency as the pathogenic mechanism. J. Med. Genet. 41: e113, 2004). SAL-Like 4 protein overexpression is associated with the promotion, growth and metastasis of a number of cancers, including lung cancer, gastric cancer, liver cancer, renal cancer, myelodysplastic syndrome, germ cell-sex cord-stromal tumors including dysgerminoma, yolk sac tumor, and choriocarcinoma, and leukemia, among others. Accordingly, in certain embodiments, a compound of the present invention, or pharmaceutical salt thereof, optionally in a pharmaceutical composition as described herein is used to degrade SAL-Like 4 protein for the treatment of a cancer, including but not limited to, gastric cancer, liver cancer, renal cancer, myelodysplastic syndrome, germ cell-sex cord-stromal tumors including dysgerminoma, yolk sac tumor, and choriocarcinoma, and leukemia, among others.

A selected tricyclic compound of the present invention, or pharmaceutical salt thereof, optionally in a pharmaceutical composition as described herein can also be administered in an effective amount to a host to degrade B-Cell Lymphoma 6 (BCL6) protein. B-Cell Lymphoma 6 contains an autonomous transrepressor domain, and 2 noncontiguous regions, including the POZ motif, mediate maximum transrepressive activity. Translocations of the B-Cell Lymphoma 6 gene translocations are associated with the development of myeloproliferative disorders such as non-Hodgkin lymphomas. B-Cell Lymphoma 6 overexpression prevents increase in reactive oxygen species and inhibits apoptosis induced by chemotherapeutic reagents in cancer cells (see, e.g., Tahara et al., Overexpression of B-cell lymphoma 6 alters gene expression profile in a myeloma cell line and is associated with decreased DNA damage response. Cancer Sci. 2017 August; 108(8):1556-1564; Cardenas et al., The expanding role of the BCL6 oncoprotein as a cancer therapeutic target. Clin Cancer Res. 2017 Feb. 15; 23(4): 885-893). Accordingly, in certain embodiments, a compound of the present invention, or pharmaceutical salt thereof, optionally in a pharmaceutical composition as described herein is used to degrade B-Cell Lymphoma 6 for the treatment of a cancer, including but not limited to a hematologic or solid tumor, for example, but not limited to a B-cell leukemia or lymphoma, for example, but not limited to diffuse large B-cell lymphomas (DLBCLs) and ABC-DLBCL subtypes, B-acute lymphoblastic leukemia, chronic myeloid leukemia, breast cancer and non-small cell lung cancer.

Further, a selected tricyclic compound of the present invention, or pharmaceutical salt thereof, optionally in a pharmaceutical composition as described herein is administered in an effective amount to a host to degrade B-Cell Lymphoma 6B (BCL6B) protein. B-Cell Lymphoma 6B protein contains an N-terminal POZ domain and 5 C-terminal zinc finger motifs, and is believed to act as a transcriptional repressor (see, e.g., Okabe et al., BAZF, a novel Bcl6 homolog, functions as a transcriptional repressor. Molec. Cell. Biol. 18: 4235-4244, 1998). Overexpression of B-Cell Lymphoma 6B protein has been associated with the development of germ cell tumors (Ishii et al., FGF2 mediates mouse spermatogonial stem cell self-renewal via upregulation of Etv5and Bcl6bthrough MAP2K1activation. Development 139, 1734-1743 (2012)). Accordingly, in certain embodiments, a compound of the present invention, or pharmaceutical salt thereof, optionally in a pharmaceutical composition as described herein is used to degrade B-Cell Lymphoma 6B for the treatment of a cancer, including but not limited to, a germ cell cancer including but not limited to germinoma, including dysgerminoma and seminoma, a teratoma, yolk sac tumor, and choriocarcinomas.

Alternatively, a selected tricyclic compound of the present invention, or pharmaceutical salt thereof, optionally in a pharmaceutical composition as described herein can be administered in an effective amount to a host to degrade Early Growth Response 1 (EGR1) protein. Early Growth Response 1 protein directly controls transforming growth factor-beta-1 gene expression, and has been shown to be involved in the proliferation and survival of prostate cancer cells by regulating several target genes, including cyclin D2 (CCND2), p19(Ink4d), and Fas, as well as glioma cells (see, e.g., Virolle et al., Erg1 promotes growth and survival of prostate cancer cells: identification of novel Egr1 target genes. J. Biol. Chem. 278: 11802-11810, 2003; Chen et al., Inhibition of EGR1 inhibits glioma proliferation by targeting CCND1 promoter. Journal of Experimental & Clinical Cancer Research Volume 36, Article number: 186 (2017)). One mechanism used by Egr1 to confer resistance to apoptotic signals was the ability of Egr1 to inhibit Fas expression, leading to insensitivity to FasL. Accordingly, in certain embodiments, a compound of the present invention, or pharmaceutical salt thereof, optionally in a pharmaceutical composition as described herein is used to degrade Early Growth Response 1 protein for the treatment of a cancer, including but not limited to a prostate cancer or glioma including, but not limited to, pilocytic astrocytoma, diffuse astrocytoma, anaplastic astrocytoma, glioblastoma multiforme.

In yet another aspect, a selected tricyclic compound of the present invention, or pharmaceutical salt thereof, optionally in a pharmaceutical composition as described herein can be administered in an effective amount to a host to degrade Early Growth Response 4 (EGR4) protein. Early Growth Response 4 protein contains 3 zinc fingers of the C2/H2 subtype near the carboxy terminus (see, e.g., Crosby et al., Neural-specific expression, genomic structure, and chromosomal localization of the gene encoding the zinc-finger transcription factor NGFI-C. Proc. Nat. Acad. Sci. 89: 4739-4743, 1992). Overexpression of Early Growth Response 4 protein has been associated with the development of cholangiocarcinoma (see, e.g., Gong et al., Gramicidin inhibits cholangiocarcinoma cell growth by suppressing EGR4. Artificial Cells, Nanomedicine, and Biotechnology, 48:1, 53-59 (2019)). Accordingly, in certain embodiments, a compound of the present invention, or pharmaceutical salt thereof, optionally in a pharmaceutical composition as described herein is used to degrade Early Growth Response 4 protein for the treatment of a cancer, including but not limited to cholangiocarcinoma.

In certain aspects, a selected tricyclic compound of the present invention, or pharmaceutical salt thereof, optionally in a pharmaceutical composition as described herein can be administered in an effective amount to a host to degrade Sal-Like 1 (SALL1) protein.

In an alternative embodiment, a selected tricyclic compound of the present invention, or pharmaceutical salt thereof, optionally in a pharmaceutical composition as described herein can be administered in an effective amount to a host to degrade Sal-Like 3 (SALL3) protein. The SALL3 protein contains 4 double zinc finger (DZF) domains, each of which contains sequences identical or closely related to the SAL box, a characteristic stretch of 8 amino acids within the second zinc finger motif.

In yet another embodiment, a selected tricyclic compound of the present invention, or pharmaceutical salt thereof, optionally in a pharmaceutical composition as described herein can be administered in an effective amount to a host to degrade Tumor protein p63 (TP63). Tumor protein p63 overexpression has been associated with lung cancer development and poor prognosis, radiation resistance in oral cancers and head and neck cancers, squamous cell carcinoma of the skin (see, e.g., Massion et al., Significance of p63 amplification and overexpression in lung cancer development and prognosis. Cancer Res. 2003 Nov. 1; 63(21): 7113-21; Moergel et al., Overexpression of p63 is associated with radiation resistance and prognosis in oral squamous cell carcinoma. Oral Oncol. 2010 September; 46(9):667-71). Accordingly, in certain embodiments, a compound of the present invention, or pharmaceutical salt thereof, optionally in a pharmaceutical composition as described herein is used to degrade Tumor protein p63 for the treatment of a cancer, including but not limited to non-small cell lung cancer, small cell lung cancer, head and neck cancer, and squamous cell carcinoma of the skin.

In yet another embodiment, a selected tricyclic compound of the present invention, or pharmaceutical salt thereof, optionally in a pharmaceutical composition as described herein can be administered in an effective amount to a host to degrade Widely-Interspaced Zinc Finger-Containing (WIZ) Protein.

A selected tricyclic compound of the present invention, or pharmaceutical salt thereof, optionally in a pharmaceutical composition as described herein can also be administered in an effective amount to a host to degrade Zinc Finger and BTB Domain Containing Protein 7A (ZBTB7A). Zinc Finger and BTB Domain Containing Protein 7A expression is associated with a number of cancers, including prostate cancer, non-small cell lung cancer, bladder, breast cancer, prostate, ovarian, oral squamous cell carcinoma, and hepatocellular carcinoma (see, e.g., Han et al., ZBTB7A Mediates the Transcriptional Repression Activity of the Androgen Receptor in Prostate Cancer. Cancer Res 2019; 79:5260-71; Molloy et al., ZBTB7A governs estrogen receptor alpha expression in breast cancer. Journal of Molecular Cell Biology, Volume 10, Issue 4, August 2018, Pages 273-284). Accordingly, in certain embodiments, a compound of the present invention, or pharmaceutical salt thereof, optionally in a pharmaceutical composition as described herein is used to degrade Zinc Finger and BTB Domain Containing Protein 7A for the treatment of a cancer, including but not limited to prostate cancer, non-small cell lung cancer, breast cancer, oral squamous cell carcinoma, prostate, ovarian, glioma, bladder, and hepatocellular carcinoma.

In other aspects, a selected tricyclic compound of the present invention, or pharmaceutical salt thereof, optionally in a pharmaceutical composition as described herein can be administered in an effective amount to a host to degrade Zinc Finger and BTB Domain Containing Protein 7B (ZBTB7B). Zinc Finger and BTB Domain Containing Protein 7B expression has been associated with breast, prostate, urothelial, cervical, and colorectal cancers. Accordingly, in certain embodiments, a compound of the present invention, or pharmaceutical salt thereof, optionally in a pharmaceutical composition as described herein is used to degrade Zinc Finger and BTB Domain Containing Protein 7B for the treatment of a cancer, including but not limited to breast, prostate, urothelial, cervical, and colorectal cancers.

A selected tricyclic compound of the present invention, or pharmaceutical salt thereof, optionally in a pharmaceutical composition as described herein can be administered in an effective amount to a host to degrade casein kinase I, alpha I (CK1α or CK1-alpha). CK1-alpha is a bifunctional regulator of NF-kappa-B (see, e.g., Bidere et al., Casein kinase 1-alpha governs antigen-receptor-induced NF-kappa-B activation and human lymphoma cell survival. Nature 458: 92-96, 2009). CK1-alpha dynamically associates with the CBM complex on T cell receptor engagement to participate in cytokine production and lymphocyte proliferation. However, CK1-alpha kinase activity has a contrasting role by subsequently promoting the phosphorylation and inactivation of CARMA1. CK1-alpha has thus a dual 'gating' function which first promotes and then terminates receptor-induced NF-kappa-B. ABC DLBCL cells required CK1-alpha for constitutive NF-kappa-B activity, indicating that CK1-alpha functions as a conditionally essential malignancy gene. Expression of CK1-alpha has been associated with myelodysplastic disease with depletion of 5q (del(5q) MDS (see, e.g., Kronke, et al., Lenalidomide induces ubiquitination and degradation of CK1-alpha in del(5q) MDS. Nature 523: 183-188, 2015), colorectal cancer, breast cancer, leukemia, multiple myeloma, lung cancer, diffuse large B cell lymphoma, non-small cell lung cancer, and pancreatic cancer, amongst others (see, e.g., Richter et al., CK1α overexpression correlates with poor survival in colorectal cancer. BMC Cancer. 2018; 18: 140; Jiang et al., Casein kinase 1α: biological mechanisms and theranostic potential. Cell Commun Signal. 2018; 16: 23). Accordingly, in some embodiments, a compound of the present invention, or pharmaceutical salt thereof, optionally in a pharmaceutical composition as described herein is used to degrade casein kinase I, alpha I for the treatment of a cancer, including but not limited to colorectal cancer, breast cancer, leukemia, multiple myeloma, lung cancer, diffuse large B cell lymphoma, non-small cell lung cancer, pancreatic cancer, myelodysplastic syndromes including but not limited to 5q-syndrome, refractory cytopenia with unilineage dysplasia, refractory anemia, refractory neutropenia, and refractory thrombocytopenia, refractory anemia with ring sideroblasts, refractory cytopenia with multilineage dysplasia (RCMD), refractory anemias with excess blasts (REAB) I and II, refractory anemia with excess blasts in transformation (RAEB-T), chronic myelomonocytic leukemia (CMML), myelodysplasia unclassifiable, refractory cytopenia of childhood (dysplasia in childhood).

A selected tricyclic compound of the present invention, or pharmaceutical salt thereof, optionally in a pharmaceutical composition as described herein can also be administered in an effective amount to a host to degrade Family with Sequence Similarity 83, Member H (FAM83H). FAM83H is believed to be involved in the progression of human cancers in conjunction with tumor-associated molecules, such as MYC and β-catenin, and overexpression has been associated with lung, breast, colon, liver, ovary, pancreas, prostate, oesophageal, glioma, hepatocellular carcinoma, thyroid, renal cell carcinoma, osteosarcoma, and stomach cancers (see, e.g., Kim et al., FAM83H is involved in stabilization of β-catenin and progression of osteosarcomas. Journal of Experimental & Clinical Cancer Research volume 38, Article number: 267 (2019)). Accordingly, in some embodiments, a compound of the present invention, or pharmaceutical salt thereof, optionally in a pharmaceutical composition as described herein is used to degrade FAM83H for the treatment of a cancer, including but not limited to, lung, breast, colon, liver, ovary, pancreas, prostate, oesophageal, glioma, thyroid, liver cancer, including but not limited to hepatocellular carcinoma, renal cell carcinoma, osteosarcoma, and stomach cancers.

Alternatively, a selected tricyclic compound of the present invention, or pharmaceutical salt thereof, optionally in a pharmaceutical composition as described herein can be administered in an effective amount to a host to degrade Zinc-finger and BTB domain containing protein 16 (ZBTB16). Overexpression and translocation of ZBTB16 has been associated with the development of various hematological cancers, including acute promyelocytic leukemia (see, e.g., Zhang et al., Genomic sequence, structural organization, molecular evolution, and aberrant rearrangement of promyelocytic leukemia zinc finger gene. Proc. Nat. Acad. Sci. 96: 11422-11427, 1999). Accordingly, in some embodiments, a compound of the present invention, or pharmaceutical salt thereof, optionally in a pharmaceutical composition as described herein is used to degrade ZBTB16 for the treatment of a cancer, including but not limited to a hematological cancer including but not limited to a leukemia or lymphoma, including but not limited to acute promyelocytic leukemia, acute lymphoblastic leukemia, Adult T-cell lymphoma/ATL, and Burkitt's lymphoma.

In an alternative embodiment, a selected tricyclic compound of the present invention, or pharmaceutical salt thereof, optionally in a pharmaceutical composition as described herein can be administered in an effective amount to a host to degrade AT-Rich Interaction Domain-Containing Protein 2 (ARID2). ARID2 is a subunit of the PBAF chromatin-remodeling complex, which facilitates ligand-dependent transcriptional activation by nuclear receptors (see, e.g., Yan et al., PBAF chromatin-remodeling complex requires a novel specificity subunit, BAF200, to regulate expression of selective interferon-responsive genes. Genes Dev. 19: 1662-1667, 2005).

In another aspect, a selected tricyclic compound of the present invention, or pharmaceutical salt thereof, optionally in a pharmaceutical composition as described herein can be administered in an effective amount to a host to degrade Polybromo associated BAF (PBAF). Mutations in PBAF have been associated with the development of synovial sarcomas and multiple myeloma (see, e.g., Alfert et al., The BAF complex in development and disease. Epigenetics & Chromatin volume 12, Article number: 19 (2019)). Accordingly, in some embodiments, a compound of the present invention, or pharmaceutical salt thereof, optionally in a pharmaceutical composition as described herein is used to degrade PBAF for the treatment of a cancer, including but not limited to synovial sarcoma and multiple myeloma.

In other embodiments, the selected tricyclic compound of the present invention when administered after binding to and forming a neomorphic surface with cereblon, is capable of binding a number of neosubstrates resulting in a form of "poly-pharmacology." For example, the tricyclic compound may bind and degrade IRAK4, IKZF1 and/or 3, and or Aiolos. In other examples, the tricyclic compound, when administered, is able to degrade two or more of the proteins named above or herein, for example, SALL4 and IKZF 1/3 or IKZF2/4.

In certain embodiments, a tricyclic compound of the present invention has degradation selectivity in vitro for IKZF2 and/or IKZF4 over IKZF1 and/or IKZF3 of at least about 1.5, 2, 3, 5, or even 10-fold in a standard HiBiT bioluminescence assay. The HiBiT assay is a well known assay that has been thoroughly described in the literature.

IV. Combination Therapy

A selected compound of Formula I or a pharmaceutically acceptable salt thereof can be used in an effective amount, either alone or in combination, to treat a patient as described further herein.

The disclosed compounds described herein can be used in an effective amount alone or in combination with another compound of the present invention or another bioactive agent or second therapeutic agent to treat a patient such as a human with a disorder, including but not limited to those described herein.

The term "bioactive agent" is used to describe an agent, other than the selected compound according to the present invention, which can be used in combination or alternation with a compound of the present invention to achieve a desired result of therapy. In certain embodiments, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a patient in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDIO680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In certain embodiments the checkpoint inhibitor is selected from nivolumab/OPDIVO®; pembrolizumab/KEYTRUDA®; and pidilizumab/CT-011, MPDL3280A/RG7446; MEDI4736; MSB0010718C; BMS 936559, a PDL2/lg fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including, but not limited to, a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including, but not limited to a selective androgen receptor modulator, a selective androgen receptor degrader, a complete androgen receptor degrader, or another form of partial or complete androgen antagonist. In certain embodiments, the prostate or testicular cancer is androgen-resistant.

Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In certain embodiments, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In certain embodiments, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In certain embodiments, the bioactive agent is an HER-2 inhibitor. Examples of HER-2 inhibitors include trastuzumab, lapatinib, ado-trastuzumab emtansine, and pertuzumab.

In certain embodiments, the bioactive agent is a CD20 inhibitor. Examples of CD20 inhibitors include obinutuzumab, rituximab, fatumumab, ibritumomab, tositumomab, and ocrelizumab.

In certain embodiments, the bioactive agent is a JAK3 inhibitor. Examples of JAK3 inhibitors include tasocitinib.

In certain embodiments, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole;

methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In certain embodiments, the bioactive agent is a kinase inhibitor. In certain embodiments, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include, but are not limited to, Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl] oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl) amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl) phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4] triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile) (dactolisib), XL-765 (N-(3-(N-(3-(3,5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10,11-hexahydroindeno[4.5 h]isochromen-10-yl]acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422).

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, but are not limited to, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl] methyl dihydrogen phosphate), fostamatinib disodium salt (sodium (6-((5-fluoro-2-((3,4,5-trimethoxyphenyl)amino) pyrimidin-4-yl)amino)-2,2-dimethyl-3-oxo-2H-pyrido[3,2-b][1,4]oxazin-4(3H)-yl)methyl phosphate), BAY 61-3606

(2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In certain embodiments, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In certain embodiments, the bioactive agent is a Raf inhibitor. Raf inhibitors are known and include, for example, Vemurafinib (N-[3-[[5-(4-Chlorophenyl)-1H-pyrrolo[2,3-b] pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl] pyridin-4-yl]oxy-N-[4-(trifluoromethyl)phenyl] benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino] phenoxy]-N-Methyl-2pyridinecarboxaMide 1-Oxide), PLX-4720, dabrafenib (GSK2118436), GDC-0879, RAF265, AZ 628, Sf590885, ZM336372, GW5074, TAK-632, CEP-32496, LY3009120, and GX818 (Encorafenib).

In certain embodiments, the bioactive agent is an AKT inhibitor, including, but not limited to, MK-2206, GSK690693, Perifosine, (KRX-0401), GDC-0068, Triciribine, AZD5363, Honokiol, PF-04691502, and Miltefosine, a FLT-3 inhibitor, including, but not limited to, P406, Dovitinib, Quizartinib (AC220), Amuvatinib (MP-470), Tandutinib (MLN518), ENMD-2076, and KW-2449, or a combination thereof.

In certain embodiments, the bioactive agent is an mTOR inhibitor. Examples of mTOR inhibitors include, but are not limited to, rapamycin and its analogs, everolimus (Afinitor), temsirolimus, ridaforolimus, sirolimus, and deforolimus. Examples of MEK inhibitors include but are not limited to tametinib/GSKl120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2- fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In certain embodiments, the bioactive agent is a RAS inhibitor. Examples of RAS inhibitors include but are not limited to Reolysin and siG12D LODER.

In certain embodiments, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhbitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, of atumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In certain embodiments the compound is administered in combination with ifosfamide.

In certain embodiments, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™).

Examples of additional suitable chemotherapeutic agents include, but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or other chemical compound useful in the treatment of cancer). Examples of chemotherapeutic agents include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-1 1); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example combination dosing regimes are described in Saltz et al., Proc. Am. Soc. Clin. Oncol. 18:233a (1999) and Douillard et al., Lancet 355(9209): 1041-1047 (2000).

Additional therapeutic agents that can be administered in combination with a Compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In certain embodiments, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In some embodiments, the bioactive agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-l-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The combination therapy may include a therapeutic agent which is a non-drug treatment. For example, the compound could be administered in addition to radiation therapy, cryotherapy, hyperthermia, and/or surgical excision of tumor tissue.

In certain embodiments the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

In certain embodiments the second therapeutic agent is administered on a different dosage schedule than the compound of the present invention. For example the second therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In another embodiment the first therapeutic agent has a treatment holiday. For example the first therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In certain embodiments both the first and second therapeutic have a treatment holiday.

V. Pharmaceutical Compositions

The compound of Formula I as described herein can be administered as the neat chemical, but are more typically administered as a pharmaceutical composition, that includes an effective amount for a patient, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the pharmaceutical composition is in a dosage form that contains from about 0.005 mg to about 2000 mg, from about 1 mg to about 1000 mg, from about 10 mg to about 800 mg, or from about 20 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.005, 0.01, 0.025, 0.05, 0.1, 1, 5, 10, 25, 50, 100, 200, 250, 300, 400, 500, 600, 700, or 750 mg of active compound, or its salt and at most about 1 gram of active compound or its salt.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments the compound of the present invention is administered with a treatment holiday in between treatment cycles. For example the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

In some embodiments a loading dose is administered to begin treatment. For example, the compound may be administered in a dosage that is at least about 1.5×, 2×, 2.5×, 3×, 3.5×, 4×, 4.5×, 5×, 5.5×, 6×, 6.5×, 7×, 7.5×, 8×, 8.5×, 9×, 9.5×, or 10× higher dose to initiate treatment than the maintenance dose treatment cycle. Additional exemplary loading doses include at least about 1.5×, 2×, 2.5×, 3×, 3.5×, 4×, 4.5×, 5×, 5.5×, 5×, 6.5×, 7×, 7.5×, 8×, 8.5×, 9×, 9.5×, or 10× higher dose on the first 1, 2, 3, 4, 5, 6, 7, 8, 9, or 10 days of treatment followed by the maintenance dose on the remaining days of treatment in the treatment cycle.

The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent.

These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

A pharmaceutically or therapeutically effective amount of the composition will be delivered to the patient. The precise effective amount will vary from patient to patient, and will depend upon the species, age, the subject's size and health, the nature and extent of the condition being treated, recommendations of the treating physician, and the therapeutics or combination of therapeutics selected for administration. The effective amount for a given situation can be determined by routine experimentation.

In certain embodiments a therapeutic amount may for example be in the range of about 0.0001 mg/kg to about 25 mg/kg body weight. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In certain embodiments the dose ranges from about 0.001-10 mg/kg of patient bodyweight, for example about 0.0001 mg/kg, about 0.0005 mg/kg, about 0.001 mg/kg, about 0.005 mg/kg, about 0.01 mg/kg, about 0.05 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 1 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10 mg/kg.

In certain embodiments a therapeutic amount may for example be in the range of about 0.01 mg/kg to about 250 mg/kg body weight, more typically about 0.1 mg/kg to about 10 mg/kg, in at least one dose. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In certain embodiments the dose ranges from about 0.01-100 mg/kg of patient bodyweight, for example about 0.01 mg/kg, about 0.05 mg/kg, about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packed tablets, capsules, and powders in vials or ampoules. Also, the unit dosage form can be a capsule, tablet, cachet, or lozenge itself, or it can be the appropriate number of any of these in packaged form.

In certain embodiments the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Thus, the composition of the disclosure can be administered as a pharmaceutical formulation including one suitable for oral (including buccal and sub-lingual), rectal, nasal, topical, transdermal, pulmonary, vaginal or parenteral (including intramuscular, intra-arterial, intrathecal, subcutaneous and intravenous), injections, inhalation or spray, intra-aortal, intracranial, subdermal, intraperitioneal, subcutaneous, or by other means of administration containing conventional pharmaceutically acceptable carriers. A typical manner of administration is oral, topical or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sublingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. The compositions will include an effective amount of the selected drug in combination with a pharmaceutically acceptable carrier and, in addition, can include other pharmaceutical agents, adjuvants, diluents, buffers, and the like.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to adjuvants, binders, buffering agents, coloring agents, diluents, disintegrants, excipients, emulsifiers, flavorants, gels, glidents, lubricants, preservatives, stabilizers, surfactants, solubilizer, tableting agents, wetting agents or solidifying material.

Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited, to liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in Remington's Pharmaceutical Sciences, 18th Edition (Easton, Pennsylvania: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment provided is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

In certain embodiments the excipient is selected from butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The pharmaceutical compositions/combinations can be formulated for oral administration. For oral administration, the composition will generally take the form of a tablet, capsule, a softgel capsule or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In certain embodiments, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Formulations suitable for rectal administration are typically presented as unit dose suppositories. These may be prepared by admixing the active compound with one or more conventional solid carriers, for example, cocoa butter, and then shaping the resulting mixture.

In certain embodiments, the pharmaceutical composition is suitable for topical application to the skin using a mode of administration and defined above.

In certain embodiments, the pharmaceutical composition is suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound.

In certain embodiments, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

VI. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure or enriched enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in certain embodiments. A wide variety of chiral stationary phases are commercially available.

General Synthesis Scheme 1

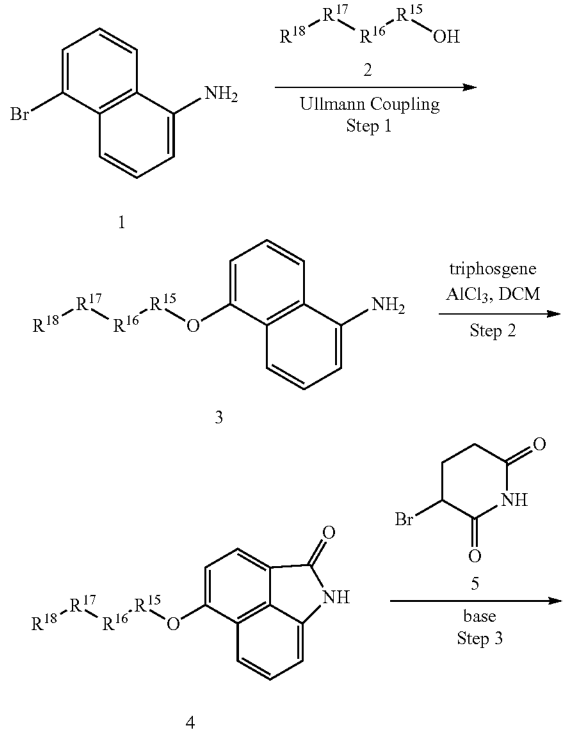

1

3

4

-continued

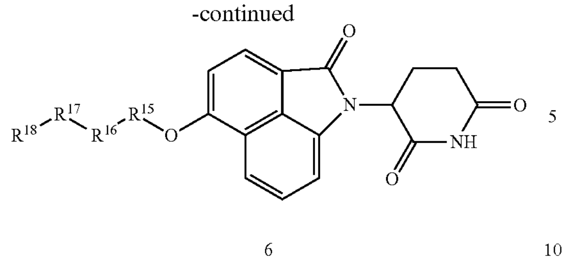

6

In some aspects, a compound of Formula I can be synthesized according to the route provided in General Synthesis Scheme 1. In step 1, intermediate 1 is reacted with 2 in the presence of a copper catalyst (for example, copper(I) iodide, copper(I) chloride, or alternatively another suitable copper catalyst used in Ullmann coupling conditions), a ligand (for example, bipyridine, 1,10-phenanthroline, dimethylethylenediamine, or alternatively another suitable ligand used in Ullmann coupling conditions), and a base (for example, cesium carbonate, potassium carbonate, tribasic potassium phosphate, or alternatively another suitable base used in Ullmann coupling conditions) in organic solvent (for example, dimethylsulfoxide, acetonitrile, or dioxane) at elevated temperature to afford 3. In step 2, 3 is reacted with triphosgene in the presence of aluminum trichloride in dichloromethane to afford 4. In step 3, intermediate 4 is reacted with a base (for example, sodium hydride) in an organic solvent (for example, tetrahydrofuran or dichloromethane) followed by the addition of 5 to afford 6.

General Synthesis Scheme 2

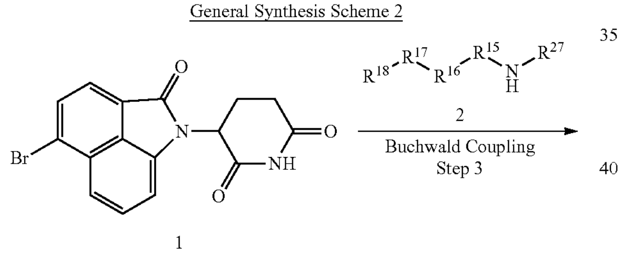

1

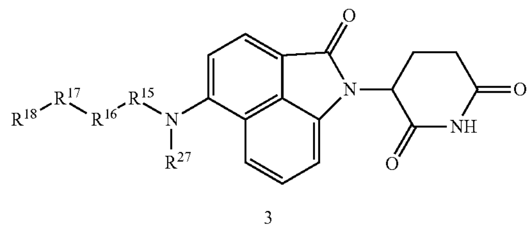

3

In some aspects, a compound of Formula I can be synthesized according to the route provided in General Synthesis Scheme 2. In step 1, intermediate 1 is reacted with 2 in the presence of a palladium catalyst (for example, palladium(II) acetate, $Pd_2(dba)_3$, or alternatively another suitable palladium catalyst used in Buchwald-Hartwig coupling conditions), a phosphine ligand (for example, BINAP, XantPhos, or alternatively another suitable phosphine ligand used in Buchwald-Hartwig coupling conditions), and a base (for example, potassium tert-butoxide, cesium carbonate, or alternatively another suitable base used in Buchwald-Hartwig coupling conditions) in organic solvent (for example, toluene, THF, dioxane, or DMF) at elevated temperature to afford 3.

General Synthesis Scheme 3

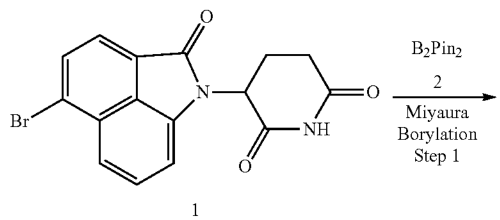

1

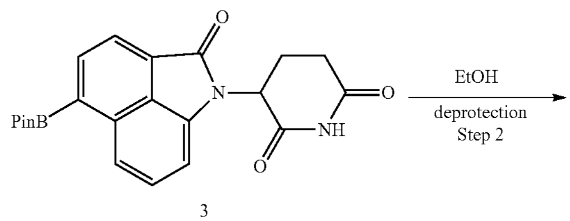

3

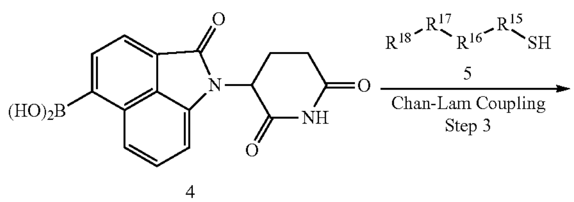

4

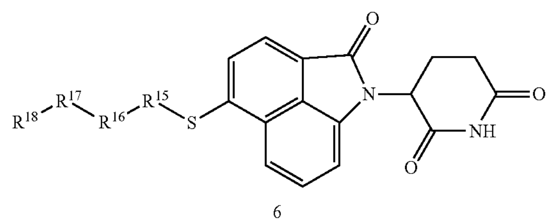

6

In some aspects, a compound of Formula I can be synthesized according to the route provided in General Synthesis Scheme 3. In step 1, intermediate 1 is reacted with 2 in the presence of a palladium catalyst (for example, $PdCl_2$(dppf), $PdCl_2(PPh_3)$, or alternatively another suitable palladium catalyst used in Miyaura coupling conditions), a ligand (for example, XPhos, $PPh_3$, or alternatively another suitable ligand used in Miyaura coupling conditions), and a base (for example, potassium acetate, potassium ethoxide, potassium carbonate, or alternatively another suitable base used in Miyaura coupling conditions) in organic solvent (for example, toluene, DMA, or dioxane) at elevated temperature to afford 3. In step 2, intermediate 3 is reacted with EtOH at elevated temperature to afford 4. In step 3, compound 4 is reacted with 5 in the presence of a copper catalyst (for example, copper(II) bromide, copper(II) acetate, or alternatively another suitable copper catalyst used in Chan-Lam coupling conditions) and a base (for example, pyridine, 4-dimethylaminopyridine, potassium tert-butoxide, or alternatively another suitable base used in Chan-Lam coupling conditions) in organic solvent (for example, methanol, acetonitrile, or dichloromethane) under ambient air to afford 6.

General Synthesis Scheme 4

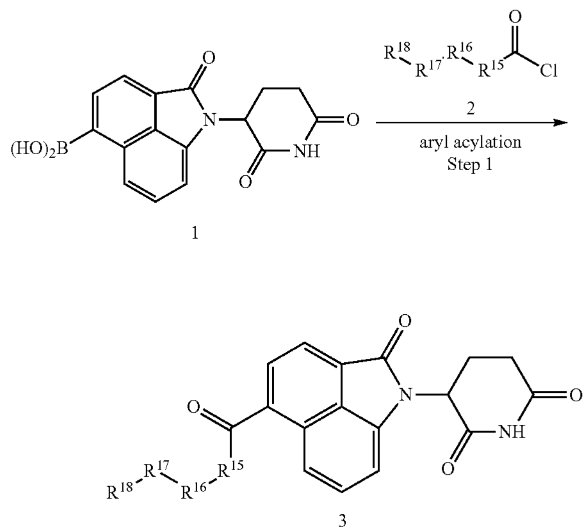

In some aspects, a compound of Formula I can be synthesized according to the route provided in General Synthesis Scheme 4. In step 1, intermediate 1 is reacted with 2 in the presence of a palladium catalyst (for example, $Pd(OAc)_2$, $Pd(PPh_3)_4$, or alternatively another suitable palladium catalyst), a ligand (for example, P(p-MeOPh)$_3$, $PPh_3$, $PCy_3$ or alternatively another suitable ligand), water, and pivalic anhydride in organic solvent (for example, dimethoxyethane, THF, or toluene) at elevated temperature to afford 3.

General Synthesis Scheme 5

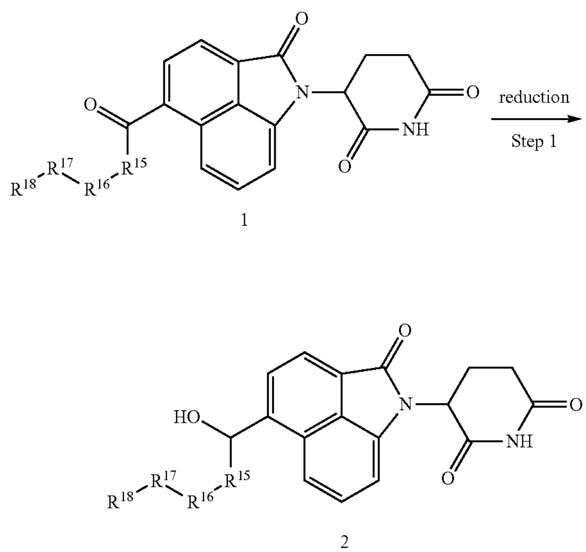

In some aspects, a compound of Formula I can be synthesized according to the route provided in General Synthesis Scheme 5. In step 1, intermediate 1 is reacted with a suitable carbonyl reductant (for example, sodium borohydride) in organic solvent (for example, ethanol or methanol) to afford General Synthesis Scheme 6

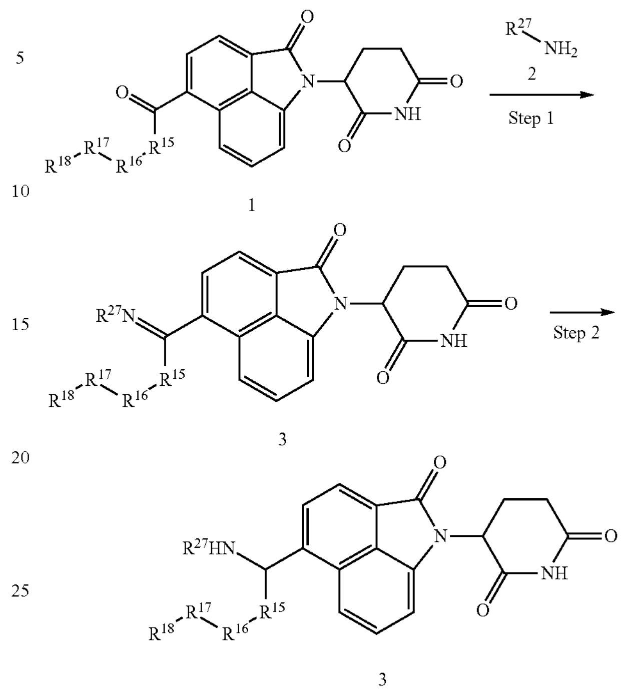

In some aspects, a compound of Formula I can be synthesized according to the route provided in General Synthesis Scheme 6. In step 1, intermediate 1 is reacted with 2 in the presence of a suitable desiccant (for example, molecular sieves or $MgSO_4$) in organic solvent (for example, dichloromethane or toluene) to afford 3. In step 2, the imine of 3 is reduced to an amino group with an appropriate reducing agent.

General Synthesis Scheme 7

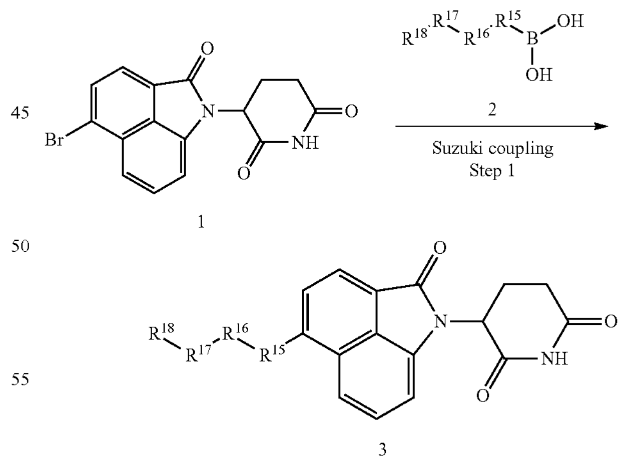

In some aspects, a compound of Formula I can be synthesized according to the route provided in General Synthesis Scheme 7. In step 1, intermediate 1 is reacted with 2 in the presence of a palladium catalyst (for example, $Pd(OAc)_2$, $Pd_2dba_3$, or alternatively another suitable palladium catalyst used in Suzuki coupling conditions), a ligand (for example, XPhos, $PCy_3$, or alternatively another suitable ligand used in Suzuki coupling conditions), and a base (for example, sodium carbonate, tribasic potassium phosphate, potassium carbonate, or alternatively another suitable base used in Suzuki coupling conditions) in aqueous organic solvent (for example, 10:1 toluene:water, 5:1 THF:water, or 1:1 ethanol:water) at elevated temperature to afford 3.

General Synthesis Scheme 8

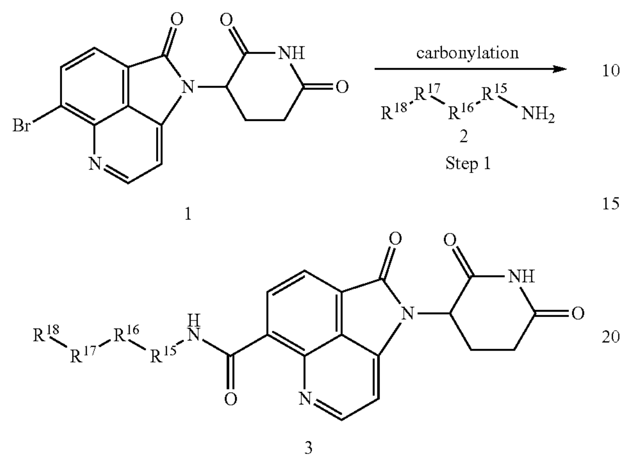

1

3

In some aspects a compound of Formula 1 can be synthesized according to the route provided in General Synthesis Scheme 8. In step 1, intermediate 1 is reacted with intermediate 2 in the presence of a palladium precatalyst (for example, for example, $Pd(OAc)_2$, $Pd_2dba_3$, or alternatively another suitable palladium catalyst used in palladium catalyzed carbonylations), a base (for example triethylamine, diisopropyl ethylamine, or alternatively another base used in palladium catalyzed carbonylations), CO gas, and a ligand (For example, for example, XantPhos, $PCy_3$, or alternatively another suitable ligand used in palladium catalyzed carbonylation reactions) in organic solvent (for example, DMF) at elevated temperature to afford 3.

Example 1. Compound 1 and 5-(4,4,5,5-Tetramethyl-1,3,2-dioxaborolan-2-yl)benzo[cd]indol-2(1H)-one

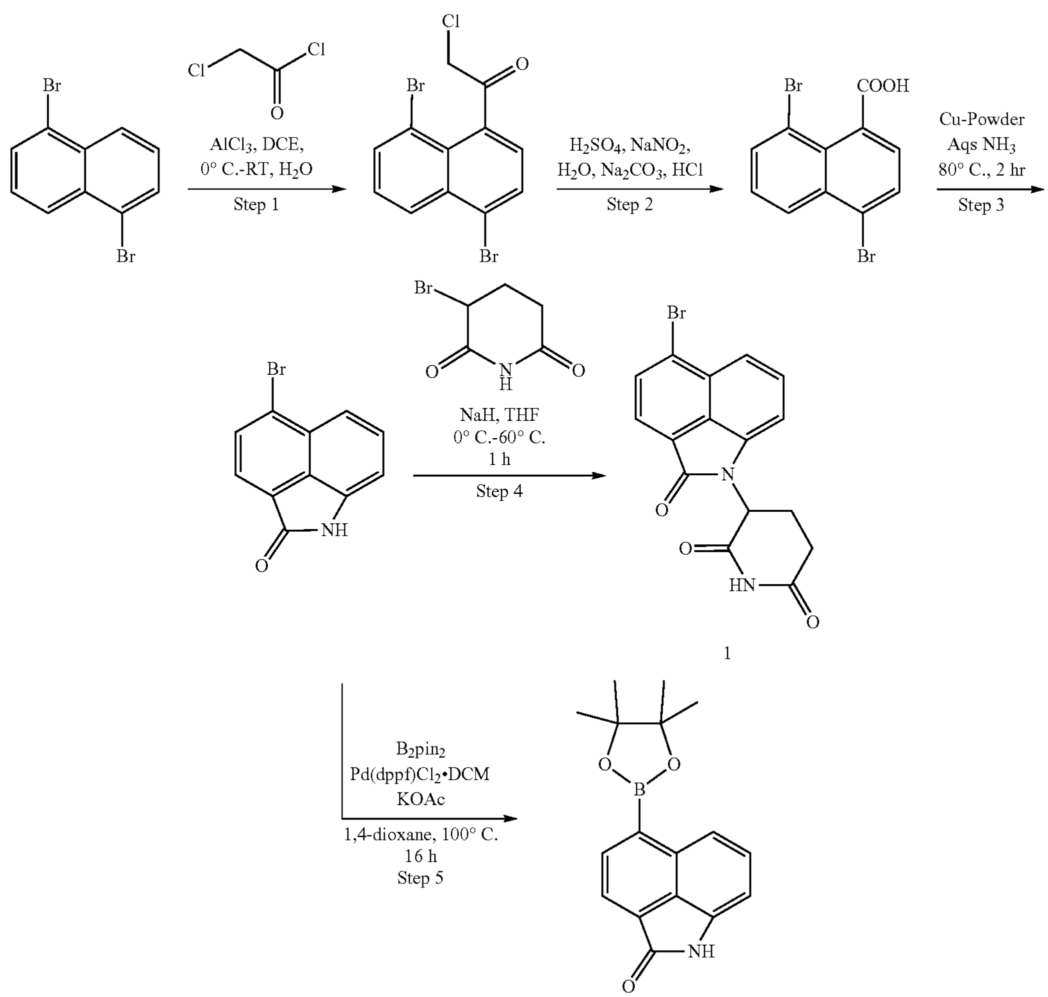

Step-1: Synthesis of 2-Chloro-1-(4,8-dibromonaphthalen-1-yl)ethan-1-one: A stirred solution of 1,5-dibromonaphthalene (162 g, 566.51 mmol) in DCE (2000 mL) was cooled to 0° C. and 2-chloroacetyl chloride (83.18 g, 736.46 mmol, 58.57 mL) was added dropwise. The resultant solution was stirred at 0° C. for 15 minutes followed by portion-wise addition of anhydrous aluminum chloride (98.20 g, 736.46 mmol, 40.25 mL). The resultant reaction mixture was then slowly warmed to room temperature and stirred for 16 hours. After completion (monitored by TLC) the reaction mixture was poured into ice cold water and extracted with DCM (twice). The combined organic extract was further washed with water and brine, dried over sodium sulfate, filtered and concentrated under reduced pressure. The crude thus obtained was purified by column chromatography (100-200 Silica; Gradient: 0-5% EtOAc in hexane) to afford 2-chloro-1-(4,8-dibromo-1-naphthyl)ethanone (150 g, 390 mmol) as an off-white solid. Yield-69%. $^1$H NMR (d$^6$-DMSO, 400 MHZ) δ 8.36 (dd, J=8.48, 0.72 Hz, 1H), 8.11-8.07 (m, 2H), 7.69 (t, J=8.04 Hz, 1H), 7.59 (d, J=7.8 Hz, 1H), 5.05 (s, 2H);

Step-2: Synthesis of 4,8-Dibromo-1-naphthoic acid: To a stirred solution of 2-chloro-1-(4,8-dibromo-1-naphthyl) ethanone (151 g, 416.62 mmol) in sulfuric acid (1.8 L) was added sodium nitrite (30.27 g, 438.75 mmol) at room temperature and the resultant reaction mixture was stirred at 65° C. for 45 minutes. After completion (monitored by TLC) the reaction mixture was poured into cold water (2 litres) and the resulting solid was filtered off. The solid thus obtained was added to a 10% sodium carbonate solution (4 lit) and stirred for 30 minutes at room temperature. The mixture was filtered; the filtrate was cautiously acidified with concentrated HCl under vigorous stirring and filtered again to remove insoluble impurity. The filtrate (aqueous) was then extracted with ethyl acetate (twice). The combined organic extract was further washed with brine, dried over sodium sulfate and concentrated under reduced pressure to afford 4,8-dibromonaphthalene-1-carboxylic acid (110 g, 299 mmol) as a light brown solid. Yield-72%. $^1$H NMR (d$^6$-DMSO, 400 MHZ) δ 13.48 (br s, 1H), 8.33 (d, J=8.36 Hz, 1H), 8.09 (d, J=7.4 Hz, 1H), 8.01 (d, J=7.72 Hz, 1H), 7.65 (t, J=8.0 Hz, 1H), 7.59 (d, J=7.72 Hz, 1H); LC MS [M−H]$^-$ 328.90.

Step-3: Synthesis of 5-Bromobenzo[cd]indol-2(1H)-one: To a stirred suspension of 4,8-dibromonaphthalene-1-carboxylic acid (65 g, 196.99 mmol) in aqueous ammonia (700 mL),) was added copper powder (3.25 g, 51.22 mmol) and the resultant reaction mixture was stirred at 80° C. for 2 hours. After completion (monitored by TLC) the reaction mixture was poured into ice-cooled water and was slowly acidified with concentrated HCl (pH-2) under vigorous stirring. The resulting yellow precipitate was filtered off and was further dried under reduced pressure to afford 5-bromo-1H-benzo[cd]indol-2-one (39 g, 151.68 mmol) as brown solid. Yield-77%. $^1$H NMR (d$^6$-DMSO, 400 MHZ) δ 10.88 (s, 1H), 8.05 (d, J=7.44 Hz, 1H), 7.88 (d, J=7.4 Hz, 1H), 7.61 (t, J=7.8 Hz, 1H), 7.53 (d, J=8.56 Hz, 1H), 7.04 (d, J=7.0 Hz, 1H); LC MS [M+H]$^+$ 248.2, 250.1.

Step-4: Synthesis of 3-(5-Bromo-2-oxobenzo[cd]indol-1(2H)-yl)piperidine-2,6-dione (Compound 1): To a suspension of 5-bromo-1H-benzo[cd]indol-2-one (25 g, 100.78 mmol) in dry THF (250 mL), sodium hydride (60% dispersion in mineral oil) (38.61 g, 1.01 mol) was added portion-wise while the temperature was maintained below 5° C. Once the addition was over, the resultant mixture was slowly warmed to room temperature and stirred for 15 minutes. The reaction mixture was again cooled to 0° C. and 3-bromopiperidine-2,6-dione (96.75 g, 503.88 mmol) was added to portion-wise. The resulting reaction mixture was heated at 70° C. for 1 hour. After completion (monitored by TLC), the reaction mixture was slowly poured in crushed ice and extracted with ethyl acetate (×3). The combined organic extract was dried over sodium sulfate and concentrated under reduced pressure. The crude thus obtained was triturated with diethyl ether and pentane to afford the desired compound 3-(5-bromo-2-oxo-benzo[cd]indol-1-yl)piperidine-2,6-dione (16 g, 34.27 mmol) as a light yellow solid. Yield-34%. $^1$H NMR (d$^6$-DMSO, 400 MHZ) δ 11.14 (s, 1H), 8.12 (d, J=7.48 Hz, 1H), 7.99 (d, J=7.44 Hz, 1H), 7.72-7.62 (m, 2H), 7.26 (d, J=6.92 Hz, 1H), 5.46 (dd, J=12.84, 5.28 Hz, 1H), 2.99-2.90 (m, 1H), 2.81-2.63 (m, 2H), 2.12-2.07 (m, 1H); LC MS [M+H]$^+$ 359.07, 361.02.

Step-5: Synthesis of 5-(4,4,5,5-Tetramethyl-1,3,2-dioxaborolan-2-yl)benzo[cd]indol-2(1H)-one: To a stirred solution of 5-bromo-1H-benzo[cd]indol-2-one (200 mg, 806 μmol, 1 eq) in 1,4 dioxane (10 mL) was added bis(pinacolato) diboron (307 mg, 1.21 mmol, 1.5 eq) followed by well-dried potassium acetate (237 mg, 2.42 mmol, 3 eq). The resultant reaction mixture was degassed well with argon for 15 minutes. Pd(dppf)$Cl_2$.DCM (66 mg, 81 μmol, 0.1 eq) was then added and the reaction mixture was heated at 100° C. for 16 hours. After completion of the reaction (monitored by TLC), the reaction mixture was cooled to room temperature and filtered through a celite pad with EtOAc washings. The combined filtrate was then washed with cold water, dried over sodium sulfate and concentrated under reduced pressure to afford crude 5-(4,4,5,5-tetramethyl-1,3,2-dioxaborolan-2-yl)-1H-benzo[cd]indol-2-one (200 mg, 406 μmol, 60% purity) as a crude brown gum which was used without further purification. Yield 35%. LC MS [M+H]$^+$ 296.2.

Example 2. 5-Chloromethyl-1-(4-methoxy-benzyl)-1H-benzo[cd]indol-2-one

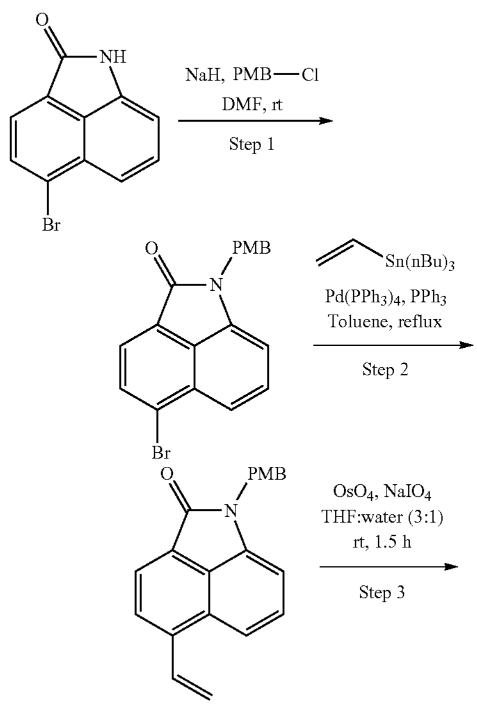

-continued

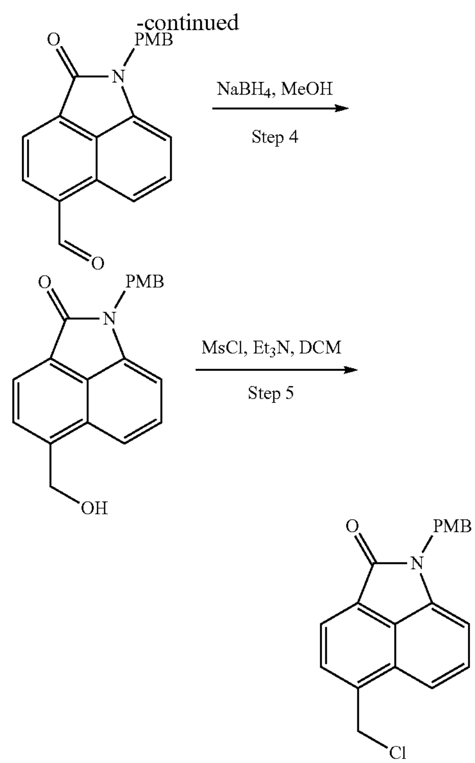

Step-1: Synthesis of 5-Bromo-1-(4-methoxy-benzyl)-1H-benzo[cd]indol-2-one: To a stirred solution of 5-bromo-1H-benzo[cd]indol-2-one (50.0 g, 201.532 mmol) in DMF (150 mL) was added sodium hydride (60% dispersion in mineral oil) (7.255 g, 302.297 mmol) at 0° C. and the reaction mixture was stirred at same temperature for 30 minutes. 4-Methoxy benzyl chloride (32.806 mL, 241.8 mmol) was then added and the reaction mixture was slowly warmed to room temperature and stirred for another 30 minutes. After reaction completion (monitored by TLC) the reaction mass was quenched with crushed ice and extracted with EtOAc. The organic extract was further washed with water and brine, dried over sodium sulfate and concentrated under reduced pressure. The crude thus obtained was purified by column chromatography (100-200 Silica; gradient: 0-1% EtOAc in DCM) to afford 5-bromo-1-(4-methoxy-benzyl)-1H-benzo[cd]indol-2-one (66 g, 179.36 mmol) as yellow solid. Yield 89%. $^1$H NMR ($d^6$-DMSO, 400 MHZ) δ 8.09 (d, J=7.44 Hz, 1H), 7.98 (d, J=7.44 Hz, 1H), 7.65-7.56 (m, 2H), 7.32 (d, J=8.56 Hz, 2H), 7.19 (d, J=6.96 Hz, 1H), 6.87 (d, J=8.56 Hz, 2H), 5.03 (s, 2H), 3.69 (s, 3H); LC MS $[M+H]^+$ 367.80, 369.84.

Step-2: Synthesis of 1-(4-Methoxy-benzyl)-5-vinyl-1H-benzo[cd]indol-2-one: To a stirred solution of 5-bromo-1-(4-methoxy-benzyl)-1H-benzo[cd]indol-2-one (66 g, 179.348 mmol) in toluene (800 mL), argon was purged for 20 minutes. Tributyl vinyl tin (55.037 mL, 188.315 mmol), triphenylphosphine (2.352 g, 8.967 mmol) and tetrakis(triphenylphosphine)palladium (10.363 g, 8.967 mmol) were added and the reaction mixture was heated at 110° C. for 16 hours. After completion of the reaction (monitored by TLC), the solvent was evaporated under reduced pressure and the crude thus obtained was purified by column chromatography (100-200 Silica; gradient: 0-20% EtOAc in hexane) to afford 1-(4-methoxy-benzyl)-5-vinyl-1H-benzo[cd]indol-2-one (45 g, 141.68 mmol) as yellow solid. Yield 79%. $^1$H NMR ($d^6$-DMSO, 400 MHZ) δ 8.07-8.03 (m, 2H), 7.85 (d, J=8.64 Hz, 1H), 7.59-7.49 (m, 2H), 7.31 (d, J=8.6 Hz, 2H), 7.12 (d, J=7.12 Hz, 1H), 6.87 (d, J=8.56 Hz, 2H), 6.15 (d, J=17.44 Hz, 1H), 5.66 (d, J=11.16 Hz, 1H), 3.69 (s, 3H); LC MS $[M+H]^+$ 316.02

Step-3: Synthesis of 1-(4-Methoxy-benzyl)-2-oxo-1,2-dihydro-benzo[cd]indole-5-carbaldehyde: To a stirred solution of 1-(4-methoxy-benzyl)-5-vinyl-1H-benzo[cd]indol-2-one (45 g, 112.5 mmol) in water (100 mL) and THF (300 mL) was added 4% solution of $OsO_4$ in water (572 mg, 507.35 μmol, 14.3 mL) and the reaction mixture was stirred at room temperature for 20 minutes before sodium periodate (60.157 g, 281.25 mmol) was added. The resultant reaction mixture was then stirred at room temperature for 1 hour. After completion of the reaction (monitored by TLC) the reaction mixture was filtered through a celite bed and washed with THE and EtOAc. The filtrate collected was then dried over sodium sulfate and concentrated under reduced pressure to afford 1-(4-methoxy-benzyl)-2-oxo-1,2-dihydro-benzo[cd]indole-5-carbaldehyde (28 g, 87.75 mmol) as brown solid. Yield-78%. $^1$H NMR ($d^6$-DMSO, 400 MHZ) δ 10.48 (s, 1H), 8.41 (d, J=7.12 Hz, 1H), 8.37 (d, J=8.64 Hz, 1H), 8.27 (d, J=7.08 Hz, 1H), 7.65-7.61 (m, 1H), 7.33 (d, J=8.6 Hz, 2H), 7.18 (d, J=7.2 Hz, 1H), 6.88 (d, J=8.6 Hz, 2H), 5.03 (s, 2H), 3.69 (s, 3H); LC MS $[M+H]^+$ 317.98

Step-4: Synthesis of 5-Hydroxymethyl-1-(4-methoxy-benzyl)-1H-benzo[cd]indol-2-one: To a stirred solution of 1-(4-methoxy-benzyl)-2-oxo-1,2-dihydro-benzo[cd]indole-5-carbaldehyde (28 g, 88.324 mmol) in methanol (250 mL), sodium borohydride (10.024 g, 264.984 mmol) was added slowly at 0° C. and the resultant reaction mixture was stirred at room temperature for 16 hours. After completion (monitored by TLC) the reaction mass was concentrated under reduced pressure and was slowly poured into crushed ice. The solid precipitate that formed was filtered off and dried properly under reduced pressure. The crude thus obtained was purified by column chromatography (100-200 Silica; gradient: 0-5% MeOH in DCM) to afford 5-hydroxymethyl-1-(4-methoxy-benzyl)-1H-benzo[cd]indol-2-one (22 g, 68.89 mmol) as a yellow solid. Yield 78%. $^1$H NMR ($d_6$-DMSO, 400 MHZ) δ 8.05 (d, J=7.2 Hz, 1H), 7.82 (d, J=7.12 Hz, 1H), 7.70 (d, J=8.48 Hz, 1H), 7.47 (t, J=7.84 Hz, 1H), 7.30 (d, J=8.48 Hz, 2H), 7.09 (d, J=7.12 Hz, 1H), 6.87 (d, J=8.56 Hz, 2H), 5.53 (t, J=5.52 Hz, 1H), 5.05-5.02 (m, 4H), 3.69 (s, 3H); LC MS $[M+H]^+$ 319.8

Step-5: Synthesis of 5-Chloromethyl-1-(4-methoxy-benzyl)-1H-benzo[cd]indol-2-one: To a stirred suspension of 5-hydroxymethyl-1-(4-methoxy-benzyl)-1H-benzo[cd]indol-2-one (22 g, 68.966 mmol) in DCM (350 mL), $Et_3N$ (28.837 mL, 206.897 mmol) and methanesulfonyl chloride (206.897 mmol, 16.015 mL) were added at 0° C. and the resultant reaction mixture was stirred at room temperature for 16 hours. After completion (monitored by TLC) the reaction mixture was diluted with ethyl acetate, washed with water, saturated sodium bicarbonate solution and brine, dried over sodium sulfate and concentrated under reduced pressure to afford 5-chloromethyl-1-(4-methoxy-benzyl)-1H-benzo[cd]indol-2-one (19 g, 56.55 mmol) as yellow solid. Yield-82%. $^1$H NMR ($d^6$-DMSO, 400 MHZ) δ 8.07 (d, J=7.12 Hz, 1H), 7.90 (d, J=7.16 Hz, 1H), 7.80 (d, J=8.6 Hz, 1H), 7.55 (t, J=7.88 Hz, 1H), 7.31 (d, J=8.6 Hz, 2H), 7.13 (d, J=7.16 Hz, 1H), 6.87 (d, J=8.6 Hz, 2H), 5.30 (s, 2H), 5.03 (s, 2H), 3.69 (s, 3H);

Example 3. Synthesis of 3-(2-oxo-5-vinyl-benzo[cd]indol-1-yl)piperidine-2,6-dione (Compound 2) 1-(2,6-dioxo-3-piperidyl)-2-oxo-benzo[cd]indole-5-carbaldehyde (Compound 3)

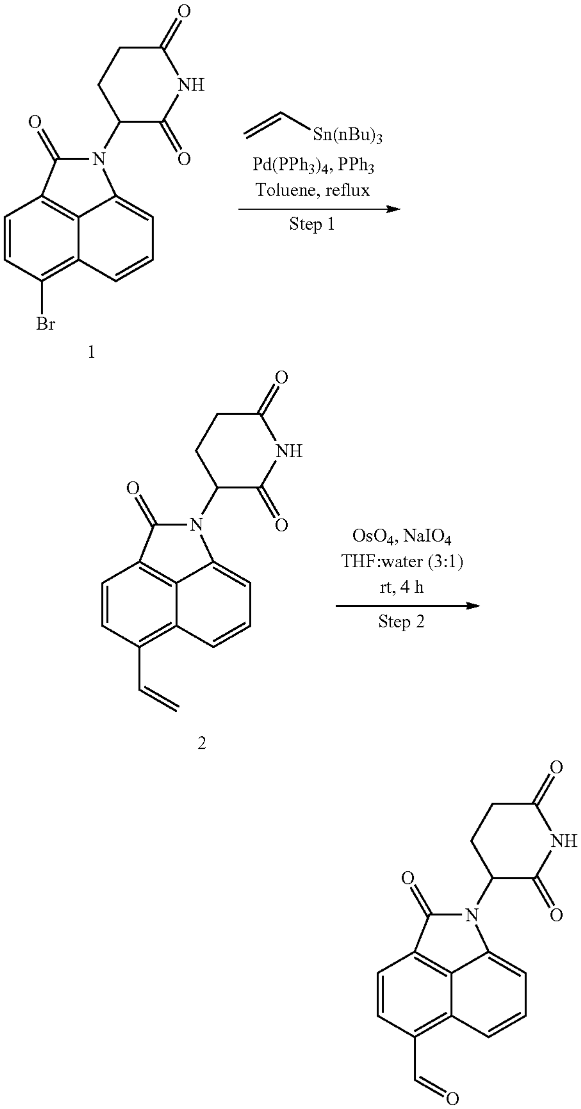

3

Step-1: Synthesis of 3-(2-oxo-5-vinyl-benzo[cd]indol-1-yl)piperidine-2,6-dione (Compound 2): To a stirred solution of 3-(5-bromo-2-oxo-benzo[cd]indol-1-yl)piperidine-2,6-dione (20 g, 55.68 mmol) in toluene (500 mL), argon was purged for 20 minutes. Tributyl vinyl tin (22.95 g, 72.39 mmol, 21.06 mL), triphenylphosphine (730.26 mg, 2.78 mmol) and tetrakis(triphenylphosphine)palladium (3.22 g, 2.78 mmol) were added and the reaction mixture was heated at 110° C. for 16 hours. After completion of the reaction (monitored by TLC), the solvent was evaporated under reduced pressure and the crude thus obtained was purified by column chromatography (100-200 Silica; Gradient: 0-10% MeOH in DCM) to afford 3-(2-oxo-5-vinyl-benzo[cd]indol-1-yl)piperidine-2,6-dione (14.3 g, 32.85 mmol) as yellow solid. Yield 59%. LC MS $[M+H]^+$ 307.2

Step-2: Synthesis of 1-(2,6-dioxo-3-piperidyl)-2-oxo-benzo[cd]indole-5-carbaldehyde: To a stirred solution of 3-(2-oxo-5-vinyl-benzo[cd]indol-1-yl)piperidine-2,6-dione (14 g, 45.70 mmol) in water (12 mL) and THF (36 mL) was added 4% solution of $OsO_4$ in water (572 mg, 507.35 μmol, 2 mL) and the reaction mixture was stirred at room temperature for 20 minutes before sodium periodate (24.44 g, 114.26 mmol) was added. The resultant reaction mixture was then stirred at room temperature for 4 hours. After completion of the reaction (monitored by TLC) the reaction mixture was filtered through a celite bed, washed with THE and 20% IPA in DCM. The filtrate collected was then dried over sodium sulfate and concentrated under reduced pressure. Crude thus obtained was purified by column chromatography (100-200 Silica; gradient: 0-5% MeOH in DCM) to afford 1-(2,6-dioxo-3-piperidyl)-2-oxo-benzo[cd]indole-5-carbaldehyde (8 g, 16.91 mmol) as a yellow solid. Yield-37%. $^1H$ NMR (d6-DMSO, 400 MHZ) δ 11.16 (s, 1H), 10.52 (s, 1H), 8.46-8.43 (m, 2H), 8.31-8.30 (m, 1H), 7.71-7.67 (m, 1H), 7.27-7.25 (m, 1H), 5.48 (dd, J=12.48, 4.84 Hz, 1H), 2.95-2.90 (m, 1H), 2.79-2.74 (m, 1H), 2.68-2.63 (m, 1H), 2.13-2.08 (m, 1H); LC MS $[M+H]^+$ 309.0.

Example 4. 3-[5-(Benzhydrylideneamino)-2-oxo-benzo[cd]indol-1-yl]piperidine-2,6-dione (Compound 4), 3-(5-amino-2-oxo-benzo[cd]indol-1-yl)piperidine-2,6-dione (Compound 4), and 3-(5-fluoro-2-oxo-benzo[cd]indol-1-yl)piperidine-2,6-dione (Compound 5)

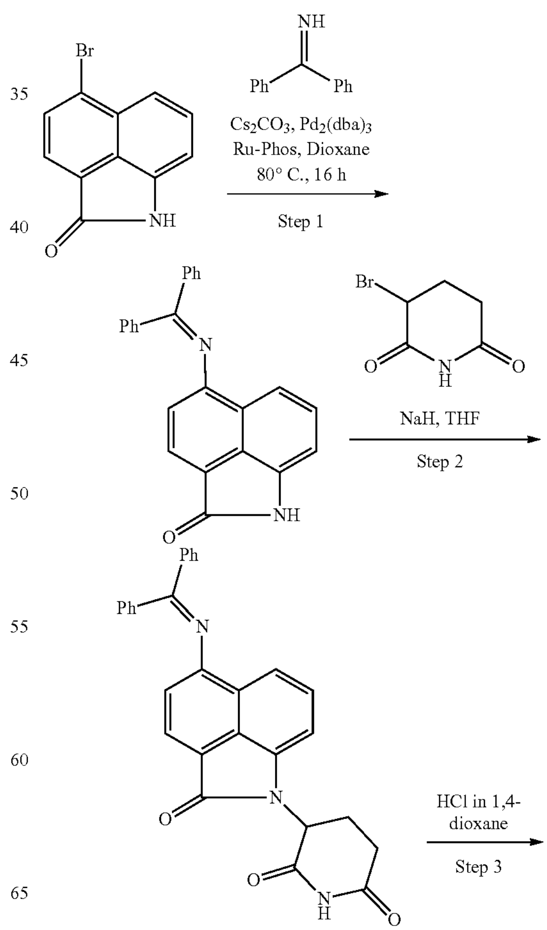

-continued

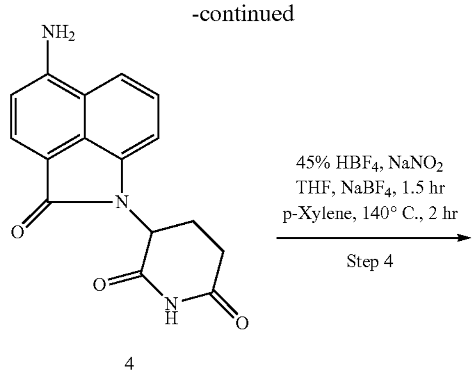

4

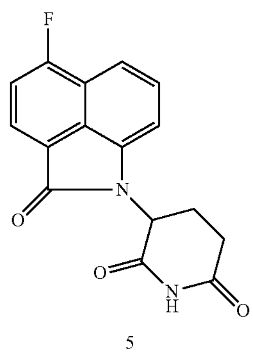

5

Step-1: Synthesis of 5-(Benzhydrylideneamino)-1H-benzo[cd]indol-2-one: To a stirred solution of 5-bromo-1H-benzo[cd]indol-2-one (25 g, 100.78 mmol), diphenylmethanimine (36.53 g, 201.55 mmol, 33.82 mL) in toluene (1500 mL) was added sodium tert-butoxide (29.05 g, 302.33 mmol) and the resultant reaction mixture was degassed with argon for 10 minutes. Then (5-diphenylphosphanyl-9,9-dimethyl-xanthen-4-yl)-diphenyl-phosphane (11.66 g, 20.16 mmol) and (1E, 4E)-1,5-diphenylpenta-1,4-dien-3-one palladium (9.23 g, 10.08 mmol) were added and the reaction mixture was heated at 80° C. for 16 hours. After completion of the reaction (monitored by TLC and LCMS) the reaction mixture was diluted with cold water extracted with EtOAc (×2). The crude extract was then dried over sodium sulfate and concentrated under reduced pressure. Crude thus obtained was purified by column chromatography (100-200 Silica; Gradient: 0-20% EtOAc in hexane) to afford 5-(benzhydrylideneamino)-1H-benzo[cd]indol-2-one (20 g, 41.31 mmol) as yellow solid. Yield-41%. LC MS $[M+H]^+$ 349.40.

Step-2: Synthesis of 3-[5-(Benzhydrylideneamino)-2-oxo-benzo[cd]indol-1-yl]piperidine-2,6-dione (Compound 4): To a stirred suspension of 5-(benzhydrylideneamino)-1H-benzo[cd]indol-2-one (10 g, 28.70 mmol) in THF (100 mL) was added sodium hydride (60% dispersion in mineral oil) (16.50 g, 430.54 mmol) in a portion-wise manner at 0° C. After completion of the addition, the reaction mixture was slowly warmed to room temperature and stirred for 1 hour. The reaction mixture was again cooled to 0° C. and 3-bromo-glutarimide (33.07 g, 172.22 mmol) was added in portions. The reaction mixture was again warmed to room temperature and was heated at 70° C. for 4 hours. After completion (monitored by TLC), the reaction mixture was slowly poured in crushed ice. The aqueous portion was the extracted with ethyl acetate (×3) and the combined organic layers were separated, dried over sodium sulfate and concentrated under reduced pressure. The crude thus obtained was triturated with diethyl ether and pentane to afford the desired compound 3-[5-(benzhydrylideneamino)-2-oxo-benzo[cd]indol-1-yl]piperidine-2,6-dione (10 g, 21.81 mmol) as a yellow solid. Yield-76%. LC MS $[M+H]^+$ 460.0.

Step-3: Synthesis of 3-(5-Amino-2-oxo-benzo[cd]indol-1-yl)piperidine-2,6-dione (Compound 4): To a stirred solution of 3-[5-(benzhydrylideneamino)-2-oxo-benzo[cd]indol-1-yl]piperidine-2,6-dione (10 g, 21.76 mmol) in THF (100 mL) was added 15 mL aqueous HCl (2N) and the resultant reaction mixture was stirred at room temperature for 2 hours. After completion (monitored by TLC) the reaction mixture was concentrated to dryness and 20 mL of HCl in 1,4-dioxane (4N) was added and the reaction was stirred for 30 min. The reaction mixture was again concentrated to dryness and was triturated with ether to remove the impurities. The crude was then basified with saturated sodium bicarbonate solution and washed with 30% EtOAc in hexane. The insoluble material that was found in the junction of aqueous and organic layer was filtered off and dried properly to afford the desired compound 3-(5-amino-2-oxo-benzo[cd]indol-1-yl)piperidine-2,6-dione (5.5 g, 18.71 mmol) as yellow solid. Yield-86%. $^1$H NMR ($d^6$-DMSO, 400 MHZ) δ 11.03 (s, 1H), 7.78 (d, J=8.52 Hz, 1H), 7.72 (d, J=7.88 Hz, 1H), 7.29 (t, J=7.86 Hz, 1H), 7.13 (br s, 2H), 6.98 (d, J=7.2 Hz, 1H), 6.73 (d, J=7.88 Hz, 1H), 5.34 (dd, J=12.64, 5.2 Hz, 1H), 2.98-2.88 (m, 1H), 2.76-2.69 (m, 1H), 2.66-2.60 (m, 1H), 2.03-1.98 (m, 1H); LC MS $[M+H]^+$ 296.2.

Step-4: Synthesis of 3-(5-Fluoro-2-oxo-benzo[cd]indol-1-yl)piperidine-2,6-dione (Compound 5): To a stirred solution of 3-(5-amino-2-oxo-benzo[cd]indol-1-yl)piperidine-2,6-dione (4 g, 13.55 mmol) in THF (8 mL) was added 48% trifluoroborane hydrofluoride (1.19 g, 13.55 mmol, 40 mL) at 0° C. followed by a solution of sodium nitrite (2.80 g, 40.64 mmol, 1.29 mL) in water (4 mL). After the addition was over, the reaction mixture was stirred at that temperature for 1 hour followed by the addition of sodium tetrafluoroborate (7.44 g, 67.73 mmol, 3.01 mL). The resultant reaction mixture was then warmed to room temperature and was filtered off. The solid collected was further washed with diethyl ether and dried under high vacuum to afford the corresponding diazonium salt as a brown solid. Resulting solid was then suspended top-xylene (50 mL) and was heated at 140° C. for 2 hours. After completion (monitored by TLC), the reaction mixture was cooled to room temperature and was concentrated under reduced pressure. The crude thus obtained was purified by column chromatography (100-200 Silica; Gradient: 0-15% EtOAc in hexane) to afford 3-(5-fluoro-2-oxo-benzo[cd]indol-1-yl)piperidine-2,6-dione (2.2 g, 7.18 mmol) as a yellow solid. Yield-53%. $^1$H NMR (d6-DMSO, 400 MHZ) δ 11.14 (s, 1H), 8.15-8.12 (m, 1H), 7.71-7.69 (m, 1H), 7.65-7.60 (m, 2H), 7.26 (d, J=7.08 Hz, 1H), 5.46 (dd, J=12.84, 5.2 Hz, 1H), 2.99-2.90 (m, 1H), 2.80-2.73 (m, 1H), 2.70-2.63 (m, 1H), 2.13-2.12 (m, 1H); LC MS $[M+H]^+$ 299.0

Example 5. General Procedure for Amine-Containing Tricyclic Glutarimide Compounds

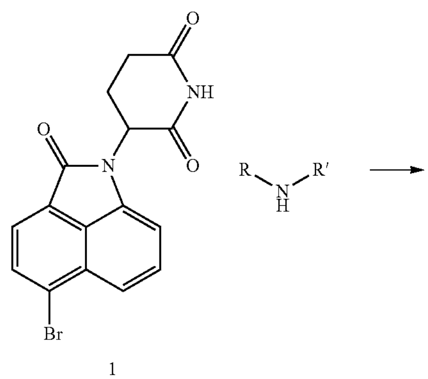

1

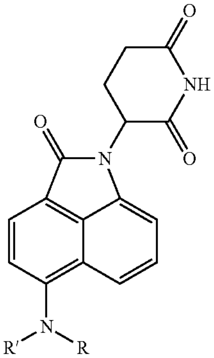

3-(5-Bromo-2-oxobenzo[cd]indol-1(2H)-yl)piperidine-2,6-dione (Compound 1) is coupled to the appropriate amine. Isolation and purification procedures affords amine substituted compounds, for example Compound 7-Compound 16.

Example 6: 3-(2-Oxo-5-(-2-(trifluoromethyl)pyrrolidin-1-yl)benzo[cd]indol-1(2H)-yl)piperidine-2,6-dione (Compound 6)

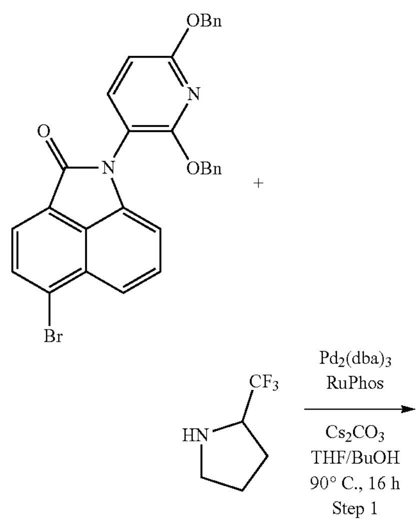

-continued

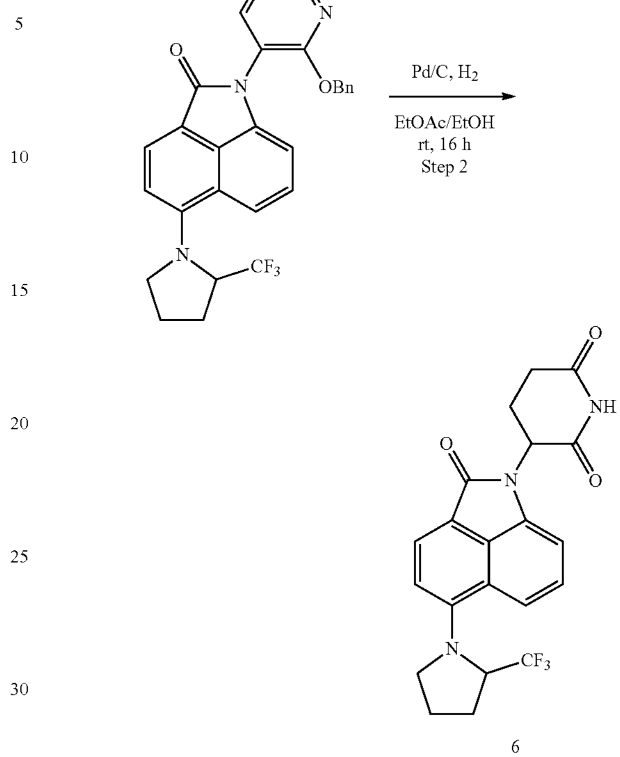

6

Step 1: Synthesis of 1-(2,6-Bis(benzyloxy)pyridin-3-yl)-5-(2-(trifluoromethyl)pyrrolidin-1-yl)benzo[cd]indol-2(1H)-one: To a stirred solution of 1-(2,6-bis(benzyloxy)pyridin-3-yl)-5-bromobenzo[cd]indol-2(1H)-one (200 mg, 372 μmol, 1 eq) was added amine 2-(trifluoromethyl)pyrrolidine (51 mg, 372 μmol, 1 eq), $Cs_2CO_3$ (242 mg, 744 μmol, 2 eq), $Pd_2(dba)_3$ (34 mg, 37 μmol, 0.1 eq) and RuPhos (34 mg, 74 μmol, 0.2 eq) in THF/tBuOH (4 mL, 1:1, 0.093 M). The solution was then degassed with argon before the mixture was heated to 90° C. for 16 hours. Upon reaction completion the mixture was filtered through a frit and washed through with EtOAc. The filtrate was then concentrated to a crude residue which was purified via Combiflash® normal phase column chromatography 0-100% EtOAc in hexane to afford 1-(2,6-dibenzyloxy-3-pyridyl)-5-[(2S)-2-(trifluoromethyl)pyrrolidin-1-yl]benzo[cd]indol-2-one as a solid (100 mg, 100 μmol). Yield-27%. LC MS ES+$[M+H]^+$ 596.2.

Step 2: Synthesis of 3-(2-Oxo-5-(2-(trifluoromethyl)pyrrolidin-1-yl)benzo[cd]indol-1(2H)-yl)piperidine-2,6-dione (Compound 6): To a degassed stirred solution of 1-(2,6-dibenzyloxy-3-pyridyl)-5-[(2S)-2-(trifluoromethyl)pyrrolidin-1-yl]benzo[cd]indol-2-one as a solid (100 mg, 100 μmol, 1 eq) in EtOAc/EtOH (10 mL, 1:1, 0.02 M) was added Pd/C (178 mg, 10% dry, 1 mmol, 10 eq) before a hydrogen balloon was attached to the reaction vessel and the mixture was allowed to stir at room temperature for 16 hours. Upon reaction completion the mixture was filtered through a celite pad before the filtrate was concentrated to a crude residue which was purified via RP-HPLC to afford the product 3-(2-oxo-5-(2-(trifluoromethyl)pyrrolidin-1-yl)benzo[cd]indol-1(2H)-yl)piperidine-2,6-dione (4 mg, 9.5 μmol). Yield-6%. LC MS ES+ $[M+H]^+$ 418.1.

Compound 8-Compound 16 were made using the same procedure as described in Example 6 for the preparation of 3-(2-oxo-5-(2-(trifluoromethyl)pyrrolidin-1-yl)benzo[cd]indol-1(2H)-yl)piperidine-2,6-di one (Compound 7) using the appropriate amine starting material from the table.

| Amine starting material | Compound | LCMS |
|---|---|---|
| 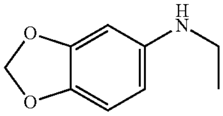 | 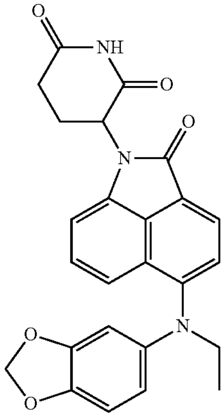 [SMILES: CCN(c1ccc2c(c1)OCO2)c1ccc2c3c(cccc13)N(C1CCC(=O)NC1=O)C2=O] 3-(5-(benzo[d][1,3]dioxol-5-yl(ethyl)amino)-2-oxobenzo[cd]indol-1(2H)-yl)piperidine-2,6-dione (Compound 7) | ES+ $[M + H]^+$ 444.2 |
| 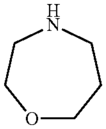 | 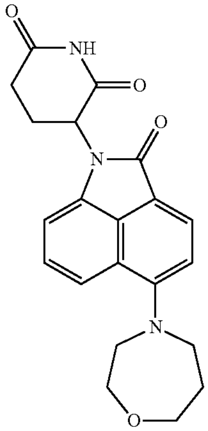 [SMILES: O=C1CCC(N2C(=O)c3ccc(N4CCCOCC4)c4cccc2c34)C(=O)N1] 3-(5-(1,4-oxazepan-4-yl)-2-oxobenzo[cd]indol-1(2H)-yl)piperidine-2,6-dione (Compound 8) | ES+ $[M + H]^+$ 380.2 |
| 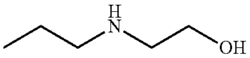 | 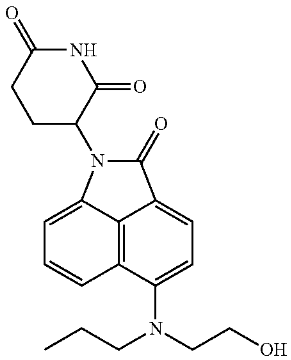 [SMILES: CCCN(CCO)c1ccc2c3c(cccc13)N(C1CCC(=O)NC1=O)C2=O] 3-(5-((2-hydroxyethyl)(propyl)amino)-2-oxobenzo[cd]indol-1(2H)-yl)piperidine-2,6-dione (Compound 9) | ES+ $[M + H]^+$ 382.2 |

-continued
| Amine starting material | Compound | LCMS |
| --- | --- | --- |
| 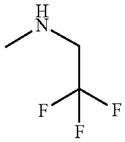 | 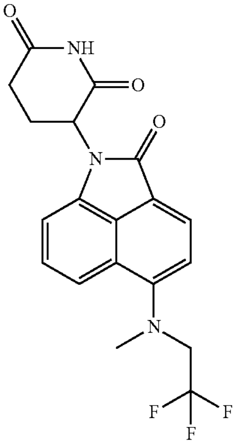 [SMILES: CN(CC(F)(F)F)c1ccc2c3c(cccc13)N(C1CCC(=O)NC1=O)C2=O]<br>3-(5-(methyl(2,2,2-trifluoroethyl)amino)-2-oxobenzo[cd]indol-1(2H)-yl)piperidine-2,6-dione (Compound 10) | ES+ [M + H]$^+$ 392.2 |
| 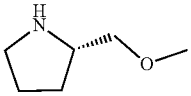 | 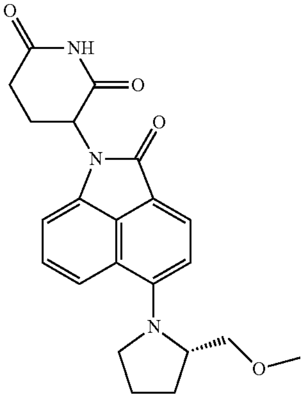 [SMILES: COC[C@@H]1CCCN1c1ccc2c3c(cccc13)N(C1CCC(=O)NC1=O)C2=O]<br>3-(5-((S)-2-(methoxymethyl)pyrrolidin-1-yl)-2-oxobenzo[cd]indol-1(2H)-yl)piperidine-2,6-dione (Compound 11) | ES+ [M + H]$^+$ 394.3 |
| 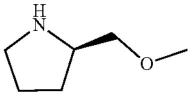 | 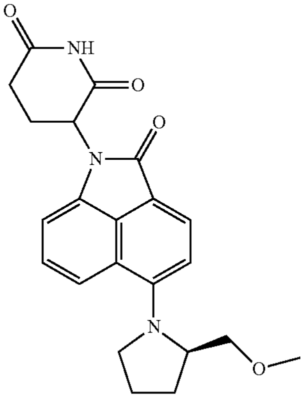 [SMILES: COC[C@H]1CCCN1c1ccc2c3c(cccc13)N(C1CCC(=O)NC1=O)C2=O]<br>3-(5-((R)-2-(methoxymethyl)pyrrolidin-1-yl)-2-oxobenzo[cd]indol-1(2H)-yl)piperidine-2,6-dione (Compound 12) | ES+ [M + H]$^+$ 394.1 |

-continued
| Amine starting material | Compound | LCMS |
|---|---|---|
| 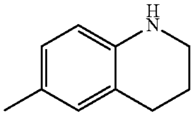 | 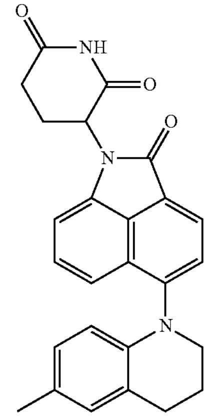 [SMILES: Cc1ccc2c(c1)CCCN2c1ccc2c3c(cccc13)N(C1CCC(=O)NC1=O)C2=O]<br>3-(5-(6-methyl-3,4-dihydroquinolin-1(2H)-yl)-2-oxobenzo[cd]indol-1(2H)-yl)piperidine-2,6-dione (Compound 13) | ES+ $[M + H]^+$ 426.0 |
| 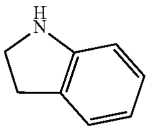 | 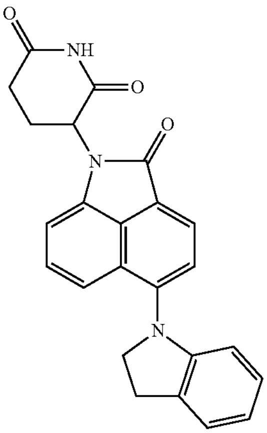 [SMILES: O=C1CCC(N2C(=O)c3ccc(N4CCc5ccccc54)c4cccc2c34)C(=O)N1]<br>3-(5-(indolin-1-yl)-2-oxobenzo[cd]indol-1(2H)-yl)piperidine-2,6-dione (Compound 14) | ES+ $[M + H]^+$ 398.0 |

-continued
| Amine starting material | Compound | LCMS |
|---|---|---|
| 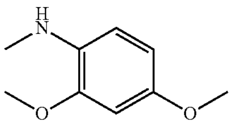 | 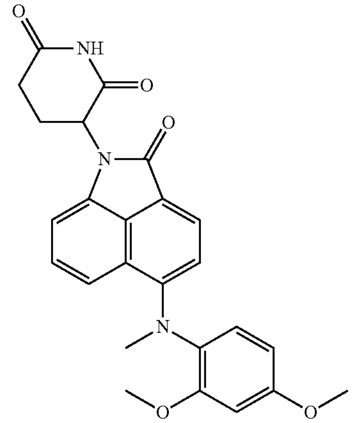 [SMILES: COc1ccc(N(C)c2ccc3c4c(cccc24)N(C2CCC(=O)NC2=O)C3=O)c(OC)c1] 3-(5-((2,4-dimethoxyphenyl)(methyl)amino)-2-oxobenzo[cd]indol-1(2H)-yl)piperidine-2,6-dione (Compound 15) | ES+ $[M + H]^+$ 446.4 |
| 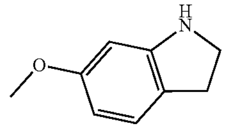 | 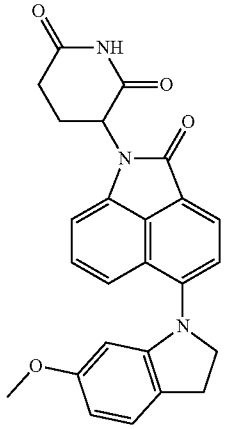 [SMILES: COc1ccc2c(c1)N(c1ccc3c4c(cccc14)N(C1CCC(=O)NC1=O)C3=O)CC2] 3-(5-(6-methoxyindolin-1-yl)-2-oxobenzo[cd]indol-1(2H)-yl)piperidine-2,6-dione (Compound 16) | ES+ $[M + H]^+]$ 428.1 |

Example 7. 3-(2-Oxo-5-((S)-2-phenylpyrrolidin-1-yl)benzo[cd]indol-1(2H)-yl)piperidine-2,6-dione (Compound 18)

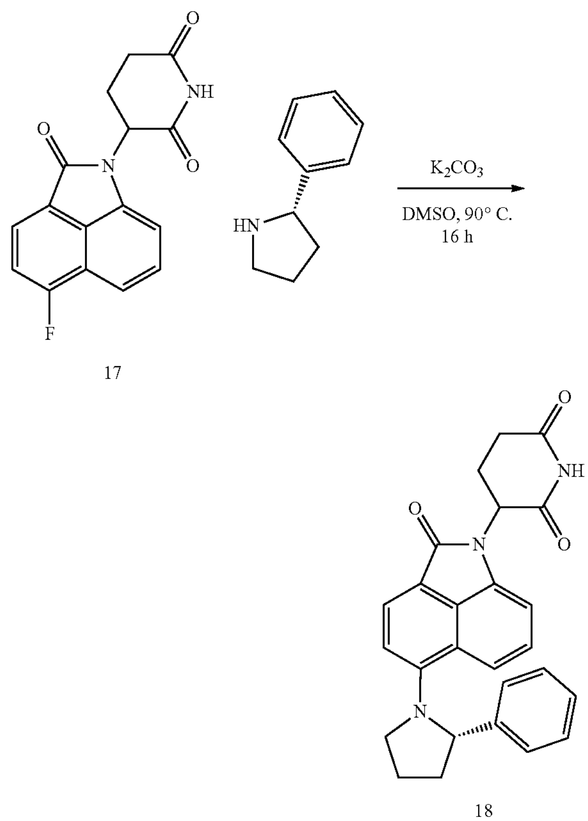

17

18

To a stirred solution of 3-(5-fluoro-2-oxobenzo[cd]indol-1(2H)-yl)piperidine-2,6-dione (Compound 17) (50 mg, 167 μmol, 1 eq) and (2S)-2-phenylpyrrolidineamine (25 mg, 167 μmol, 1 eq) in DMSO (0.08 M) was added potassium carbonate (46 mg, 335 μmol, 2 eq) before the reaction mixture was degassed with argon and stirred for 16 hours at 90° C. The reaction was monitored by LCMS. upon reaction completion the reaction mixture was filtered off and the filtrated was concentrated to a crude residue. The crude thus obtained was purified by CombiFlash® normal phase column chromatography 0-100% EtOAc in hexane to afford the product 3-(2-oxo-5-((S)-2-phenylpyrrolidin-1-yl)benzo[cd]indol-1(2H)-yl)piperidine-2,6-dione (18 mg, 42 μmol) as a solid. Yield-43%. LC MS ES+ $[M+H]^+$ 426.2.

Compound 19-Compound 25 were made using the same procedure as described in Example 7 for the preparation of 3-(2-oxo-5-((S)-2-phenylpyrrolidin-1-yl)benzo[cd]indol-1(2H)-yl)piperidine-2,6-dione (Compound 18) using the appropriate amine starting material from the table.

| Amine starting material | Product | LCMS |
| --- | --- | --- |
| 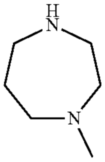 | 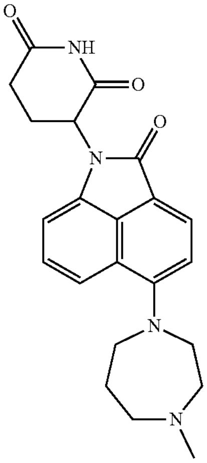 [SMILES: CN1CCCN(c2ccc3c4c(cccc24)N(C2CCC(=O)NC2=O)C3=O)CC1] 3-(5-(4-methyl-1,4-diazepan-1-yl)-2-oxobenzo[cd]indol-1(2H)-yl)piperidine-2,6-dione (Compound 19) | ES+ $[M + H]^+$ 393.1 |

-continued
| Amine starting material | Product | LCMS |
|---|---|---|
| 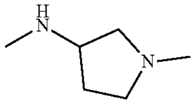 | 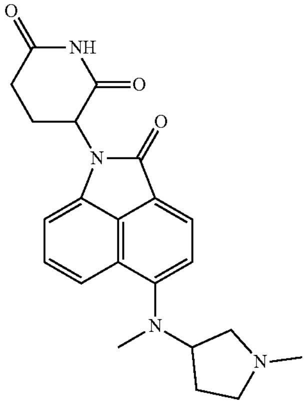 [SMILES: CN1CCC(N(C)c2ccc3c4c(cccc24)N(C2CCC(=O)NC2=O)C3=O)C1] 3-(5-(methyl(1-methylpyrrolidin-3-yl)amino)-2-oxobenzo[cd]indol-1(2H)-yl)piperidine-2,6-dione (Compound 20) | ES+ $[M+H]^+$ 393.1 |
| 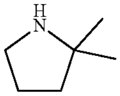 | 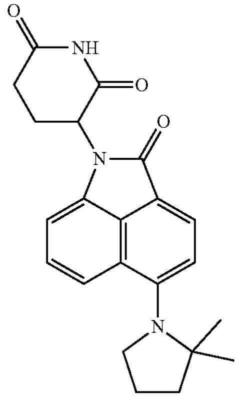 [SMILES: CC1(C)CCCN1c1ccc2c3c(cccc13)N(C1CCC(=O)NC1=O)C2=O] 3-(5-(2,2-dimethylpyrrolidin-1-yl)-2-oxobenzo[cd]indol-1(2H)-yl)piperidine-2,6-dione (Compound 21) | ES+ $[M+H]^+$ 378.1 |
| 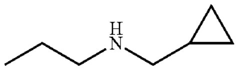 | 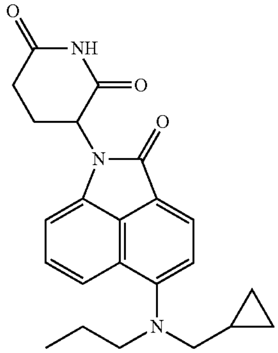 [SMILES: CCCN(CC1CC1)c1ccc2c3c(cccc13)N(C1CCC(=O)NC1=O)C2=O] 3-(5-((cyclopropylmethyl)(propyl)amino)-2-oxobenzo[cd]indol-1(2H)-yl)piperidine-2,6-dione (Compound 22) | ES+ $[M+H]^+$ 392.1 |

-continued
| Amine starting material | Product | LCMS |
|---|---|---|
| 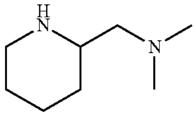 | 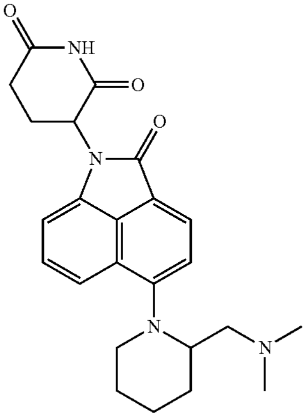 [SMILES: CN(C)CC1CCCCN1c1ccc2c3c(cccc13)N(C1CCC(=O)NC1=O)C2=O]<br>3-(5-(2-((dimethylamino)methyl)piperidin-1-yl)-2-oxobenzo[cd]indol-1(2H)-yl)piperidine-2,6-dione (Compound 23) | ES+ $[M + H]^+$ 421.3 |
| 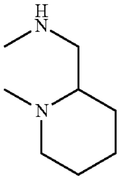 | 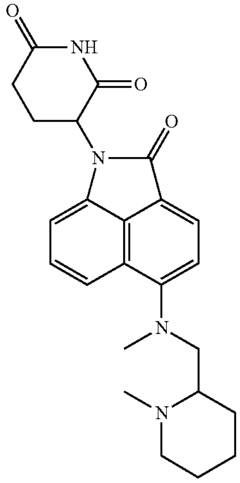 [SMILES: CN(CC1CCCCN1C)c1ccc2c3c(cccc13)N(C1CCC(=O)NC1=O)C2=O]<br>3-(5-(methyl((1-methylpiperidin-2-yl)methyl)amino)-2-oxobenzo[cd]indol-1(2H)-yl)piperidine-2,6-dione (Compound 24) | ES+ $[M + H]^+$ 421.5 |

-continued

| Amine starting material | Product | LCMS |
| --- | --- | --- |
| 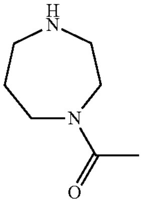 | 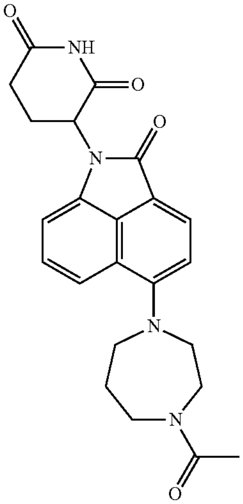 [SMILES: CC(=O)N1CCCN(c2ccc3c4c(cccc24)N(C2CCC(=O)NC2=O)C3=O)CC1] 3-(5-(4-acetyl-1,4-diazepan-1-yl)-2-oxobenzo[cd]indol-1(2H)-yl)piperidine-2,6-dione (Compound 25) | ES+ $[M + H]^+$ 421.2 |

Example 8. 3-(2-Oxo-5-(2-(pyridin-3-yl)pyrrolidin-1-yl)benzo[cd]indol-1(2H)-yl)piperidine-2,6-dione (Compound 26)

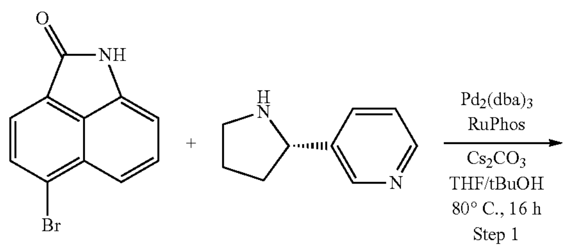

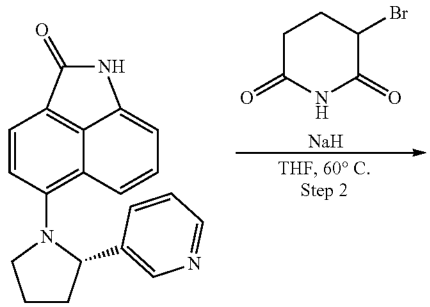

-continued

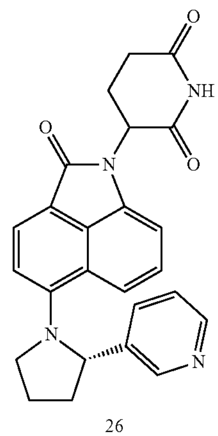

26

Step 1: Synthesis of (S)-5-(2-(Pyridin-3-yl)pyrrolidin-1-yl)benzo[cd]indol-2(1H)-one: To a stirred solution of 5-bromobenzo[cd]indol-2(1H)-one (200 mg, 806 μmol, 1 eq) was added 3-pyrrolidin-2-ylpyridine (119 mg, 806 μmol, 1 eq), $Cs_2CO_3$ (525 mg, 1.61 mmol, 2 eq), $Pd_2(dba)_3$ (74 mg, 81 μmol, 0.1 eq) and RuPhos (75 mg, 161 μmol, 0.2 eq) in THF/tBuOH (4 mL, 1:1, 0.093 M). The solution was then degassed with argon before the mixture was heated to 90° C. for 16 hours. Upon reaction completion the mixture was filtered through a frit and washed through with EtOAc. The filtrate was then concentrated to a crude residue which was purified via Combiflash® normal phase column chromatography 0-100% EtOAc in hexane to afford 5-[2-(3-pyridyl)pyrrolidin-1-yl]-1H-benzo[cd]indol-2-one as a solid (90 mg, 241 μmol). Yield-30%. LC MS ES+ $[M+H]^+$ 316.1.

Step 2: Synthesis of 3-(2-Oxo-5-(2-(pyridin-3-yl)pyrrolidin-1-yl)benzo[cd]indol-1(2H)-yl)piperidine-2,6-dione (Compound 26): To a cooled solution of 5-[2-(3-pyridyl)pyrrolidin-1-yl]-1H-benzo[cd]indol-2-one (45 mg, 142 μmol, 1 eq) in THF (10 mL, 0.01 M) was added NaH (54 mg, 1.43 mmol, 60% oil dispersion, 10 eq) portion-wise while maintaining a temperature of less than 5° C. Upon complete addition, the mixture was stirred at room temperature for a further 15 minutes before the mixture was again cooled to 0° C. and 3-bromo-piperidine-2,6-dione (137 mg, 713 μmol, 5 eq) was added. The mixture was heated to 70° C. for 1 hour. Upon reaction completion, the mixture was cooled to 0° C. and quenched with ice water. The mixture was then extracted with EtOAc (3×). The combined organic layers were separated, dried over sodium sulfate and concentrated to a crude residue which was purified via RP-HPLC to afford 3-[2-oxo-5-[2-(3-pyridyl)pyrrolidin-1-yl]benzo[cd]indol-1-yl]piperidine-2,6-dione as a solid (5.1 mg, 12 μmol). Yield-8%. LC MS ES+ $[M+H]^+$ 427.2.

Compound 27 was made using the same procedure as described in Example 8 for the preparation of 3-(2-oxo-5-(2-(pyridin-3-yl)pyrrolidin-1-yl)benzo[cd]indol-1(2H)-yl)piperidine-2,6-dione (Compound 26) using the appropriate amine starting material in the table.

| Amine starting material | Product | LCMS |
| --- | --- | --- |
| 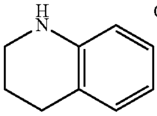 | 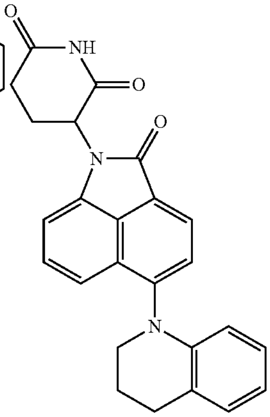 3-(5-(3,4-dihydroquinolin-1(2H)-yl)-2-oxobenzo[cd]indol-1(2H)-yl)piperidine-2,6-dione (Compound 27) | ES+ $[M + H]^+$ 412.4 |

Example 9. tert-Butyl 4-(1-(2,6-dioxopiperidin-3-yl)-2-oxo-1,2-dihydrobenzo[cd]indol-5-yl)-3,6-dihydropyridine-1(2H)-carboxylate (Compound 28), tert-Butyl 4-(1-(2,6-dioxopiperidin-3-yl)-2-oxo-1,2-dihydrobenzo[cd]indol-5-yl)piperidine-1-carboxylate (Compound 29), and 3-(2-Oxo-5-(piperidin-4-yl)benzo[cd]indol-1(2H)-yl)piperidine-2,6-dione (Compound 30)

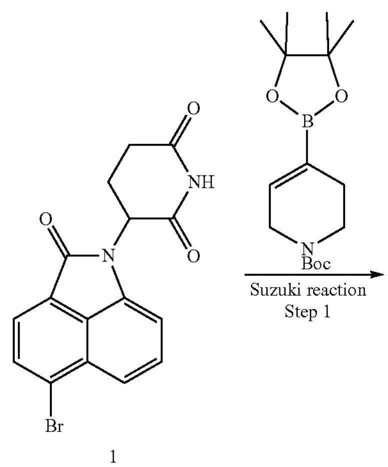

1

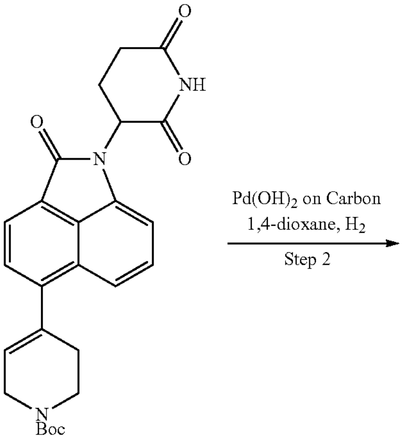

28

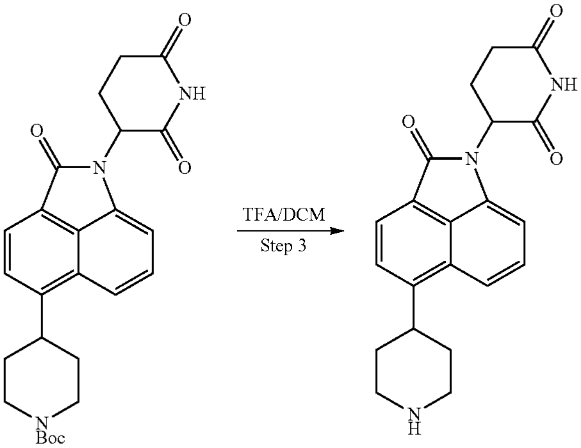

29

30

Step 1: Synthesis of tert-Butyl 4-(1-(2,6-dioxopiperidin-3-yl)-2-oxo-1,2-dihydrobenzo[cd]indol-5-yl)-3,6-dihydro-pyridine-1(2H)-carboxylate (Compound 28): To a solution of 3-(5-bromo-2-oxo-benzo[cd]indol-1-yl)piperidine-2,6-dione (Compound 1) (200 mg, 556.83 μmol) in DMF (3 mL) was added tert-butyl 4-(4,4,5,5-tetramethyl-1,3,2-dioxaborolan-2-yl)-3,6-dihydro-2H-pyridine-1-carboxylate (206.61 mg, 668.20 μmol) and cesium fluoride (126.87 mg, 835.25 μmol, 30.79 μL) at 25° C. and the reaction mixture was degased with nitrogen for 5 minutes. Cyclopentyl (diphenyl)phosphane dichloromethane dichloropalladium: iron (45.47 mg, 55.68 μmol) was added and again the reaction mixture was degased with nitrogen for 5 minutes. The reaction mixture was allowed to stirred at 80° C. for 10 hours. The reaction was monitored by LCMS and upon completion, the reaction mixture was allowed to cool to room temperature and then poured on water (10 mL), extracted with ethyl acetate (2×10 mL), washed with brine (10 ml), dried over anhydrous sodium sulfate and concentrated on rotavapor. The crude residue was purified by flash chromatography using 25 g silica and 0-100% ethylacetate in hexane as the eluent to provide tert-butyl 4-[1-(2,6-dioxo-3-piperidyl)-2-oxo-benzo[cd]indol-5-yl]-3,6-dihydro-2H-pyridine-1-carboxylate (Compound 28) (105 mg, 179.46 μmol, 32% yield) as a a yellow solid. Desired product was confirmed by $^1$HNMR and LCMS (m/z=462.0 [M+H] with purity 78%).

Step 2: Synthesis of tert-Butyl 4-[1-(2,6-dioxo-3-piperidyl)-2-oxo-benzo[cd]indol-5-yl]piperidine-1-carboxylate (Compound 29): Into a 25 mL single-necked round-bottomed flask containing a well-stirred suspension of tert-butyl 4-[1-(2,6-dioxo-3-piperidyl)-2-oxo-benzo[cd]indol-5-yl]-3,6-dihydro-2H-pyridine-1-carboxylate (Compound 28) (170 mg, 368.36 μmol) in 1,4-dioxane (10 mL) was added palladium hydroxide on carbon, 20 wt. % 50% water (103.46 mg, 736.74 μmol) at ambient temperature under nitrogen atmosphere. The resulting suspension was stirred at ambient temperature under hydrogen atmosphere (bladder) for 16 hours. After complete consumption of the starting material as indicated by TLC, the reaction mixture was filtered through a pad of Celite and the Celite bed was washed with 1,4-dioxane (10 mL) and 1:1 EtOAc/DCM (20 mL). Combined filtrate was concentrated under reduced pressure to provide a crude residue which was triturated with $Et_2O$ (2×15 mL) to afford tert-butyl 4-[1-(2,6-dioxo-3-piperidyl)-2-oxo-benzo[cd]indol-5-yl]piperidine-1-carboxylate (Compound 29) (155 mg, 238.56 μmol, 64% yield) as a yellow solid. LCMS (ESI): m/z 408.3 $[M+H-{}^{t}Bu]^+$.

Step 3: Synthesis of 3-[2-Oxo-5-(4-piperidyl)benzo[cd]indol-1-yl]piperidine-2,6-dione (Compound 30): To a stirred solution of tert-butyl 4-[1-(2,6-dioxo-3-piperidyl)-2-oxo-benzo[cd]indol-5-yl]piperidine-1-carboxylate (Compound 29) (0.140 g, 302.03 μmol, 000) in DCM (3 mL) was added TFA (413.27 mg, 3.62 mmol, 279.23 μL) at 0° C. The reaction mixture was stirred at 25° C. for 2 hours. The progress of the reaction was monitored by LCMS/TLC. After reaction completion, the reaction mixture was concentrated under reduced pressure. The crude product was triturated with diethyl ether (20 mL) to afford 3-[2-oxo-5-(4-piperidyl)benzo[cd]indol-1-yl]piperidine-2,6-dione (Compound 30) (0.1 g, 244.90 μmol, 81% yield) as pale yellow solid. The formed product was confirmed by LCMS.

Example 10: 3-[5-(1-Benzyl-4-piperidyl)-2-oxo-benzo[cd]indol-1-yl]piperidine-2,6-dione (Compound 32)

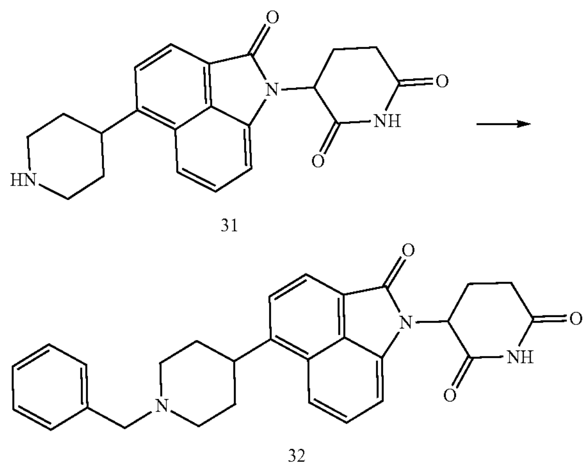

31

32

To a stirred solution of 3-[2-oxo-5-(4-piperidyl)benzo[cd]indol-1-yl]piperidine-2,6-dione (Compound 31) (0.060 g, 150.05 μmol) in THF (2 mL) was added benzaldehyde (15.92 mg, 150.05 μmol) and then the solution was stirred for 10 minutes. Later, triethyl amine (30.37 mg, 300.10 μmol, 41.83 μL) was added and the reaction mixture was stirred at room temperature for 30 minutes. Next, sodium cyanoborohydride (23.57 mg, 375.12 μmol) was added and the reaction mixture was stirred at room temperature for 16 hours. The progress of the reaction was monitored by TLC and after reaction completion, the reaction mixture was diluted with ethyl acetate and washed with water and brine. The separated organic layer was dried over anhydrous sodium sulfate, filtered and concentrated under reduced pressure. The crude compound was purified by column chromatography, eluting with 1 to 5% MeOH in DCM and then purified by Prep.HPLC to provide 3-[5-(1-benzyl-4-piperidyl)-2-oxo-benzo[cd]indol-1-yl]piperidine-2,6-dione (Compound 32) (8 mg, 16.75 μmol, 11% yield) as a yellow solid. $^1$HNMR (400 MHz, DMSO-$d_6$): δ 11.11 (s, 1H), 8.04-8.02 (d, J=8 Hz, 1H), 7.84-7.82 (d, J=8 Hz, 1H), 7.74-7.72 (d, J=8 Hz, 1H), 7.55-7.51 (m, 1H), 7.35-7.25 (m, 5H), 7.15-7.13 (s, J=8 Hz, 1H), 5.44-5.42(m 1H), 3.56 (s, 2H), 3.32-3.30 (m, 1H), 3.02-2.97 (m, 3H), 2.76-2.73 (m, 1H), 2.66-2.63 (m, 1H), 2.24-2.21 (m, 1H), 2.07 (m, 1H), 1.89-1.86 (m, 5H). LC-MS:($ES^+$)=454.2 [M+H]+

Example 11. 3-[5-[1-[(2-Methoxypyrimidin-5-yl)methyl]-4-piperidyl]-2-oxo-benzo[cd]indol-1-yl]piperidine-2,6-dione (Compound 33)

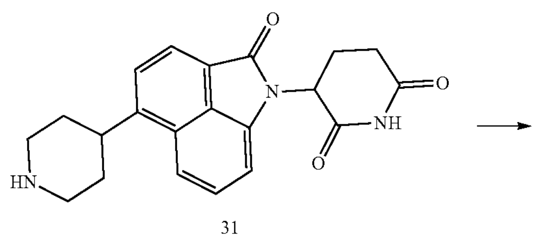

31

-continued

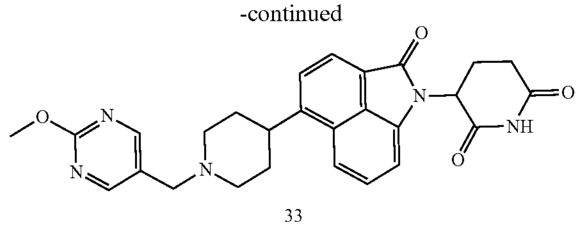

33

To a stirred solution of 3-[2-oxo-5-(4-piperidyl)benzo[cd]indol-1-yl]piperidine-2,6-dione (Compound 31) (0.060 g, 150.05 μmol) in THF (2 mL) was added triethyl amine (30.37 mg, 300.10 μmol, 41.83 μL) followed by 2-methoxy-pyrimidine-5-carbaldehyde (20.73 mg, 150.05 μmol). The solution was stirred for 30 minutes. Sodium cyanoborohydride (23.57 mg, 375.12 μmol) was added and the reaction was stirred at room temperature for 16 hours. The progress of the reaction was monitored by TLC and after reaction completion, the reaction mixture was diluted with ethyl acetate and washed with brine. The separated organic layer was dried over anhydrous sodium sulfate, filtered and concentrated under reduced pressure. The resulting crude compound was purified by column chromatography, eluting with 1 to 5% MeOH in DCM, to provide 3-[5-[1-[(2-methoxy-pyrimidin-5-yl)methyl]-4-piperidyl]-2-oxo-benzo[cd]indol-1-yl]piperidine-2,6-dione (Compound 33) (10 mg, 20.25 μmol, 13% yield) as off-white solid. $^1$HNMR (400 MHz, DMSO-d6): δ 11.11 (s, 1H), 8.56 (S, 2H), 8.04-8.02 (d, J=8 Hz, 1H), 7.85-7.82 (d, J=12 Hz, 1H), 7.73-7.71 (d, J=8 Hz, 1H), 7.55-7.51 (m, 1H), 7.15-7.13 (d, J=8 Hz, 1H), 5.44-5.42 (m, 1H), 3.91 (s, 3H), 3.55-3.41 (m, 4H), 2.98-2.96 (m, 3H), 2.76-2.74 (m, 1H), 2.66-2.62 (m, 1H), 2.32-2.25 (m, 2H), 2.09-2.08 (m, 1H), 1.96-1.93 (m, 3H). LC-MS:(ES$^+$)=486.2 [M+H]+

Example 12. 3-[5-[1-[(3-Morpholinosulfonylphenyl)methyl]-4-piperidyl]-2-oxo-benzo[cd]indol-1-yl]piperidine-2,6-dione (Compound 34)

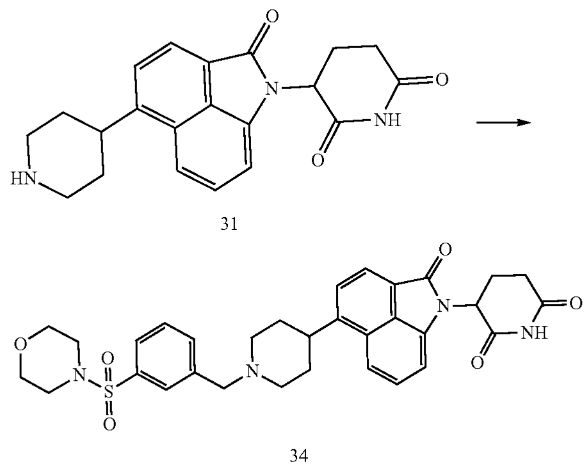

31

34

To a stirred solution of 3-[2-oxo-5-(4-piperidyl)benzo[cd]indol-1-yl]piperidine-2,6-dione (Compound 31) (0.075 g, 187.56 μmol) in THF (5 mL) was added triethylamine (37.96 mg, 375.12 μmol, 52 μL) followed by 3-morpholinosulfonylbenzaldehyde (47.88 mg, 187.56 μmol) and the reaction was stirred at room temperature for 30 minutes. Sodium cyanoborohydride (29.47 mg, 468.90 μmol) was added and the stirring was continued for another 16 hours. The progress of the reaction was monitored by TLC and after reaction completion, the mixture was dissolved in ethyl acetate. The solution washed with sodium bicarbonate followed by brine. The organic layer was separated and dried over anhydrous sodium sulfate, filtered and concentrated under reduced pressure. The crude compound was purified by Prep.HPLC chromatography to provide 3-[5-[1-[(3-morpholinosulfonylphenyl)methyl]-4-piperidyl]-2-oxo-benzo[cd]indol-1-yl]piperidine-2,6-dione (Compound 34) (32 mg, 52.70 μmol, 28% yield) as a yellow solid. THNMR (400 MHz, DMSO-d6): δ 11.10 (s, 1H), 8.05-8.03 (d, J=8 Hz, 1H), 7.85-7.82 (d, J=12 Hz, 1H), 7.76-7.74 (m, 3H), 7.55-7.51 (m, 2H), 7.15-7.13 (d, J=8 Hz, 1H), 5.45-5.41 (m, 1H), 3.70 (m, 2H), 3.62 (m, 4H), 3.44 (m, 1H), 2.99-2.97 (m, 3H), 2.91-2.87 (m, 4H), 2.77-2.76 (m, 1H), 2.66-2.63 (m, 2H), 2.32 (m, 2H), 2.09-2.06 (m, 1H), 1.88 (m, 4H).

LC-MS:(ES$^+$)=603.2 [M+H]+

Example 13. 3-[5-[1-[(3-Fluoro-4-methyl-phenyl)methyl]-4-piperidyl]-2-oxo-benzo[cd]indol-1-yl]piperidine-2,6-dione (Compound 35)

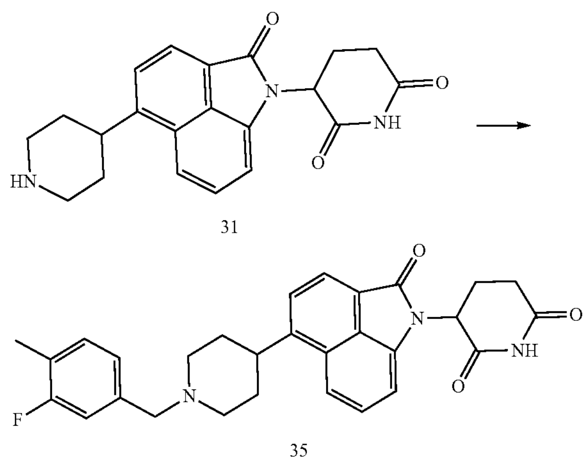

31

35

To a stirred solution of 3-[2-oxo-5-(4-piperidyl)benzo[cd]indol-1-yl]piperidine-2,6-dione (Compound 31) (75 mg, 187.56 μmol) in THF (2 mL) was added 3-fluoro-4-methyl-benzaldehyde (25.91 mg, 187.56 μmol, 22.93 μL) followed by triethylamine (37.96 mg, 375.12 μmol, 52 μL). The reaction mixture was then stirred at room temperature for 30 minutes before sodium cyanoborohydride (29.47 mg, 468.90 μmol) was added and the reaction mixture was stirred for another 16 hour at room temperature. The progress of the reaction was monitored by TLC and after reaction completion, the mixture was dissolved in ethyl acetate and washed with sodium bicarbonate and brine. The separated organic layer was dried over anhydrous sodium sulfate, filtered, and concentrated under reduced pressure to provide the crude compound, which was purified by column chromatography (1 to 5% MeOH in DCM) and then Prep.HPLC to provide 3-[5-[1-[(3-fluoro-4-methyl-phenyl)methyl]-4-piperidyl]-2-oxo-benzo[cd]indol-1-yl]piperidine-2,6-dione (Compound 35) (6 mg, 11.74 μmol, 6% yield) as off-white solid. $^1$HNMR (400 MHz, DMSO-$d_6$): δ 11.12 (s, 1H), 8.04-8.03 (d, J=4 Hz, 1H), 7.84-7.82 (d, J=8 Hz, 1H), 7.75-7.73 (d, J=8 Hz, 1H), 7.53 (m, 1H), 7.26-7.22 (m, 1H), 7.15-7.07 (m, 3H), 3.54 (s, 2H), 3.39-3.30 (m, 2H), 2.98-2.95 (m, 3H), 2.76-2.73 (m, 1H), 2.66-2.62 (m, 1H), 2.21 (m, 4H), 2.07 (m, 1H), 1.85 (m, 4H) 1.73 (m, 1H). LC-MS:(ES$^+$)=486.3 [M+H]+

Example 14. 3-[5-[1-[(2-Morpholinopyrimidin-5-yl)methyl]-4-piperidyl]-2-oxo-benzo[cd]indol-1-yl]piperidine-2,6-dione (Compound 36)

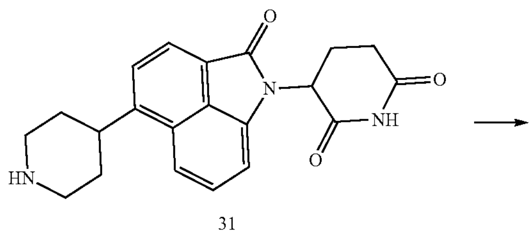

31

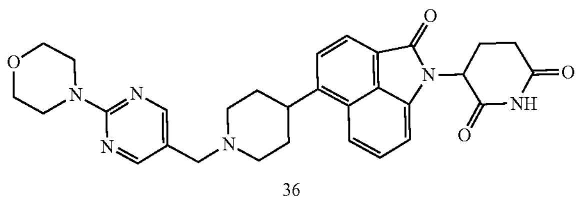

36

To a stirred solution of 3-[2-oxo-5-(4-piperidyl)benzo[cd]indol-1-yl]piperidine-2,6-dione (Compound 31) (0.075 g, 187.56 μmol) in THF (5 mL) was added 2-morpholinopyrimidine-5-carbaldehyde (36.24 mg, 187.56 μmol) and then triethyl amine (37.96 mg, 375.12 μmol, 52.28 μL). The reaction mixture was stirred at room temperature for 30 minutes before sodium cyanoborohydride (29.47 mg, 468.90 μmol) was added. The reaction mixture was stirred at room temperature for 16 hours. The progress of the reaction was monitored by TLC and after reaction completion, the reaction mixture was dissolved in ethyl acetate and given subsequent sodium bicarbonate and brine washes. The separated organic layer was dried over anhydrous sodium sulfate, filtered and concentrated under reduced pressure. The resulting crude compound was purified by Prep.HPLC to provide 3-[5-[1-[(2-morpholinopyrimidin-5-yl)methyl]-4-piperidyl]-2-oxo-benzo[cd]indol-1-yl]piperidine-2,6-dione (Compound 36) (25 mg, 45.48 μmol, 24% yield) as a light yellow solid. $^1$HNMR (400 MHz, DMSO-$d_6$): δ 11.08 (s, 1H), 8.34 (s, 2H), 8.04-8.02 (d, J=8 Hz, 1H), 7.84-7.82 (d, J=8 Hz, 1H), 7.72-7.70 (d, J=8 Hz, 1H), 7.54-7.50 (m, 1H), 7.15-7.13 (d, J=8 Hz, 1H), 3.67-3.66 (m, 6H), 3.34 (s, 2H), 2.98-2.91 (m, 2H), 2.79-2.73 (m, 1H), 2.66 (m, 1H), 2.62-2.59 (m, 1H), 2.37-2.32 (m, 1H), 2.22-2.20 (m, 2H), 2.09 (m, 1H), 1.98 (m, 1H), 1.85-1.75 (m, 6H). LC-MS:(ES$^+$)=541.3 [M+H]+

Example 15. 3-[5-[1-(1H-Indazol-5-ylmethyl)-4-piperidyl]-2-oxo-benzo[cd]indol-1-yl]piperidine-2,6-dione (Compound 37)

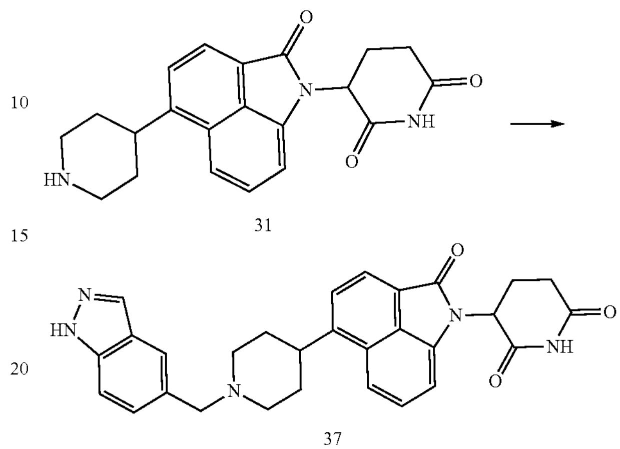

31

37

To a stirred solution of 3-[2-oxo-5-(4-piperidyl)benzo[cd]indol-1-yl]piperidine-2,6-dione (Compound 31) (0.075 g, 187.56 μmol) in THF (5 mL) was added triethyl amine (37.96 mg, 375.12 μmol, 52.28 μL). The reaction was stirred at room temperature for 30 minutes and then sodium cyanoborohydride (29.47 mg, 468.90 μmol) was added and the reaction was stirred at room temperature for 16 hours. The progress of the reaction was monitored by TLC and after reaction completion, r the mixture was dissolved in ethyl acetate and washed with sodium bicarbonate and brine. The organic layer was separated and dried over anhydrous sodium sulfate, filtered and concentrated under reduced pressure. The crude compound was purified by silica gel column chromatography (0 to 5% MeOH in DCM) followed by Prep.HPLC purification to provide 3-[5-[1-(1H-indazol-5-ylmethyl)-4-piperidyl]-2-oxo-benzo[cd]indol-1-yl]piperidine-2,6-dione (Compound 37) (30 mg, 58.49 μmol, 31% yield, 96%) as light yellow solid. $^1$HNMR (400 MHz, DMSO-d6): δ 13.01 (s, 1H), 11.10 (s, 1H), 8.04-8.03 (m, 2H), 7.84-7.82 (m, 1H), 7.73-7.71 (m, 2H), 7.55-7.51 (m, 2H), 7.39-7.37 (m, 1H), 7.15-7.13 (d, J=8 Hz, 1H), 5.45-5.41 (m, 1H), 3.70 (s, 2H), 3.44 (m, 1H), 3.05 (m, 2H), 2.97-2.91 (m, 1H), 2.79-2.73 (m, 1H), 2.66-2.62 (m, 2H), 2.32 (m, 2H), 2.09-2.07 (m, 1H), 1.88 (m, 3H).

LC-MS:(ES$^+$)=494.2 [M+H]+

Example 16. 3-[5-[1-(1H-Indol-2-ylmethyl)-4-piperidyl]-2-oxo-benzo[cd]indol-1-yl]piperidine-2,6-dione (Compound 38)

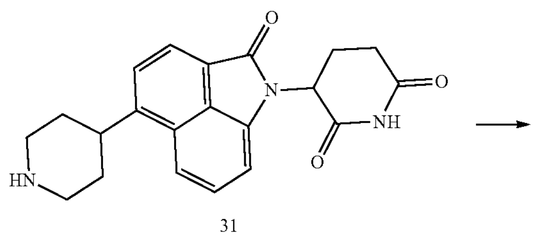

31

-continued

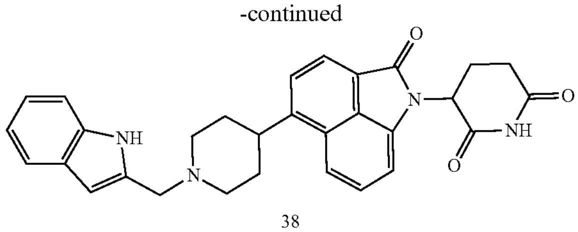

38

To a stirred solution of 3-[2-oxo-5-(4-piperidyl)benzo[cd]indol-1-yl]piperidine-2,6-dione (Compound 31) (0.090 g, 225.07 μmol) in THF (5 mL) was added triethylamine (45.55 mg, 450.15 μmol, 62.74 μL), followed by 1H-indole-2-carbaldehyde (39.21 mg, 270.09 μmol), phenylsilane (121.78 mg, 1.13 mmol) and dibutyltin dichloride (341.94 mg, 1.13 mmol). The reaction was stirred at 60° C. for 16 hours. The progress of the reaction was monitored by TLC. After reaction completion, the reaction mixture was dissolved in ethyl acetate and then washed with sodium bicarbonate followed by brine. The organic layer was separated and dried over anhydrous sodium sulfate, filtered and concentrated under reduced pressure. The crude compound awas purified by Prep.HPLC to provide 3-[5-[1-(1H-indol-2-ylmethyl)-4-piperidyl]-2-oxo-benzo[cd]indol-1-yl]piperidine-2,6-dione (Compound 38) (24 mg, 46.90 μmol, 20% yield) as yellow solid. $^1$HNMR (400 MHz, DMSO-d6): δ 11.10 (brs, 1H), 11.01 (s, 1H), 8.05-8.03 (d, J=8 Hz, 1H), 7.85-7.82 (d, J=12 Hz, 1H), 7.72-7.70 (d, J=8 Hz, 1H), 7.54-7.50 (m, 1H), 7.46-7.44 (d, J=6 Hz, 1H), 7.34-7.32 (d, J=8 Hz, 1H), 7.15-7.13 (d, J=8 Hz, 1H), 7.04-7.00 (m, 1H), 6.96-6.92 (m, 1H), 6.30 (s, 1H), 5.45-5.41 (m, 1H), 3.71 (s, 2H), 3.42-3.40 (m, 2H), 3.06-3.03 (m, 2H), 2.98-2.97 (m, 1H), 2.91-2.90 (m, 1H), 2.69-2.60 (m, 1H), 2.31-2.27 (m, 1H), 2.09-2.06 (m, 1H), 1.90-1.88 (m, 4H). LC-MS:(ES$^+$)=493.2 [M+H]+

Example 17. 3-[5-[1-(1H-Indazol-4-ylmethyl)-4-piperidyl]-2-oxo-benzo[cd]indol-1-yl]piperidine-2,6-dione (Compound 39)

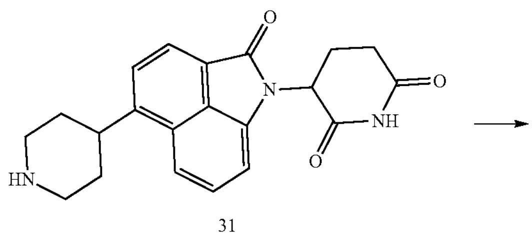

31

-continued

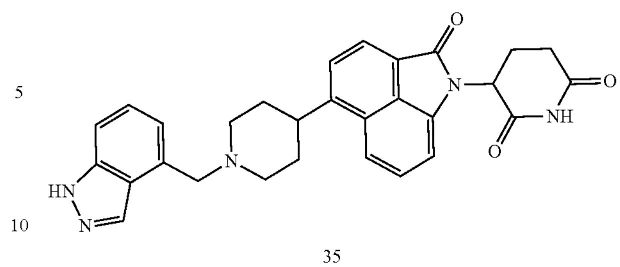

35

To a stirred solution of 3-[2-oxo-5-(4-piperidyl)benzo[cd]indol-1-yl]piperidine-2,6-dione (Compound 39) (0.075 g, 187.56 μmol) in THF (5 mL) was added triethyl amine (37.96 mg, 375.12 μmol, 52.28 μL) and the reaction was stirred for 30 minutes. Later, sodium cyanoborohydride (29.47 mg, 468.90 μmol) was added and the reaction mixture was stirred at room temperature for 16 hours. The progress of the reaction was monitored by TLC and after reaction completion, the reaction mixture was dissolved in ethyl acetate and washed with sodium bicarbonate and brine. The organics were separated and dried over anhydrous sodium sulfate, filtered and concentrated under reduced pressure to afford the crude compound. The crude material was purified by silica gel column chromatography (0 to 5% MeOH in DCM), followed by prep.HPLC purification to provide 3-[5-[1-(1H-indazol-4-ylmethyl)-4-piperidyl]-2-oxo-benzo[cd]indol-1-yl]piperidine-2,6-dione (Compound 39) (11 mg, 22.07 μmol, 11% yield) as a light yellow solid. $^1$HNMR (400 MHz, DMSO-$d_6$): δ 13.04 (s, 1H), 11.12 (s, 1H), 8.30 (s, 1H), 8.04-8.03 (d, J=4 Hz, 1H), 7.84-7.82 (d, J=8 Hz, 1H), 7.75-7.74 (d, J=4 Hz, 1H), 7.55-7.51 (m, 1H), 7.44-7.42 (m, 1H), 7.31-7.29 (m, 1H), 7.15-7.13 (m, 1H), 7.08 (m, 1H), 5.44-5.43 (m, 1H), 3.88 (s, 2H), 3.42 (m, 1H), 3.03 (m, 2H), 2.94-2.91 (m, 1H), 2.86-2.80 (m, 1H), 2.76-2.73 (m, 1H), 2.66-2.62 (m, 1H), 2.32 (m, 2H), 2.07 (m, 1H), 1.87 (m, 3H). LC-MS:(ES$^+$)=494.4 [M+H]+

Example 18. 4-(2,6-Bis(benzyloxy)pyridin-3-yl)-8-bromopyrrolo[2,3,4-de]quinolin-5(4H)-one (Compound 40)

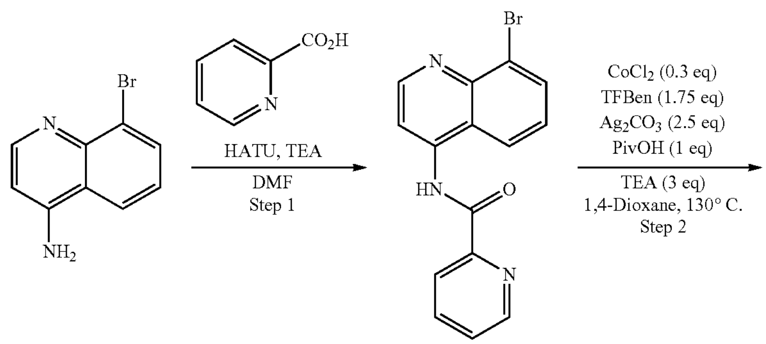

-continued

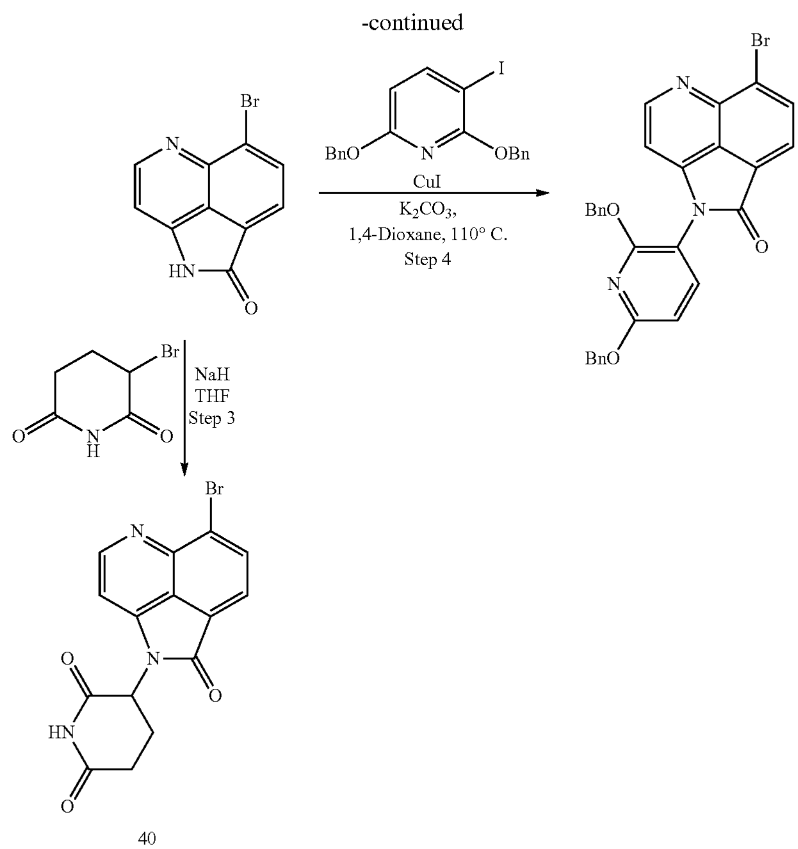

40

Step 1: Synthesis of N-(8-Bromoquinolin-4-yl)picolinamide: To a stirred suspension of 8-bromoquinolin-4-amine (CAS: 65340-75-2) in DMF (10 vol eq) is added picolinic acid (1 eq), TEA (3 eq) followed by HATU (1.1 eq) and the mixture is stirred at room temperature. Upon completion of reaction, the mixture is quenched, worked up and purified using standard protocols to afford N-(8-bromoquinolin-4-yl) picolinamide.

Step 2: Synthesis of 8-Bromopyrrolo[2,3,4-de]quinolin-5(4H)-one: A suspension of N-(8-bromoquinolin-4-yl)picolinamide (1 eq), $CoCl_2$ (0.3 eq), $Ag_2CO_3$ (2.5 eq), benzene-1,3,5-triyl triformate (TFBen, 1.75 eq), PivOH (1 eq) and TEA (3 eq) in 1,4-dioxane (10 vol eq) is heated at 130° C. for 20 hours according to procedures from *Org. Lett.* 2019, 21, 5694-5698. Upon reaction completion, the mixture is worked up and purified using standard protocols to afford 8-bromopyrrolo[2,3,4-de]quinolin-5(4H)-one.

Step 3: Synthesis of 3-(8-Bromo-5-oxopyrrolo[2,3,4-de]quinolin-4(5H)-yl)piperidine-2,6-dione: To a stirred solution of 8-bromopyrrolo[2,3,4-de]quinolin-5(4H)-one in THF (10 vol eq) at 0° C. is added NaH (5 eq). The reaction is stirred at this temperature for 15 minutes before the addition of 3-bromopiperidine-2,6-dione (1 eq). The reaction mixture is slowly heated to 60° C. and stirred at this temperature until completion of the reaction. A standard workup and purification provides 3-(8-bromo-5-oxopyrrolo[2,3,4-de]quinolin-4(5H)-yl)piperidine-2,6-dione.

Step 4: Synthesis of 4-(2,6-Bis(benzyloxy)pyridin-3-yl)-8-bromopyrrolo[2,3,4-de]quinolin-5(4H)-one (Compound 40): In a sealed tube, 3-bromopyridine (1 eq) is combined with 8-bromopyrrolo[2,3,4-de]quinolin-5(4H)-one (1 eq), copper (I) iodide (0.1 eq), potassium carbonate (2 eq) and N,N'-dimethylethylenediamine (0.2 eq) in 1,4-dioxane (0.3 M) according to procedures from Aebi, J. et. al. (2013) and PCT Application No. WO 2013079452. The reaction mixture is heated at 110° C. overnight or until completion of reaction. A standard workup and purification provides 4-(2,6-bis(benzyloxy)pyridin-3-yl)-8-bromopyrrolo[2,3,4-de]quinolin-5(4H)-one.

Example 19. 3-(5-Oxo-8-((S)-2-oxoindolin-3-yl)pyrrolo[2,3,4-de]quinolin-4(5H)-yl)piperidine-2,6-dione (Compound 43A) and 3-(5-oxo-8-((R)-2-oxoindolin-3-yl)pyrrolo[2,3,4-de]quinolin-4(5H)-yl)piperidine-2,6-dione (Compound 43B)

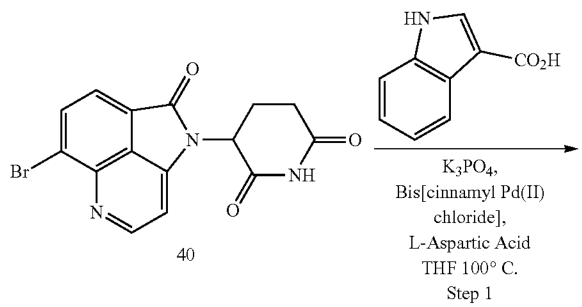

40

-continued

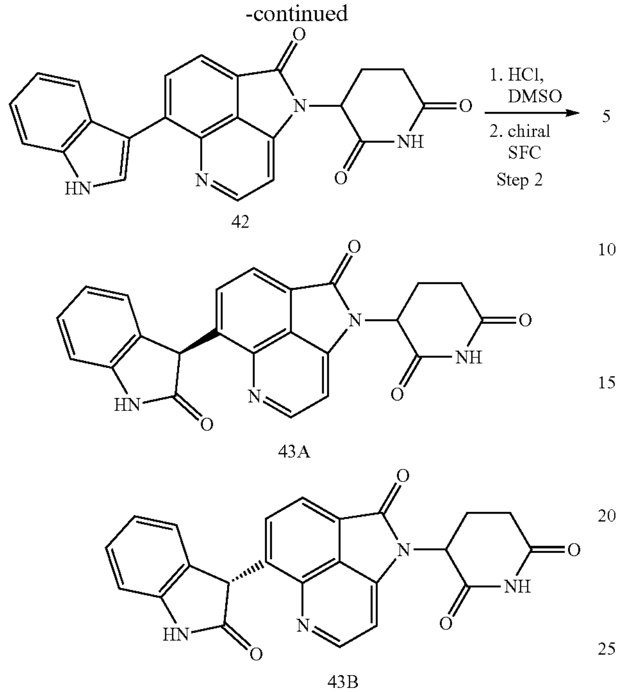

42

43A

43B

Step 1: Synthesis of 3-(8-(1H-Indol-3-yl)-5-oxopyrrolo[2,3,4-de]quinolin-4(5H)-yl)piperidine-2,6-dione (Compound 42): Following an analogous procedure described in Lokhande et al. (*Advanced Synthesis* & *Catalysis,* 362(14), 2857-2863), a stirred and degassed solution of 1H-indole-3-carboxylic acid (1 eq), 3-(8-bromo-5-oxopyrrolo[2,3,4-de]quinolin-4(5H)-yl)piperidine-2,6-dione (Compound 40) (1.0 eq), $K_3PO_4$ (2 eq.), palladium, di-μ-chlorobis[(1,2,3-η)-1-phenyl-2-propen-1-yl]di-(0.2 eq.), and L-aspartic acid (1.0 eq.) in THF (0.2 M) is sealed and is stirred for 24 hours at 100° C. Upon reaction completion, the reaction is concentrated and sequentially purified by column chromatography (DCM, MeOH) to provide 3-(8-(1H-indol-3-yl)-5-oxopyrrolo[2,3,4-de]quinolin-4(5H)-yl)piperidine-2,6-dione (Compound 42).

Step 2: Synthesis of 3-(5-Oxo-8-((S)-2-oxoindolin-3-yl)pyrrolo[2,3,4-de]quinolin-4(5H)-yl)piperidine-2,6-dione (Compound 43A) and 3-(5-oxo-8-((R)-2-oxoindolin-3-yl)pyrrolo[2,3,4-de]quinolin-4(5H)-yl)piperidine-2,6-dione (Compound 43B): 3-(8-(1H-indol-3-yl)-5-oxopyrrolo[2,3,4-de]quinolin-4(5H)-yl)piperidine-2,6-dione (Compound 42) (1.0 mmol) is dissolved in dimethyl sulfoxide (10 equivalents). Concentrated hydrochloric acid (12 N, 18 equivalents) is added to the reaction mixture dropwise at room temperature. Upon reaction completion, the reaction mixture is neutralized to pH>6. Concentrated ammonium hydroxide is added to the reaction mixture. The reaction mixture is extracted with dichloromethane. The organic phases are combined. The organic phases are dried over sodium sulfate, filtered and concentrated and purified by chiral SFC to provide 3-(5-oxo-8-((S)-2-oxoindolin-3-yl)pyrrolo[2,3,4-de]quinolin-4(5H)-yl)piperidine-2,6-dione (Compound 43A) and 3-(5-oxo-8-((R)-2-oxoindolin-3-yl)pyrrolo[2,3,4-de]quinolin-4(5H)-yl)piperidine-2,6-dione (Compound 43B).

Example 20. 3-(5-Oxo-8-((S)-1,2,3,4-tetrahydroisoquinolin-3-yl)pyrrolo[2,3,4-de]quinolin-4(5H)-yl)piperidine-2,6-dione (Compound 44)

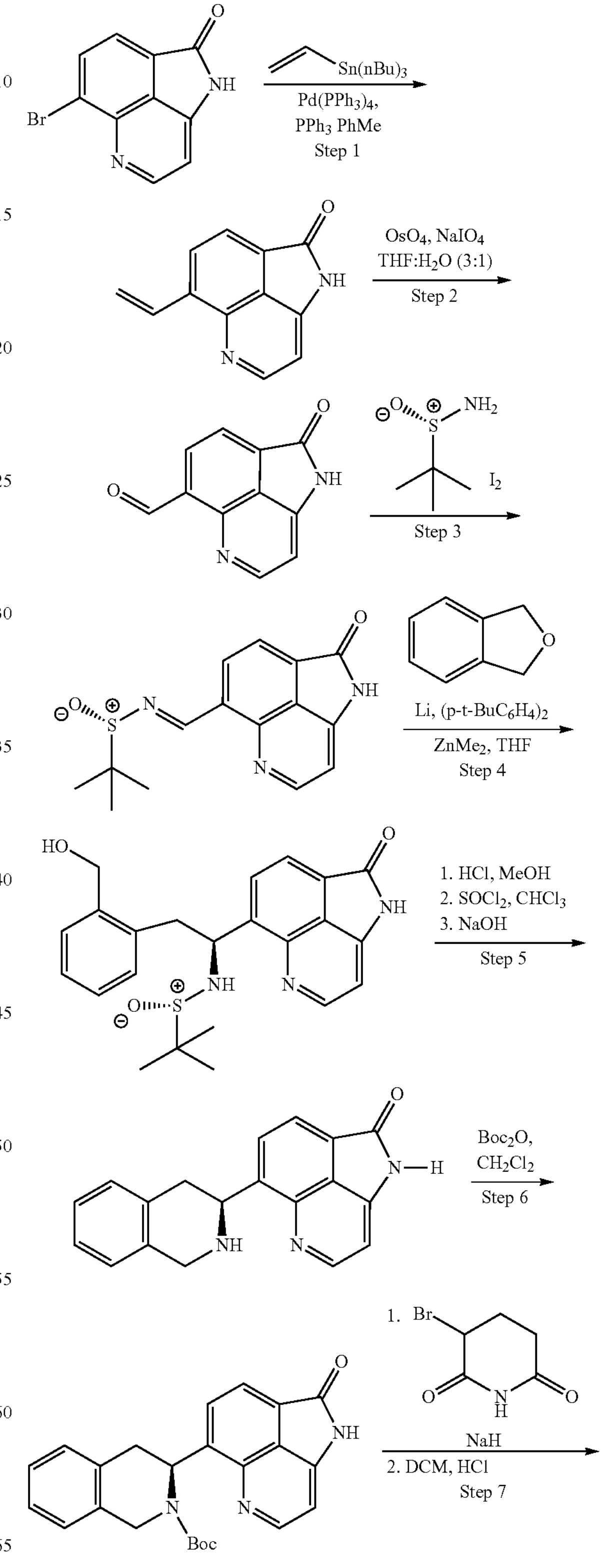

-continued

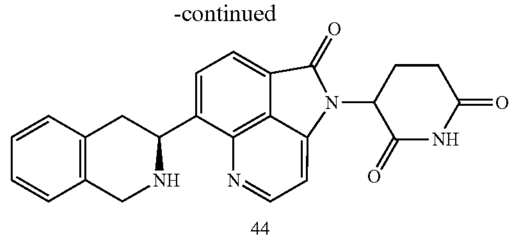

44

Step 1: Synthesis of 8-Vinylpyrrolo[2,3,4-de]quinolin-5(4H)-one: A stirred solution of 8-bromopyrrolo[2,3,4-de]quinolin-5(4H)-one (179.348 mmol) in toluene (800 mL) was purged with argon for 20 minutes before tributyl vinyl tin (55.037 mL, 188.315 mmol), triphenylphosphine (2.352 g, 8.967 mmol) and tetrakis(triphenylphosphine)palladium (10.363 g, 8.967 mmol) are added. The reaction mixture is heated at 110° C. for 16 hours. After completion of the reaction (monitor by TLC), the solution is evaporated under reduced pressure and the crude reside is purified by column chromatography (100-200 Silica; Gradient: 0-20% EtOAc in hexane) to obtain 8-vinylpyrrolo[2,3,4-de]quinolin-5(4H)-one.

Step 2: Synthesis of 5-Oxo-4,5-dihydropyrrolo[2,3,4-de]quinoline-8-carbaldehyde: To a stirred solution of 8-vinylpyrrolo[2,3,4-de]quinolin-5(4H)-one (112.5 mmol) in water (100 mL) and THF (300 mL) is added a 4% solution of tetraoxoosmium in water (572 mg, 507.35 µmol, 14.3 mL) and the reaction is stirred at room temperature for 20 minutes. Sodium periodate (60.157 g, 281.25 mmol) is added and the reaction is stirred at room temperature for 1 hour. After completion of the reaction (monitor by TLC), the solution is filtered through a celite bed and washed with THF and EtOAc. The organics are dried over sodium sulfate and concentrated under reduced pressure to afford 5-oxo-4,5-dihydropyrrolo[2,3,4-de]quinoline-8-carbaldehyde X.

Step 3: Synthesis of (E)-2-Methy-N-((5-oxo-4,5-dihydropyrrolo[2,3,4-de]quinolin-8-yl)methylene)propane-2-sulfinamide: A mixture of 2-methyl-2-propanesulfinanide (61 mg, 0.5 mmol), 5-oxo-4,5-dihydropyrrolo[2,3,4-de]quinoline-8-carbaldehyde (0.5 mmol) and elemental iodine (13 mg, 0.05 mmol) is placed in a 5 mL grinding steel jar. The reaction mixture is milled for 20 minutes at 30 Hz. The reaction mixture is dissolved in dichloromethane (20 mL). The reaction mixture is washed with a saturated solution of $Na_2S_2O_8$ (10 mL), brine (10 mL), The organic phase is dried over anhydrous $MgSO_4$. The reaction mixture is filtered and evaporated under reduced pressure. The residue is purified by flash chromatography (EtOAc/n-hexane) to obtain (E)-2-methyl-N-((5-oxo-4,5-dihydropyrrolo[2,3,4-de]quinolin-8-yl)methylene)propane-2-sulfinamide.

Step 4: Synthesis of N—((S)-2-(2-(Hydroxymethyl)phenyl-1-(5-oxo-4,5-dihydropyrrolo[2,3,4-de]quinolin-8-yl)ethyl)-2-methylpropane-2-sulfinamide: A solution of phthalan (360 mg) is added dropwise to a blue suspension of lithium powder (140 mg, 20.0 mmol) and a catalytic amount of DTBB (80.0 mg, 0.3 mmol) in THF (5 mL) under argon. The mixture is stirred at 0° C. for 45 minutes. The excess lithium is filtered off (by cannula under argon and use a filter plate). A solution of $ZnMe_2$ (3.0 mL, 1.0 M in hexane) is added dropwise to the mixture. Stirring of the mixture is continued for 15 minutes at room temperature. The reaction mixture is cooled to −65° C. A solution of N—((S)-2-(2-(hydroxymethyl)phenyl)-1-(5-oxo-4,5-dihydropyrrolo[2,3,4-de]quinolin-8-yl)ethyl)-2-methylpropane-2-sulfinamide (1.0 mmol) in THF (0.4 mL) is added dropwise to the mixture. After 12 hours, at −65° C., the reaction mixture is hydrolyzed with water (5 mL). The mixture is extracted with ethyl acetate (3×15 mL) at room temperature. The mixture is dried with anhydrous $MgSO_4$. The mixture is evaporated (15 Torr). The residue is purified by column chromatography (silica gel, hexane/ethyl acetate) to obtain N—((S)-2-(2-(hydroxymethyl)phenyl)-1-(5-oxo-4,5-dihydropyrrolo[2,3,4-de]quinolin-8-yl)ethyl)-2-methylpropane-2-sulfinamide.

Step 5: Synthesis of (S)-8-(1,2,3,4-Tetrahydroisoquinolin-3-yl)pyrrolo[2,3,4-de]quinolin-5(4H)-one: A 4M HCl (1 mL) solution in dioxane is added to a stirred solution of N—((S)-2-(2-(hydroxymethyl)phenyl)-1-(5-oxo-4,5-dihydropyrrolo[2,3,4-de]quinolin-8-yl)ethyl)-2-methylpropane-2-sulfinamide (0.50 mmol) in MeOH (6 mL) at 0° C. The mixture is stirred for 3 hours at 0° C. A saturated $NaHCO_3$ solution is added to the mixture. The reaction mixture is extracted with ethyl acetate (3×10 mL). The mixture is dried with anhydrous $MgSO_4$. The mixture is evaporated (15 Torr). The residue is taken up in chloroform (5 mL). Thionyl chloride (1.7 mmol) is added to the mixture at 0° C. The solution is stirred at 50° C. for 4 hours. The solvent is evaporated (15 Torr) The resulting residue is dissolved in THF (5 mL). A 5 M sodium hydroxide solution (10 mL) is added to the mixture. The resulting mixture is stirred vigorously for 10 hours at 20° C. The mixture is dried with anhydrous $MgSO_4$. The mixture is evaporated (15 Torr). The residue is purified by column chromatography (silica gel, chloroform/methanol) to obtain (S)-8-(1,2,3,4-tetrahydroisoquinolin-3-yl)pyrrolo[2,3,4-de]quinolin-5(4H)-one.

Step 6: Synthesis of tert-Butyl (S)-3-(5-oxo-4,5-dihydropyrrolo[2,3,4-de]quinolin-8-yl)-3,4-dihydroisoquinoline-2(1H)-carboxylate: To a stirred solution of (S)-8-(1,2,3,4-tetrahydroisoquinolin-3-yl)pyrrolo[2,3,4-de]quinolin-5(41H)-one (5.25 mmol) in dioxane (50 mL) is added di-tert-butyl dicarbonate (114.68 mg, 525.45 µmol, 120.59 µL) dropwise at room temperature over 10 minutes. The reaction mixture is stirred at room temperature for an additional 5 hours. After completion of the reaction, the solvent is evaporated under reduced pressure to provide a crude residue which is then dissolved in DCM and extracted with water. The organic solvent is dried over anhydrous $Na_2SO_4$, filtered and concentrated under reduced pressure at 50° C. to provide the crude tert-butyl (S)-3-(5-oxo-4,5-dihydropyrrolo[2,3,4-de]quinolin-8-yl)-3,4-dihydroisoquinoline-2(1H)-carboxylate, which is used in the next step without further purification after drying well.

Step 7: Synthesis of 3-(5-Oxo-8-((S)-1,2,3,4-tetrahydroisoquinolin-3-yl)pyrrolo[2,3,4-de]quinolin-4(5H)-yl)piperidine-2,6-dione (Compound 44): To a solution of tert-butyl (S)-3-(5-oxo-4,5-dihydropyrrolo[2,3,4-de]quinolin-8-yl)-3,4-dihydroisoquinoline-2(11H)-carboxylate (1 eq) in THF (10 vol eq) at 0° C. is added NaH (60% in mineral oil, 5 eq) and the reaction is stirred at this temperature for 15 minutes before the addition of 3-bromopiperidine-2,6-dione (1 eq). The reaction mixture is slowly heated to 60° C. and stirred at this temperature until completion of the reaction. A standard workup and purification will provide tert-butyl ((3S)-3-(4-(2,6-dioxopiperidin-3-yl)-5-oxo-4,5-dihydropyrrolo[2,3,4-de]quinolin-8-yl)-3,4-dihydroisoquinolin-2(1H)-yl) carbonate. To a stirred a solution of tert-butyl ((3S)-3-(4-(2,6-dioxopiperidin-3-yl)-5-oxo-4,5-dihydropyrrolo[2,3,4-de]quinolin-8-yl)-3,4-dihydroisoquinolin-2(1H)-yl) carbonate (7.33 mmol) in DCM (10 mL) at 0° C. is added hydrogen chloride solution 4.0 M in dioxane (7.33 mmol, 20 mL) and the reaction is stirred room temperature for 3 hours. The reaction is monitored by LCMS. After completion of the reaction, the solvent is evaporated under vacuum to obtain the crude. The crude is washed with diethyl ether (50 mL) to afford 3-(5-oxo-8-((S)-1,2,3,4-tetrahydroisoquinolin-3-yl)pyrrolo[2,3,4-de]quinolin-4(5H)-yl)piperidine-2,6-dione (Compound 44).

Example 21. 3-(5-Oxo-8-((R)-1,2,3,4-tetrahydroisoquinolin-3-yl)pyrrolo[2,3,4-de]quinolin-4(5H)-yl)piperidine-2,6-dione (Compound 45)

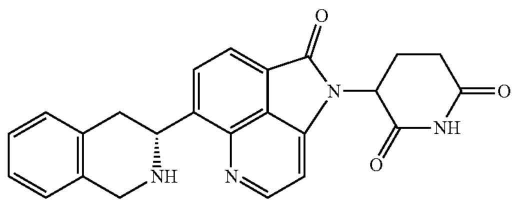

Compound 45 can be prepared by a similar method to that for the preparation of Compound 44 above using the opposite enantiomer of 2-methyl-2-propanesulfinamide in Step 3.

Example 22. 3-(6-((1-Benzylazetidin-3-yl)methyl)-2-oxobenzo[cd]indol-1(2H)-yl)piperidine-2,6-dione (Compound 49) and 3-(6-((1-methylazetidin-3-yl)methyl)-2-oxobenzo[cd]indol-1(2H)-yl)piperidine-2,6-dione (Compound 50)

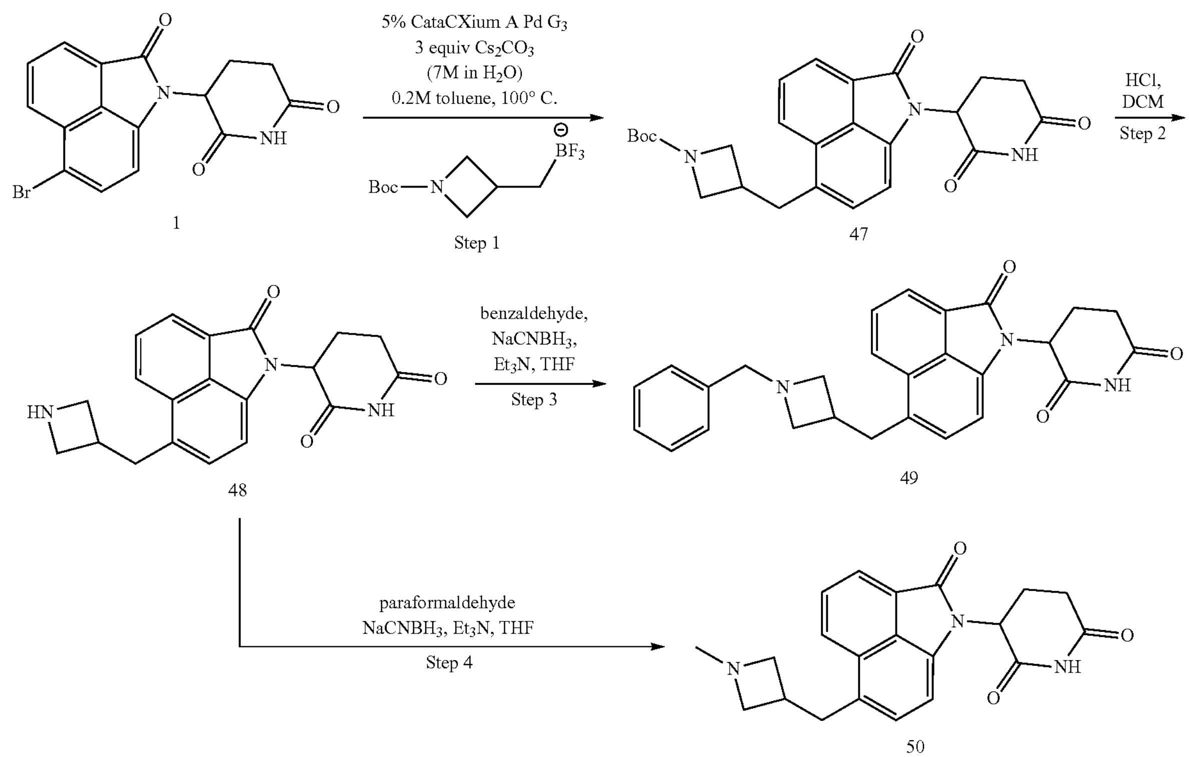

1

47

48

49

50

Step 1: Synthesis of tert-Butyl 3-((1-(2,6-dioxopiperidin-3-yl)-2-oxo-1,2-dihydrobenzo[cd]indol-6-yl)methyl)azetidine-1-carboxylate (Compound 47): ((1-(tert-Butoxycarbonyl)azetidin-3-yl)methyl)trifluoroborate (1.3 equiv, 0.13 mmol) and CataCXium A Pd G3 (5 mol %, 3.6 mg, 4.9×10-3 mmol) is weighed into a 4 mL vial and purged with nitrogen. A solution of 3-(6-bromo-2-oxobenzo[cd]indol-1(2H)-yl)piperidine-2,6-dione (Compound 1) (1 equiv, 0.10 mmol) in 0.45 mL of toluene is added. A nitrogen sparged $Cs_2CO_3$ solution (3 equiv, 7 M in $H_2O$, 43 μL) is added and the reaction is stirred at 100° C. for 72 hours. Upon completion, the reaction is concentrated, taken up in 1:1 MeOH/DMSO and filtered through Celite. The product is purified by reverse phase HPLC to provide tert-butyl 3-((1-(2,6-dioxopiperidin-3-yl)-2-oxo-1,2-dihydrobenzo[cd]indol-6-yl)methyl)azetidine-1-carboxylate (Compound 47).

Step 2: Synthesis of 3-(6-(Azetidin-3-ylmethyl)-2-oxobenzo[cd]indol-1(2H)-yl)piperidine-2,6-dione (Compound 48): To a stirred a solution of tert-butyl 3-((1-(2,6-dioxopiperidin-3-yl)-2-oxo-1,2-dihydrobenzo[cd]indol-6-yl)methyl)azetidine-1-carboxylate (Compound 47) (7.33 mmol) in DCM (10 mL) at 0° C. is added hydrogen chloride solution 4.0 M in dioxane (7.33 mmol, 20 mL) and the reaction is stirred room temperature for 3 hours. The reaction is monitored by LCMS. After completion of the reaction, the solvent is evaporated under vacuum to obtain the crude material. The crude is washed with diethyl ether (50 mL) to afford 3-(6-(azetidin-3-ylmethyl)-2-oxobenzo[cd]indol-1(2H)-yl)piperidine-2,6-dione (Compound 48).

Step 3: Synthesis of 3-(6-((1-Benzylazetidin-3-yl)methyl)-2-oxobenzo[cd]indol-1(2H)-yl)piperidine-2,6-dione (Compound 49): To a stirred solution of 3-(6-(azetidin-3-ylmethyl)-2-oxobenzo[cd]indol-1(2H)-yl)piperidine-2,6-dione (Compound 48) in THF (2 mL) is added benzaldehyde (15.92 mg, 150.05 μmol) and the solution is stirred for 10 minutes. Triethyl amine (30.37 mg, 300.10 μmol, 41.83 μL) is added and the reaction mixture is stirred at room temperature for 30 minutes. Next, sodium cyanoborohydride (23.57 mg, 375.12 μmol) is added the reaction mixture is stirred at room temperature for 16 hours. The progress of the reaction is monitored by TLC and after reaction completion, the reaction mixture is diluted with ethyl acetate and washed with water and brine. The separated organic layer is dried over anhydrous sodium sulfate, filtered and concentrated under reduced pressure. The crude compound is purified by column chromatography, eluting with 1 to 5% MeOH in DCM and then purified by Prep.HPLC to provide 3-(6-((1-benzylazetidin-3-yl)methyl)-2-oxobenzo[cd]indol-1(2H)-yl)piperidine-2,6-dione as a yellow solid.

Step 4: Synthesis of 3-(6-((1-Methylazetidin-3-yl)methyl)-2-oxobenzo[cd]indol-1(2H)-yl)piperidine-2,6-dione (Compound 50): To a stirred solution of 3-(6-(azetidin-3-ylmethyl)-2-oxobenzo[cd]indol-1(2H)-yl)piperidine-2,6-dione (Compound 48) in THF (2 mL) is added paraformaldehyde (150.05 μmol) and the solution is stirred for 10 minutes. Triethyl amine (30.37 mg, 300.10 μmol, 41.83 μL) is added and the reaction mixture is stirred at room temperature for 30 minutes. Next, sodium cyanoborohydride (23.57 mg, 375.12 μmol) is added and the reaction mixture is stirred at room temperature for 16 hours. The progress of the reaction is monitored by TLC and after reaction completion, the reaction mixture is diluted with ethyl acetate and given a water and brine wash. The separated organic layer is dried over anhydrous sodium sulfate, filtered and concentrated under reduced pressure. The crude compound is purified by column chromatography, eluting with 1 to 5% MeOH in DCM and then purified by Prep.HPLC to provide 3-(6-((1-methylazetidin-3-yl)methyl)-2-oxobenzo[cd]indol-1(2H)-yl)piperidine-2,6-dione (Compound 50) as a yellow solid.

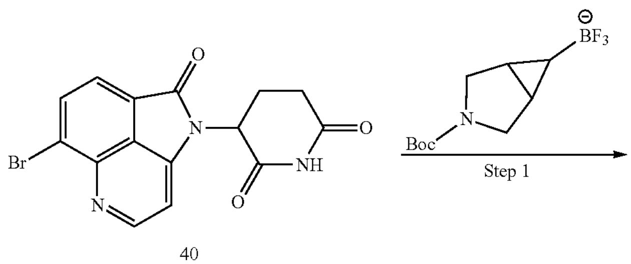

40

Example 23. 3-(8-((1-Benzylazetidin-3-yl)methyl)-5-oxopyrrolo[2,3,4-de]quinolin-4(5H)-yl)piperidine-2,6-dione (Compound 51)

51

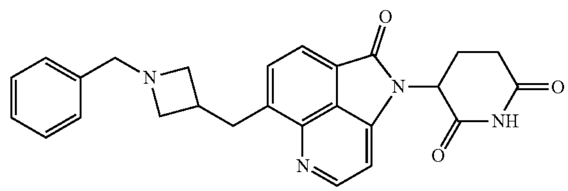

Compound 51 can be made from procedure for Compound 49 using 3-(8-bromo-5-oxopyrrolo[2,3,4-de]quinolin-4(5H)-yl)piperidine-2,6~dione in Step 1.

Example 24. 3-(8-((1-Methylazetidin-3-yl)methyl)-5-oxopyrrolo[2,3,4-de]quinolin-4(5H)-yl)piperidine-2,6-dione (Compound 52)

52

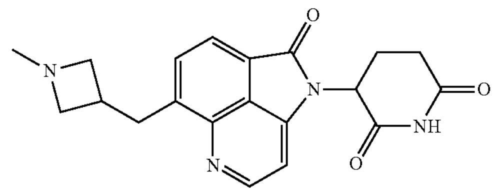

Compound 52 can be made from procedure for Compound 50 using 3-(8-bromo-5-oxopyrrolo[2,3,4-de]quinolin-4(5H)-yl)piperidine-2,6-dione in Step 1.

Example 25. 3-(8-(3-Benzyl-3-azabicyclo[3.1.0]hexan-6-yl)-5-oxopyrrolo[2,3,4-de]quinolin-4(5H)-yl)piperidine-2,6-dione (Compound 56) and 3-(8-(3-Methyl-3-azabicyclo[3.1.0]hexan-6-yl)-5-oxopyrrolo[2,3,4-de]quinolin-4(5H)-yl)piperidine-2,6-dione (Compound 57)

-continued

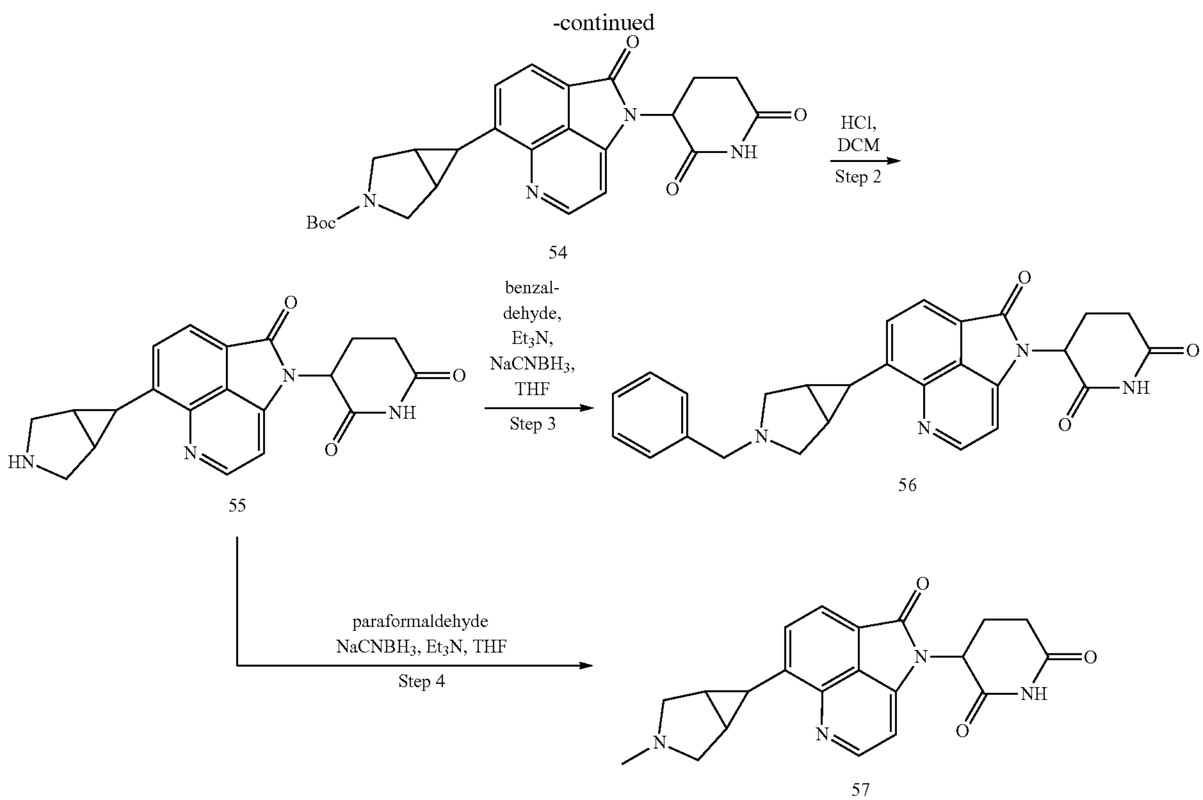

54

55

56

57

Step 1: Synthesis of 6-(4-(2,6-Dioxopiperidin-3-yl)-5-oxo)-4,5-dihydropyrrolo[2,3,4-de]quinolin-8-yl)-3-azabicyclo[3.1.0]hexane-3-carboxylate (Compound 54): To a sealed test-tube is added corresponding (3-(tert-butoxycarbonyl)-3-azabicyclo[3.1.0]hexan-6-yl)trifluoroborate (Compound 40) (0.503 mmol, 1.2 equiv, synthesized from 1H-pyrrole-1-carboxylic acid, 2,5-dihrydro-, 1,1-dimethylethyl ester by the methods of Charette el al. (*Synlett*, (11) 1779-1782; 2005)), 3-(8-bromo-5-oxopyrrolo)[2,3,4-de]quinolin-4(5H)-yl)piperidine-2,6-dione (0.419 mmol, 1.0 equiv), $K_3PO_4$ (2904 mg, 1.385 mmol, 3.3 equiv), $Pd(OAC)_2$ (2.8 mg, 0.013 mmol, 0.03 equiv), 2-biphenyldicyclohexylphosphine (8.8 mg, 0.027 mmol, 0.06 equiv) and 1.7 mL toluene-$H_2O$ (3:1 v/v) under argon atmosphere. The reaction mixture is stirred at 100° C. for 20 hours. The reaction is cooled to room temperature and quenched by the addition of water. The mixture is then transferred to an extraction funnel with $Et_2O$ and the organic phase was, removed. The aqueous phase is extracted with $Et_2O$ (2×15 mL), the combined organic phases are dried with $Na_2SO_4$, filtered and concentrated under reduced pressure. The crude cyclopropane is purified by flash chromatography (EtOAc-hexanes) to afford corresponding tert-butyl 6-(4-(2,6-dioxopiperidin-3-yl)-5-oxo-4,5-dihydropyrrolo[2,3,4-de]quinolin-8-yl)-3-azabicyclo[3.1.0]hexane-3-carboxylate (Compound 54).

Step 2: Synthesis of 3-(8-(3-Azabicyclo[3.1.0]hexan-6-yl)-5-oxopyrrolo[2,3,4-de]quinolin-4(5H)-yl)piperidine-2,6-dione (Compound 55): To a stirred a solution of tert-butyl 6-(4-(2,6-dioxopiperidin-3-yl)-5-oxo-4,5-dihydropyrrolo[2,3,4-de]quinolin-8-yl)-3-azabicyclo[3.1.0]hexane-3-carboxylate (Compound 54) (7.33 mmol) in DCM (10 mL) at 0° C. is added hydrogen chloride solution 4.0 M in dioxane (7.33 mmol, 20 mL) and the reaction is stirred room temperature for 3 hours. The reaction is monitored by LCMS. After completion of the reaction, the solvent is evaporated under vacuum to obtain the crude. The crude is washed with diethyl ether (50 mL) to afford 3-(8-(3-azabicyclo[3.1.0]hexan-6-yl)-5-oxopyrrolo[2,3,4-de]quinolin-4(5H)-yl)piperidine-2,6-dione (Compound 55).

Step 3: Synthesis of 3-(8-(3-Benzyl-3-azabicyclo[3.1.0]hexan-6-yl)-5-oxopyrrolo[2,3,4-de]quinolin-4(5H)-yl)piperidine-2,6-dione (Compound 56): To a stirred solution of 3-(8-(3-azabicyclo[3.1.0]hexan-6-yl)-5-oxopyrrolo[2,3,4-de]quinolin-4(5H)-yl)piperidine-2,6-dione (Compound 55) in THF (2 mL) is added benzaldehyde (15.92 mg, 150.05 μmol μmol) and the solution is stirred for 10 minutes. Triethyl amine (30.37 mg, 300.10 μmol, 41.83 μL) is added and the reaction mixture is stirred at room temperature for 30 minutes. Next, sodium cyanoborohydride (23.57 mg, 375.12 μmol) is added and the reaction mixture is stirred at room temperature for 16 hours. The progress of the reaction is monitored by TLC and after reaction completion, the reaction mixture is diluted with ethyl acetate and washed with water and brine. The separated organic layer is dried over anhydrous sodium sulfate, filtered and concentrated under reduced pressure. The crude compound is purified by column chromatography, eluting with 1 to 5% MeOH in DCM and then purified by Prep.HPLC to provide 3-(8-(3-benzyl-3-azabicyclo[3.1.0]hexan-6-yl)-5-oxopyrrolo[2,3,4-de]quinolin-4(5H)-yl)piperidine-2,6-dione (Compound 56) as a yellow solid.

Step 4: Synthesis of 3-(8-(3-Methyl-3-azabicyclo[3.1.0]hexan-6-yl)-5-oxopyrrolo[2,3,4-de]quinolin-4(5H)-yl)piperidine-2,6-dione (Compound 57): To a stirred solution of 3-(8-(3-azabicyclo[3.1.0]hexan-6-yl)-5-oxopyrrolo[2,3,4-de]quinolin-4(5H)-yl)piperidine-2,6-dione (Compound 55) in THF (2 mL) is added paraformaldehyde (150.05 μmol) and the solution is stirred for 10 minutes. Triethyl amine (30.37 mg, 300.10 μmol, 41.83 μL) is added and the reaction mixture is stirred at room temperature for 30 minutes. Next, sodium cyanoborohydride (23.57 mg, 375.12 μmol) is added and the reaction mixture is stirred at room temperature for 16 hours. The progress of the reaction is monitored by TLC and after reaction completion, the reaction mixture is diluted with ethyl acetate and washed with water and brine. The separated organic layer is dried over anhydrous sodium sulfate, filtered and concentrated under reduced pressure. The crude compound is purified by column chromatography, eluting with 1 to 5% MeOH in DCM and then purified by Prep.HPLC to provide 3-(8-(3-methyl-3-azabicyclo[3.1.0]hexan-6-yl)-5-oxopyrrolo[2,3,4-de]quinolin-4(5H)-yl)piperidine-2,6-dione (Compound 57) as a yellow solid.

Example 26. 3-(5-(3-Benzyl-3-azabicyclo[3.1.0]hexan-6-yl)-2-oxobenzo[cd]indol-1(2H)-yl)piperidine-2,6-dione (Compound 58)

58

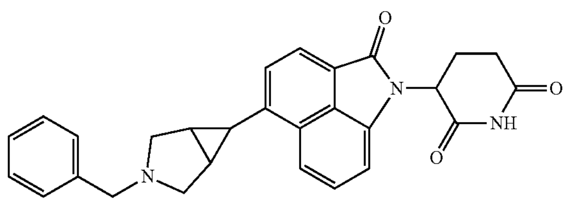

Compound 58 can be made from procedure for Compound 56 using 3-(6-bromo-2-oxobenzo[cd]indol-1(2H)-yl)piperidine-2,6-dione in Step 1.

Example 27. 3-(5-(3-Methyl-3-azabicyclo[3.1.0]hexan-6-yl)-2-oxobenzo[cd]indol-1(2H)-yl)piperidine-2,6-dione

59

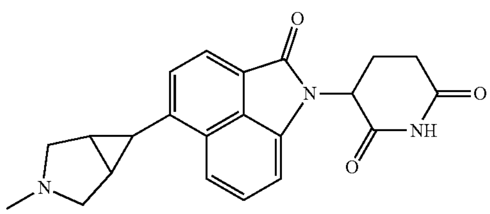

Compound 59 can be made from procedure for Compound 57 using 3-(6-bromo-2-oxobenzo[cd]indol-1(2H)-yl)piperidine-2,6-dione in Step 1.

Example 28. 3-(8-(1-Benzylpiperidin-4-yl)-5-oxopyrrolo[2,3,4-de]quinolin-4(5H)-yl)piperidine-2,6-dione (Compound 60)

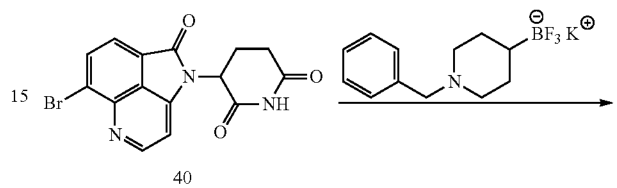

40

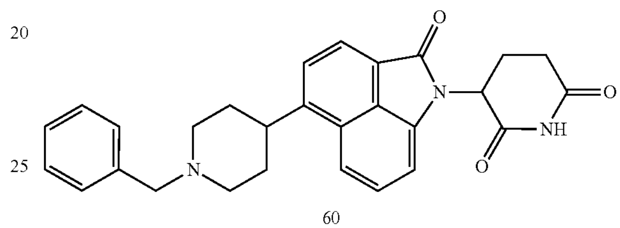

60

To a sealed test-tube is added potassium (1-benzylpiperidin-4-yl)trifluoroborate (1.2 equiv), aryl bromide (1.0 eq), $K_3PO_4$ (3.3 eq), $Pd(OAc)_2$ (0.03 eq), 2-biphenyldicyclohexylphosphine (0.06 eq) (Compound 40) and toluene/$H_2O$ (3:1 v/v, 0.1 M) under an argon atmosphere. The reaction mixture is stirred at 100° C. for 20 hours. The reaction is cooled to room temperature and quenched by the addition of water. The mixture is then extracted with $Et_2O$ (×3) before the combined organic layers are washed with brine (×1) and dried over sodium sulfate before being filtered and concentrated to a crude residue. The crude material is then purified using flash column chromatography to afford the product 3-(8-(1-benzylpiperidin-4-yl)-5-oxopyrrolo[2,3,4-de]quinolin-4(5H)-yl)piperidine-2,6-dione (Compound 60).

Compound 61-Compound 71 was made using the same procedure as described in Example 28 for the preparation of 3-(8-(1-benzylpiperidin-4-yl)-5-oxopyrrolo[2,3,4-de]quinolin-4(5H)-yl)piperidine-2,6-dione (Compound 60) using the appropriate starting materials in the table.

| Aryl bromide | Trifluoroborate salt |
|---|---|
| 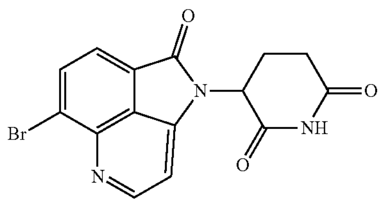 [SMILES: O=C1CCC(N2C(=O)c3ccc(Br)c4nccc2c34)C(=O)N1] | 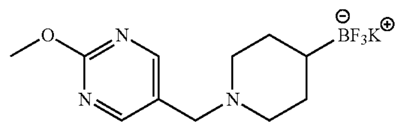 |

-continued
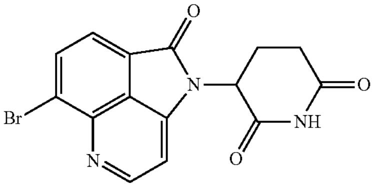 [SMILES: O=C1CCC(N2C(=O)c3ccc(Br)c4nccc2c34)C(=O)N1]
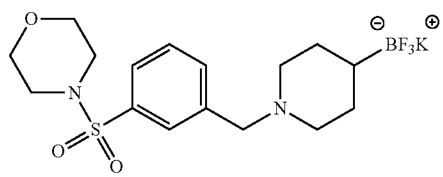
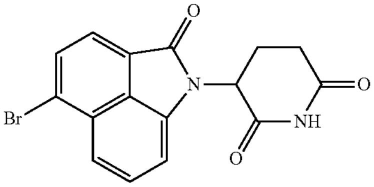
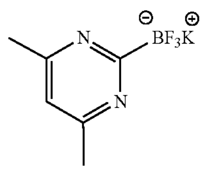
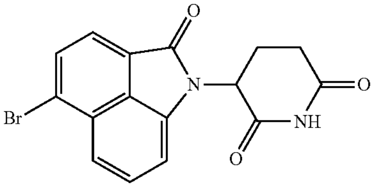 [SMILES: O=C1CCC(N2C(=O)c3ccc(Br)c4cccc2c34)C(=O)N1]
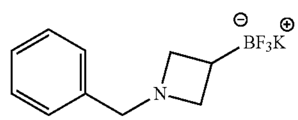
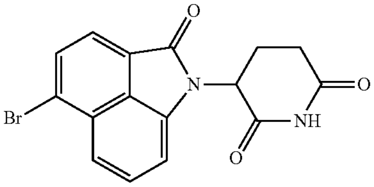
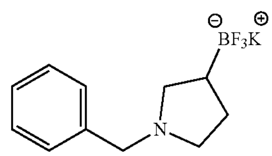
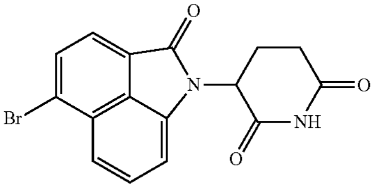 [SMILES: O=C1CCC(N2C(=O)c3ccc(Br)c4cccc2c34)C(=O)N1]
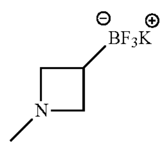
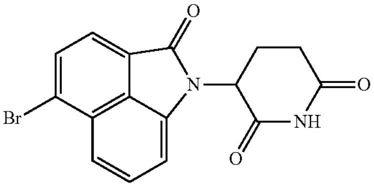 [SMILES: O=C1CCC(N2C(=O)c3ccc(Br)c4cccc2c34)C(=O)N1]
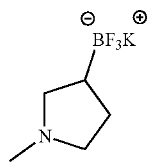
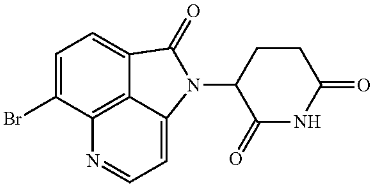
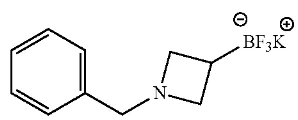
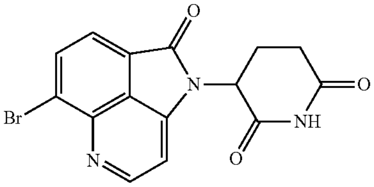
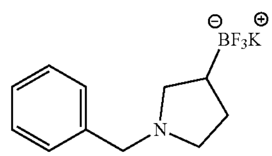

-continued
| | |
|---|---|
| 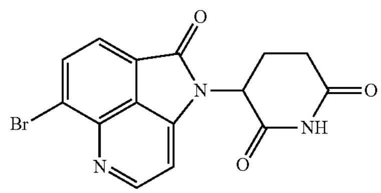 [SMILES: O=C1CCC(N2C(=O)c3ccc(Br)c4nccc2c34)C(=O)N1] | 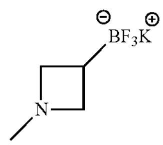 |
| 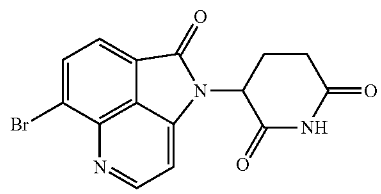 | 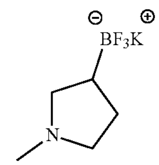 |
| Product |
|---|
| 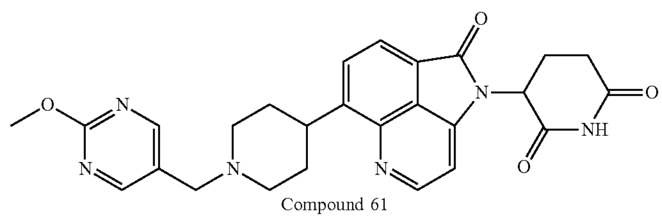 Compound 61 |
| 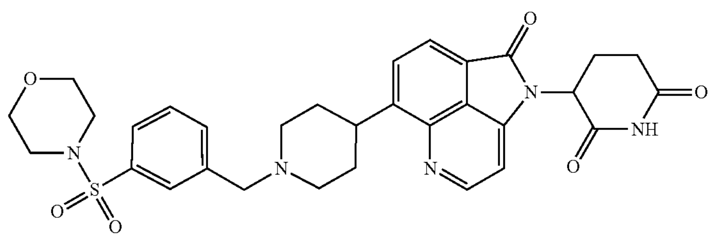 Compound 62 |
| 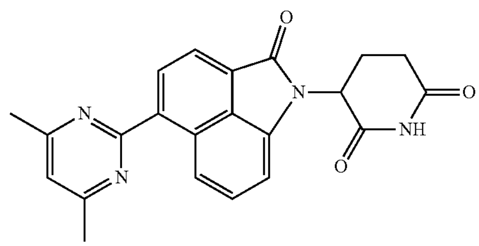 [SMILES: Cc1cc(C)nc(-c2ccc3c4c(cccc24)N(C2CCC(=O)NC2=O)C3=O)n1] Compound 63 |
| 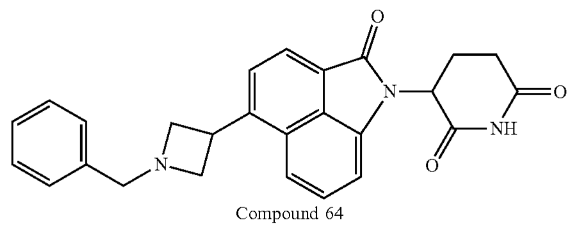 Compound 64 |
| 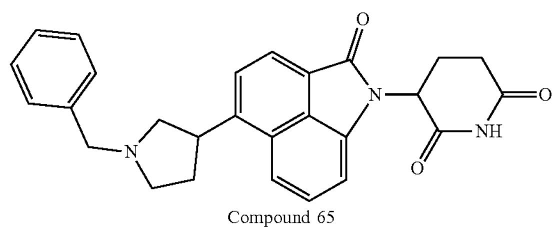 Compound 65 |

-continued
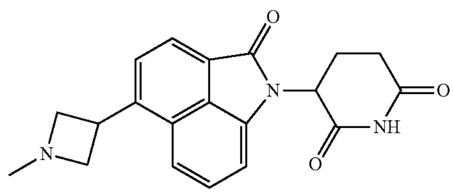
Compound 66
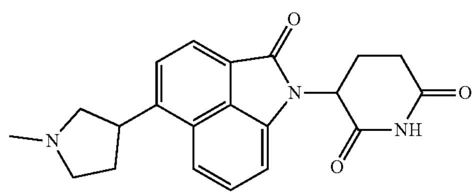
Compound 67
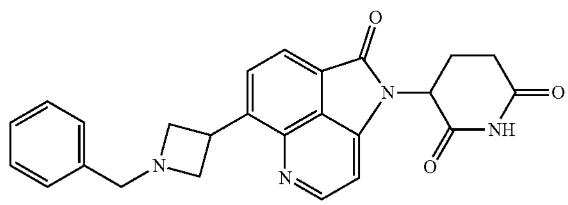 [SMILES: O=C1CCC(N2C(=O)c3ccc(C4CN(Cc5ccccc5)C4)c4cccc2c34)C(=O)N1]
Compound 68
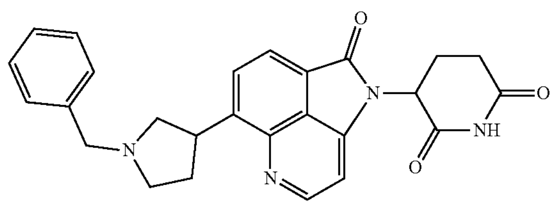
Compound 69
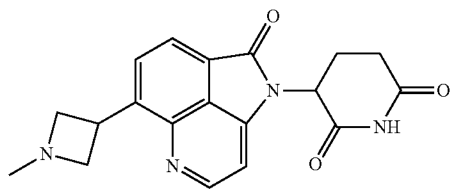 [SMILES: CN1CC(c2ccc3c4c(cccc24)N(C2CCC(=O)NC2=O)C3=O)C1]
Compound 70
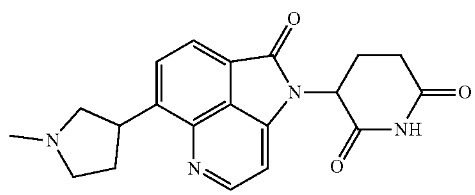 [SMILES: CN1CCC(c2ccc3c4c(ccnc24)N(C2CCC(=O)NC2=O)C3=O)C1]
Compound 71

Compound 72-Compound 75 were made using the same procedure as described in Example 7 for the preparation of 3-(2-oxo-5-((S)-2-phenylpyrrolidin-1-yl)benzo[cd]indol-1(2H)-yl)piperidine-2,6-di one (Compound 18) using the appropriate amine starting material from the table.

| Amine starting material | Product |
|---|---|
| 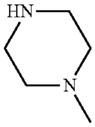 | 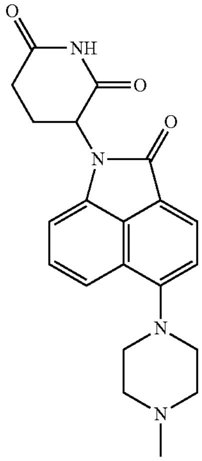 [SMILES: CN1CCN(c2ccc3c4c(cccc24)N(C2CCC(=O)NC2=O)C3=O)CC1] Compound 72 |
| 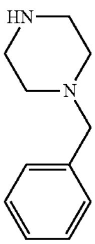 [SMILES: c1ccc(CN2CCNCC2)cc1] | 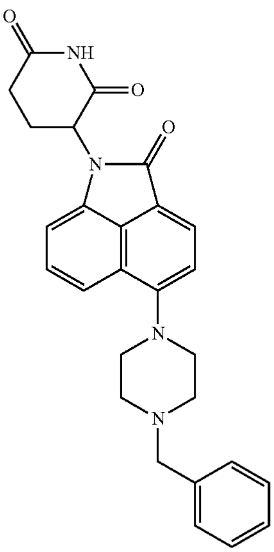 [SMILES: O=C1CCC(N2C(=O)c3ccc(N4CCN(Cc5ccccc5)CC4)c4cccc2c34)C(=O)N1] Compound 73 |

-continued

| Amine starting material | Product |
|---|---|
| 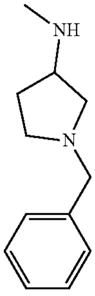 | 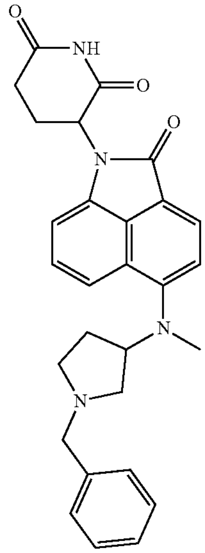 [SMILES: CN(c1ccc2c3c(cccc13)N(C1CCC(=O)NC1=O)C2=O)C1CCN(Cc2ccccc2)C1] Compound 74 |
| 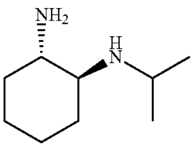 | 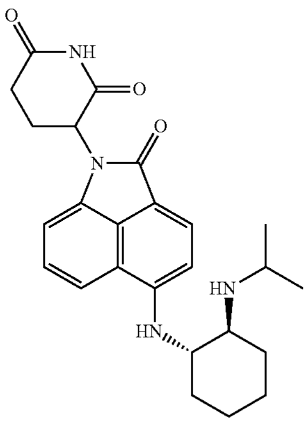 [SMILES: CC(C)N[C@H]1CCCC[C@@H]1Nc1ccc2c3c(cccc13)N(C1CCC(=O)NC1=O)C2=O] Compound 75 |

Example 29. 3-(5-(((trans)-2-(3-(3-Fluorophenoxy)azetidin-1-yl)cyclohexyl)oxy)-2-oxobenzo[cd]indol-1(2H)-yl)piperidine-2,6-dione (Compound 76)

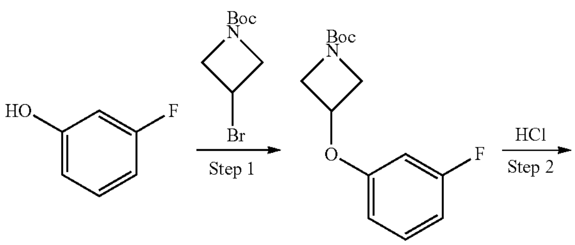

-continued

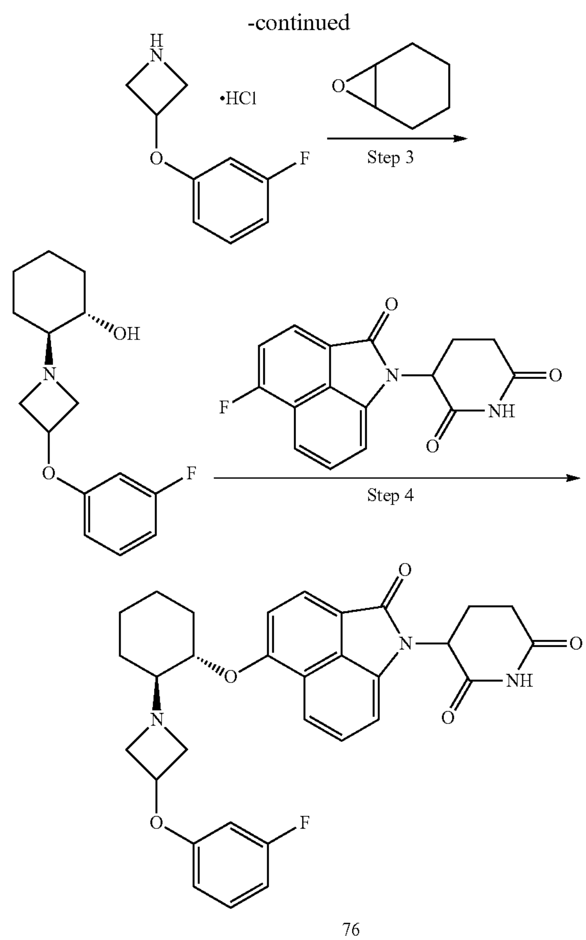

76

Step 1: tert-Butyl 3-(3-fluorophenoxy)azetidine-1-carboxylate: To a cooled (0° C.) solution of 3-fluorophenol (1 eq) in THF (0.1 M) is added NaH (2 eq, 60% dispersion in mineral oil) portion-wise before a solution of tert-butyl 3-bromoazetidine-1-carboxylate (1 eq in THF) is added dropwise to the reaction mixture. The mixture is then stirred with monitoring by LCMS/TLC. Upon reaction completion the mixture is cooled to 0° C. and quenched with water. Standard work up and purification procedures will deliver the product tert-butyl 3-(3-fluorophenoxy)azetidine-1-carboxylate.

Step 2: 3-(3-Fluorophenoxy)azetidine hydrochloride: tert-butyl 3-(3-fluorophenoxy)azetidine-1-carboxylate (1 eq) is suspended in HCl (4 M in 1,4-dioxane, 20 eq) and stirred at room temperature with monitoring by LCMS/TLC. Upon reaction completion, the mixture is concentrated to dryness as a 3-(3-fluorophenoxy)azetidine hydrochloride and used without further purification.

Step 3: (trans)-2-(3-(3-Fluorophenoxy)azetidin-1-yl)cyclohexan-1-ol: 3-(3-fluorophenoxy)azetidine hydrochloride (1 eq) is suspended in DMSO (0.1 M) after which $K_2CO_3$ (3 eq) is added portion wise. 7-Oxabicyclo[4.1.0]heptane (1 eq) is then added to the mixture and the suspension is heated to 100° C. until the starting materials are consumed. Upon reaction completion the mixture is cooled to room temperature and quenched with $H_2O$. Standard work up and purification procedures delivers the product (trans)-2-(3-(3-fluorophenoxy)azetidin-1-yl)cyclohexan-1-ol.

Step 4: 3-(5-(((trans)-2-(3-(3-Fluorophenoxy)azetidin-1-yl)cyclohexyl)oxy)-2-oxobenzo[cd]indol-1(2H)-yl)piperidine-2,6-dione (Compound 76): To a suspension of (trans)-2-(3-(3-Fluorophenoxy)azetidin-1-yl)cyclohexan-1-ol (1 eq) in DMSO (0.1 M) is added DIPEA (3 eq) followed by Compound 17 (1 eq). The reaction mixture is heated to 100° C. with stirring until the starting materials are consumed as evidenced by TLC/LCMS. Upon reaction completion the mixture is cooled to room temperature and quenched with $H_2O$. Standard work up and purification procedures delivers the product 3-(5-(((trans)-2-(3-(3-fluorophenoxy)azetidin-1-yl)cyclohexyl)oxy)-2-oxobenzo[cd]indol-1(2H)-yl)piperidine-2,6-dione (Compound 76).

Example 30. 3-(8-(((trans)-2-(3-(3-Fluorophenoxy)azetidin-1-yl)cyclohexyl)oxy)-5-oxopyrrolo[2,3,4-de]quinolin-4(5H)-yl)piperidine-2,6-dione (Compound 77)

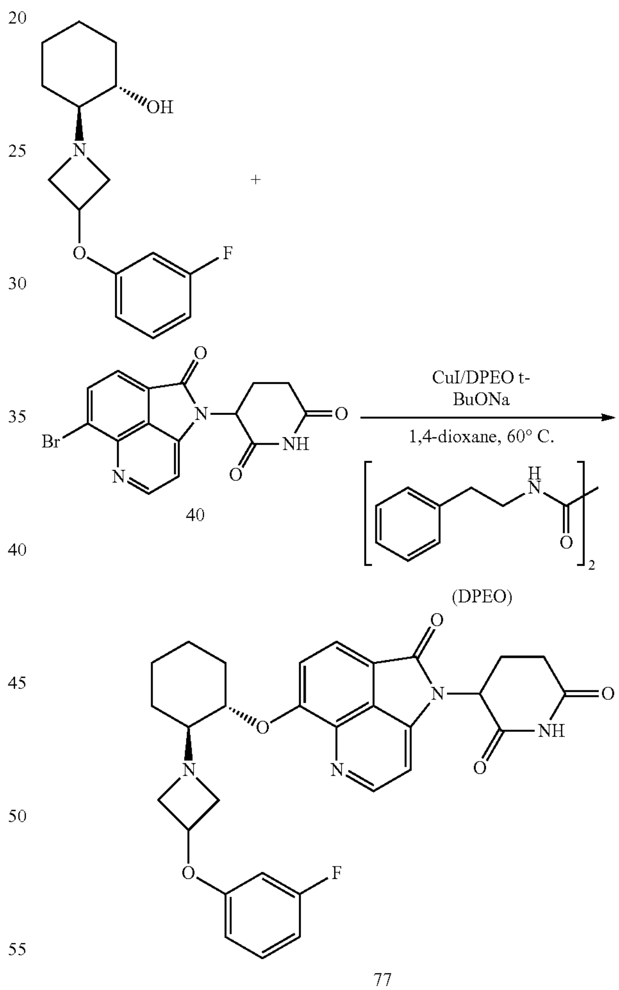

77

As described in Chen et. al. (*J. Am. Chem. Soc.* 2019, 141, 3541-3549), 3-(8-bromo-5-oxopyrrolo[2,3,4-de]quinolin-4(5H)-yl)piperidine-2,6-dione (Compound 40) (1 eq), CuI (0.01 eq), t-BuONa (1.2 eq), DPEO (0.01 eq), (trans)-2-(3-(3-fluorophenoxy)azetidin-1-yl)cyclohexan-1-ol (1 eq), 4 Å MS (400-500 mg/5 mmol SM) are suspended in 1,4-dioxane (2 M) under an argon atmosphere. The mixture is then heated to 80° C. for 24 hours with vigorous stirring. Upon reaction completion the mixture is cooled to room temperature and acidified with $NH_4Cl$ (aq) before being diluted with EtOAc and extracted (×3). The combined organic layers are washed with brine (×1) and dried over sodium sulfate before being filtered and concentrated to a crude residue which is purified using standard column chromatography to afford 3-(8-(((trans)-2-(3-(3-fluorophenoxy)azetidin-1-yl)cyclohexyl)oxy)-5-oxopyrrolo[2,3,4-de]quinolin-4(5H)-yl)piperidine-2,6-dione.

Example 31. 4-(2,6-Dioxopiperidin-3-yl)-5-oxo-N-((3R, 5S)-1,3,5-trimethylpiperidin-4-yl)-4,5-dihydropyrrolo[2,3,4-de]quinoline-8-carboxamide (Compound 78)

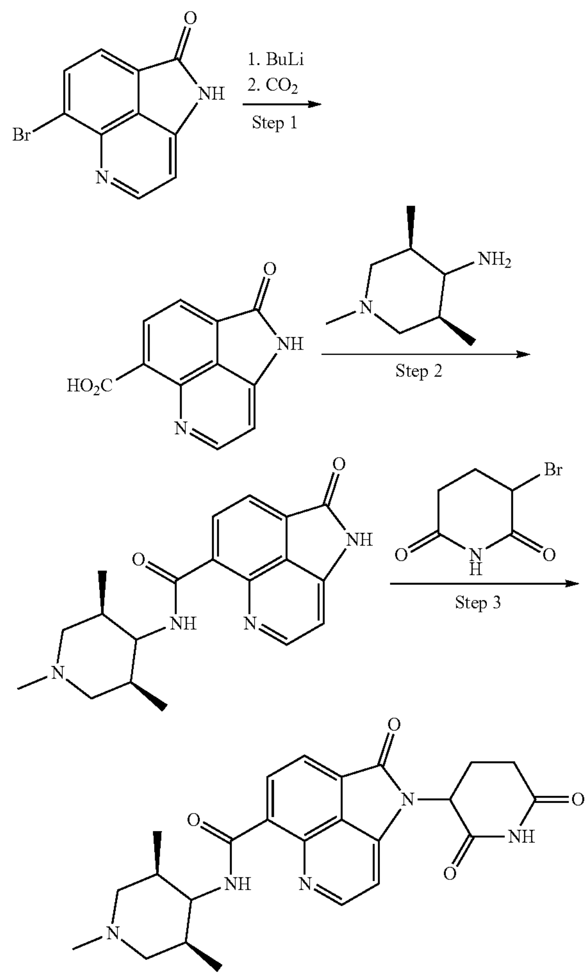

78

Step 1: 5-Oxo-4,5-dihydropyrrolo[2,3,4-de]quinoline-8-carboxylic acid: To a cooled solution (−78° C.) of 8-bromopyrrolo[2,3,4-de]quinolin-5(4H)-one (1 eq) in $Et_2O$ (0.1 M) is added (n-BuLi solution, 3 eq) and the mixture is allowed to stir for 30 minutes. $CO_2$ gas is then canulated into the solution (dry ice expellant dried through a calcium chloride plug) and the reaction is monitored until the starting materials are consumed. Upon reaction completion the solution is slowly warmed to room temperature before being carefully quenched with $NH_4Cl$ aqueous solution. Standard work up and purification procedures will afford 5-oxo-4,5-dihydropyrrolo[2,3,4-de]quinoline-8-carboxylic acid as the product.

Step 2: 4-(2,6-Dioxopiperidin-3-yl)-5-oxo-N-((3R, 5S)-1,3,5-trimethylpiperidin-4-yl)-4,5-dihydropyrrolo[2,3,4-de]quinoline-8-carboxamide: To a solution of 5-oxo-4,5-dihydropyrrolo[2,3,4-de]quinoline-8-carboxylic acid (1 eq) in DMF (0.1 M) is added (3R, 5S)-1,3,5-trimethylpiperidin-4-amine (1 eq), DIPEA (2 eq) and HATU (1 eq) at room temperature. The reaction is then monitored via TLC/LCMS and upon reaction completion the mixture is quenched by the addition of $H_2O$. Standard work up and purification procedures will afford 4-(2,6-dioxopiperidin-3-yl)-5-oxo-N-((3R, 5S)-1,3,5-trimethylpiperidin-4-yl)-4,5-dihydropyrrolo[2,3,4-de]quinoline-8-carboxamide as the product.

Step 3: 4-(2,6-Dioxopiperidin-3-yl)-5-oxo-N-((3R, 5S)-1,3,5-trimethylpiperidin-4-yl)-4,5-dihydropyrrolo[2,3,4-de]quinoline-8-carboxamide (Compound 78): To a solution of 4-(2,6-dioxopiperidin-3-yl)-5-oxo-N-((3R, 5S)-1,3,5-trimethylpiperidin-4-yl)-4,5-dihydropyrrolo[2,3,4-de]quinoline-8-carboxamide (1 eq) in THF (0.1 M) is added NaH (60% dispersion in mineral oil (10 eq) portion wise at 0° C. Upon complete addition, the resulting mixture is then warmed to room temperature and 3-bromopiperidine-2,6-dione (5 eq) is added. The mixture is then stirred with heating at 70° C. until the starting material is consumed. Upon reaction completion the mixture is quenched through the addition of crushed ice. Standard work up and purification procedures will afford 4-(2,6-dioxopiperidin-3-yl)-5-oxo-N-((3R, 5S)-1,3,5-trimethylpiperidin-4-yl)-4,5-dihydropyrrolo[2,3,4-de]quinoline-8-carboxamide (Compound 78) as the product.

Compound 79 was made using the same procedure as described in Example 31 for the preparation of 4-(2,6-dioxopiperidin-3-yl)-5-oxo-N-((3R, 5S)-1,3,5-trimethylpiperidin-4-yl)-4,5-dihydropyrrolo[2,3,4-de]quinoline-8-carboxamide (Compound 78) using the appropriate amine starting material from the table.

| Step 2 Amine starting material | Step 3 Product |
| --- | --- |
| 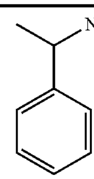 | 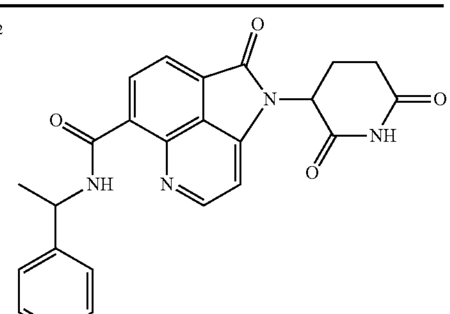 Compound 79 |

Example 32. 3-(8-Fluoro-5-oxopyrrolo[2,3,4-de]quinolin-4(5H)-yl)piperidine-2,6-dione (Compound 80)

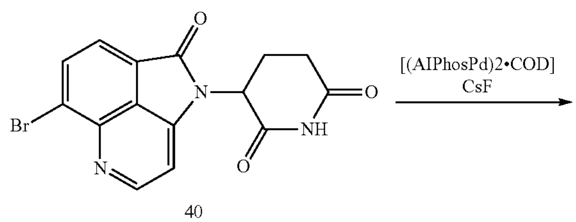

40

-continued

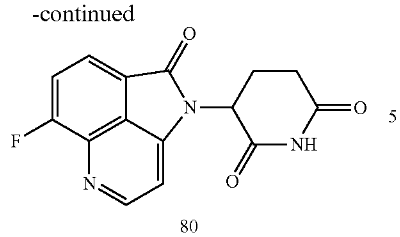

80

As described in procedures from Sather et al (J. Am. Chem. Soc. 2015, 137, 13433-13438), to a solution of 3-(8-bromo-5-oxopyrrolo[2,3,4-de]quinolin-4(5H)-yl)piperidine-2,6-dione (Compound 40) (1 eq) in toluene (0.1 M) is added CsF (3 eq) and [$(AlPhosPd)_2$•COD] (0.01 eq) under an inert atmosphere. The mixture is then allowed to stir at room temperature until the reaction is complete. Upon reaction completion the mixture is filtered through a celite pad. The crude filtrate is concentrated to a residue which is purified using standard flash chromatography to afford 3-(8-fluoro-5-oxopyrrolo[2,3,4-de]quinolin-4(5H)-yl)piperidine-2,6-dione (Compound 80) as the product.

Compound 81-Compound 82 were made using the same procedure as described in Example 32 for the preparation of 3-(2-oxo-5-((S)-2-phenylpyrrolidin-1-yl)benzo[cd]indol-1(2H)-yl)piperidine-2,6-dione (Compound 18) using 3-(8-fluoro-5-oxopyrrolo[2,3,4-de]quinolin-4(5H)-yl)piperidine-2,6-dione (Compound 80) and the appropriate amine starting material from the table.

-continued

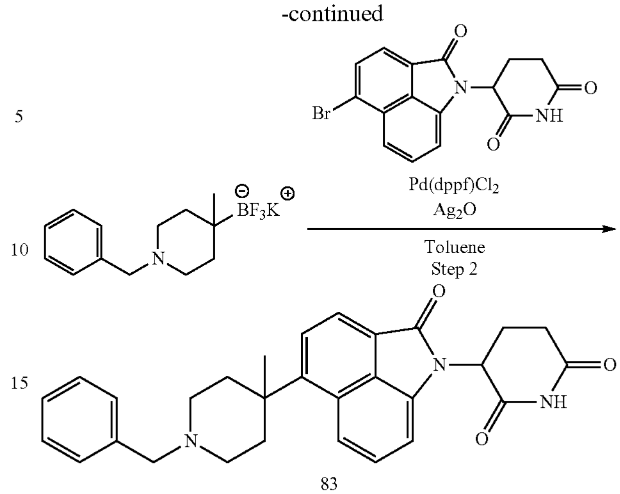

83

Step 1: Potassium (1-benzyl-4-methylpiperidin-4-yl)trifluoroborate: 1-Benzyl-4-methyl-4-(4,4,5,5-tetramethyl-1,3,2-dioxaborolan-2-yl)piperidine is prepared according to the reported procedure from Friese et. al. *Angew. Chem. Int. Ed.* 2019, 58, 9561-9564 and converted to potassium (1-benzyl-4-methylpiperidin-4-yl)trifluoroborate according to the standard reported procedures from Lennox et. al. *Angew. Chem. Int. Ed.* 2012, 51, 9385-9388.

Step 2: 3-(5-(1-Benzyl-4-methylpiperidin-4-yl)-2-oxobenzo[cd]indol-1(2H)-yl)piperidine-2,6-dione: A solution of potassium (1-benzyl-4-methylpiperidin-4-yl)trifluoroborate (1 eq), Pd(dppf)$Cl_2$ (0.1 eq), $Ag_2O$ (2 eq) and Compound 1 (1 eq) in toluene (0.1 M) is heated at 100° C. under an inert atmosphere. The reaction is monitored by TLC/LCMS and upon consumption of the starting materials the mixture is diluted with EtOAc and filtered through a celite pad. Standard workup and purification procedures will furnish 3-(5-(1-benzyl-4-methylpiperidin-4-yl)-2-oxobenzo[cd]indol-1(2N)-yl)piperidine-2,6-dione (Compound 83) as the product.

Compound 84-Compound 86 were made using the same procedure as described in Example 33 for the preparation of 3-(5-(1-benzyl-4-methylpiperidin-4-yl)-2-oxobenzo[cd]indol-1(2H)-yl)piperidine-2,6-dione (Compound 83) using the appropriate boronic esters and aryl bromides from the table.

| Amine starting material | Product |
|---|---|
| 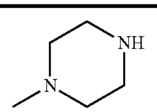 | 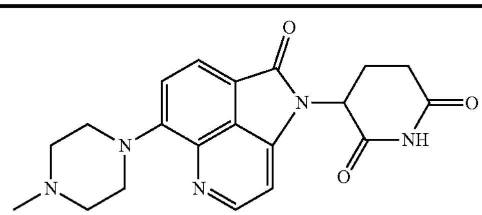 Compound 81 |
| 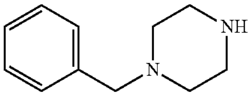 [SMILES: c1ccc(CN2CCNCC2)cc1] | 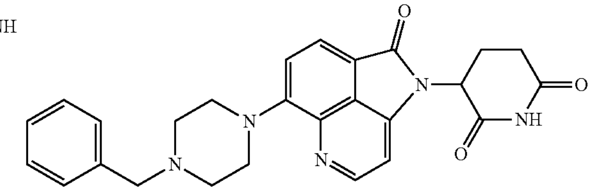 Compound 82 |

Example 33. 3-(5-(1-Benzyl-4-methylpiperidin-4-yl)-2-oxobenzo[cd]indol-1(2H)-yl)piperidine-2,6-dione (Compound 83

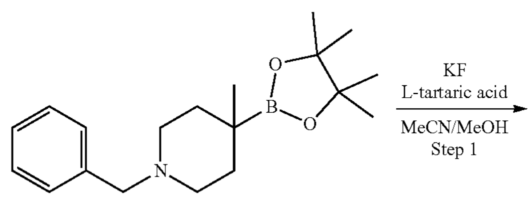

| Step 1 Boronic ester starting material | Step 2 aryl bromide |
|---|---|
| 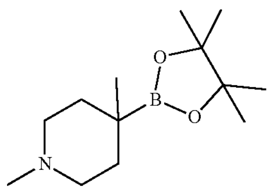 | 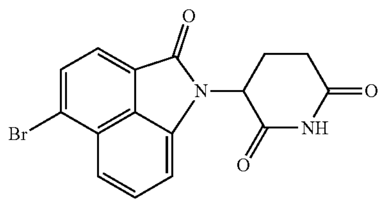 [SMILES: O=C1CCC(N2C(=O)c3ccc(Br)c4cccc2c34)C(=O)N1] |
| 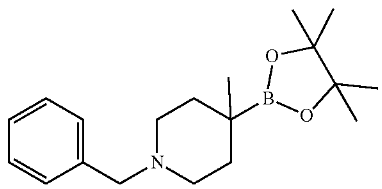 [SMILES: CC1(B2OC(C)(C)C(C)(C)O2)CCN(Cc2ccccc2)CC1] | 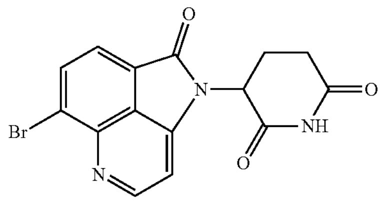 [SMILES: O=C1CCC(N2C(=O)c3ccc(Br)c4nccc2c34)C(=O)N1] |
| 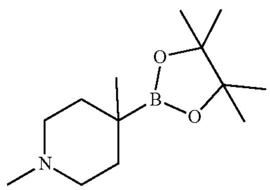 | 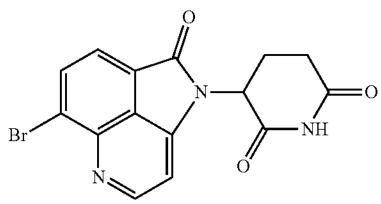 [SMILES: O=C1CCC(N2C(=O)c3ccc(Br)c4nccc2c34)C(=O)N1] |
| Product |
|---|
| 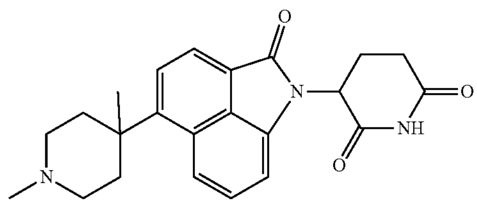 [SMILES: CN1CCC(C)(c2ccc3c4c(cccc24)N(C2CCC(=O)NC2=O)C3=O)CC1]<br>Compound 84 |
| 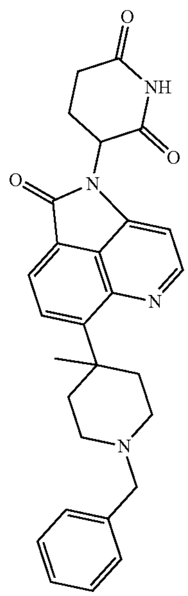 [SMILES: CC1(c2ccc3c4c(ccnc24)N(C2CCC(=O)NC2=O)C3=O)CCN(Cc2ccccc2)CC1]<br>Compound 85 |

-continued

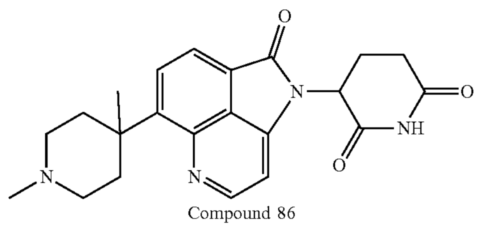

Compound 86

Example 34. 3-(5-(1-Benzyl-4-fluoropiperidin-4-yl)-2-oxobenzo[cd]indol-1(2H)-yl)piperidine-2,6-dione (Compound 87)

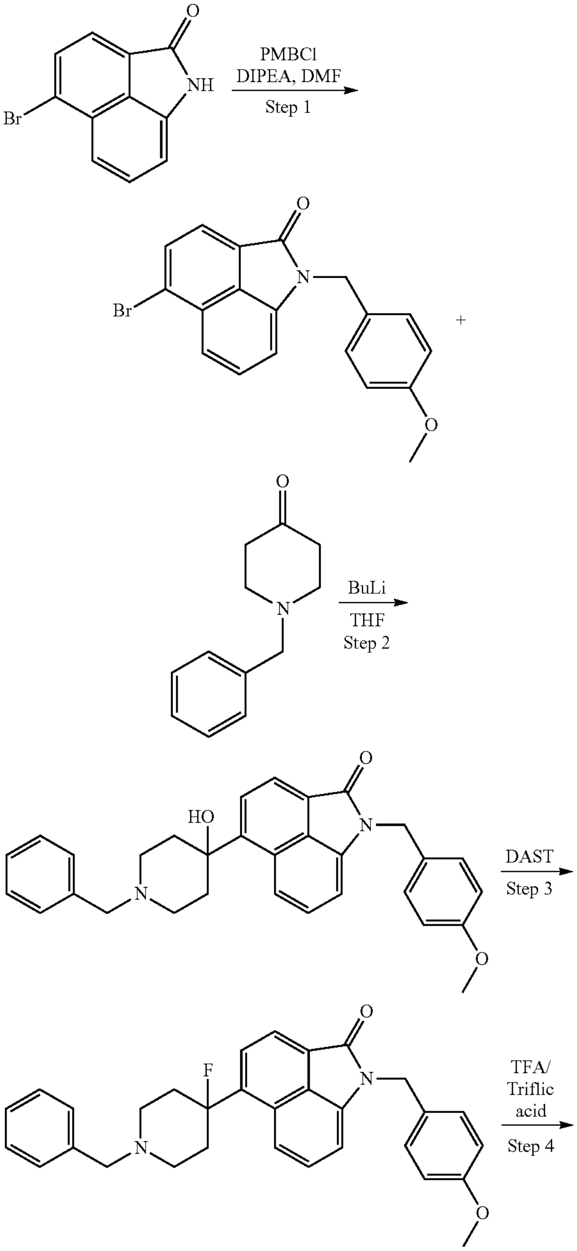

-continued

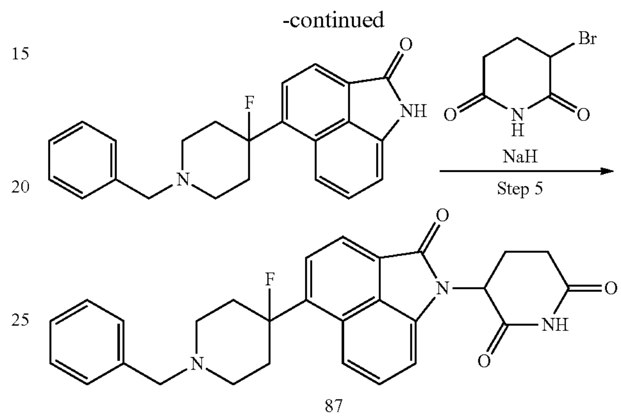

87

Step 1: 5-Bromo-1-(4-methoxybenzyl)benzo[cd]indol-2(1H)-one: To a solution of 5-bromobenzo[cd]indol-2(1H)-one (1 eq) in DMF (0.1 M) is added DIPEA (2 eq) followed by PMBCl (1.1 eq) at room temperature. The mixture is stirred with monitoring by TLC/LCMS. Upon reaction completion the mixture is quenched through the addition of $H_2O$. Standard work up and purification procedures will afford 5-bromo-1-(4-methoxybenzyl)benzo[cd]indol-2(1H)-one as the product.

Step 2: 5-(1-Benzyl-4-hydroxypiperidin-4-yl)-1-(4-methoxybenzyl)benzo[cd]indol-2(1H)-one: To a cooled (−78° C.) solution of 5-bromo-1-(4-methoxybenzyl)benzo[cd]indol-2(1H)-one (1 eq) in THF (0.1 M) is added BuLi (2 eq) dropwise and the mixture is allowed to stir for 30 minutes. 1-benzylpiperidin-4-one (1 eq) is then subsequently added to the reaction mixture and stirring is continued at ambient temperature until reaction completion is evident. Upon reaction completion the mixture is cooled to 0° C. before being carefully quenched through the addition of $H_2O$. Standard workup and purification procedures will afford 5-(1-benzyl-4-hydroxypiperidin-4-yl)-1-(4-methoxybenzyl)benzo[cd]indol-2(1H)-one as the product.

Step 3: 5-(1-Benzyl-4-fluoropiperidin-4-yl)-1-(4-methoxybenzyl)benzo[cd]indol-2(1H)-one: To a cooled (0° C.) solution of 5-(1-benzyl-4-hydroxypiperidin-4-yl)-1-(4-methoxybenzyl)benzo[cd]indol-2(1H)-one (1 eq) in DCM (0.1 M) is added DAST (1.5 eq) dropwise. The reaction mixture is allowed to stir at room temperature until reaction completion is evident. Upon reaction completion the mixture is concentrated to dryness. Standard workup and purification procedures will afford 5-(1-benzyl-4-fluoropiperidin-4-yl)-1-(4-methoxybenzyl)benzo[cd]indol-2(1H)-one as the product.

Step 4: 5-(1-Benzyl-4-fluoropiperidin-4-yl)benzo[cd]indol-2(1H)-one: 5-(1-Benzyl-4-fluoropiperidin-4-yl)-1-(4-methoxybenzyl)benzo[cd]indol-2(1H)-one (1 eq) is suspended in TFA (0.1 M) at room temperature before triflic acid (5 eq) is then added dropwise and the reaction mixture is heated to reflux until the starting material is consumed. Upon reaction completion the mixture is cooled to room temperature and concentrated to dryness. Standard workup and purification procedures will afford 5-(1-benzyl-4-fluoropiperidin-4-yl)benzo[cd]indol-2(1H)-one as the product.

Step 5: 3-(5-(1-Benzyl-4-fluoropiperidin-4-yl)-2-oxobenzo[cd]indol-1(2H)-yl)piperidine-2,6-dione (Compound 87): To a cooled (0° C.) solution of 5-(1-benzyl-4-fluoropiperidin-4-yl)benzo[cd]indol-2(1H)-one (1 eq) in THF is added NaH (10 eq, 60% dispersion in mineral oil) portion wise. The mixture is allowed to warm to room temperature and subsequently 3-bromopiperidine-2,6-dione (5 eq) is added before the mixture is heated to reflux until reaction completion is evident. Upon reaction completion the mixture is cooled to 0° C. before being carefully quenched with $H_2O$. Standard workup and purification procedures will afford 3-(5-(1-benzyl-4-fluoropiperidin-4-yl)-2-oxobenzo[cd]indol-1(2H)-yl)piperidine-2,6-dione as the product.

Compound 88-Compound 95 were made using the same procedure as described in Example 34 for the preparation of 3-(5-(1-benzyl-4-fluoropiperidin-4-yl)-2-oxobenzo[cd]indol-1(2H)-yl)piperidine-2,6-di one (Compound 87) using the appropriate aryl bromides and ketones from the table.

| Step 1 aryl bromide | Step 2 ketone |
| --- | --- |
| 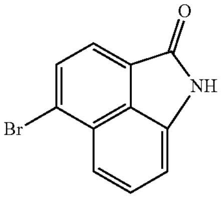 [SMILES: O=C1Nc2cccc3c(Br)ccc1c23] | 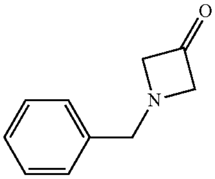 [SMILES: O=C1CN(Cc2ccccc2)C1] |
| 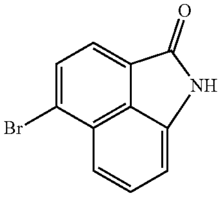 [SMILES: O=C1Nc2cccc3c(Br)ccc1c23] | 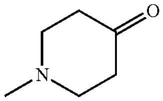 |
| 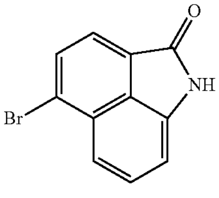 [SMILES: O=C1Nc2cccc3c(Br)ccc1c23] | 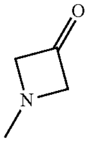 |
| 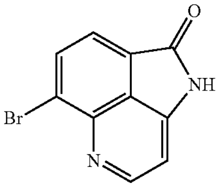 [SMILES: O=C1Nc2ccnc3c(Br)ccc1c23] | 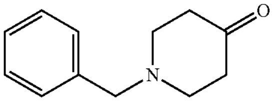 [SMILES: O=C1CCN(Cc2ccccc2)CC1] |
| 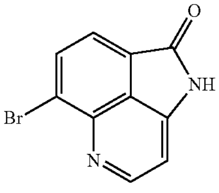 [SMILES: O=C1Nc2ccnc3c(Br)ccc1c23] | 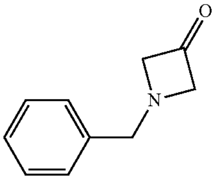 [SMILES: O=C1CN(Cc2ccccc2)C1] |
| 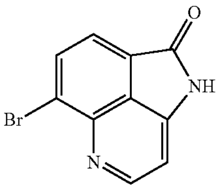 [SMILES: O=C1Nc2ccnc3c(Br)ccc1c23] | 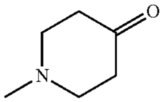 |

-continued
| | |
|---|---|
| 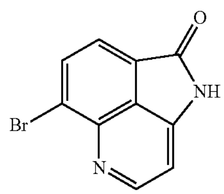 [SMILES: O=C1Nc2ccnc3c(Br)ccc1c23] | 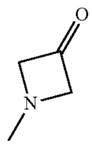 |
Product
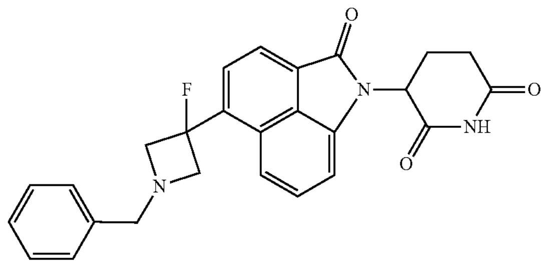 [SMILES: O=C1CCC(N2C(=O)c3ccc(C4(F)CN(Cc5ccccc5)C4)c4cccc2c34)C(=O)N1]
Compound 89
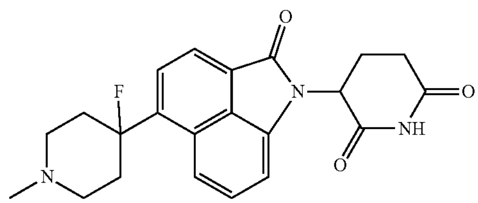 [SMILES: CN1CCC(F)(c2ccc3c4c(cccc24)N(C2CCC(=O)NC2=O)C3=O)CC1]
Compound 90
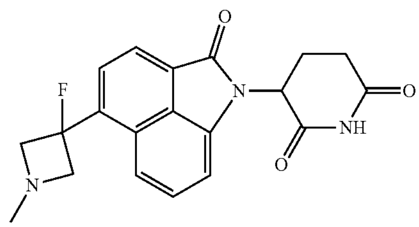 [SMILES: CN1CC(F)(c2ccc3c4c(cccc24)N(C2CCC(=O)NC2=O)C3=O)C1]
Compound 91
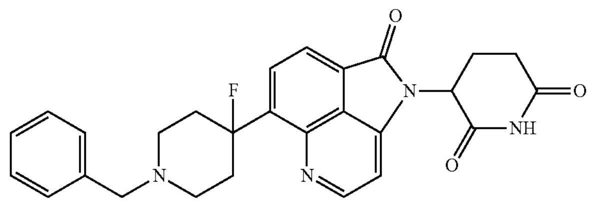 [SMILES: O=C1CCC(N2C(=O)c3ccc(C4(F)CCN(Cc5ccccc5)CC4)c4nccc2c34)C(=O)N1]
Compound 92
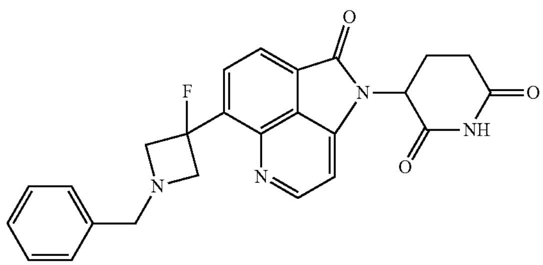 [SMILES: O=C1CCC(N2C(=O)c3ccc(C4(F)CN(Cc5ccccc5)C4)c4nccc2c34)C(=O)N1]
Compound 93

-continued

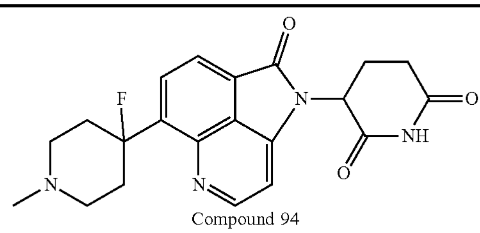

Compound 94

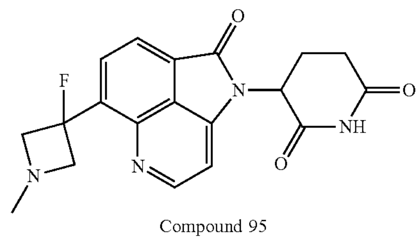

Compound 95

Example 35: 3-[5-(1-benzyl-4-fluoro-4-piperidyl)-2-oxo-benzo[cd]indol-1-yl]piperidine-2,6-dione (Compound 96)

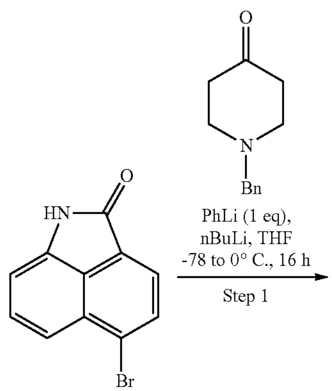

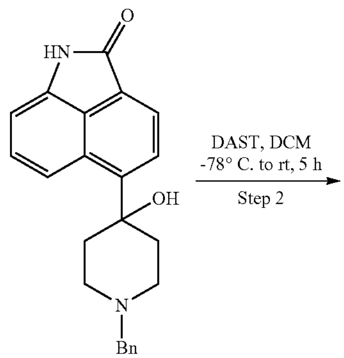

-continued

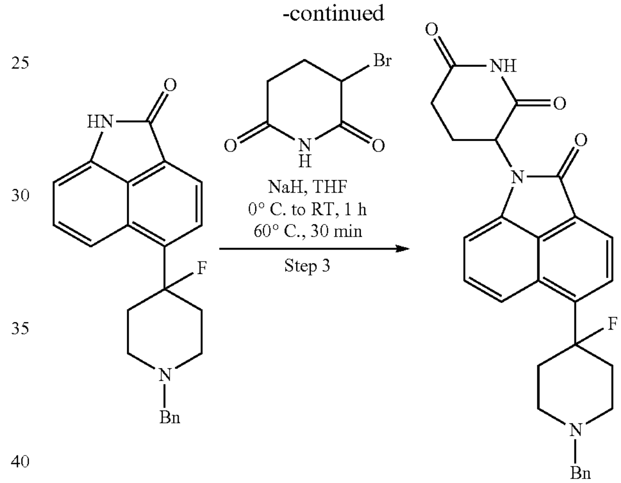

Step 1: To the stirred solution of 5-bromo-1H-benzo[cd]indol-2-one (400 mg, 1.61 mmol) in dry THF (5.0 mL) was added phenyllithium, 1.8M in di-n-butyl ether (135.52 mg, 1.61 mmol, 167.30 μL) at −78° C. under inert atmosphere and the reaction was stirred at the same temperature for 30 minutes followed by the addition of butyllithium (113.62 mg, 1.77 mmol) at the same temperature. After addition, the temperature was allowed to increase to −40° C. and the reaction mixture was stirred at the same temperature for 30 minutes. Then a solution of 1-benzylpiperidin-4-one (305.16 mg, 1.61 mmol, 287.88 μL) in dry THF (5.0 mL) was added at −78° C. and the reaction mixture was allowed to warm to room temperature and stirred for additional 16 hours. After the reaction was complete, the reaction mixture was quenched with ammonium chloride solution and diluted with ethyl acetate (50 mL). The combined organic layer was washed with water/brine and separated, dried over anhydrous sodium sulfate, and evaporated under reduced pressure. The resulting crude product was purified by flash chromatography using 0-5% MeOH-DCM to afford 5-(1-benzyl-4-hydroxy-4-piperidyl)-1H-benzo[cd]indol-2-one (255 mg, 569.15 μmol, 35% yield) asbrown solid. $^{1}$H NMR (400 MHz, DMSO-$d_6$) δ 10.68 (s, 1H), 8.20 (d, J=8.84 Hz, 1H), 7.93 (d, J=7.4 Hz, 1H), 7.88 (d, J=7.44 Hz, 1H), 7.44 (t, J=7.2 Hz, 1H), 7.33-7.30 (m, 5H), 6.93 (d, J=7.04 Hz, 1H), 5.4 (br m, 1H), 3.64 (br, 2H), 2.74-2.66 (br, 4H), 2.32 (br m, 2H), 1.94-1.90 (m, 2H).

Step 2: To a solution of 5-(1-benzyl-4-hydroxy-4-piperidyl)-1H-benzo[cd]indol-2-one (150 mg, 418.49 μmol) in anhydrous DCM (15.0 mL) was added N-ethyl-N-(trifluoro-$1^{4}-sulfanyl)ethanamine (337.28 mg, 2.09 mmol, 276.46 μL) dropwise at −78° C. under inert atmosphere and the reaction mixture was stirred at room temperature for an additional 5 hours. After completion of the reaction, the reaction mixture was diluted with 10% MeOH-DCM (20 mL) and quenched with saturated sodium bicarbonate solution. The organic phase was washed with water/brine and separated, dried over anhydrous sodium sulfate, and evaporated under reduced pressure. The crude product was purified by flash column chromatography using 0-5% MeOH-DCM to afford 5-(1-benzyl-4-fluoro-4-piperidyl)-1H-benzo[cd]indol-2-one (70 mg, 185.28 μmol, 44% yield) as a brownish gum. LC-MS ($ES^+$): m/z 361.39 $[M+H]^+$.

Step 3: To a cooled solution of 5-(1-benzyl-4-fluoro-4-piperidyl)-1H-benzo[cd]indol-2-one (70 mg, 194.22 μmol) in dry THF (5 mL), sodium hydride (60% dispersion in mineral oil) (74.42 mg, 1.94 mmol) was added portion wise, maintaining the temp <5° C. After addition, the resulting mixture was stirred for 15 minutes at room temperature. The reaction mixture was again cooled to 0° C. and 3-bromopiperidine-2,6-dione (186.46 mg, 971.08 μmol) was added portion wise. The resulting solution was heated at 70° C. for 1 hr. After completion, the reaction mixture was cooled to 0° C. and quenched with the addition of ice-cold water (10 mL). The aqueous layer was extracted with ethyl acetate (3×50 mL). The combined organics was separated, dried over anhydrous sodium sulfate, filtered and concentrated under reduced pressure to afford crude 3-[5-(1-benzyl-4-fluoro-4-piperidyl)-2-oxo-benzo[cd]indol-1-yl]piperidine-2,6-dione which was purified by PREP TLC to afford 3-[5-(1-benzyl-4-fluoro-4-piperidyl)-2-oxo-benzo[cd]indol-1-yl]piperidine-2,6-dione (Compound 96, 36 mg, 74.00 μmol, 38% yield) as a yellow solid. $^1H$ NMR (400 MHz, DMSO-$d_6$) δ 11.12 (s, 1H), 8.07 (d, J=6.88 Hz, 1H), 7.94 (d, J=8.28 Hz, 1H), 7.88 (d, J=7.36 Hz, 1H), 7.56 (t, J=7.52 Hz, 1H), 7.37-7.33 (m, 4H), 7.28-7.27 (m, 1H), 7.17 (d, J=7.0 Hz, 1H), 5.46-5.44 (m, 1H), 3.60 (s, 2H), 2.97-2.85 (m, 4H), 2.77-2.63 (m, 3H), 2.49-2.18 (m, 4H), 2.09 (m, 1H); LC-MS ($ES^+$): m/z 472.28 $[M+H]^+$.

3-[5-(4-fluoro-1-methyl-4-piperidyl)-2-oxo-benzo[cd]indol-1-yl]piperidine-2,6-dione (Compound 97)

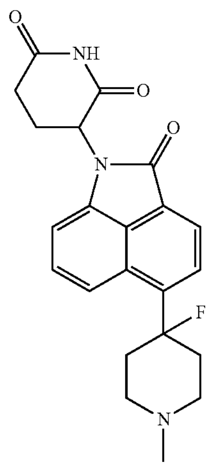 [SMILES: CN1CCC(F)(c2ccc3c4c(cccc24)N(C2CCC(=O)NC2=O)C3=O)CC1]

Compound 97 was prepared substantially following the synthesis of Compound 96.

$^1H$ NMR (400 MHz, DMSO-$d_6$) δ 11.12 (s, 1H), 8.08 (d, J=7.12 Hz, 1H), 7.93 (d, J=8.76 Hz, 1H), 7.87 (d, J=7.48 Hz, 1H), 7.55 (t, J=7.24 Hz, 1H), 7.17 (d, J=7.24 Hz, 1H), 5.45 (dd, J=12.32, 4.84 Hz, 1H), 2.94-2.91 (m, 3H), 2.79-2.49 (m, 3H), 2.43-2.32 (s, 4H), 2.28 (s, 3H), 2.2-2.07 (m, 2H); LC-MS ($ES^+$): m/z 396.37 $[M+H]^+$.

Example 36: Synthesis of 5-(1-chloropyrrolidin-3-yl)-1H-benzo[cd]indol-2-one

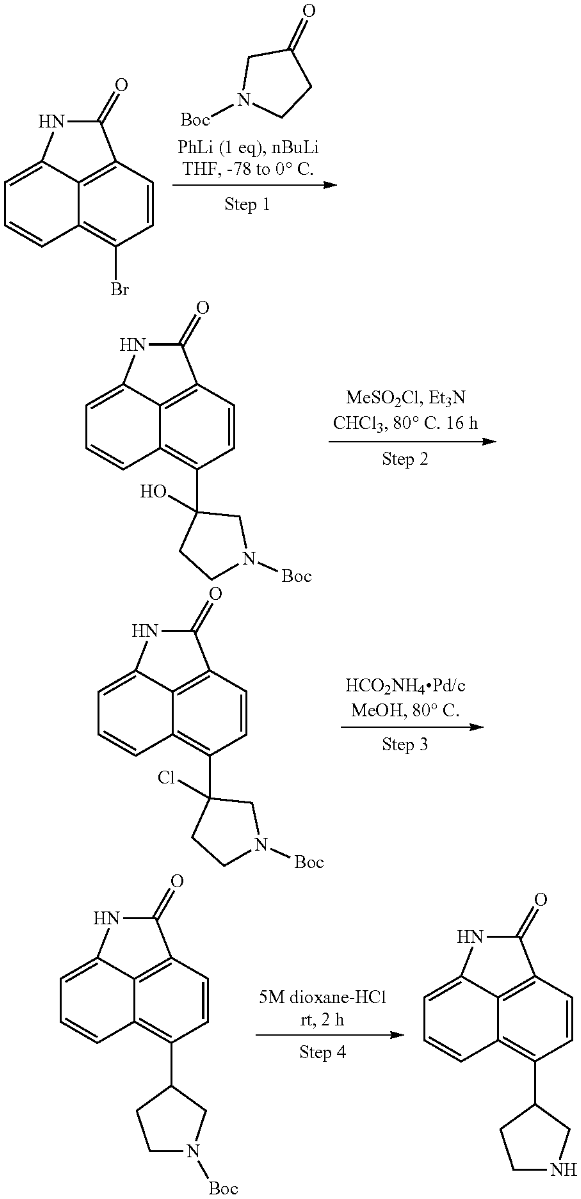

Step 1: In a flame dried 100 mL two necked round-bottom flask under $N_2$, 5-bromo-1H-benzo[cd]indol-2-one (1 g, 4.03 mmol) was dissolved in in dry THF (10.0 mL) and phenyllithium in di-n-butyl ether (1.9 M, 2.12 mL) was added at −78° C. The resulting solution was stirred at the same temperature for 30 minutes followed by the addition of butyllithium (1.66 M, 2.67 mL) at −78° C. After complete addition, the temperature was allowed to increase to −40° C. and the reaction mixture was stirred at the same temperature for another 30 minutes. A solution of tert-butyl 3-oxopyrrolidine-1-carboxylate (746.63 mg, 4.03 mmol) in dry THF (10.0 mL) was added at −78° C. and the reaction mixture was allowed to warm to room temperature and stirred for additional 16 hours. After completion of the reaction, the reaction mixture was quenched with ammonium chloride solution (20 mL) and extracted with ethyl acetate (40×2 ml). The combined organic layer was separated, dried over anhydrous sodium sulfate, and evaporated under reduced pressure. Crude reaction mass was purified by flash chromatography using 0-5% MeOH-DCM to afford tert-butyl 3-hydroxy-3-(2-oxo-1H-benzo[cd]indol-5-yl)pyrrolidine-1-carboxylate (490.0 mg, 1.10 mmol, 27% yield) as brown solid. LC-MS ($ES^+$): m/z 299.17 $[M-tBu+H]^+$.

Step 2: To a solution of tert-butyl 3-hydroxy-3-(2-oxo-1H-benzo[cd]indol-5-yl)pyrrolidine-1-carboxylate (386 mg, 1.09 mmol) in HPLC grade $CHCl_3$ (10.0 mL) was added triethylamine, 99% (440.85 mg, 4.36 mmol, 607.23 μL) at 0° C. followed by the addition of methanesulfonyl chloride (509.24 mg, 4.36 mmol, 344.08 μL) and the resulting reaction mixture was refluxed at 80° C. for 16 hours. After completion of the reaction, the reaction mixture was diluted with DCM (30 mL) and organic layer was washed with saturated sodium bicarbonate solution followed by water and brine solution. The combined organic phase was separated, dried over anhydrous sodium sulfate and evaporated under reduced pressure to obtain tert-butyl 3-chloro-3-(2-oxo-1H-benzo[cd]indol-5-yl)pyrrolidine-1-carboxylate (400 mg, 1.07 mmol, 99% yield) which was used directly in the next step without purification and characterization.

Step 3: To a stirred solution of crude tert-butyl 3-chloro-3-(2-oxo-1H-benzo[cd]indol-5-yl)pyrrolidine-1-carboxylate (400 mg, 1.07 mmol) in methanol (6.0 mL) was added ammonium formate, 99% (676.53 mg, 10.73 mmol, 528.54 μL), Pd/C (45.62 mg, 375.66 μmol) at room temperature and the resulting reaction mixture was heated at 70° C. for 4 hours in a sealed vial. After completion of reaction, the reaction mixture was filtered through a pad of celite and washed with 10% MeOH-DCM. The combined filtrate was then washed with cold water, dried over anhydrous sodium sulphate and concentrated under reduced pressure to obtain tert-butyl 3-(2-oxo-1H-benzo[cd]indol-5-yl)pyrrolidine-1-carboxylate (360 mg, 531.92 μmol, 50% yield) as crude compound which was used directly in the next step. LC-MS ($ES^+$): m/z 339.1 $[M+H]^+$.

Step 4: To the stirred solution of tert-butyl 3-(2-oxo-1H-benzo[cd]indol-5-yl)pyrrolidine-1-carboxylate (360.0 mg, 1.06 mmol) in dioxane (2 mL), was added 4 M dioxane-HCl (10 mL) at 0° C. and the resulting solution was stirred for another 2 hours at room temperature. After completion of the reaction, the volatiles were removed under reduced pressure and the solid obtained was washed with ether and pentane to afford 5-(1-chloropyrrolidin-3-yl)-1H-benzo[cd]indol-2-one hydrochloride (290.0 mg, 931.86 μmol, 88% yield) as a brown solid which was used the next step without purification. LC-MS ($ES^+$): m/z 239.1 $[M+H]^+$.

Example 37: Synthesis of 3-[5-(1-methylpyrrolidin-3-yl)-2-oxo-benzo[cd]indol-1-yl]piperidine-2,6-dione (Compound 98)

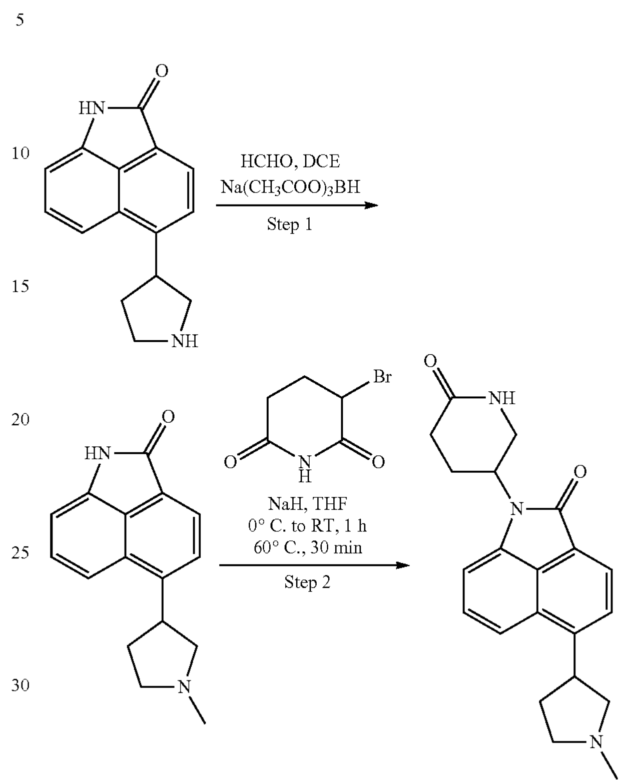

Step 1: To an oven dried 50 ml round bottom flask, 5-pyrrolidin-3-yl-1H-benzo[cd]indol-2-one; hydrochloride (290 mg, 1.06 mmol) and formaldehyde (31.69 mg, 1.06 mmol, 29.35 μL) were dissolved in methanol (2.0 mL)-DCM (5.0 mL). To this solution, triethylamine (106.81 mg, 1.06 mmol, 147.12 μL) and acetic acid (126.77 mg, 2.11 mmol, and 120.73 μL) were added and the resulting reaction mixture was allowed to stir at room temperature for 5-6 hours. The reaction mixture was then cooled at 0° C. and sodium; triacetoxyboranide (1.12 g, 5.28 mmol) was added and stirring was continued for 16 hours at room temperature. After completion of the reaction, the reaction mixture was evaporated under reduced pressure and the crude compound was purified by flash column chromatography using 0-10% MeOH-DCM to afford 8-(1-methylpyrrolidin-3-yl)-15,16-diazatricyclododeca-1(8),2(9),3(10),4(15),11-pentaen-14-one (110 mg, 269.25 μmol, 26% yield) as yellow solid. LC-MS ($ES^+$): m/z 253.34 $[M+H]^+$.

Step 2: To a cooled solution of 5-(1-methylpyrrolidin-3-yl)-1H-benzo[cd]indol-2-one (110 mg, 435.97 μmol) in dry THF (5 mL), sodium hydride (60% dispersion in mineral oil) (417.62 mg, 10.44 mmol) was added portion wise, maintaining the temp <5° C. The resulting mixture was stirred for 15 minutes at room temperature. Then the reaction mixture was again cooled to 0° C. and 3-bromopiperidine-2,6-dione (1.00 g, 5.23 mmol) was added portion wise. After complete addition, the resulting solution was heated at 70° C. for 1 hr. After complete consumption of 5-(1-methylpyrrolidin-3-yl)-1H-benzo[cd]indol-2-one, the reaction mixture was cooled to 0° C. and quenched with the addition of ice-cold water (5 mL) and extracted with ethyl acetate (3×50 mL). Combined organics was separated, dried over anhydrous sodium sulfate and concentrated under reduced pressure. Crude reaction mass was purified by PREP TLC to afford 3-[5-(1-methylpyrrolidin-3-yl)-2-oxo-benzo[cd]indol-1-yl]piperidine-2,6-dione (Compound 98, 10.0 mg, 26.00 μmol, 6% yield) as yellow solid. $^1$H NMR (400 MHz, DMSO-$d_6$) δ 11.12 (s, 1H), 8.05 (d, J=7.36 Hz, 1H), 7.92 (d, J=8.68 Hz, 1H), 7.83 (d, J=7.4 Hz, 1H), 7.53 (t, J=7.68 Hz, 1H), 7.14 (d, J=7.2 Hz, 1H), 5.44 (dd, J=12.84, 5.32 Hz, 1H), 4.16 (m, 1H), 2.96-2.62 (m, 6H), 2.77-2.62 (m, 2H), 2.32 (s, 3H), 2.07 (m, 1H), 1.90 (m, 1H). LC-MS (ES$^+$): m/z 364.25 [M+H]$^+$.

3-[5-(1-benzylpyrrolidin-3-yl)-2-oxo-benzo[cd]indol-1-yl]piperidine-2,6-dione (Compound

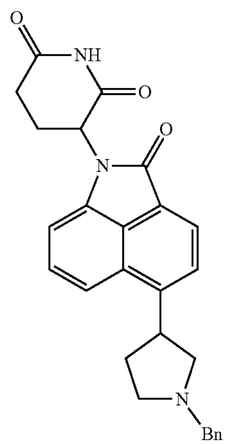 [SMILES: O=C1CCC(N2C(=O)c3ccc(C4CCN(Cc5ccccc5)C4)c4cccc2c34)C(=O)N1]

Compound 99 was prepared substantially following the synthesis of Compound 98.

LC-MS (ES$^+$): m/z 440.3 [M+H]$^+$.

$^1$H NMR (400 MHz, DMSO-$d_6$) δ 11.10 (s, 1H), 8.04 (d, J=7.32 Hz, 1H), 7.95 (d, J=8.68 Hz, 1H), 7.83 (d, J=7.36 Hz, 1H), 7.52 (t, J=8.08 Hz, 1H), 7.38 (br d, J=7.04 Hz, 2H), 7.33 (t, J=7.28 Hz, 2H), 7.26-7.24 (m, 1H), 7.13 (d, J=7.16 Hz, 1H), 5.44 (dd, J=12.84, 5.32 Hz, 1H), 4.16 (m, 1H), 3.72-3.69 (br m, 2H), 2.96-2.89 (m, 5H), 2.8-2.73 (m, 2H), 2.49-2.44 (m, 1H), 2.09-2.06 (m, 1H), 1.94-1.90 (m, 1H).

Example 38: Synthesis of 5-(3-hydroxyazetidin-3-yl)-1H-benzo[cd]indol-2-one

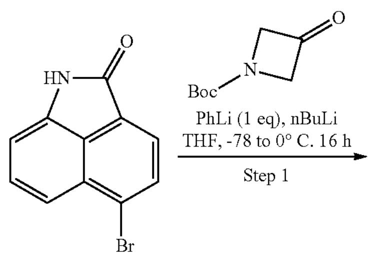

-continued

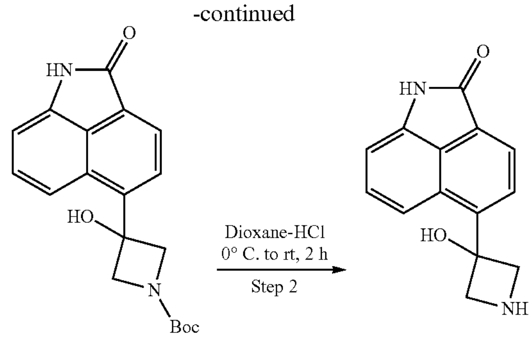

Step 1: In a flamed dried two necked round bottom flask under $N_2$ atmosphere, 5-bromo-1H-benzo[cd]indol-2-one (1.0 g, 4.03 mmol) was dissolved in dry THF (5.0 mL) and cooled at −78° C. To this chilled solution, phenyllithium in di-n-butyl ether (1.8 M, 2.24 mL) was added and the reaction was stirred at the same temperature for 30 minutes followed by the addition of butyllithium (1.62 M, 2.74 mL) at same temperature. After addition, the temperature was allowed to increase to −40° C. and the reaction mixture was stirred at the same temperature for 30 minutes. A solution of tert-butyl 3-oxoazetidine-1-carboxylate (690.09 mg, 4.03 mmol, 287.88 μL) in dry THF (5.0 mL) at −78° C. was added and then the reaction mixture was allowed to warm at room temperature and stirred for another 16 hours. After formation of new spot as evidenced from TLC, the reaction mixture was quenched with ammonium chloride solution and diluted with ethyl acetate (100 mL). The combined organic layer was washed with water/brine and separated, dried over anhydrous sodium sulfate, and evaporated under reduced pressure. The crude product was then purified by flash column chromatography using 0-5% MeOH-DCM to afford tert-butyl 3-hydroxy-3-(2-oxo-1H-benzo[cd]indol-5-yl)azetidine-1-carboxylate (339 mg, 870.78 μmol, 22% yield) as brown solid. LC-MS (ES$^+$): m/z 341.35 [M+H]$^+$.

Step 2: 4 M dioxane-HCl (10 mL) was added to the cooled solution of tert-butyl 3-hydroxy-3-(2-oxo-1H-benzo[cd]indol-5-yl)azetidine-1-carboxylate (340 mg, 998.91 μmol) in dioxane (3 mL) at 0° C. and stirred for 2 hours at room temperature. After completion of the reaction, the volatiles were removed to afford crude 5-(3-hydroxyazetidin-3-yl)-1H-benzo[cd]indol-2-one hydrochloride (280 mg, 715.25 μmol, 72% yield) which was neutralized with triethylamine (pH~7) before being used in the next step. LC-MS (ES$^+$): m/z 241.16 [M+H]$^+$.

Example 39: Synthesis of 3-[5-(1-benzyl-3-fluoro-azetidin-3-yl)-2-oxo-benzo[cd]indol-1-yl]piperidine-2,6-dione (Compound 100)

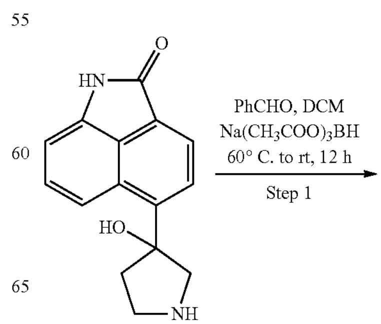

-continued

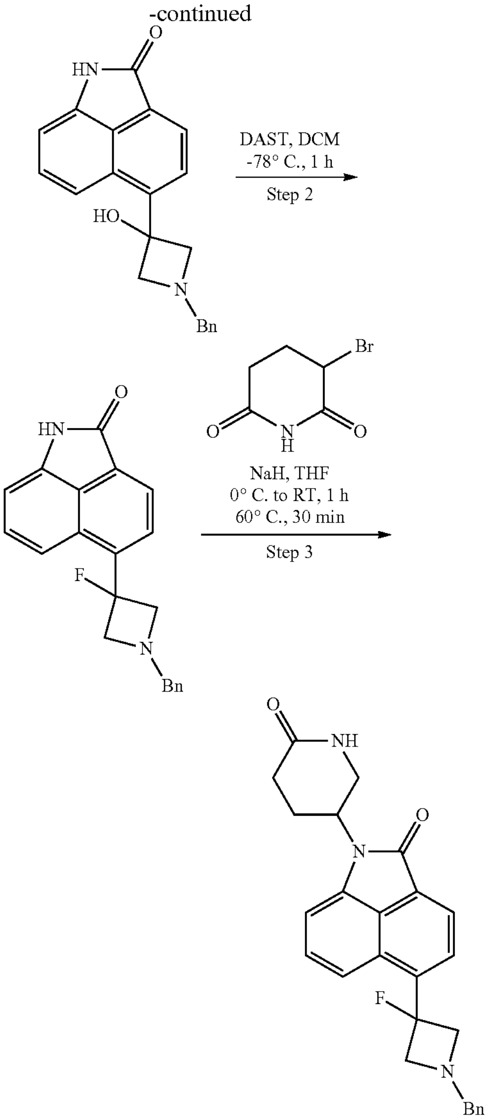

Step 1: To a well stirred solution of 5-(3-hydroxyazetidin-3-yl)-1H-benzo[cd]indol-2-one (120 mg, 499.47 μmol) in anhydrous DCM (5.0 mL) were added benzaldehyde (79.51 mg, 749.20 μmol, 76.45 μL) followed by acetic acid (59.99 mg, 998.93 μmol, 57.13 μL) under nitrogen atmosphere. After heating the reaction mixture at 60° C. for 2 hours, it was cooled at room temperature and sodium; triacetoxyboranuide (529.29 mg, 2.50 mmol) was added at 0° C. After addition, the reaction mixture was stirred for another 12 hours at room temperature. After completion of the reaction, the reaction mass was diluted with DCM (25 mL) and neutralized with $NaHCO_3$ solution. The organic phase was washed with water/brine and separated, dried over anhydrous sodium sulfate, filtered, and concentrated under reduced pressure. Resulting crude mass was purified by flash column chromatography to afford 5-(1-benzyl-3-hydroxy-azetidin-3-yl)-1H-benzo[cd]indol-2-one (105 mg, 310.48 μmol, 62% yield). LC-MS (ES⁺): m/z 331.37 [M+H]⁺.

Step 2: To the solution of 5-(1-benzyl-3-hydroxy-azetidin-3-yl)-1H-benzo[cd]indol-2-one (84 mg, 254.25 μmol) in anhydrous DCM (10.0 mL) was added N-ethyl-N-(trifluoro-$1^{4}-sulfanyl)ethanamine (204.92 mg, 1.27 mmol, 167.96 μL) dropwise via syringe at −78° C. and stirred at the same temperature for 1 hr. After completion, the reaction mixture was diluted with DCM (20 mL) and neutralized with $NaHCO_3$ solution. The organic phase was separated, dried over anhydrous sodium sulfate, filtered, concentrated and dried under reduced pressure to afford 5-(1-benzyl-3-fluoro-azetidin-3-yl)-1H-benzo[cd]indol-2-one (80 mg, 161.27 μmol, 63% yield) which was used for the next step reaction without further purification. LC-MS (ES⁺): m/z 333.38 [M+H]⁺.

Step 3: To a cooled solution of 5-(1-benzyl-3-fluoro-azetidin-3-yl)-1H-benzo[cd]indol-2-one (84 mg, 252.73 μmol) in dry THF (5 mL), Sodium hydride (60% dispersion in mineral oil) (96.84 mg, 2.53 mmol) was added portion wise, maintaining the temp <5° C. After addition, the resulting mixture was stirred for 15 minutes at room temperature. Then the reaction mixture was again cooled to 0° C. and 3-bromopiperidine-2,6-dione (242.63 mg, 1.26 mmol) was added to it portion wise. After addition, the resulting solution was heated at 70° C. for 1 hour. After complete consumption of 5-(1-benzyl-3-fluoro-azetidin-3-yl)-1H-benzo[cd]indol-2-one, the reaction mixture was cooled to 0° C. and quenched with the addition of ice-cold water (10 mL). The aqueous layer was extracted with ethyl acetate (3×50 mL), and the combined organics was separated, dried over anhydrous sodium sulfate, and concentrated under reduced pressure. The crude product was purified by PREP TLC to afford 3-[5-(1-benzyl-3-fluoro-azetidin-3-yl)-2-oxo-benzo[cd]indol-1-yl]piperidine-2,6-dione (Compound 100, 15.2 mg, 32.72 μmol, 12.95% yield) as yellow solid. $^1$H NMR (400 MHz, DMSO-$d_6$) δ 11.14 (s, 1H), 8.16 (br, 1H), 8.0 (br, 1H), 7.65-7.63 (m, 1H), 7.58 (t, J=7.28 Hz, 1H), 7.39 (br, 5H), 7.22 (d, J=7.04 Hz, 1H), 5.48 (dd, J=12.84, 5.2 Hz, 1H), 5.1 (s, 2H), 3.8-4.0 (br, 4H), 2.95-2.92 (m, 1H), 2.79-2.78 (m, 1H), 2.68-2.65 (m, 1H), 2.12-2.10 (m, 1H); LC-MS (ES⁺): m/z 444.30 [M+H]⁺.

3-[5-(3-fluoro-1-methyl-azetidin-3-yl)-2-oxo-benzo[cd]indol-1-yl]piperidine-2,6-dione (Compound 101)

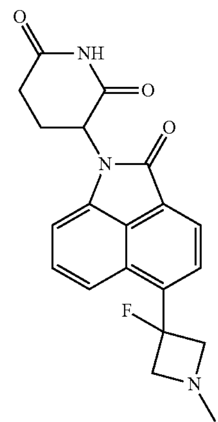 [SMILES: CN1CC(F)(c2ccc3c4c(cccc24)N(C2CCC(=O)NC2=O)C3=O)C1]

Compound 101 was prepared substantially following the synthesis of Compound 100.

LC-MS (ES⁺): m/z 368.27 [M+H]⁺.

$^1$H NMR (400 MHz, DMSO-$d_6$) δ 11.13 (s, 1H), 8.12 (d, J=7.56 Hz, 1H), 7.96-7.95 (m, 1H), 7.68-7.66 (m, 1H), 7.57 (t, J=7.28 Hz, 1H), 7.2 (d, J=7.12 Hz, 1H), 5.45 (dd, J=12.8, 5.2 Hz, 1H), 3.94-3.8 (m, 4H), 2.95-2.92 (m, 1H), 2.79-2.78 (m, 1H), 2.68-2.67 (m, 1H), 2.40 (s, 3H), 2.12-2.10 (m, 1H).

Example 40: Synthesis of 3-[5-(1-methylazetidin-3-yl)-2-oxo-benzo[cd]indol-1-yl]piperidine-2,6-dione (Compound 102)

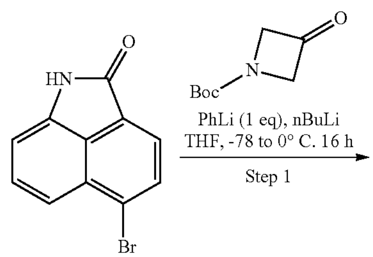

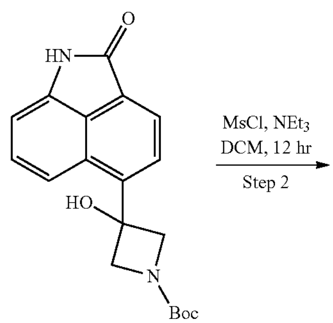

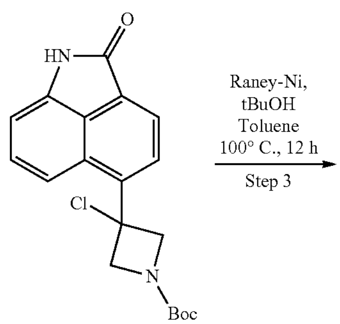

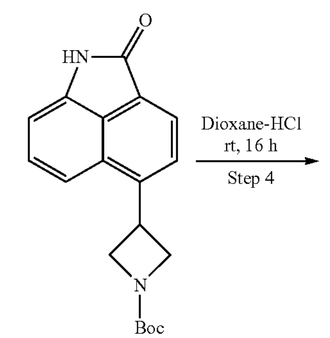

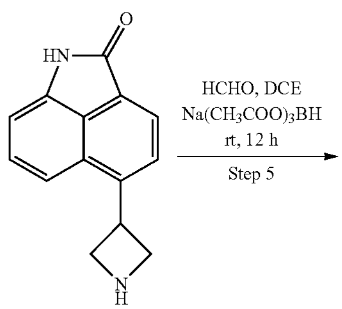

-continued

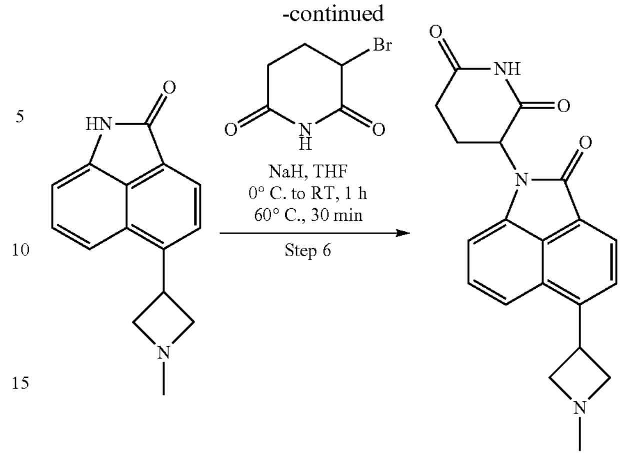

Step 1: To the stirred solution of 5-bromo-1H-benzo[cd]indol-2-one (lg, 4.03 mmol) in dry THF (10.0 mL) was added phenyllithium in di-n-butyl ether (1.9 M, 2.12 mL) at −78° C. under argon atmosphere and the reaction was stirred at the same temperature for 30 minutes followed by the addition of butyllithium (1.62 M, 2.74 mL) at −78° C. After addition, the temperature was allowed to increase to −40° C. and the reaction mixture was stirred at the same temperature for 30 minutes. A solution of tert-butyl 3-oxoazetidine-1-carboxylate (690.09 mg, 4.03 mmol) in THF (10.0 mL) was added at −78° C. and then the reaction mixture was allowed to warm to room temperature and stirred for another 16 hours. After completion of the reaction, the reaction mixture was quenched with ammonium chloride solution and diluted with ethyl acetate (100 mL). Combined organic phase was washed with water and separated, dried over anhydrous sodium sulfate and evaporated under reduced pressure. Crude reaction was purified by flash column chromatography using 0-5% MeOH-DCM to afford tert-butyl 3-hydroxy-3-(2-oxo-1H-benzo[cd]indol-5-yl)azetidine-1-carboxylate (390.0 mg, 1.05 mmol, 26% yield) as brown solid. LC-MS ($ES^+$): m/z 341.39 $[M+H]^+$.

Step 2: To a solution of tert-butyl 3-hydroxy-3-(2-oxo-1H-benzo[cd]indol-5-yl)azetidine-1-carboxylate (360 mg, 1.06 mmol) in HPLC grade $CHCl_3$ (10.0 mL) was added Triethylamine, 99% (428.10 mg, 4.23 mmol, 589.67 μL) at 0° C. and stirred for 10 minutes followed by the addition of methanesulfonyl chloride (484.63 mg, 4.23 mmol, 327.45 μL). The resulting solution was then heated at 80° C. for 16 hours. After completion of the reaction, the reaction mixture was diluted with ethyl acetate (100 mL) and washed with sodium bicarbonate solution/brine. The organic phase was separated, dried over anhydrous sodium sulfate and evaporated under reduced pressure to obtain crude tert-butyl 3-chloro-3-(2-oxo-1H-benzo[cd]indol-5-yl)azetidine-1-carboxylate (428 mg, 644.11 μmol, 61% yield) as a brown solid which was used in the next step without purification. LC-MS ($ES^+$): m/z 359.32 $[M+H]^+$.

Step 3: To a suspension of tert-butyl 3-chloro-3-(2-oxo-1H-benzo[cd]indol-5-yl)azetidine-1-carboxylate (428 mg, 1.19 mmol) in tert-butanol (4 mL) and toluene (4 mL) was added Raney Nickel 2800, slurry, in $H_2O$, active catalyst (1.02 g, 11.93 mmol) and the reaction mixture was degassed for 10 minutes prior to heating at 100° C. for 12 hr. After completion, the reaction mixture was cooled to room temperature, filtered through a pad of celite, washed with 10% MeOH/DCM. The combined filtrate was then concentrated under reduced pressure to afford tert-butyl 3-(2-oxo-1H- benzo[cd]indol-5-yl)azetidine-1-carboxylate (370 mg, 489.34 μmol, 41% yield) which was used directly in the next step without purification. LC-MS ($ES^+$): m/z 325.39 $[M+H]^+$.

Step 4: To the stirred solution of tert-butyl 3-(2-oxo-1H-benzo[cd]indol-5-yl)azetidine-1-carboxylate (370.0 mg, 1.14 mmol) in 1,4-dioxane (3 mL), 4 M dioxane-HCl (1.14 mmol, 10 mL) was added at 0° C. and the reaction mixture was stirred for 16 hours at room temperature. After completion, the volatiles were removed under reduced pressure to obtain a solid which was washed with ether and pentane to afford 5-(1-chloroazetidin-3-yl)-1H-benzo[cd]indol-2-one hydrochloride (290.0 mg, 478.16 μmol, 42% yield) as yellow solid which was used in the next step without purification. LC-MS ($ES^+$): m/z 225.36 $[M+H]^+$.

Step 5: To a well stirred solution of 5-(1-chloroazetidin-3-yl)-1H-benzo[cd]indol-2-one.HCl (90.0 mg, 1.11 mmol) in HPLC grade DCM-MeOH (5:2, v/v, 7 mL) was added triethylamine, 99% (112.55 mg, 1.11 mmol, 155.03 μL) and then the reaction mixture was stirred at room temperature for 10 minutes followed by the addition of formaldehyde (66.81 mg, 2.22 mmol, 61.86 μL) and acetic acid (133.59 mg, 2.22 mmol, 127.23 μL). The resulting reaction mixture was then heated at 60° C. for 3 hours and it was brought to room temperature prior to the addition of sodium; triacetoxyboranuide (1.22 g, 5.75 mmol). After complete addition, the reaction mixture was allowed to stir at same temperature for an additional 12 hours. After completion of reaction, the reaction mixture was diluted with 10% MeOH in DCM (50 mL) and washed with saturated sodium bicarbonate solution followed by water/brine solution. The organic portion was separated, dried over sodium sulfate, and concentrated under reduced pressure. The crude product was purified by combi-flash column chromatography to afford 5-(1-methylazetidin-3-yl)-1H-benzo[cd]indol-2-one (60.0 mg, 188.85 μmol, 17% yield). LC-MS ($ES^+$): m/z 239.02 $[M+H]^+$.

Step 6: To a cooled solution of 5-(1-methylazetidin-3-yl)-1H-benzo[cd]indol-2-one (160.0 mg, 671.47 μmol) in dry THF (5 mL) was added portionwise, maintaining the temp <5° C. After addition, the resulting mixture was stirred for 15 minutes at room temperature. Then the reaction mixture was again cooled to 0° C. and 3-bromopiperidine-2,6-dione (128.93 mg, 671.47 μmol) was added portion wise. After complete addition, resulting solution was heated at 70° C. 1 hr. After completion, the reaction mixture was cooled to 0° C. and quenched with the addition of ice-cold water (5 mL). The aqueous layer was extracted with ethyl acetate (3×50 mL), the combined organics was separated, dried over anhydrous sodium sulfate, and concentrated under reduced pressure. The crude product was purified by PREP-TLC to afford 3-[5-(1-methylazetidin-3-yl)-2-oxo-benzo[cd]indol-1-yl]piperidine-2,6-dione (Compound 102, 5.8 mg, 15.85 μmol, 2% yield).

$^1H$ NMR (400 MHz, DMSO-$d_6$) δ 11.11 (s, 1H), 8.07 (d, J=7.28 Hz, 1H), 7.79 (d, J=7.12 Hz, 1H), 7.62 (d, J=8.48 Hz, 1H), 7.51 (t, J=7.32 Hz, 1H), 7.14 (d, J=7.16 Hz, 1H), 5.44-5.42 (m, 1H), 4.38-4.35 (m, 1H), 3.91 (m, 2H), 3.43 (m, 2H), 2.94-2.91 (m, 1H), 2.77-2.62 (m, 2H), 2.32 (s, 3H), 2.10-2.07 (m, 1H); LC-MS ($ES^+$): m/z 350.1 $[M+H]^+$.

Example 41: 3-[5-[(1-benzylazetidin-3-yl)methyl]-2-oxo-benzo[cd]indol-1-yl]piperidine-2,6-dione (Compound 103)

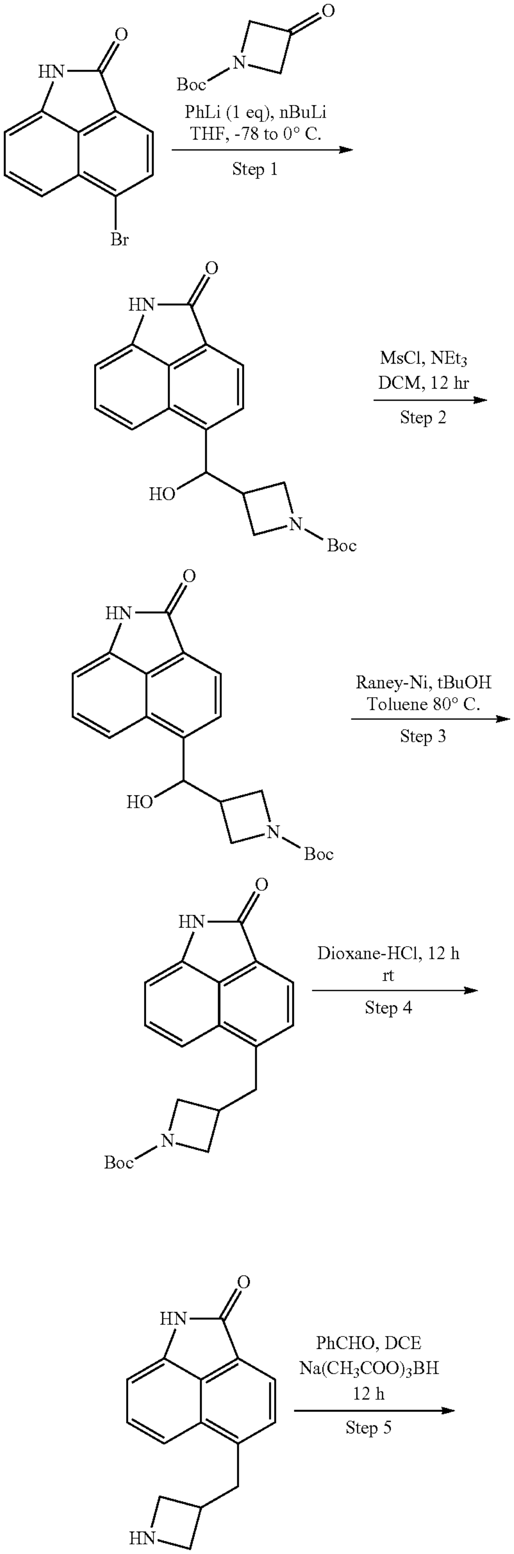

-continued

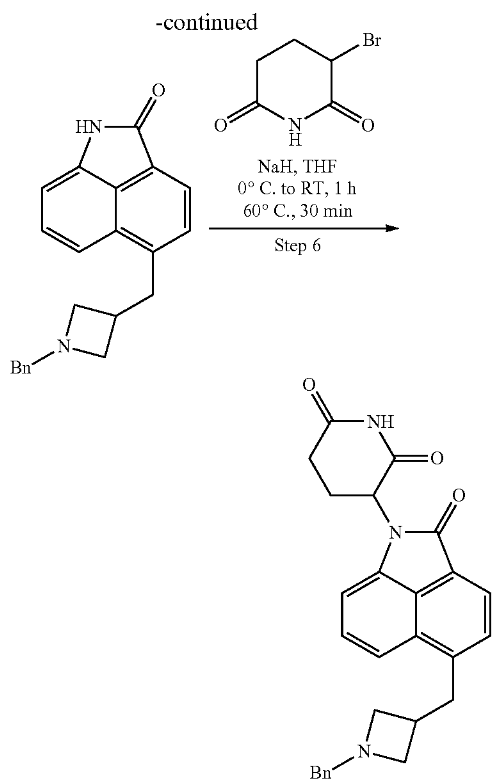

Step 1: To the stirred solution of 5-bromo-1H-benzo[cd]indol-2-one (1.0 g, 4.03 mmol) in dry THF (5.0 mL) was added phenyllithium in di-n-butyl ether (1.8 M, 2.24 mL) at −78° C. under argon atmosphere and the reaction was stirred at the same temperature for 30 minutes followed by the addition of butyllithium (1.62 M, 2.74 mL) at −78° C. The reaction was allowed to warm to −40° C. and stirred at this temperature for 30 minutes. Then a solution of tert-butyl 3-formylazetidine-1-carboxylate (746.63 mg, 4.03 mmol, 287.88 μL) in dry THF (5.0 mL) was added at −78° C. and stirring continued at room temperature for 16 hours. After completion, the reaction mixture was quenched with ammonium chloride solution and diluted with ethyl acetate (100 mL). The combined organic layer was washed with water/brine, dried over anhydrous sodium sulfate, and concentrated under reduced pressure. The crude product was purified by flash column chromatography using 0-5% MeOH-DCM to afford tert-butyl 3-[hydroxy-(2-oxo-1H-benzo[cd]indol-5-yl)methyl]azetidine-1-carboxylate (470 mg, 1.19 mmol, 30% yield) as brown solid. $^1$H NMR (400 MHz, DMSO-$d_6$) δ 10.7 (s, 1H), 7.96 (d, J=7.2 Hz, 1H), 7.84-7.81 (m, 2H), 7.48 (t, J=7.6 Hz, 1H), 6.96 (d, J=7.04 Hz, 1H), 5.92 (d, J=4.32 Hz, 1H), 5.44-5.42 (m, 1H), 3.91 (br m, 1H), 3.75-3.67 (m, 3H), 3.0-2.95 (m, 1H), 1.36 (s, 9H). LC-MS (ES$^+$): m/z 255.2 [M−Boc+H]$^+$.

Step 2: To flame dried 100 mL round bottomed flask, a solution of tert-butyl 3-[hydroxy-(2-oxo-1H-benzo[cd]indol-5-yl)methyl]azetidine-1-carboxylate (350 mg, 987.59 μmol) in HPLC grade $CHCl_3$ (10.0 mL) was cooled to 0° C. To this chilled solution was added triethylamine (440399.74 mg, 3.95 mmol, 550.60 μL) followed by methanesulfonyl chloride (452.51 mg, 3.95 mmol, 305.75 μL). The resulting reaction mixture was refluxed at 80° C. for 4 hours. After completion, the reaction mixture was diluted with DCM (30 mL) and the organic layer was washed with saturated sodium bicarbonate solution followed by water/brine solution. The combined organic phase was dried over anhydrous sodium sulfate and evaporated under reduced pressure to afford tert-butyl 3-chloro-3-(2-oxo-1H-benzo[cd]indol-5-yl) pyrrolidine-1-carboxylate (400 mg, 1.07 mmol, 99% yield) which was used directly in the next step without purification. LC-MS (ES$^+$): m/z 317.25 [M−tBu+H]$^+$.

Step 3: To a suspension of tert-butyl 3-[chloro-(2-oxo-1H-benzo[cd]indol-5-yl)methyl]azetidine-1-carboxylate (400 mg, 1.07 mmol) in tert-butanol (5 mL) and toluene (5 mL) was added Raney Nickel 2800, slurry in $H_2O$, active catalyst (459.57 mg, 5.36 mmol) and the reaction mixture was degassed for 10 minutes prior to heating at 100° C. for 12 hours. After completion, the reaction mixture was cooled to room temperature, filtered through a pad of celite, and washed with 10% MeOH/DCM. The filtrate was washed with cold water, dried over anhydrous sodium sulfate and concentrated under reduced pressure to afford tert-butyl 3-[chloro-(2-oxo-1H-benzo[cd]indol-5-yl)methyl]azetidine-1-carboxylate (450 mg, 1.21 mmol) which was used in the next step without purification or characterization.

Step 4: A solution of tert-butyl 3-[(2-oxo-1H-benzo[cd]indol-5-yl)methyl]azetidine-1-carboxylate (306 mg, 904.26 μmol) in dioxane (4 mL) was treated with 4 M dioxane-HCl (9.04 mmol, 2.0 mL) at 0° C. and stirred at room temperature for 12 hours. After completion of the reaction, the volatiles were removed under reduced pressure and the crude product was washed with pentane/diethyl ether and dried well to afford 5-(azetidin-3-ylmethyl)-1H-benzo[cd]indol-2-one; hydrochloride (250 mg, 482.00 μmol, 53% yield) which was used for the next step reaction without purification. LC-MS (ES$^+$): m/z 239.45 [M+H]$^+$.

Step 5: To a suspension of 5-(azetidin-3-ylmethyl)-1H-benzo[cd]indol-2-one (150 mg, 629.50 μmol) in MeOH (5 mL)-DCE (5 mL), triethylamine was added until pH~7. To this solution was added acetic acid (113.41 mg, 1.89 mmol, 108.01 μL) followed by benzaldehyde (133.61 mg, 1.26 mmol) and the resulting solution was heated at 60° C. for 3 hours. The mixture was then cooled to room temperature before sodium triacetoxyborohydride (667.09 mg, 3.15 mmol) was added portion wise at 0° C. The reaction mixture was stirred for an additional 12 hours at room temperature. After completion, the volatiles were removed, and the residue was redissolved in ethyl acetate (50 mL). The organic layer was washed with sodium bicarbonate solution, dried over anhydrous sodium sulfate, filtered, and concentrated under reduced pressure. The crude product was purified by combi-flash column chromatography to afford 5-[(1-benzylazetidin-3-yl)methyl]-1H-benzo[cd]indol-2-one (100 mg, 249.69 μmol, 40% yield). LC-MS (ES$^+$): m/z 329.0 [M+H]$^+$.

Step 6: To a cooled solution of 5-[(1-benzylazetidin-3-yl)methyl]-1H-benzo[cd]indol-2-one (50 mg, 152.25 μmol) in dry THF (5 mL), sodium hydride (60% dispersion in mineral oil) (58.34 mg, 1.52 mmol) was added portionwise, maintaining the temperature <5° C. The resulting mixture was stirred at room temperature for 15 minutes. Then the reaction mixture was cooled to 0° C. and 3-bromopiperidine-2,6-dione (146.17 mg, 761.25 μmol) was added portionwise and the solution was heated at 70° C. for 1 hour. After complete consumption of the starting material, the reaction mixture was cooled to 0° C. and quenched with the addition of ice-cold water (5 mL). The aqueous layer was extracted with ethyl acetate (3×50 mL). The combined organic layer was dried over anhydrous sodium sulfate and concentrated under reduced pressure. The crude product was purified by PREP TLC to afford 3-[5-[(1-benzylazetidin-3-yl)methyl]-2-oxo-benzo[cd]indol-1-yl]piperidine-2,6-dione (Compound 103, 15 mg, 34.13 μmol, 22% yield) as yellow solid. LC-MS ($ES^+$): m/z 440.30 $[M+H]^+$.

$^1H$ NMR (400 MHz, DMSO-$d_6$) δ 11.12 (s, 1H), 7.99 (d, J=7.0 Hz, 1H), 7.78 (d, J=8.28 Hz, 1H), 7.62 (d, J=6.68 Hz, 1H), 7.53 (t, J=7.72 Hz, 1H), 7.28-7.25 (m, 5H), 7.14 (d, J=7.16 Hz, 1H), 5.44 (dd, J=11.28, 3.32 Hz, 1H), 3.55 (s, 2H), 3.39-3.37 (m, 2H), 3.29-3.27 (m, 2H), 2.94 (br m, 3H), 2.80-2.62 (m, 3H), 2.09 (m, 1H).

Example 42: Synthesis of tert-butyl 3-[[1-(2,6-dioxo-3-piperidyl)-2-oxo-benzo[cd]indol-5-yl]methyl]azetidine-1-carboxylate (Compound 104)

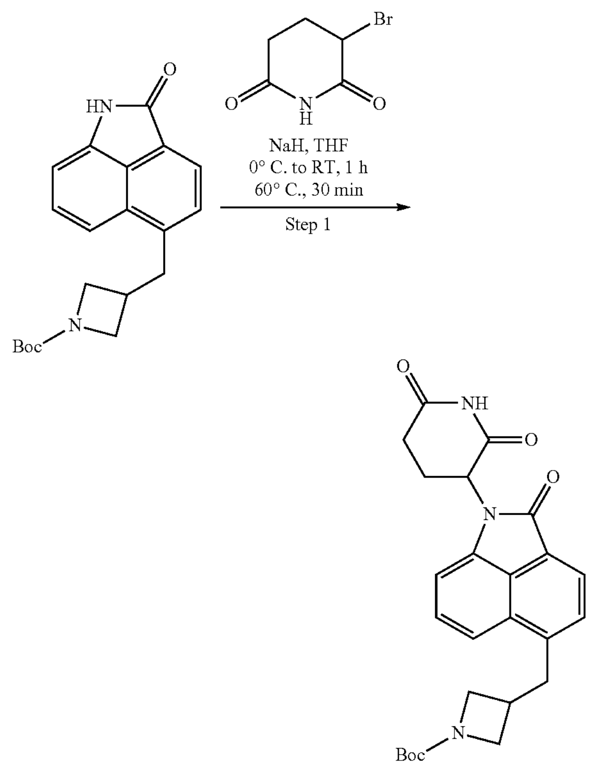

Compound tert-butyl 3-[(2-oxo-1H-benzo[cd]indol-5-yl)methyl]azetidine-1-carboxylate was prepared in Example 41.

To a cooled solution of tert-butyl 3-[(2-oxo-1H-benzo[cd]indol-5-yl)methyl]azetidine-1-carboxylate (95 mg, 280.73 μmol) in dry THF (5 mL), sodium hydride (60% dispersion in mineral oil) (107.57 mg, 2.81 mmol) was added portion wise, maintaining the temperature <5° C. After addition, the resulting mixture was stirred for 15 minutes at room temperature. Then the reaction mixture was again cooled to 0° C. and 3-bromopiperidine-2,6-dione (269.52 mg, 1.40 mmol) was added portion wise. After complete addition, resulting solution was heated at 70° C. 1 hr. After complete consumption of the starting material, the reaction mixture was cooled to 0° C. and quenched with the addition of ice-cold water (10 mL). The aqueous layer was extracted with ethyl acetate (3×50 mL). The combined organics was separated, dried over anhydrous sodium sulfate, and concentrated under reduced pressure. The crude product was purified by PREP TLC to afford tert-butyl 3-[[1-(2,6-dioxo-3-piperidyl)-2-oxo-benzo[cd]indol-5-yl]methyl]azetidine-1-carboxylate (Compound 104, 9.6 mg, 20.82 μmol, 7% yield) as yellow solid. $^1H$ NMR (400 MHz, DMSO-$d_6$) δ 11.12 (s, 1H), 8.01 (d, J=7.12 Hz, 1H), 7.81 (d, J=8.56 Hz, 1H), 7.68 (d, J 7.2 Hz, 1H), 7.55 (t, J=7.4 Hz, 1H), 7.15 (d, J=7.24 Hz, 1H), 5.45 (dd, J=12.84, 5.44 Hz, 1H), 3.83 (m, 2H), 3.65 (m, 2H), 3.43 (d, J 7.84 Hz, 2H), 2.97-2.9 (m, 2H), 2.77-2.63 (m, 2H), 2.10-2.07 (m, 1H), 1.36 (s, 9H); LC-MS ($ES^-$): m/z 448.36 $[M-H]^-$.

Example 43: Synthesis of 3-[5-[(1-methylazetidin-3-yl)methyl]-2-oxo-benzo[cd]indol-1-yl]piperidine-2,6-dione (Compound 105)

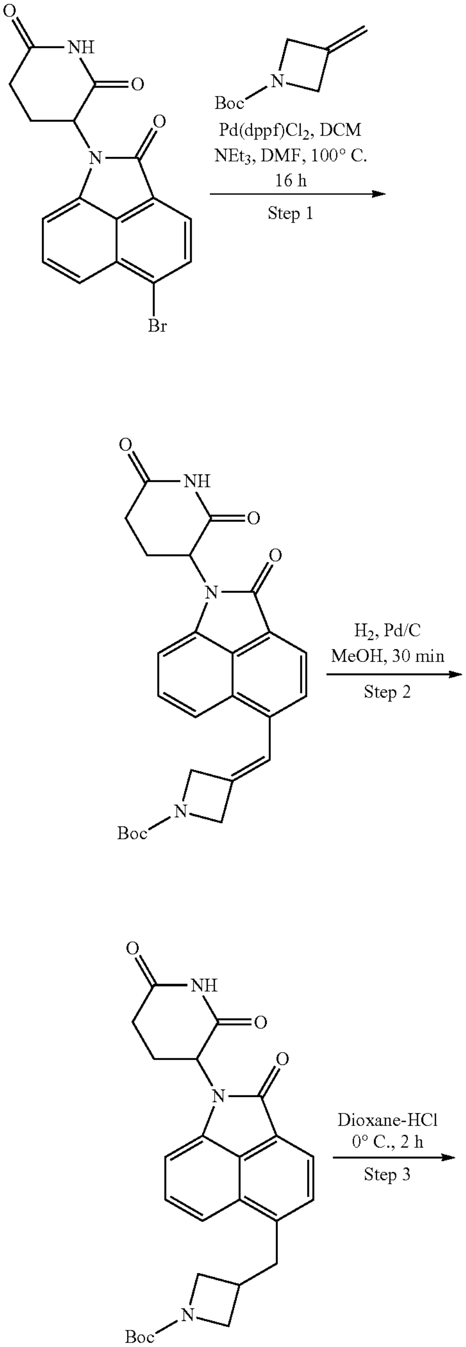

-continued

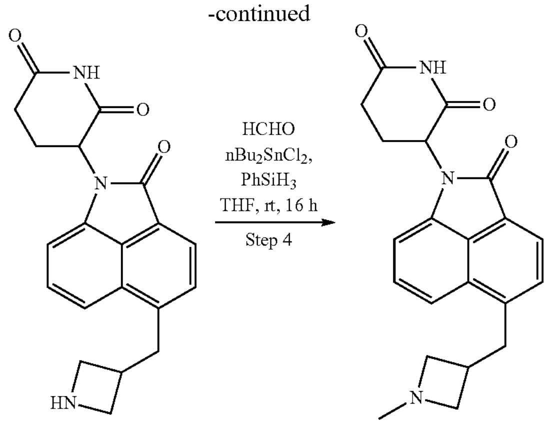

Step 1: To an oven dried, nitrogen purged sealed vial, 3-(5-bromo-2-oxo-benzo[cd]indol-1-yl)piperidine-2,6-dione (450 mg, 1.25 mmol) and tert-butyl 3-methyleneazetidine-1-carboxylate (636.04 mg, 3.76 mmol) were dissolved in HPLC grade DMF (3.0 mL). To this solution, triethylamine (633.89 mg, 6.26 mmol, 873.13 μL) was added and the reaction mixture was purged with argon gas for 10 minutes followed by the addition of [1,1'-bis(diphenylphosphino)ferrocene]dichloropalladium(II) (102.31 mg, 125.29 μmol). The resulting reaction mixture was heated at 100° C. for 16 hours. After completion of reaction, the reaction mixture was allowed to cool to room temperature and diluted with ethyl acetate (40 mL). The combined organic layer was washed with cold water/brine several times. The organic layer was separated, dried over anhydrous sodium sulfate, evaporated under reduced pressure to afford the crude product which was purified by column chromatography (100-200 mesh silica gel, 40%-50% ethyl acetate in DCM) to afford tert-butyl 3-[[1-(2,6-dioxo-3-piperidyl)-2-oxo-benzo[cd]indol-5-yl]methylene]azetidine-1-carboxylate (420 mg, 750.87 μmol, 60% yield) as a light brownish solid. LC-MS (ES$^+$): m/z 348.2 [M−Boc+H]$^+$.

Step 2: To a well degassed solution of tert-butyl 3-[[1-(2,6-dioxo-3-piperidyl)-2-oxo-benzo[cd]indol-5-yl]methylene]azetidine-1-carboxylate (420 mg, 938.59 μmol) in Ethanol (5.0 mL)-EtOAc (5.0 mL) was added 10% Pd/C (569.97 mg, 4.69 mmol) and resulting mixture was hydrogenated at room temperature under hydrogen balloon pressure for 1 hour. After completion, reaction mixture was filtered through a pad of celite, washed with ethyl acetate and THF. The filtrate was concentrated under reduced pressure and the crude product was triturated with n-pentane to afford tert-butyl 3-[[1-(2,6-dioxo-3-piperidyl)-2-oxo-benzo[cd]indol-5-yl]methyl]azetidine-1-carboxylate (350 mg, 583.98 μmol, 62% yield). LC-MS (ES$^+$): m/z 350.2 [M−Boc+H]$^+$.

Step 3: To the stirred solution of tert-butyl 3-[[1-(2,6-dioxo-3-piperidyl)-2-oxo-benzo[cd]indol-5-yl]methyl]azetidine-1-carboxylate (420 mg, 934.38 μmol) in dioxane (3 mL) was added 4 M Dioxane-HCl (15 mL) and the reaction mixture was stirred at room temperature for 2 hours. After completion of the reaction, the volatiles were evaporated under reduced pressure to obtain a solid which was washed with diethyl ether and pentane to afford 3-[5-[(1-chloroazetidin-3-yl)methyl]-2-oxo-benzo[cd]indol-1-yl]piperidine-2,6-dione hydrochloride (400.0 mg, 527.58 μmol, 56% yield) as a yellow solid which was used in the next step without purification. LC-MS (ES$^+$): m/z 350.0 [M+H]$^+$.

Step 4: To the stirred solution of 3-[5-(azetidin-3-ylmethyl)-2-oxo-benzo[cd]indol-1-yl]piperidine-2,6-dione (200 mg, 572.44 μmol) and formaldehyde (38.99 mg, 1.14 mmol, 47.84 μL) in dry THF (5 mL), dibutyltin dichloride (260.90 mg, 858.66 μmol, 191.84 μL) was added portion wise and the mixture was stirred for 20 minutes at 60° C. in a sealed vial. Subsequently, the reaction mixture was cooled to room temperature and phenylsilane (61.94 mg, 572.44 μmol, 70.55 μL) was added. The resulting reaction mixture was heated at 80° C. for 12 hours. After completion of the reaction, the volatiles were removed under reduced pressure and redissolved in 5% MeOH-DCM (20 mL). Organic portion was washed with water/brine and separated, dried over sodium sulfate, and concentrated. The crude product was purified by PREP-TLC to afford 3-[5-[(1-methylazetidin-3-yl)methyl]-2-oxo-benzo[cd]indol-1-yl]piperidine-2,6-dione (Compound 105, 13.1 mg, 32.59 μmol, 6% yield). LC-MS (ES$^+$): m/z 364.31 [M+H]$^+$. $^1$H NMR (400 MHz, DMSO-$d_6$) δ 11.12 (s, 1H), 8.04 (d, J=7 Hz, 1H), 7.83 (d, J=8.72 Hz, 1H), 7.65 (d, J=7.28 Hz, 1H), 7.57 (t, J=7.4 Hz, 1H), 7.17 (d, J=7.16 Hz, 1H), 5.45-5.43 (m, 1H), 3.86-3.85 (m, 2H), 3.69 (m, 2H), 3.47 (d, J=7.44 Hz, 2H), 3.07-3.03 (m, 2H), 2.76-2.73 (m, 1H), 2.68 (br s, 4H), 2.10-2.08 (m, 1H).

Example 44: Synthesis of 3-[5-(4,6-dimethylpyrimidin-2-yl)-2-oxo-benzo[cd]indol-1-yl]piperidine-2,6-dione (Compound 106)

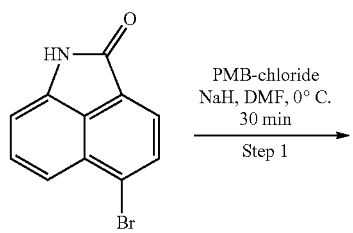

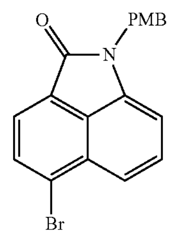

PdCl2dppf•DCM, KOAc
Bispinacolatodiboron
Dioxane, 90° C., 16 h
Step 2

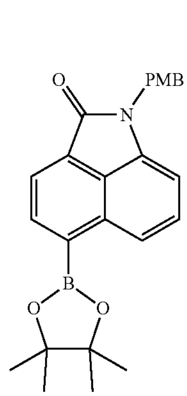

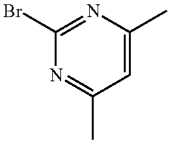

PdCl2dppf•DCM
K2CO3
Dioxane-water, 12 h
RT
Step 3

-continued

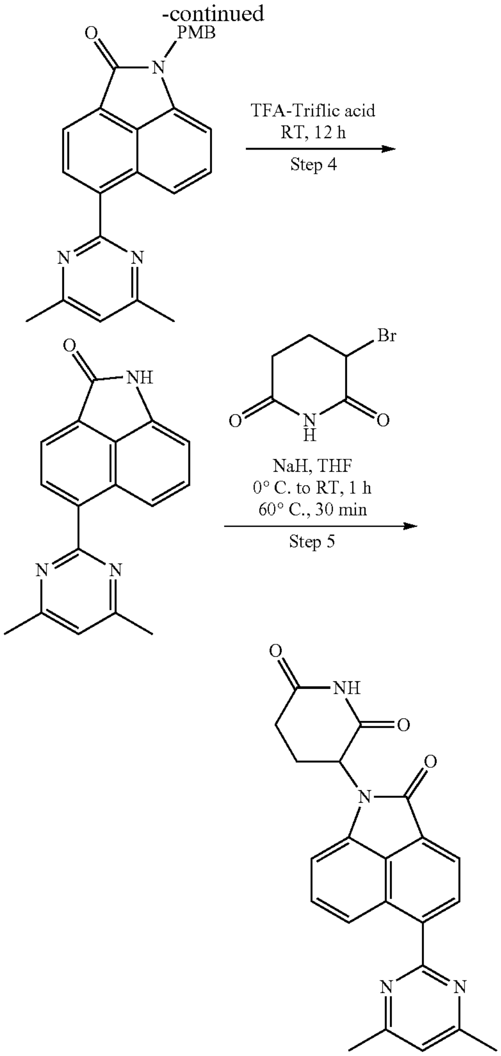

Step 1: To a stirred solution of 5-bromo-1H-benzo[cd]indol-2-one (6.0 g, 24.19 mmol) in dry DMF (10 mL), sodium hydride (60% dispersion in mineral oil) (1.39 g, 36.28 mmol) was added at 0° C. The reaction mixture was stirred for 30 minutes at the same temperature under inert atmosphere. 1-(chloromethyl)-4-methoxy-benzene (4.55 g, 29.02 mmol, and 3.79 mL) was then added to the reaction mixture and stirred for another 30 minutes at room temperature. After completion, ethyl acetate (100 mL) was added to the reaction mixture. The organic layer was washed with cold water (3×30 mL) followed by brine solution. The organic layer was separated, dried over sodium sulfate, filtered, and concentrated under reduced pressure. The crude product was purified by combi-flash column chromatography to afford 5-bromo-1-[(4-methoxyphenyl)methyl]benzo[cd]indol-2-one (6.0 g, 15.81 mmol, 65% yield) as yellow solid. LC-MS ($ES^+$): m/z 370.2 $[M+H]^+$.

Step 2: In an oven dried sealed vial under nitrogen atmosphere, 5-bromo-1-[(4-methoxyphenyl)methyl]benzo[cd]indol-2-one (3.0 g, 8.15 mmol) was dissolved in 1,4 dioxane (60 mL) followed by the addition of bis(pinacolato) diboron (3.10 g, 12.22 mmol) and potassium acetate (2.40 g, 24.44 mmol). The resulting reaction mixture was purged with argon for 15 minutes. Cyclopentyl(diphenyl)phosphane; dichloromethane; dichloropalladium; iron (665.34 mg, 814.72 μmol) was added to the reaction mixture and the mixture was heated at 100° C. for 16 hours. After completion of the reaction, the reaction mixture was cooled to room temperature, filtered through a pad of celite, washed with ethyl acetate. The filtrate was washed with cold water (2×40 mL), dried over sodium sulfate, and concentrated under reduced pressure. The crude residue was purified by flash column chromatography to afford 1-[(4-methoxyphenyl)methyl]-5-(4,4,5,5-tetramethyl-1,3,2-dioxaborolan-2-yl)benzo[cd]indol-2-one (2.9 g, 6.98 mmol, 86% yield) as a yellow solid. LC-MS ($ES^+$): m/z 416.4 $[M+H]^+$.

Step 3: A mixture of 1-[(4-methoxyphenyl)methyl]-5-(4,4,5,5-tetramethyl-1,3,2-dioxaborolan-2-yl)benzo[cd]indol-2-one (200 mg, 481.59 μmol), 2-bromo-4,6-dimethyl-pyrimidine (75.06 mg, 401.33 μmol) and potassium carbonate (166.40 mg, 1.20 mmol) were suspended in a mixture of dioxane (4 mL) and water (1 mL). The resulting reaction mixture was degassed with argon for 10 minutes, followed by the addition of Pd(dppf)Cl2.DCM (32.77 mg, 40.13 μmol) and the mixture was stirred at room temperature for 12 hours. After completion of the reaction, the reaction mixture was filtered through filter cartridge and the filtrate was evaporated to dryness. The crude product was diluted with ethyl acetate (50 mL) and washed with water/brine. The organic phase was separated, dried over anhydrous sodium sulfate, filtered and concentrated under reduced pressure to afford 5-(4,6-dimethylpyrimidin-2-yl)-1-[(4-methoxyphenyl)methyl]benzo[cd]indol-2-one (110 mg, 250.35 μmol, 62% yield) which was used for the next step reaction without further purification. LC-MS ($ES^+$): m/z 396.4 $[M+H]^+$.

Step 4: To a stirred solution of 5-(4,6-dimethylpyrimidin-2-yl)-1-[(4-methoxyphenyl)methyl]benzo[cd]indol-2-one (158 mg, 399.54 μmol) in TFA (5.0 mL), triflic acid (1.20 g, 7.99 mmol, 701.33 μL) was added dropwise at 0° C. and stirred for 16 hours at room temperature. After completion of the reaction, the reaction mixture was evaporated and quenched with saturated sodium bicarbonate solution. Aqueous phase was extracted with ethyl acetate (3×25 mL) and washed with water/brine solution. The organic phase was separated, dried over sodium sulfate, and concentrated to afford crude 5-(4,6-dimethylpyrimidin-2-yl)-1H-benzo[cd]indol-2-one (67 mg, 238.50 μmol, 60% yield) as a brown solid which was used in the next step without purification. LC-MS ($ES^+$): m/z 276.2 $[M+H]^+$.

Step 5: To a cooled solution of 5-(4,6-dimethylpyrimidin-2-yl)-1H-benzo[cd]indol-2-one (67.06 mg, 243.60 μmol) in dry THF (5 mL), sodium hydride (60% dispersion in mineral oil) (93.34 mg, 2.44 mmol) was added portion wise, maintaining the temp <5° C. Once the addition is over, the resulting mixture was stirred for 15 minutes at room temperature. Then the reaction mixture was again cooled to 0° C. and 3-bromopiperidine-2,6-dione (233.87 mg, 1.22 mmol) was added to it portion wise. After complete addition, resulting solution was heated at 70° C. 1 hr. After completion, the reaction mixture was cooled to 0° C. and quenched with the addition of ice-cold water. The aqueous layer was extracted with ethyl acetate (3×50 mL). The combined organics was separated, dried over anhydrous sodium sulfate and concentrated under reduced pressure to give the crude product which was purified by PREP-TLC to afford 3-[5-(4,6-dimethylpyrimidin-2-yl)-2-oxo-benzo[cd]indol-1-yl]piperidine-2,6-dione (Compound 106, 20 mg, 51.76 μmol, 21% yield) as yellow solid. LC-MS ($ES^+$): m/z 387.3 $[M+H]^+$. $^1H$ NMR (400 MHz, DMSO-$d_6$) δ 11.15 (s, 1H), 8.68 (dd, J=8.8, 7.44 Hz, 2H), 8.21 (d, J=7.36 Hz, 1H), 7.59 (t, J=7.32 Hz, 1H), 7.36 (s, 1H), 7.20 (d, J=7.08 Hz, 1H), 5.49 (dd, J=1.334, 5.08 Hz, 1H), 2.95-2.91 (br m, 1H), 2.8-2.77 (m, 2H), 258 (s, 6H), 2.13-2.08 (m, 1H).

Example 45: Synthesis of 1-(2,6-dioxo-3-piperidyl)-2-oxo-N-(1-phenylethyl)benzo[cd]indole-5-carboxamide (Compound 107)

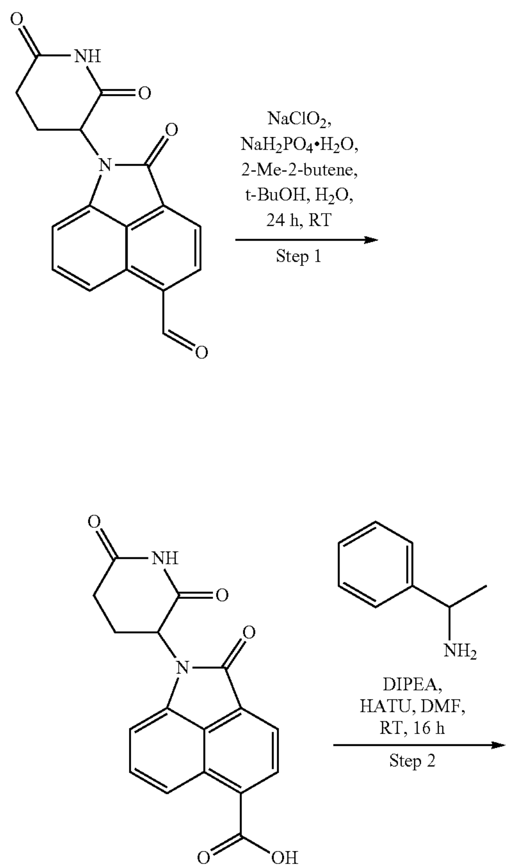

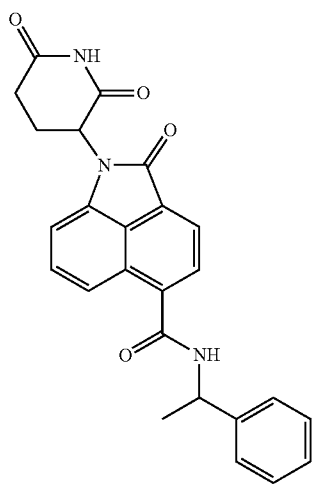

Step 1: 2-Methylbut-2-ene (682.45 mg, 9.73 mmol, 1.03 mL) was added to a stirred solution of 1-(2,6-dioxo-3-piperidyl)-2-oxo-benzo[cd]indole-5-carbaldehyde (200 mg, 648.74 μmol) in tert-butanol (12 mL) at 0-5° C. To this mixture, an aqueous solution of sodium chlorite (293.36 mg, 3.24 mmol) and sodium dihydrogen phosphate hydrate (447.61 mg, 3.24 mmol) were added dropwise, and stirring was continued for 16 hours at room temperature. After completion, the reaction mixture was evaporated to dryness under reduced pressure and 10 mL of 10 (M) NaOH was added. The resulting solution was extracted with ethyl acetate, the organic layer was discarded and the aqueous layer was acidified using 1 N HCl solution. The observed yellow precipitate was filtered off and dried under vacuum to afford 1-(2,6-dioxo-3-piperidyl)-2-oxo-benzo[cd]indole-5-carboxylic acid (120 mg, 336.74 μmol, 52% yield); LC-MS ($ES^+$): m/z 325 $[M+H]^+$.

Step 2: To a stirred solution of 1-(2,6-dioxo-3-piperidyl)-2-oxo-benzo[cd]indole-5-carboxylic acid (30 mg, 92.51 μmol) in DMF (1 mL) were added DIPEA (23.91 mg, 185.02 μmol, 32.23 μL) and HATU (35.18 mg, 92.51 μmol) and the mixture was stirred at room temperature for 15 minutes. 1-Phenylethanamine (12.33 mg, 101.76 μmol, 13.05 μL) was added and the mixture stirred at room temperature for 16 hours. After completion of the reaction, the reaction mixture was purified by reverse phase prep HPLC to afford 1-(2,6-dioxo-3-piperidyl)-2-oxo-N-(1-phenylethyl)benzo[cd]indole-5-carboxamide (Compound 107, 8.92 mg, 20.87 μmol, 23% yield). LC-MS ($ES^+$): m/z 428 $[M+H]^+$. $^1H$ NMR (400 MHz, DMSO-$d_6$) δ 11.09 (br.s, 1H), 9.20 (d, J=8 Hz, 1H), 8.16 (d, J=8 Hz, 1H), 8.00 (dd, J=8 Hz, 0.8 Hz, 1H), 7.81 (dd, J=8 Hz, 4 Hz, 1H), 7.55 (t, J=8 Hz, 1H), 7.46 (d, J=8 Hz, 2H), 7.37 (t, J=8 Hz, 2H), 7.26 (t, J=8 Hz, 1H), 7.20 (d, J=8 Hz, 1H), 5.46 (q, J=8 Hz, 1H), 2.96-2.90 (m, 1H), 2.78 (t, J=8 Hz, 1H), 2.67-2.64 (m, 1H), 2.13-2.08 (m, 1H), 1.51 (d, J=8 Hz, 3H).

Compound 108-Compound 112 were prepared substantially following the synthesis of Compound 107.

N-(1-cyclohexylethyl)-1-(2,6-dioxopiperidin-3-yl)-2-oxo-1,2-dihydrobenzo[cd]indole-5-carboxamide (Compound 108)

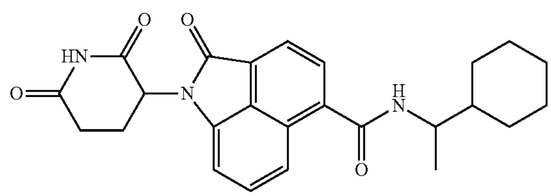 [SMILES: CC(NC(=O)c1ccc2c3c(cccc13)N(C1CCC(=O)NC1=O)C2=O)C1CCCCC1]

LC-MS ($ES^+$): m/z 434 $[M+H]^+$.

$^1H$ NMR (400 MHz, DMSO-$d_6$) δ 11.13 (s, 1H), 8.50 (d, J=8 Hz, 1H), 8.14 (d, J=8 Hz, 1H), 7.91 (d, J=8 Hz, 1H), 7.83 (d, J=8 Hz, 1H), 7.57 (t, J=8 Hz, 1H), 7.19 (d, J=8 Hz, 1H), 5.46 (q, J=4 Hz, 1H), 3.94 (q, J=8 Hz, 1H), 2.92 (t, J=8 Hz, 1H), 2.79-2.75 (m, 1H), 2.66 (d, J=16 Hz, 1H), 2.11-2.13 (m, 1H), 1.84-1.72 (m, 4H), 1.64 (s, 1H), 1.44 (d, J=8 Hz, 1H), 1.23-1.19 (m, 8H).

1-(2,6-dioxopiperidin-3-yl)-N-(1-(2-methoxyphenyl)ethyl)-2-oxo-1,2-dihydrobenzo[cd]indole-5-carboxamide (Compound 109)

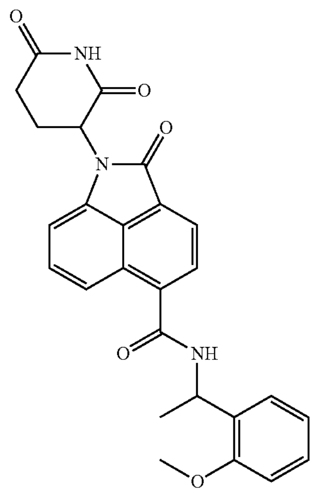

LC-MS ($ES^+$): m/z 458 $[M+H]^+$.

$^1H$ NMR (400 MHz, DMSO-$d_6$) δ 11.18 (br.s, 1H), 9.14 (d, J=8 Hz, 1H), 8.17 (d, J=8 Hz, 1H), 8.01 (d, J=8 Hz, 1H), 7.80 (d, J=8 Hz, 1H), 7.55 (m, 1H), 7.40 (d, J=8 Hz, 1H), 7.25 (d, J=8 Hz, 1H), 7.18 (d, J=8 Hz, 1H), 7.02 (d, J=8 Hz, 1H), 6.96 (d, J=8 Hz, 1H), 5.52 (t, J=8 Hz, 1H), 5.46 (t, J=8 Hz, 1H), 3.87 (s, 3H), 2.95-2.91 (m, 1H), 2.79-2.75 (m, 1H), 2.66 (d, J=12 Hz, 1H); 2.13-2.10 (m, 1H), 1.74 (s, 2H), 1.42 (d, J=8 Hz, 3H).

1-(2,6-dioxopiperidin-3-yl)-2-oxo-N-(2,2,2-trifluoro-1-phenylethyl)-1,2-dihydrobenzo[cd]indole-5-carboxamide (Compound 110)

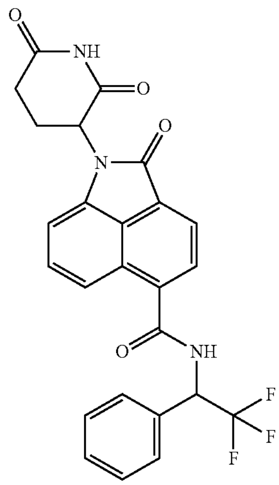 [SMILES: O=C1CCC(N2C(=O)c3ccc(C(=O)NC(c4ccccc4)C(F)(F)F)c4cccc2c34)C(=O)N1]

LC-MS ($ES^+$): m/z 482 $[M+H]^+$.

$^1H$ NMR (400 MHz, DMSO-$d_6$) δ 11.15 (br.s, 1H), 10.06 (d, J=8 Hz, 1H), 8.19 (d, J=8 Hz, 1H), 7.99 (d, J=8 Hz, 1H), 7.71 (d, J=8 Hz, 3H), 7.59 (t, J=8 Hz, 1H), 7.46 (d, J=8 Hz, 3H), 7.22 (d, J=8 Hz, 1H), 6.15 (t, J=8 Hz, 1H), 5.46 (d, J=8 Hz, 1H), 2.95-2.92 (m, 1H), 2.82-2.73 (m, 1H), 2.66 (d, J=8 Hz, 1H), 2.12-2.08 (m, 1H).

1-(2,6-dioxopiperidin-3-yl)-N-(2-methyl-1-phenylpropyl)-2-oxo-1,2-dihydrobenzo[cd]indole-5-carboxamide (Compound 111)

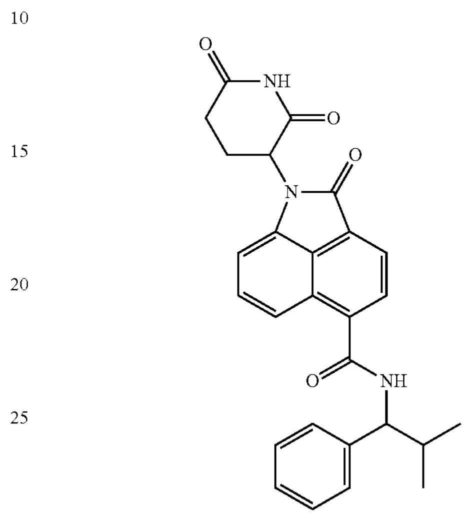

LC-MS ($ES^+$): m/z 456 $[M+H]^+$.

$^1H$ NMR (400 MHz, DMSO-$d_6$) δ 11.12 (s, 1H), 9.14 (d, J=8 Hz, 1H), 8.16 (d, J=8 Hz, 1H), 7.91 (q, J=4 Hz, 1H), 7.70 (t, J=8 Hz, 1H), 7.53 (t, J=8 Hz, 1H), 7.43 (d, J=8 Hz, 1H), 7.36 (t, J=8 Hz, 1H), 7.27 (d, J=8 Hz, 1H), 7.18 (d, J=8 Hz, 1H), 5.46 (q, J=8 Hz, 1H), 4.82 (t, J=8 Hz, 1H), 2.99-2.90 (m, 1H), 2.81-2.71 (m, 1H), 2.66 (d, J=16 Hz, 1H), 2.13-2.08 (m, 2H), 1.05 (d, J=8 Hz, 3H), 0.78 (d, J=8 Hz, 3H).

1-(2,6-dioxopiperidin-3-yl)-N-isopropyl-2-oxo-1,2-dihydrobenzo[cd]indole-5-carboxamide (Compound 112)

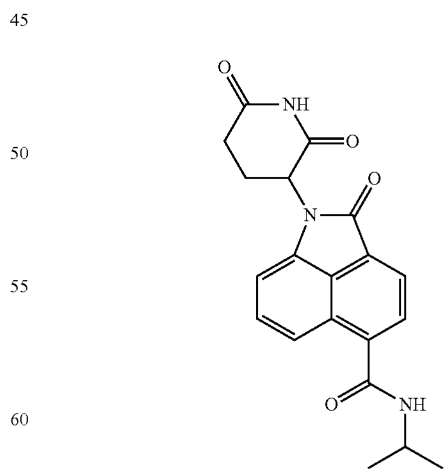

LC-MS ($ES^+$): m/z 366 $[M+H]^+$.

$^1H$ NMR (400 MHz, DMSO-$d_6$) δ 11.11 (br.s, 1H), 8.59 (d, J=8 Hz, 1H), 8.13 (d, J=8 Hz, 1H), 7.92 (d, J=8 Hz, 1H), 7.86 (d, J=8 Hz, 1H), 7.57 (t, J=8 Hz, 1H), 7.19 (d, J=8 Hz,

1H), 5.49-5.44 (m, 1H), 4.21-4.15 (m, 1H), 2.98-2.95 (m, 1H), 2.82-2.63 (m, 2H), 2.13-2.10 (m, 1H), 1.23-1.15 (m, 6H).

Example 46: Synthesis of 1-(2,6-dioxopiperidin-3-yl)-2-oxo-1,2-dihydrobenzo[cd]indole-5-carboxylic acid (Compound 113)

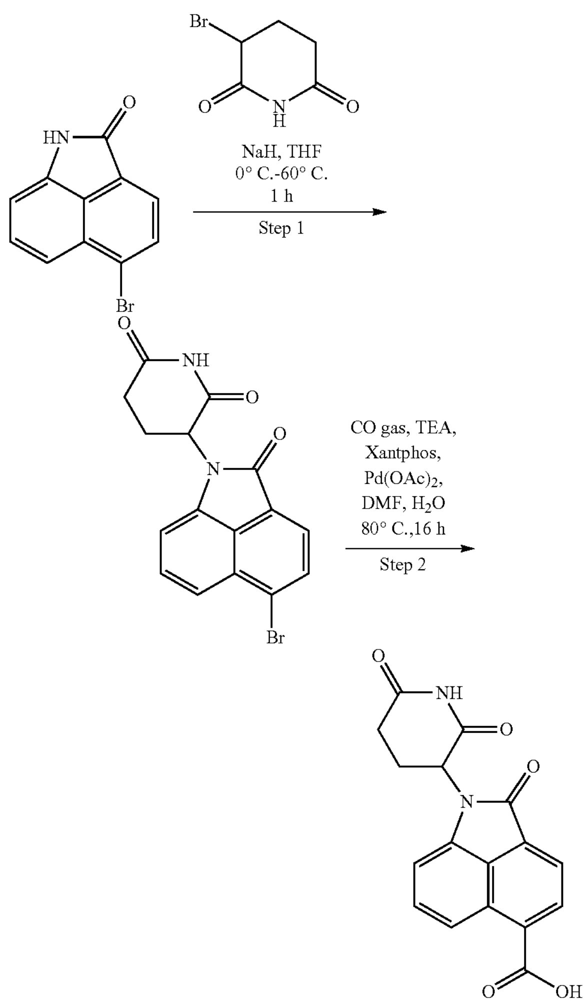

Step 1: To an ice-cold solution of 5-bromo-1H-benzo[cd]indol-2-one (5 g, 20.16 mmol) in THF (70 mL) was added NaH (60% dispersion in mineral oil) (23.17 g, 604.66 mmol) and the reaction was stirred at room temperature for 15 minutes. The reaction was then cooled to 0° C. and 3-bromo-glutarimide (27.09 g, 141.09 mmol) was added slowly to the mixture and it was heated to reflux for 1 hour. After completion, the reaction mixture was diluted with ethyl acetate and poured into ice-cold water. The separated organic layer was dried over anhydrous sodium sulfate, filtered and concentrated to give a residue which was purified by combi-flash column chromatography (45% EtOAc in DCM) to afford 3-(5-bromo-2-oxo-benzo[cd]indol-1-yl)piperidine-2,6-dione (6 g, 15.87 mmol, 79% yield) as a light yellow solid. LC-MS (ES*): m/z 359 $[M+H]^+$.

Step 2: To a solution of 3-(5-bromo-2-oxo-benzo[cd]indol-1-yl)piperidine-2,6-dione (300 mg, 835.25 μmol) in DMF-H2O mixture (25:1, 5.2 mL) was added triethylamine (127.34 mg, 1.26 mmol, 175.40 μL) and the resulting solution was degassed and back-filled with argon for 5 minutes. Then Xantphos (83.30 mg, 143.97 μmol) and $Pd(OAc)_2$ (28.25 mg, 125.84 μmol) were added and this mixture was degassed and back-filled with argon for 2 minutes. The reaction mixture was purged with a carbon monoxide filled balloon and heated at 80° C. for 16 hours under this atmosphere. After completion of the reaction, the reaction mixture was purified by reverse-phase prep purification to afford 1-(2,6-dioxo-3-piperidyl)-2-oxo-benzo[cd]indole-5-carboxylic acid (Compound 113, 20.29 mg, 62.57 mol, 7% yield). LC-MS ($ES^+$): m/z 325 $[M+H]^+$. $^1H$ NMR (400 MHz, DMSO-$d_6$) δ 11.15 (s, 1H), 8.40 (d, J=8 Hz, 2H), 8.14 (d, J=8 Hz, 1H), 7.60 (q, J=4 Hz, 1H), 7.20 (d, J=8 Hz, 1H), 5.47 (t, J=8 Hz, 1H), 2.93 (d, J=12 Hz, 1H), 2.76 (d, J=12 Hz, 1H), 2.65 (d, J=16 Hz, 1H), 2.11 (d, J=8 Hz, 1H).

Example 47: Synthesis of 3-(5-fluoro-2-oxo-benzo[cd]indol-1-yl)piperidine-2,6-dione

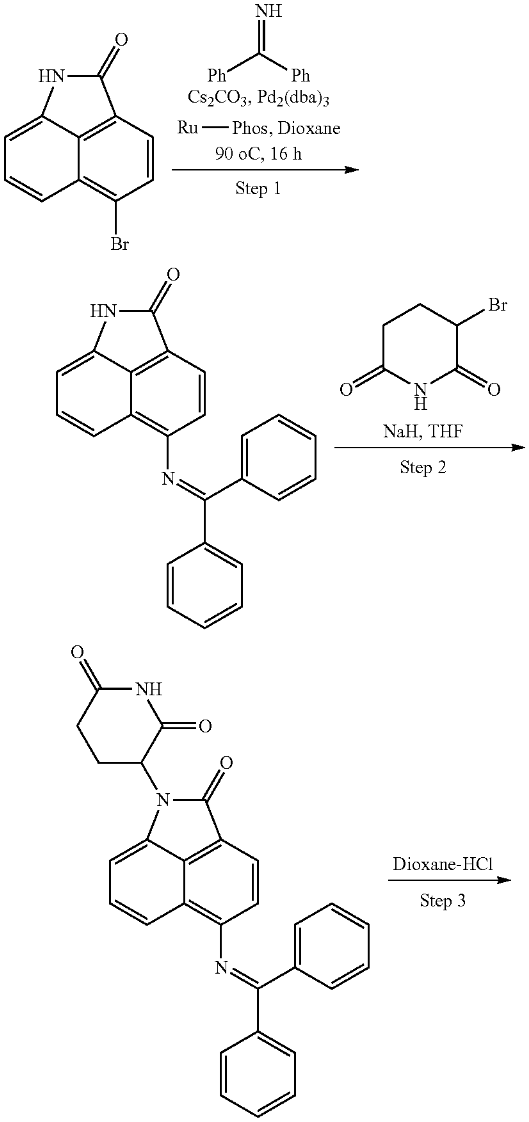

-continued

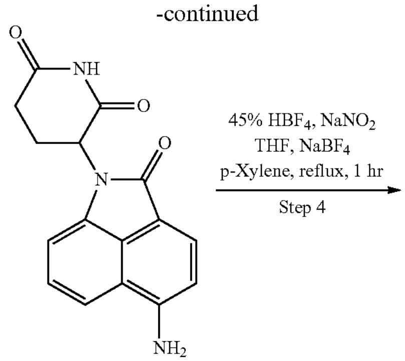

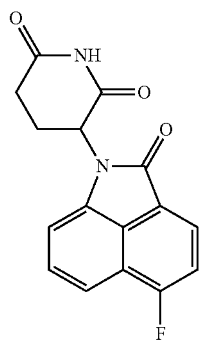

Step 1: To a stirred solution of 5-bromo-1H-benzo[cd]indol-2-one (25 g, 100.78 mmol), diphenylmethanimine (36.53 g, 201.55 mmol, 33.82 mL) in toluene (1500 mL) was added sodium tert-butoxide (29.05 g, 302.33 mmol) and the resulting reaction mixture was degassed with argon for 10 minutes. Then (5-diphenylphosphanyl-9,9-dimethyl-xanthen-4-yl)-diphenyl-phosphane (11.66 g, 20.16 mmol) and (1E,4E)-1,5-diphenylpenta-1,4-dien-3-one; palladium (9.23 g, 10.08 mmol) were added and the reaction mixture was heated at 80° C. for 16 hours. After completion, the reaction mixture was diluted with cold water and extracted twice with ethyl acetate. The organic layer was then dried over anhydrous sodium sulphate and concentrated under reduced pressure. The obtained crude product was purified by flash column chromatography (100-200 mesh silica gel, 0-20% EtOAc in Hexane) to afford 5-(benzhydrylideneamino)-1H-benzo[cd]indol-2-one (20 g, 42% yield) as a yellow solid. LC-MS ($ES^+$): m/z 349.4 $[M+H]^+$.

Step 2: To a stirred suspension of 5-(benzhydrylideneamino)-1H-benzo[cd]indol-2-one (10 g, 28.70 mmol) in THF (100 mL) was added sodium hydride (60% dispersion in mineral oil) (16.50 g, 430.54 mmol) portionwise at 0° C. Then the reaction mixture was slowly warmed up to room temperature and stirred for 1 hour before being cooled to 0° C. and adding 3-bromo-glutarimide (33.07 g, 172.22 mmol) portionwise. The reaction mixture was warmed to room temperature and heated at 70° C. for 4 hours. After completion of the reaction, the reaction mixture was slowly poured into crushed ice. The aqueous layer was extracted with ethyl acetate (3×) and the combined organic layer was separated, dried over sodium sulfate, and concentrated under reduced pressure. The crude product was triturated with diethyl ether and pentane to afford the desired compound 3-[5-(benzhydrylideneamino)-2-oxo-benzo[cd]indol-1-yl]piperidine-2,6-dione (10 g, 76% yield) as a yellow solid. LC-MS ($ES^+$): m/z 460.0 $[M+H]^+$.

Step 3: To a stirred solution of 3-[5-(benzhydrylideneamino)-2-oxo-benzo[cd]indol-1-yl]piperidine-2,6-dione (10 g, 21.76 mmol) in THF (100 mL) was added 15 mL aqueous HCl (2N) and the resulting reaction mixture was stirred at room temperature for 2 hours. After completion, the reaction mixture was evaporated to dryness and dioxane-HCl (20 mL) was added and stirred for 30 minutes. The mixture was concentrated in vacuo and the residue was triturated with ether, basified with saturated sodium bicarbonate solution, and washed with 30% EtOAc in Hexane. The solid was filtered and dried under vacuum to afford 3-(5-amino-2-oxo-benzo[cd]indol-1-yl)piperidine-2,6-dione (5.5 g, 86% yield) as a yellow solid. LC-MS ($ES^+$): m/z 296.2 $[M+H]^+$.

Step 4: To a stirred solution of 3-(5-amino-2-oxo-benzo[cd]indol-1-yl)piperidine-2,6-dione (4 g, 13.55 mmol) in THF (8 mL) was added 48% trifluoroborane hydrofluoride (1.19 g, 13.55 mmol, 40 mL) at 0° C. followed by a solution of sodium nitrite (2.80 g, 40.64 mmol, 1.29 mL) in water (4 mL). The reaction mixture was stirred at that temperature for 1 hour before the addition of sodium tetrafluoroborate (7.44 g, 67.73 mmol). The resulting reaction mixture was then warmed up to room temperature. The solid precipitation was filtered, washed with diethyl ether, and dried under high vacuum to afford the corresponding diazonium salt as a brown solid. The resulting solid was then suspended in p-xylene (50 mL) and the mixture was heated at 140° C. for 2 hours. After completion of the reaction, the reaction mixture was cooled to room temperature and concentrated under reduced pressure. The crude product was purified by column chromatography (100-200 mash silica gel, 0-15% EtOAc in Hexane) to afford 3-(5-fluoro-2-oxo-benzo[cd]indol-1-yl)piperidine-2,6-dione (2.2 g, 53% yield) as a yellow solid. LC-MS ($ES^+$): m/z 299.0 $[M+H]^+$.

Example 48: Synthesis of 3-[5-(4-methylpiperazin-1-yl)-2-oxo-benzo[cd]indol-1-yl]piperidine-2,6-dione (Compound 114)

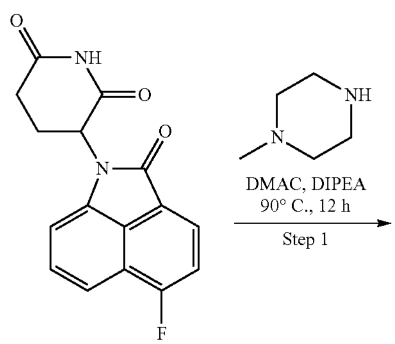

-continued

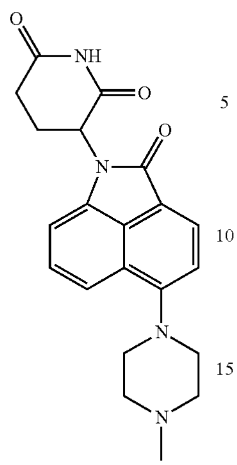

To the stirred solution of 1-methylpiperazine (20.15 mg, 201.16 μmol, 22.31 μL) (20.15 mg, 201.16 μmol, 22.31 μL) in HPLC grade DMAC (0.5 mL), DIPEA (21.67 mg, 167.63 μmol, 29.20 μL) was added and stirred for 30 min followed by the addition of 3-(5-fluoro-2-oxo-benzo[cd]indol-1-yl) piperidine-2,6-dione (50 mg, 167.63 μmol). Resulting solution was further heated at 90° C. for 12 hr. After completion of reaction, ice cooled water (10 mL) was added to the reaction mixture and extracted with ethyl acetate (3×25 mL). The organic layer was separated, dried over anhydrous Sodium sulfate, filtered and evaporated under reduced pressure to get crude residue which was purified by PREP-TLC to afford 3-[5-(4-methylpiperazin-1-yl)-2-oxo-benzo[cd]indol-1-yl]piperidine-2,6-dione (Compound 114, 37 mg, 97.77 μmol, 58% yield) as white solid. LC-MS ($ES^+$): m/z 379.34 $[M+H]^+$. $^1H$ NMR (400 MHz, DMSO-$d_6$) δ 11.09 (s, 1H), 7.95 (d, J=7.72 Hz, 1H), 7.60 (d, J=8.64 Hz, 1H), 7.43 (t, J=7.36 Hz, 1H), 7.16 (d, J=7.72 Hz, 1H), 7.07 (d, J=7.12 Hz, 1H), 5.40 (dd, J=12.48, 5.12 Hz, 1H), 2.96-2.93 (m, 1H), 2.78-2.71 (m, 1H), 2.62 (br s, 5H), 2.49 (br s, 4H), 2.18 (s, 3H), 1.98 (m, 1H).

Compound 115 and Compound 116 were prepared substantially following the synthesis of Compound 114 in Example 48 using the appropriate amine starting material.

3-[5-(4-benzylpiperazin-1-yl)-2-oxo-benzo[cd]indol-1-yl]piperidine-2,6-dione (Compound 115)

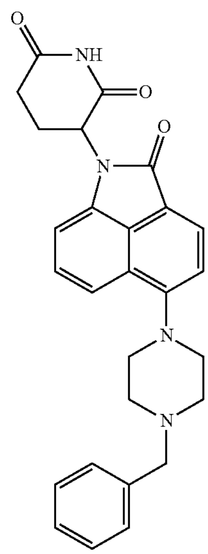 [SMILES: O=C1CCC(N2C(=O)c3ccc(N4CCN(Cc5ccccc5)CC4)c4cccc2c34)C(=O)N1]

LC-MS ($ES^+$): m/z 455.36 $[M+H]^+$.

$^1H$ NMR (400 MHz, DMSO-$d_6$) δ 11.08 (s, 1H), 7.95 (d, J=7.68 Hz, 1H), 7.60 (d, J=8.6 Hz, 1H), 7.42 (t, J=7.64 Hz, 1H), 7.36-7.33 (m, 3H), 7.29-7.28 (m, 2H), 7.16 (d, J=7.76 Hz, 1H), 7.07 (d, J=7.16 Hz, 1H), 5.40 (dd, J=12.44, 4.64 Hz, 1H), 3.60 (s, 2H), 3.38-3.31 (br, 4H), 2.98-2.94 (m, 1H), 2.78-2.71 (m, 1H), 2.67 (br, 5H), 2.06-2.03 (m, 1H).

3-[5-[(1-benzylpyrrolidin-3-yl)-methyl-amino]-2-oxo-benzo[cd]indol-1-yl]piperidine-2,6-dione (Compound 116)

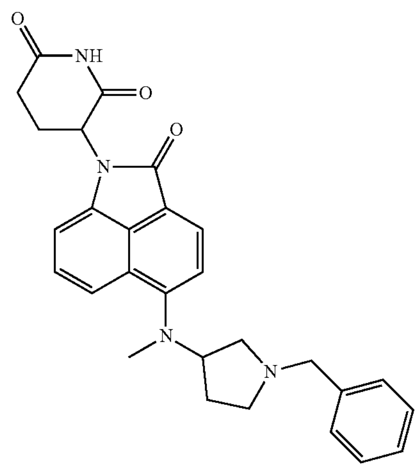 [SMILES: CN(c1ccc2c3c(cccc13)N(C1CCC(=O)NC1=O)C2=O)C1CCN(Cc2ccccc2)C1]

LC-MS ($ES^+$): m/z 469.3 $[M+H]^+$.

$^1H$ NMR (400 MHz, DMSO-$d_6$) δ 11.08 (s, 1H), 7.95 (d, J=7.68 Hz, 1H), 7.60 (d, J=8.6 Hz, 1H), 7.42 (t, J=7.64 Hz, 1H), 7.36-7.33 (m, 3H), 7.29-7.28 (m, 2H), 7.16 (d, J=7.76 Hz, 1H), 7.07 (d, J=7.16 Hz, 1H), 5.40 (dd, J=12.44, 4.64 Hz, 1H), 3.60 (s, 2H), 3.38-3.31 (br, 4H), 2.98-2.94 (m, 1H), 2.78-2.71 (m, 1H), 2.67 (br, 5H), 2.06-2.03 (m, 1H).

Example 49: Synthesis of 3-[5-[(1R)-2-[3-(3-fluorophenoxy)azetidin-1-yl]cyclohexoxy]-2-oxo-benzo[cd]indol-1-yl]piperidine-2,6-dione (Compound 117)

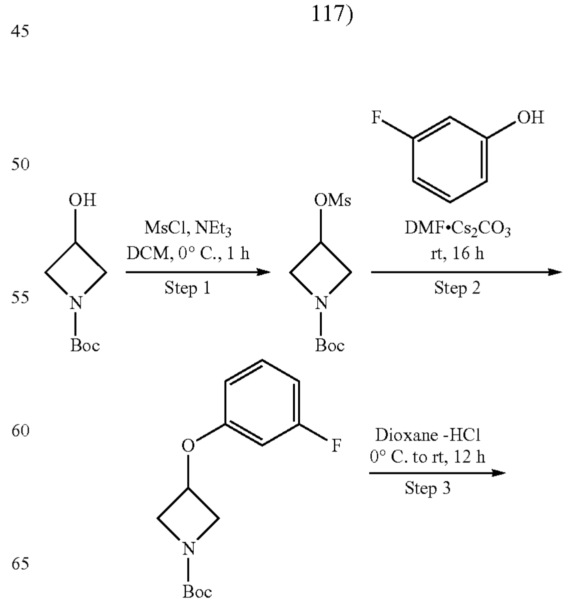

-continued

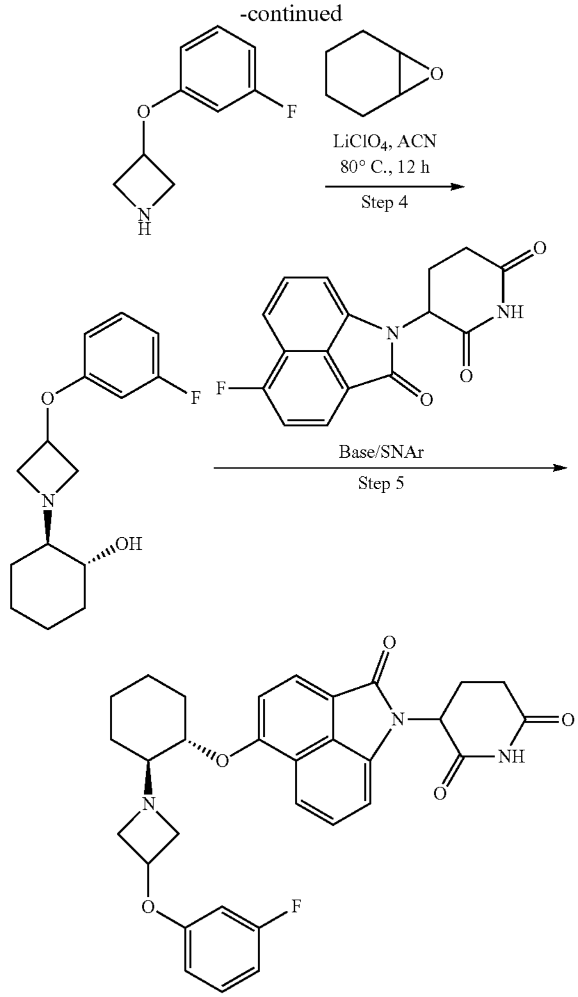

Step 1: To a flame-dried 100 mL round bottom flask under argon atmosphere, tert-butyl 3-hydroxyazetidine-1-carboxylate (3 g, 17.32 mmol) was dissolved in dry DCM (4 mL) and cooled to 0° C. To this chilled solution, triethylamine (2.63 g, 25.98 mmol, 3.62 mL) was added dropwise and the mixture was stirred at the same temperature for 30 mins. Then methanesulfonyl chloride (2.38 g, 20.78 mmol, 1.61 mL) was added via syringe and the resulting reaction mixture was stirred for another 16 hours at room temperature. After completion, the reaction mixture was diluted with DCM (25 mL) and washed with saturated sodium bicarbonate solution and brine solution. The organic phase was separated, dried over sodium sulfate, filtered and concentrated under reduced pressure to obtain tert-butyl 3-methylsulfonyloxyazetidine-1-carboxylate (3.5 g, 11.84 mmol, 68% yield) which was used for the next step without any purification. $^1$H NMR (400 MHz, DMSO-$d_6$) δ 5.27-5.22 (m, 1H), 4.23-4.19 (m, 2H), 3.93-3.90 (m, 2H), 3.24 (s, 3H), 1.36 (s, 9H).

Step 2: To a well stirred solution of 3-fluorophenol (807.88 mg, 7.21 mmol, 651.52 μL) in HPLC grade DMF (10 mL) was added cesium carbonate (3.20 g, 9.83 mmol) at room temperature. After stirring at this temperature for 20 minutes, tert-butyl 3-methylsulfonyloxyazetidine-1-carboxylate (2 g, 6.55 mmol) was added and the reaction was stirred overnight. After completion, the reaction mixture was diluted with ethyl acetate (30 mL) and poured into ice-water (25 mL). The organic phase was washed with brine solution and separated, dried over anhydrous sodium sulfate, filtered and concentrated under reduced pressure to give the crude product which was purified by flash column chromatography to afford tert-butyl 3-(3-fluorophenoxy)azetidine-1-carboxylate (1.6 g, 4.01 mmol, 61% yield). LC-MS (ES$^+$): m/z 212.2 [M−tBu+H]$^+$.

Step 3: To tert-butyl 3-(3-fluorophenoxy)azetidine-1-carboxylate (1.5 g, 5.61 mmol) was added 4 M dioxane-HCl (14.03 mL) at 0° C. After stirring for 30 minutes at this temperature, the reaction mixture was allowed to warm up to room temperature slowly and stirred for another 12 hours. After completion, the volatiles were removed under reduced pressure to yield a semi-solid, which was triturated with pentane and dried under vacuum to afford 3-(3-fluorophenoxy)azetidine hydrochloride (1 g, 2.46 mmol, 44% yield) as a yellowish-white solid which was used for the next step reaction without further purification. LC-MS (ES$^+$): m/z 168.22 [M+H]$^+$.

Step 4: To a well stirred solution of 7-oxabicyclo[4.1.0]heptane (616.40 mg, 6.28 mmol) in HPLC grade acetonitrile (10 mL) was added lithium perchlorate (222.73 mg, 2.09 mmol) at room temperature. After stirring for 10 minutes, 3-(3-fluorophenoxy)azetidine (700 mg, 4.19 mmol, 2.89 mL) was added and the resulting mixture was heated at 80° C. overnight. After completion, the solvent was removed under reduced pressure to give a crude residue which was then diluted with ethyl acetate (25 mL) and washed with water and brine. The organic phase was separated, dried over anhydrous sodium sulfate, filtered and concentrated under reduced pressure. The crude product was triturated with pentane and dried under vacuum to afford 2-[[3-(3-fluorophenoxy)cyclobutyl]amino]cyclohexanol (900 mg, 2.90 mmol, 69% yield) as a yellow solid which was used for the next step without further purification. LC-MS (ES$^+$): m/z 266.19 [M+H]$^+$.

Step 5: To a cooled solution of (1R)-2-[3-(3-fluorophenoxy)azetidin-1-yl]cyclohexanol (80 mg, 301.52 μmol) in dry THF (5 mL), sodium hydride (60% dispersion in mineral oil) (115.53 mg, 3.02 mmol) was added portionwise, maintaining the temp <5° C. The resulting mixture was stirred at room temperature for 15 minutes. The reaction mixture was cooled to 0° C. and 3-(5-fluoro-2-oxo-benzo[cd]indol-1-yl)piperidine-2,6-dione (89.93 mg, 301.52 μmol) was added portionwise before it was heated at 70° C. for 1 hour. After complete consumption of the starting material, the reaction mixture was cooled to 0° C. and quenched with ice-cold water (10 mL). The aqueous layer was extracted with ethyl acetate (3×50 mL). The combined organics was separated, dried over anhydrous sodium sulfate, and concentrated under reduced pressure. The crude product was purified by PREP-TLC to afford 3-[5-[(1R)-2-[3-(3-fluorophenoxy)azetidin-1-yl]cyclohexoxy]-2-oxo-benzo[cd]indol-1-yl]piperidine-2,6-dione (Compound 117, 27 mg, 49.24 μmol, 16% yield) as yellow solid. LC-MS (ES$^+$): m/z 544.36 [M+H]$^+$. $^1$H NMR (400 MHz, DMSO-$d_6$) δ 11.10 (s, 1H), 8.02 (d, J=7.88 Hz, 1H), 7.66 (d, J=8.4 Hz, 1H), 7.45 (t, J=7.28 Hz, 1H), 7.32 (d, J=8.2 Hz, 1H), 7.28-7.24 (m, 1H), 7.12 (d, J=6.92 Hz, 1H), 6.73 (t, J=8.08 Hz, 1H), 6.66-6.62 (m, 2H), 5.42-5.40 (m, 1H), 4.72-4.71 (m, 1H), 4.59 (br, 1H), 3.79 (br m, 1H), 3.70 (m, 1H), 3.28-3.07 (m, 1H), 2.94-2.91 (m, 1H), 2.75-2.61 (m, 3H), 2.08 (br m, 2H), 1.90-1.88 (m, 1H), 1.69 (m, 2H), 1.45 (m, 2H), 1.22-1.17 (m, 3H).

Example 50: Synthesis of 3-[2-oxo-5-[[(1S,2S)-2-(isopropylamino)cyclohexyl]amino]benzo[cd]indol-1-yl]piperidine-2,6-dione (Compound 118)

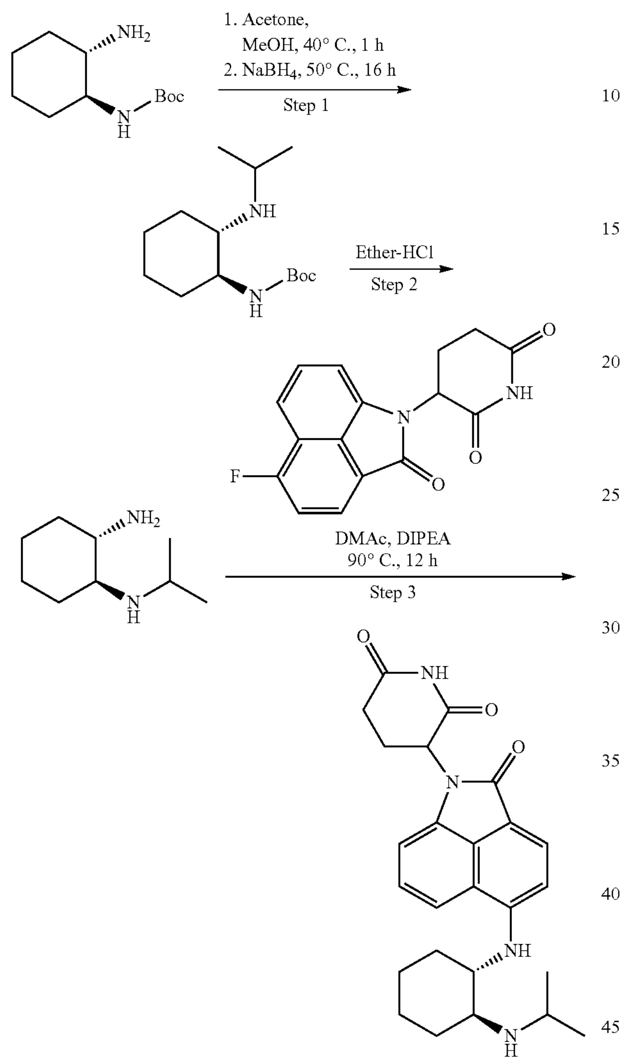

Step 1: To a stirred solution of tert-butyl N-[(1S,2S)-2-aminocyclohexyl]carbamate (0.25 g, 1.17 mmol) and acetone (203.26 mg, 3.50 mmol, 256.97 μL) in methanol (2.5 mL), sodium borohydride (44.13 mg, 1.17 mmol, 41.25 μL) was added at 0° C. Then the reaction mixture was allowed to warm up to ambient temperature and stirred for 16 hours. After completion of the reaction, the reaction mixture was quenched with saturated ammonium chloride solution and the volatiles were evaporated under reduced pressure. The aqueous layer was extracted with ethyl acetate. The organic layer was separated, washed with saturated brine solution, dried over anhydrous sodium sulfate, filtered, and concentrated under reduced pressure to afford tert-butyl N-[(1S,2S)-2-(isopropylamino)cyclohexyl] carbamate (0.2 g, 741.08 mol, 64% yield) as a colorless liquid. LC-MS ($ES^+$): m/z 257.5 $[M+H]^+$.

Step 2: Ether-HCl (2M, 4 mL) was added to tert-butyl N-[(1S,2S)-2-(isopropylamino)cyclohexyl]carbamate (200 mg, 780.08 μmol) at 0° C. under argon atmosphere. The reaction mixture was then warmed up to room temperature and stirred for 16 hours. The reaction mixture was concentrated under reduced pressure, co-distilled with DCM and n-pentane, then dried under vacuum to afford (1S,2S)—N2-isopropylcyclohexane-1,2-diamine hydrochloride (140 mg, 653.77 μmol, 84% yield) as a colorless gum. LC-MS ($ES^+$): m/z 157.0 $[M+H]^+$.

Step 3: To a stirred solution of (1S,2S)—N2-isopropylcyclohexane-1,2-diamine (140 mg, 895.90 μmol) in DMAc (5 mL) was added DIPEA (347.37 mg, 2.69 mmol, 468.15 μL) followed by 3-(5-fluoro-2-oxo-benzo[cd]indol-1-yl)piperidine-2,6-dione (267.22 mg, 895.90 μmol) and the resulting mixture was heated at 90° C. for 12 hours. After completion, the reaction mixture was purified by reverse phase prep-HPLC to afford 3-[2-oxo-5-[[(1S,2S)-2-(isopropylamino)cyclohexyl]amino]benzo[cd]indol-1-yl]piperidine-2,6-dione (Compound 118, 4.38 mg, 9.77 mol, 1% yield). LC-MS ($ES^+$): m/z 435.35 $[M+H]^+$. $^1$H NMR (400 MHz, DMSO-$d_6$) δ 11.05 (s, 1H), 8.32 (br.s, 1H), 7.88 (d, J=8.0 Hz, 1H), 7.82 (d, J=8.6 Hz, 1H), 7.40 (t, J=7.4 Hz, 1H), 7.10-7.04 (m, 2H), 6.88 (d, J=8.0 Hz, 1H), 5.39-5.35 (m, 1H), 3.78 (br.s, 1H), 3.55 (br.s, 1H), 3.33 (br.s, 1H), 2.97-2.90 (m, 1H), 2.79-2.61 (m, 3H), 2.24 (d, J=10.2 Hz, 1H), 2.12 (d, J=11.4 Hz, 1H), 2.07-2.00 (m, 1H), 1.83 (d, J=11.0 Hz, 1H), 1.73 (d, J=10.5 Hz, 1H), 1.47-1.30 (m, 4H), 1.28-1.24 (m, 2H), 1.26 (t, J=8.0 Hz, 3H).

3-[2-oxo-5-[[(1R,2R)-2-(isopropylamino)cyclohexyl]amino]benzo[cd]indol-1-yl]piperidine-2,6-dione (Compound 119)

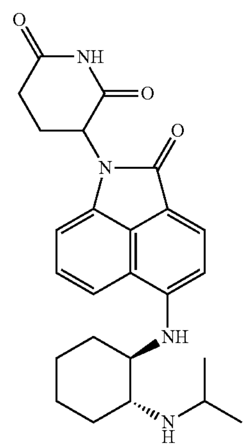 [SMILES: CC(C)N[C@@H]1CCCC[C@H]1Nc1ccc2c3c(cccc13)N(C1CCC(=O)NC1=O)C2=O]

Compound 119 was prepared substantially following the synthesis of Compound 118.

LC-MS ($ES^+$): m/z 435.35 $[M+H]^+$.

$^1$H NMR (400 MHz, DMSO-$d_6$) δ 11.05 (s, 1H), 8.32 (br.s, 1H), 7.88 (d, J=8.0 Hz, 1H), 7.82 (d, J=8.6 Hz, 1H), 7.40 (t, J=7.4 Hz, 1H), 7.10-7.04 (m, 2H), 6.88 (d, J=8.0 Hz, 1H), 5.39-5.35 (m, 1H), 3.78 (br.s, 1H), 3.55 (br.s, 1H), 3.33 (br.s, 1H), 2.97-2.90 (m, 1H), 2.79-2.61 (m, 3H), 2.24 (d, J=10.2 Hz, 1H), 2.12 (d, J=11.4 Hz, 1H), 2.07-2.00 (m, 1H), 1.83 (d, J=11.0 Hz, 1H), 1.73 (d, J=10.5 Hz, 1H), 1.47-1.30 (m, 4H), 1.28-1.24 (m, 2H), 1.26 (t, J=8.0 Hz, 3H).

Example 51: Synthesis of 3-[18-(4-benzylpiperazin-1-yl)-24-oxo-26,30-diazatricyclododeca-5,7(19),8(26),17(20),18(21)-pentaen-30-yl]piperidine-2,6-dione (Compound 120)

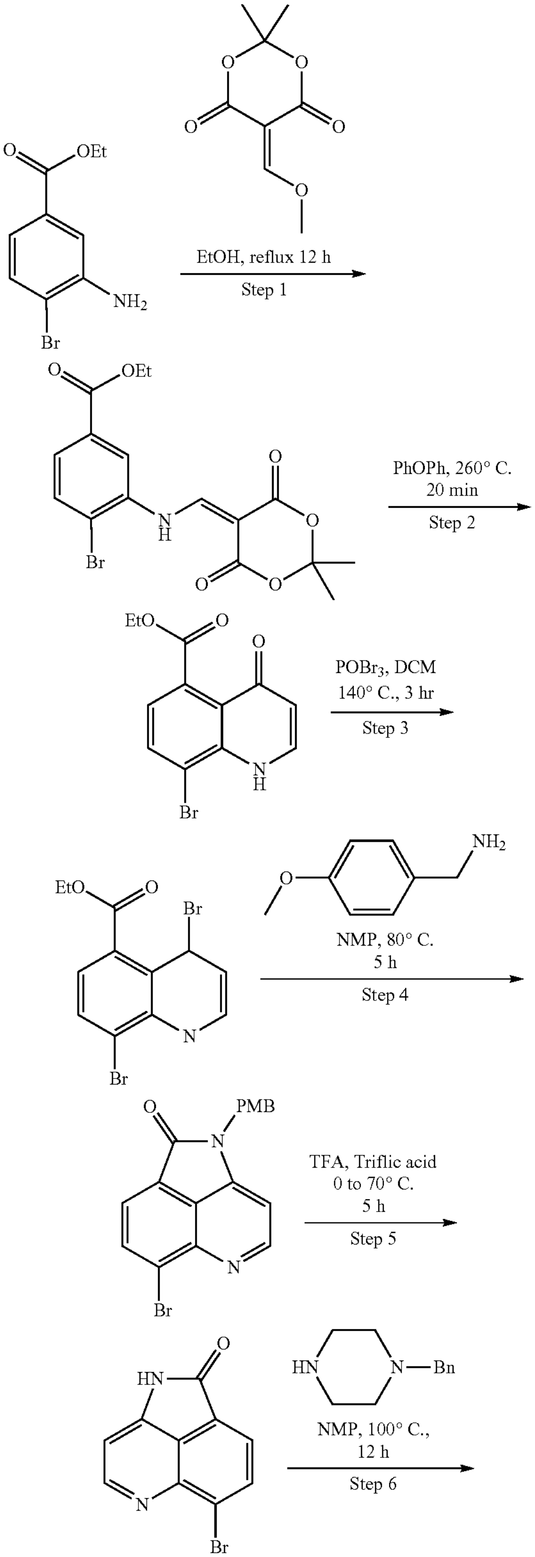

-continued

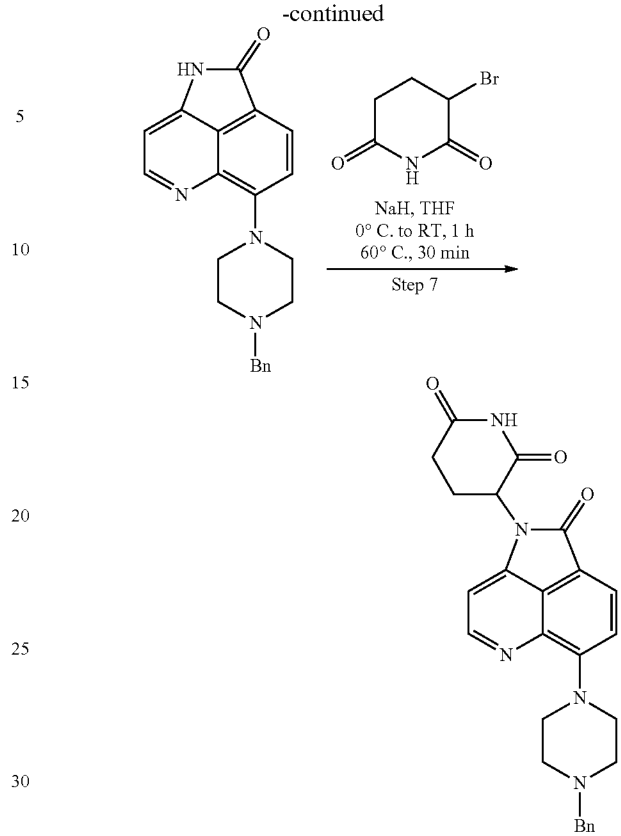

Step 1: To a well stirred solution of ethyl 3-amino-4-bromo-benzoate (20 g, 81.94 mmol) in ethanol (100 mL) was added 5-(methoxymethylene)-2,2-dimethyl-1,3-dioxane-4,6-dione (12.00 g, 64.46 mmol) and the reaction mixture was heated at 80° C. overnight. After completion, the solvent was removed under reduced pressure to obtain crude residue which was then washed with pentane followed by 50% $Et_2O$/Pentane to afford ethyl 4-bromo-3-[(2,2-dimethyl-4,6-dioxo-1,3-dioxan-5-ylidene)methylamino]benzoate (25 g, 50.23 mmol, 61% yield) as yellow solid. $^1H$ NMR (400 MHz, DMSO-$d_6$) δ 11.51 (d, J=13.8 Hz, 1H), 8.74 (t, J=7.2 Hz, 1H), 8.22 (d, J=1.16 Hz, 1H), 7.91 (d, J=8.32 Hz, 1H), 7.74-7.71 (m, 1H), 4.39-4.33 (q, 2H), 1.7 (s, 6H), 1.34 (t, J=7.08 Hz, 1H).

Step 2: Solution of ethyl 4-bromo-3-[(2,2-dimethyl-4,6-dioxo-1,3-dioxan-5-ylidene)methylamino]benzoate (20 g, 50.23 mmol) in $Ph_2O$ (40 mL) was heated at 260° C. for 20 minutes. The reaction mass was cooled to room temperature and poured into hexane. The resulting semi solid was filtered and washed with hexane, followed by 50% pentane/$Et_2O$ several time to afford ethyl 8-bromo-4-oxo-1H-quinoline-5-carboxylate (12 g, 31.61 mmol, 63% yield) which was used for the next step without further purification. LC-MS ($ES^+$): m/z 296.24 $[M+H]^+$.

Step 3: A solution of ethyl 8-bromo-4-oxo-1H-quinoline-5-carboxylate (12 g, 40.52 mmol) and phosphoryl bromide (69.71 g, 243.15 mmol, 24.72 mL) in HPLC grade DCM (25 mL) was heated at 140° C. for 3 hours. After completion, the reaction mix was diluted with DCM (200 mL) and washed with saturated $NaHCO_3$ solution followed by brine solution. The organic phase was separated, dried over anhydrous sodium sulfate, filtered, and evaporated under reduced pressure. The resulting crude mass was purified by column chromatography (hexane to 100% DCM as eluent) to give ethyl 4,8-dibromoquinoline-5-carboxylate (8.5 g, 23.68 mmol, 70% yield) as a colorless solid. LC-MS (ES$^+$): m/z 360.15 [M+H]$^+$.

Step 4: To a solution of ethyl 4,8-dibromoquinoline-5-carboxylate (5.5 g, 15.32 mmol) in HPLC grade NMP (30 mL) was added 4-methoxybenzylamine (4.20 g, 30.64 mmol, 4.00 mL) and the reaction mixture was heated at 80° C. for 5 h. After completion, the reaction was diluted with ethyl acetate (200 mL) and then washed with water and brine. The organic layer was separated, dried over anhydrous sodium sulfate, filtered and then concentrated under reduced pressure to yield a crude residue which was then purified by silica-gel column chromatography to afford 14-bromo-19-[(4-methoxyphenyl)methyl]-18,19-diazatricyclododeca-5(12),6(14),7(13),8(18),15-pentaen-17-one (4.5 g, 9.99 mmol, 65% yield) as white solid. LC-MS (ES$^+$): m/z 371.1 [M+H]$^+$.

Step 5: To the solid compound 14-bromo-19-[(4-methoxyphenyl)methyl]-18,19-diazatricyclododeca-5(12),6(14),7(13),8(18),15-pentaen-17-one (4 g, 10.83 mmol) was added TFA (10.0 mL) followed by trifluoromethanesulfonic acid (16.26 g, 108.34 mmol, 9.51 mL) at 0° C. and stirred for 30 minutes at the same temperature. The reaction mixture was further allowed to heat at 70° C. for 5 hours. After completion, the reaction was diluted with DCM (150 mL) and slowly poured into ice-cold water. The resulting solution was then neutralized with $Na_2CO_3$ solution. The organic phase was separated, dried over anhydrous sodium sulfate, filtered, and then concentrated under reduced pressure to give the crude residue which was then purified by silica gel column chromatography to get 6-bromo-10,11-diazatricyclododeca-(4),1(6),2(5),3(10),7-pentaen-9-one (2 g, 4.58 mmol, 42% yield) as white solid. LC-MS (ES$^+$): m/z 248.8 [M+H]$^+$.

Step 6: To a well stirred solution of 6-bromo-10,11-diazatricyclododeca-(4),1(6),2(5),3(10),7-pentaen-9-one (100.40 mg, 403.10 μmol) in HPLC grade NMP (250.00 μL), 1-benzylpiperazine (142.10 mg, 806.21 μmol) was added and the reaction mass was heated at 100° C. overnight in a sealed vial. After completion, the solution was cooled to room temperature and poured into ice-cold water (5 mL). The aqueous portion was extracted with ethyl acetate (3×25 mL), separated, dried over anhydrous sodium sulfate, filtered and concentrated under reduced pressure to get crude residue which was then purified by flash chromatography to obtain pure compound 17-(4-benzylpiperazin-1-yl)-21,22-diazatricyclododeca-5(15),6(17),7(16),8(21),18-pentaen-20-one (100 mg, 284.55 μmol, 71% yield) as white solid. LC-MS (ES$^+$): m/z 345.36 [M+H]$^+$.

Step 7: To a cooled solution of 17-(4-benzylpiperazin-1-yl)-21,22-diazatricyclododeca-5,7(16),8(21),15(18),17(19)-pentaen-20-one (85 mg, 246.80 μmol) in dry THF (15 mL), Sodium hydride (60% dispersion in mineral oil) (296.13 mg, 7.40 mmol) was added portion wise, maintaining the temp <5° C. After addition, the resulting mixture was stirred for 15 minutes at room temperature. Then the reaction mixture was again cooled to 0° C. and 3-bromopiperidine-2,6-dione (568.66 mg, 2.96 mmol) was added to it portion wise and the resulting solution was heated at 70° C. for 1 hour. After complete consumption of 17-(4-benzylpiperazin-1-yl)-21,22-diazatricyclododeca-5,7(16),8(21),15(18),17(19)-pentaen-20-one, the reaction mixture was cooled to 0° C. and quenched with the addition of ice-cold water (5 mL). The aqueous layer was extracted with ethyl acetate (3×50 mL). Combined organics was separated, dried over anhydrous sodium sulfate and concentrated under reduced pressure to afford crude compound which was purified by PREP TLC to afford 3-[18-(4-benzylpiperazin-1-yl)-24-oxo-26,30-diazatricyclododeca-5,7(19),8(26),17(20),18(21)-pentaen-30-yl]piperidine-2,6-dione (Compound 120, 19 mg, 38.44 μmol, 16% yield) as yellow solid. $^1$H NMR (400 MHz, DMSO-$d_6$) δ 11.11 (s, 1H), 8.65 (d, J=4.68 Hz, 1H), 7.89 (d, J=8.0 Hz, 1H), 7.36-7.35 (m, 4H), 7.27 (br m, 1H), 7.12-7.07 (m, 2H), 5.40 (dd, J=12.4, 5.28 Hz, 1H), 4.08-4.01 (m, 4H), 3.56 (s, 2H), 2.95-2.92 (m, 1H), 2.75-2.61 (m, 6H), 2.08-1.98 (m, 1H). LC-MS (ES$^+$): m/z 456.31 [M+H]$^+$.

3-[12-(4-methylpiperazin-1-yl)-18-oxo-20,24-diazatricyclododeca-1,3(13),4(20),11(14),12(15)-pentaen-24-yl]piperidine-2,6-dione (Compound 121)

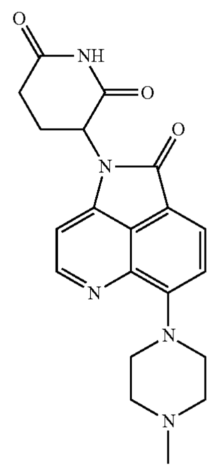 [SMILES: CN1CCN(c2ccc3c4c(ccnc24)N(C2CCC(=O)NC2=O)C3=O)CC1]

Compound 121 was prepared substantially following the synthesis of Compound 120.

LC-MS (ES$^+$): m/z 380.39 [M+H]$^+$. $^1$H NMR (400 MHz, DMSO-$d_6$) δ 11.11 (s, 1H), 8.67 (d, J=4.68 Hz, 1H), 7.90 (d, J=8.28 Hz, 1H), 7.13-7.09 (m, 2H), 5.40 (dd, J=11.84, 3.48 Hz, 1H), 3.95 (br s, 4H), 3.31 (br, 4H), 2.92-2.89 (m, 1H), 2.72-2.56 (m, 2H), 2.32 (s, 3H), 2.08-2.06 (m, 1H).

Example 52: 27-(2,6-dioxo-3-piperidyl)-20-oxo-N-(1-phenylethyl)-24,27-diazatricyclododeca-6,8(15),9(24),13(16),14(17)-pentaene-14-carboxamide (Compound 122)

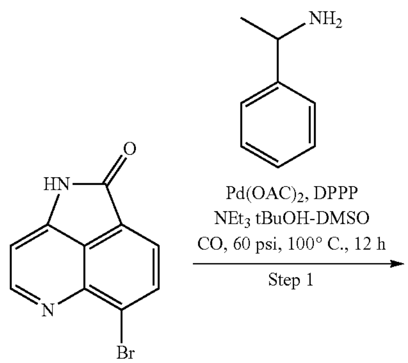

-continued

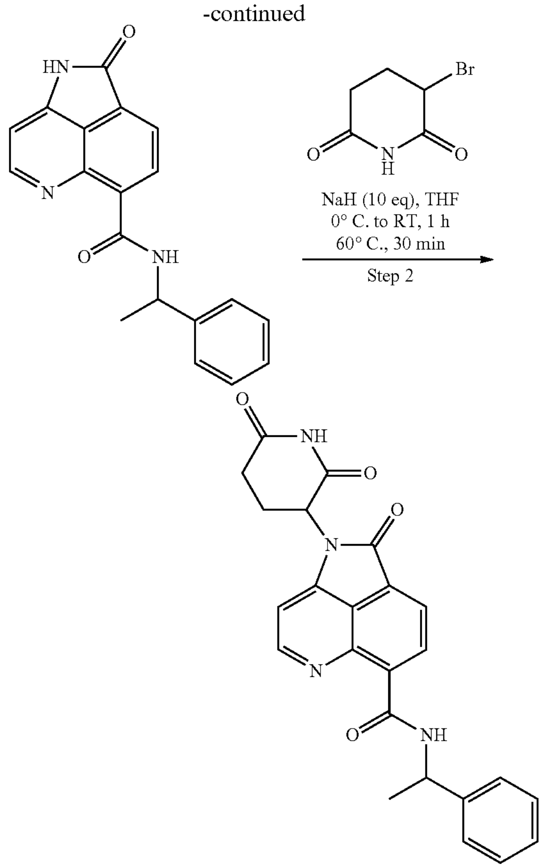

Step 1: To a stirred solution of 5-bromo-13$1^{3}-broma-10-azatricyclododeca-(4),1(5),2(8),3(13),6-pentaen-9-one (300 mg, 952.50 μmol) and 1-phenylethan-1-amine (173 mg, 1.43 mmol) in a mixed solvent of HPLC grade t-BuOH (8 mL) and DMSO (0.8 mL), 3-diphenylphosphanylpropyl (diphenyl)phosphane (58.93 mg, 142.88 μmol) was added and resulting solution was degassed with argon for 15 min. To this solution, diacetoxypalladium (32.08 mg, 142.88 μmol) was added and resulting reaction mixture was heated at 100° C. in 60 psi of CO gas for 12 hr. After completion, the reaction mixture was diluted with ethyl acetate (50 mL) and washed with water and brine solution several times. The organic phase was separated, dried over anhydrous sodium sulfate, and concentrated under reduced pressure. The crude reaction mass was purified by column chromatography (100-200 mesh silica gel, 10-15% EtOAc in hexane) to afford 16-oxo-N-(1-phenylethyl)-19,20-diazatricyclododeca-6(11),7(12),8(13),9(19),14-pentaene-12-carboxamide (40 mg, 113.44 μmol, 12% yield) as a colorless gum. LC-MS (ES+): m/z 318.3 $[M+H]^+$.

Step 2: To a cooled solution of 16-oxo-N-(1-phenylethyl)-19,20-diazatricyclododeca-6,8(13),9(19),11(14),12(15)-pentaene-12-carboxamide (40 mg, 126.05 μmol) in dry THF (5 mL), sodium hydride (60% dispersion in mineral oil) (48.30 mg, 1.26 mmol) was added portion wise, maintaining the temp <5° C. After addition, the resulting mixture was stirred for 15 minutes at room temperature. Then the reaction mixture was again cooled to 0° C. and 3-bromopiperidine-2,6-dione (121.01 mg, 630.24 μmol) was added portion wise. The resulting solution was heated at 70° C. for 1 hr. After complete consumption of 16-oxo-N-(1-phenylethyl)-19,20-diazatricyclododeca-6,8(13),9(19),11(14),12(15)-pentaene-12-carboxamide, the reaction mixture was cooled to 0° C. and quenched with the addition of ice-cold water (5 mL). The aqueous layer was extracted with ethyl acetate (3×50 mL). The combined organics was separated, dried over anhydrous sodium sulfate, and concentrated under reduced pressure. The crude product was purified by PREP TLC to afford 27-(2,6-dioxo-3-piperidyl)-20-oxo-N-(1-phenylethyl)-24,27-diazatricyclododeca-6,8(15),9(24),13(16),14(17)-pentaene-14-carboxamide (Compound 122, 21 mg, 48.04 μmol, 38% yield) as yellow solid. $^1$H NMR (400 MHz, DMSO-$d_6$) δ 11.20 (s, 1H), 11.06 (d, , J=7.76 Hz, 1H), 9.01 (d, J=4.96 Hz, 1H), 8.63 (d, J=7.32 Hz, 1H), 8.25 (d, J=7.28 Hz, 1H), 7.47-7.45 (m, 2H), 7.36 (t, J=7.28 Hz, 3H), 7.26 (t, J=7.28 Hz, 1H), 5.50 (dd, J=11.84, 3.48 Hz, 1H), 5.32-5.28 (m, 1H), 2.94 (m, 1H), 2.76-2.65 (m, 2H), 2.17-2.15 (m, 1H), 1.59 (d, J=6.88 Hz, 3H); LC-MS ($ES^+$): m/z 429.4 $[M+H]^+$.

Example 53 Synthesis of 3-[18-(1-benzyl-4-fluoro-4-piperidyl)-24-oxo-27,30-diazatricyclododeca-5(17),6(18),7(19),8(27),20-pentaen-30-yl]piperidine-2,6-dione (Compound 123)

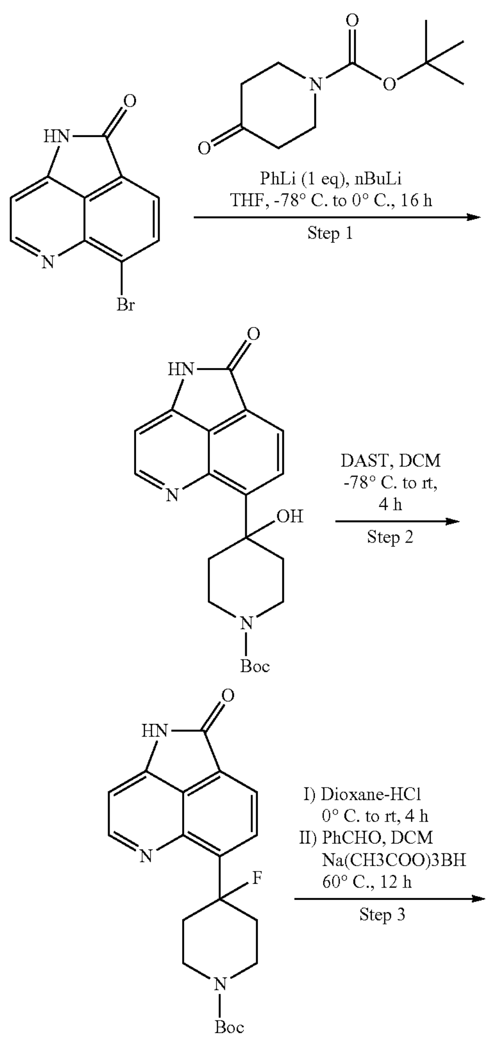

-continued

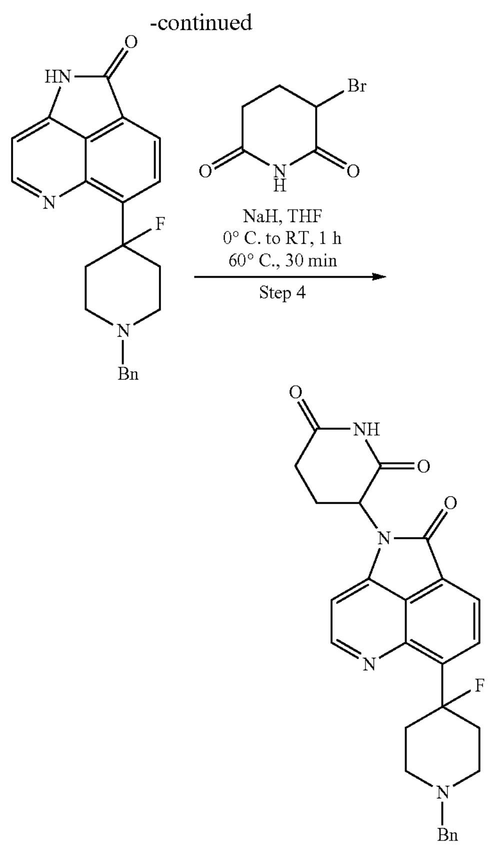

Step 1: To a flame-dried round-bottom flask under nitrogen atmosphere, 6-bromo-10,11-diazatricyclododeca-,2(5), 3(10),4(7),6(8)-pentaen-9-one (400 mg, 1.61 mmol) was dissolved in dry THF (10.0 mL) and the flask was cooled to −78° C. To this solution phenyllithium, 1.8 M in di-n-butyl ether (683.64 mg, 8.13 mmol, 844.00 μL) was added drop wise and resulting reaction mixture was stirred at same temperature for 30 minutes followed by the addition of butyllithium (1.34 M, 882.00 μL) at −78° C. After addition, the temperature was allowed to increase to −40° C. and the reaction mixture was stirred at the same temperature for an additional 30 minutes. A solution of tert-butyl 4-oxopiperidine-1-carboxylate (319.99 mg, 1.61 mmol) in dry THF (10.0 mL) was added at −78° C. and then the reaction mixture was allowed to warm to room temperature and stirred for 16 hours at room temperature. After completion of the reaction, the mixture was quenched with ammonium chloride solution and diluted with ethyl acetate (100 mL). The combined organic phase was washed with water/brine and separated, dried over anhydrous sodium sulfate and evaporated under reduced pressure to obtain the crude compound which was purified by flash chromatography using 0-5% MeOH-DCM to afford tert-butyl 4-hydroxy-4-(16-oxo-20,21-diazatricyclododeca-3,5(13),6(20),11(14),12 (15)-pentaen-12-yl)piperidine-1-carboxylate (500 mg, 947.45 μmol, 59% yield) as brown solid. LC-MS ($ES^+$): m/z 370.4 $[M+H]^+$.

Step 2: To a well stirred solution of tert-butyl 4-hydroxy-4-(16-oxo-20,21-diazatricyclododeca-3(11),4(12),5(13),6 (20),14-pentaen-12-yl)piperidine-1-carboxylate (300 g, 812.10 mmol) in anhydrous DCM (15.0 mL) was added N-ethyl-N-(trifluoro-$1^{4}-sulfanyl)ethanamine (261.80 g, 1.62 mol, 214.59 mL) drop wise at −78° C. After complete addition, the reaction mixture was allowed to warm up to room temperature and was stirred for another 4 hours. After the reaction was complete, the reaction mixture was poured slowly into ice-cold aqueous $NaHCO_3$ (sat.). The aqueous layer was extracted with DCM (3×20 mL). The organic layer was separated, dried over anhydrous sodium sulfate, concentrated, and dried under vacuum to afford crude tert-butyl 4-fluoro-4-(16-oxo-20,21-diazatricyclododeca-3(11),4(12), 5(13),6(20),14-pentaen-12-yl)piperidine-1-carboxylate (200 mg, 301.56 μmol, 4% yield) which was used in the next step without purification. LC-MS ($ES^+$): m/z 372.4 $[M+H]^+$.

Step 3: To the stirred solution of -butyl 4-fluoro-4-(16-oxo-20,21-diazatricyclododeca-3(11),4(12),5(13),6(20),14-pentaen-12-yl)piperidine-1-carboxylate (200 mg, 301.56 μmol) in dioxane (4 mL), 4 M dioxane-HCl was added (9.04 mmol, 2.0 mL) at 0° C. and the reaction mixture was stirred at room temperature for 4 h. After completion, the volatiles were removed under reduced pressure and the residue was washed with pentane/diethyl ether and dried under vacuum to afford 9-(4-fluoro-4-piperidyl)-15,17-diazatricyclododeca-(8),1(9),2(10),3(15),11-pentaen-13-one (109 mg, 401.79 μmol) which was redissolved in dry DCM (5.0 mL) and neutralized with triethylamine (pH~7). To this solution, benzaldehyde (85.28 mg, 803.57 μmol, and 82.00 μL) was added followed by acetic acid (48.25 mg, 803.57 μmol, and 45.96 μL) and the resulting mixture stirred at 60° C. for 2 hr. The reaction mixture was then cooled to room temperature and sodium; triacetoxyboranuide (425.77 mg, 2.01 mmol) was added and stirring was continued for another 12 hours. After completion, volatiles were removed under vacuum and the resulting mixture was extracted with ethyl acetate (40 mL). The organic phase was washed with water/brine and separated, dried over sodium sulfate and concentrated under reduced pressure to afford the crude product which was subjected to flash chromatography using (30-40% EtOAc/DCM as eluent) to afford 16-(1-benzyl-4-fluoro-4-piperidyl)-22,23-diazatricyclododeca-5(15),6(16),7(17),8(22), 18-pentaen-20-one (90 mg, 209.18 μmol, 52% yield) as brown gum. LC-MS ($ES^+$): m/z 362.2 $[M+H]^+$.

Step 4: To a chilled solution of 16-(1-benzyl-4-fluoro-4-piperidyl)-22,23-diazatricyclododeca-5(15),6(16),7(17),8 (22),18-pentaen-20-one (57.76 mg, 159.82 μmol) in dry THF (5 mL) was added sodium hydride (60% dispersion in mineral oil) (153.09 mg, 4.00 mmol, 60% purity) portion-wise, maintaining the temp <5° C. After addition, the resulting mixture was stirred for 15 minutes at room temperature. Then the reaction mixture was again cooled to 0° C. and 3-bromopiperidine-2,6-dione (368.24 mg, 1.92 mmol) was added to it portion wise. After complete addition, resulting solution was heated at 70° C. 1 hr. After completion, the reaction mixture was cooled to 0° C. and quenched with the addition of ice-cold water (5 mL). The aqueous layer was extracted with ethyl acetate (3×50 mL). The combined organics was separated, dried over anhydrous sodium sulfate, and concentrated under reduced pressure. The crude product was purified by PREP-TLC to afford 3-[18-(1-benzyl-4-fluoro-4-piperidyl)-24-oxo-27,30-diazatricyclododeca-5(17),6(18),7(19),8(27),20-pentaen-30-yl] piperidine-2,6-dione (Compound 123, 26.3 mg, 55.66 μmol, 35% yield). $^1H$ NMR (400 MHz, DMSO-$d_6$) δ 11.17 (s, 1H), 8.92 (d, J=4.84 Hz, 1H), 8.15 (d, J=7.36 Hz, 1H), 8.05 (d, J=7.4 Hz, 1H), 7.38-7.34 (m, 4H), 7.29-7.24 (m, 2H), 5.44 (dd, J=11.28, 3.32 Hz, 1H), 3.59 (s, 2H), 3.28-3.19 (m, 2H), 2.85-2.64 (m, 5H), 2.49-41 (m, 2H), 2.07 (m, 1H), 1.88-1.82 (m, 2H); LC-MS ($ES^+$): m/z 473.3 $[M+H]^+$.

3-[16-(1-benzyl-3-fluoro-azetidin-3-yl)-22-oxo-25,28-diazatricyclododeca-5(15),6(16),7(17),8(25),18-pentaen-28-yl]piperidine-2,6-dione (Compound 124)

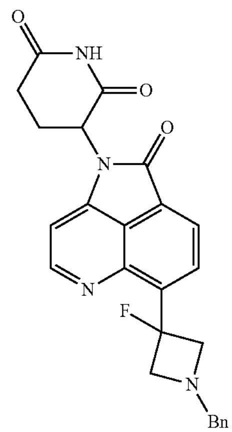 [SMILES: O=C1CCC(N2C(=O)c3ccc(C4(F)CN(Cc5ccccc5)C4)c4nccc2c34)C(=O)N1]

Compound 124 was prepared substantially following the synthesis of Compound 123.

$^1$H NMR (400 MHz, DMSO-$d_6$) δ 11.15 (s, 1H), 8.86 (d, J=4.84 Hz, 1H), 8.14 (d, J=7.2 Hz, 1H), 8.04-8.01 (m, 1H), 7.35-7.32-7.29 (m, 4H), 7.24-7.21 (m, 2H), 5.45 (dd, J=12.68, 5.16 Hz, 1H), 4.10-4.02 (m, 2H), 3.95-3.88 (m, 2H), 3.77 (s, 2H), 2.95-2.91 (m, 1H), 2.76-2.48 (m, 2H), 2.13-2.03 (m, 1H); LC-MS ($ES^+$): m/z 445.24 $[M+H]^+$.

Example 54: Synthesis of 3-[15-(1-benzylazetidin-3-yl)-23-oxo-25,28-diazatricyclododeca-5,7(17),8(25),15(19),16(18)-pentaen-28-yl]piperidine-2,6-dione (Compound 125)

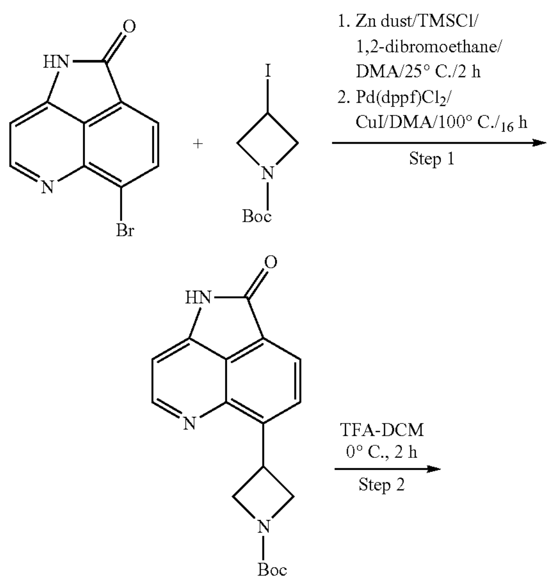

-continued

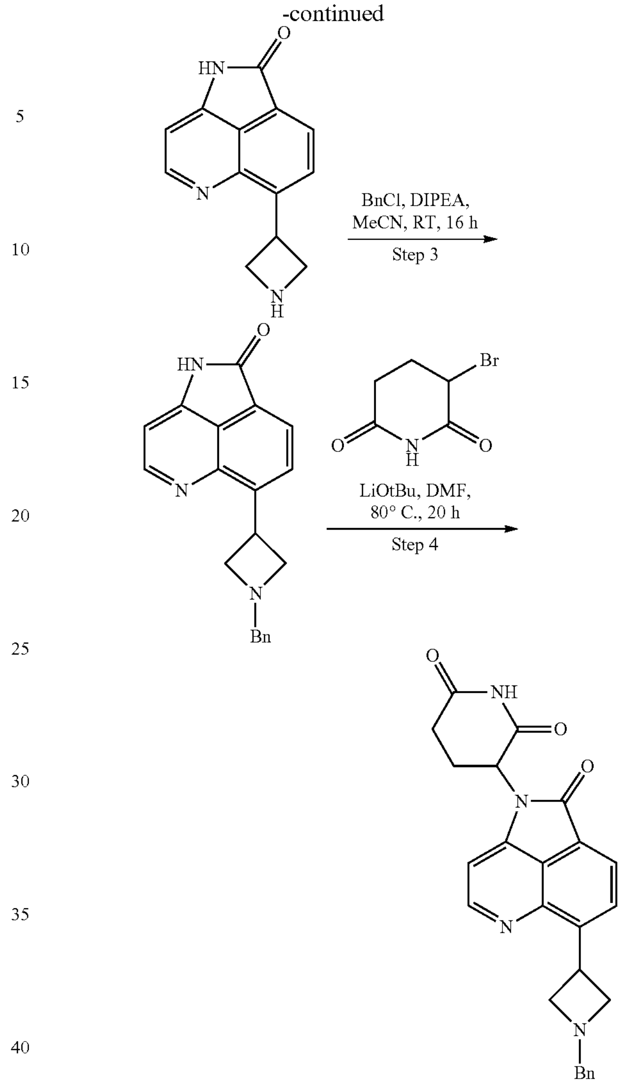

Step 1: To a stirred solution of freshly activated Zinc powder (1.60 g, 24.52 mmol) in DMAc (3 mL) were added chloro(trimethyl)silane (129.69 μL, 1.02 mmol) and 1,2-dibromoethane (123.28 μL, 1.43 mmol) at room temperature. The resulting mixture was stirred under inert atmosphere for 10 min at room temperature. To the above mixture, a solution of tert-butyl-3-iodoazetidine-1-carboxylate (5.79 g, 20.44 mmol) in DMAc (15 mL) was added dropwise at room temperature and continued to stir for 2 h at room temperature. The reaction mixture was then added into a degassed solution of 6-bromo-10,11-diazatricyclododeca-2(5),3(10),4(7),6(8)-pentaen-9-one (509 mg, 2.04 mmol), $PdCl_2$(dppf) (74.77 mg, 102.18 μmol) and CuI (19.46 mg, 102.18 μmol) in DMAc (2 mL) under inert condition. The resulting reaction mixture was heated at 100° C. for 16 hours. After completion, the reaction mixture was filtered through a short pad of celite and washed with ethyl acetate. The combined organic layer was washed with water, brine, dried over anhydrous sodium sulfate, filtered, and concentrated under reduced pressure. The crude product was purified by column chromatography (50% ethyl acetate-dichloromethane) to afford tert-butyl-3-(15-oxo-18,19-diazatricyclododeca-3,5(11),6(18),9(13),10(12)-pentaen-9-yl) azetidine-1-carboxylate (350 mg, 1.08 mmol, 53% yield). LC-MS ($ES^+$): m/z 326.2 $[M+H]^+$.

Step 2: To a stirred solution of tert-butyl-3-(15-oxo-18,19-diazatricyclododeca-3,5(11),6(18),9(13),10(12)-pentaen-9-yl)azetidine-1-carboxylate (350 mg, 1.08 mmol) in DCM (3 mL), trifluoroacetic acid (3.50 mL, 45.43 mmol) was added dropwise at 0° C. The resulting mixture was warmed to room temperature and stirred for 2 hours. After completion, the reaction mixture was concentrated under reduced pressure and triturated with n-pentane to afford 6-(azetidin-3-yl)-13,15-diazatricyclododeca-,2(8),3(13),6(10),7(9)-pentaen-12-one trifluoroacetate (200 mg, 589.50 mol, 55% yield). LC-MS ($ES^+$): m/z 226.26 $[M+H]^+$.

Step 3: To a stirred solution of 6-(azetidin-3-yl)-13,15-diazatricyclododeca-,2(8),3(13),6(10),7(9)-pentaen-12-one (200 mg, 589.50 mol) (150 mg, 442.13 μmol) in MeCN (15 mL) was added benzyl chloride (50.88 μL, 442.13 μmol) and DIPEA (154.02 μL, 884.25 μmol) at 0° C. The resulting mixture was stirred at room temperature for 16 hours. After completion, the reaction mixture was concentrated, diluted with 5% MeOH in DCM and washed with water and brine, dried over anhydrous sodium sulfate, filtered and concentrated under reduced pressure to afford 8-(1-benzylazetidin-3-yl)pyrrolo[2,3,4-de]quinolin-5(4H)-one (70 mg, 221.07 μmol, 50% yield), which was used in the next step without any further purification. LC-MS ($ES^+$): m/z 316.2 $[M+H]^+$.

Step 4: To a stirred solution of 13-(1-benzylazetidin-3-yl)-20,21-diazatricyclododeca-5,7(15),8(20),13(17),14(16)-pentaen-19-one (70 mg, 221.96 μmol) in DMF (5 mL) in a sealed tube was added lithium tert-butoxide (71.08 mg, 887.85 μmol) at 0° C. followed by 3-bromopiperidine-2,6-dione (85.24 mg, 443.93 μmol). The resulting mixture was heated at 80° C. for 20 hours. After completion, the reaction mixture was diluted with water and extracted with ethyl acetate. The combined organic layer was washed with brine, dried over anhydrous sodium sulfate, filtered, and concentrated under reduced pressure. The crude product was purified by reverse phase prep HPLC to afford 3-[15-(1-benzylazetidin-3-yl)-23-oxo-25,28-diazatricyclododeca-5,7(17),8(25),15(19),16(18)-pentaen-28-yl]piperidine-2,6-dione (Compound 125, 3.25 mg, 6.56 mol, 3% yield). LC-MS ($ES^+$): m/z 427.32 $[M+H]^+$.

Example 55: Synthesis of 3-[17-(1-benzyl-4-piperidyl)-25-oxo-27,30-diazatricyclododeca-5(17),6(18),7(19),8(27),20-pentaen-30-yl]piperidine-2,6-dione (Compound 126)

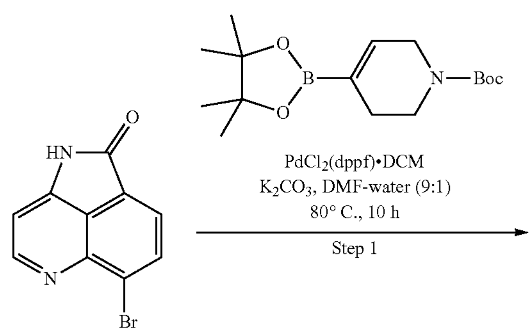

-continued

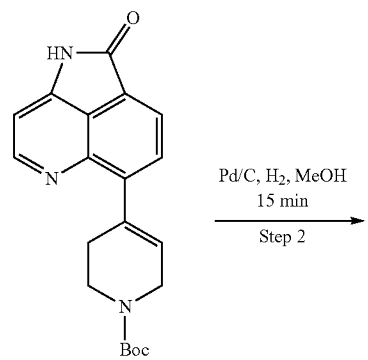

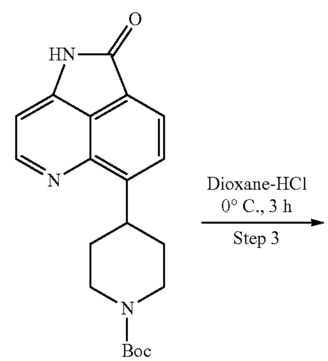

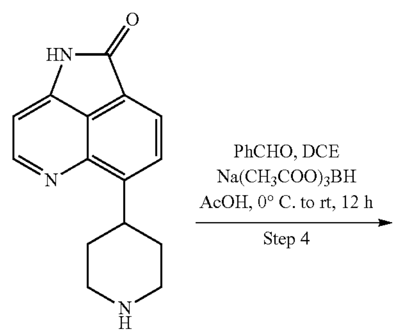

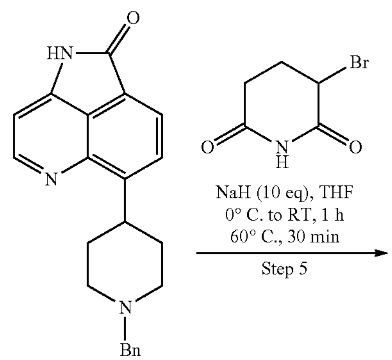

-continued

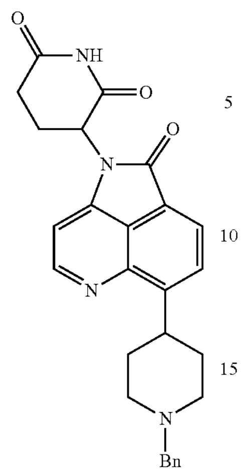

Step 1: To a degassed solution of 6-bromo-10,11-diazatricyclododeca-(4),1(6),2(5),3(10),7-pentaen-9-one (580.0 mg, 2.33 mmol) and tert-butyl 4-(4,4,5,5-tetramethyl-1,3,2-dioxaborolan-2-yl)-3,6-dihydro-2H-pyridine-1-carboxylate (1.08 g, 3.49 mmol) in dioxane-water (4:1, v/v, 10 mL), cyclopentyl(diphenyl)phosphane; dichloromethane; dichloropalladium; iron (190.17 mg, 232.87 μmol) and potassium carbonate (965.53 mg, 6.99 mmol) were added and the resulting reaction mixture was heated at 100° C. for 16 hours. After completion, the reaction mixture was concentrated in vacuo and the crude product was purified by column chromatography (10-20% EtOAc/DCM) to afford tert-butyl 4-(17-oxo-20,21-diazatricyclododeca-3(11),4(12),5(13),6(20),14-pentaen-12-yl)-3,6-dihydro-2H-pyridine-1-carboxylate (3) (600 mg, 1.67 mmol, 72% yield) as an off-white solid. LC-MS ($ES^+$): m/z 352.2 $[M+H]^+$.

Step 2: A solution of tert-butyl 4-(18-oxo-21,22-diazatricyclotrideca-3(12),4(13),5(14),6(21),15-pentaen-13-yl)-3,6-dihydro-2H-pyridine-1-carboxylate (500 mg, 1.42 mmol) in methanol (2 mL) was degassed with argon gas for 10 minutes followed by the addition of 10% Pd/C (91.74 mg, 86.20 μmol). The resulting reaction mixture was hydrogenated under balloon pressure at room temperature for 30 minutes. The reaction mixture was then filtered through a pad of celite and washed with 10% MeOH/DCM. The filtrate was evaporated under reduced pressure and the crude product was purified by flash column chromatography (50-60% EtOAc/Hexane) to obtain tert-butyl 4-(18-oxo-21,22-diazatricyclotrideca-3(12),4(13),5(14),6(21),15-pentaen-12-yl)piperidine-1-carboxylate (480 mg, 84% yield) as a brown solid. LC-MS ($ES^+$): m/z 354.34 $[M+H]^+$.

Step 3: To tert-butyl 4-(17-oxo-20,21-diazatricyclododeca-3(11),4(12),5(13),6(20),14-pentaen-11-yl)piperidine-1-carboxylate (470 mg, 1.33 mmol), 4 M dioxane-HCl (5.32 mmol, 0.5 mL) was added at 0° C. and stirred for 3 hours at room temperature. After completion of the reaction, the volatiles were removed under reduced pressure to afford 8-(4-piperidyl)-15,17-diazatricyclododeca-(8),1(9),2(10),3(15),11-pentaen-14-one (220 mg, 781.69 μmol, 59% yield) which was used in the next step without purification. LC-MS ($ES^+$): m/z 254.2 $[M+H]^+$.

Step 4: To a stirred suspension of 8-(1-chloro-4-piperidyl)-15,16-diazatricyclododeca-(8),1(9),2(10),3(15),11-pentaen-14-one (170 mg, 586.69 μmol) in DCM (5.0 mL) and methanol (2.0 mL) was added triethylamine (pH~7). Then benzaldehyde (124.52 mg, 1.17 mmol, 119.73 μL) and acetic acid (70.46 mg, 1.17 mmol, 67.11 μL) were added under nitrogen atmosphere. The resulting solution was stirred for 4 hours at room temperature before sodium; triacetoxyboranuide (621.72 mg, 2.93 mmol) was added portion wise at 0° C. The reaction mixture was heated at 60° C. for another 12 hours. After completion, the reaction mixture was diluted with 20% MeOH-DCM (30 mL) and washed with saturated sodium bicarbonate solution, water, and brine. The organic phase was separated, dried over sodium sulfate and concentrated to give the crude product which was purified by flash column chromatography (0-10% MeOH-DCM) to afford 15-(1-benzyl-4-piperidyl)-22,23-diazatricyclododeca-5(15),6(16),7(17),8(22),18-pentaen-21-one (80 mg, 151.42 μmol, 26% yield). LC-MS ($ES^+$): m/z 344.28 $[M+H]^+$.

Step 5: To a chilled solution of 15-(1-benzyl-4-piperidyl)-22,23-diazatricyclododeca-5(15),6(16),7(17),8(22),18-pentaen-21-one (80 mg mg, 232.95 μmol) in dry THF (5 mL), sodium hydride (60% dispersion in mineral oil) (89.26 mg, 2.33 mmol) was added portionwise, maintaining the temp <5° C. After addition, the resulting mixture was stirred for 15 minutes at room temperature. Then the reaction mixture was cooled to 0° C. and 3-bromopiperidine-2,6-dione (223.64 mg, 1.16 mmol) was added portion wise and the mixture was heated at 70° C. for 1 hour. After completion, the reaction mixture was cooled to 0° C. and quenched with the addition of ice-cold water (5 mL) and extracted with ethyl acetate (3×50 mL). The combined organic layers were separated, dried over anhydrous sodium sulfate and concentrated under reduced pressure. The crude product was purified by PREP-TLC to afford 3-[17-(1-benzyl-4-piperidyl)-25-oxo-27,30-diazatricyclododeca-5(17),6(18),7(19),8(27),20-pentaen-30-yl]piperidine-2,6-dione (Compound 126, 21.3 mg, 46.86 μmol, 20% yield) as yellow solid. LC-MS ($ES^+$): m/z 455.33 $[M+H]^+$. $^1H$ NMR (400 MHz, DMSO-$d_6$) δ 11.15 (s, 1H), 8.86 (d, J=4.76 Hz, 1H), 8.08 (d, J=7.32 Hz, 1H), 7.86 (d, J=7.36 Hz, 1H), 7.35-7.32 (m, 4H), 7.27-7.24 (m, 1H), 7.21 (d, J=4.8 Hz, 1H), 5.44 (dd, J=12.8, 5.08 Hz, 1H), 3.81-3.55 (m, 1H), 3.38 (s, 2H), 3.0-2.89 (m, 3H), 2.75-2.63 (m, 2H), 2.18-2.10 (m, 3H), 1.94-1.87 (m, 4H).

Example 56: Synthesis of 3-[14-[1-[(2-methoxypyrimidin-5-yl)methyl]-4-piperidyl]-24-oxo-26,31-diazatricyclododeca-1(14),2(15),3(16),4(26),18-pentaen-31-yl]piperidine-2,6-dione (Compound 127)

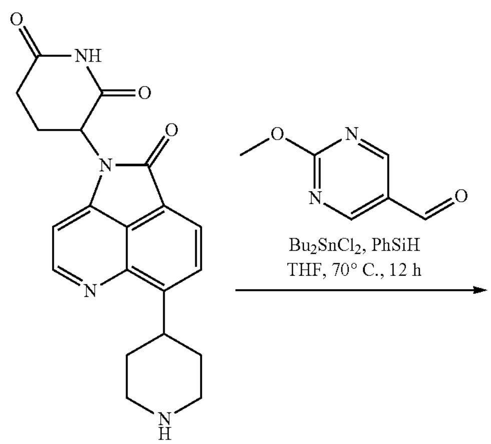

-continued

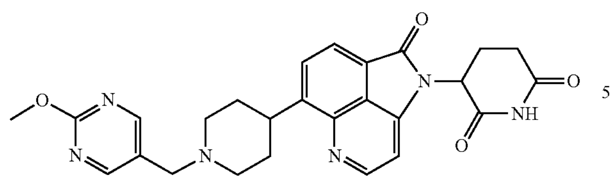

To a solution of 3-[18-oxo-10-(4-piperidyl)-20,23-diazatricyclododeca-(10),1(11),2(12),3(20),13-pentaen-23-yl]piperidine-2,6-dione (80 mg, 219.54 μmol) and 2-methoxypyrimidine-5-carbaldehyde (30.32 mg, 219.54 μmol) in dry THF (4 mL) was added dibutyltin dichloride (100 mg, 73.57 μL, 329.31 μmol) portionwise and the reaction mixture was heated at 70° C. for 1 hour. Subsequently, the reaction mixture was cooled to room temperature and phenylsilane (28.51 mg, 32.51 μL, 263.45 μmol) was added. The mixture was heated at 70° C. for another 12 hours in a sealed vial. After completion, the reaction mixture was cooled to 0° C. and quenched with the addition of ice-cold water (10 mL) and extracted with ethyl acetate (3×20 mL). The combined organics was separated, dried over anhydrous sodium sulfate and concentrated under reduced pressure. The crude product was purified by PREP-TLC to afford 3-[14-1-[(2-methoxypyrimidin-5-yl)methyl]-4-piperidyl]-24-oxo-26,31-diazatricyclododeca-1(14),2(15),3(16),4(26),18-pentaen-31-yl]piperidine-2,6-dione (Compound 127, 8.5 mg, 17.44 μmol, 8% yield) as an off-white solid. LC-MS ($ES^+$): m/z 487.2 $[M+H]^+$. $^1H$ NMR (400 MHz, DMSO-$d_6$) δ 11.15 (s, 1H), 8.86 (d, J=4.68 Hz, 1H), 8.55 (s, 2H), 8.08 (d, J=7.28 Hz, 1H), 7.84 (d, J=7.4 Hz, 1H), 7.21 (d, J=4.76 Hz, 1H), 5.43 (m, 1H), 3.91 (s, 3H), 3.79 (m, 1H), 3.53 (s, 2H), 2.99-2.97 (br m, 6H), 2.19-2.16 (m, 3H), 1.90 (m, 3H).

Example 57: Synthesis of 3-[21-[1-[(3-morpholinosulfonylphenyl)methyl]-4-piperidyl]-29-oxo-31,35-diazatricyclododeca-3(21),4(22),5(23),6(31),24-pentaen-35-yl]piperidine-2,6-dione (Compound 128)

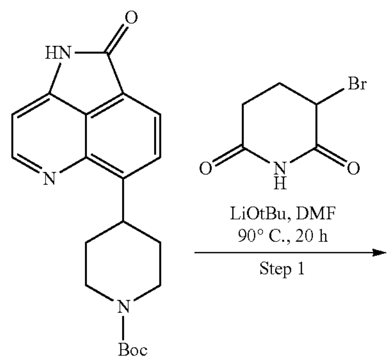

-continued

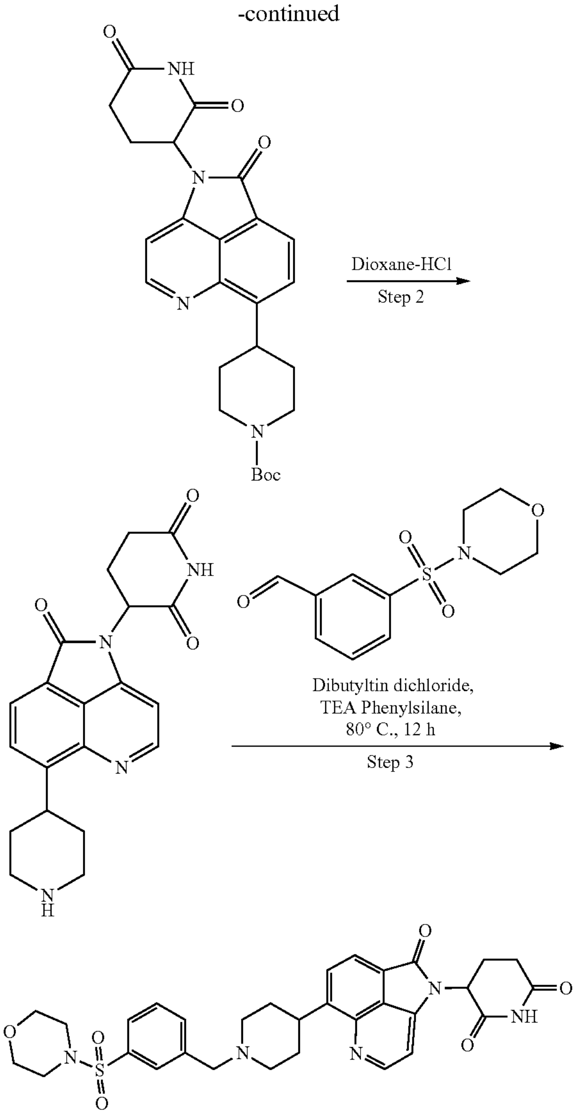

Step 1: To a stirred solution of tert-butyl 4-(17-oxo-20,21-diazatricyclododeca-3,5(13),6(20),11(15),12(14)-pentaen-11-yl)piperidine-1-carboxylate (100 mg, 282.95 mol) in DMF (5 mL), lithium tert-butoxide, (90.61 mg, 1.13 mmol) was added at 0° C., followed by 3-bromopiperidine-2,6-dione (108.66 mg, 565.91 mol). The resulting reaction mixture was heated at 90° C. for 16 hours. After completion, the reaction mixture was quenched with saturated $NH_4Cl$ solution and extracted with ethyl acetate. The organic layer was dried over anhydrous sodium sulfate and concentrated under reduced pressure. The crude product was purified by combi-flash column chromatography (50% EtOAc in DCM) to afford tert-butyl 4-[28-(2,6-dioxo-3-piperidyl)-21-oxo-25,28-diazatricyclododeca-3,5(15),6(25),13(17),14(16)-pentaen-13-yl]piperidine-1-carboxylate (25 mg, 38.75 μmol, 14% yield). LC-MS ($ES^+$): m/z 465 $[M+H]^+$.

Step 2: To a stirred solution of tert-butyl 4-[28-(2,6-dioxo-3-piperidyl)-21-oxo-25,28-diazatricyclododeca-3,5(15),6(25),13(17),14(16)-pentaen-13-yl]piperidine-1-carboxylate (25 mg, 53.82 mol) in 1,4-dioxane (0.5 mL), dioxane-HCl (4 M, 30 L) was added dropwise at 0° C. The reaction mixture was stirred for 3 hours at the same temperature. After completion, the mixture was evaporated to dryness to give 3-[18-oxo-10-(4-piperidyl)-20,23-diazatricyclododeca-,2(12),3(20),10(14),11(13)-pentaen-23-yl]piperidine-2,6-dione hydrochloride (15 mg crude, 37.42 μmol, 70% yield). LC-MS ($ES^+$): m/z 365 $[M+H]^+$.

Step 3: To a stirred solution of 3-[18-oxo-10-(4-piperidyl)-20,23-diazatricyclododeca-,2(12),3(20),10(14),11(13)-pentaen-23-yl]piperidine-2,6-dione hydrochloride (15 mg, 37.42 mol), 3-morpholinosulfonylbenzaldehyde (9.55 mg, 37.42 mol) in THF (3 mL), dibutyltin dichloride (13.64 mg, 44.90 μmol, 10.03 μL) and $Et_3N$ (7.57 mg, 74.84 mol, 10.43 L) were added and the reaction mixture was stirred for 1 hour at 60° C. This mixture was cooled to ambient temperature and phenylsilane (6.07 mg, 56.13 mol) was added. The resulting solution was heated at 80° C. for another 12 hours. The crude product was purified by reverse phase prep-HPLC to afford 3-[21-[1-[(3-morpholinosulfonylphenyl)methyl]-4-piperidyl]-29-oxo-31,35-diazatricyclododeca-3(21),4(22),5(23),6(31),24-pentaen-35-yl]piperidine-2,6-dione (Compound 128, 2.94 mg, 4.69 μmol, 13% yield). LC-MS ($ES^+$): m/z 604 $[M+H]^+$. $^1H$ NMR (400 MHz, DMSO-$d_6$) δ 11.16 (s, 1H), 8.86 (d, J=8 Hz, 1H), 8.10 (t, J=8 Hz, 1H), 7.86 (s, 1H), 7.73 (s, 1H), 7.64 (s, 1H), 7.22 (d, J=8 Hz, 1H), 5.44 (dd, J=12 Hz, 4 Hz, 1H), 4.55 (s, 1H), 3.85 (s, 1H), 3.69 (s, 1H), 3.63 (s, 4H), 2.97-2.94 (m, 2H), 2.88 (s, 4H), 2.75-2.63 (m, 2H), 2.32-2.24 (m, 2H), 2.13-2.10 (m, 1H), 1.90 (s, 3H), two aliphatic protons were unresolved.

Example 58: Synthesis of 29-(2,6-dioxo-3-piperidyl)-N-(2-methyl-1-phenyl-propyl)-21-oxo-26,29-diazatricyclododeca-7,9(16),10(26),14(17),15(18)-pentaene-15-carboxamide (Compound 129)

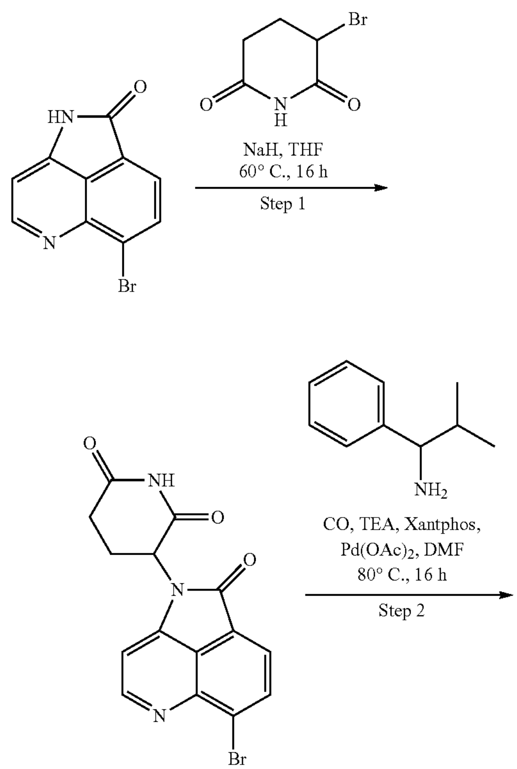

-continued

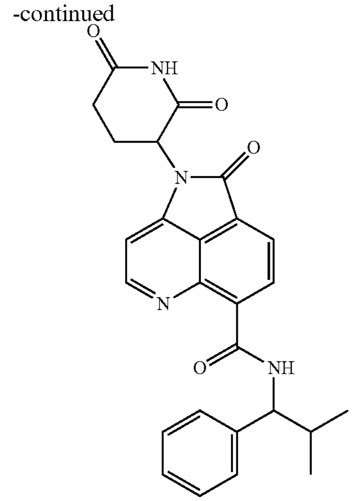

Step 1: To a solution of 6-bromo-10,11-diazatricyclododeca-,2(5),3(10),4(7),6(8)-pentaen-9-one (0.5 g, 2.01 mmol) in THF (5 mL) NaH (60% dispersion in mineral oil) (92.31 mg, 4.02 mmol, 6.69 mL) was added portionwise at room temperature and the resulting solution was heated at 60° C. for 1 hour. In another flask, a stirred solution of 3-bromopiperidine-2,6-dione (578.20 mg, 3.01 mmol) in THF (5 mL) was heated at 60° C. and the former mixture was added slowly to this solution. Heating was continued at the same temperature for an additional 16 hours. After completion, the reaction mixture was quenched with saturated ammonium chloride solution and extracted with ethyl acetate. The combined organic layer was washed with water, saturated brine solution, dried over anhydrous sodium sulfate, filtered, and concentrated under reduced pressure. The crude product was purified by combi-flash column chromatography (50% ethyl acetate-DCM) to afford 3-(8-bromo-13-oxo-15,17-diazatricyclododeca-,2(7),3(15),6(9),8(10)-pentaen-17-yl)piperidine-2,6-dione (100 mg, 263.77 mol, 13% yield). LC-MS ($ES^+$): m/z 360 $[M+H]^+$.

Step 2: To a solution of 3-(8-bromo-13-oxo-15,17-diazatricyclododeca-,2(7),3(15),6(9),8(10)-pentaen-17-yl)piperidine-2,6-dione (50 mg, 138.83 μmol) in DMF (0.5 mL) were added triethylamine (56.19 mg, 555.31 μmol, 77.40 μL) and 2-methyl-1-phenyl-propan-1-amine (31.08 mg, 208.24 mol). The resulting solution was degassed and back-filled with argon for 5 minutes before Xantphos (16.07 mg, 27.77 μmol) and $Pd(OAc)_2$ (12.47 mg, 55.53 μmol) were added. This mixture was again degassed and back-filled with argon for 2 minutes. The reaction mixture was purged with a carbon monoxide-filled balloon and heated at 80° C. for 16 hours under this atmosphere. After completion of the reaction, the reaction mixture was purified by reverse phase prep purification to afford 29-(2,6-dioxo-3-piperidyl)-N-(2-methyl-1-phenyl-propyl)-21-oxo-26,29-diazatricyclododeca-7,9(16),10(26),14(17),15(18)-pentaene-15-carboxamide (Compound 129, 2.43 mg, 5.02 mol, 4% yield). LC-MS ($ES^+$): m/z 457 $[M+H]^+$. $^1H$ NMR (400 MHz, DMSO-$d_6$) δ 11.28 (s, 1H), 11.16 (br.s, 1H), 9.08 (d, J=8 Hz, 1H), 8.83 (d, J=8 Hz, 1H), 8.24 (d, J=8 Hz, 1H), 7.40-7.32 (m, 5H), 7.26 (s, 1H), 5.51 (dd, J=12 Hz, 4 Hz, 1H), 5.07 (q, J=8 Hz, 1H), 2.94-2.90 (m, 1H), 2.78-2.73 (m, 2H), 2.68 (d, J=16 Hz, 1H), 2.22-2.15 (m, 2H), 1.23 (s, 2H), 0.99-0.94 (m, 6H).

Compound 130-Compound 133 were prepared substantially following the synthesis of Compound 129.

28-(2,6-dioxo-3-piperidyl)-N-[1-(2-methoxyphenyl)ethyl]-21-oxo-25,28-diazatricyclododeca-6,8(15),9(25),12(17),14(18)-pentaene-14-carboxamide (Compound 130)

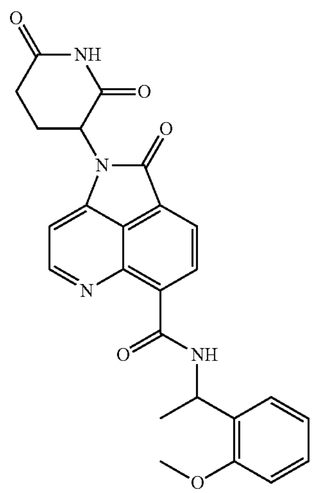 [SMILES: COc1ccccc1C(C)NC(=O)c1ccc2c3c(ccnc13)N(C1CCC(=O)NC1=O)C2=O]

LC-MS (ES$^+$): m/z 459.2 [M+H]$^+$.

$^1$H NMR (400 MHz, DMSO-$d_6$) δ 11.23 (d, J=8.3 Hz, 1H), 9.06 (d, J=5.0 Hz, 1H), 8.65 (d, J=7.3 Hz, 1H), 8.25 (d, J=7.3 Hz, 1H), 7.37-7.34 (m, 2H), 7.26 (dt, J=6.6, 1.4 Hz, 1H), 7.05 (d, J=8.1 Hz, 1H), 6.91 (t, J=7.3 Hz, 1H), 5.53-5.48 (m, 1H), 3.92 (s, 3H), 2.91-2.85 (m, 1H), 2.77-2.64 (m, 2H), 2.18-2.16 (m, 1H), 1.53 (d, J=6.9 Hz, 3H).

27-(2,6-dioxo-3-piperidyl)-19-oxo-N-(2,2,2-trifluoro-1-phenyl-ethyl)-24,27-diazatricyclododeca-5,7(14),8(24),12(15),13(16)-pentaene-13-carboxamide (Compound 131)

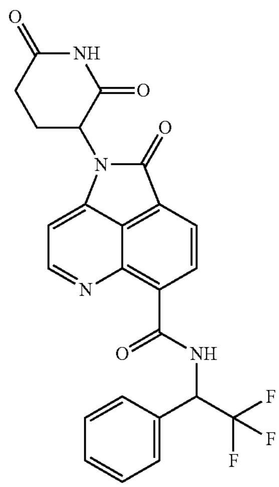 [SMILES: O=C1CCC(N2C(=O)c3ccc(C(=O)NC(c4ccccc4)C(F)(F)F)c4nccc2c34)C(=O)N1]

LC-MS (ES$^+$): m/z 483.2 [M+H]$^+$.

N-(1-cyclohexylethyl)-27-(2,6-dioxo-3-piperidyl)-20-oxo-24,27-diazatricyclododeca-1,3(14),4(24),12(15),13(16)-pentaene-13-carboxamide (Compound 132)

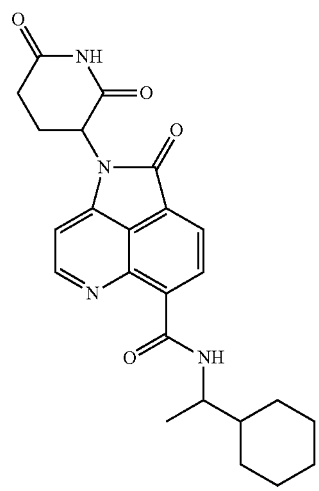 [SMILES: CC(NC(=O)c1ccc2c3c(ccnc13)N(C1CCC(=O)NC1=O)C2=O)C1CCCCC1]

LC-MS (ES$^+$): m/z 435.3 [M+H]$^+$.

$^1$H NMR (400 MHz, DMSO-$d_6$) δ 11.20 (s, 1H), 10.59 (d, J=8.5 Hz, 1H), 8.99 (d, J=5.0 Hz, 1H), 8.65 (d, J=7.3 Hz, 1H), 8.25 (d, J=7.3 Hz, 1H), 7.34 (dd, J=4.9, 1.3 Hz, 1H), 5.51-5.47 (m, 1H), 4.08-4.03 (m, 1H), 2.93-2.65 (m, 3H), 2.16-2.13 (m, 1H), 1.86-1.52 (m, 6H), 1.24-1.06 (m, 4H), 1.22 (d, J=6.7 Hz, 3H)

22-(2,6-dioxo-3-piperidyl)-N-isopropyl-15-oxo-19,22-diazatricyclododeca-2,4(10),5(19),8(11),9(12)-pentaene-9-carboxamide (Compound 133)

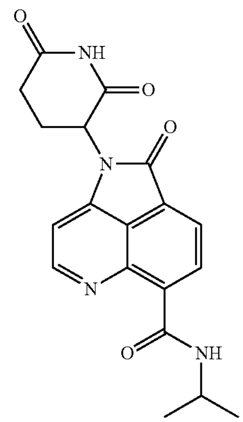 [SMILES: CC(C)NC(=O)c1ccc2c3c(ccnc13)N(C1CCC(=O)NC1=O)C2=O]

LC-MS (ES$^+$): m/z 367.2 [M+H]$^+$.

$^1$H NMR (400 MHz, DMSO-$d_6$) δ 11.20 (s, 1H), 10.47 (d, J=7.36 Hz, 1H), 8.98 (d, J=4.92 Hz, 1H), 8.65 (d, J=7.36 Hz, 1H), 8.25 (d, J=Hz, 1H), 7.35 (d, J=7.32 Hz, 1H), 5.55-5.45 (m, 1H), 4.21-4.20 (m, 1H), 3.21-2.90 (m, 1H), 2.78-2.61 (m, 2H), 2.19-2.10 (m, 1H), 1.29 (d, J=6.56 Hz, 6H).

Example 59: Synthesis of N2-(2,6-dioxo-3-piperidyl)-N5-(1-phenylethyl)pyridine-2,5-dicarboxamide (Compound 134)

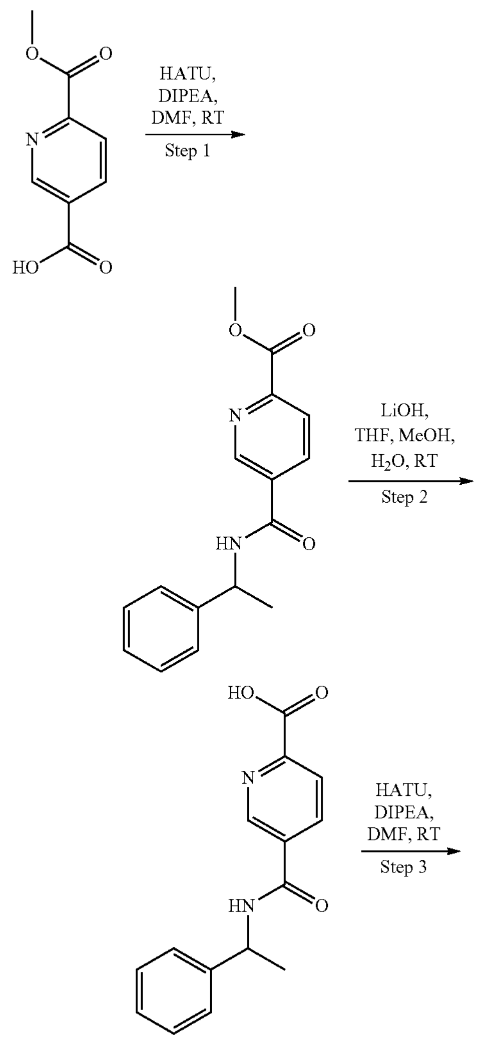

Step 1: To a stirred solution of 6-methoxycarbonylpyridine-3-carboxylic acid (500 mg, 2.76 mmol) in DCM (10 mL) was added N-ethyl-N-isopropyl-propan-2-amine (713.48 mg, 5.52 mmol, 961.56 μL) and HATU (1.06 g, 2.76 mmol) and the reaction mixture was stirred at room temperature for 15 minutes. 1-Phenylethanamine (334.48 mg, 2.76 mmol, 353.95 μL) was added to the solution and the resulting mixture was stirred for another 16 hours. After completion of the reaction, the reaction mixture was diluted with water and the separated organic layer was washed with water, saturated brine solution, dried over anhydrous sodium sulfate, filtered, and evaporated under reduced pressure. The crude product was purified by combi-flash column chromatography (50% EtOAc in hexane) to afford methyl 5-(1-phenylethylcarbamoyl)pyridine-2-carboxylate (500 mg, 1.60 mmol, 58% yield). LC-MS ($ES^+$): m/z 285 $[M+H]^+$.

Step 2: To a stirred solution of methyl 5-(1-phenylethylcarbamoyl)pyridine-2-carboxylate (250 mg, 879.32 μmol) in THF-MeOH—$H_2O$ (3.5 mL, 4:2:1) mixture at 10° C. was added $LiOH{\cdot}H_2O$ (55.35 mg, 1.32 mmol). The resulting mixture was stirred at room temperature for 16 hours. After completion, the reaction mixture was concentrated in vacuo, diluted with water, and washed with ethyl acetate. The organic layer was discarded, and the aqueous layer was cooled and acidified with 1N HCl until pH~2. It was then re-extracted with ethyl acetate and the organic phase was dried over anhydrous sodium sulfate, concentrated in vacuo to afford 5-(1-phenylethylcarbamoyl)pyridine-2-carboxylic acid (160 mg, 561.19 μmol, 64% yield) LC-MS ($ES^+$): m/z 271 $[M+H]^+$.

Step 3: To a stirred solution of 5-(1-phenylethylcarbamoyl)pyridine-2-carboxylic acid (100 mg, 369.98 μmol) in DMF (3 mL) was added HATU (141.42 mg, 369.98 μmol) and DIPEA (95.64 mg, 739.97 μmol, 128.89 μL) and the mixture was stirred at room temperature for 15 minutes. Subsequently, 3-amino-2,6-piperidinedione (47.41 mg, 369.98 μmol) was added and the resulting mixture was stirred at room temperature for another 16 hours. After completion of the reaction, the reaction mixture was purified by reverse phase prep-HPLC to afford N2-(2,6-dioxo-3-piperidyl)-N5-(1-phenylethyl)pyridine-2,5-dicarboxamide (Compound 134, 40.17 mg, 105.60 μmol, 29% yield). LC-MS ($ES^+$): m/z 381 $[M+H]^+$. $^1H$ NMR (400 MHz, DMSO-$d_6$) δ 10.86 (s, 1H), 9.18 (d, J=8 Hz, 2H), 9.07 (s, 1H), 8.45 (d, J=8 Hz, 1H), 8.15 (d, J=8 Hz, 1H), 7.41 (d, J=8 Hz, 2H), 7.34 (t, J=8 Hz, 2H), 7.25 (d, J=8 Hz, 1H), 5.19 (t, J=8 Hz, 1H), 4.81 (m, 1H), 2.80 (d, J=16 Hz, 1H), 2.24 (d, J=8 Hz, 1H), 2.01 (m, 1H), 1.50 (d, J=8 Hz, 3H), one proton is merged with solvent residual peak.

Example 60

3-(8-(4,6-dimethylpyrimidin-2-yl)-5-oxopyrrolo[2,3,4-de]quinolin-4(5H)-yl)piperidine-2,6-dione (Compound 135)

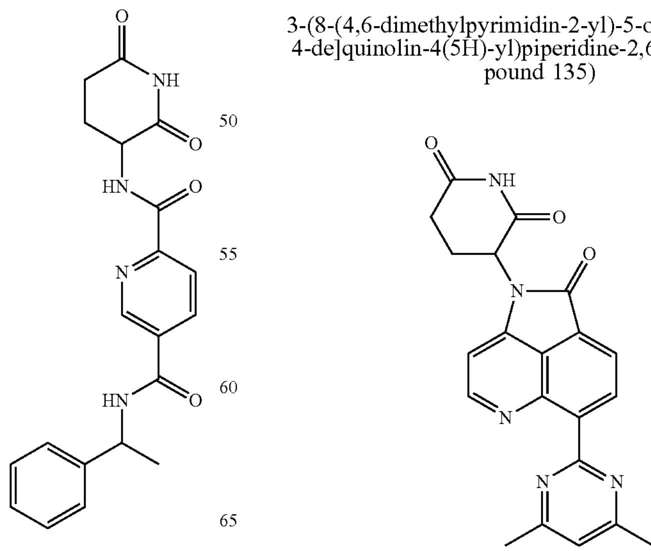

Compound 135 is prepared substantially following the synthesis of Compound 106 in Example 44, but using 14-bromo-19-[(4-methoxyphenyl)methyl]-18,19-diazatricyclododeca-5(12),6(14),7(13),8(18),15-pentaen-17-one as starting material in Step 2.

Example 61 IKZF2 Degradation Assay

HiBit Method

Materials

RPMI 1640 Medium without phenol red and fetal bovine serum (FBS) were purchased from Gibco (Grand Island, NY, USA). Nano-Glo® HiBiT Lytic Assay System was purchased from Promega (Madison, WI, USA). JURKAT.21 (IKZF2-HiBiT) cell line, endogenously expressing IKZF2 with HiBiT fusion tag via CRISPR, was purchasing from Synthego (Menlo Park, CA, USA). Cell culture flasks and 384-well microplates were acquired from VWR (Radnor, PA, USA).

IKZF2 Degradation Analysis

IKZF2 degradation was determined based on quantification of luminescent signal using Nano-Glo® HiBiT Lytic Assay kit. Test compounds were added to the 384-well plate from a top concentration of 10 μM with 11 points, half log titration in duplicates. JURKAT.216 cells were added into 384-well plates at a cell density of 5000 cells per well. The plates were kept at 37° C. with 5% $CO_2$ for 6 or 24 hours. The cells treated in the absence of the test compound were the negative control and the cells without Nano-Glo® HiBiT Lytic reagent were the positive control. After 6-hour or 24-hour incubation, Nano-Glo® HiBiT Lytic Assay reagents were added to the cells. Luminescence was acquired on EnVision™ Multilabel Reader (PerkinElmer, Santa Clara, CA, USA).

Example 62 GSPT1 Degradation Assay

HiBit Method

Materials

DMEM no-phenol red medium and fetal bovine serum (FBS) were purchased from Gibco (Grand Island, NY, USA). Nano-Glo® HiBiT Lytic Assay System was purchased from Promega (Madison, WI, USA). 293T.114 (HiBiT-GSPT1) cell line was generated in house, endogenously expressing GSPT1 with HiBiT fusion tag via CRISPR. Cell culture flasks and 384-well microplates were acquired from VWR (Radnor, PA, USA).

GSPT1 Degradation Analysis

GSPT1 degradation was determined based on quantification of luminescent signal using Nano-Glo® HiBiT Lytic Assay kit. Test compounds were added to the 384-well plate from a top concentration of 10 M with 11 points, half log titration in duplicates. 293T.114 cells were added into 384-well plates at a cell density of 6000 cells per well. The plates were kept at 37° C. with 5% $CO_2$ for 6 hours. The cells treated in the absence of the test compound were the negative control and the cells without Nano-Glo® HiBiT Lytic reagent were the positive control. After 6-hour incubation, Nano-Glo® HiBiT Lytic Assay reagents were added to the designated wells. Luminescence was acquired on EnVision™ Multilabel Reader (PerkinElmer, Santa Clara, CA, USA).

TABLE 1

| Cmpd | | HiBiT-Degradation | | | |
|---|---|---|---|---|---|
| | | 293T.114 GSPT1 6 hours | | JURKAT.21 IKZF2 6 hours | |
| # | Structure | $DC_{50}$ nM | $E_{max}$ | $DC_{50}$ nM | $E_{max}$ |
| 96 | 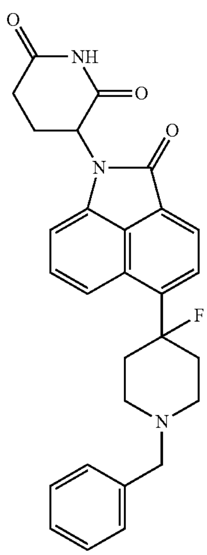 [SMILES: O=C1CCC(N2C(=O)c3ccc(C4(F)CCN(Cc5ccccc5)CC4)c4cccc2c34)C(=O)N1] | + | ++ | + | ++ |

TABLE 1-continued
| Cmpd # | Structure | HiBiT-Degradation 293T.114 GSPT1 6 hours DC$_{50}$ nM | E$_{max}$ | JURKAT.21 IKZF2 6 hours DC$_{50}$ nM | E$_{max}$ |
|---|---|---|---|---|---|
| 97 | 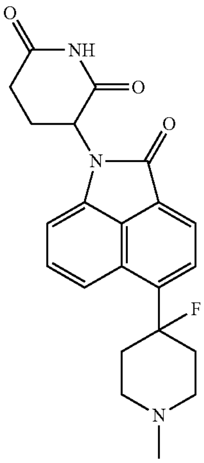 [SMILES: CN1CCC(F)(c2ccc3c4c(cccc24)N(C2CCC(=O)NC2=O)C3=O)CC1] | + | ++ | + | ++ |
| 98 | 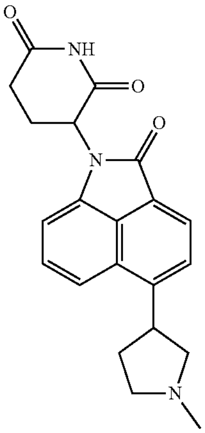 [SMILES: CN1CCC(c2ccc3c4c(cccc24)N(C2CCC(=O)NC2=O)C3=O)C1] | + | + | + | ++ |
| 99 | 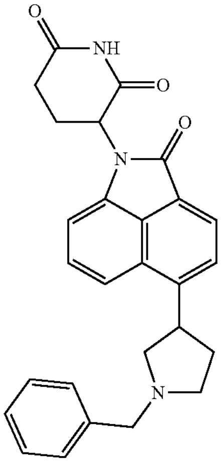 [SMILES: O=C1CCC(N2C(=O)c3ccc(C4CCN(Cc5ccccc5)C4)c4cccc2c34)C(=O)N1] | + | + | + | ++ |

TABLE 1-continued
| Cmpd # | Structure | HiBiT-Degradation 293T.114 GSPT1 6 hours DC$_{50}$ nM | E$_{max}$ | JURKAT.21 IKZF2 6 hours DC$_{50}$ nM | E$_{max}$ |
|---|---|---|---|---|---|
| 100 | 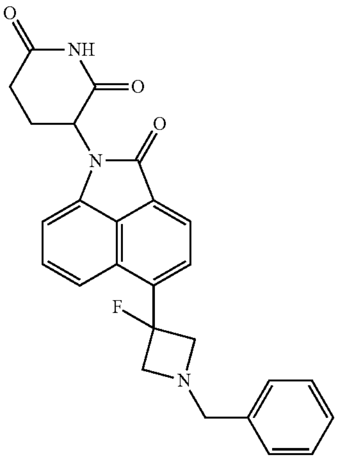 [SMILES: O=C1CCC(N2C(=O)c3ccc(C4(F)CN(Cc5ccccc5)C4)c4cccc2c34)C(=O)N1] | + | + | + | ++ |
| 101 | 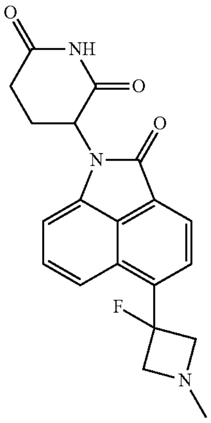 [SMILES: CN1CC(F)(c2ccc3c4c(cccc24)N(C2CCC(=O)NC2=O)C3=O)C1] | + | + | + | ++ |
| 102 | 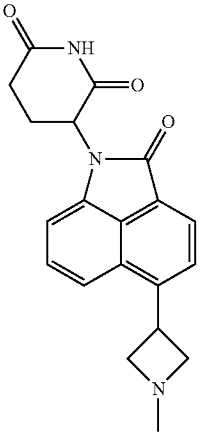 [SMILES: CN1CC(c2ccc3c4c(cccc24)N(C2CCC(=O)NC2=O)C3=O)C1] | + | ++ | + | ++ |

TABLE 1-continued
| Cmpd # | Structure | HiBiT-Degradation 293T.114 GSPT1 6 hours DC$_{50}$ nM | E$_{max}$ | JURKAT.21 IKZF2 6 hours DC$_{50}$ nM | E$_{max}$ |
|---|---|---|---|---|---|
| 103 | 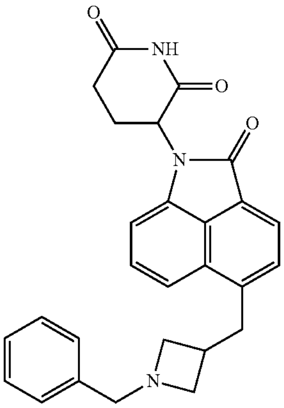 [SMILES: O=C1CCC(N2C(=O)c3ccc(CC4CN(Cc5ccccc5)C4)c4cccc2c34)C(=O)N1] | + | ++ | + | ++ |
| 104 | 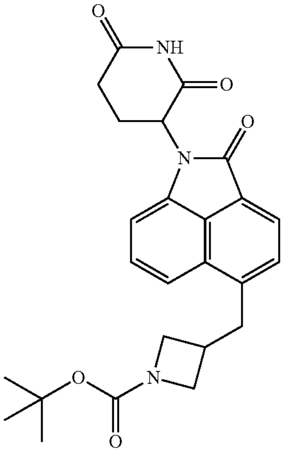 [SMILES: CC(C)(C)OC(=O)N1CC(Cc2ccc3c4c(cccc24)N(C2CCC(=O)NC2=O)C3=O)C1] | + | ++ | + | ++ |
| 105 | 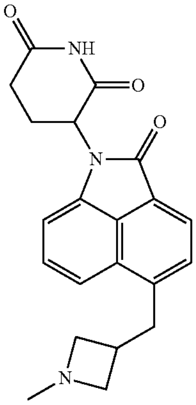 [SMILES: CN1CC(Cc2ccc3c4c(cccc24)N(C2CCC(=O)NC2=O)C3=O)C1] | + | + | + | ++ |

TABLE 1-continued
| Cmpd # | Structure | HiBiT-Degradation 293T.114 GSPT1 6 hours DC$_{50}$ nM | E$_{max}$ | HiBiT-Degradation JURKAT.21 IKZF2 6 hours DC$_{50}$ nM | E$_{max}$ |
|---|---|---|---|---|---|
| 106 | 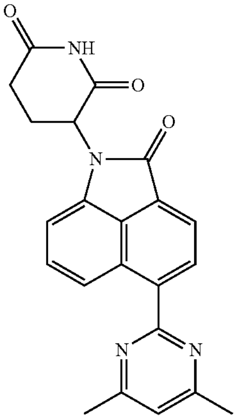 | + | ++ | +++ | +++ |
| 107 | 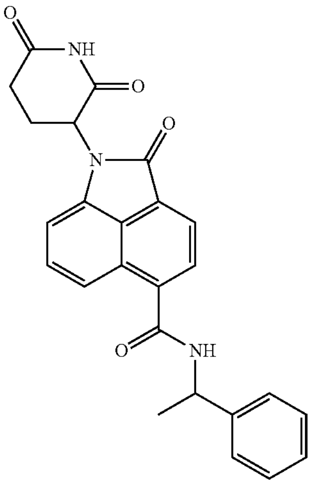 | + | ++ | + | ++ |
| 109 | 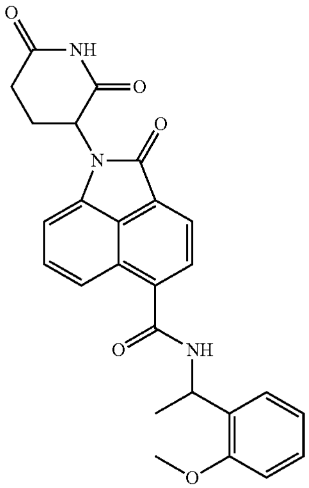 | + | ++ | | |

TABLE 1-continued
| Cmpd # | Structure | HiBiT-Degradation 293T.114 GSPT1 6 hours DC$_{50}$ nM | E$_{max}$ | JURKAT.21 IKZF2 6 hours DC$_{50}$ nM | E$_{max}$ |
|---|---|---|---|---|---|
| 110 | 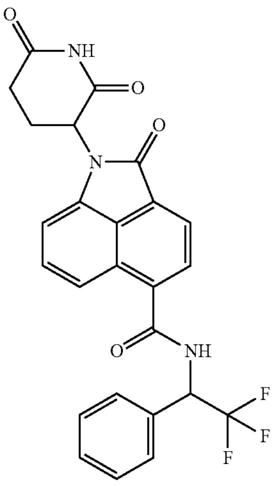 [SMILES: O=C1CCC(N2C(=O)c3ccc(C(=O)NC(c4ccccc4)C(F)(F)F)c4cccc2c34)C(=O)N1] | | | + | ++ |
| 112 | 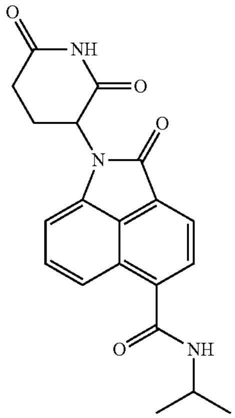 [SMILES: CC(C)NC(=O)c1ccc2c3c(cccc13)N(C1CCC(=O)NC1=O)C2=O] | + | ++ | + | ++ |
| 114 | 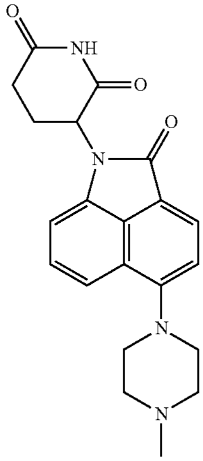 [SMILES: CN1CCN(c2ccc3c4c(cccc24)N(C2CCC(=O)NC2=O)C3=O)CC1] | + | ++ | | |

TABLE 1-continued
| Cmpd # | Structure | HiBiT-Degradation 293T.114 GSPT1 6 hours DC$_{50}$ nM | E$_{max}$ | HiBiT-Degradation JURKAT.21 IKZF2 6 hours DC$_{50}$ nM | E$_{max}$ |
|---|---|---|---|---|---|
| 115 | 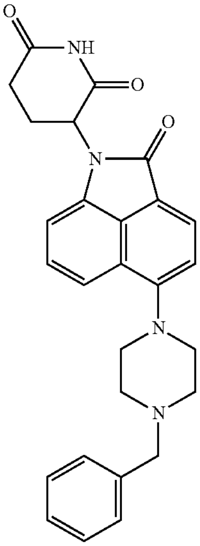 [SMILES: O=C1CCC(N2C(=O)c3ccc(N4CCN(Cc5ccccc5)CC4)c4cccc2c34)C(=O)N1] | | | + | ++ |
| 116 | 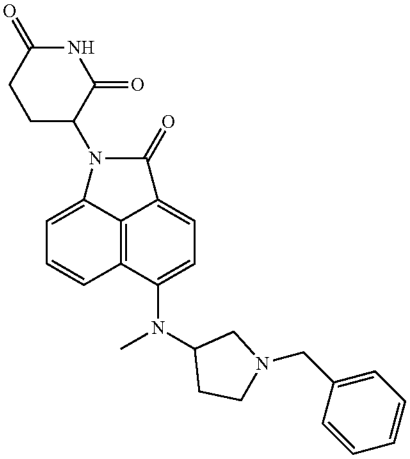 [SMILES: CN(c1ccc2c3c(cccc13)N(C1CCC(=O)NC1=O)C2=O)C1CCN(Cc2ccccc2)C1] | + | ++ | | |
| 117 | 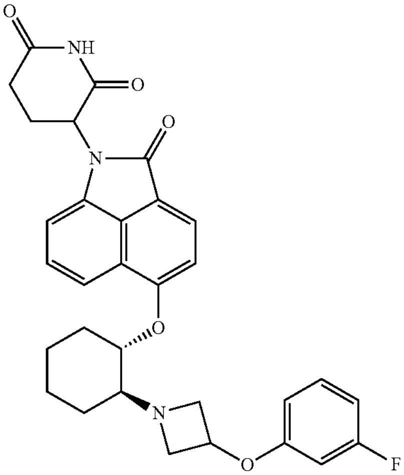 [SMILES: O=C1CCC(N2C(=O)c3ccc(O[C@H]4CCCC[C@@H]4N4CC(Oc5cccc(F)c5)C4)c4cccc2c34)C(=O)N1] | | | + | ++ |

TABLE 1-continued
| Cmpd # | Structure | HiBiT-Degradation 293T.114 GSPT1 6 hours DC$_{50}$ nM | E$_{max}$ | JURKAT.21 IKZF2 6 hours DC$_{50}$ nM | E$_{max}$ |
| --- | --- | --- | --- | --- | --- |
| 120 | 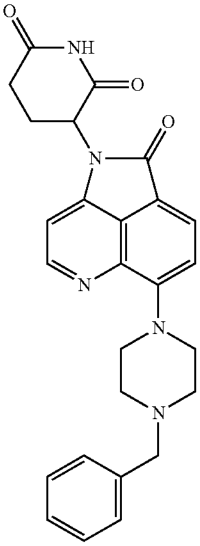 [SMILES: O=C1CCC(N2C(=O)c3ccc(N4CCN(Cc5ccccc5)CC4)c4nccc2c34)C(=O)N1] | + | ++ | + | ++ |
| 121 | 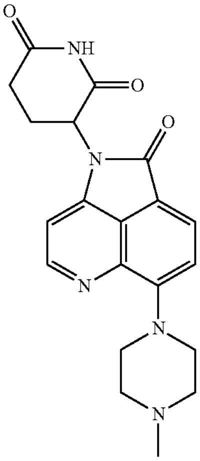 [SMILES: CN1CCN(c2ccc3c4c(ccnc24)N(C2CCC(=O)NC2=O)C3=O)CC1] | + | ++ | + | + |

TABLE 1-continued
| Cmpd # | Structure | HiBiT-Degradation 293T.114 GSPT1 6 hours DC$_{50}$ nM | E$_{max}$ | HiBiT-Degradation JURKAT.21 IKZF2 6 hours DC$_{50}$ nM | E$_{max}$ |
| --- | --- | --- | --- | --- | --- |
| 122 | 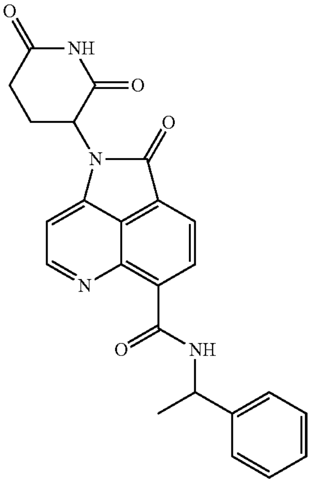 [SMILES: CC(NC(=O)c1ccc2c3c(ccnc13)N(C1CCC(=O)NC1=O)C2=O)c1ccccc1] | + | ++ | + | ++ |
| 123 | 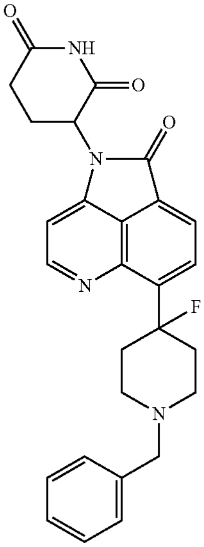 [SMILES: O=C1CCC(N2C(=O)c3ccc(C4(F)CCN(Cc5ccccc5)CC4)c4nccc2c34)C(=O)N1] | + | ++ | | |

TABLE 1-continued
| Cmpd # | Structure | HiBiT-Degradation 293T.114 GSPT1 6 hours DC$_{50}$ nM | HiBiT-Degradation 293T.114 GSPT1 6 hours E$_{max}$ | HiBiT-Degradation JURKAT.21 IKZF2 6 hours DC$_{50}$ nM | HiBiT-Degradation JURKAT.21 IKZF2 6 hours E$_{max}$ |
|---|---|---|---|---|---|
| 124 | 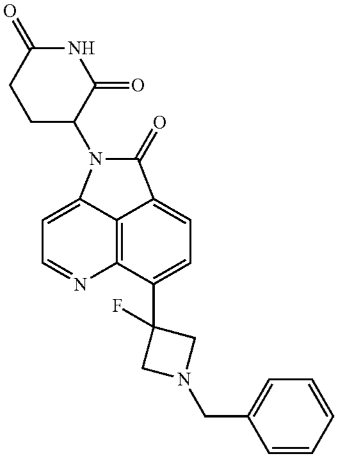 [SMILES: O=C1CCC(N2C(=O)c3ccc(C4(F)CN(Cc5ccccc5)C4)c4nccc2c34)C(=O)N1] | | | | |
| 126 | 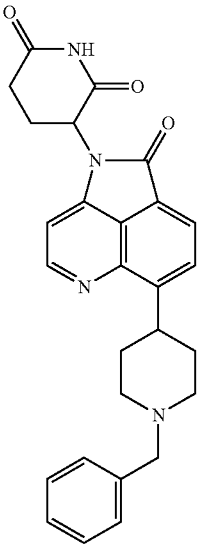 [SMILES: O=C1CCC(N2C(=O)c3ccc(C4CCN(Cc5ccccc5)CC4)c4nccc2c34)C(=O)N1] | | | + | ++ |

TABLE 1-continued
| Cmpd # | Structure | HiBiT-Degradation 293T.114 GSPT1 6 hours DC$_{50}$ nM | E$_{max}$ | HiBiT-Degradation JURKAT.21 IKZF2 6 hours DC$_{50}$ nM | E$_{max}$ |
|---|---|---|---|---|---|
| 127 | 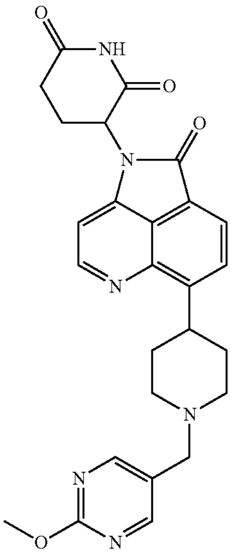 [SMILES: COc1ncc(CN2CCC(c3ccc4c5c(ccnc35)N(C3CCC(=O)NC3=O)C4=O)CC2)cn1] | + | + | + | ++ |
| 128 | 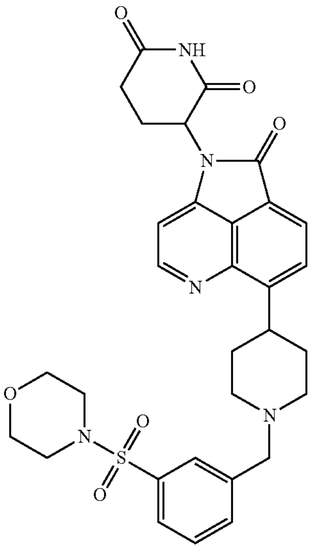 [SMILES: O=C1CCC(N2C(=O)c3ccc(C4CCN(Cc5cccc(S(=O)(=O)N6CCOCC6)c5)CC4)c4nccc2c34)C(=O)N1] | + | ++ | + | ++ |
As used in the table above for IC$_{50}$ values <500 nM = +++, 500-10,000 nM = ++, >10,000 nM = +
For Emax values <45% = ++++, 45-60% = +++, 60% = ++, >95% = +

As used in the table above for $IC_{50}$ values <500 nM=+++, 500-10,000 nM=++, >10,000 nM=+

For Emax values <45%=++++, 45-60%=+++, 60-95%=++, >95%=+

TABLE 2

| Cmpd # | Structure | HiBiT-Degradation JURKAT.21 IKZF2 24 hours DC$_{50}$ nM | E$_{max}$ |
|---|---|---|---|
| 102 | 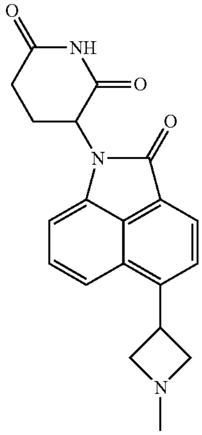 [SMILES: CN1CC(c2ccc3c4c(cccc24)N(C2CCC(=O)NC2=O)C3=O)C1] | + | ++ |
| 106 | 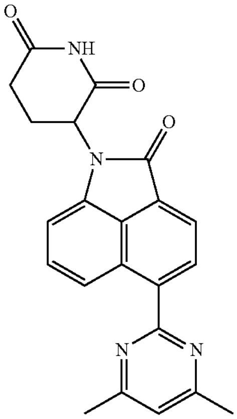 [SMILES: Cc1cc(C)nc(-c2ccc3c4c(cccc24)N(C2CCC(=O)NC2=O)C3=O)n1] | +++ | ++++ |

TABLE 2-continued

| Cmpd # | Structure | HiBiT-Degradation JURKAT.21 IKZF2 24 hours DC$_{50}$ nM | E$_{max}$ |
|---|---|---|---|
| 128 | 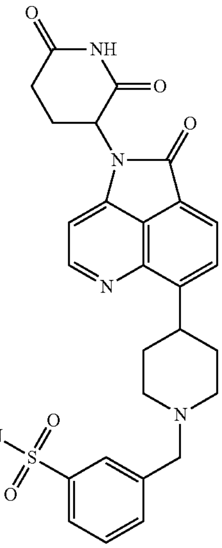 | + | ++ |

As used in the table above for $IC_{50}$ values <500 nM = +++, 500-10,000 nM = ++, >10,000 nM = +
For Emax values <45% = ++++, 45-60% = +++, 60% = ++, >95% = +

As used in the table above for $IC_{50}$ values <500 nM=+++, 500-10,000 nM=++, >10,000 nM=+
For Emax values <45%=++++, 45-60%=+++, 60-95%=++, >95%=+

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modifications may be made thereto without departing form the spirt or scope of the invention as defined in the claims and embodiments.

We claim:

1. A compound of Formula:

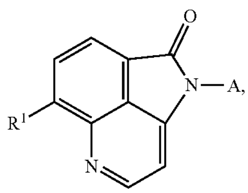

or a pharmaceutically acceptable salt thereof;

wherein:

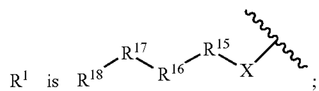

X is selected from the group consisting of a bond, alkyl, heterocycle, aryl, heteroaryl, bicycle, —$NR^{27}$—, —$NR^{10}$—, —$CR^{40}R^{41}$—, —O—, —C(O)—, —C($NR^{27}$)—, —C(S)—, —S(O)—, —$S(O)_2$— and —S—; each of which is optionally substituted, as allowed by valence, to form a stable compound, with 1, 2, 3, or 4 substituents independently selected from $R^{40}$;

$R^{15}$, $R^{16}$, and $R^{17}$ are independently at each occurrence selected from the group consisting of a bond, alkyl, —C(O)—, —C(O)O—, —OC(O)—, —$SO_2$—, —S(O)—, —C(S)—, —C(O)$NR^{27}$—, —$NR^{27}$C(O)—, —O—, —S—, —$NR^{27}$—, —$NR^{10}$—, —C($R^{40}R^{41}$)—, bicycle, alkene, alkyne, haloalkyl, alkoxy, aryl, heterocycle, cycloalkyl, and heteroaryl; each of which is optionally substituted, as allowed by valence to form a stable compound, with 1, 2, 3, or 4 substituents independently selected from $R^{40}$; and wherein no more than two of $R^{15}$, $R^{16}$, and $R^{17}$ are selected to be bond;

$R^{18}$ is selected from the group consisting of hydrogen, halogen, cyano, —C(O)$R^{27}$, —C(O)$OR^{27}$, alkyl, —C(O)$NR^{10}R^{27}$, —$NR^{27}$C(O)$R^{27}$, —$NR^{10}R^{27}$, —$OR^{27}$, —$SR^{27}$, alkene, alkyne, haloalkyl, alkoxy, aryl, heterocycle, and heteroaryl; each of which is optionally substituted, as allowed by valence to form a stable compound, with 1, 2, 3, or 4 substituents independently selected from $R^{40}$;

$R^{27}$ is independently at each occurrence selected from the group consisting of hydrogen, alkyl, arylalkyl, heteroarylalkyl, alkene, alkyne, aryl, heteroaryl, heterocycle, and cycloalkyl;

$R^{40}$ is independently at each occurrence selected from the group consisting of hydrogen, cyano, nitro, alkyl, halogen, haloalkyl, —$OR^{10}$, —$SR^{10}$, —S(O)$R^{12}$, —$SO_2R^{12}$, and —$NR^{10}R^{11}$;

$R^{41}$ is aryl, heteroaryl, or hydrogen;

A is selected from the group consisting of:

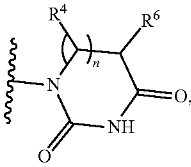
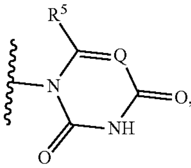
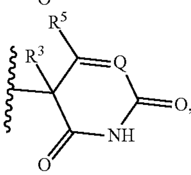
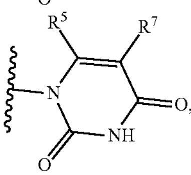
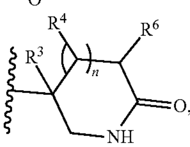
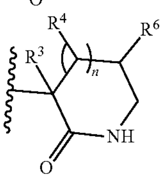
,
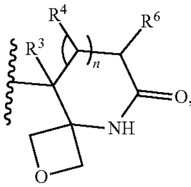
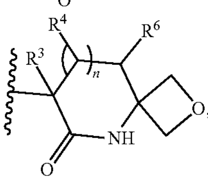
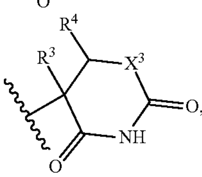
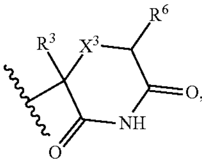
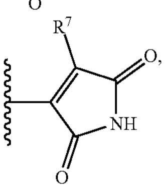
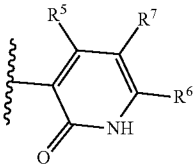
,
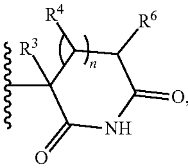
and
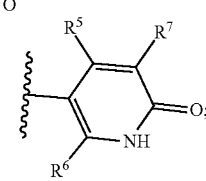

n is 0, 1, or 2;

$X^3$ is $NR^{10}$, $NR^{6'}$, O, or S;

Q is $CR^7$ or N;

$R^3$ is hydrogen, alkyl, halogen, or haloalkyl;

or $R^3$ and $R^6$ are combined to form a 1 or 2 carbon attachment;

or $R^3$ and $R^4$ are combined to form a 1, 2, 3, or 4 carbon attachment;

or $R^3$ and an $R^4$ group adjacent to $R^3$ are combined to form a double bond;

$R^4$ and $R^5$ are independently selected from the group consisting of hydrogen, alkyl, halogen, haloalkyl, —$OR^{10}$, —$SR^{10}$, —$S(O)R^{12}$, —$SO_2R^{12}$, and —$NR^{10}R^{11}$;

$R^6$ and $R^7$ are independently selected from the group consisting of hydrogen, alkyl, halogen, haloalkyl, —$OR^{10}$, —$SR^{10}$, —$S(O)R^{12}$, —$SO_2R^{12}$, and —$NR^{10}R^{11}$;

$R^{6'}$ is hydrogen, alkyl, or haloalkyl;

or $R^3$ and $R^{6'}$ are combined to form a 1 or 2 carbon attachment;

each $R^{10}$ and $R^{11}$ are independently selected from the group consisting of hydrogen, alkyl, haloalkyl, heterocycle, aryl, heteroaryl, —$C(O)R^{12}$, —$S(O)R^{12}$, and —$SO_2R^{12}$;

each $R^{12}$ is independently selected from the group consisting of hydrogen, alkyl, haloalkyl, heterocycle, aryl, heteroaryl, —$NR^{13}R^{14}$, and $OR^{13}$; and each instance of $R^{13}$ and $R^{14}$ is independently selected from the group consisting of hydrogen, alkyl, and haloalkyl.

2. The compound of claim 1, wherein the compound is selected from the group consisting of:

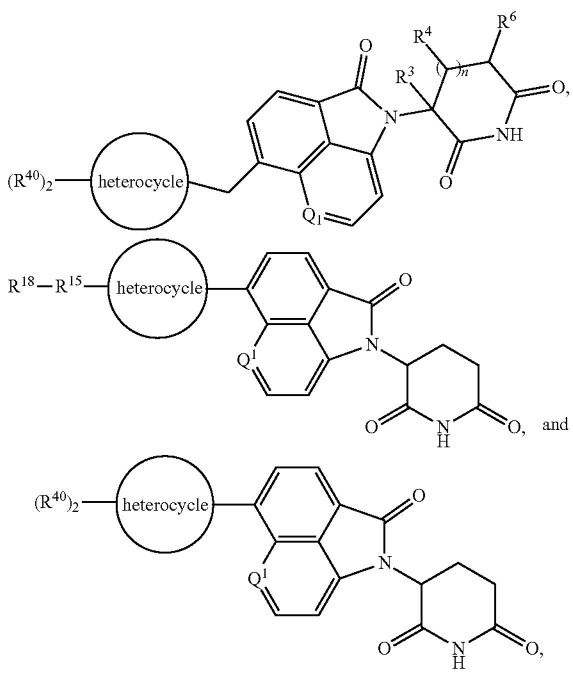

wherein $Q^1$ is N;

or a pharmaceutically acceptable salt thereof.

3. The compound of claim 2, wherein n is 1.

4. The compound of claim 3, wherein $R^4$ is hydrogen.

5. The compound of claim 4, wherein $R^3$ is hydrogen.

6. The compound of claim 5, wherein $R^6$ is hydrogen.

7. The compound of claim 1, wherein X is —C(O)—.

8. The compound of claim 1, wherein X is a bond.

9. The compound of claim 6, wherein $R^{15}$ is a bond, alkyl, haloalkyl, heterocycle, aryl, heteroaryl, or bicycle.

10. The compound of claim 1, wherein $R^{16}$ is a bond, alkyl, haloalkyl, heterocycle, aryl, heteroaryl, bicycle, —$S(O)_2$—, —C(O)—, —C(O)O—, —OC(O)—, —O—, or —$NR^{10}$—.

11. The compound of claim 1, wherein $R^{17}$ is a bond, alkyl, haloalkyl, heterocycle, aryl, heteroaryl, or bicycle.

12. The compound of claim 6, wherein $R^{18}$ is hydrogen, halogen, —$C(O)R^{27}$, —$C(O)OR^{27}$, —$C(O)NR^{10}R^{27}$, —$N^{27}C(O)R^{27}$, —$NR^{10}R^{27}$, or —$OR^{27}$.

13. The compound of claim 6, wherein $R^{18}$ is aryl, heterocycle, or heteroaryl, each of which is optionally substituted, as allowed by valence to form a stable compound, with 1, 2, 3, or 4 substituents independently selected from $R^{40}$.

14. The compound of claim 1, wherein the compound is selected from the group consisting of:

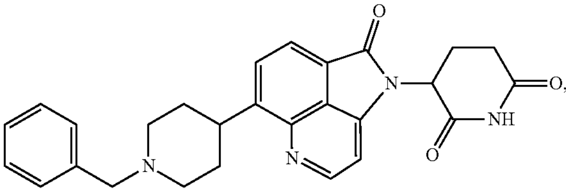

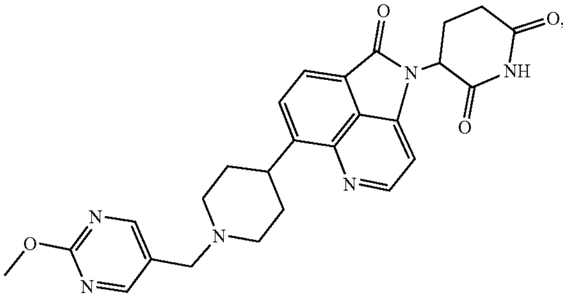

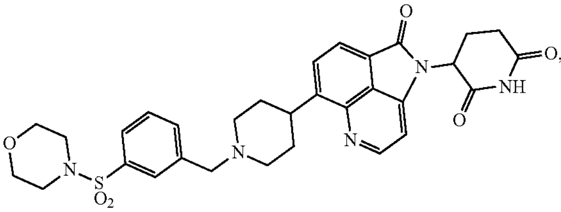

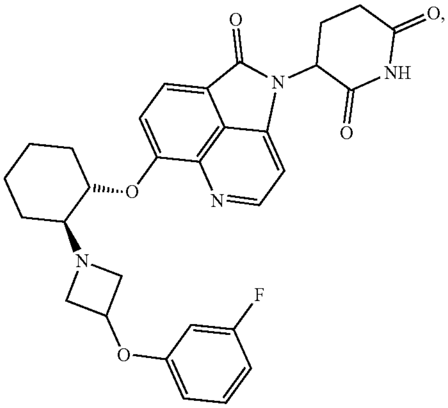

-continued
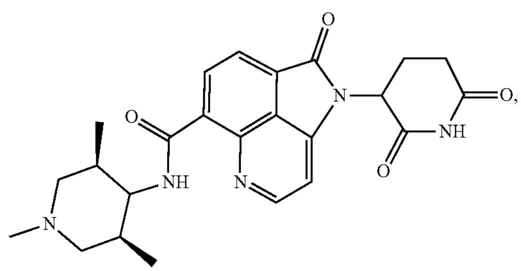
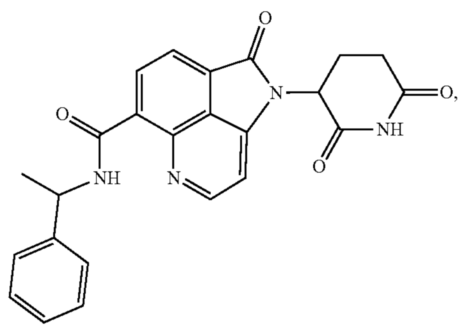
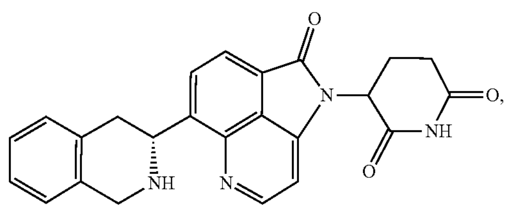
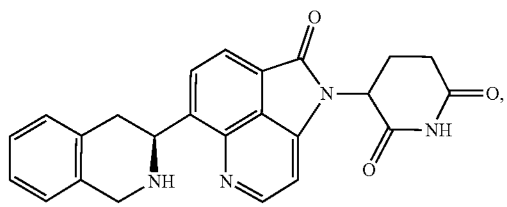
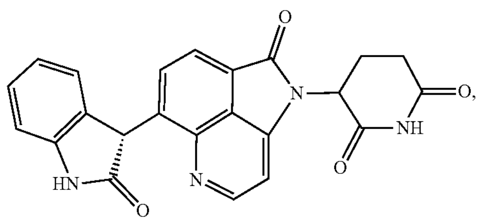
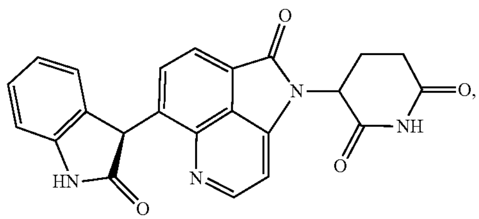
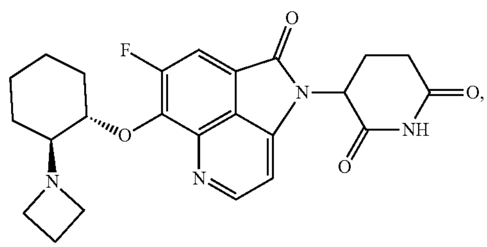
-continued
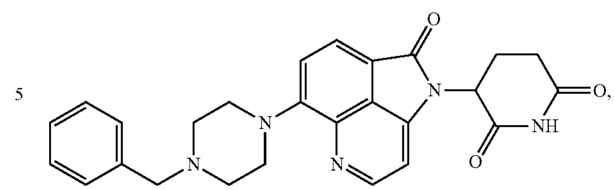
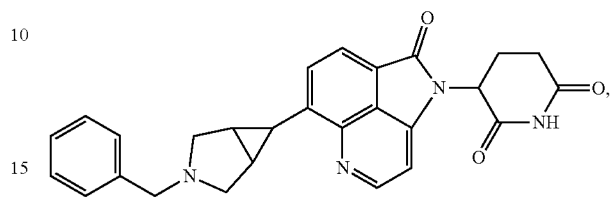
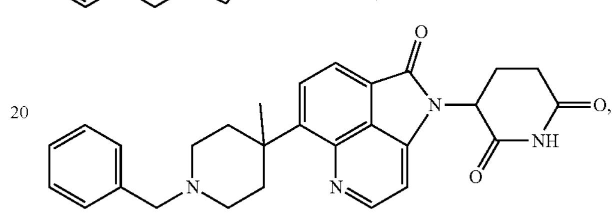
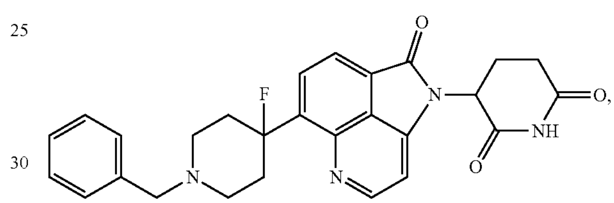
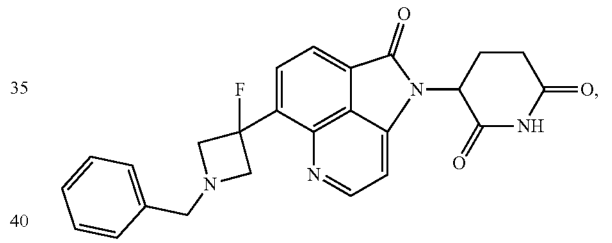
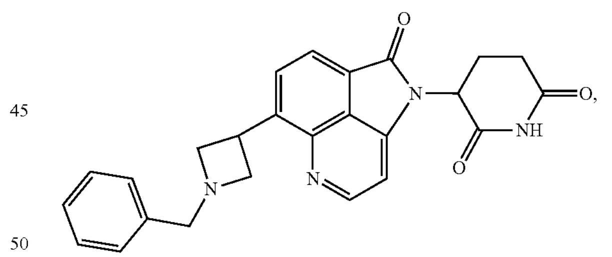
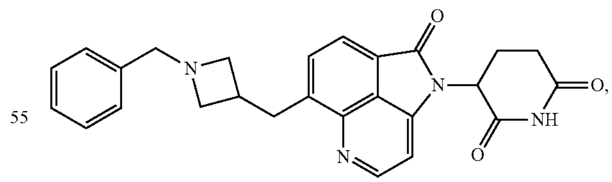
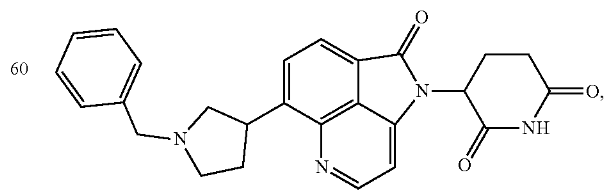

-continued
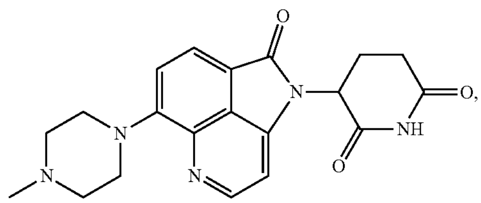
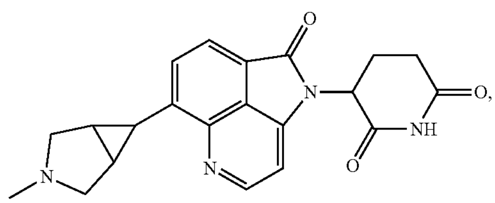
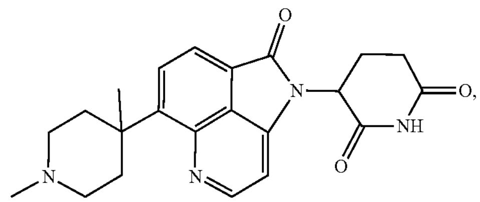
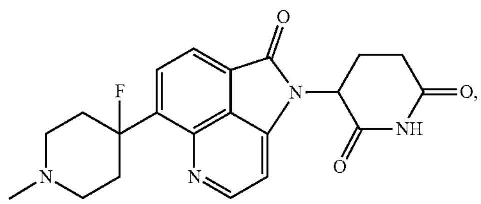
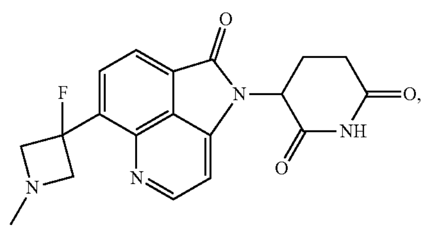
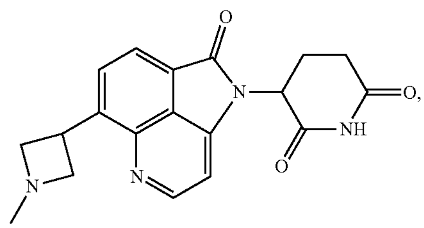
-continued
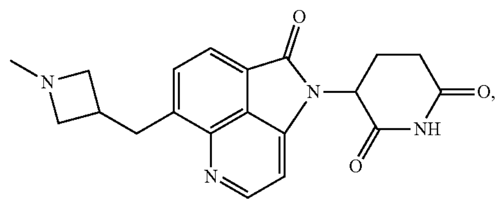
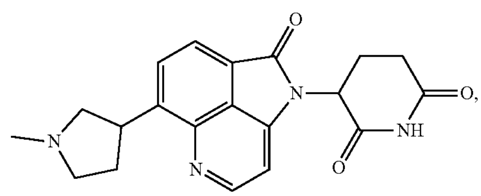
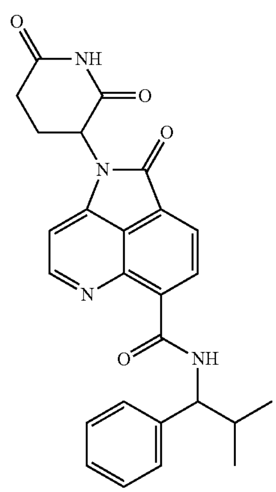
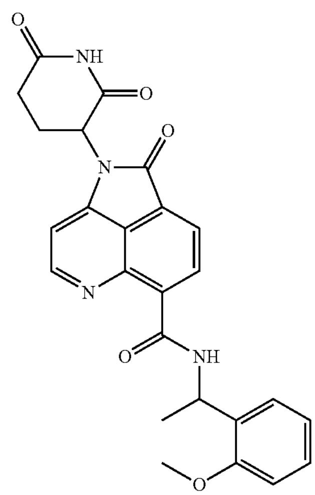

-continued

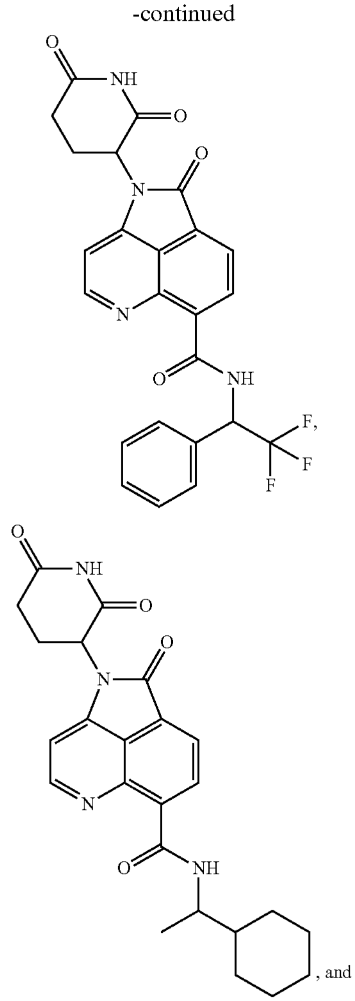

, and

-continued

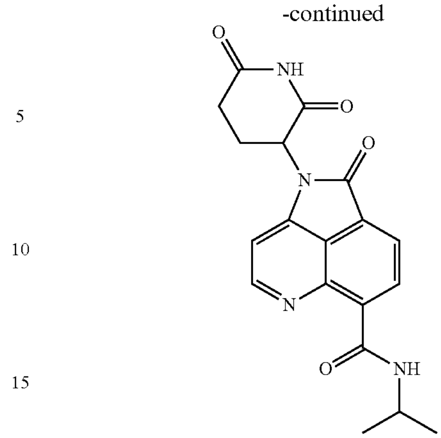

;

or a pharmaceutically acceptable salt thereof.

15. A pharmaceutical composition comprising a compound of claim 1 or a pharmaceutically acceptable salt thereof and a pharmaceutically acceptable excipient.

16. A method of treating a disorder mediated by cereblon, IKZF2, or IKZF4 in a human comprising administering an effective dose of a compound of claim 1 or a pharmaceutically acceptable salt or composition thereof to a human in need thereof.

17. The method of claim 16, wherein the disorder is a cancer or tumor.

18. The method of claim 16, wherein the disorder is an immune, autoimmune, or inflammatory disorder.

19. The method of claim 16, wherein the disorder is a hematological malignancy.

20. The method of claim 16, wherein the disorder is small cell lung carcinoma, non-small cell lung carcinoma, melanoma, breast cancer, triple negative breast cancer, multiple myeloma, leukemia, chronic myeloid leukemia, acute myeloid leukemia, acute lymphoblastic leukemia, chronic lymphoblastic leukemia, or a myelodysplastic syndrome.

* * * * *

SEQUENCE LISTING

```
Sequence total quantity: 3
SEQ ID NO: 1           moltype = AA  length = 6
FEATURE                Location/Qualifiers
source                 1..6
                       mol_type = protein
                       organism = Homo sapiens
SEQUENCE: 1
QCXXCG                                                             6

SEQ ID NO: 2           moltype = AA  length = 23
FEATURE                Location/Qualifiers
source                 1..23
                       mol_type = protein
                       organism = Homo sapiens
SEQUENCE: 2
QCXXCGXXXF XXXXXLXXHX XXH                                          23

SEQ ID NO: 3           moltype = AA  length = 17
```

-continued

```
FEATURE                 Location/Qualifiers
source                  1..17
                        mol_type = protein
                        organism = Homo sapiens
SEQUENCE: 3
QCXXCXXCGX XCXXXXX                                          17
```